US011427869B2

(12) United States Patent
Regev et al.

(10) Patent No.: US 11,427,869 B2
(45) Date of Patent: Aug. 30, 2022

(54) T CELL BALANCE GENE EXPRESSION, COMPOSITIONS OF MATTERS AND METHODS OF USE THEREOF

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US); THE BRIGHAM AND WOMEN'S HOSPITAL, INC., Boston, MA (US); THE REGENTS OF THE UNIVERSITY OF CALIFORNIA, Oakland, CA (US)

(72) Inventors: Aviv Regev, Cambridge, MA (US); Vijay K. Kuchroo, Boston, MA (US); Jellert Gaublomme, Cambridge, MA (US); Youjin Lee, Boston, MA (US); Chao Wang, Boston, MA (US); Nir Yosef, Oakland, CA (US); Hongkun Park, Cambridge, MA (US); James Kaminski, Oakland, CA (US)

(73) Assignees: The Broad Institute, Inc., Cambridge, MA (US); Massachusetts Institute of Technology, Cambridge, MA (US); President and Fellows of Harvard College, Cambridge, MA (US); The Brigham and Women's Hospital, Inc., Boston, MA (US); The Regents of the University of California, Oakland, CA (US)

( * ) Notice: Subject to any disclaimer, the term of this patent is extended or adjusted under 35 U.S.C. 154(b) by 201 days.

(21) Appl. No.: 15/687,089

(22) Filed: Aug. 25, 2017

(65) Prior Publication Data
US 2017/0349950 A1    Dec. 7, 2017

Related U.S. Application Data

(63) Continuation-in-part of application No. PCT/US2016/019949, filed on Feb. 26, 2016.

(60) Provisional application No. 62/386,073, filed on Nov. 16, 2015, provisional application No. 62/181,697, filed on Jun. 18, 2015, provisional application No. 62/176,796, filed on Feb. 26, 2015.

(51) Int. Cl.
*C12Q 1/6883* (2018.01)
*C12Q 1/6881* (2018.01)
*G01N 33/50* (2006.01)

(52) U.S. Cl.
CPC ........ *C12Q 1/6883* (2013.01); *C12Q 1/6881* (2013.01); *G01N 33/5023* (2013.01); *C12Q 2600/106* (2013.01); *C12Q 2600/112* (2013.01); *C12Q 2600/158* (2013.01)

(58) Field of Classification Search
CPC ...................................................... C12Q 1/68
See application file for complete search history.

(56) References Cited

U.S. PATENT DOCUMENTS

| 4,683,195 | A  | 7/1987  | Mullis et al. |
| 4,683,202 | A  | 7/1987  | Mullis |
| 5,989,431 | A  | 11/1999 | Evans et al. |
| 6,548,256 | B2 | 4/2003  | Lienau et al. |
| 7,041,481 | B2 | 5/2006  | Anderson et al. |
| 7,708,949 | B2 | 5/2010  | Stone et al. |
| 8,697,359 | B1 | 4/2014  | Zhang |
| 8,771,945 | B1 | 7/2014  | Zhang |
| 8,795,965 | B2 | 8/2014  | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015  | Cong et al. |

(Continued)

FOREIGN PATENT DOCUMENTS

| EP | 2047910 A2 | 4/2009 |
| EP | 2264182 A1 | 12/2010 |

(Continued)

OTHER PUBLICATIONS

Handbook of Chemistry and Physics, 49th Edition, 1968, Weast (ed.), The Chemical Rubber Co., Cleveland, Ohio, p. A-245.*

(Continued)

*Primary Examiner* — Ethan C Whisenant
(74) *Attorney, Agent, or Firm* — F. Brent Nix, Esq.; Johnson, Marcou, Isaacs & Nix, LLC; Michael B. Scher, Esq.

(57) ABSTRACT

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

5 Claims, 25 Drawing Sheets

(56) References Cited

U.S. PATENT DOCUMENTS

| | | |
|---|---|---|
| 8,945,839 B2 | 2/2015 | Zhang |
| 2005/0172476 A1 | 8/2005 | Stone et al. |
| 2007/0195127 A1 | 8/2007 | Ahn et al. |
| 2008/0003142 A1 | 1/2008 | Link et al. |
| 2008/0014589 A1 | 1/2008 | Link et al. |
| 2010/0022414 A1 | 1/2010 | Link et al. |
| 2010/0137163 A1 | 6/2010 | Link et al. |
| 2010/0172803 A1 | 7/2010 | Stone et al. |
| 2012/0122714 A1 | 5/2012 | Samuels et al. |
| 2012/0219947 A1 | 8/2012 | Yurkovetsky et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |

FOREIGN PATENT DOCUMENTS

| | | |
|---|---|---|
| EP | 2764103 A2 | 8/2014 |
| EP | 2771468 A1 | 9/2014 |
| EP | 2784162 A1 | 10/2014 |
| WO | 2004002627 A2 | 1/2004 |
| WO | 2007089541 A2 | 8/2007 |
| WO | 2012048265 A2 | 4/2012 |
| WO | 2013074691 A1 | 5/2013 |
| WO | 2013074812 A1 | 5/2013 |
| WO | 2013074825 A1 | 5/2013 |
| WO | 2014018423 A2 | 1/2014 |
| WO | 2014041800 A1 | 3/2014 |
| WO | 2014041804 A1 | 3/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014/134351 A2 | 9/2014 |
| WO | 2014/145992 A1 | 9/2014 |
| WO | 2014145631 A1 | 9/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2015130968 A2 | 9/2015 |

OTHER PUBLICATIONS

Caprioli et al. Th17 immune response in IBD: A new pathogenic mechanism. J. of Crohn's and Colitis 2 : 291-295 (Year: 2008).*

J. Gaublomme, et al., Single-Cell Genomics Unveils Critical Regulators of Th17 Cell Pathogenicity, Cell, (Nov. 19, 2015) vol. 163, No. 6, p. 1400-1412.

N. Yosef, et al., Dynamic Regulatory Network Controlling TH17 Cell Differentiation, Nature (Mar. 6, 2013) vol. 496, No. 7446, p. 461-468.

N. Yosef, et al., Supplementary Information: Dynamic Regulatory Network Controlling TH17 Cell Differentiation, Nature (Mar. 6, 2013) vol. 496, No. 7446, p. 461-468.

Youjin Lee, et al., Induction and Molecular Signatur of Pathogenic TH17 Cells, Nature Immunology (Sep. 9, 2012) vol. 13, No. 10, p. 991-999.

Toshimasa Aranami, et al., Th17 Cells and Autoimmune Encephalomyelitis (EAE/MS) Allergology International (Jan. 1, 2008) vol. 57, No. 2, p. 115-120.

Furuzawa-Carballeda, et al., Autoimmune Inflamation from the Th17 Perspective, Autoimmune Reviews, Elsevier, Amsterdam, Nl (Feb. 5, 2007) vol. 6,No. 3, p. 169-175.

Abadja, et al., "Significance of T helper 17 immunity in transplantation", Curr Opin Organ Transplant, 17(1), 2012, pp. 8-14.

Ahmed, et al., "IL-17 in obesity and adipogenesis", \Cytokine & growth factor reviews, 21, 2010, pp. 449-453.

Amit, et al., "A module of negative feedback regulators defines growth factor signaling," Nature Genetics, 39(4), 2007, pp. 503-512.

Annunziato, et al., "Phenotypic and functional features of human Th17 cells", The Journal of experimental medicine, 204, 2007, pp. 1849-1861.

Antebi, et al., "Mapping differentiation under mixed culture conditions reveals a tunable continuum of T cell fates", PLoS biology 11, 2013, 14 pages.

Arpaia, et al., "Metabolites produced by commensal bacteria promote peripheral regulatory T-cell generation", Nature, 504, 2013, pp. 451-455.

Aust, et al., "CXCR6 within T-helper (Th) and T-cytotoxic (Tc) type 1 lymphocytes in Graves' disease (GD)", European journal of endocrinology, 152, 2005, pp. 635-643.

Awasthi, et al., "Cutting edge: IL-23 receptor gfp reporter mice reveal distinct populations of IL-17-producing cells", Journal of immunology, 182, 2009, pp. 5904-5908.

Bachmann, et al., "CD2 sets quantitative thresholds in T cell activation", The Journal of experimental medicine, 190, 1999, pp. 1383-1392.

Baeten, et al., "How Cytokine Networks Fuel Inflammation: Interleukin-17 and a Tale of Two Autoimmune Diseases", Nature Medicine, vol. 19, 2013, 824-825.

Bending, et al., "Highly purified Th17 cells from BDC2.5NOD mice convert into Th1-like cells in NOD/SCID recipient mice", The Journal of clinical investigation, 119, 2009, pp. 565-572.

Berod, et al., "De Novo Fatty Acid Synthesis Controls the Fate Between Regulatory T and T helper 17 Cells", Nature Medicine, vol. 20, No. 11, 2014, 1327-1333.

Bettelli, et al., "Myelin oligodendrocyte glycoprotein-specific T cell receptor transgenic mice develop spontaneous autoimmune optic neuritis", The Journal of experimental medicine, 197, 2003, pp. 1073-1081.

Bettelli, et al., "Reciprocal Developmental Pathways for the Generation of Pathogenic Effector Th17 and Regulatory T Cells", Nature, vol. 441, May 2006, 235-238.

Blaschitz, et al., "Th17 Cytokines and the Gut Mucosal Barrier", J. Clin. Immunol., vol. 30, Feb. 2, 2010, 196-203.

Brenner, et al., "Toso controls encephalitogenic immune responses by dendritic cells and regulatory T cells", Proceedings of the National Academy of Sciences of the United States of America, 111, 2014, pp. 1060-1065.

Cellot, et al., "Zfx: At the Crossroads of Survival and Self-Renewal", Cell, vol. 129, 40/20/2007, 239-241.

Chai, et al., "Immobilized Anti-CD3 mAB Induces Anergy in Murine Naive and Memory CD4+ T Cells in Vitro", Intl. Immunol., vol. 9, No. 7, 1997, 935-944.

Chen, et al., "hmChIP: a database and web server for exploring publicly available human and mouse ChIP-seq and ChIP-chip data", Bioinformatics, 27, 2011, pp. 1447-1448.

Cho, et al., "The genetics and immunopathogenesis of inflammatory bowel disease", Nature reviews Immunology, 8, 2008, pp. 458-466.

(56) References Cited

OTHER PUBLICATIONS

Chung, et al., "Critical regulation of early Th17 cell differentiation by interleukin-1 signaling", Immunity, 30, 2009, pp. 576-587.
Ciofani, et al., "A validated regulatory network for Th17 cell specification", Cell, vol. 151, No. 2, Oct. 1, 2012, 289-303.
Codarri, et al., "RORgammat Drives Production of the Cytokine GM-CSF in Helper T Cells, Which is Essential for the Effector Phase of Autoimmune Neuroinflammation", Nature Immunology, vol. 12, Jun. 2011, 560-567.
Crawford, et al., "Molecular and transcriptional basis of CD4(+) T cell dysfunction during chronic infection", Immunity, 40, 2014, pp. 289-302.
Dang, et al., "Control of T(H)17/T(reg) balance by hypoxia-inducible factor 1", Cell, 146, 2011, pp. 772-784.
Dolfi, et al., "Late signals from CD27 prevent Fas-dependent apoptosis of primary CD8+ T cells", Journal of immunology ,180, 2008, pp. 2912-2921.
El-Behi, et al., "The encephalitogenicity of T(H)17 cells is dependent on IL-1- and IL-23-induced production of the cytokine GM-CSF", Nature immunology, 12, 2011, pp. 568-575.
Esfandiari, et al., "A Proinflammatory Role of IL-18 in the Development of Spontaneous Autoimmune Disease", J Immunol., vol. 157, 2001, 5338-5347.
Fang, et al., "The Zinc Finger Transcription Factor ZFX is Required for Maintaining the Tumorigenic Potential of Glioblastoma Stem Cells", Stem Cells, vol. 32, No. 8, Aug. 2014, 2033-2047.
Franke, et al., "Genome-wide meta-analysis increases to 71 the number of confirmed Crohn's disease susceptibility loci", Nature genetics, 42, 2010, pp. 1118-1125.
Gaffen, et al., "IL-17 signaling in host defense against Candida albicans", Immunologic research, 50, 2011, pp. 181-187.
Galan-Caridad, et al., "Zfx Controls the Self-Renewal of Embryonic and Hematopoietic Stem Cells", Cell, vol. 129, Apr. 20, 2007, 345-347.
Gattinoni, et al., "Wnt Signaling Arrests Effector T Cell Differentiation and Generates CD8+ Memory Stem Cells", Nat. Med, vol. 7, No. 7, Jul. 2009, 808-813.
Genovese, et al., "LY2439821, a humanized anti-interleukin-17 monoclonal antibody, in the treatment of patients with rheumatoid arthritis: A phase I randomized, double-blind, placebo-controlled, proof-of-concept study", Arthritis & Rheumatology, vol. 62, No. 4, 2010, 929-939.
Ghoreschi, et al., "Generation of pathogenic T(H)17 cells in the absence of TGF-beta signaling", Nature, 467, 2010, pp. 967-971.
Ghosh, et al., "Design, Synthesis, and Progress Toward Optimization of Potent Small Molecule Antagonists of CC Chemokine Receptor 8 (CCR8)", J. Med. Chem., vol. 49, No. 9, May 4, 2006, 2669-2672.
Gilmore, et al., "The c-Rel Transcription Factor in Development and Disease", Genes & cancer, 2, 2011, pp. 695-711.
Hamann, et al., "Therapeutic Targeting of Chemokine Signaling in Multiple Sclerosis", Journ of Neurologica Sciences, vol. 274, Nov. 25, 2008, 31-38.
Harant, et al., "Negative Cross-Talk Between the Human Orphan Nuclear Receptor Nur77/NAK-1/TR3 and Nuclear Factor-kappaB", Nucleic Acids Research, vol. 32, No. 17, 2004, 5280-5290.
Harel, et al., "ZFX Controls the Self Renewal of Human Embryonic Stem Cells", PLoS One, vol. 7, Issue 8, Aug. 2012, 1-10.
Harrington, et al., "Memory CD4 T Cells Emerge from Effector T-Cell Progenitors", Nature, vol. 452, No. 7185, Mar. 2008, 356-360.
Hendriks, "CD27 is Required for Generation and Long-Term Maintenance of T Cell Immunity", Nature Immunol., vol. 1, 2000, 433-440.
Hendriks, et al., "CD27 Promotes Survival of Activated T Cells and Complement CD28 in Generation and Establishment of the Effector T Cell Pool", The Journal of Experimental Medicine, vol. 198, No. 9, Nov. 3, 2003, 1369-1380.
Hernandez-Santos, et al., "Th17 Cells in Immunity to Candida albicans", Cell Host Microbe, vol. 11, No. 5, May 17, 2012, 425-435.
Hilliard, et al., "Critical roles of c-Rel in autoimmune inflammation and helper T cell differentiation", The Journal of clinical investigation, 110, 2002, pp. 843-850.
Hitoshi, et al., "Toso, a Cell Surface, Specific Regulator of Fas-Induced Apoptosis in T cells", Immunity, 1998, pp. 461-471.
Hock, et al., "Gfi-1 Restricts Proliferation and Preserves Functional Integrity of Haematopoietic Stem Cells", Nature, vol. 431, 2004, 1002-1007—Abstract.
Hueber, et al., "Secukinumab, a human anti-IL-17A monoclonal antibody, for moderate to severe Crohn's disease: unexpected results of a randomised, double-blind placebo-controlled trial", Gut, 61, 2012, pp. 1693-1700.
Hundt, et al., "Impaired Activation and Localization of LAT in Anergic T Cells as a Consequence of a Selective Palmitoylation Defect", Immunity, vol. 24, May 2006, 513-522.
Ichii, et al., "Bcl6 is Essential for the Generation of Long-term Memory CD4+ T Cells", International Immunology, vol. 19, No. 4, Feb. 16, 2007, 427-433.
Pepper, et al., "Different Routes of Bacterial Infection Induce Long-Lived Th1 Memory Cells and Short-Lived Th-17 Cells", Nat Immunol., vol. 11, No. 1, Jan. 2010, 83-89.
Peters, et al., "Podoplanin negatively regulates CD4+ effector T cell responses", The Journal of clinical investigation, 125(1), 2014, pp. 129-140.
Quintana, et al., "Aiolos Promotes Th17 Differentiation by Directly Silencing Il2 Expression", Nat Immunol., vol. 13, No. 8, Aug. 2001, 770-777.
Reya, et al., "A Role for Wnt Signalling in Self-Renewal of Haematopoietic Stem Cells", Nature, vol. 423,, May 22, 2003, 409-414.
Rocha, et al., "Med12 is Essential for Early Mouse Development and for Canonical Wnt and Wnt/PCP Signaling", Development, vol. 137, 2010, 2723-2731.
Sallusto, et al., "Two Subsets of Memory T Lymphocytes with Distinct Homing Potentials and Effector Functions", Nature, vol. 401, Oct. 14, 1999, 708-712.
Salminen, et al., "Control of p53 and NF-(kappa)B Signaling by WIP1 and MIF: Role in Cellular Senescence and Organismal Aging", Cell Signal, vol. 23, No. 5, May 2011, 747-752.
Sanjurjo, et al., "The Human CD5L/AIM-CD36 Axis: A novel Autophagy Inducer in Macrophages that Modulates Inflammatory Responses", Autophagy, 2015, pp. 487-502.
Santori, et al., "Identification of Natural ROR(gamma_ Ligands that Regulate the Development of Lymphoid Cells", Cell Metabolism, vol. 21, Feb. 3, 2015, 286-297.
Sarkar, et al., "Functional and Genomic Profiling of Effector CD8 T Cell Subsets with Distinct Memory Fates", The Journ. of Exp. Med., vol. 205, No. 3, Mar. 17, 2008, 625-640.
Sarrias, et al., "The Scavenger Receptor Cysteine-Rich (SRCR) Domain: An Ancient and Highly Conserved Protein Module of the Innate Immune Systme", Crit. Rev. Immunol., vol. 24, No. 1, 2004, 1-37.
Segal, et al., "Module Networks: Identifying Regulatory Modules and Their Condition-Specific Regulators from Gene Expression Data", Nature Genetics, vol. 34, No. 2, Jun. 2003, 166-167.
Sester, et al., "PD-1 Expression and IL-2 Loss of Cytomegalovirus-Specific T Cells Correlates with Viremia and Reversible Functional Anergy", American Journal of Transplantation, vol. 8, 2008, 1486-1497.
Shi, et al., "HIF1alpha-dependent glycolytic pathway orchestrates a metabolic checkpoint for the differentiation of TH17 and Treg cells", The Journal of experimental medicine, vol. 208, No. 7, 2011, 1367-1376.
Shin, et al., "T-Bet Expression is Regulated by EGR1-Mediated Signaling in Activated T Cells", Clin Immunol., vol. 131, No. 3, Jun. 2009, 385-394.
Shinohara, et al., "Engagement of the Type 1 Interferon Receptor on Dendritic Cells Inhibits T Helper 17 Cell Development: Role of Intracellular Osteopontin", Immunity, vol. 29, Jul. 18, 2008, 68-78.

(56) References Cited

OTHER PUBLICATIONS

Snyder, et al., "Memory Inflation During Chronic Viral Infection is Maintained by Continous Production of Short-Lived, Functional Cells", Immunity, vol. 29, Oct. 17, 2008, 650-659.
Song, et al., "The Mouse Cell Surface Protein TOSO Regulates Fa/Fas Ligand-Induced Apoptosis through Its Binding to Fas-Associated Death Domain", Journ. of Biol. Chem., vol. 280, No. 10, Mar. 11, 2005, 9618-9626.
Soroosh, et al., "Oxysterols are agonist ligands of RORγt and drive Th17 cell differentiation", PNAS, vol. 111, No. 33, Aug. 19, 2014, 12163-12168.
Stumhofer, et al., "Interleukins 27 and 6 induce STAT3-mediated T cell production of interleukin 10", Nature Immunology, vol. 8, No. 12, 2007, 1363-1371.
Sutton, et al., "A Crucial Role for Interleukin (IL)-1 in the Induction of IL-17-Producing T Cells that Mediate Autoimmune Encephalitis", JEM, vol. 203, No. 7, 2006, 1685-1691.
Symons, et al., "Are Th17 Cells in the Gut Pathogenic or Protective", Mucosal Immunol., vol. 5, No. 1, Jan. 2012, 4-6.
The Broad Institute, Inc., et al., "Communication Pursuant to Rule 164(2)(b) and Article 94(3) EPC", dated Sep. 24, 2018, 6 pages.
The Broad Institute, Inc., et al., "Search Results under Rule 164(2)(b) EPC for EP 16714607", dated Sep. 17, 2018, 4 pages.
The Broad Institute, Inc., Communication Pursuant to Article 94(3) EPC for EP 16714607.5, dated Aug. 14, 2019, pp. 1-6.
Thierfelder, et al., "Requirement for Stat4 in Interleukin-12-Mediated Responses of Natural Killer and T Cells", Nature, vol. 382, Jul. 11, 1996, 171-174.
Trimble, et al., "CD3Gamma and CD28 Down-Modulation on CD8 T Cells During Viral Infection", Blood, vol. 96, No. 3, Aug. 1, 2000, 1021-1029.
Tsuzuki, et al., "TEL (ETV6)-A<L1 (RUNX1) Initiates Self-Renewing Fetal Pro-B Cells in Association wiht a Transcriptional Program Shared with Embryonic Stem Cells in Mice", Stem Cells, vol. 31, 2013, 236-247.
Veldhoen, et al., "TGFbeta in the context of an inflammatory cytokine milieu supports de novo differentiation of IL-17-producing T cells", Immunity, vol. 24, Issue 2, Feb. 2006, 179-189.
Waite, et al., "Th17 Response and Inflammatory Autoimmunce Diseases", Int. J. of Inflammation; vol. 2012, 2012, 1-10.
Wang, et al., "CD5L/AIM Regulates Lipid Biosynthesis and Restrains Th17 Cell Pathogenicity", Cell, 2015, pp. 1413-1427.
Wang, et al., "The Transcription Factor Foxp1 is a Critical Negative Regulator of the Differentiation of Follicular Helper T Cells", Nat. Immunol., vol. 15, May 25, 2014, 667-675.
Wei, et al., "Global Mapping of H3K4me3 and H3K27me3 Reveals Specificity and Plasticity in Lineage Fate Determination of Differentiating CD4+ T Cells", Immunity, vol. 30, No. 1, 2009, 155-167.
Weisberg, et al., "ZFX Controls Propagation and Prevents Differentiation of Acute T-Lymphoblastic and Myeloid Leukemia", Cell Reports, vol. 6, Feb. 13, 2014, 528-540.
Welford, et al., "HIF1apha Delays Premature Senescence Through the Activation of MIF", GensDevelop., vol. 20, 2006, 3366-3371.
Wells, et al., "Signalling through CD289 and CTLA-4 Controls Two Distinct Forms of T Cell Anergy", Journal of Clinical Investigation, vol. 108, No. 6, Sep. 15, 2001, 895-904.
Wherry, et al., "Molecular Signature of CD8+ T Cell Exhaustion During Chronic Viral Infection", Immunity, vol. 27, No. 4, Oct. 1, 2007, 670-684.
Willinger, et al., "Human Naive CD8 T Cells Down-Regulate Expression of the WNT Pathway Transcrioption Factors Lymphoid Enhancer Binding Factor 1 and Transcription Factor 7 (T Cell Factor) Following Antigen Encounter in Vitro and In Vivo", The Journ. of Immunology, vol. 176, 2006, 1439-1446.
Winer, et al., "Obesity predisposes to Th17 bias", European Journal of Immunology, vol. 39, Issue 9, Sep. 2009, 2629-2635.
Wu, et al., "Induction of Pathogenic Th17 Cells by Inducible Salt Sensing Kinase SGK1", Nature, vol. 496, No. 7446, Apr. 25, 2013, 513-517.
Xiao, et al., "Small-Molecule RORγt Antagonists Inhibit T Helper 17 Cell Transcriptional Network by Divergent Mechanisms", Immunity, vol. 40, No. 4, Apr. 2014, 477-489.
Xu, et al., "c-Maf Regulates IL-10 Expression during Th17 Polarization", The Journal of Immunology, vol. 182, No. 10, 2009, 6226-6236.
Ye, et al., "The role and regulation of human Th17 cells in tumor immunity", Am J Pathol., 182(1), 2013, pp. 10-20.
Zhou, et al., "IL-6 Programs Th-17 Cell Differentiation by Promoting Sequential Engagement of the IL-21 and IL-23", Nat. Immunol., vol. 8, No. 9, Sep. 2007, 967-974.
Zingoni, et al., "Cutting Edge: The Chemokine Receptor CCR8 is Preferentially Expressed in Th2 but not Th1 Cells", Journ Immunol., vol. 161, 1998, 547-551.
Nika et al., "Constitutively Active Lck Kinase in T Cells Drives Antigen Receptor Signal Transduction," Immunity, 32(6), 2010, p. 766-777.
Yang, et al., "Focused Specificity of Intestinal Th17 Cells towards Commensal Bacterial Antigens," Nature, 510(7503), 2014, pp. 152-156.
The Broad Institute, Inc., "Communication pursuant to Article 94(3) EPC for EP 16714607.5", May 14, 2020, 7 pages.
International Genetics of Ankylosing Spondylitis, et al., "Identification of multiple risk variants for ankylosing spondylitis through high-density genotyping of immune-related loci", Nature genetics, 45, 2013, pp. 730-738.
International Multiple Sclerosis Genetics, et al., "Genetic risk and a primary role for cell-mediated immune mechanisms in multiple sclerosis", Nature, 476, 2013, pp. 214-219.
Ioannidis, et al., "The B-Catenin-TCF-1 Pathway Ensures CD4+ CD8+ Thymocyte Survival", Nature Immunology, vol. 2, No. 8,, Aug. 2001, 691-697.
Isakov, et al., "LcK Protein Kinase is a Key Regulator of T-Cell Activation and a Target for Signal Intervention by Herpesvirus saimiri and other Viral Gene Products", Eur. J. Biochem., vol. 267, 2000, 3413-3421.
Ivanov, et al., "Induction of intestinal Th17 cells by segmented filamentous bacteria", Cell, vol. 139, No. 3, 2009, 485-498.
Jager, et al., "Th1, Th17, and Th9 effector cells induce experimental autoimmune encephalomyelitis with different pathological phenotypes", The Journal of Immunology, vol. 183, No. 11, 2009, 7169-7177.
Jarboe, et al., "MARCKS Regulates Growth, Radiation Sensitivity and is a Novel Prognostic Factor for Glioma", Clin. Cancer Res., vol. 18, No. 11, Jun. 1, 2012, 3030-3041.
Jhun, et al., "Obesity aggravates the joint inflammation in a collagen-induced arthritis model through deviation to Th17 differentiation", Experimental & Molecular Medicine, vol. 44, No. 7, Jul. 2012, 424-431.
Jin, et al., "Structural Basis for Hydroxycholesterols as Natural Ligands of Orphan Nuclear Receptor ROR(gamma)", Molecular Endocrinology, vol. 24, 2010, 923-929.
Jostins, et al., "Host-microbe interactions have shaped the genetic architecture of inflammatory bowel disease", Nature, vol. 491, No. 7422, Nov. 1, 2012, 119-124.
Kandasamy, et al., "NetPath: A Public Resource of Curated Signal Transduction Pathways", Genome Biology, vol. 11, No. R3, 2010, 1-9.
Kaplan, et al., "Impaired IL-12 Responses and Enhanced Development of TH2 Cells in Stat4-Deficient Mice", Nature, vol. 382, No. 11, Jul. 11, 1996, 174-177.
Komatsu, et al., "Pathogenic Conversion of Foxp3+ T Cells into Th17 Cells in Autoimmune Arthritis", Nature Medicine, vol. 20, No. 1, Jan. 2014, 62-71.
Konkel, et al., "Balancing acts: the role of TGF-beta in the mucosal immune system", Trends in Molecular Medicine, vol. 17, No. 11, 2011, 668-676.
Korn, et al., "IL-17 and Th17 Cells", Annual Review of Immunology, vol. 27, Jan. 1, 2009, 485-517.
Korn, et al., "IL-21 initiates an alternative pathway to induce proinflammatory T(H)17 cells", Nature, vol. 448, No. 7152, Jul. 26, 2007, 484-487.

(56) References Cited

OTHER PUBLICATIONS

Kryczek, et al., "Human Th17 Cells are Long-Lived Effector Memory Cells", Sci Transl Med, vol. 3, No. 104, Oct. 12, 2011, 1-11.
Kurachi, et al., "The Transcription Factor BATF Operates as an Essential Differentiation Checkpoint in Early Effector CD8+ T Cells", Nat Immunol., vol. 15, No. 4, Apr. 2014, 373-383.
Kurokawa et al., "Macrophage-Derived AIM Is Endocytosed into Adipocytes and Decreases Lipid Droplets via Inhibition of Fatty Acid Synthase Activity," Cell Metabolism, 11, Jun. 9, 2010, pp. 479-492.
Lachmann, et al., "ChEA: Transcription Factor Regulation Inferred from Integrating Genome-Wide ChIP-X experiments", Bioinformatics, vol. 26, No. 19, 2010, 2438-2444.
Lang, et al., "Involvement of Toso in Activation of Monocytes, Macrophages, and Granulocytes", PNAS, vol. 110, No. 7, Feb. 12, 2013, 2593-2598.
Latta, et al., "CXCR6 is Expressed on T Cells in Both T Helper Type 1 (TH1) Inflammation and Allergen-Induced Th2 Lung Inflammation but is Only a Weak Mediated of Chemotaxes", Immunology, vol. 121, 2007, 555-564.
Laurence, et al., "Interleukin-2 signaling via STAT5 constrains T helper 17 cell generation", Immunity, vol. 26, No. 3, Mar. 2007, 371-381.
Lee, et al., "Late Developmental Plasticity in the T Helper 17 Lineage", Immunity, vol. 30, No. 1, Jan. 1, 2009, 92-107.
Lees, et al., "New IBD genetics: common pathways with other diseases", Gut, vol. 60, No. 12, 2011, 1739-1753.
Leonardi, et al., "Anti-interleukin-17 monoclonal antibody ixekizumab in chronic plaque psoriasis", The New England Journal of Medicine, vol. 366, No. 13, 2012, 1190-1199.
Liberzon, et al., "Molecular Signatures Database (MSigDB) 3.0.", Bioinformatics, vol. 27,No. 12, 2011, 1739-1740.
Lin, et al., "Th1-Th17 Cells Mediate Protective Adaptive Immunity Against Staphylococcus aureus and Candida albicans Infection in Mice", PLoS Pathogens, vol. 5, Iss. 12, Dec. 2009, 1-10.
Linhart, et al., "Transcription factor and microRNA motif discovery: the Amadeus platform and a compendium of metazoan target sets", Genome research, vol. 18, Jul. 2008, 1180-1189.
Liu, et al., "Modulation of T Cell Cytokine Production by miR-144* with Elevated Expression in Patients with Pulmonary Tuberculosis", Molec. Immunol., vol. 9-10, May 2011, 1084-1090.
Mahad, et al., "The Role of MCP-1 (CCL2) and CCR2 in Multiple Sclerosis and Experimental Autoimmune Encephalomyelitis (EAE)", Seminars in Immunology, vol. 15, Iss. 1, Feb. 2003, 23-32.
Maity, et al., "HIF and MIF—A Nifty Way to Delay Senescence", Genes and Development, vol. 20, 2006, 3337-3341.
Martinez, et al., "The Macrophage Soluble Receptor AIM/Api6/CD5L Displays a Broad Pathogen Recognition Spectrum and is Involved in Early Response to Microbial Aggression", Cellular & Molecular Immunology, vol. 11, 2014, 343-354.
Mathews, et al., "Induction of IL-17A Precedes Development of Airway Hyperresponsiveness during Diet-Induced Obesity and Correlates with Complement Factor D", Frontiers in Immunology, vol. 5, Article 440, 2014, 09 pages.
Maynard, et al., "Regulatory T cells expressing interleukin 10 develop from Foxp3+ and Foxp3− precursor cells in the absence of interleukin 10", Nature Immunology, vol. 8, No. 9, 2007, 931-941.
McGeachy, et al., "Interleukin 23 Receptor is Essential for the Terminal Differentiation of Effector T Helper Type 17 Cells in Vivo", Nat Immunol., vol. 10, No. 3, Mar. 2009, 314-324.
Miaw, et al., "ROG, repressor of GATA, regulates the expression of cytokine genes", Immunity, vol. 12, No. 3, Mar. 2000, 323-333.
Miyazaki, et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily", The Journal of Experimental Medicine, vol. 189, No. 2, Jan. 18, 1999, 413-422.
Mo, et al., "Stat4 Isoforms Differentially Regulate Inflammation and Demyelination_in_Experimental_Allergic_Encephalitis", Journal of Immunology, vol. 181, 2008, 5681-5690.
Monk, et al., "n3 PUFAs Reduce Mouse CD4+ T-Cell Ex Vivo_Polarization_Into_Th17 Cells 1-3", Journal of Nutrition, vol. 143, 2013, 1501-1508.
Monk, et al., "Th17 Cell Accuulation is Decreased during Chronic Experimental Coliitis by (n-3) PUFA in Fat-1 Mice", Journal of Nutrition, vol. 142, 2012, 117-124.
Muranski, et al., "Th17 Cells Are Long-Lived and Retain a Stem Cell-Like Molecular Signature", Immunity, vol. 35, Dec. 23, 2011, 972-985.
Nakae, et al., "Phenotypic Differences between Th1 and Th17 Cells and Negative Regulation on Th1 Cell Differentiation by IL-17", Journal of Leukocyte Biology, 2007, pp. 1258-1268.
Nguyen, et al., "Toso Regulates the Balance Between Apoptotic and Nonapoptotic Death Receptor Signaling by Facilitating RIP1 Ubiquitination", Blood Journal, vol. 118, No. 3, Jul. 21, 2011, 598-608.
Nishikomori, et al., "Activated STAT4 has an Essential Role in Th1 Differentiation and Proliferation that is Independent of Its Role in the Maintenance of IL-12R Beta2 Chain Expression and Signaling", Journal of Immunology, vol. 169, 2002, 4388-4398.
Novershtern, et al., "Densely Interconnected Transcriptional Circuits Control Cell States in Human Hematopoiesis", Cell, vol. 144, No. 2, Jan. 21, 2011, 296-309.
Nurieva, et al., "Essential Autocrine Regulation by Il-21 in the Generation of Inflammatory T Cells", Nature. vol. 448, Jul. 26, 2007, 480-484.
Palmer, et al., "Autoimmunity: Increasing Suspects in the CD4+ T Cell Lineup", Nature Immunology, vol. 11, 2010, 36-40.
Papp, et al., "Brodalumab, an Anti-Interleukin-17-Receptor Antibody for Psoriasis", The New England Journal of Medicine, vol. 366, No. 13, Mar. 29, 2012, 1181-1189.
Patel, et al., "Effect of IL-17A blockade with secukinumab in autoimmune diseases", Annals of the Rheumatic Diseases, vol. 72, Suppl 2, 2013, ii116-ii123.

* cited by examiner

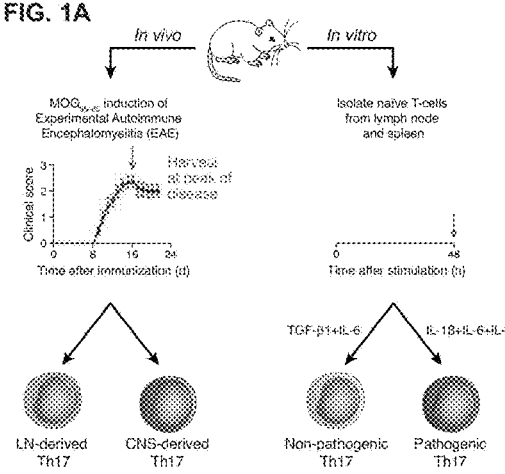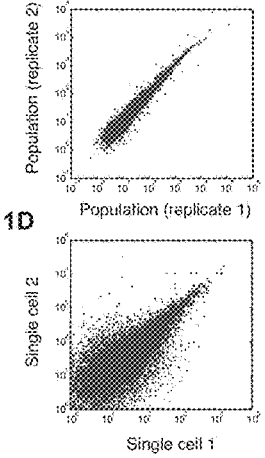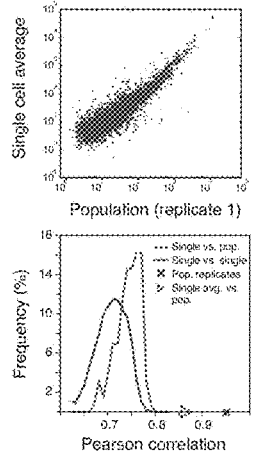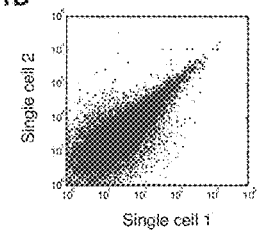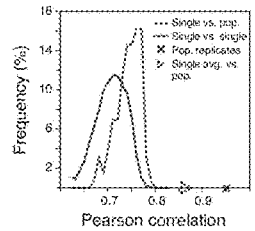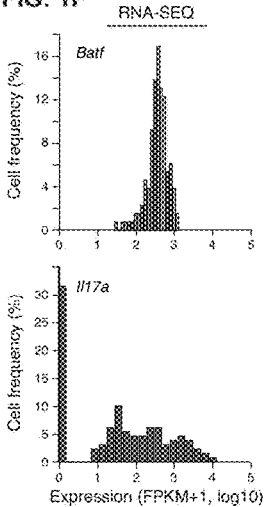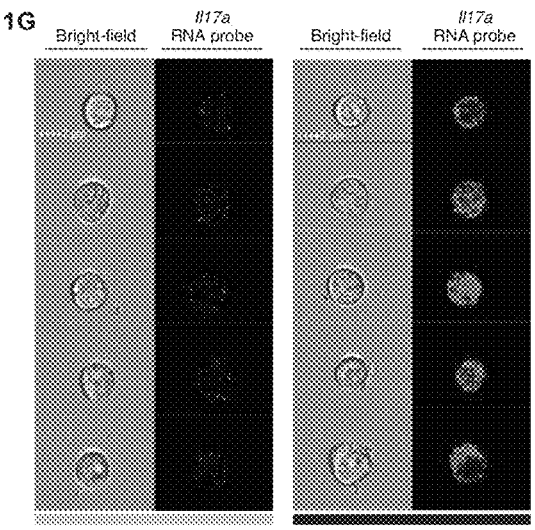

FIG. 2A
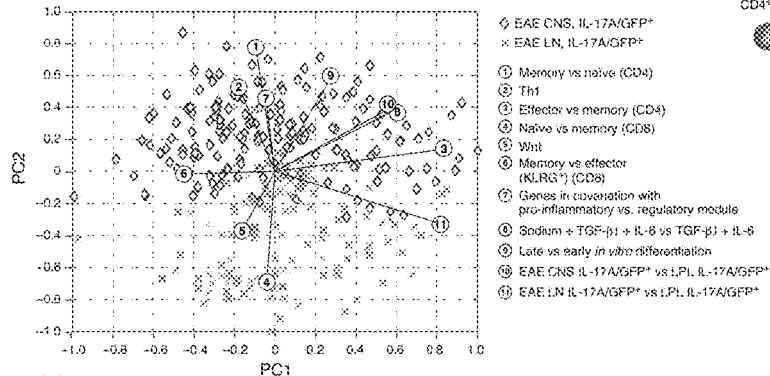
FIG. 2B
FIG. 2C
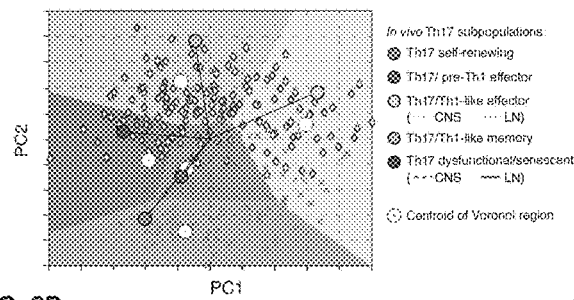
FIG. 2D
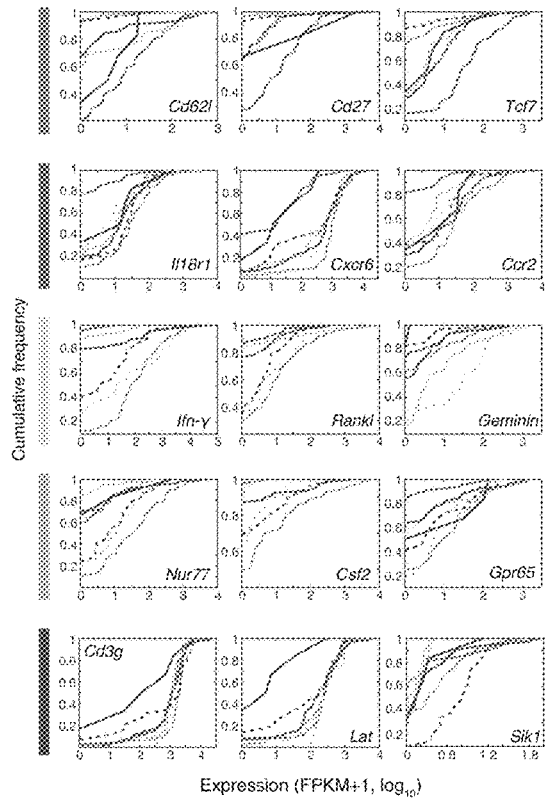
FIG. 2E
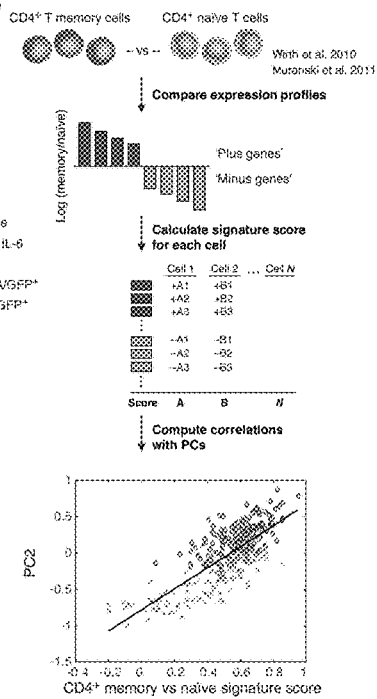
FIG. 2F
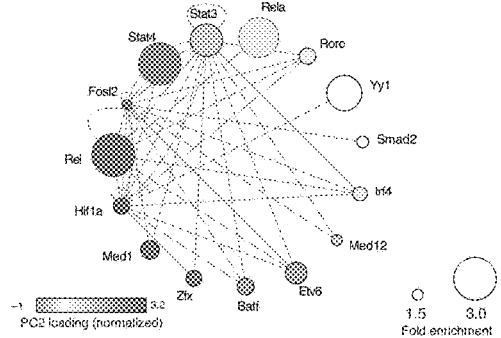
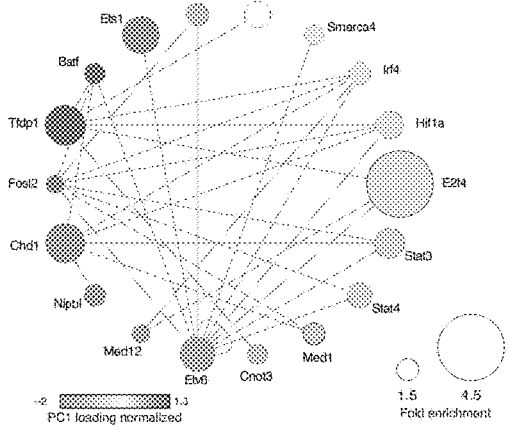

*In vivo* Th17/Th1 memory subpopulation signature

*In vivo* Th17 self-renewing subpopulation signature

Pathogenicity signature

*Il10*

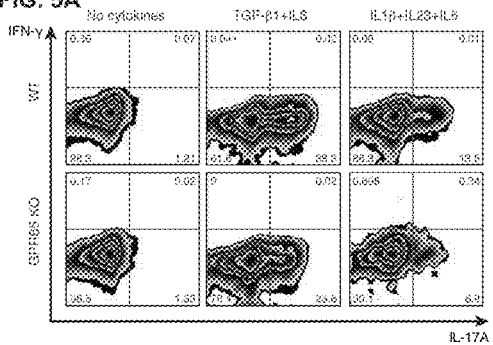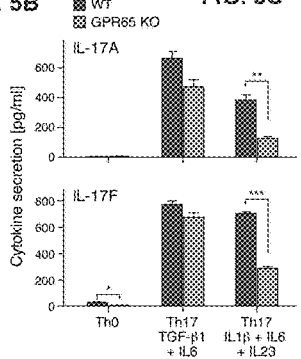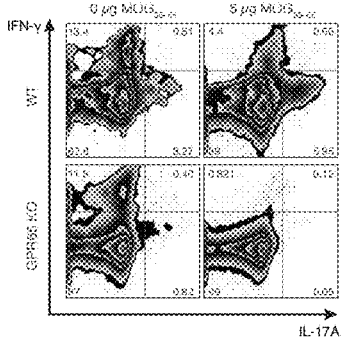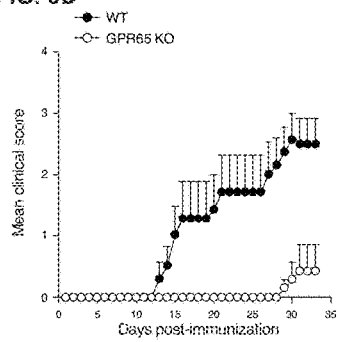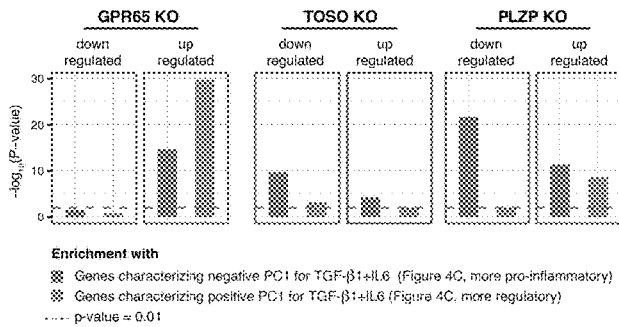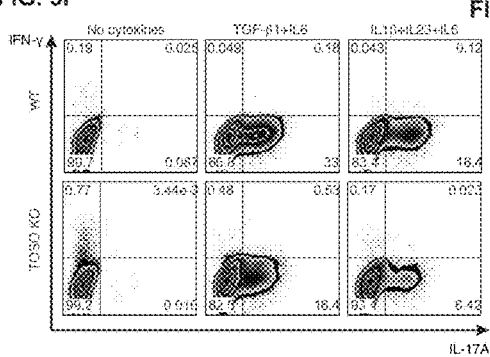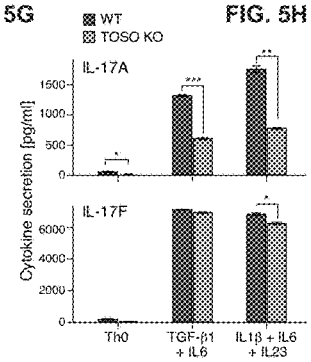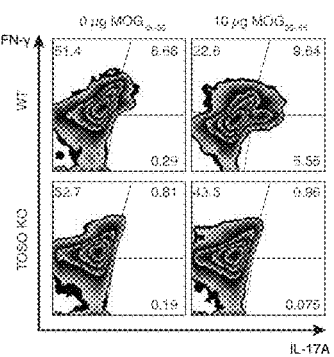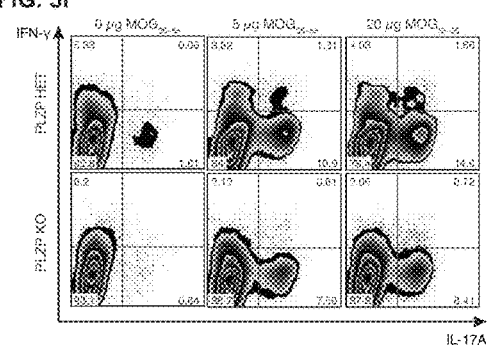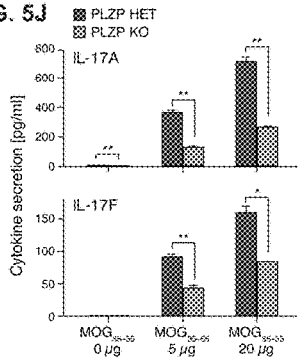

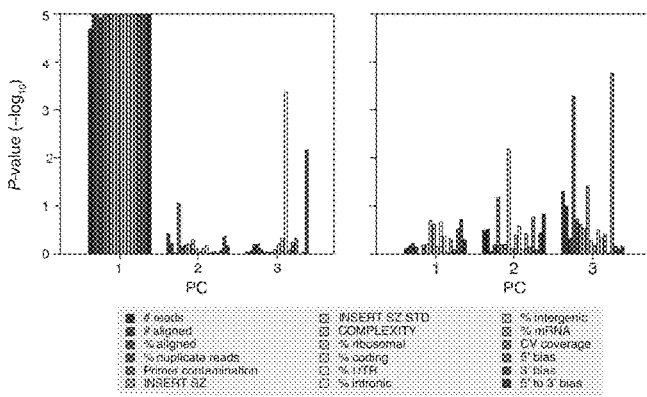
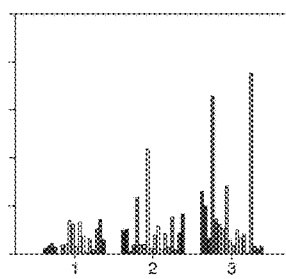
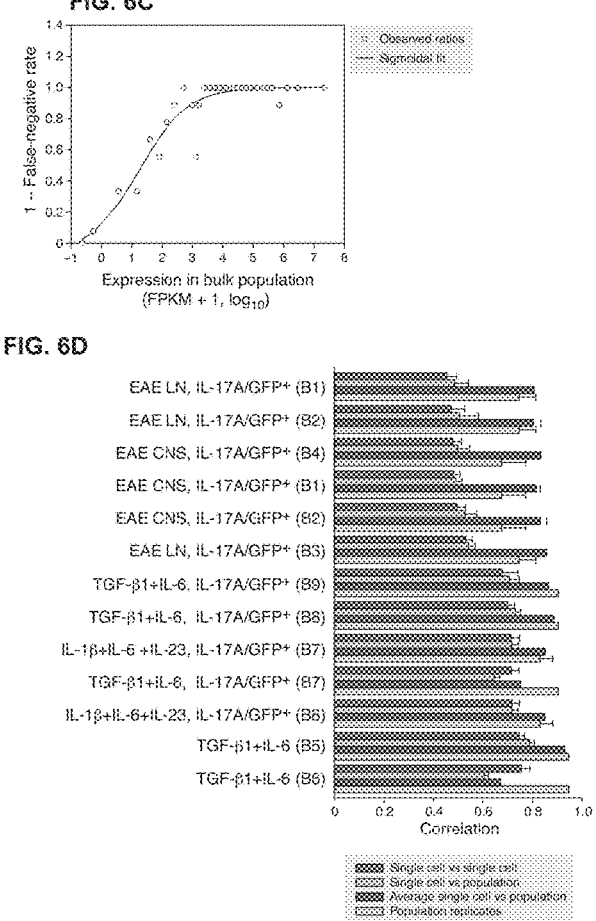
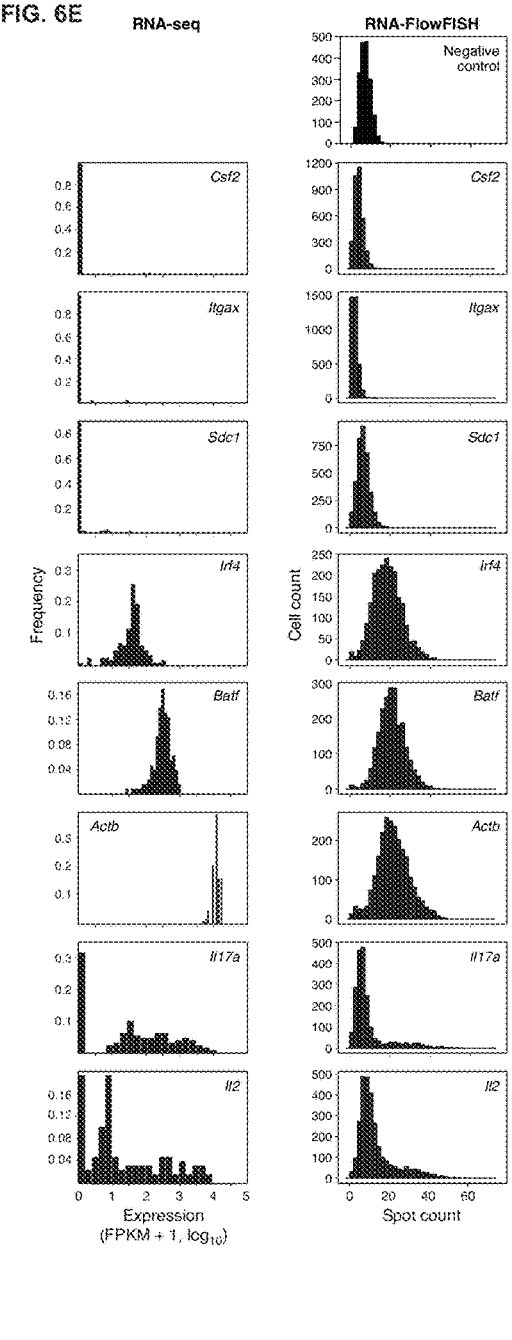

FIG. 7A FIG. 7B
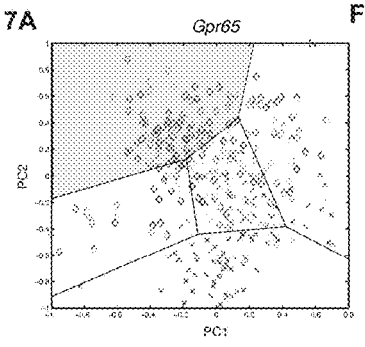
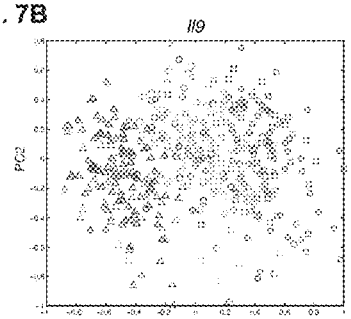
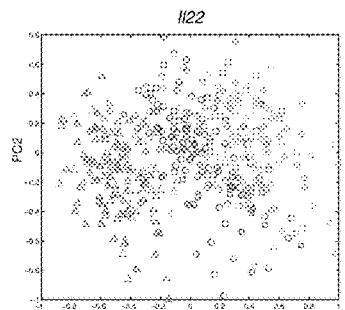
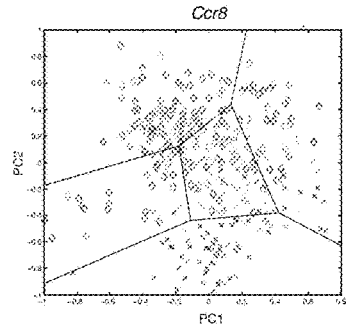
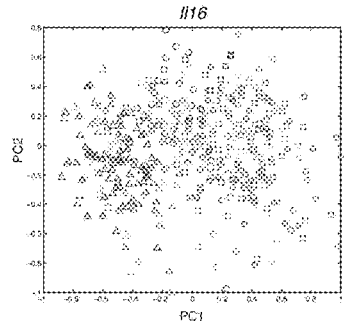
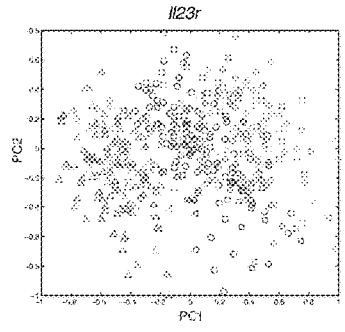
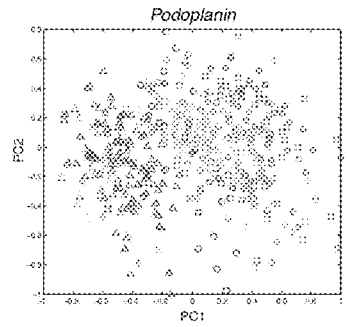
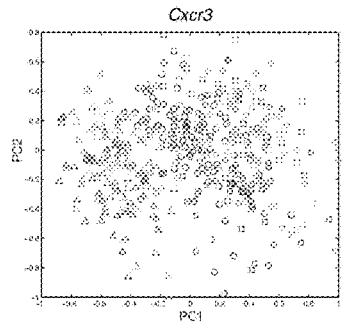
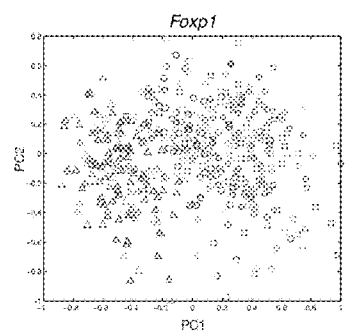
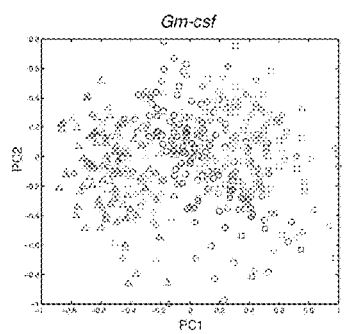
△ In vitro IL-1β+IL-6+IL-23, IL-17A/GFP+
○ In vitro TGF-β1+IL-6
□ In vitro TGF-β1+IL-6, IL-17A/GFP+
◇ EAE CNS, IL-17A/GFP+
× EAE LN, IL-17A/GFP+
Low High

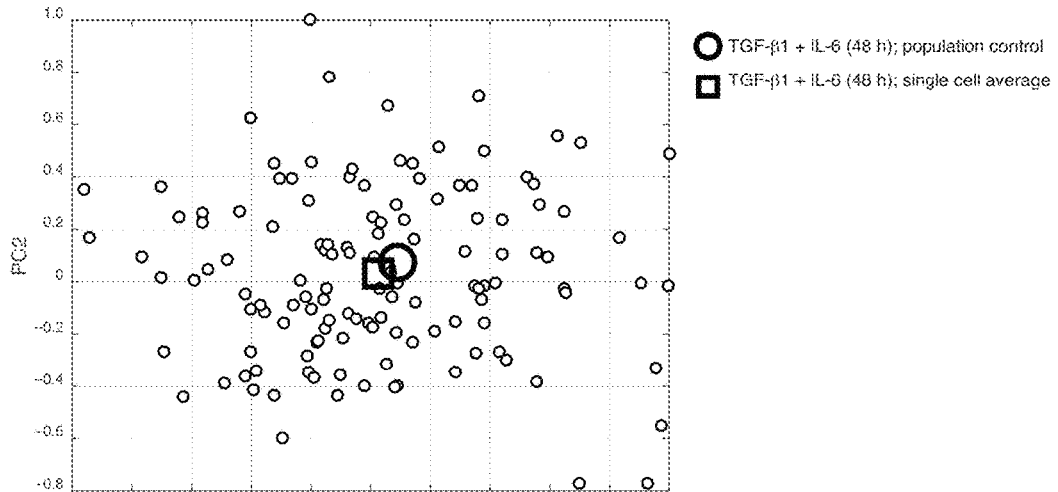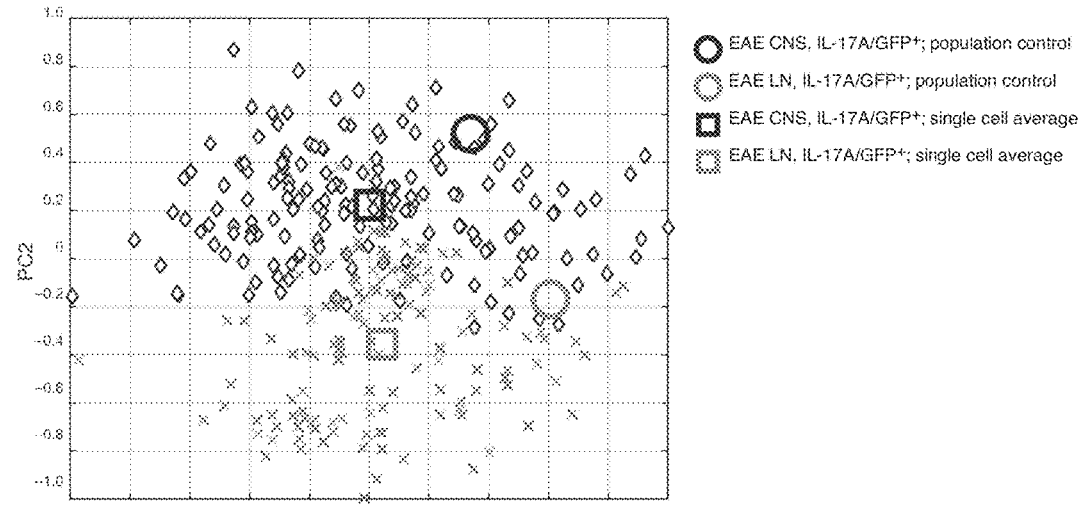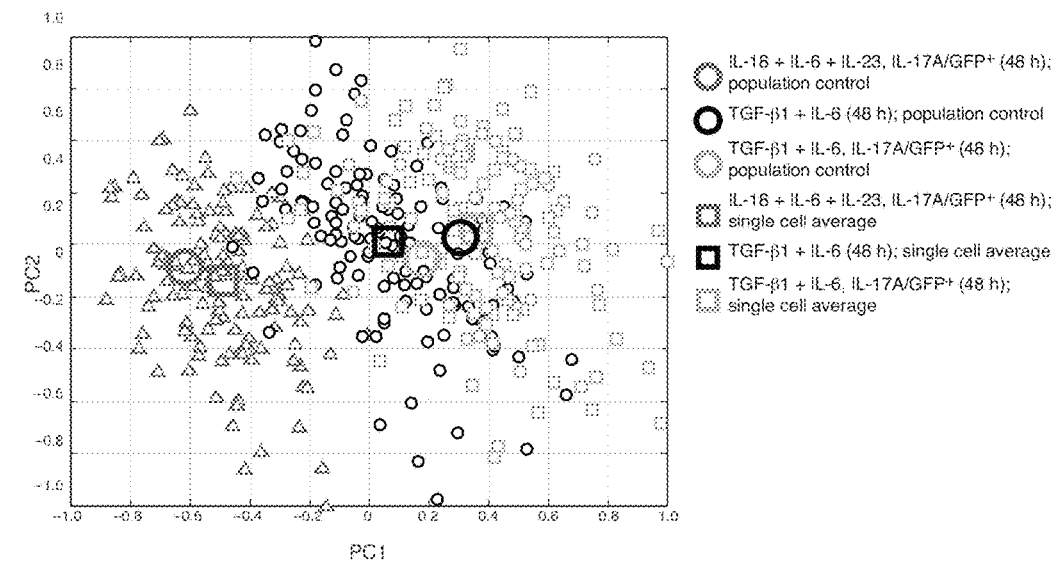

FIG. 11A
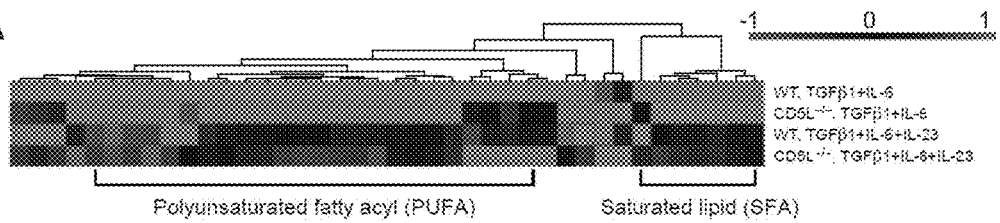
FIG. 11B
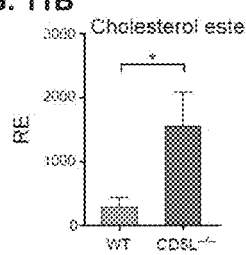
FIG. 11C
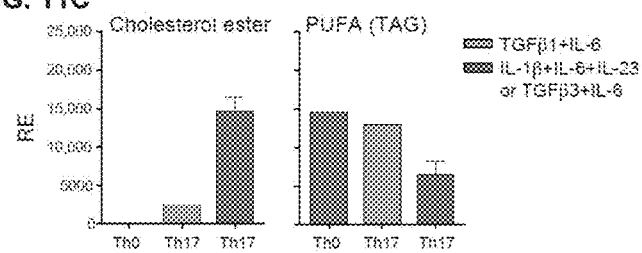
FIG. 11D   FIG. 11E
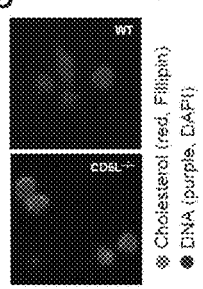 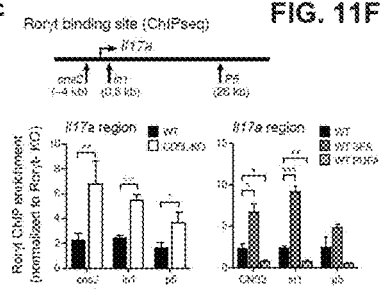
FIG. 11F
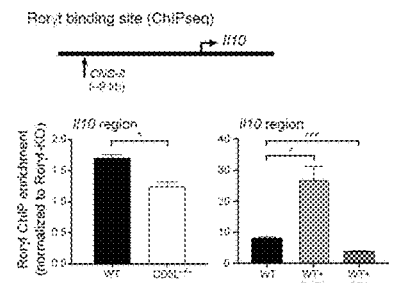
FIG. 11G
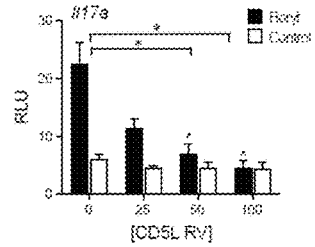
FIG. 11H
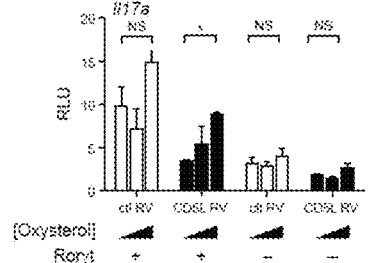
FIG. 11I
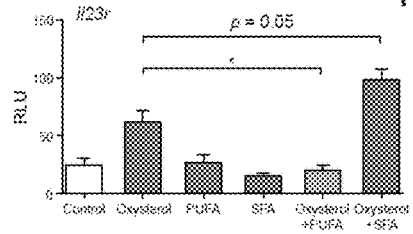
FIG. 11J
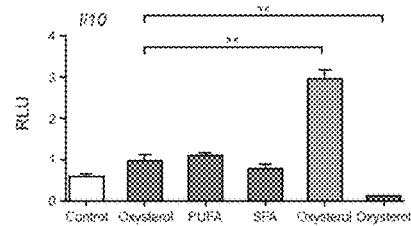

FIG. 12A 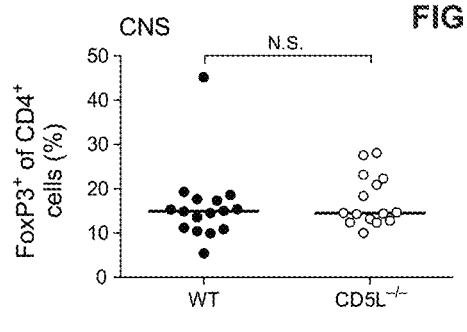 FIG. 12B 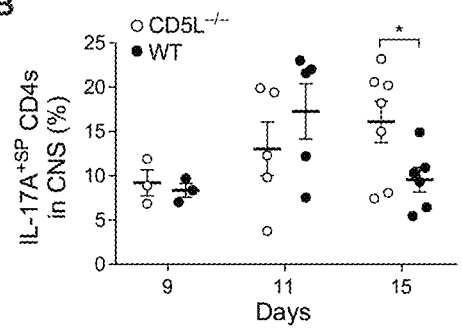
FIG. 12C 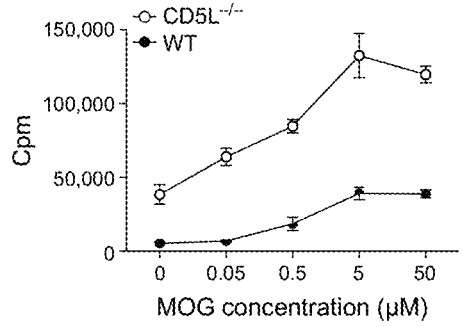 FIG. 12D 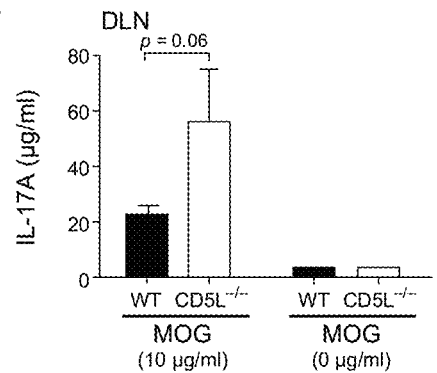
FIG. 12E 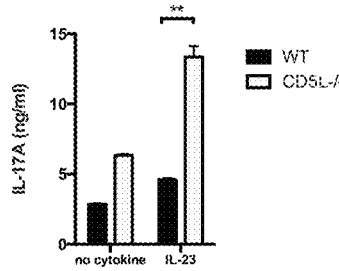 FIG. 12F 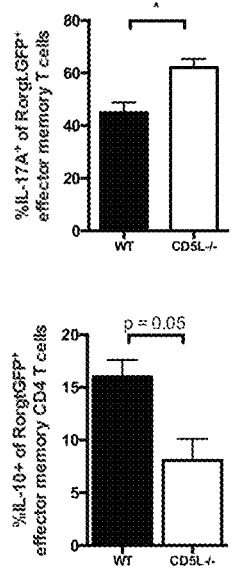
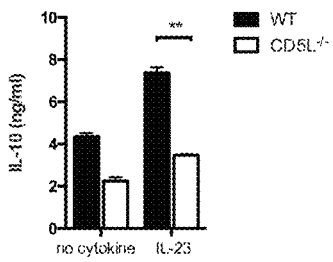

FIG. 16H

FIG. 18A 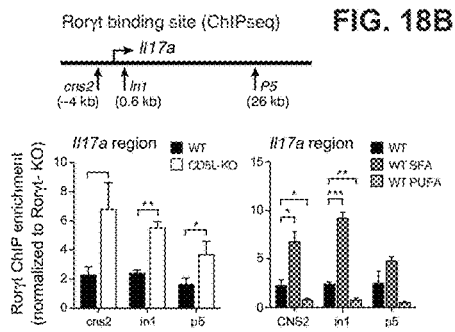 FIG. 18B 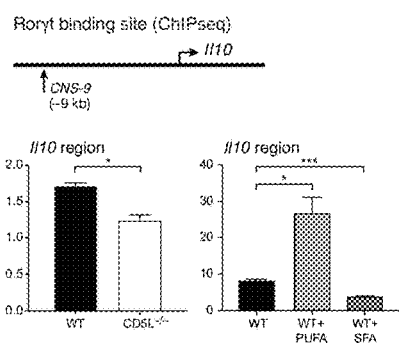
FIG. 18C 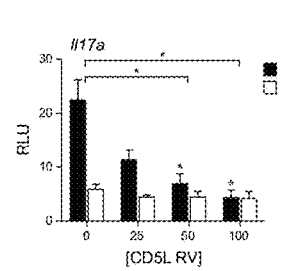 FIG. 18D 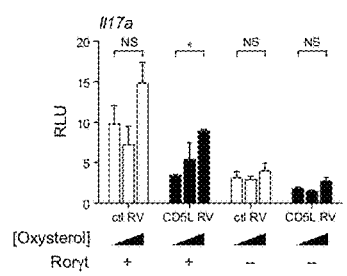
FIG. 18E 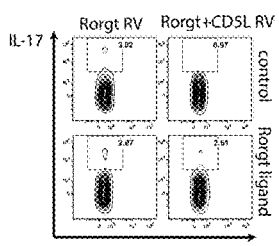 FIG. 18F 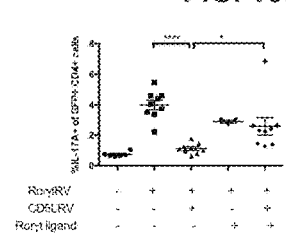 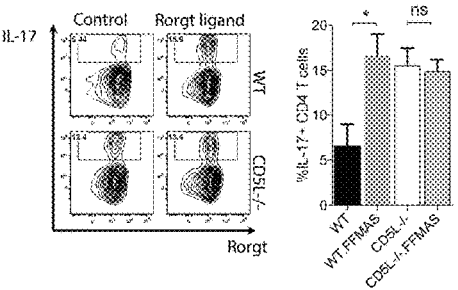

FIG. 19A
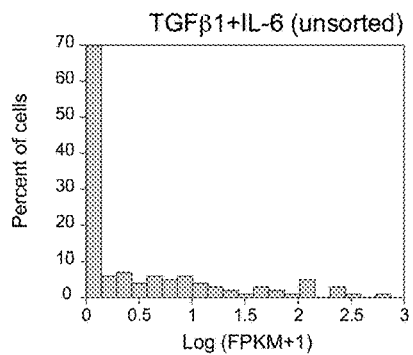
FIG. 19B
FIG. 19C
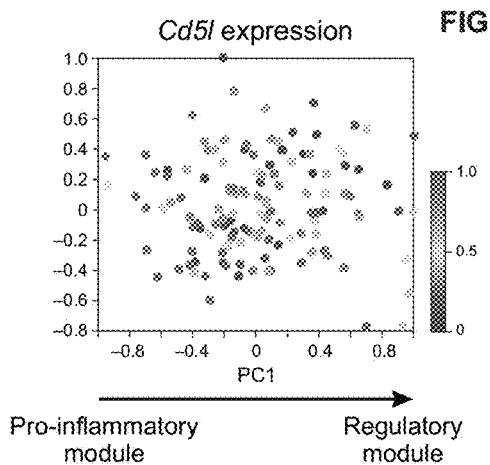
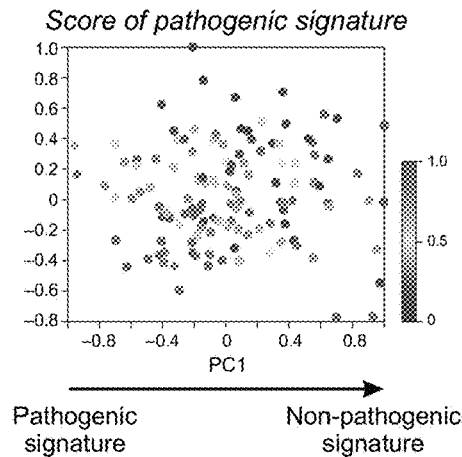
FIG. 19D
FIG. 19E
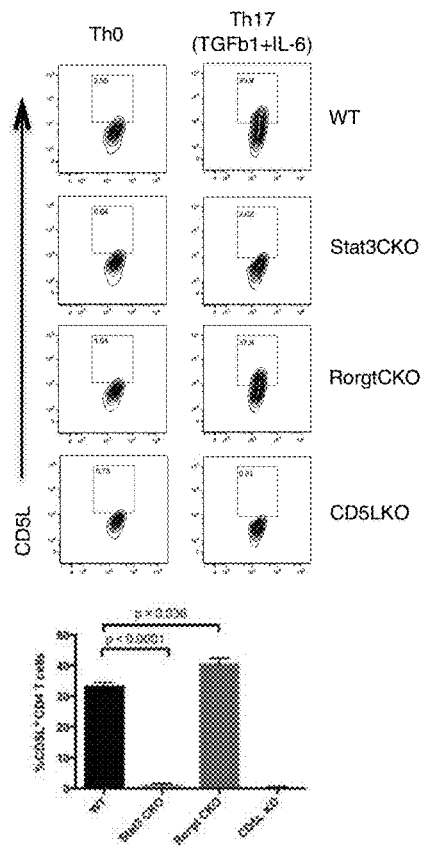
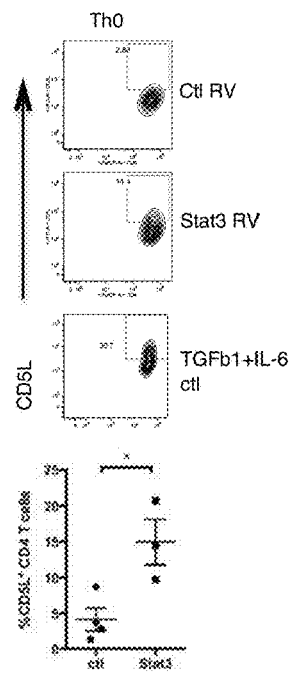

FIG. 20A 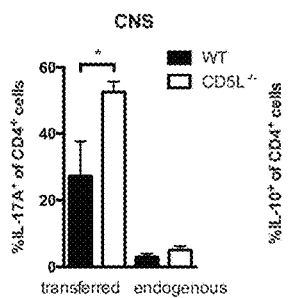 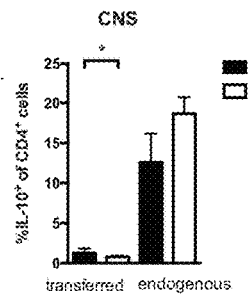

| Name | P value |
|------|---------|
| SMs | 0.000999 |
| CEs | 0.000999 |
| PCs | 0.000999 |
| LPCs | 0.000999 |
| TAGs | 0.000999 |

US 11,427,869 B2

T CELL BALANCE GENE EXPRESSION, COMPOSITIONS OF MATTERS AND METHODS OF USE THEREOF

RELATED APPLICATIONS AND INCORPORATION BY REFERENCE

This application is a continuation-in-part of International patent application Serial No. PCT/US2016/019949 filed Feb. 26, 2016 and published as PCT Publication No. WO2016/138488 on Sep. 1, 2016 and which claims priority to U.S. provisional patent application 62/176,796, filed Feb. 26, 2015; U.S. provisional patent application 62/181,697, filed Jun. 18, 2015 and U.S. provisional patent application 62/386,073, filed Nov. 16, 2015.

STATEMENT AS TO FEDERALLY SPONSORED RESEARCH

This invention was made with government support under Grant Nos. OD003958, HG006193, HG005062, OD003893, NS030843, NS045937, AI073748, A1045757 and AI056299 awarded by National Institutes of Health. The government has certain rights in the invention.

Reference is also made to PCT application PCT/US2015/017826, filed Feb. 26, 2015 and published on Sep. 3, 2015 as WO2015130968; WO/2012/048265; WO/2014/145631; WO/2014/134351; and U.S. provisional patent application 61/945,641, filed Feb. 27, 2014; and Wang et al., CD5L/AIM Regulates Lipid Biosynthesis and Restrains Th17 Cell Pathogenicity. Cell Volume 163, Issue 6, p 1413-1427, 3 Dec. 2015 and Gaublomme et al., Single-Cell Genomics Unveils Critical Regulators of Th17 Cell Pathogenicity. Cell Volume 163, Issue 6, p 1400-1412, 3 Dec. 2015, incorporated herein by reference.

The foregoing applications, and all documents cited therein or during prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Appln cited documents, herein cited documents, all documents herein referenced or cited, and all documents indicated to be incorporated herein by reference, are incorporated by reference to the same extent as if each individual document was specifically and individually set forth herein in full and indicated to be incorporated by reference when or where cited or referenced.

FIELD OF THE INVENTION

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

BACKGROUND OF THE INVENTION

Despite their importance, the molecular circuits that control the balance of T cells, including the differentiation of naïve T cells, remain largely unknown. Recent studies that reconstructed regulatory networks in mammalian cells have focused on short-term responses and relied on perturbation-based approaches that cannot be readily applied to primary T cells. Accordingly, there exists a need for a better understanding of the dynamic regulatory network that modulates, controls, or otherwise influences T cell balance, including Th17 cell differentiation, maintenance and function, and means for exploiting this network in a variety of therapeutic and diagnostic methods. Citations herein are not intended as an admission that anything cited is pertinent or prior art; nor does it constitute any admission as to the contents or date of anything cited.

SUMMARY OF THE INVENTION

The invention has many utilities. The invention pertains to and includes methods and compositions therefrom of Drug Discovery, as well as for detecting patients or subjects who may or may not respond or be responding to a particular treatment, therapy, compound, drug or combination of drugs or compounds; and accordingly ascertaining which drug or combination of drugs may provide a particular treatment or therapy as to a condition or disease or infection or infectious state, as well as methods and compositions for selecting patient populations (e.g., by detecting those who may or may not respond or be responding), or methods and compositions involving personalized treatment—a combination of Drug Discovery and detecting patients or subjects who may not respond or be responding to a particular treatment, therapy, compound, drug or combination of drugs or compounds (e.g., by as to individual(s), so detecting response, nor responding, potential to respond or not, and adjusting particular treatment, therapy, compound, drug or combination of drugs or compounds to be administered or administering a treatment, therapy, compound, drug or combination of drugs or compounds indicated from the detecting).

The invention provides a method of diagnosing, prognosing and/or staging an immune response involving T cell balance, comprising detecting a first level of expression, activity and/or function of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5 or one or more products of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l and comparing the detected level to a control of level of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l or gene product expression, activity and/or function, wherein a difference in the detected level and the control level indicates that the presence of an immune response in the subject.

The invention also provides a method of monitoring an immune response in a subject comprising detecting a level of expression, activity and/or function of Toso, advantageously Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l at a first time point, detecting a level of expression, activity and/or function of one or more signature genes or one or more products of Toso, advantageously Ctla2b, Gatm, Bdh2, Bcat1, Zfp36, Acsl4, Acat3, Adi1, Dot1l, Mett10d, Sirt6, Sc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l at a second time point, and comparing the first detected level of expression, activity and/or function with the second detected level of expression, activity and/or function, wherein a change in the first and second detected levels indicates a change in the immune response in the subject.

The invention also provides a method of identifying a patient population at risk or suffering from an immune response comprising detecting a level of expression, activity and/or function of Toso, advantageously Ctla2b, Gatm, Bdh2, Bcat1, Zfp36, Acsl4, Acat3, Adi1, Dot1l, Mett10d, Sirt6, Sc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l or one or more products of Toso, advantageously Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the patient population and comparing the level of expression, activity and/or function of one or more signature genes or one or more products of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in a patient population not at risk or suffering from an immune response, wherein a difference in the level of expression, activity and/or function of one or more of Toso, advantageously Ctla2b, Gatm, Bdh2, Bcat1, Zfp36, Acsl4, Acat3, Adi1, Dot1l, Mett10d, Sirt6, Sc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l or one or more products of Toso, advantageously Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the patient populations identifies the patient population as at risk or suffering from an immune response.

The invention also provides a method for monitoring subjects undergoing a treatment or therapy specific for a target gene selected from the group consisting of candidates Toso, advantageously Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l for an aberrant immune response to determine whether the patient is responsive to the treatment or therapy comprising detecting a level of expression, activity and/or function of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the absence of the treatment or therapy and comparing the level of expression, activity and/or function of Toso, advantageously Ctla2h, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the presence of the treatment or therapy, wherein a difference in the level of expression, activity and/or function of Toso, advantageously Ctla2b, Gatm, Bdh2, Bcat1, Zfp36, Acsl4, Acat3, Adi1, Dot1l, Mett10d, Sirt6, Slc25a13. Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l or products of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the presence of the treatment or therapy indicates whether the patient is responsive to the treatment or therapy.

In these methods the immune response is an autoimmune response or antiinflammatory response; or the inflammatory response is associated with an autoimmune response, an infectious disease and/or a pathogen-based disorder; or the signature genes are Th17-associated genes; or the treatment or therapy is an antagonist as to expression of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce differentiation toward regulatory T cells (Tregs), Th1 cells, or a combination of Tregs and Th1 cells; or the treatment or therapy is an agonist that enhances or increases the expression of Toso, advantageously Ctla2h, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce T cell differentiation toward Th17 cells; or the treatment or therapy is an antagonist of a target gene selected from the group consisting of Toso, advantageously Ctla2b, Gatm, Bdh2, Bcat1, Zfp36, Acsl4, Acat3, Adi1, Dot11, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a pathogenic to non-pathogenic signature; or the treatment or therapy is an agonist that enhances or increases the expression of a target gene selected from the group consisting of Toso, advantageously Ctla2h, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a non-pathogenic to a pathogenic signature; or the T cell modulating agent is an antibody, a soluble polypeptide, a polypeptide agent, a peptide agent, a nucleic acid agent, a nucleic acid ligand, or a small molecule agent.

The invention also provides a method of modulating T cell balance, the method comprising contacting a T cell or a population of T cells with a T cell modulating agent in an amount sufficient to modify differentiation, maintenance and/or function of the T cell or population of T cells by altering balance between Th17 cells, regulatory T cells (Tregs) and other T cell subsets as compared to differentiation, maintenance and/or function of the T cell or population of T cells in the absence of the T cell modulating agent; wherein the T cell modulating agent is an antagonist for or of Toso, advantageously Ctla2b, Gatm, Bdh2, Bcat1, Zfp36, Acsl4, Acat3, Adi1, Dot11, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5 in any combination of Gpr65, Plzp, Toso or Cd5l in an amount sufficient to induce differentiation toward regulatory T cells (Tregs), Th1 cells, or a combination of Tregs and Th1 cells, or wherein the T cell modulating agent is an agonist that enhances or increases the expression of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65. Plzp, Toso or Cd5l in an amount sufficient to induce T cell differentiation toward Th17 cells, or wherein the T cell modulating agent is specific for a target gene selected from the group consisting of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5, or wherein the T cell modulating agent is an antagonist of a target gene selected from the group consisting of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr6S, Plzp or Cd5l in any combination of Gpr65, Plzp, Toso or Cd5l in an amount sufficient to switch Th17 cells from a pathogenic to non-pathogenic signature, or wherein the T cell modulating agent is an agonist that enhances or increases the expression of a target gene selected from the group consisting of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a non-pathogenic to a pathogenic signature. In these methods the T cell modulating agent is an antibody, a soluble polypeptide, a polypeptide agent, a peptide agent, a nucleic acid agent, a nucleic acid ligand, or a small molecule agent; or the T cells are naïve T cells, partially differentiated T cells, differentiated T cells, a combination of naïve T cells and partially differentiated T cells, a combination of naïve T cells and differentiated T cells, a combination of partially differentiated T cells and differentiated T cells, or a combination of naïve T cells, partially differentiated T cells and differentiated T cells.

The invention also provides a method of enhancing Th17 differentiation in a cell population, increasing expression, activity and/or function of one or more Th17-associated cytokines or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines or non-Th17-associated transcription regulators selected from FOXP3, interferon gamma (IFN-γ), GATA3, STAT4 and TBX21, comprising contacting a T cell with an agent that enhances expression, activity and/or function of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l.

In methods herein the agent enhances expression, activity and/or function of at least Toso. The agent can be an antibody, a soluble polypeptide, a polypeptide agonist, a peptide agonist, a nucleic acid agonist, a nucleic acid ligand, or a small molecule agonist; advantageously an antibody, such as a monoclonal antibody; or an antibody that is a chimeric, humanized or fully human monoclonal antibody.

The invention comprehends use of an antagonist for or of Toso, advantageously Ctla2b, Gatm, Bdh2, Bcat1, Zfp36, Acsl4, Acat3, Adi1, Dot11, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce differentiation toward regulatory T cells (Tregs), Th1 cells, or a combination of Tregs and Th1 cells for treating or Drug Discovery of or formulating or preparing a treatment for an aberrant immune response in a patient.

The invention comprehends use of an agonist that enhances or increases the expression of Toso, advantageously Ctla2b, Gatm, Bdh2, Bcat1, Zfp36, Acsl4, Acat3, Adi1, Dot1, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65. Plzp, Toso or Cd5l in an amount sufficient to induce T cell differentiation toward Th17 cells for treating or Drug Discovery of or formulating or preparing a treatment for an aberrant immune response in a patient.

The invention comprehends use of an antagonist of a target gene selected from the group consisting of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a pathogenic to non-pathogenic signature for treating or Drug Discovery of or formulating or preparing a treatment for an aberrant immune response in a patient.

The invention comprehends use of an agonist that enhances or increases the expression of a target gene selected from the group consisting of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a non-pathogenic to a pathogenic signature for treating or Drug Discovery of or formulating or preparing a treatment for an aberrant immune response in a patient.

The invention comprehends a treatment method or Drug Discovery method or method of formulating or preparing a treatment comprising any one of the methods or uses herein discussed.

The invention comprehends a method of drug discovery for the treatment of a disease or condition involving an immune response involving T cell balance in a population of cells or tissue which express a target gene selected from the group consisting of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l comprising the steps of (a) providing a compound or plurality of compounds to be screened for their efficacy in the treatment of said disease or condition; (b) contacting said compound or plurality of compounds with said population of cells or tissue; (c) detecting a first level of expression, activity and/or function of a target gene selected from the group consisting of Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of a target gene selected from the group consisting of Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65.Plzp or Cd5l in any combination of Gpr65, Plzp, Toso or Cd5l; (d) comparing the detected level to a control of level of a target gene selected from the group consisting of Toso. Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65. Plzp or Cd5l in any combination thereof Gpr65, Plzp, Toso or Cd5 or gene product expression, activity and/or function; (e) evaluating the difference between the detected level and the control level to determine the immune response elicited by said compound or plurality of compounds.

The invention provides compositions and methods for modulating T cell balance. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products.

As used herein, the term "modulating T cell balance" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell, controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other CD4+ T cell differentiation: controlling or otherwise influencing the networks that regulate other CD4+ T cell maintenance; controlling or otherwise influencing the networks that regulate other CD4+ T cell function; manipulating or otherwise influencing the ratio of T cells such as, for example, manipulating or otherwise influencing the ratio of Th17 cells to other T cell types such as Tregs or other CD4+ T cells; manipulating or otherwise influencing the ratio of different types of Th17 cells such as, for example, pathogenic Th17 cells and non-pathogenic Th17 cells; manipulating or otherwise influencing at least one function or biological activity of a T cell; manipulating or otherwise influencing at least one function or biological activity of Th cell; manipulating or otherwise influencing at least one function or biological activity of a Treg cell; manipulating or otherwise influencing at least one function or biological activity of a Th17 cell; and/or manipulating or otherwise influencing at least one function or biological activity of another CD4+ T cell.

The invention provides T cell modulating agents that modulate T cell balance. For example, in some embodiments, the invention provides T cell modulating agents and methods of using these T cell modulating agents to regulate, influence or otherwise impact the level(s) of and/or balance between T cell types, e.g., between Th17 and other T cell types, for example, regulatory T cells (Tregs), and/or Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

For example, in some embodiments, the invention provides T cell modulating agents and methods of using these T cell modulating agents to regulate, influence or otherwise impact the level of and/or balance between Th17 phenotypes, and/or Th17 activity and inflammatory potential. Suitable T cell modulating agents include an antibody, a soluble polypeptide, a polypeptide agent, a peptide agent, a nucleic acid agent, a nucleic acid ligand, or a small molecule agent.

For example, in some embodiments, the invention provides T cell modulating agents and methods of using these T cell modulating agents to regulate, influence or otherwise impact the level of and/or balance between Th17 cell types, e.g., between pathogenic and nonpathogenic Th17 cells. For example, in some embodiments, the invention provides T cell modulating agents and methods of using these T cell modulating agents to regulate, influence or otherwise impact the level of and/or balance between pathogenic and non-pathogenic Th17 activity.

For example, in some embodiments, the invention provides T cell modulating agents and methods of using these T cell modulating agents to influence or otherwise impact the differentiation of a population of T cells, for example toward Th17 cells, with or without a specific pathogenic distinction, or away from Th17 cells, with or without a specific pathogenic distinction.

For example, in some embodiments, the invention provides T cell modulating agents and methods of using these T cell modulating agents to influence or otherwise impact the differentiation of a population of T cells, for example toward a non-Th17 T cell subset or away from a non-Th17 cell subset. For example, in some embodiments, the invention provides T cell modulating agents and methods of using these T cell modulating agents to induce T-cell plasticity, i.e., converting Th17 cells into a different subtype, or into a new state.

For example, in some embodiments, the invention provides T cell modulating agents and methods of using these T cell modulating agents to induce T cell plasticity, e.g., converting Th17 cells into a different subtype, or into a new state.

For example, in some embodiments, the invention provides T cell modulating agents and methods of using these T cell modulating agents to achieve any combination of the above.

In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

The T cell modulating agents are used to modulate the expression of one or more target genes or one or more products of one or more target genes that have been identified as genes responsive to Th17-related perturbations. These target genes are identified, for example, by contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or Table 2 of WO/2014/134351, incorporated herein by reference; alone or with those of other herein disclosed methods.

In some embodiments, the target gene is one or more Th17-associated cytokine(s) or receptor molecule(s) selected from those listed in Table 3 of WO/2014/134351, incorporated herein by reference; alone or with those of other herein disclosed methods. In some embodiments, the target gene is one or more Th17-associated transcription regulator(s) selected from those shown in Table S3 (Gaublomme 2015) or listed in Table 4 of WO/2014/134351, incorporated herein by reference; alone or with those of other herein disclosed methods.

In some embodiments, the target gene is one or more Th17-associated transcription regulator(s) selected from those shown in Table S3 (Gaublomme 2015) or Table 5 of WO/2014/134351, incorporated herein by reference: alone or with those of other herein disclosed methods. In some embodiments, the target gene is one or more Th17-associated receptor molecule(s) selected from those listed in Table 6 of WO/2014/134351, incorporated herein by reference; alone or with those of other herein disclosed methods. In some embodiments, the target gene is one or more Th17-associated kinase(s) selected from those listed in Table 7 of WO/2014/134351, incorporated herein by reference; alone or with those of other herein disclosed methods. In some embodiments, the target gene is one or more Th17-associated signaling molecule(s) selected from those listed in Table 8 of WO/2014/134351, incorporated herein by reference; alone or with those of other herein disclosed methods. In some embodiments, the target gene is one or more Th17-associated receptor molecule(s) selected from those listed in Table 9 of WO/2014/134351, incorporated herein by reference; alone or with those of other herein disclosed methods. In some embodiments, the target gene is one or more target genes involved in induction of Th17 differentiation such as, for example one or more of the target genes listed in Table 2 herein or Table 5 of WO/2014/134351, incorporated herein by reference (alone or with those of other herein disclosed methods), as being associated with the early stage of Th17 differentiation, maintenance and/or function. In some embodiments, the target gene is one or more target genes involved in onset of Th17 phenotype and amplification of Th17 T cells such as, for example, one or more of the target genes listed in Table 2 herein or Table 5 of WO/2014/134351, incorporated herein by reference (alone or with those of other herein disclosed methods), as being associated with the intermediate stage of Th17 differentiation, maintenance and/or function. In some embodiments, the target gene is one or more target genes involved in stabilization of Th17 cells and/or modulating Th17-associated interleukin 23 (IL-23) signaling such as, for example, one or more of the target genes listed in Table 2 herein or Table 5 of WO/2014/134351, incorporated herein by reference (alone or with those of other herein disclosed methods), as being associated with the late stage of Th17 differentiation, maintenance and/or function. In some embodiments, the target gene is one or more of the target genes listed in Table 6 of WO/2014/134351, incorporated herein by reference (alone or with those of other herein disclosed methods), as being associated with the early stage of Th17 differentiation. In some embodiments, the target gene is one or more of the target genes listed in Table 6 of WO/2014/134351, incorporated herein by reference (alone or with those of other herein disclosed methods), as being associated with the intermediate stage of Th17 differentiation, maintenance and/or function. In some embodiments, the target gene is one or more of the target genes listed in Table 6 of WO/2014/134351, incorporated herein by reference (alone or with those of other herein disclosed methods), as being associated with the late stage of Th17 differentiation, maintenance and/or function. In some embodiments, the target gene is one or more of the target genes listed in Table 7 herein or Table 7 of WO/2014/134351, incorporated herein by reference (alone or with those of other herein disclosed methods), as being associated with the early stage of Th17 differentiation, maintenance and/or function. In some embodiments, the target gene is one or more of the target genes listed in Table 7 of WO/2014/134351, incorporated herein by reference (alone or with those of other herein disclosed methods), as being associated with the intermediate stage of Th17 differentiation, maintenance and/or function. In some embodiments, the target gene is one or more of the target genes listed in Table 7 of WO/2014/134351, incorporated herein by reference (alone or with those of other herein disclosed methods), as being associated with the late stage of Th17 differentiation, maintenance and/or function. In some embodiments, the target gene is one or more of the target genes listed in Table 8 of WO/2014/134351, incorporated herein by reference (alone or with those of other herein disclosed methods), as being associated with the early stage of Th17 differentiation, maintenance and/or function. In some embodiments, the target gene is one or more of the target genes listed in Table 8 of WO/2014/134351, incorporated herein by reference (alone or with those of other herein disclosed methods), as being associated with the intermediate stage of Th17 differentiation, maintenance and/or function. In some embodiments, the target gene is one or more of the target genes listed in Table 8 of WO/2014/134351, incorporated herein by reference (alone or with those of other herein disclosed methods), as being associated with the late stage of Th17 differentiation, maintenance and/or function. In some embodiments, the target gene is one or more of the target genes listed in Table 9 of WO/2014/134351, incorporated herein by reference (alone or with those of other herein disclosed methods), as being associated with the early stage of Th17 differentiation, maintenance and/or function. In some embodiments, the target gene is one or more of the target genes listed in Table S6 (Gaublomme 2015), Table 7 or in Table 9 of WO/2014/134351, incorporated herein by reference (alone or with those of other herein disclosed methods), as being associated with the intermediate stage of Th17 differentiation, maintenance and/or function. In some embodiments, the target gene is one or more of the target genes listed in Table S6 (Gaublomme 2015), Table 7 or Table 9 of WO/2014/134351, incorporated herein by reference (alone or with those of other herein disclosed methods), as being associated with the late stage of Th17 differentiation, maintenance and/or function.

In some embodiments, the target gene is one or more target genes that is a promoter of Th17 cell differentiation. In some embodiments, the target gene is GPR65. In some embodiments, the target gene is also a promoter of pathogenic Th17 cell differentiation and is selected from the group consisting of CD5L, DEC1, PLZP and TCF4.

In some embodiments, the target gene is one or more target genes that is a promoter of pathogenic Th17 cell differentiation. In some embodiments, the target gene is selected from the group consisting of CD5L, DEC1, PUP and TCF4.

The desired gene or combination of target genes is selected, and after determining whether the selected target gene(s) is overexpressed or under-expressed during Th17 differentiation and/or Th17 maintenance, a suitable antagonist or agonist is used depending on the desired differentiation, maintenance and/or function outcome. For example, for target genes that are identified as positive regulators of Th17 differentiation, use of an antagonist that interacts with those target genes will shift differentiation away from the Th17 phenotype, while use of an agonist that interacts with those target genes will shift differentiation toward the Th17 phenotype. For target genes that are identified as negative regulators of Th17 differentiation, use of an antagonist that interacts with those target genes will shift differentiation toward from the Th17 phenotype, while use of an agonist that interacts with those target genes will shift differentiation away the Th17 phenotype. For example, for target genes that are identified as positive regulators of Th17 maintenance, use of an antagonist that interacts with those target genes will reduce the number of cells with the Th17 phenotype, while use of an agonist that interacts with those target genes will increase the number of cells with the Th17 phenotype. For target genes that are identified as negative regulators of Th17 differentiation, use of an antagonist that interacts with those target genes will increase the number of cells with the Th17 phenotype, while use of an agonist that interacts with those target genes will reduce the number of cells with the Th17 phenotype. Suitable T cell modulating agents include an antibody, a soluble polypeptide, a polypeptide agent, a peptide agent, a nucleic acid agent, a nucleic acid ligand, or a small molecule agent.

In some embodiments, the positive regulator of Th17 differentiation is a target gene selected from MINA, TRPS1, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3, and combinations thereof. In some embodiments, the positive regulator of Th17 differentiation is a target gene selected from MINA, PML, POU2AF1, PROCR, SMARCA4, ZEB1, EGR2, CCR6, FAS and combinations thereof.

In some embodiments, the negative regulator of Th17 differentiation is a target gene selected from SP4, ETS2, IKZF4, TSC22D3, IRF1 and combinations thereof. In some embodiments, the negative regulator of Th17 differentiation is a target gene selected from SP4, IKZF4, TSC22D3 and combinations thereof.

In some embodiments, the T cell modulating agent is a soluble Fas polypeptide or a polypeptide derived from FAS. In some embodiments, the T cell modulating agent is an agent that enhances or otherwise increases the expression, activity, and/or function of FAS in Th17 cells. As shown herein, expression of FAS in T cell populations induced or otherwise influenced differentiation toward Th17 cells. In some embodiments, these T cell modulating agents are useful in the treatment of an immune response, for example, an autoimmune response or an inflammatory response. In some embodiments, these T cell modulating agents are useful in the treatment of an infectious disease or other pathogen-based disorders. In some embodiments, the T cell modulating agent is an antibody, a soluble polypeptide, a polypeptide agonist, a peptide agonist, a nucleic acid agonist, a nucleic acid ligand, or a small molecule agonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells. In some embodiments, the T cell modulating agent is an agent that inhibits the expression, activity and/or function of FAS. Inhibition of FAS expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, these T cell modulating agents are useful in the treatment of autoimmune diseases such as psoriasis, inflammatory bowel disease (IBD), ankylosing spondylitis, multiple sclerosis, Sjögren's syndrome, uveitis, and rheumatoid arthritis, asthma, systemic lupus erythematosus, transplant rejection including allograft rejection, and combinations thereof. In addition, enhancement of Th17 cells is also useful for clearing fungal infections and extracellular pathogens. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells that express additional cytokines. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR5. Inhibition of CCR5 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an inhibitor or neutralizing agent. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR6. Inhibition of CCR6 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR1. Inhibition of EGR1 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR2. Inhibition of EGR2 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

For example, in some embodiments, the invention provides T cell modulating agents and methods of using these T cell modulating agents to regulate, influence or otherwise impact the phenotype of a Th17 cell or population of cells, for example, by influencing a naïve T cell or population of cells to differentiate to a pathogenic or non-pathogenic Th17 cell or population of cells, by causing a pathogenic Th17 cell or population of cells to switch to a non-pathogenic Th17 cell or population of T cells (e.g., populations of naïve T cells, partially differentiated T cells, differentiated T cells and combinations thereof), or by causing a non-pathogenic Th17 cell or population of T cells (e.g., populations of naïve T cells, partially differentiated T cells, differentiated T cells and combinations thereof) to switch to a pathogenic Th17 cell or population of cells.

In some embodiments, the invention comprises a method of drug discovery for the treatment of a disease or condition involving an immune response involving T cell balance in a population of cells or tissue of a target gene comprising the steps of providing a compound or plurality of compounds to be screened for their efficacy in the treatment of said disease or condition, contacting said compound or plurality of compounds with said population of cells or tissue, detecting a first level of expression, activity and/or function of a target gene, comparing the detected level to a control of level of a target gene, and evaluating the difference between the detected level and the control level to determine the immune response elicited by said compound or plurality of compounds. For example, the method contemplates comparing tissue samples which can be inter alia infected tissue, inflamed tissue, healthy tissue, or combinations of tissue samples thereof.

In one embodiment of the invention, the reductase null animals of the present invention may advantageously be used to modulate T cell balance in a tissue or cell specific manner. Such animals may be used for the applications hereinbefore described, where the role of T cell balance in product/drug metabolism, detoxification, normal homeostasis or in disease etiology is to be studied. It is envisaged that this embodiment will also allow other effects, such as drug transporter-mediated effects, to be studied in those tissues or cells in the absence of metabolism, e.g., carbon metabolism. Accordingly the animals of the present invention, in a further aspect of the invention may be used to modulate the functions and antibodies in any of the above cell types to generate a disease model or a model for product/drug discovery or a model to verify or assess functions of T cell balance.

In another embodiment, the method contemplates use of animal tissues and/or a population of cells derived therefrom of the present invention as an in vitro assay for the study of any one or more of the following events/parameters: (i) role of transporters in product uptake and efflux; (ii) identification of product metabolites produced by T cells; (iii) evaluate whether candidate products are T cells; or (iv) assess drug/drug interactions due to T cell balance.

The terms "pathogenic" or "non-pathogenic" as used herein are not to be construed as implying that one Th17 cell phenotype is more desirable than the other. As described herein, there are instances in which inhibiting the induction of pathogenic Th17 cells or modulating the Th17 phenotype towards the non-pathogenic Th17 phenotype is desirable. Likewise, there are instances where inhibiting the induction of non-pathogenic Th17 cells or modulating the Th17 phenotype towards the pathogenic Th17 phenotype is desirable.

As used herein, terms such as "pathogenic Th17 cell" and/or "pathogenic Th17 phenotype" and all grammatical variations thereof refer to Th17 cells that, when induced in the presence of TGF-$\beta$3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-$\beta$3-induced Th17 cells. As used herein, terms such as "non-pathogenic Th17 cell" and/or "non-pathogenic Th17 phenotype" and all grammatical variations thereof refer to Th17 cells that, when induced in the presence of TGF-$\beta$3, express a decreased level of one or more genes selected from IL6st, IL1rn, Ikzf3, Maf, Ahr, IL9 and IL10, as compared to the level of expression in a TGF-$\beta$3-induced Th17 cells.

In some embodiments, the T cell modulating agent is an agent that enhances or otherwise increases the expression, activity and/or function of Protein C Receptor (PROCR, also called EPCR or CD201) in Th17 cells. As shown herein, expression of PROCR in Th17 cells reduced the pathogenicity of the Th17 cells, for example, by switching Th17 cells from a pathogenic to non-pathogenic signature. Thus, PROCR and/or these agonists of PROCR are useful in the treatment of a variety of indications, particularly in the treatment of aberrant immune response, for example in autoimmune diseases and/or inflammatory disorders. In some embodiments, the T cell modulating agent is an antibody, a soluble polypeptide, a polypeptide agonist, a peptide agonist, a nucleic acid agonist, a nucleic acid ligand, or a small molecule agonist.

In some embodiments, the T cell modulating agent is an agent that inhibits the expression, activity and/or function of the Protein C Receptor (PROCR, also called EPCR or CD201). Inhibition of PROCR expression, activity and/or function in Th17 cells switches non-pathogenic Th17 cells to pathogenic Th17 cells. Thus, these PROCR antagonists are useful in the treatment of a variety of indications, for example, infectious disease and/or other pathogen-based disorders. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cell modulating agent is a soluble Protein C Receptor (PROCR, also called EPCR or CD201) polypeptide or a polypeptide derived from PROCR. In some embodiments, the invention provides a method of inhibiting Th17 differentiation, maintenance and/or function in a cell population and/or increasing expression, activity and/or function of one or more non-Th17-associated cytokines, one or more non-Th17 associated receptor molecules, or non-Th17-associated transcription regulators selected from FOXP3, interferon gamma (IFN-γ), GATA3, STAT4 and TBX21, comprising contacting a T cell with an agent that inhibits expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of inhibiting Th17 differentiation in a cell population and/or increasing expression, activity and/or function of one or more non-Th17-associated cytokines, one or more non-Th17-associated receptor molecules, or non-Th17-associated transcription factor selected from FOXP3, interferon gamma (IFN-γ), GATA3, STAT4 and TBX21, comprising contacting a T cell with an agent that enhances expression, activity and/or function of SP4, ETS2, IKZF4, TSC22D3, IRF1 or combinations thereof. In some embodiments, the agent enhances expression, activity and/or function of at least one of SP4, IKZF4, TSC22D3 or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of enhancing Th17 differentiation in a cell population increasing expression, activity and/or function of one or more Th17-associated cytokines, one or more Th17-associated receptor molecules, or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, comprising contacting a T cell with an agent that inhibits expression, activity and/or function of SP4, ETS2, IKZF4, TSC22D3, IRF1 or combinations thereof. In some embodiments, the agent inhibits expression, activity and/or function of at least one of SP4, IKZF4, TSC22D3 or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 T cell phenotype.

In some embodiments, the invention provides a method of enhancing Th17 differentiation in a cell population, increasing expression, activity and/or function of one or more Th17-associated cytokines, one or more Th17-associated receptor molecules, and/or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, comprising contacting a T cell with an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent enhances expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the antibody is a chimeric, humanized or fully human monoclonal antibody. In some embodiments, the agent is administered in an amount sufficient to inhibit Foxp3, IFN-γ, GATA3, STAT4 and/or TBX21 expression, activity and/or function. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of identifying genes or genetic elements associated with Th17 differentiation comprising: a) contacting a T cell with an inhibitor of Th17 differentiation or an agent that enhances Th17 differentiation; and b) identifying a gene or genetic element whose expression is modulated by step (a). In some embodiments, the method also comprises c) perturbing expression of the gene or genetic element identified in step b) in a T cell that has been in contact with an inhibitor of Th17 differentiation or an agent that enhances Th17 differentiation; and d) identifying a gene whose expression is modulated by step c). In some embodiments, the inhibitor of Th17 differentiation is an agent that inhibits the expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the inhibitor of Th17 differentiation is an agent that enhances expression, activity and/or function of SP4, ETS2, IKZF4, TSC22D3, IRF1 or combinations thereof. In some embodiments, the agent enhances expression, activity and/or function of at least one of SP4, IKZF4 or TSC22D3. In some embodiments, the agent that enhances Th17 differentiation is an agent that inhibits expression, activity and/or function of SP4, ETS2, IKZF4, TSC22D3, IRF1 or combinations thereof. In some embodiments, wherein the agent that enhances Th17 differentiation is an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent is an antibody, a soluble polypeptide, a polypeptide antagonist, a peptide antagonist, a nucleic acid antagonist, a nucleic acid ligand, or a small molecule antagonist.

In some embodiments, the invention provides a method of modulating induction of Th17 differentiation comprising contacting a T cell with an agent that modulates expression, activity and/or function of one or more target genes or one or more products of one or more target genes selected from IRF1, IRF8, IRF9, STAT2, STAT3, IRF7, STAT1, ZFP281, IFI35, REL, TBX21, FLI1, BATF, IRF4, one or more of the target genes listed in Table 2 herein or Table 5 of WO/2014/134351, incorporated herein by reference (alone or with those of other herein disclosed methods), as being associated with the early stage of Th17 differentiation, maintenance and/or function, e.g., AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STAT5B, STAT6, TFEB, TP53, TRIM24, and/or ZFP161, or any combination thereof.

In some embodiments, the invention provides a method of modulating onset of Th17 phenotype and amplification of Th17 T cells comprising contacting a T cell with an agent that modulates expression, activity and/or function of one or more target genes or one or more products of one or more target genes selected from one or more of the target genes listed in Table 2 herein or Table 5 of WO/2014/134351, incorporated herein by reference (alone or with those of other herein disclosed methods), as being associated with the intermediate stage of Th17 differentiation, maintenance and/or function. In some embodiments, the invention provides a method of modulating stabilization of Th17 cells and/or modulating Th17-associated interleukin 23 (IL-23) signaling comprising contacting a T cell with an agent that modulates expression, activity and/or function of one or more target genes or one or more products of one or more target genes selected from one or more of the target genes listed in Table 2 herein or Table 5 of WO/2014/134351 (alone or with those of other herein disclosed methods), incorporated herein by reference, as being associated with the late stage of Th17 differentiation, maintenance and/or function. In some embodiments, the invention provides a method of modulating one or more of the target genes listed in Table S6 (Gaublomme 2015), Table 7 or in Table 6 of WO/2014/134351, incorporated herein by reference (alone or with those of other herein disclosed methods), as being associated with the early stage of Th17 differentiation, maintenance and/or function. In some embodiments, the invention provides a method of modulating one or more of the target genes listed in Table S6 (Gaublomme 2015), Table 7 herein or Table 6 of WO/2014/134351, incorporated herein by reference (alone or with those of other herein disclosed methods), as being associated with the intermediate stage of Th17 differentiation, maintenance and/or function. In some embodiments, the invention provides a method of modulating one or more of the target genes listed in Table S6 (Gaublomme 2015), Table 7 herein or Table 6 of WO/2014/134351 (alone or with those of other herein disclosed methods), incorporated herein by reference, as being associated with the late stage of Th17 differentiation, maintenance and/or function. In some embodiments, the invention provides a method of modulating one or more of the target genes listed in Table 7 of WO/2014/134351 (alone or with those of other herein disclosed methods), incorporated herein by reference, as being associated with the early stage of Th17 differentiation, maintenance and/or function. In some embodiments, the invention provides a method of modulating one or more of the target genes listed in Table 7 of WO/2014/134351, incorporated herein by reference (alone or with those of other herein disclosed methods), as being associated with the intermediate stage of Th17 differentiation, maintenance and/or function. In some embodiments, the invention provides a method of modulating one or more of the target genes listed in Table 7 of WO/2014/134351, incorporated herein by reference (alone or with those of other herein disclosed methods), as being associated with the late stage of Th17 differentiation, maintenance and/or function. In some embodiments, the invention provides a method of modulating is one or more of the target genes listed in Table 8 of WO/2014/134351, incorporated herein by reference (alone or with those of other herein disclosed methods), as being associated with the early stage of Th17 differentiation, maintenance and/or function. In some embodiments, the invention provides a method of modulating one or more of the target genes listed in Table 8 of WO/2014/134351, incorporated herein by reference (alone or with those of other herein disclosed methods), as being associated with the intermediate stage of Th17 differentiation, maintenance and/or function. In some embodiments, the invention provides a method of modulating one or more of the target genes listed in Table 8 of WO/2014/134351, incorporated herein by reference (alone or with those of other herein disclosed methods), as being associated with the late stage of Th17 differentiation, maintenance and/or function. In some embodiments, the invention provides a method of modulating one or more of the target genes listed in Table 9 of WO/2014/134351, incorporated herein by reference (alone or with those of other herein disclosed methods), as being associated with the early stage of Th17 differentiation, maintenance and/or function. In some embodiments, the invention provides a method of modulating one or more of the target genes listed in Table 9 of WO/2014/134351, incorporated herein by reference (alone or with those of other herein disclosed methods), as being associated with the intermediate stage of Th17 differentiation, maintenance and/or function. In some embodiments, the invention provides a method of modulating one or more of the target genes listed in Table 9 of WO/2014/134351, incorporated herein by reference (alone or with those of other herein disclosed methods), as being associated with the late stage of Th17 differentiation, maintenance and/or function. In some embodiments, the invention provides a method of inhibiting tumor growth in a subject in need thereof by administering to the subject a therapeutically effective amount of an inhibitor of Protein C Receptor (PROCR). In some embodiments, the inhibitor of PROCR is an antibody, a soluble polypeptide, a polypeptide agent, a peptide agent, a nucleic acid agent, a nucleic acid ligand, or a small molecule agent. In some embodiments, the inhibitor of PROCR is one or more agents selected from the group consisting of lipopolysaccharide; cisplatin; fibrinogen; 1,10-phenanthroline; 5-N-ethylcarboxamido adenosine; cystathionine; hirudin; phospholipid; Drotrecogin alfa; VEGF; Phosphatidylethanolamine; serine; gamma-carboxyglutamic acid; calcium; warfarin; endotoxin; curcumin; lipid; and nitric oxide.

In some embodiments, the invention provides a method of diagnosing an immune response in a subject, comprising detecting a level of expression, activity and/or function of one or more signature genes or one or more products of one or more signature genes selected from those listed in Table 1 or 2 of WO/2014/134351, incorporated herein by reference (alone or with those of other herein disclosed methods), and comparing the detected level to a control of level of signature gene or gene product expression, activity and/or function, wherein a difference between the detected level and the control level indicates that the presence of an immune response in the subject. In some embodiments, the immune response is an autoimmune response. In some embodiments, the immune response is an inflammatory response, including inflammatory response(s) associated with an autoimmune response and/or inflammatory response(s) associated with an infectious disease or other pathogen-based disorder.

In some embodiments, the invention provides a method of monitoring an immune response in a subject, comprising detecting a level of expression, activity and/or function of one or more signature genes or one or more products of one or more signature genes, e.g., one or more signature genes selected from those listed in Table 1 or 2 of WO/2014/134351, incorporated herein by reference (alone or with those of other herein disclosed methods), at a first time point, detecting a level of expression, activity and/or function of one or more signature genes or one or more products of one or more signature genes, e.g., one or more signature genes selected from those listed in Table 1 or 2 of WO/2014/134351 (alone or with those of other herein disclosed methods), incorporated herein by reference, at a second time point, and comparing the first detected level of expression, activity and/or function with the second detected level of expression, activity and/or function, wherein a change between the first and second detected levels indicates a change in the immune response in the subject. In some embodiments, the immune response is an autoimmune response. In some embodiments, the immune response is an inflammatory response.

In some embodiments, the invention provides a method of monitoring an immune response in a subject, comprising isolating a population of T cells from the subject at a first time point, determining a first ratio of T cell subtypes within the T cell population at a first time point, isolating a population of T cells from the subject at a second time point, determining a second ratio of T cell subtypes within the T cell population at a second time point, and comparing the first and second ratio of T cell subtypes, wherein a change in the first and second detected ratios indicates a change in the immune response in the subject. In some embodiments, the immune response is an autoimmune response. In some embodiments, the immune response is an inflammatory response.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal. The immunoglobulin superfamily occupies a central importance in this coordination of immune responses, and the CD28/cytotoxic T-lymphocyte antigen-4 (CTLA-4):B7.1/B7.2 receptor/ligand grouping represents the archetypal example of these immune regulators (see e.g., Korman A J, Peggs K S, Allison J P, "Checkpoint blockade in cancer immunotherapy." Adv Immunol. 2006, 90:297-339). In part the role of these checkpoints is to guard against the possibility of unwanted and harmful self-directed activities. While this is a necessary function, aiding in the prevention of autoimmunity, it may act as a barrier to successful immunotherapies aimed at targeting malignant self-cells that largely display the same array of surface molecules as the cells from which they derive. The expression of immune-checkpoint proteins can be dysregulated in a disease or disorder and can be an important immune resistance mechanism. Therapies aimed at overcoming these mechanisms of peripheral tolerance, in particular by blocking the inhibitory checkpoints, offer the potential to generate therapeutic activity, either as monotherapies or in synergism with other therapies.

Thus, the present invention relates to a method of engineering T-cells, especially for immunotherapy, comprising modulating T cell balance to inactivate or otherwise inhibit at least one gene or gene product involved in the immune check-point.

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown in Table 10 of WO/2014/134351, incorporated herein by reference (alone or with those of other herein disclosed methods), of the specification.

One skilled in the art will appreciate that the T cell modulating agents have a variety of uses. For example, the T cell modulating agents are used as therapeutic agents as described herein. The T cell modulating agents can be used as reagents in screening assays, diagnostic kits or as diagnostic tools, or these T cell modulating agents can be used in competition assays to generate therapeutic reagents.

In some embodiments, the invention provides a method of diagnosing, prognosing and/or staging an immune response involving Th17 T cell balance, comprising detecting a first level of expression of one or more of saturated fatty acids (SFA) and/or polyunsaturated fatty acids (PUFA) in Th17 cells, and comparing the detected level to a control level of saturated fatty acids (SFA) and/or polyunsaturated fatty acids (PUFA), wherein a change in the first level of expression and the control level detected indicates a change in the immune response in the subject. In one embodiment, a shift towards polyunsaturated fatty acids (PUFA) and away from saturated fatty acids (SFA) indicates a non-pathogenic Th17 response.

In some embodiments, the invention provides a method for monitoring subjects undergoing a treatment or therapy involving T cell balance comprising, detecting a first level of expression of one or more of saturated fatty acids (SFA) and/or polyunsaturated fatty acids (PUFA) in Th17 cells in the absence of the treatment or therapy and comparing the detected level to a level of saturated fatty acids (SFA) and/or polyunsaturated fatty acids (PUFA) in the presence of the treatment or therapy, wherein a difference in the level of expression in the presence of the treatment or therapy indicates whether the subject is responsive to the treatment or therapy.

In another embodiment, the invention provides a method for monitoring subjects undergoing a treatment or therapy involving T cell balance comprising detecting a first level of expression of one or more of saturated fatty acids (SFA) and polyunsaturated fatty acids (PUFA) in Th17 cells in the absence of the treatment or therapy and comparing the ratio of detected level to a ratio of detected level of saturated fatty acids (SFA) and polyunsaturated fatty acids (PUFA) in the presence of the treatment or therapy, wherein a shift in the ratio in the presence of the treatment or therapy indicates whether the subject is responsive to the treatment or therapy. Not being bound by a theory, a shift in the ratio towards polyunsaturated fatty acids (PUFA) and away from saturated fatty acids (SFA) indicates a non-pathogenic Th17 response.

In another embodiment, the therapy may be a lipid, preferably a mixture of lipids of the present invention. The lipids may be synthetic. Not being bound by a theory, a treatment comprising lipids may shift T cell balance.

In another embodiment, the treatment or therapy involving T cell balance is for a subject undergoing treatment or therapy for cancer. Not being bound by a theory, shifting Th17 balance towards a pathogenic phenotype would allow a stronger immune response against a tumor.

In some embodiments, the invention provides a method of drug discovery for the treatment of a disease or condition involving an immune response involving Th17 T cell balance in a population of cells or tissue comprising: (a) providing a compound or plurality of compounds to be screened for their efficacy in the treatment of said disease or condition; (b) contacting said compound or plurality of compounds with said population of cells or tissue; (c) detecting a first level of expression of one or more of saturated fatty acids (SFA) and/or polyunsaturated fatty acids (PUFA) in Th17 cells, optionally calculating a ratio; (d) comparing the detected level to a control level of saturated fatty acids (SFA) and/or polyunsaturated fatty acids (PUFA), optionally comparing the shift in ratio; and, (e) evaluating the difference between the detected level and the control level to determine the immune response elicited by said compound or plurality of compounds.

In some embodiments, a panel of lipids is detected. The panel may include saturated fatty acids (SFA) and/or polyunsaturated fatty acids (PUFA) whose expression is changed at least 1.5 fold when comparing wild type Th17 cells to CD5L$^{-/-}$ Th17 cells after treatment with non-pathogenic inducing cytokines. The non-pathogenic inducing cytokines may be TGF-β1+IL-6. The panel may include lipids whose expression is changed upon differentiation into a pathogenic or non-pathogenic Th17 cell. In another embodiment single saturated fatty acids (SFA) and/or polyunsaturated fatty acids (PUFA) representative of lipids whose expression is changed in response to CD5L loss or differentiation are detected. In a preferred embodiment, the SFA is a cholesterol ester or palmitic acid and the PUFA is a PUFA-containing triacylglyceride or arachidonic acid. In one embodiment only a single SFA or PUFA is detected.

In some embodiments, the treatment or therapy is a formulation comprising at least one lipid. The at least one lipid may be a synthetic lipid. Not being bound by a theory an autoimmune disease may be treated with polyunsaturated fatty acids (PUFA) and a disease requiring an enhanced immune response may be treated with saturated fatty acids (SFA).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any such subject matter.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is to be construed as a promise.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A-1G. Single-cell RNA-seq of Th17 cells in vivo and in vitro. (FIG. 1A) Experimental setup; left: Procedure to isolate Th17 cells from in vivo tissues. EAE was induced by MOG immunization of IL-17A reporter mice, and CD3$^+$CD4$^+$IL-17A/GFP$^+$ cells were harvested at the peak of disease (inset cartoon graph: Y axis: disease score; X axis—days; Red arrow: the peak at clinical score 2.5-3) from the draining LNs and CNS and analyzed by single-cell RNA-Seq. Right: Procedure to differentiate Th17 cells in vitro. Naïve CD4$^+$CD62L$^+$CD44$^-$ T cells were isolated from the LN and the spleen of non-immunized mice and subsequently differentiated by CD3/CD28 activation and either TGF-β1+IL-6 to derive non-pathogenic Th17 cells, or IL-1β+IL-6+IL-23 to derive more pathogenic cells. Single-cell RNA-seq was performed at 48h into differentiation. (FIG. 1B-FIG. 1E) Quality of single-cell RNA-seq. Scatter plots (B-D) compare transcript expression (FPKM+1, log$_{10}$) from the in vitro TGF-β1+IL-6 48 hr condition, between two bulk population replicates (FIG. 1B), the 'average' of single-cell profile and a matched bulk population control (FIG. 1C), or two single cells (FIG. 1D). Histograms (FIG. 1E) depict the distributions of Pearson correlation coefficients (X axis) between single cells and their matched population control (red) and between pairs of single cells (blue). The Pearson correlation coefficient between the two replicates or between the single cell average and the matched population profile are marked by a blue cross and red triangle, respectively. (FIG. 1F, FIG. 1G) Agreement between single-cell RNA-Seq and RNA Flow-FISH. (FIG. 1F) Comparison between expression distributions measured by RNA-seq (left) and transcript count distributions measured by RNA Flow-FISH (right) for the unimodally expressed gene Batf (top) and the bi-modally expressed Il17a (bottom). As a negative control, expression of the bacterial DapB gene was measured (light green). (FIG. 1G) Bright-field images of RNA Flow-FISH samples (n=5,000 cells) with the corresponding fluorescence channel for cells negative for Il17a transcripts (yellow) and positive for Il17a transcript (brown). Scale bar in the bright-field images is 7 μm. See also FIG. 6, Table S1, related FIG. 1.

FIG. 2A-2F. Th17 cells span a progressive trajectory of states from the LN to the CNS. (FIG. 2A) Principal component analysis (PCA) separates CNS-derived cells (purple diamonds) from LN-derived cells (orange crosses). Shown are 302 cells in the space of the first two PCs. Numbered circles are selected features (signatures) that significantly correlate with PC1 or PC2 (p<10$^{-6}$, Table S2(Gaublomme 2015) positioned based on the values of their Pearson correlation coefficient with each PC (axis values; to facilitate this view, the plotted PC values were normalized to be in the range between −1 and 1). Features were identified by the analysis depicted in (FIG. 2B) as either significantly diverse within a condition (with GSEA; FDR<0.05); or between conditions (with a KS test comparing CNS and LN, FDR<10$^1$). (FIG. 2B) Functional annotation scheme. From top to bottom. Gene signatures are defined from literature (e.g., by comparing CD4$^+$ memory and naïve T cells, top) distinguishing 'plus' and 'minus' genes (e.g., genes that are, respectively, high and low in CD4$^+$ memory vs. naïve cells; bar plot). A signature score is calculated for each signature in each single cell, as the difference inweighted z scores between the 'plus' and 'minus' genes in the signature (Experimental Procedures). Finally (bottom), for each signature and PC Applicants compute the Pearson correlation coefficient between the signature score for each cell, and the loading on the PC for each cell. Applicants plot these Pearson correlation coefficients on the PCA plot (circled numbers in (FIG. 2A)). (FIG. 2C) Five progressive Th17-cell states from the LN to the CNS. Shown is the PCA plot as in A, but where Voronoi cells (defined by the signatures characterizing the cells populating the extremities of PCA space; Experimental Procedures (colored circles, Table S2 (Gaublomme 2015)) define five feature-specific subpopulations: Th17 self-renewing (green, defined by a LCMV-specific CD4 signature comparing naïve cells to cells isolated 8 days post acute LCMV infection, GSE30431), Th17/pre-Th1 effector (pink, defined by a signature using TRP1 CD4$^+$ T cells comparing 5 day ex vivo Th17-polarized and stimulated cells to day 0 Th17 in vitro cells, GSE26030), Th17/Th1-like effector (yellow, LCMV-specific CD4 signature comparing cells isolated 8 days vs. 30 days post chronic LCMV infection, GSE30431), Th17/Th1-like memory (light blue, LCMV-specific CD4 signature comparing cells isolated 30 days post chronic infection to naïve cells, GSE30431), and Th17 dysfunctional/senescent (moss grey, inverse of a LCMV-specific CD4 signature comparing cells isolated 30 days post acute vs. chronic infection, GSE30431). The self-renewing state was observed in two technical replicates of one of the two in vivo biological replicates, potentially due to differences in disease induction or progression. (FIG. 2D) Example genes that distinguish each sub-population. For each of the five subpopulations in (C) (color coded rows) shown are cumulative distribution function (CDF) plots of expression for key selected genes. In each case, the gene's CDF is shown for cells from each sub-population. For the subpopulations that have a substantial mixture of LN and CNS cells, the dotted curve corresponds to cells from the CNS, and the solid line for cells from the LN of that subpopulation (FIG. 2E, FIG. 2F) Transcription factors (nodes) whose targets are significantly enriched in PC2 (E) or PC1 (F). Nodes are sized proportionally to fold enrichment (Table S3 Gaublomme 2015) and colored according to the loading of the encoding gene in the respective PC (red and green: high and low PC loading, respectively; loadings were normalized to have zero mean and standard deviation of 1). See also FIGS. 7 and 13-14, Table S2-5 (Gaublomme 2015), Table 2 and 6, related to FIG. 2.

(FIG. 3B-FIG. 3D) Key signatures related to pathogenicity. CDFs of the single-cell scores for key signatures for the three in vitro populations (colored as in A):
(FIG. 3B) a signature distinguishing the in vivo Th17/Th1-like memory sub-population (blue in FIG. 2C);
(FIG. 3C) a signature distinguishing the in vivo Th17 self-renewing sub-population (green in FIG. 2C);
and (FIG. 3D) a signature of pathogenic Th17 cells (Lee et al., 2012).
(FIG. 3E) CDFs of expression level (FPKM+1, $\log_{10}$) of Il10 for the three in vitro populations. See also Table S2 (Gaublomme 2015) related to FIG. 3.

(FIG. 4A) Single-cell expression distribution of genes. The heat map shows for each gene (row) its expression distribution across single cells differentiated under the TGF-β1+IL-6 condition for 48h (without further IL-17A-based sorting). Color scale: proportion of cells expressing in each of the 17 expression bins (columns). Genes are sorted from more unimodal (top) to bimodal (bottom). (FIG. 4B) Modules co-varying with pro-inflammatory and regulatory genes. Heat map of the Spearman correlation coefficients between the single-cell expression levels of signature genes of pathogenic T cells (Lee et al., 2012) or of other CD4$^+$ lineages (columns) and the single-cell expression of any other bimodally expressed gene (rows) in cells differentiated under the TGF-β1+IL-6 condition at 48h. Genes are clustered by similarity of these correlations, revealing two diametrically opposed modules of co-varying genes: a pro-inflammatory module (orange; e.g., Il17a, Il21, Ccl20) and a regulatory module (green, e.g., Il10, Il24, Il27ra). (FIG. 4C) The modules co-varying with pro-inflammatory and regulatory genes distinguish key variation. Each cell (TGF-β1+IL-6, 48h) is colored by a signature score comparing the two co-variation modules. Shown is a PCA plot (first two PCs) with the cells differentiated under the TGF-β1+IL-6 condition at 48h, where each cell is colored by a signature score (by the method of FIG. 2B) comparing the two modules from FIG. 4B (color code). Other signatures correlated to the PCs are marked by numbered circles. (FIG. 4D) Expression of key module genes. Each panel shows the PCA plot of (C) where cells are colored by an expression ranking score of a key gene, denoted on top. (from top left corner clockwise: Il10, Toso, Il17a, and Plzp. (FIG. 4E) A ranking of the top 100 candidate genes co-varying with pro-inflammatory or regulatory genes (out of 184; Table 2 herein), sorting from high (left) to lower (right) ranking scores (bar chart). Bar chart (top) indicates ranking score deduced from single-cell data (Experimental Procedures). Genes are ordered from high (left) to low (right) scores. Purple-white heat map (middle) shows ranking scores for (top to bottom row): pathogenicity, pro-inflammatory vs. regulatory co-variation module and in vitro and in vivo PC's. Bottom matrix indicates 'known' (black, top row) genes previously associated with Th17 function; 'novel validated' (black, middle) genes that were tested and validated by follow-up experiments, and assignment to the 'pro-inflammatory/regulatory module' (orange & green, bottom) determined in this study. See also FIGS. 10 and 15, Table S2 (Gaublomme 2015) & S8 related to FIG. 4.

FIG. 5A-5J. GPR65, TOSO and PLZP are validated as T-cell pathogenicity regulators. (FIG. 5A, FIG. 5B) Reduction in IL17A-producing cells in GPR65$^{-/-}$ T-cells differentiated in vitro. (FIG. 5A) Intracellular cytokine staining for IFN-γ (Y axis) and IL-17a (X axis) of CD4$^+$ T cells from respective WT (top) or GPR65$^{-/-}$ (bottom) cells activated in vitro for 96h with anti-CD3 and anti-CD28, either without (Th0; left) or with Th17-polarizing cytokines (TGF-β1+IL-6, middle; or IL-1β+IL-6+IL-23, right). (FIG. 5B) Quantification of secreted IL-17A and Il-17F (Y axis) by cytometric bead assays (CBA) in corresponding samples (X axis). * p<0.05,  p<0.01, * p<0.001. (FIG. 5C) Reduced IL-17A and IFN-γ production by GPR65-memory (CD62L$^-$CD44$^+$ CD4$^+$) T cells in a recall assay. Rag1$^{-/-}$ mice were reconstituted with 2×10$^6$ naïve CD4 T cells from WT or GPR65$^{-/-}$ mice, and, immunized with MOG$_{35-55}$/CFA one week post transfer. Draining LN and spleen cells were isolated 8 days after immunization and cultured ex vivo for 4 days with MOG$_{35-55}$ for recall assay (Experimental Procedures). These cells were subsequently analyzed for production of IFN-γ (Y axis) and IL-17A (X axis). (FIG. 5D) Loss of GPR65 reduces tissue inflammation and autoimmune disease in vivo. Rag-1$^{-/-}$ mice (n=10 per category) reconstituted with 2×10$^6$ naïve CD4 T-cells from WT or GPR65$^{-/-}$ mice, then induced with EAE one week post transfer. Shown is the mean clinical score (Y axis) at days post immunization (X axis) for WT (black circles) or GPR65$^{-/-}$ (open circles) mice. Error bars indicate the standard deviation of the mean clinical score. (FIG. 5E) Transcriptional impact of a loss of GPR65, TOSO and PLZP. Shown is the significance of enrichment ($-\log_{10}$ (P-value); hypergeometric test, Y axis) of genes that are dysregulated compared to WT during the TGF-β1+IL-6 differentiation of GPR65$^{-/-}$ (96h), PLZP (48h) and TOSO$^{-/-}$ (96h) cells. Red (blue) bars represent genes characterizing PC1 of FIG. 4C negatively (positively). Dashed red line: p=0.01. (FIG. 5F, FIG. 5G) Reduction in IL17A-producing cells in TOSO$^{-/-}$ T cells differentiated in vitro. (FIG. 5F) Intracellular cytokine staining as in (A) but for WT or TOSO$^{-/-}$ CD4$^+$ T-cells, activated in vitro for 96h. (FIG. 5G) Quantification of secreted IL-17A and Il-17F for CD4$^+$ T cells from respective WT (dark green) or TOSO$^{-/-}$ (light green) mice as in (B) but at 48h. * p<0.05,  p<0.01, * p<0.001. (FIG. 5H) Reduced IL-17A production by TOSO$^{-/-}$ LN memory T cells in a recall assay as in (C). (FIG. 5I) Hampered IL-17A production by PLZP$^{-/-}$ CD4+ T cells in an in vitro recall assay. PLZP$^{-/-}$ (bottom row) and littermate controls (top row) were immunized with 100 μg of MOG$_{35-55}$/CFA. Cells were harvested from the draining LNs and spleen 8 days post immunization and cultured ex vivo for 4 days with progressive concentrations of MOG$_{35-55}$ (left column: 0 μg, middle: 5 μg and right: 20 μg) and 20 ng/ml of IL-23. CD4$^+$ T cells were analyzed for IFN-γ (Y axis) and IL-17A (X axis) production by intracellular cytokine staining. (FIG. 5J) Quantification of secreted IL-17A and IL-17F of a MOG$_{35-55}$ recall assay for littermate controls (dark green) and PLZP$^{-/-}$ mice (light green) at 96h post ex vivo.

Figure 3A:
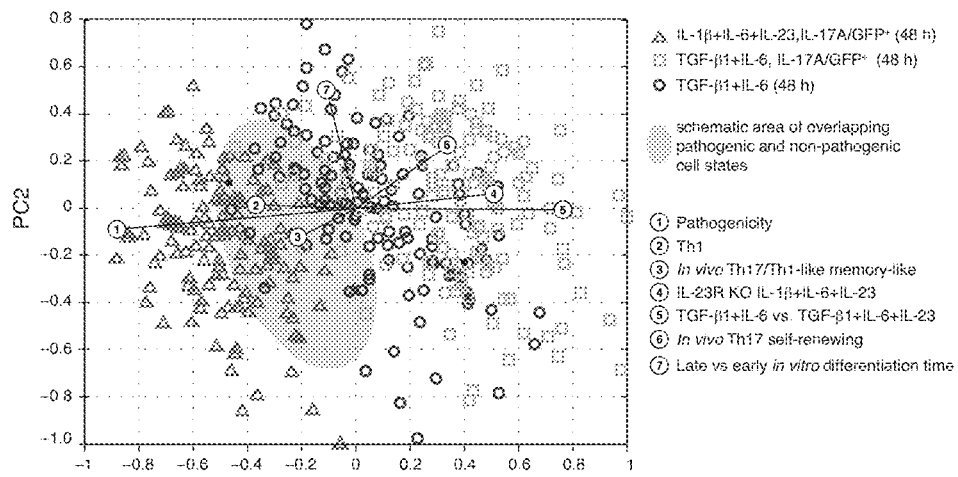
FIG. 3A-3E. A spectrum of pathogenicity states in vitro (FIG. 3A) PCA plot of Th17 cells differentiated in vitro. PC1 separates cells from most (left) to least (right) pathogenic, as indicated both by the differentiation condition (color code), and by the correlated signatures (numbered circles). PC2 separates IL-17a+ sorted Th17 cells differentiated under pathogenic conditions (red triangles) from non-pathogenic cells (Light blue squares) and non-pathogenic cells not sorted to be IL-17A positive (Black circles) at 48h. Presented are features that correlate with PC1 or PC2 (p<0.05); and that were identified as significantly diverse within a condition (using GSEA; with an FDR cutoff of 0.05); or between conditions (using KS-test to compare CNS and LN, with an FDR cutoff of 1e-4).

All experiments are a representative of at least three independent experiments with at least three experimental replicates per group.

FIG. 6A-6I. related to FIG. 1. Single-cell RNA-seq quality control. (FIG. 6A, FIG. 6B) Correlation between the first three PCs (X axis), and different RNA-seq quality measures (colored bars). (FIG. 6A) Before filtering and normalization, the main PCs highly correlate with various library quality scores (Legend below panel A & B), indicating that the dominant signal in the pre-normalization data may reflect experimental artifacts. (FIG. 6B) Normalization strongly reduces these correlations. Applicants find that before filtering and normalization (panel A) the main PCs highly correlate with the various library quality scores, as opposed to post-normalization (panel B). These results indicate that the dominant signal in the pre-normalization data might reflect experimental artifacts. (FIG. 6C) An example of a cell-specific false-negative curve (FNC). The false-negative rate (Y axis, percentage of genes in an expression bin that are detected in this cell (non zero estimated abundance)) is depicted as a function of transcript abundance in the bulk population (X axis, average expression level of genes within each bin). Each blue circle corresponds to a set of housekeeping genes (stratified according to their bulk-population expression levels). The false-negative curve (black solid line) is derived using a logistic function fit. (FIG. 6D) Correlations between single-cell and bulk population profiles. Bar chart depicts the Spearman correlations coefficients (X axis) for each experimental batch (Y axis), where cells from each batch originate from a single mouse. A unique batch identifier is indicated in parentheses. Shown are Spearman correlations of gene expression profiles between pairs of single cells (blue bars, mean and standard deviation); between each single cell and a matched bulk population (orange bars, mean and standard deviation); between an average over all single cells and a matched bulk population (red bars); and between two bulk population replicates (green bars). (FIG. 6E) RNA Flow-Fish validation of expression distribution obtained by RNA-seq. Shown are the single-cell expression distributions for a set of select genes (rows) by RNA-seq (left column) and RNA Flow-Fish (right column). For RNA-seq distributions, the frequency of cells (Y axis) is shown as a function of expression (X axis, FPKM+1, $\log_{10}$), whereas RNA Flow-Fish is plotted as number of cells (Y axis) as a function of transcript (spot) count (X axis). Applicants find agreement for a variety of distributions, ranging from non-expressing (Csf2, Itgax, Sdc1) to unimodal distributions (Irf4, Batf, Actb) and bimodal distributions (Il7a, Il2). (FIG. 6F) Constitutively expressed genes are enriched for housekeeping functions. Shown is the fold enrichment of housekeeping genes among all the non-bimodally expressed genes (X axis) for each condition (Y axis) (FIG. 6G) As in (A), corresponding p-values (hypergeometric test). (FIG. 6H, FIG. 6I) Applicants find greater variation in expression levels for key immune genes. (H) Standard deviation (Y axis) of all the detectably expressed genes in the non-pathogenic (TGF-β1+IL-6) condition is plotted vs. their single-cell average expression (X axis). Shown are housekeeping genes (green crosses), immune-response-related genes (red crosses, based on Gene Ontology) and other genes (blue dots). Selected outliers are highlighted by black squares. (I) As in (G), but where the standard deviation (Y axis) and mean (X axis) of every gene are computed only for cells that express it (defined as those cells that are associated with the Gaussian distribution in our mixture model).

FIG. 7A-7E. Population controls compared to single cell profiles. (FIG. 7A) Gene expression levels of selected genes for in vivo derived cells projected on PCs. Cells (CNS cells: diamonds, LN cells: crosses) are shown in a PCA plot as in FIG. 2C and each cell is colored proportionally to the ranked expression of the denoted gene in this cell relative to the other cells (blue—low expression; red—high expression). Top: Gpr65 is predominantly expressed in the CNS, and particularly high in the Th17/Th1-like memory subpopulation (light blue). Bottom: Ccr8, previously associated with Th2 cells but not Th1/Th17 cells, is also highly expressed in most CNS derived cells. (FIG. 7B) Gene expression levels of selected genes for in vitro derived cells projected on PCs. Similar analysis as in (A) but for the different differentiation conditions in vitro and plotted on a PCA plot as in FIG. 3A; (Left column) regulatory genes (IL-9, IL-16, Podoplanin and Foxp1) show high expression in the non-pathogenic condition (TGF-β1+IL-6), whereas inflammatory genes such as IL-22, IL-23r, Cxcr3 and Gm-csf are more highly expressed in the pathogenic differentiation condition (IL-1β+IL-6+IL-23). FIG. 7 is sometimes also referred to as Supplementary FIG. 2. (FIG. 7C, FIG. 7D, FIG. 7E) Shown are PCA plots based on single cell profiles (small circles, triangles, squares and crosses) along with projected matching population controls (large circles) and single cell averages (large squares) for (FIG. 7C) In vitro Th17 single cells only from the non-pathogenic conditions (TGF-β1+IL-6); (FIG. 7D) In vivo Th17 cells (CNS: purple, LN: orange); and (FIG. 7E) In vitro Th17 cells from all conditions: pathogenic (IL-1β+IL-6+IL-23; red icons); and non-pathogenic conditions (TGF-β1+IL-6. Black icons: cells not sorted for IL-17A/GFP+; light blue icons: IL-17A/GFP+ cells).

FIG. 8A-8D. (FIG. 8A) GPR65$^{-/-}$ memory cells express less IL-17A upon IL-23 reactivation. Sorted memory (CD62L$^-$CD44$^+$CD4$^+$) T cells from wild type (WT, top row) and GPR65$^{-/-}$ (bottom row) mice were reactivated with IL-23 (20 ng/ml) for 96 h. Intracellular cytokine (ICC) analysis shows a reduction of ~45% IL-17A-positive cells (X axis) for GPR65$^{-/-}$ cells when compared to WT (FIG. 8B) IL-17A and IFN-γ production is hampered in vivo for GPR65$^{-/-}$ cells. A reduced frequency of IL-17A (X axis) and IFN-γ (Y axis) positive cells from the draining LNs and spleen of MOG$_{35-55}$/CFA-immunized RAG-1$^{-/-}$ mice reconstituted with WT (top row) or GPR65$^{-/-}$ (bottom row) naïve CD4$^+$ T-cells 30 days post EAE induction (FIG. 8C) GPR65$^{-/-}$ CD4$^+$ T-cells express less IL-17A and more IL-10. Quantification of secreted cytokines (Y axis) by cytometric bead assays (CBAs) for differentiation conditions (X axis) either without (Th0; left) or with Th17 polarizing cytokines (TGF-β1+IL-6, middle; or IL-1β+IL-6+IL-23, right) for GPR65$^4$ cells (light green) and littermate control cells (dark green). * p<0.05,  p<0.01, * p<0.001. All data presented here are a representative of three independent experiments, with at least 3 replicates per experiment. (FIG. 8D) Linear regression analysis of EAE disease progression for GPR65 KO vs. WT mice. Mean clinical score (Y axis) is shown as a function of days post immunization (X axis) for WT (solid line) and GPR65$^1$ mice (dotted line). *** p<0.001. Data presented here is a representative of at least three independent experiments.

Figure 9A:
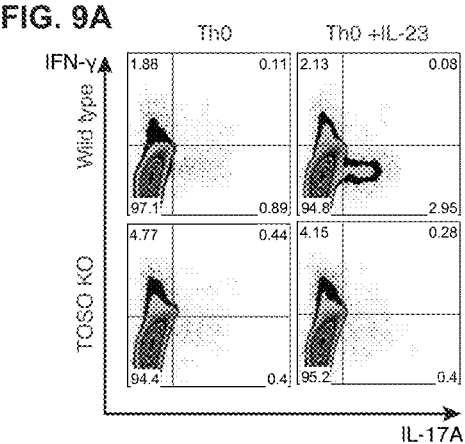
Figure 9B:
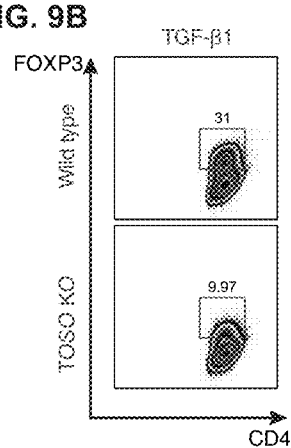
Figure 9C:
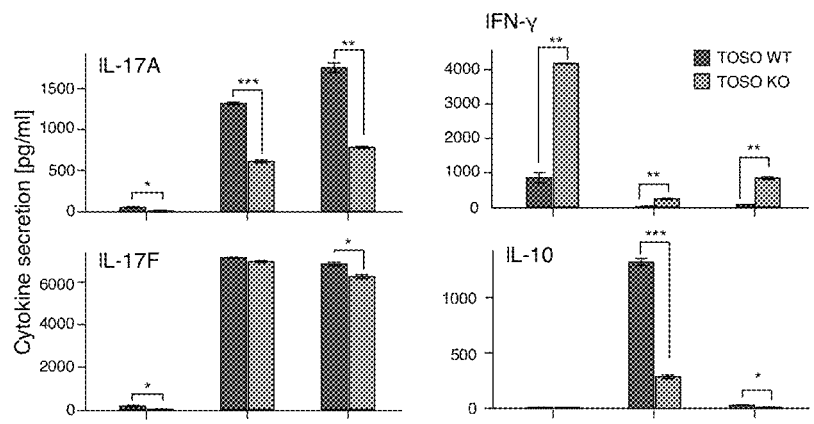

FIG. 9A-9C. (FIG. 9A) TOSO$^{-/-}$ cells express less IL-17A but more IFN-γ upon IL-23 reactivation. Sorted memory (CD62L$^-$CD44$^+$CD4$^+$) T cells from WT and TOSO$^{-/-}$ mice were reactivated (anti-CD3/CD28) with IL-23 (20 ng/ml) for 96 h. The ICC analysis shows hardly any IL-17A (X axis) positive cells amongst TOSO$^{-/-}$ cells (bottom row) whereas WT does show a small IL-17A positive population (top row). On the other hand, IFN-γ (Y axis) gets induced to a larger extend in the TOSO$^{-/-}$ cells. (FIG. 9B) TOSO$^{-/-}$ cells exhibit lower FOXP3 levels during Treg differentiation. Naïve CD4$^+$ T-cells from WT (top row) and TOSO$^{-/-}$ mice (bottom row) were differentiated in vitro with TGF-β1 (2 ng/ml) for 96h, and subsequently stained and analyzed by ICC for intracellular FOXP3 expression (Y axis) and CD4 expression (X axis). (FIG. 9C) TOSO$^{-/-}$ cells secrete less IL-17A, less IL-10, but more IFN-γ. Quantification of secreted cytokines (Y axis) by CBA for a 96h differentiation in conditions (X axis) without (Th0; left) or with Th17 polarizing cytokines (TGF-β1+IL-6, middle; or IL-1β+IL-6+IL-23, right) for TOSO$^{-/-}$ cells (light green) and WT cells (dark green). * $p<0.05$,  $p<0.01$, * $p<0.001$. All data presented here are a representative of three independent experiments, with at least three replicates per experiment.

Figure 10A:
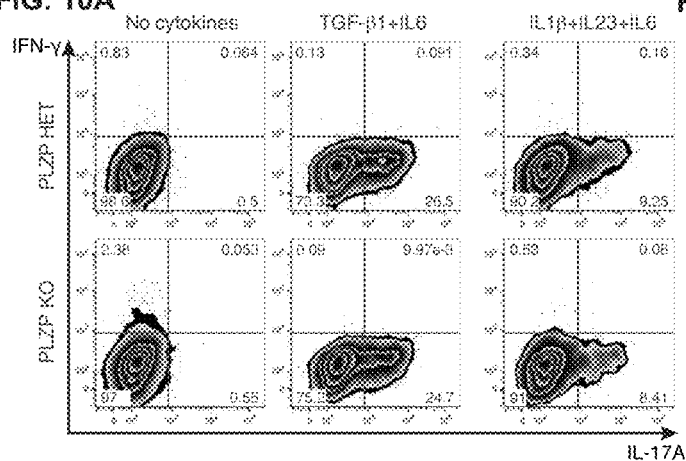
Figure 10B:
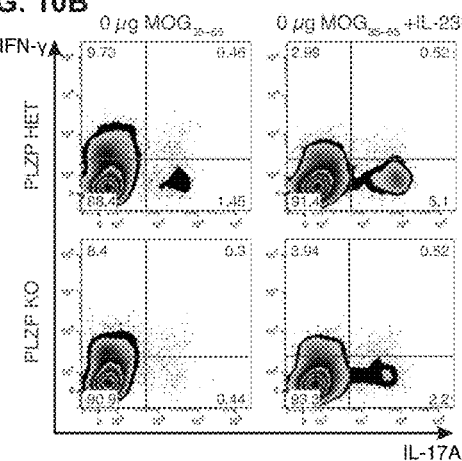
Figure 10C:
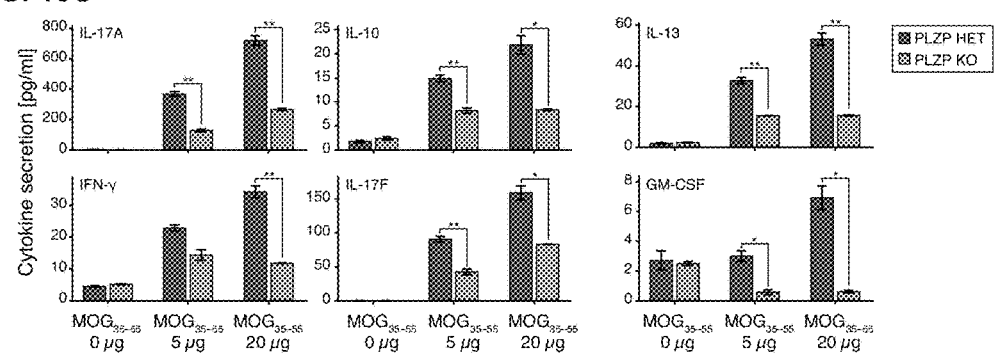

FIG. 10A-10C. (FIG. 10A) PLZP. T cells show comparable IL-17A and IFN-γ production to littermate controls (PLZP HET). ICC staining for IFN-γ (Y axis) and IL-17A (X axis) of CD4$^+$ T cells from respective littermate controls (top) or PLZP$^{-/-}$ (bottom) cells activated in vitro for 48h with anti-CD3 and anti-CD28 either without (Th0; left) or with Th17 polarizing cytokines (TGF-β1+IL-6, middle; or IL-1β+IL-6+IL-23, right). (FIG. 10B) PLZP$^{-/-}$ cells produce less IL-17A cells upon IL-23 stimulation. PLZP$^{-/-}$ mice and littermate controls were immunized with 100 μg of MOG$_{35-55}$/CFA. Cells harvested 8 days after immunization from the draining LNs and spleen were cultured ex vivo for 4 days with (right column) or without (left) IL-23 (20 ng/ml). CD4$^+$ T cells were analyzed for IFN-γ and IL-17A production by ICC staining. (FIG. 10C) PLZP$^{-/-}$ cells express significantly less pro-inflammatory cytokines in a MOG recall assay. Quantification of secreted cytokines (Y axis) by CBA in a MOG recall assay with different MOG$_{35-55}$ concentrations (X axis) for PLZP. mice (light green) and littermate controls (dark green). * $p<0.05$,  $p<0.01$, * $p<0.001$, showing significant reduction of cytokine expression under MOG reactivation conditions. All data presented here are a representative of three independent experiments, with at least 3 replicates per experiment.

Figure 11K:
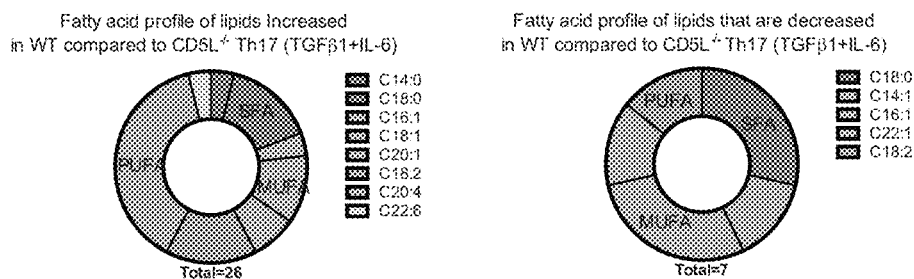

FIG. 11A-11M. CD5L shifts Th17 cell lipidome balance from saturated to unsaturated lipid, modulating Rorγt ligand availability and function. FIG. 11A, B show Lipidome analysis of Th17 cells. (FIG. 11A) WT and CD5L$^{-/-}$ naïve T cells were differentiated. Cells and supernatant were harvested at 96 hours and subjected to MS/LC. Three independent mouse experiments were performed. Data shown are median expression of each metabolite identified that have at least 1.5 fold differences between WT and CD5L$^{-/-}$ under the TGFβ1+IL-6 condition. (FIG. 11B, FIG. 1C) Expression of representative metabolites including cholesterol ester and a PUFA-containing TAG species. (FIG. 11D) Microscopy of wt and CD5L$^{-/-}$ cells stained for free cholesterol. (E,F) Rorγt ChIP from Th17 cells differentiated as described in A. under various conditions as indicated. (FIG. 11G-FIG. 11J) Dual luciferase reporter assays. (FIG. 11G, FIG. 11H) Dual luciferase reporter assays were performed in EL4 cells stably transfected with a control vector or Rorγt vector. CD5L retroviral vector was cotransfected in G. (FIG. 11H). CD5L retroviral vector was cotransfected at 0, 25, 50 and 100 ng/well. (FIG. 11I-FIG. 11J) 10 μM of either arachidonic acid (PUFA) or 20 μM of palmitic acid (SFA) were used whenever a single dose was indicated. All ChIP and luciferase assay are representative of at least 3 independent experiments. Representative metabolites were used, including a cholesterol ester and a PUFA-containing TAG species. (FIG. 11K) Lipids from the two clusters in (A) are partitioned based on the length and saturation of their fatty acyl (FA) side chains. Those carrying more than one FA are further grouped by their FAs with the least saturation or longest carbon chain (in that order). Complete FA profile is shown in (FIG. 11L) Ratio of specific lipids in WT vs. CD5L$^{-/-}$ Th17 cells carrying various PUFA side chains. Phospholipids included in this analysis: phosphatidylcholine, phosphatidylethanolamine, phosphatidylserine and their respective lyso-metabolites. Neutral lipid included in this analysis: Triacylglyceride, diacylglyceride and monoacylglyceride. Asterisk (*) denotes to $p<0.05$ in Student's t-test. (FIG. 11M) Expression of cyp51 and sc4mol mRNA in WT or CD5L$^{-/-}$ Th17 cells (TGF-β1+IL-6, left panels) or WTTh17 cells (TGF-β1+IL-6 with control or IL-23, right panels). SFA (palmitic acid, 25 uM) or PUFA (arachidonic acid, 25 uM) was added at 48h and cells analyzed at 96h.

FIG. 12A-12F. Characterization of WT and CD5L−/− mice with EAE. Mice were immunized (FIG. 12A) 15 days post immunization, lymphocytes from CNS were isolated and directly stained and analyzed with flow cytometry for the expression of FoxP3. (FIG. 12B) Cells from CNS as in A were restimulated with PMA/ionomycin with Brefeldin A for 4 hours and profiled for cytokine production by flow cytometry. (FIG. 12C) Cells were isolated from Inguinal LN of mice 10 days after immunization. 3H Thymidine incorporation assays was used to determine T cell proliferation in response to MOG35-55 peptide; (FIG. 12D) Supernatant from C were harvested and the amount of IL-17 was determined by ELISA. (FIG. 12E, FIG. 12F) Summary data for FIG. 17 G, H respectively.

Figure 13:
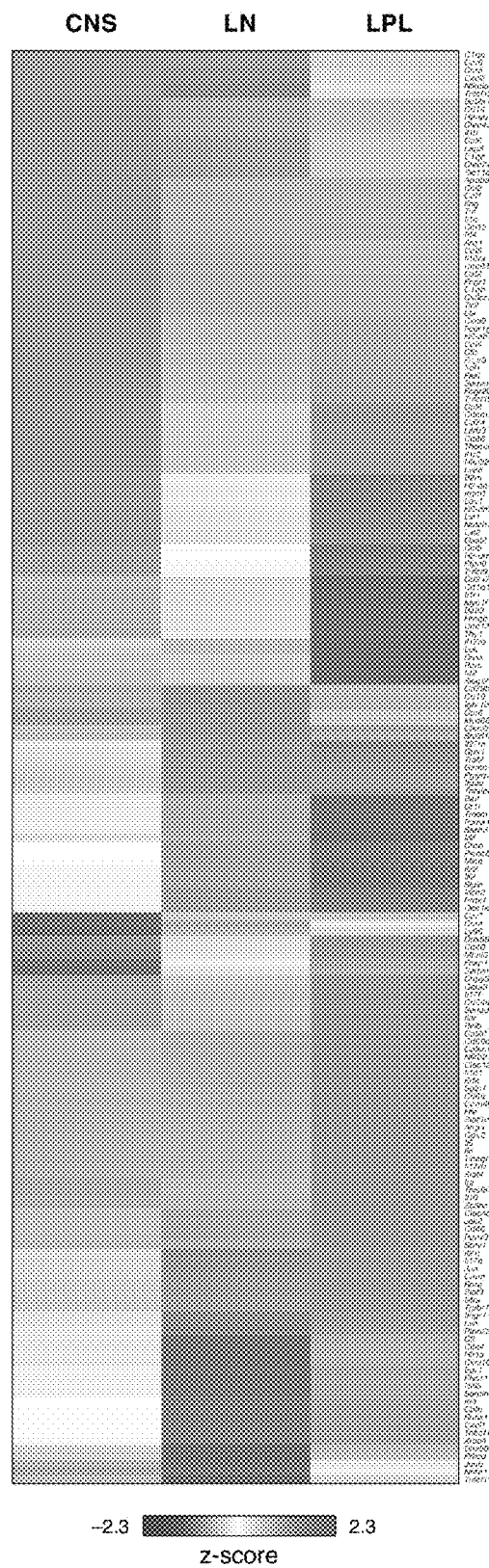
Figure 14A:
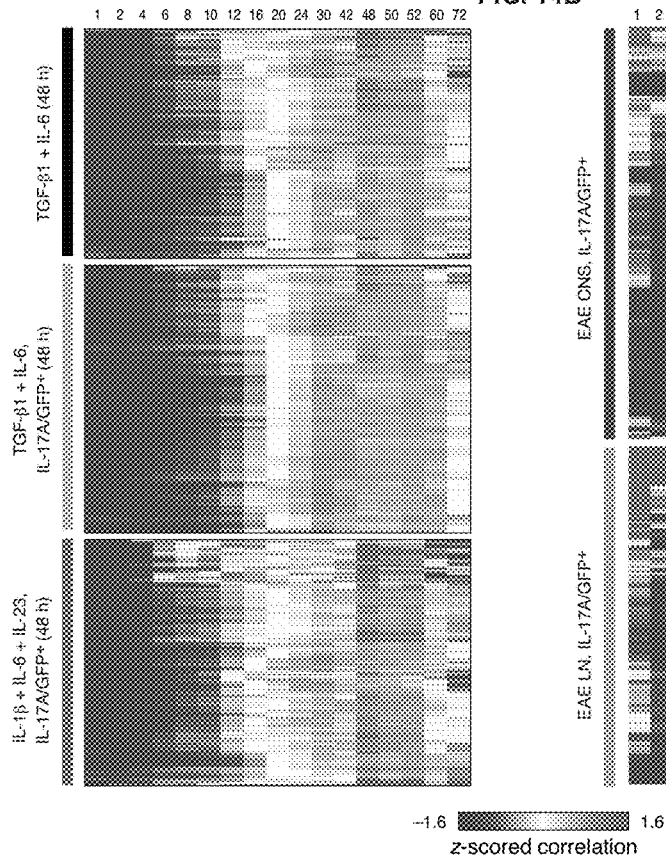
Figure 14B:
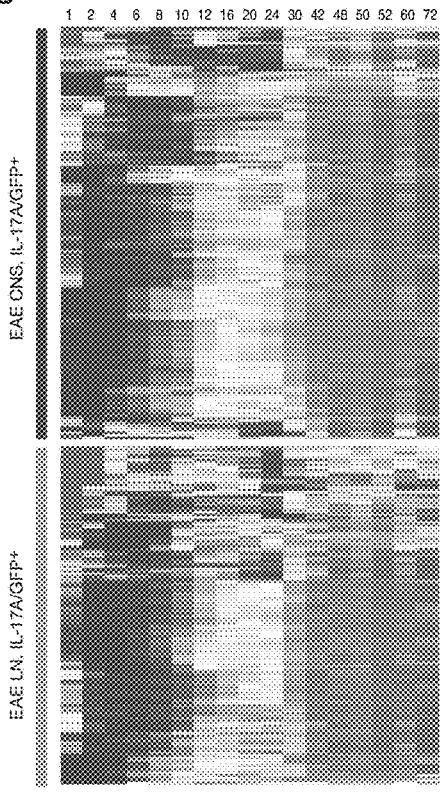
Figure 14C:
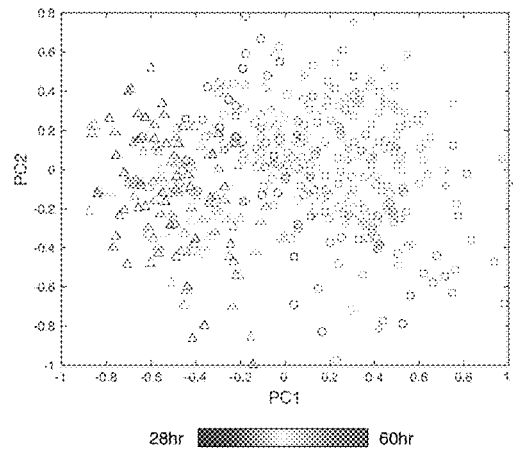
Figure 14D:
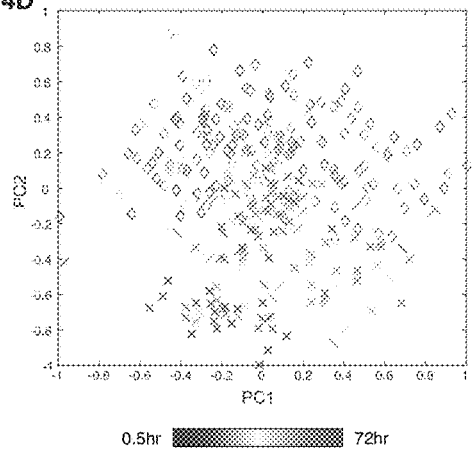

FIG. 13, related to FIG. 2. Differential gene expression of Th17 cells derived from LPL, LN and CNS. Shown are the expression levels of immune response related genes (rows; Z normalized per row) that are differentially expressed between bulk population samples from CNS, LN and LPL derived Th17 cells (columns).

FIG. 14A-14D, related to FIGS. 2 and 3. Temporal asynchrony between individual cells in vivo and in vitro. (FIG. 14A, FIG. 14B) Weighted Pearson correlation coefficient (red: positive; blue: negative) of each single cell's profile (row) with bulk profiles at each of 18 time points (columns) along a 72h time course of Th17 cell differentiation, previously collected with microarrays (Yosef et al., 2013). The weighted Pearson correlation weighs down the effect of false negatives, as done in the weighted PCA, and z-normalized per row. Cells collected in vitro (A) show more synchrony than those from in vivo samples (B). (FIG. 14C, FIG. 14D) Some of the cell-to-cell variation likely reflects time of differentiation. Shown are the PCA plots for in vitro cells (C, asin FIG. 3; IL-1β+IL-6+IL-23, triangles, TGF-β1+IL-6, squares and circles) and in vivo cells (D, as in FIG. 2; CNS cells: diamonds, LN cells: crosses). Each cell (point) is colored proportionally to the ranked associated time point of this cell's maximal correlation from the analysis in (A, B) (blue: early time points; red: late time points).

Figure 15A:
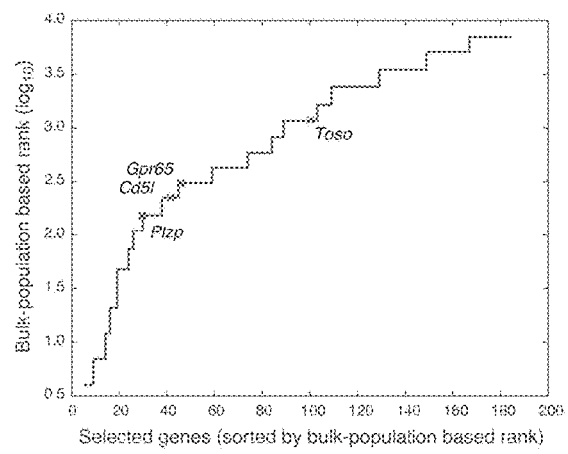
Figure 15B:
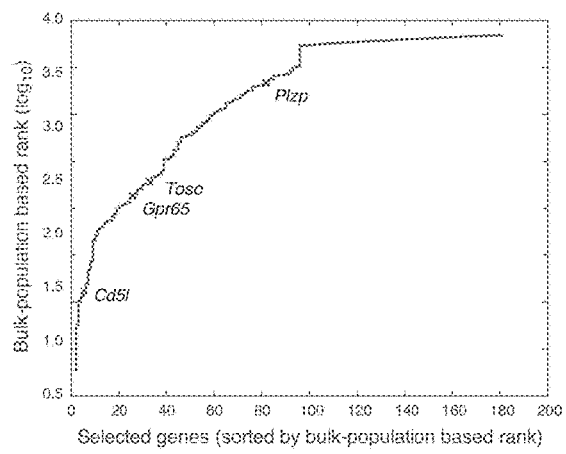

FIG. 15A-15B, related to FIG. 4. Population based studies do not prioritize genes that have top ranks for Th17 pathogenicity by single cell data Shown are the 184 genes from our co-variation matrix (rows, FIG. 4B), ordered according to population based ranking (X-axis) along with their rank (log 10 (#genes that are ranked equal to or better); Y-axis) based on either (FIG. 15A) a compendium of 41 studies of Th17 cells, or (FIG. 15B) a literature based ranking (Ciofani et al., 2012). Red crosses: our top ranking candidates that we followed up on. While the 184 genes from our covariation matrix are more highly ranked than the other 7,000 genes from the single cells in vitro ($p<10^{-10}$ and ~0.015 for A and B, respectively: Wilcoxon Rank Sum Test), they do not necessarily stand out.

FIG. 16A-16I. CD5L is a candidate regulator of Th17 cell functional states. (FIG. 16A-FIG. 16C) Single-cell RNA-seq analysis. (FIG. 16A) Cd5l expression of single-cells from in-vitro generated and in-vivo sorted Th17 cells (IL-17.GFP+) from mice at the peak of EAE. (FIG. 16B, FIG. 16C) Correlation of Cd5l expression in non-pathogenic Th17 cells (TGF-β1+IL-6) with (B) the cell pathogenicity score (based on the pathogenic signature of (Lee et al., 2012)). p=2.63×10-5 (Wilcoxon Rank Sum Test, comparing signature scores of Cd5l expressing vs. non-expressing cells); (FIG. 16C) the founding signature genes of the single-cell based proinflammatory (red) and regulatory (green) modules (Solid bars, significant correlation (p<0.05); striked bars, none significant correlation). (FIG. 16D-FIG. 16F) Validation of CD5L expression in vitro. Naïve T cells (CD4+CD62L+CD44−CD25−) were sorted and differentiated as indicated and analyzed by qPCR for CD5L expression at 48h (D) and 72h (E) and by flow cytometry at 48h (F); (E) IL-23 or control was added at 48h in fresh media. (FIG. 16G-FIG. 16I) Validation of Cd5l expression in vivo. (G,H) IL-17A.GFP reporter mice were immunized to induce EAE. Cells were sorted from spleen (G) and CNS (H) at the peak of disease. Cd5l and Il17a expression are measured by qPCR. Figure shown is representative data of three technical replicates from two independent experiments. (I) Cells were sorted from the gut of naïve mice and the number of RNA transcripts measured by nanostring nCounter platform.

Figure 17A:
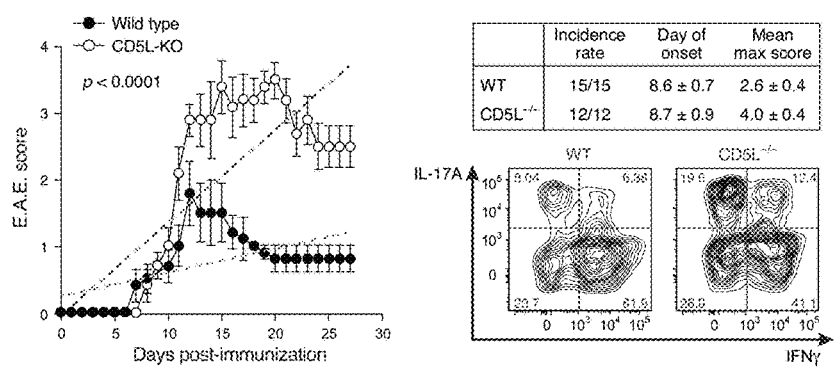
Figure 17B:
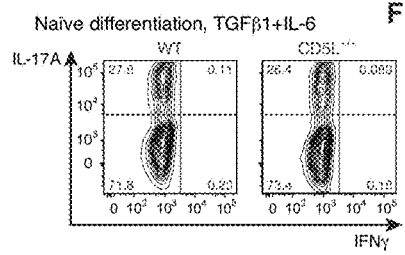
Figure 17C:
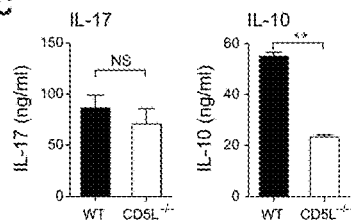
Figure 17D:
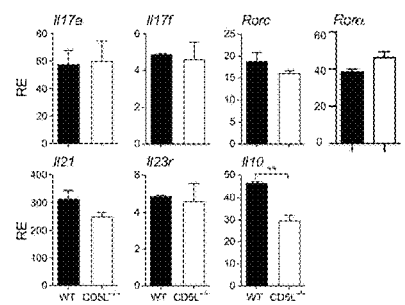
Figure 17E:
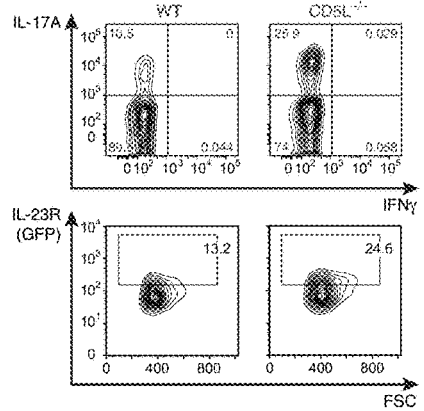
Figure 17F:
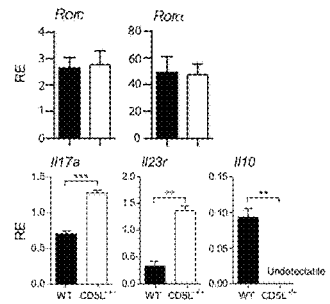
Figure 17G:
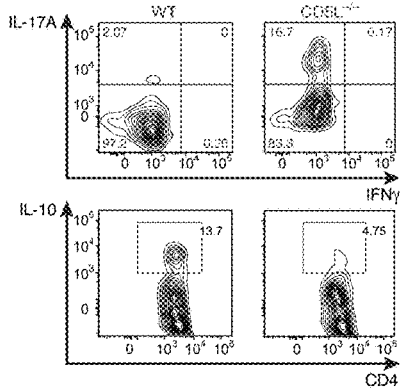

FIG. 17A-17H. CD5L represses effector functions without affecting Th17 cell differentiation. (FIG. 17A) EAE was induced by MOG/CFA (40 µg) immunization. Left panel is pooled results from 3 independent experiments. Right panel: cytokine profile of CD4 T cells isolated from CNS at day 15 post immunization. (FIG. 17B-FIG. 17D) Naïve splenic T cells were sorted and differentiated with TGF-β1+IL-6 for 48h. Th17 cell signature genes were measured by flow cytometry (FIG. 17B), ELISA (FIG. 17C) and qPCR (FIG. 17D). (FIG. 17E-FIG. 17F) Effector Th17 cells were differentiated as in B and resuspended in fresh media with no cytokines for 72h followed by restimulation. Gene profile was measured by flow cytometry (FIG. 17E) and qPCR (FIG. 17F). (FIG. 17G-FIG. 17H) Effector memory T cells (CD4+CD62L−CD44+) (FIG. 17G) or Effector memory Th17 cells (CD4+CD62L−CD44+RorγtGFP+) (FIG. 17H) were sorted from spleen of naïve mice and activated with TCR stimulation.

FIG. 18A-18F. CD5L and PUFA/SFA profile regulate Rorγt function in a ligand-dependent manner. (FIG. 18A, FIG. 18B) Rorγt ChIP-PCR analyses in WT and CD5L−/− Th17 cells. WT, CD5L−/− and Rorγt−/− Th17 cells were differentiated with TGF-1+IL-6 for 96h. Enrichment of Rorγt binding to genomic regions of Il17 (FIG. 18A) and Il10 (FIG. 18B) is measured using qPCR. For fatty acid experiments, 10 µM of either SFA (palmitic acid) or PUFA (arachidonic acid or docosahexaenoic acid showed similar results) was added to WT Th17 cell culture at day 0. Three independent experiments were performed. (FIG. 18C, FIG. 18D) Rorγt transcriptional activity was measured by luciferase reporter of Il17 promoter in EL4 cells transfected with CD5L-RV at 0, 25, 50, 100 ng (FIG. 18C) or 100 ng with 7,27 dihydroxycholesterol (5, 0.5 or 0.05 uM) (FIG. 18D). (FIG. 18E) Naïve WT T cells were activated without polarizing cytokines (Th0) and infected with retrovirus expressing Rorγt in the presence of control-RV or CD5L-RV with or without FF-MAS (5 uM) as a source of Rorγt ligand. Each dot represents an independent infection. (FIG. 18F) WT or CD5L−/− naïve cells were differentiated with TGF-β1+IL-6. At 48h, cells were replated in fresh media with either control or FF-MAS (5 uM) as a source of Rorγt ligand. Cells were harvested for FACS analysis 72h later. 100961 FIG. 19A-19E. Single cell RNA-seq identifies Cd5l as a gene in covariance with the pathogenic module within non-pathogenic Th17 cells. (FIG. 19A) Histogram of Cd5l expression in single cell from unsorted in-vitro derived Th17 cells differentiated under the TGF-β1+IL-6 condition. (FIG. 19B) The expression of Cd5l within single cell is shown in covariance with the first PC of in-vitro derived cells as in (FIG. 19A) where it correlates with the pro-inflammatory module. (FIG. 19C) Within the same PC space as in (FIG. 19B), score of pathogenic signature is shown to also correlate with PC1 as defined in the text. (FIG. 19D, FIG. 19E) Regulation of CD5L expression. (FIG. 19D) Naïve CD4 T cells were sorted from WT, Stat3CD4Cre−/−, RorgtCD4Cre−/− and CD5L−/− and differentiated under Th0 or Th17 (TGFb1+IL-6) condition as in FIG. 17D. CD5L expression was measured intracellularly at 48 hour post differentiation. Upper panel: representative FACS plot; Lower panel: summary results from three independent experiments. (FIG. 19E) Naïve CD4 T cells were differentiated under Th0 condition and transfected with retrovirus carrying Stat3 construct to overexpress STAT3. CD5L expression was measured as in D.

FIG. 20A-20F. CD5L antagonizes pathogenicity of Th17 cells. (FIG. 20A, FIG. 20B) (FIG. 20A) Summary data for Cytokine profile of WT and CD5L−/− 2D2 cells isolated from CNS at day 27 post transfer. Cells were gated on Va3.2+CD4+. (FIG. 20B) Summary data for Cytokine profile of CD45.1 WT recipients that received 100,000 naïve WT or CD5L−/− 2D2 T cells and were immunized the following day with MOG/CFA without pertussis toxin. Cytokine profile of 2D2 T cells was examined on day 10 in draining LN (FIG. 20C-FIG. 20F) Passive EAE is induced. Briefly, naïve 2D2 cells were sorted from WT mice and differentiated under the pathogenic Th17 differentiation conditions with IL-1β+IL-6+IL-23. At 24h, either CD5L-RV or control-RV retrovirus was used to infect the activated cells. The expression of CD5L was analyzed at day 3 post-infection. 50% of cells expressed GFP in both groups. (FIG. 20C) Representative flow cytometry analysis of cytokine profile prior to transfer; (FIG. 20D) Weight loss curve after transfer; (FIG. 20E) EAE score; Dotted green and red lines are linear regression analysis performed as in FIG. 17A. (FIG. 20F) Representative flow cytometry data of cytokine profile of CD4+ T cells from CNS at day 30 post transfer.

FIG. 21A-21E. CD5L regulates lipid metabolism in Th17 cells and modulate Rorγt ligand. (FIG. 21A) Lipidomics analysis. Entire set of 39 lipids (rows) resolved from cell lysates (columns) that have significantly different levels among any Th17 cell conditions and are with a fold difference of at least 1.5. (FIG. 21B) The ratio of specific lipids (from all those resolved) between WT and CD5L−/− Th17 cells (both in TGF-β1+IL-6 conditions) (Y-axis) partitioned by their PUFA content (X axis). (FIG. 21C) Left panel: The ratio of a particular lipid with specific SFA or MUFA content in WT vs CD5L−/− Th17 cells (TGF-81+IL-6) is shown. Right panel, same data as left panel, segregating phospholipid from neutral lipids (FIG. 21D) MEVA analysis of all lipid species resolved (rows) comparing cell lysates or media in different Th17 cell conditions (1-6, legend). CE, cholesterol ester; LPC, lysophosphatidylcholine; PC, phosphatidylcholine; SM, sphingomyelin; TAG, triacylglyceride.

B623: IL-1β+IL-6+IL-23 condition; T16: TGF-β+IL-6 condition. (FIG. 21E) Expression of free cholesterol in Th17 cells. WT and CD5L−/− Th17 cells were differentiated with TGF-β1+IL-6 for 48 hours and harvested for confocal microscopy. Cells were fixed using paraformaldehyde and stained with Filipin for 30 minutes, washed and sealed with DAPI-coated cover slides and analyzed by confocal microscopy.

DETAILED DESCRIPTION

This invention relates generally to compositions and methods for identifying the regulatory networks that control T cell balance, T cell differentiation, T cell maintenance and/or T cell function, as well compositions and methods for exploiting the regulatory networks that control T cell balance, T cell differentiation, T cell maintenance and/or T cell function in a variety of therapeutic and/or diagnostic indications.

The invention provides compositions and methods for modulating T cell balance. The invention provides T cell modulating agents that modulate T cell balance. For example, in some embodiments, the invention provides T cell modulating agents and methods of using these T cell modulating agents to regulate, influence or otherwise impact the level of and/or balance between T cell types, e.g., between Th17 and other T cell types, for example, regulatory T cells (Tregs). For example, in some embodiments, the invention provides T cell modulating agents and methods of using these T cell modulating agents to regulate, influence or otherwise impact the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

These compositions and methods use T cell modulating agents to regulate, influence or otherwise impact the level and/or balance between T cell types, e.g., between Th17 and other T cell types, for example, regulatory T cells (Tregs).

The invention provides methods and compositions for modulating T cell differentiation, for example, helper T cell (Th cell) differentiation. The invention provides methods and compositions for modulating T cell maintenance, for example, helper T cell (Th cell) maintenance. The invention provides methods and compositions for modulating T cell function, for example, helper T cell (Th cell) function. These compositions and methods use T cell modulating agents to regulate, influence or otherwise impact the level and/or balance between Th17 cell types, e.g., between pathogenic and non-pathogenic Th17 cells. These compositions and methods use T cell modulating agents to influence or otherwise impact the differentiation of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the maintenance of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the differentiation of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the maintenance of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the differentiation of a population of T cells, for example toward a non-Th17 T cell subset or away from a non-Th17 cell subset. These compositions and methods use T cell modulating agents to influence or otherwise impact the maintenance of a population of T cells, for example toward a non-Th17 T cell subset or away from a non-Th17 cell subset.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

These compositions and methods use T cell modulating agents to influence or otherwise impact the function and/or biological activity of a T cell or T cell population. These compositions and methods use T cell modulating agents to influence or otherwise impact the function and/or biological activity of a helper T cell or helper T cell population. These compositions and methods use T cell modulating agents to influence or otherwise impact the function and/or biological activity of a Th17 cell or Th17 cell population. These compositions and methods use T cell modulating agents to influence or otherwise impact the function and/or biological activity of a non-Th17 T cell or non-Th17 T cell population, such as, for example, a Treg cell or Treg cell population, or another CD4+ T cell or CD4+ T cell population. These compositions and methods use T cell modulating agents to influence or otherwise impact the plasticity of a T cell or T cell population, e.g., by converting Th17 cells into a different subtype, or into a new state.

The methods provided herein combine transcriptional profiling at high temporal resolution, novel computational algorithms, and innovative nanowire-based tools for performing perturbations in primary T cells to systematically derive and experimentally validate a model of the dynamic regulatory network that controls Th17 differentiation. See e.g., Yosef et al., "Dynamic regulatory network controlling Th17 cell differentiation, Nature, vol. 496: 461-468 (2013)/ doi. 10.1038/naturel 1981, the contents of which are hereby incorporated by reference in their entirety. The network consists of two self-reinforcing, but mutually antagonistic, modules, with novel regulators, whose coupled action may be essential for maintaining the level and/or balance between Th17 and other CD4+ T cell subsets. Overall, 9,159 interactions between 71 regulators and 1,266 genes were active in at least one network; 46 of the 71 are novel. The examples provided herein identify and validate 39 regulatory factors, embedding them within a comprehensive temporal network and reveals its organizational principles, and highlights novel drug targets for controlling Th17 differentiation.

A "Th17-negative" module includes regulators such as SP4, ETS2, IKZF4, TSC22D3 and/or, IRF1. It was found that the transcription factor Tsc22d3, which acts as a negative regulator of a defined subtype of Th17 cells, co-localizes on the genome with key Th17 regulators. The "Th17 positive" module includes regulators such as MINA, PML, POU2AF1, PROCR, SMARCA4, ZEB1, EGR2, CCR6, and/or FAS. Perturbation of the chromatin regulator Mina was found to up-regulate Foxp3 expression, perturbation of the co-activator Pou2af1 was found to up-regulate IFN-γ production in stimulated naïve cells, and perturbation of the TNF receptor Fas was found to up-regulate IL-2 production in stimulated naïve cells. All three factors also control IL-17 production in Th17 cells.

The immune system must strike a balance between mounting proper responses to pathogens and avoiding uncontrolled, autoimmune reaction. Pro-inflammatory IL-17-producing Th17 cells area prime case in point: as a part of the adaptive immune system, Th17 cells mediate clearance of fungal infections, but they are also strongly implicated in the pathogenesis of autoimmunity (Korn et al., 2009). In mice, although Th17 cells are present at sites of tissue inflammation and autoimmunity (Korn et al., 2009), they are also normally present at mucosal barrier sites, where they maintain barrier functions without inducing tissue inflammation (Blaschitz and Raffatellu, 2010). In humans, functionally distinct Th17 cells have been described; for instance, Th17 cells play a protective role in clearing different types of pathogens like *Candida albicans* (Hernandez-Santos and Gaffen, 2012) or *Staphylococcus aureus* (Lin et al., 2009), and promote barrier functions at the mucosal surfaces (Symons et al., 2012), despite their pro-inflammatory role in autoimmune diseases such as rheumatoid arthritis, multiple sclerosis, psoriasis systemic lupus erythematous and asthma (Waite and Skokos, 2012). Thus, there is considerable diversity in the biological function of Th17 cells and in their ability to induce tissue inflammation or provide tissue protection.

Mirroring this functional diversity, depending on the cytokines used for differentiation, in vitro polarized Th17 cells can either cause severe autoimmune responses upon adoptive transfer ('pathogenic Th17 cells') or have little or no effect in inducing autoimmune disease ('non-pathogenic cells')(Ghoreschi et al., 2010; Lee et al., 2012). In vitro differentiation of naïve CD4 T cells in the presence of TGF-β1+IL-6 induces an IL-17A and IL-10 producing population of Th17 cells, that are generally nonpathogenic, whereas activation of naïve T cells in the presence IL-1β+ IL-6+IL-23 induces a T cell population that produces IL-17A and IFN-γ, and are potent inducers of autoimmune disease induction (Ghoreschi et al., 2010).

Charting this functional heterogeneity of Th17 cells to understand the molecular circuits that control it is thus of both fundamental and clinical importance. Previous transcriptional profiling studies have identified sets of genes, dubbed 'pathogenicity signatures', that consist of genes differentially expressed between 'pathogenic' vs. 'non-pathogenic' in vitro differentiated Th17 cells (Ghoreschi et al., 2010; Lee et al., 2012). However, such studies relied either on genomic profiling of cell populations, which are limited in their ability to detect distinct cellular states within a cell mixture, or on tracking a handful of pre-selected markers by fluorescence-based flow cytometry (Perfetto et al., 2004), which cannot discover novel molecular factors that regulate Th17 cell function. Emerging technological and computational approaches for single-cell RNA-seq (Shalek et al., 2013; Shalek et al., 2014; Trapnell et al., 2014) have opened up the exciting possibility of a more unbiased and principled interrogation into the regulatory circuits underlying different cell states. Single-cell RNA-seq also facilitates the genomic study of samples with limited cell availability, such as in vivo derived Th17 cells from the sites of tissue inflammation during an autoimmune reaction.

Here, single-cell RNA-seq was performed of 806 mouse Th17 cells from in vivo and in vitro models and computationally analyzed the data to dissect the molecular basis of different functional Th17 cell states. It was found that Th17 cells isolated from the draining LNs and CNS at the peak of EAE span a spectrum of states ranging from self renewing cells in the LN to Th1-like effector/memory cells and a dysfunctional, senescent-like cell phenotype in the CNS. In vitro polarized Th17 cells also spanned a pathogenicity spectrum from potentially pathogenic to more regulatory cells. Genes associated with these opposing states include not only canonical regulators that were identified at a population level, but also novel candidates that have not been previously detected by population-level expression approaches (Ciofani et al., 2012; Yosef et al., 2013), which were prioritized for functional analysis. Testing four high-ranking candidates—Gpr6S, Plzp, Toso and Cd5l—with knockout mice, substantial effects were found both on in vitro Th17-cell differentiation and on the development of EAE in vivo. This work provides novel insights into Th17 cellular and functional states in vivo leading to the discovery of novel regulators for targeted manipulation of pathogenic functions of Th17 cells in autoimmune disease.

The T cell modulating agents are used to modulate the expression of one or more target genes or one or more products of one or more target genes that have been identified as genes responsive to Th17-related perturbations. These target genes are identified, for example, by contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or 2 of WO/2014/134351, incorporated herein by reference (alone or with those of other herein disclosed methods).

In some embodiments, the target gene is one or more Th17-associated cytokine(s) or receptor molecule(s) selected from those listed in Table 3 of WO/2014/134351, incorporated herein by reference (alone or with those of other herein disclosed methods). In some embodiments, the target gene is one or more Th17-associated transcription regulator(s) selected from those shown in Table S3 (Gaublomme 2015) or Table 4 of WO/2014/134351, incorporated herein by reference (alone or with those of other herein disclosed methods).

In some embodiments, the target gene is one or more Th17-associated transcription regulator(s) selected from those shown in Table S3 (Gaublomme 2015) or Table 5 of WO/2014/134351, incorporated herein by reference (alone or with those of other herein disclosed methods). In some embodiments, the target gene is one or more Th17-associated receptor molecule(s) selected from those listed in Table 6 of WO/2014/134351, incorporated herein by reference (alone or with those of other herein disclosed methods). In some embodiments, the target gene is one or more Th17-associated kinase(s) selected from those listed in Table 7 of WO/2014/134351, incorporated herein by reference (alone or with those of other herein disclosed methods). In some embodiments, the target gene is one or more Th17-associated signaling molecule(s) selected from those listed in Table 8 of WO/2014/134351, incorporated herein by reference (alone or with those of other herein disclosed methods). In some embodiments, the target gene is one or more Th17-associated receptor molecule(s) selected from those listed in Table 9 of WO/2014/134351, incorporated herein by reference (alone or with those of other herein disclosed methods).

Automated Procedure for Selection of Signature Genes

The invention also provides methods of determining gene signatures that are useful in various therapeutic and/or diagnostic indications. The goal of these methods is to select a small signature of genes that will be informative with respect to a process of interest. The basic concept is that different types of information can entail different partitions of the "space" of the entire genome (>20 k genes) into subsets of associated genes. This strategy is designed to have the best coverage of these partitions, given the constraint on the signature size. For instance, in some embodiments of this strategy, there are two types of information: (i) temporal expression profiles; and (ii) functional annotations. The first information source partitions the genes into sets of co-expressed genes. The information source partitions the genes into sets of co-functional genes. A small set of genes is then selected such that there are a desired number of representatives from each set, for example, at least 10 representatives from each co-expression set and at least 10 representatives from each co-functional set. The problem of working with multiple sources of information (and thus aiming to "cover" multiple partitions) is known in the theory of computer science as Set-Cover. While this problem cannot be solved to optimality (due to its NP-hardness) it can be approximated to within a small factor. In some embodiments, the desired number of representatives from each set is one or more, at least 2, 5 or more, 10 or more, 15 or more, 20 or more, 25 or more, 30 or more, 35 or more, 40 or more, 50 or more, 60 or more, 70 or more, 80 or more, 90 or more, or 100 or more.

An important feature of this approach is that it can be given either the size of the signature (and then find the best coverage it can under this constraint); or the desired level of coverage (and then select the minimal signature size that can satisfy the coverage demand).

An exemplary embodiment of this procedure is the selection of the 275-gene signature (Table 1 of WO/2014/134351, incorporated herein by reference), which combined several criteria to reflect as many aspect of the differentiation program as was possible. The following requirements were defined: (1) the signature must include all of the TFs that belong to a Th17 microarray signature (comparing to other CD4+ T cells, see e.g., Wei et al., in Immunity vol. 30 155-167 (2009)), see Methods in WO/2014/134351, incorporated herein by reference); that are included as regulators in the network and are at least slightly differentially expressed; or that are strongly differentially expressed; (2) it must include at least 10 representatives from each cluster of genes that have similar expression profiles; (3) it must contain at least 5 representatives from the predicted targets of each TF in the different networks; (4) it must include a minimal number of representatives from each enriched Gene Ontology (GO) category (computed over differentially expressed genes); and, (5) it must include a manually assembled list of ~100 genes that are related to the differentiation process, including the differentially expressed cytokines, receptor molecules and other cell surface molecules. Since these different criteria might generate substantial overlaps, a set-cover algorithm was used to find the smallest subset of genes that satisfies all of five conditions. 18 genes whose expression showed no change (in time or between treatments) in the microarray data were added to this list.

Use of Signature Genes

The invention provides T cell related gene signatures for use in a variety of diagnostic and/or therapeutic indications. For example, the invention provides Th17 related signatures that are useful in a variety of diagnostic and/or therapeutic indications. "Signatures" in the context of the present invention encompasses, without limitation nucleic acids, together with their polymorphisms, mutations, variants, modifications, subunits, fragments, and other analytes or sample-derived measures.

Exemplary signatures are shown in Tables 1 and 2 of WO/2014/134351, incorporated herein by reference, and are collectively referred to herein as, inter alia, "Th17-associated genes," "Th17-associated nucleic acids," "signature genes," or "signature nucleic acids." These signatures are useful in methods of diagnosing, prognosing and/or staging an immune response in a subject by detecting a first level of expression, activity and/or function of one or more signature genes or one or more products of one or more signature genes selected from those listed in Table 1 or 2 of WO/2014/134351, incorporated herein by reference, and comparing the detected level to a control of level of signature gene or gene product expression, activity and/or function, wherein a difference in the detected level and the control level indicates that the presence of an immune response in the subject.

These signatures are useful in methods of monitoring an immune response in a subject by detecting a level of expression, activity and/or function of one or more signature genes or one or more products of one or more signature genes selected from those listed in Table 1 or 2 of WO/2014/134351, incorporated herein by reference, at a first time point, detecting a level of expression, activity and/or function of one or more signature genes or one or more products of one or more signature genes selected from those listed in Table 1 or 2 of WO/2014/134351, incorporated herein by reference, at a second time point, and comparing the first detected level of expression, activity and/or function with the second detected level of expression, activity and/or function, wherein a change in the first and second detected levels indicates a change in the immune response in the subject.

These signatures are useful in methods of identifying patient populations at risk or suffering from an immune response based on a detected level of expression, activity and/or function of one or more signature genes or one or more products of one or more signature genes selected from those listed in Table 1 or Table 2 of WO/2014/134351, incorporated herein by reference. These signatures are also useful in monitoring subjects undergoing treatments and therapies for aberrant immune response(s) to determine efficaciousness of the treatment or therapy. These signatures are also useful in monitoring subjects undergoing treatments and therapies for aberrant immune response(s) to determine whether the patient is responsive to the treatment or therapy. These signatures are also useful for selecting or modifying therapies and treatments that would be efficacious in treating, delaying the progression of or otherwise ameliorating a symptom of an aberrant immune response. The signatures provided herein are useful for selecting a group of patients at a specific state of a disease with accuracy that facilitates selection of treatments.

The present invention also comprises a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or DNA chips or a sandwich ELISA or any other method as known in the art. Alternatively, the kit contains a nucleic acid substrate array comprising one or more nucleic acid sequences.

Use of T Cell Modulating Agents

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown in Table 10 of WO/2014/134351, incorporated herein by reference.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed., Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, are used to treat or alleviate a symptom associated with an immune-related disorder or an aberrant immune response. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, T cell modulating agents are useful therapeutic tools in the treatment of autoimmune diseases and/or inflammatory disorders. In certain embodiments, the use of T cell modulating agents that modulate, e.g., inhibit, neutralize, or interfere with, Th17 T cell differentiation is contemplated for treating autoimmune diseases and/or inflammatory disorders. In certain embodiments, the use of T cell modulating agents that modulate, e.g., enhance or promote, Th17 T cell differentiation is contemplated for augmenting Th17 responses, for example, against certain pathogens and other infectious diseases. The T cell modulating agents are also useful therapeutic tools in various transplant indications, for example, to prevent, delay or otherwise mitigate transplant rejection and/or prolong survival of a transplant, as it has also been shown that in some cases of transplant rejection, Th17 cells might also play an important role. (See e.g., Abadja F, Sarraj B, Ansari M J., "Significance of T helper 17 immunity in transplantation." Curr Opin Organ Transplant. 2012 February; 17(1):8-14. doi: 10.1097/MOT.0b013e32834ef4e4). The T cell modulating agents are also useful therapeutic tools in cancers and/or anti-tumor immunity, as Th17/Treg balance has also been implicated in these indications. For example, some studies have suggested that IL-23 and Th17 cells play a role in some cancers, such as, by way of non-limiting example, colorectal cancers. (See e.g., Ye J, Livergood R S, Peng G. "The role and regulation of human Th17 cells in tumor immunity." Am J Pathol. 2013 January;182(1):10-20. doi: 10.1016/j.ajpath.2012.08.041. Epub 2012 Nov. 14). The T cell modulating agents are also useful in patients who have genetic defects that exhibit aberrant Th17 cell production, for example, patients that do not produce Th17 cells naturally.

The T cell modulating agents are also useful in vaccines and/or as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis herpetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

In some embodiments, T cell modulating agents are useful in treating, delaying the progression of, or otherwise ameliorating a symptom of an autoimmune disease having an inflammatory component such as an aberrant inflammatory response in a subject. In some embodiments, T cell modulating agents are useful in treating an autoimmune disease that is known to be associated with an aberrant Th17 response, e.g., aberrant IL-17 production, such as, for example, multiple sclerosis (MS), psoriasis, inflammatory bowel disease, ulcerative colitis, Crohn's disease, uveitis, lupus, ankylosing spondylitis, and rheumatoid arthritis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the T cell modulating agent confers a clinical benefit.

Administration of a T cell modulating agent to a patient suffering from an immune-related disorder or aberrant immune response is considered successful if any of a variety of laboratory or clinical objectives is achieved. For example, administration of a T cell modulating agent to a patient is considered successful if one or more of the symptoms associated with the immune-related disorder or aberrant immune response is alleviated, reduced, inhibited or does not progress to a further, i.e., worse, state. Administration of T cell modulating agent to a patient is considered successful if the immune-related disorder or aberrant immune response enters remission or does not progress to a further, i.e., worse, state.

A therapeutically effective amount of a T cell modulating agent relates generally to the amount needed to achieve a therapeutic objective. The amount required to be administered will furthermore depend on the specificity of the T cell modulating agent for its specific target, and will also depend on the rate at which an administered T cell modulating agent is depleted from the free volume other subject to which it is administered.

T cell modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where polypeptide-based T cell modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The invention comprehends a treatment method or Drug Discovery method or method of formulating or preparing a treatment comprising any one of the methods or uses herein discussed.

The present invention also relates to identifying molecules, advantageously small molecules or biologics, that may be involved in inhibiting one or more of the mutations in one or more genes selected from the group consisting of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l. The invention contemplates screening libraries of small molecules or biologics to identify compounds involved in suppressing or inhibiting expression of somatic mutations or alter the cells phenotypically so that the cells with mutations behave more normally in one or more of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd51 or any combination thereof Gpr65, Plzp or Cd51 in any combination of Gpr65, Plzp, Toso or Cd51.

High-throughput screening (HTS) is contemplated for identifying small molecules or biologics involved in suppressing or inhibiting expression of somatic mutations in one or more of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd51 or any combination thereof Gpr65, Plzp or Cd51 in any combination of Gpr65, Plzp, Toso or Cd51. The flexibility of the process has allowed numerous and disparate areas of biology to engage with an equally diverse palate of chemistry (see, e.g., Inglese et al., Nature Chemical Biology 3, 438-441 (2007)). Diverse sets of chemical libraries, containing more than 200,000 unique small molecules, as well as natural product libraries, can be screened. This includes, for example, the Prestwick library (1,120 chemicals) of off-patent compounds selected for structural diversity, collective coverage of multiple therapeutic areas, and known safety and bioavailability in humans, as well as the NINDS Custom Collection 2 consisting of a 1,040 compound-library of mostly FDA-approved drugs (see, e.g., U.S. Pat. No. 8,557, 746) are also contemplated.

The NIH's Molecular Libraries Probe Production Centers Network (MLPCN) offers access to thousands of small molecules—chemical compounds that can be used as tools to probe basic biology and advance our understanding of disease. Small molecules can help researchers understand the intricacies of a biological pathway or be starting points for novel therapeutics. The Broad Institute's Probe Development Center (BIPDeC) is part of the MLPCN and offers access to a growing library of over 330,000 compounds for large scale screening and medicinal chemistry. Any of these compounds may be utilized for screening compounds involved in suppressing or inhibiting expression of somatic mutations in one or more of Toso, advantageously Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd51 or any combination thereof Gpr65, Plzp or Cd51 in any combination of Gpr65, Plzp, Toso or Cd51.

The phrase "therapeutically effective amount" as used herein refers to a nontoxic but sufficient amount of a drug, agent, or compound to provide a desired therapeutic effect.

As used herein "patient" refers to any human being receiving or who may receive medical treatment.

A "polymorphic site" refers to a polynucleotide that differs from another polynucleotide by one or more single nucleotide changes.

A "somatic mutation" refers to a change in the genetic structure that is not inherited from a parent, and also not passed to offspring.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cardiovascular disease, and how the patient responds to the treatment. Additionally, a person having a greater risk of developing a cardiovascular disease (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a cardiovascular disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

In order to determine the genotype of a patient according to the methods of the present invention, it may be necessary to obtain a sample of genomic DNA from that patient. That sample of genomic DNA may be obtained from a sample of tissue or cells taken from that patient.

The tissue sample may comprise but is not limited to hair (including roots), skin, buccal swabs, blood, or saliva. The tissue sample may be marked with an identifying number or other indicia that relates the sample to the individual patient from which the sample was taken. The identity of the sample advantageously remains constant throughout the methods of the invention thereby guaranteeing the integrity and continuity of the sample during extraction and analysis. Alternatively, the indicia may be changed in a regular fashion that ensures that the data, and any other associated data, can be related back to the patient from whom the data was obtained. The amount/size of sample required is known to those skilled in the art.

Generally, the tissue sample may be placed in a container that is labeled using a numbering system bearing a code corresponding to the patient. Accordingly, the genotype of a particular patient is easily traceable.

In one embodiment of the invention, a sampling device and/or container may be supplied to the physician. The sampling device advantageously takes a consistent and reproducible sample from individual patients while simultaneously avoiding any cross-contamination of tissue. Accordingly, the size and volume of sample tissues derived from individual patients would be consistent.

According to the present invention, a sample of DNA is obtained from the tissue sample of the patient of interest. Whatever source of cells or tissue is used, a sufficient amount of cells must be obtained to provide a sufficient amount of DNA for analysis. This amount will be known or readily determinable by those skilled in the art.

DNA is isolated from the tissue/cells by techniques known to those skilled in the art (see, e.g., U.S. Pat. Nos. 6,548,256 and 5,989,431, Hirota et al., Jinrui Idengaku Zasshi. September 1989; 34(3):217-23 and John et al., Nucleic Acids Res. Jan. 25, 1991; 19(2):408; the disclosures of which are incorporated by reference in their entireties). For example, high molecular weight DNA may be purified from cells or tissue using proteinase K extraction and ethanol precipitation. DNA may be extracted from a patient specimen using any other suitable methods known in the art.

It is an object of the present invention to determine the genotype of a given patient of interest by analyzing the DNA from the patent, in order to identify a patient carrying specific somatic mutations of the invention that are associated with developing a cardiovascular disease. In particular, the kit may have primers or other DNA markers for identifying particular mutations such as, but not limited to, one or more genes selected from the group consisting of Toso, advantageously Ctla2h, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l.

There are many methods known in the art for determining the genotype of a patient and for identifying or analyzing whether a given DNA sample contains a particular somatic mutation. Any method for determining genotype can be used for determining genotypes in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are well known to one of skill in the art.

The methods of the present invention, such as whole exome sequencing and targeted amplicon sequencing, have commercial applications in diagnostic kits for the detection of the somatic mutations in patients. A test kit according to the invention may comprise any of the materials necessary for whole exome sequencing and targeted amplicon sequencing, for example, according to the invention. In a particular advantageous embodiment, a diagnostic for the present invention may comprise testing for any of the genes in disclosed herein. The kit further comprises additional means, such as reagents, for detecting or measuring the sequences of the present invention, and also ideally a positive and negative control.

The present invention further encompasses probes according to the present invention that are immobilized on a solid or flexible support, such as paper, nylon or other type of membrane, filter, chip, glass slide, microchips, microbeads, or any other such matrix, all of which are within the scope of this invention. The probe of this form is now called a "DNA chip". These DNA chips can be used for analyzing the somatic mutations of the present invention. The present invention further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874,219; 6,114,122; 6,238,910; 6,365,418; 6,410,229; 6,420,114; 6,432,696; 6,475,808 and 6,489,159 and PCT Publication No. WO 01/45843 A2, the disclosures of which are incorporated by reference in their entireties.

The present invention further encompasses the analysis of lipids. Lipid profiling is a targeted metabolomics platform that provides a comprehensive analysis of lipid species within a cell or tissue. Profiling based on electrospray ionization tandem mass spectrometry (ESI-MS/MS) is capable of providing quantitative data and is adaptable to high throughput analyses. Additionally, Liquid chromatography-mass spectrometry (LC-MS, or alternatively HPLC-MS) may be used.

Examples & Technologies as to the Instant Invention

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In this regard, mention is made that mutations in cells and also mutated mice for use in or as to the invention can be by way of the CRISPR-Cas system or a Cas9-expressing eukaryotic cell or Cas-9 expressing eukaryote, such as a mouse. The Cas9-expressing eukaryotic cell or eukaryote, e.g., mouse, can have guide RNA delivered or administered thereto, whereby the RNA targets a loci and induces a desired mutation for use in or as to the invention. With respect to general information on CRISPR-Cas Systems, components thereof, and delivery of such components, including methods, materials, delivery vehicles, vectors, particles, and making and using thereof, including as to amounts and formulations, as well as Cas9-expressing eukaryotic cells, Cas-9 expressing eukaryotes, such as a mouse, all useful in or as to the instant invention, reference is made to: U.S. Pat. Nos. 8,697,359, 8,771,945, 8,795,965, 8,865,406, 8,871,445, 8,889,356, 8,889,418, 8,895,308, 8,932,814, 8,945,839, 8,906,616; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser.

No. 14/104,837) and US 2014-0179006 A1 (U.S. application Ser. No. 14/183,486), US 2014-0170753 (U.S. application Ser. No. 14/183,429); European Patents/Patent Applications: EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), and:

*Multiplex genome engineering using CRISPR-Cas systems*. Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121): 819-23 (2013);

*RNA-guided editing of bacterial genomes using CRISPR-Cas systems*. Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering*. Wang H., Yang H., Shivalila C S., Dawlaty M M., Cheng A W., Zhang F., Jaenisch R. Cell May 9:153(4):910-8 (2013);

*Optical control of mammalian endogenous transcription and epigenetic states*. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature 12466. Epub 2013 Aug. 23;

*Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. *Cell* August 28. pii: S0092-8674(13)01015-5. (2013);

*DNA targeting specificity of RNA-guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system*. Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

*Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. Cell February 27. (2014). 156 (5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889,

*CRISPR-Cas9 Knockin Mice for Genome Editing and Cancer Modeling*, Platt et al., Cell 159(2): 440-455 (2014) DOI: 10.1016/j.cell.2014.09.014,

*Development and Applications of CRISPR-Cas9 for Genome Engineering*, Hsu et al, Cell 157, 1262-1278 (Jun. 5, 2014) (Hsu 2014),

*Genetic screens in human cells using the CRISPR:Cas9 system*, Wang et al., Science. 2014 January 3; 343 (6166): 80-84. doi:10.1126/science.1246981,

*Rational design of highly active sgRNAs for CIRISPR-Cas9-mediated gene inactivation*, Doench et al., Nature Biotechnology published online 3 Sep. 2014; doi: 10.1038/nbt.3026, and

*In vivo interrogation of gene function in the mammalian brain using CRISPR-Cas9*, Swiech et al, Nature Biotechnology; published online 19 Oct. 2014; doi: 10.1038/nbt.3055, each of which is incorporated herein by reference.

The invention involves a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard, technology of U.S. provisional patent application Ser. No. 62/048,227 filed Sep. 9, 2014, the disclosure of which is incorporated by reference, may be used in or as to the invention.

A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells. In this regard there can be a single-cell sequencing library which may comprise: merging one uniquely barcoded mRNA capture microbead with a single-cell in an emulsion droplet having a diameter of 75-125 µm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library. Accordingly, it is envisioned as to or in the practice of the invention provides that there can be a method for preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least six, and optimally more than twelve, such that, in the latter, there are more than 16 million unique barcodes on the surface of each bead in the pool. (See www.ncbi.nlm.nih.gov/pmc/articles/PMC206447). Likewise, in or as to the instant invention there can be an apparatus for creating a single-cell sequencing library via a microfluidic system, which may comprise: an oil-surfactant inlet which may comprise a filter and a carrier fluid channel, wherein said carrier fluid channel further may comprise a resistor; an inlet for an analyte which may comprise a filter and a carrier fluid channel, wherein said carrier fluid channel may further comprise a resistor; an inlet for mRNA capture microbeads and lysis reagent which may comprise a filter and a carrier fluid channel, wherein said carrier fluid channel may further comprise a resistor; said carrier fluid channels have a carrier fluid flowing therein at an adjustable or predetermined flow rate; wherein each said carrier fluid channels merge at a junction; and said junction being connected to a mixer, which contains an outlet for drops. Similarly, as to or in the practice of the instant invention there can be a method for creating a single-cell sequencing library which may comprise: merging one uniquely barcoded RNA capture microbead with a single-cell in an emulsion droplet having a diameter of 125 µm lysing the cell thereby capturing the RNA on the RNA capture microbead; performing a reverse transcription either after breakage of the droplets and collection of the microbeads; or inside the emulsion droplet to convert the cell's RNA to a first strand cDNA that is covalently linked to the RNA capture microbead; pooling the cDNA-attached microbeads from all cells; and preparing and sequencing a single composite RNA-Seq library; and, the emulsion droplet can be between 50-210 µm. In a further embodiment, the method wherein the diameter of the mRNA capture microbeads is from 10 µm to 95 µm. Thus, the practice of the instant invention comprehends preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T,C,G, or A); 2) repeating this process a large number of times, at least six, and optimally more than twelve, such that, in the latter, there are more than 16 million unique barcodes on the surface of each bead in the pool. The covalent bond can be polyethylene glycol. The diameter of the mRNA capture microbeads can be from 10 µm to 95 µm. Accordingly, it is also envisioned as to or in the practice of the invention that there can be a method for preparing uniquely barcoded mRNA capture microbeads, which has a unique barcode and diameter suitable for microfluidic devices which may comprise: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool. And, the diameter of the mRNA capture microbeads can be from 10 µm to 95 µm. Further, as to in the practice of the invention there can be an apparatus for creating a composite single-cell sequencing library via a microfluidic system, which may comprise: an oil—surfactant inlet which may comprise a filter and two carrier fluid channels, wherein said carrier fluid channel further may comprise a resistor; an inlet for an analyte which may comprise a filter and two carrier fluid channels, wherein said carrier fluid channel further may comprise a resistor; an inlet for mRNA capture microbeads and lysis reagent which may comprise a carrier fluid channel; said carrier fluid channels have a carrier fluid flowing therein at an adjustable and predetermined flow rate; wherein each said carrier fluid channels merge at a junction; and said junction being connected to a constriction for droplet pinch-off followed by a mixer, which connects to an outlet for drops. The analyte may comprise a chemical reagent, a genetically perturbed cell, a protein, a drug, an antibody, an enzyme, a nucleic acid, an organelle like the mitochondrion or nucleus, a cell or any combination thereof. In an embodiment of the apparatus the analyte is a cell. In a further embodiment the cell is a brain cell. In an embodiment of the apparatus the lysis reagent may comprise an anionic surfactant such as sodium lauroyl sarcosinate, or a chaotropic salt such as guanidinium thiocyanate. The filter can involve square PDMS posts; e.g., with the filter on the cell channel of such posts with sides ranging between 125-135 µm with a separation of 70-100 mm between the posts. The filter on the oil-surfactant inlet may comprise square posts of two sizes; one with sides ranging between 75-100 µm and a separation of 25-30 µm between them and the other with sides ranging between 40-50 µm and a separation of 10-15 µm. The apparatus can involve a resistor, e.g., a resistor that is serpentine having a length of 7000-9000 µm, width of 50-75 µm and depth of 100-150 mm. The apparatus can have channels having a length of 8000-12,000 µm for oil-surfactant inlet, 5000-7000 for analyte (cell) inlet, and 900-1200 µm for the inlet for microbead and lysis agent; and/or all channels having a width of 125-250 mm, and depth of 100-150 mm. The width of the cell channel can be 125-250 µm and the depth 100-150 µm. The apparatus can include a mixer having a length of 7000-9000 µm, and a width of 110-140 µm with 35-450 zig-zags every 150 µm. The width of the mixer can be about 125 µm. The oil-surfactant can be a PEG Block Polymer, such as BIORAD™ QX200 Droplet Generation Oil. The carrier fluid can be a water-glycerol mixture. In the practice of the invention or as to the invention, a mixture may comprise a plurality of microbeads adorned with combinations of the following elements: bead-specific oligonucleotide barcodes; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). The individual oligonucleotide molecules on the surface of any individual microbead may contain all three of these elements, and the third element may include both oligo-dT and a primer sequence. A mixture may comprise a plurality of microbeads, wherein said microbeads may comprise the following elements: at least one bead-specific oligonucleotide barcode; at least one additional identifier oligonucleotide barcode sequence, which varies among the oligonucleotides on an individual bead, and thereby assisting in the identification and of the bead specific oligonucleotide molecules; optionally at least one additional oligonucleotide sequences, which provide substrates for downstream molecular-biological reactions. A mixture may comprise at least one oligonucleotide sequence(s), which provide for substrates for downstream molecular-biological reactions. In a further embodiment the downstream molecular biological reactions are for reverse transcription of mature mRNAs; capturing specific portions of the transcriptome, priming for DNA polymerases and/or similar enzymes; or priming throughout the transcriptome or genome. The mixture may involve additional oligonucleotide sequence(s) which may comprise a oligo-dT sequence. The mixture further may comprise the additional oligonucleotide sequence which may comprise a primer sequence. The mixture may further comprise the additional oligonucleotide sequence which may comprise a oligo-dT sequence and a primer sequence. Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label is a fluorescent label. Examples of fluorescent labels include, but are not limited to, Atto dyes, 4-acetamido-4'-isothiocyanatostilbene-2,2'-disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide: anthranilamide; BODIPY; Brilliant Yellow; coumarin and derivatives; coumarin, 7-amino-4-methylcoumarin (AMC, Coumarin 120), 7-amino-4-(trifluoromethyl)coumarin (Coumarin 151); cyanine dyes; cyanosine; 4',6-diamidino-2-2-phenylindole (DAPI); 5'5"-Dibromopyrogallolsulfonephthalein (Bromopyrogallol Red); 7-diethylamino-3-(4'-isothiocyanatophenyl)-4-methylcoumarin;
diethylenetriamine pentaacetate; 4,4'-diisothiocyanatodihydro-stilbene-2,2'-disulfonic acid; 4,4'-diisothiocyanatostilbene-2,2'-disulfonic acid: 5-[dimethylamino]naphthalene-1-sulfonyl chloride (DNS, dansyl chloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. A fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylene. In the alternative, the fluorescent label may be a fluorescent bar code. Advantageously, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation. Advantageously, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached. Oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety. A detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art. Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties. A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag. One or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention accordingly may involve or be practiced as to high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. 104 to 105 single cells in droplets may be processed and analyzed in a single run. To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination. Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets. Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another, the expansion and/or contraction of the liquid reservoir may be combined with other flow-controlling devices and methods, e.g., as described herein. Non-limiting examples of devices able to cause the expansion and/or contraction of a liquid reservoir include pistons. Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets. Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel. Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform. Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets. A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification. A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element. A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids. Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell. Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges. The droplets within the emulsion libraries of the present invention may be contained within an immiscible oil which may comprise at least one fluorosurfactant. In some embodiments, the fluorosurfactant within the immiscible fluorocarbon oil may be a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein. The present invention can accordingly involve an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library. For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and may comprise a different aqueous fluid and a different library element, and pooling the at least first aqueous droplet and the at least second aqueous droplet within an immiscible fluorocarbon oil which may comprise at least one fluorosurfactant thereby forming an emulsion library. One of skill in the art will recognize that methods and systems of the invention are not preferably practiced as to cells, mutations, etc. as herein disclosed, but that the invention need not be limited to any particular type of sample, and methods and systems of the invention may be used with any type of organic, inorganic, or biological molecule (see, e.g., US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA. Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures). Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydro shear instrument. Generally, individual nucleic acid target molecules may be from about 40 bases to about 40 kb. Nucleic acid molecules may be single-stranded, double-stranded, or double-stranded with single-stranded regions (for example, stem- and loop-structures). A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4-(OCH2-CH2)xOH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant. Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid. Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer. A sample in or as to the instant invention may include individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. The invention protein targets may be isolated from biological samples containing a variety of other components including lipids, non-template nucleic acids, and nucleic acids. Protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue.

Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, s-carboxymethylation, acetylation, and methylation. Protein/nucleic acid complexes include cross-linked or stable protein-nucleic acid complexes. Extraction or isolation of individual proteins, protein complexes, proteins with translational modifications, and protein/nucleic acid complexes is performed using methods known in the art.

The invention can thus involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as U.S. Pat. No. RE41,780) and European publication number EP2047910 to Raindance Technologies Inc. The content of each of which is incorporated by reference herein in its entirety. The present invention may relates to systems and methods for manipulating droplets within a high throughput microfluidic system. A microfluid droplet encapsulates a differentiated cell. The cell is lysed and its mRNA is hybridized onto a capture bead containing barcoded oligo dT primers on the surface, all inside the droplet. The barcode is covalently attached to the capture bead via a flexible multi-atom linker like PEG. In a preferred embodiment, the droplets are broken by addition of a fluorosurfactant (like perfluorooctanol), washed, and collected. A reverse transcription (RT) reaction is then performed to convert each cell's mRNA into a first strand cDNA that is both uniquely barcoded and covalently linked to the mRNA capture bead. Subsequently, a universal primer via a template switching reaction is amended using conventional library preparation protocols to prepare an RNA-Seq library. Since all of the mRNA from any given cell is uniquely barcoded, a single library is sequenced and then computationally resolved to determine which mRNAs came from which cells. In this way, through a single sequencing run, tens of thousands (or more) of distinguishable transcriptomes can be simultaneously obtained. The oligonucleotide sequence may be generated on the bead surface. During these cycles, beads were removed from the synthesis column, pooled, and aliquoted into four equal portions by mass; these bead aliquots were then placed in a separate synthesis column and reacted with either dG, dC, dT, or dA phosphoramidite. In other instances, dinucleotide, trinucleotides, or oligonucleotides that are greater in length are used, in other instances, the oligo-dT tail is replaced by gene specific oligonucleotides to prime specific targets (singular or plural), random sequences of any length for the capture of all or specific RNAs. This process was repeated 12 times for a total of $4^{12}=16,777,216$ unique barcode sequences. Upon completion of these cycles, 8 cycles of degenerate oligonucleotide synthesis were performed on all the beads, followed by 30 cycles of dT addition. In other embodiments, the degenerate synthesis is omitted, shortened (less than 8 cycles), or extended (more than 8 cycles); in others, the 30 cycles of dT addition are replaced with gene specific primers (single target or many targets) or a degenerate sequence. The aforementioned microfluidic system is regarded as the reagent delivery system microfluidic library printer or droplet library printing system of the present invention. Droplets are formed as sample fluid flows from droplet generator which contains lysis reagent and barcodes through microfluidic outlet channel which contains oil, towards junction. Defined volumes of loaded reagent emulsion, corresponding to defined numbers of droplets, are dispensed on-demand into the flow stream of carrier fluid. The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil). The carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. Droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In some cases, an apparatus for creating a single-cell sequencing library via a microfluidic system provides for volume-driven flow, wherein constant volumes are injected over time. The pressure in fluidic channels is a function of injection rate and channel dimensions. In one embodiment, the device provides an oil/surfactant inlet; an inlet for an analyte; a filter, an inlet for for mRNA capture microbeads and lysis reagent; a carrier fluid channel which connects the inlets, a resistor; a constriction for droplet pinch-off; a mixer; and an outlet for drops. In an embodiment the invention provides apparatus for creating a single-cell sequencing library via a microfluidic system, which may comprise: an oil-surfactant inlet which may comprise a filter and a carrier fluid channel, wherein said carrier fluid channel may further comprise a resistor; an inlet for an analyte which may comprise a filter and a carrier fluid channel, wherein said carrier fluid channel may further comprise a resistor; an inlet for mRNA capture microbeads and lysis reagent which may comprise a filter and a carrier fluid channel, wherein said carrier fluid channel further may comprise a resistor; said carrier fluid channels have a carrier fluid flowing therein at an adjustable or predetermined flow rate; wherein each said carrier fluid channels merge at a junction; and said junction being connected to a mixer, which contains an outlet for drops. Accordingly, an apparatus for creating a single-cell sequencing library via a microfluidic system microfluidic flow scheme for single-cell RNA-seq is envisioned. Two channels, one carrying cell suspensions, and the other carrying uniquely barcoded mRNA capture bead, lysis buffer and library preparation reagents meet at a junction and is immediately co-encapsulated in an inert carrier oil, at the rate of one cell and one bead per drop. In each drop, using the bead's barcode tagged oligonucleotides as cDNA template, each mRNA is tagged with a unique, cell-specific identifier. The invention also encompasses use of a Drop-Seq library of a mixture of mouse and human cells. The carrier fluid may be caused to flow through the outlet channel so that the surfactant in the carrier fluid coats the channel walls. The fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid. Activation of sample fluid reservoirs to produce regent droplets is based on the concept of dynamic reagent delivery (e.g., combinatorial barcoding) via an on demand capability. The on demand feature may be provided by one of a variety of technical capabilities for releasing delivery droplets to a primary droplet, as described herein. From this disclosure and herein cited documents and knowledge in the art, it is within the ambit of the skilled person to develop flow rates, channel lengths, and channel geometries; and establish droplets containing random or specified reagent combinations can be generated on demand and merged with the "reaction chamber" droplets containing the samples/cells/substrates of interest. By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012. Accordingly, in or as to the invention it is envisioned that there can be the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. The invention envisions a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Being able to dynamically track individual cells and droplet treatments/combinations during life cycle experiments, and having an ability to create a library of emulsion droplets on demand with the further capability of manipulating the droplets through the disclosed process(es) are advantageous. In the practice of the invention there can be dynamic tracking of the droplets and create a history of droplet deployment and application in a single cell based environment. Droplet generation and deployment is produced via a dynamic indexing strategy and in a controlled fashion in accordance with disclosed embodiments of the present invention. Microdroplets can be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays. A plurality of biological assays as well as biological synthesis are contemplated. Polymerase chain reactions (PCR) are contemplated (see, e.g., US Patent Publication No. 20120219947). Methods of the invention may be used for merging sample fluids for conducting any type of chemical reaction or any type of biological assay. There may be merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyperbranched rolling circle amplification. In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence. To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter. Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as U.S. Pat. No. RE41,780) and European publication number EP2047910 to Raindance Technologies Inc. The content of each of which is incorporated by reference herein in its entirety. The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In some instances, the first sample fluid will include some or all of the reagents necessary for the PCR whereas the second sample fluid will contain the balance of the reagents necessary for the PCR together with the detection probes. Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid. Once mixed droplets have been produced, the droplets are thermal cycled, resulting in amplification of the target nucleic acid in each droplet. Droplets may be flowed through a channel in a serpentine path between heating and cooling lines to amplify the nucleic acid in the droplet. The width and depth of the channel may be adjusted to set the residence time at each temperature, which may be controlled to anywhere between less than a second and minutes. The three temperature zones may be used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001). The three temperature zones can be controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device. In other aspects, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature. The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing. After amplification, droplets may be flowed to a detection module for detection of amplification products. The droplets may be individually analyzed and detected using any methods known in the art, such as detecting for the presence or amount of a reporter. Generally, a detection module is in communication with one or more detection apparatuses. Detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

Examples of assays are also ELISA assays (see, e.g., US Patent Publication No. 20100022414). The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay. Single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention.

Another aspect of the invention is the combination of the technologies described herein. For example, the use of a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read, as explained above. RNA-Seq profiling of single cells (e.g. single Th17 cells) may be performed on cells isolated in vivo (e.g. isolated directly from a subject/patient, preferably without further culture steps). RNA-Seq profiling of single cells may be performed on any number of cells, including tumor cells, associated infiltrating cells into a tumor, immune derived cells, microglia, astrocytes, CD4 cells, CD8 cells, most preferably Th17 cells. Computational analysis of the high-throughput single-cell RNA-Seq data. This allows, for example, to dissect the molecular basis of different functional cellular states. This also allows for selection of signature genes as described herein. Once selection of signature genes is performed, an optional further step is the validation of the signature genes using any number of technologies for knock-out or knock-in models. For example, as explained herein, mutations in cells and also mutated mice for use in or as to the invention can be by way of the CRISPR-Cas system or a Cas9-expressing eukaryotic cell or Cas-9 expressing eukaryote, such as a mouse.

Such a combination of technologies, e.g. in particular with direct isolation from the subject/patient, provides for more robust and more accurate data as compared to in vitro scenarious which cannot take into account the full in vivo system and networking. This combination, in several instances is thus more efficient, more specific, and faster. This combination provides for, for example, methods for identification of signature genes and validation methods of the same. Equally, screening platforms are provided for identification of effective therapeutics or diagnostics.

These and other technologies may be employed in or as to the practice of the instant invention.

Example 1: Identification of Novel Regulators of Th17 Cell Pathogenicity by Single Cell Genomics Upon immunological challenge, diverse immune cells collectively orchestrate an appropriate response. Extensive cellular heterogeneity exists even within specific immune cell subtypes classified as a single lineage, but its function and molecular underpinnings are rarely characterized at a genomic scale. Here, single-cell RNA-seq was use to investigate the molecular mechanisms governing heterogeneity and pathogenicity of murine Th17 cells isolated from the central nervous system (CNS) and lymph nodes (LN) at the peak of autoimmune encephalomyelitis (EAE) or polarized in vitro under either pathogenic or non-pathogenic differentiation conditions. Computational analysis reveals that Th17 cells span a spectrum of cellular states in vivo, including a self-renewal state in the LN, and Th1-like effector/memory states and a dysfunctional/senescent state in the CNS. Relating these states to in vitro differentiated Th17 cells, novel genes governing pathogenicity and disease susceptibility were discovered. Using knockout mice, the crucial role in Th17 cell pathogenicity of four novel genes was tested: Gpr65, Plzp, Toso and Cd5l. Th17 cellular heterogeneity thus plays an important role in defining the function of Th17 cells in autoimmunity and can be leveraged to identify targets for selective suppression of pathogenic Th17 cells while sparing non-pathogenic tissue-protective ones.

RNA-Seq profiling of single Th17 cells isolated in vivo and in vitro. The transcriptome of 1,029 Th17 cells (subsequently retaining a final set of 806 cells, below), either harvested in vivo or differentiated in vitro (FIG. 1A and Table S1) was profiled. For in vivo experiments, EAE was induced by myelin oligodendrocyte glycoprotein (MOG) immunization, CD3$^+$CD4$^+$IL-17A/GFP$^+$ cells were harvested from the draining LNs at the peak of disease and profiled immediately. For in vitro experiments, cells were collected during differentiation of CD4$^+$ naïve T cells under two polarizing conditions: TGF-β1+IL-6 and IL-1β+IL-6+ IL-23; while both lead to IL-17A-producing cells, only the latter induces EAE upon adoptive transfer of cell ensembles into wild type or RAG-1 −/− mice (Chung et al., 2009; Ghoreschi et al., 2010). At least two independent biological replicates were used for each in vivo and in vitro condition, and two technical replicates for two in vivo conditions. Single-cell mRNA SMART-Seq libraries were prepared using microfluidic chips (Fluidigm $C_1$) for single-cell capture, lysis, reverse transcription, and PCR amplification, followed by transposon-based library construction. Corresponding population controls (>50,000 cells for in vitro samples; ~2,000-20,000 cells for in vivo samples, as available) were also profiled, with at least two replicates for each condition.

The libraries were filtered by a set of quality metrics, removing 223 (~21%) of the 1,029 profiled cells, and controlled for quantitative confounding factors and batch effects (FIGS. S1A, B), ~7,000 appreciably expressed genes (fragments per kilobase of exon per million (FPKM)>10) in at least 20% of each sample's cells) were retained for in vitro experiments and ~4,000 for in vivo ones. To account for expressed transcripts that are not detected (false negatives) due to the limitations of single-cell RNA-Seq (Deng et al., 2014; Shalek et al., 2014), subsequent analysis downweighted the contribution of less reliably measured transcripts (Shalek et al., 2014) (FIG. S1C. Following these filters, expression profiles were tightly correlated between population replicates (FIG. 1C), and the average expression across all single cells correlated well with the matching bulk population profile (r~0.76-0.89; FIG. 1C, FIG. S1D, red bars, and Table S1). While the average expression of single cells correlated well with the bulk population, substantial differences were found in expression between individual cells in the same condition (r~0.3-0.8; FIG. 1D and Figure S1D, blue bars) comparable to previous observations in other immune cells (Shalek et al., 2014). High-throughput, high-resolution, flow RNA-fluorescence was applied in situ hybridization (RNA Flow-Fish), an amplification-free imaging technique (Lalmansingh et al., 2013) to validate the observed patterns of gene expression heterogeneity for nine representative genes (FIG. 1F, FIG. 6E), chosen to span a wide range of expression and variation levels at 48h under the TGF-β1+IL-6 in vitro polarization condition. These experiments reveal that although canonical Th17 transcripts (e.g., Rorc, Irf4, Baf) are expressed unimodally, other key immune transcripts (e.g., Il-17a, 11-2) can vary in their expression across Th17 cells and exhibit a bimodal distribution. The analysis of this variation can provide clues on the functional states of the Th17 cells that have been associated with different disease states or specificity to various pathogens.

A functional annotation of single cell heterogeneity shows that Th17 cells span a spectrum of states in vivo. To study the main sources of cellular variation in vivo and their functional ramifications, a principal component analysis (PCA, FIG. 2A) was used followed by a novel analysis for functional annotation of the PC space based on the single cell expression of gene signatures of previously characterized T cell states (FIG. 2B). Specifically, drawing from previous studies feature-specific gene signatures were assembled for various T-cell types and perturbation states, each consisting of a set of 'plus' and 'minus' genes that are highly and lowly expressed in each signature, respectively (FIG. 2B). For every cell-signature pair, a score reflecting the difference in the average expression of 'plus' is. 'minus' genes in that cell was computed, and then estimated whether each signature score significantly varied: either (1) across cells of the same source (either LN or CNS; using a one vs. all Gene Set Enrichment Analysis (GSEA); FDR<0.05 in at least 10% of cells); or (2) between the LN and the CNS cells (KS-test, FDR<$10^4$). For the signatures with significant variation in at least one test, the correlations of the respective single cell signature scores with the projection of cells to each of the first two principal components (PCs; FIG. 2B and Table S2 (Gaublomme 2015)) were computed, and selected correlations were plotted on a normalized PCA map (FIG. 2A, numbered open circles). To identify transcription factors that may orchestrate this heterogeneity, the single-cell RNA-seq data were combined with transcription factor target enrichment analysis (Yosef et al., 2013) to find factors whose targets are strongly enriched (Fisher exact test, p< $10^{-5}$) in genes that correlated with each PC (Pearson correlation, FDR<0.05; FIG. 2E, F, Table S3 (Gaublomme 2015)).

Based on the functional annotation, the first PC (PC1) positively correlates with a recently defined effector vs.

memory signature following viral infection (Crawford et al., 2014), and negatively correlates with an independent molecular signature characterizing memory T cells (Wherry et al., 2007) (FIG. 2A, number 4 and 7, respectively; Table S2 (Gaublomme 2015)). This suggests that cells with high positive PC1 scores adopt an effector phenotype, and those with negative PC1 scores obtain a memory profile, and at the extreme—a dysfunctional/senescent profile. The second PC (PC2) separates cells by their source of origin (CNS and LN, FIG. 2A) and correlates with a transition from a naïve-like self-renewal state (negatively correlated with PC2; $p<10^{-33}$, FIG. 2A, number 5: Table S2 (Gaublomme 2015)) with low cell cycle activity (negatively correlated with PC2, FDR<5%) to a Th1-like effector or memory effector state (positively correlated with PC2, FIG. 2, number 2 and 3, $p<10^{-19}$ and $p<10^{-23}$, respectively). Consistently, an MsigDB analysis of genes that highly correlate with the PCs (Pearson correlation, FDR<5%) shows strong association with immune response (PC1; $p<1.2\times10^{-27}$ and PC2; $p<1.2\times10^{-28}$, hypergeometric test) and cell cycle stage (PC1; $p<10^{-30}$).

A trajectory of progressing cell states from the LN to the CNS. To further explore the diversity of LN and CNS cells, five of the key signatures discovered by functional annotation were used to divide the PCA space into distinct subsets of cells (FIG. 2C, Table S2 (Gaublomme 2015)). To this end, a Voronoi diagram was computed that delineates regions that are most strongly associated with each of the five signatures. The resulting putative subpopulations exhibit a gradual progression from a self-renewing state to a pre-Th1 effector phenotype in the LN and CNS, to a Th1-like effector state and a Th1-like memory state in the CNS, and finally a dysfunctional/senescent state in the CNS, as detailed below.

First, self-renewing Th17 cells in the LN (FIG. 2C, green) are characterized by: (1) a signature of Wnt signaling ($p<10^{-7}$, KS, FIG. 2A, number 6, Table S4 (Gaublomme 2015)), Table 6, a known feature critical for self-renewal of hematopoietic stem cells and survival of thymocytes (Ioannidis et al., 2001; Reya et al., 2003), and supported by high expression of Tcf7 ($p<10^{-2}$, FIG. 2D, Table S4 (Gaublomme 2015)) Table 6, a key target of the Wnt pathway. Tcf7 is a key transcription factor regulating the stem cell-like state of Th17 cells (Muranski et al., 2011), whose expression is lost when T-cells acquire an effector phenotype (Gattinoni et al., 2009; Willinger et al., 2006); (2) high expression ($p<10^{-10}$, KS-test, see Table S4 (Gaublomme 2015), Table 6) of the known naïve state marker Cd62l (De Rosa et al., 2001) (FIG. 2D); and (3) up-regulation ($p<10^{-9}$) of Cd27, a pro-survival gene lacking in short-lived T cells (Dolfi et al., 2008; Hendriks et al., 2000: Hendriks et al., 2003: Snyder et al., 2008) (FIG. 2D). Transcription factors analysis (negative PC2, FIG. 2E, green) suggests that Etv6, Med12 and Zfx specifically drive this self-renewing population. While neither of them has been linked to Th17 self-renewal, each is associated with such functions in other cells: Med12 is essential for Wnt signaling and early mouse development (Rocha et al., 2010); Etv6, a known positive regulator of Th17 cell differentiation (Ciofani et al., 2012; Yosef et al., 2013), functions as an essential regulator of hematopoietic stem cell survival (Hock et al., 2004) and an initiator of self-renewal in pro-B cells (Tsuzuki and Seto, 2013); and Zfx is required for self renewal in embryonic and hematopoietic stem cells (Galan-Caridad et al., 2007; Harel et al., 2012), and of the tumorigenic, non-differentiated state in glioblastoma stem cells (Fang et al., 2014) and acute T-lymphoblastic and myeloid leukemia (Weisberg et al., 2014).

Second, cells from the LN and CNS adopt similar (overlapping) cell states only in the central state of PCA plot (FIG. 2C, pink), reflecting effector Th17 cells with a pre-Th1 phenotype. Compared to the self-renewing subpopulation, these effector Th17 cells (1) begin to express receptors for IFN (IFNAR-1, $p<10^{-3}$, KS, Table S4 (Gaublomme 2015), Table 6) and IL-18 (IL-18R1, $p<10^{-3}$, FIG. 2D), both of which mediate differentiation of Th1 cells (Esfandiari et al., 2001; Shinohara et al., 2008); and (2) induce the Th1 associated chemokine receptor Cxcr6 ($p<10^{-3}$, KS, FIG. 2D) (Aust et al., 2005; Latta et al., 2007), and Ccr2 ($p\leq10^{-6}$, KS, FIG. 2D), associated with recruitment to the CNS in EAE/MS (Mahad and Ransohoff, 2003). Since these cells begin to express receptors that make them responsive to both IFN-γ and IL-18 and poised for recruitment to the CNS, they may therefore be the precursors that lead to the generation of Th17/Th1-like effector T cells observed in the CNS.

IL-17a/GFP+ sorted cells acquire a Th17/Th1-like effector phenotype in the CNS (FIG. 2C, yellow), as indicated by up-regulation ($p<10^{-3}$, KS, Table S4 (Gaublomme 2015), Table 6) of: (1) Ifn-γ, consistent with a Th1 phenotype (FIG. 2D); (2) Rankl (FIG. 2D), a marker of Th1 and IL-23 induced Th17 cells (Nakae et al., 2007), especially pathogenic Th17 cells in arthritis (Komatsu et al., 2014); and (3) cell cycle genes (e.g., Geminin (Codarri et al., 2011), FIG. 2D). Surprisingly, the Th1-like cells in the CNS (except dysfunctional/senescent state; FIG. 2C,D grey) also induce Ccr8 (FIG. 7A, bottom), previously described as a cell marker of Th2 cells (Zingoni et al., 1998), but not of Th17/Th1 cells (Annunziato et al., 2007). Mice deficient for Ccr8 exhibit later onset and milder signs of EAE (Ghosh et al., 2006; Hamann et al., 2008). Transcription factor analysis shows that these effector cells are associated with both canonical Th17 factors (Stat3, Irf4 and Hif1a) and Th1-associated factors, including Rel and Stat4 (Kaplan et al., 1996; Nishikomori et al., 2002; Thierfelder et al., 1996) (FIG. 2E, red), which are associated with EAE (Hilliard et al., 2002; Mo et al., 2008) or with autoimmune disease in humans (Gilmore and Gerondakis, 2011). These sorted IL-17A/GFP+ cells could either be a stable population of double producers or reflect Th17 plasticity into the Th1 lineage, as Th17 cells transition into a Th1 state.

Next, Th1-like memory cells detected in the CNS (FIG. 2C, light blue) correlate highly with both a memory phenotype (negative PC1) and a Th1-like phenotype (positive PC2). These cells are associated with an effector memory signature ($p<10^{-5}$, KS-test compared with all other subpopulations, see Table S4 (Gaublomme 2015), Table 6), and up-regulate ($p<10^{-5}$, KS) memory signature genes (e.g., Nur77; FIG. 2D, Samsn1, Il2ra, Il2rb, Tigit, Ifingr1 and 2), and inflammatory genes (Gm-csf and Gpr65; FIG. 2D). Il-Ir2 is a decoy receptor in the IL-1 pathway involved in Th17 pathogenicity (Sutton et al., 2006), the cytokine Gm-csf (FIG. 2D) is essential for Th17 encephalitogenicity (El-Behi et al., 2011) and neuroinflammation (Codarri et al., 2011). Nur77 (Nr4a1) (FIG. 2D), a transcriptional repressor of IL-2 (Harant and Lindley, 2004), is strongly up-regulated, to maintain cells in a Th17 state despite acquiring a Th1 factor (Sester et al., 2008). Note that while IL-2 is a growth factor for Th1 cells, IL-2 affects Th17 differentiation and stability. Transcription factor analysis (FIG. 2F) suggests that this cell state is in part driven by Egr1, a regulator of Tbet expression (Shin et al., 2009) that may help route Th1-like cells into the memory pool; Bcl6, a repressor of lymphocyte differentiation, inflammation, and cell cycle genes, essential for CD4 T-cell memory generation (Ichii et al., 2007); and Hif1a, crucial for controlling human Th17 cells to become long-lived effector memory cells (Kryczek et al., 2011) and particularly associated with cells that correlate highly with the memory and Th1 signatures (negative PC1, positive PC2).

Finally, Th17 cells acquire a dysfunctional, senescent-like state in the CNS (negative PC1 and PC2 scores; FIG. 2C, moss grey), with (1) down-regulation ($p<10^{-3}$) of genes critical to T-cell activation, including Cd3 (FIG. 2D) (Chai and Lechler, 1997; Lamb et al., 1987; Trimble et al., 2000), Cd28 (Trimble et al., 2000; Wells et al., 2001), Lat (FIG. 2D) (Hundt et al., 2006), Lck (Isakov and Biesinger, 2000; Nika et al., 2010), and Cd2 (Bachmann et al., 1999; Lamb et al., 1987) (Table S4 (Gaublomme 2015), Table 6); (2) up-regulation of genes associated with senescence, such as Ccrl2 (up regulated in exhausted CD8+ T-cells (Wherry et al., 2007)), Marcks (FIG. 2D) (inducer of senescence (Jarboe et al., 2012)), and Cd74 (a receptor to Mif in the Hif-Mif senescence pathway (Maity and Koumenis, 2006; Salminen and Kaarniranta, 2011; Welford et al., 2006)); and (3) association with signatures for CD28 costimulation ($p<10^{-11}$, GSEA, Table S2 (Gaublomme 2015)) and PD-1 signaling ($p<10^{-10}$, GSEA, Table S2 (Gaublomme 2015)). Among the possible regulators of this cell state is mir-144, an inhibitor of TNF-α and IFN-γ production and of T-cell proliferation (Liu et al., 2011), whose targets are enriched ($p<10^4$, hypergeometric test) in these cells.

In vitro derived cells span a broad spectrum of pathogenicity states with key similarities and distinctions from in vivo isolated cells. The analysis of in vivo Th17 cells harvested from mice undergoing EAE identified a progressive trajectory of at least five states, from self-renewing cells in the LN, through effector LN cells, effector Th1-like CNS cells, memory cells, and senescent ones. Given the limited number of cells available from in vivo samples, obtained as a mixed "snapshot" of an asynchronous process, it is difficult to determine their distinct pathogenic potential and underlying regulatory mechanisms. A complementary strategy is offered by profiling in vitro differentiated cells, where one can assess the heterogeneity of Th17 cells at the same condition (time point and cytokine stimulation). Furthermore, comparing in vivo and in vitro profiles can help uncover to what extent the in vitro differentiation conditions faithfully mirror in vivo states.

Single-cell RNA-seq profiles of 414 individual Th17 cells derived under non-pathogenic conditions (TGF-β1+IL-6, unsorted: 136 cells from 2 biological replicates, TGF-β1+IL-6, sorted for IL-17A/GFP+: 159 cells from 3 biological replicates) and pathogenic conditions (Il-1β+IL-6+IL-23, sorted for IL-17a/GFP+: 147 cells from 2 biological replicates) (FIG. 3A) were then analyzed.

Using the functional annotation approach (FIG. 2B) to annotate the cells with immune cell signatures, it was found that in vitro differentiated Th17 cells vary strongly in a key signature of pathogenicity and tolerance (Lee et al., 2012), reflecting the conditions in which they were derived (FIG. 3A, number 1, and 3D). High pathogenicity scores were associated with IL-17A/GFP+ sorted cells polarized under a pathogenic condition (FIG. 3A,D red, number 1, PC1), whereas IL-17A/GFP+ sorted cells from non-pathogenic conditions correlate highly with the expression of regulatory cytokines, such as IL-10, and their targets, which are barely detected in the pathogenic cells (FIG. 3E). Finally, a signature obtained from the T-cells harvested from IL23R knockout mice and differentiated under the IL-1β+IL-6+IL23 condition correlates highly with the cells that adopt a more regulatory profile, further confirming a crucial role of the IL-23 pathway in inducing a pathogenic phenotype in Th17 cells (FIG. 3A, number 4, positive PC1).

Importantly, there is a clear zone of overlap in cell states between the pathogenic and non-pathogenic conditions, with pathogenic-like cells present (in a small proportion) in populations differentiated in non-pathogenic conditions (FIG. 3A, red oval shading). In particular, cells polarized under the non-pathogenic (TGF-β1+IL-6) condition that were not specifically sorted to be IL-17A/GFP+ span the broadest pathogenicity spectrum: from cells resembling the least pathogenic cells in the IL-17A/GFP+ TGF-β1+LL-6 condition to those resembling more pathogenic cells in the IL-17A/GFP+IL-1β+IL-6+IL23 condition (FIG. 3D, open black circles). At one end of this spectrum Th17 cells were observed with high expression of regulatory transcripts such as IL-9, IL-16, Foxp1 and Podoplanin Peters et al. 2014) (FIG. 7B, left), and at the other end, Th17 cells were observed that express high levels of pro-inflammatory transcripts such as IL-22, IL23r, Cxcr3 and Gm-csf (FIG. 7B, right).

Figure 3B:
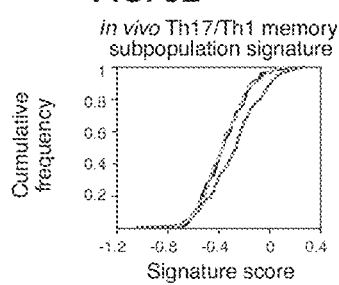
Figure 3C:
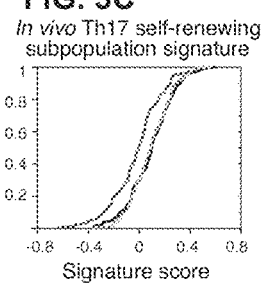
Figure 3D:
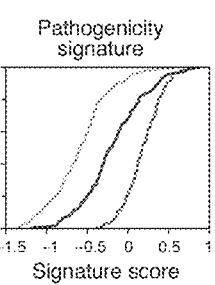
Figure 3E:
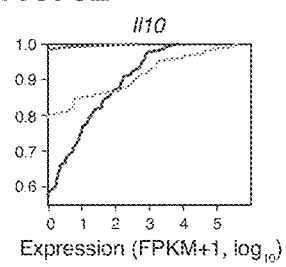

To relate the in vitro differentiated cells to the in vivo observed behavior the in vitro cells (FIG. 2B) were scored for immune related genes that characterize the in vivo identified subpopulations (FIG. 2C) (FIG. 3B,C). Cells derived in the non-pathogenic conditions scored more highly for the self-renewing signature ($p<1e-9$ KS test; Table S2 (Gaublomme 2015) and FIG. 3A, number 6, and 3C), whereas those derived in pathogenic conditions resembled more the Th-17/Th-1 like memory phenotype identified in the CNS ($p<1e-7$ KS test; Table S2 (Gaublomme 2015) and FIG. 3B).

(Co-variation with pro-inflammatory and regulatory modules in Th17 cells highlights novel candidate regulators. The cellular heterogeneity within a single population of in vitro differentiated cells was then leveraged to identify regulators that might selectively influence pathogenic vs. nonpathogenic states of Th17 cells. Focusing on the (unsorted) cells from the TGF-β1+IL-6 in vitro differentiation condition, in which the broadest spectrum of cells spanning from pathogenic to nonpathogenic-like profiles was observed, first transcriptome-wide gene expression distributions across the population were analyzed. About 35% (2,252) of the detected genes are expressed in >90% of the cells (FIG. 4A) with a unimodal distribution: these include housekeeping genes ($p<10^{-10}$, hypergeometric test, FIGS. 6F & 6G), the Th17 signature cytokine IL-17f and transcription factors (e.g., Batf Stat3 and Hif1a) that are essential for Th17 differentiation. On the other hand, bimodally expressed genes (FIG. 4A, bottom)—with high expression in at least 20% of the cells and much lower (often undetectable) levels in the rest—include cytokines like Il-17a and Il-10 and other pro-inflammatory (e.g., Il-21, Ccl20) and regulatory cytokines or their receptors (Il-24, Il-27ra, FIG. 4A). This suggests that variation in expression across Th17 cells may be related more to their (varying) pathogenicity state than to their (more uniform) differentiation state. Furthermore, while almost all cells express transcripts encoding the pioneer and master transcription factors for the Th17 lineage (Rorc, Irf4, Bat), a minority (<30%) also express transcripts encoding one or more of the transcription factors and cytokines that characterize other T-cell lineages (e.g., Stat4 for Th1 cells, and Ccr4 for Th2 cells). This may suggest the presence of "hybrid" double-positive cells, consistent with reports on plasticity in T-cell differentiation (Antebi et al., 2013), and/or reflect the previous model of duality in the Th17 transcriptional network (Yosef et al., 2013). Finally, the expression of many key immune genes varies more than the rest of the genome, even with the same mean expression level (FIG. 6H), or when only considering the expressing cells (FIG. 6I), implying a greater degree of diversity in immune gene regulation. While such patterns may be biologically important, they must be interpreted with caution. First, some (e.g., Il-17a, Il-24 and Ccl20), but not all (e.g., Il-9), of the transcripts with bi-modal patterns are also lowly expressed (on average) and thus may not be detected as reliably (Shalek et al., 2014). Second, transcription bursts coupled with instability of transcripts may lead to 'random' fluctuations in gene expression levels at any given cell.

Figure 4A:
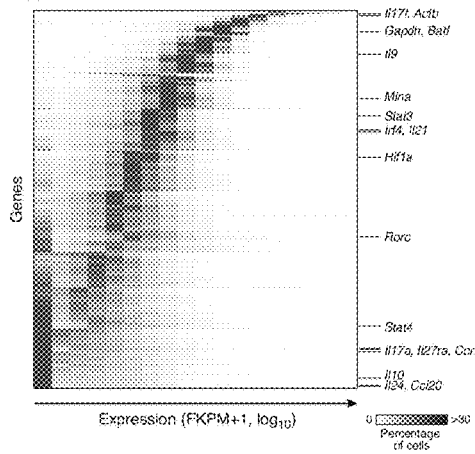
FIG. 4A-4E. Modules of genes that co-vary with pro-inflammatory and regulatory genes across single cells.
Figure 4B:
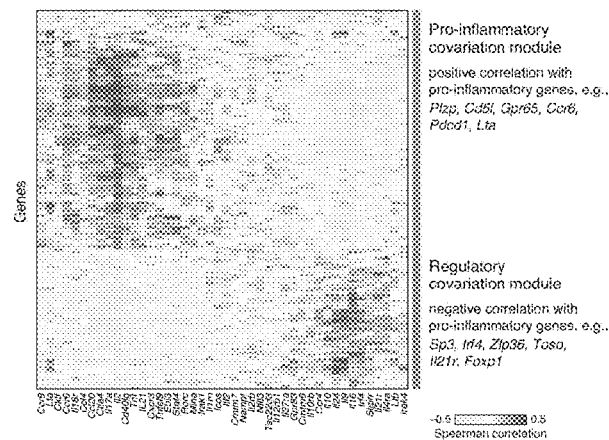

To overcome these challenges and to identify candidate regulators of pathogenicity, co-variation between transcripts across cells (FIG. 4B) was analyzed. It was reasoned that if transcript variation reflects distinct physiological cell states, entire gene modules should robustly co-vary across the cells. Furthermore, transcription factors and signaling molecules that are members of such modules may highlight new putative regulators of these modules and functional states. Focusing on significant co-variation (Spearman correlation; FDR<0.05) between each bimodally expressed transcript (expressed by less than 90% of the cells; FIG. 4B, rows) and a curated set of bimodally expressed immune response genes (cytokines, cytokine receptors, T helper cell specific signatures, FIG. 4B, columns), two key transcript modules were found: a pro-inflammatory module (FIG. 4B, orange) of transcripts that co-vary with known Th17 cytokines, such as Il-17a and Ccl-20, and a regulatory module (FIG. 4B, green) of transcripts that co-vary with known regulatory genes, such as Il-10, Il-24, and Il-9. Using these modules as signatures to annotate the original in vitro cell states (FIGS. 3A and 4C), the pro-inflammatory module (FIG. 4C, number 1) and key inflammatory genes (FIG. 4D, bottom) are correlated with the most pathogenic cells (PC1, negative correlation) and the regulatory module (FIG. 4C), and key members (FIG. 4D top), are correlated with the least pathogenic (PC1, positive correlation).

Figure 4C:
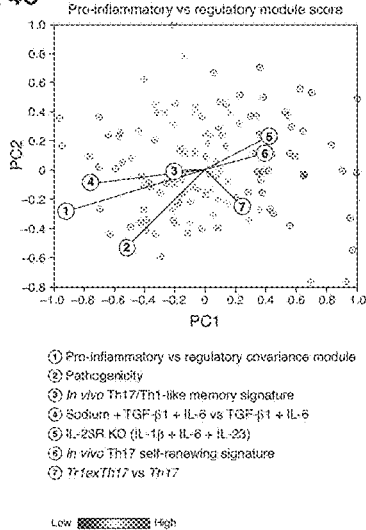
Figure 4D:
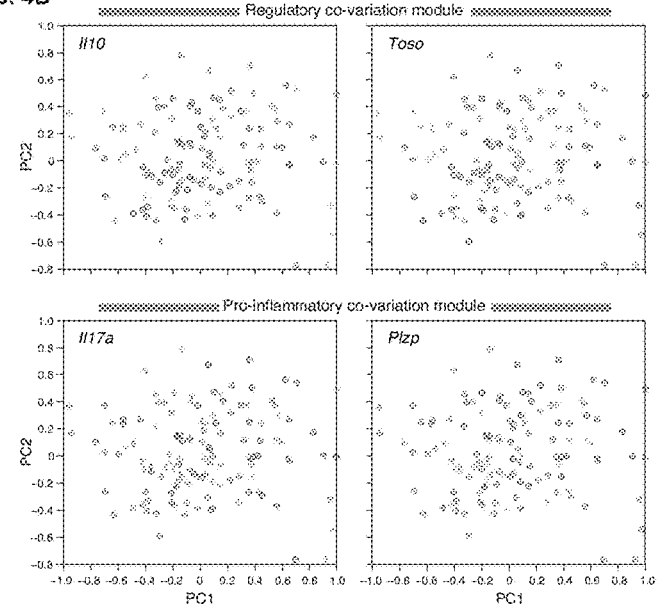
Figure 4E:
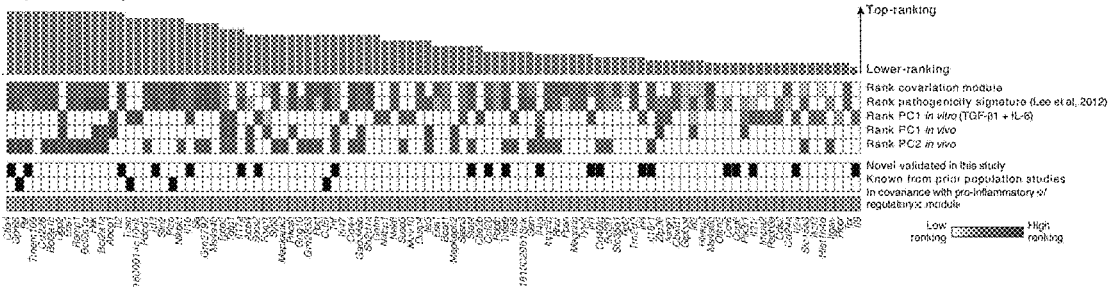
Figure 6F:
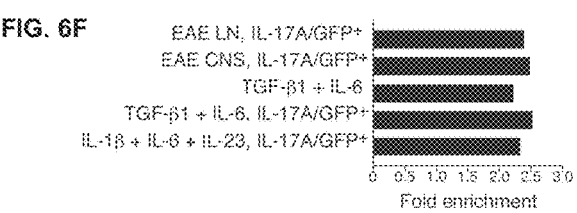
Figure 6G:
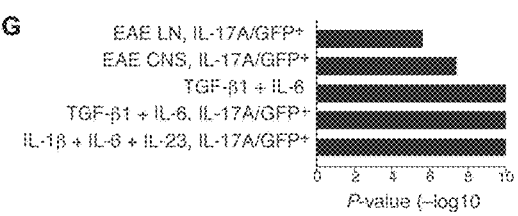
Figure 6H:
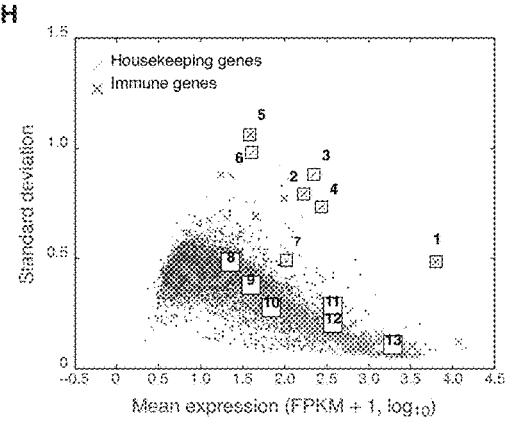
Figure 6I:
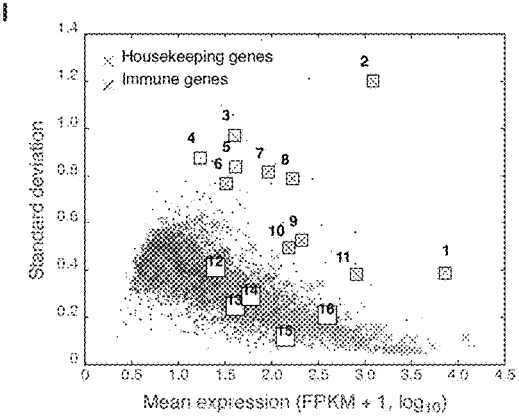
Figure 8A:
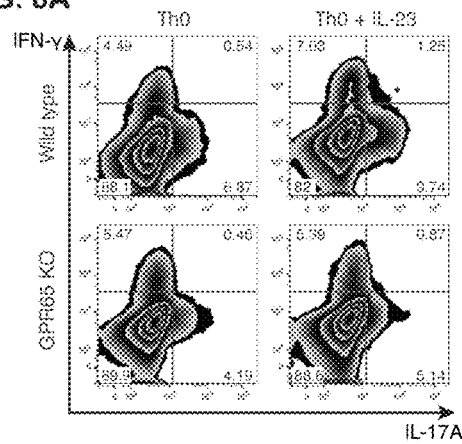
Figure 8B:
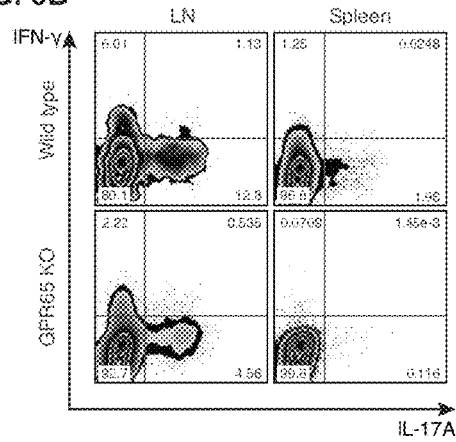
Figure 8C:
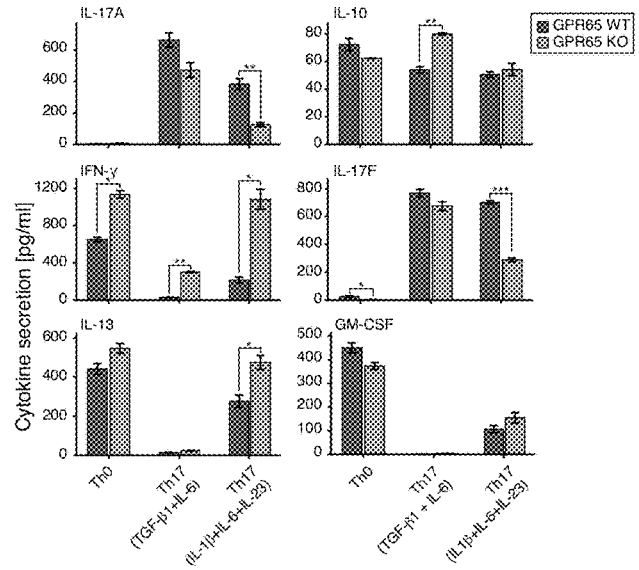
Figure 8D:
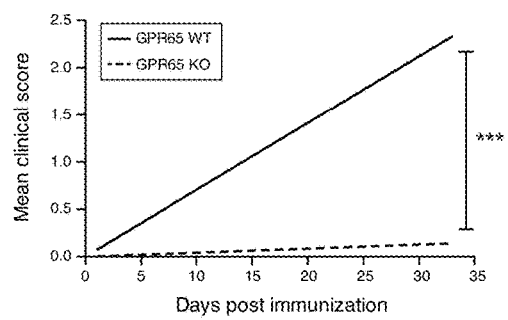

Co-variation of genes with each module highlights many novel putative regulators, many not detected by previous, population-level, approaches (Ciofani et al., 2012; Yosef et al., 2013). To select the most compelling candidate genes in the two modules (FIG. 4b, rows) for follow-up functional studies, a computational ranking scheme was developed that considers each gene's correlation with the pro-inflammatory or regulatory modules, their loading on the first in vitro PC marking for pathogenic potential, and their role in the EAE context in vivo (FIG. 4E, Table 2 herein). While the genes from our co-variation matrix (rows, FIG. 4B) tend to be highly ranked compared to all genes also in bulk-population data ($p<10^{-10}$, Wilcoxon Rank Sum test) or rankings (Ciofani et al., 2012), they do not necessarily stand out in bulk population rankings (FIG. 15), highlighting the distinct signal from single-cell profiles. Based on this ranking and availability of knockout mice, three genes were chosen for functional follow up: Plzp, Cd51 and Gpr65 that are co-expressed with the pro-inflammatory module, and Toso, co-expressed with the regulatory module. None of these genes was previously implicated in differentiation or effector function of Th17 cells.

GPR65 promotes Th17 cell pathogenicity and is essential for EAE. GPR65, a glycosphingolipid receptor, is co-expressed with the pro-inflammatory module (FIG. 4B), suggesting that it might have a role in promoting pathogenicity. GPR65 is also highly expressed in the in vivo Th17 cells harvested from the CNS that attain a Th1-like effector/memory phenotype (FIG. 2D). Importantly, genetic variants in the GPR65 locus are associated with multiple sclerosis (International Multiple Sclerosis Genetics et al., 2011), ankylosing spondylitis (International Genetics of Ankylosing Spondylitis et al., 2013), inflammatory bowel disease (Jostins et al., 2012), and Crohn's disease (Franke et al., 2010).

The role of GPR65 was tested in Th17 differentiation in vitro and in the development of autoimmunity in vivo. Naïve T-cells isolated from Gpr65−/− mice in vitro were differentiated with TGF-β1+IL-6 (non-pathogenic condition) or with IL-1β+IL-6+IL-23 (pathogenic condition) for 96 hours. In both cases, there was a ~40/a reduction of IL-17a positive cells in Gpr65$^{-/-}$ cells compared to their wild type (WT) controls as measured by intracellular cytokine staining (ICC) (FIG. 5A). Memory cells from Gpr65$^{-/-}$ mice that were reactivated with IL-23 also showed a ~45% reduction in IL-17a-positive cells when compared to wild type controls (FIG. S3A). Consistently, an enzyme-linked immunosorbent assay (ELISA) of the supernatant obtained from the activated Th17 culture showed a reduced secretion of IL-17a ($p<0.01$) and IL-17f ($p<10^{-4}$) (FIG. 5B) and increased IL-10 secretion ($p<0.01$, FIG. S3A) under pathogenic (IL-1β+IL-6+L-23) Th17 differentiation conditions in the knockout mice.

To further validate the effect of GPR65 on Th17 function, RNA-seq profiles were measured of a bulk population of Gpr65$^{-/-}$ Th17 cells, differentiated in vitro under both non-pathogenic (TGF-β1+IL-6) and pathogenic (IL-1β+IL-6+IL-23) conditions for 96 hours. Supporting a role for GPR65 as a driver of pathogenicity of Th17 cells, it was found that genes up-regulated in Gpr65$^{-/-}$ cells (compared to WT) are most strongly enriched ($P<10^{-28}$, hypergeometric test, FIG. 5E) for the genes characterizing the more regulatory cells under TGF-β1+IL-6 (positive PC1, FIG. 4C, Table S6 (Gaublomme 2015), Table 7).

To determine the effect of loss of GPR65 on tissue inflammation and autoimmune disease in vivo, RAG-1$^{-/-}$ mice were reconstituted with naïve CD4+ T-cells from wild type or Gpr65$^{-/-}$, then induced EAE with myelin oligodendrocytes glycoprotein peptide emulsified with complete Freund's adjuvant (MOG35-55/CFA). It was found that in the absence of GPR65-expressing T cells, mice are protected from EAE (FIG. 5D) and far fewer IL-17A and IFN-γ positive cells are recovered from the LN and spleen compared to wild-type controls transferred with wild-type cells (FIG. S3B). Furthermore, in vitro restimulation with MOG$_{35-55}$ of the spleen and LN cells from the immunized mice showed that loss of GPR65 resulted in dramatic reduction of MOG-specific IL-17A or IFN-7 positive cells compared to their wild-type controls (FIG. 5C), suggesting that GPR65 regulates the generation of encephalitogenic T cells in vivo. Taken together, the data strongly validates that GPR65 is a positive regulator of the pathogenic Th17 phenotype, and its loss results in protection from EAE.

TOSO is implicated in Th17-mediated induction of EAE TOSO (FAIM3) is an immune cell specific surface molecule, is known to negatively regulate Fas-mediated apoptosis (Hitoshi et al., 1998; Nguyen et al., 2011; Song and Jacob, 2005), and is co-expressed with the regulatory module in Th17 cells. Although its covariance with the regulatory module (FIG. 4B) may naïvely suggest that it positively regulates the regulatory module. Toso knockout mice were recently reported to be resistant to EAE (Lang et al., 2013). This may be consistent with a hypothesis that Toso is a negative regulator of the non-pathogenic state, co-expressed with the regulatory module, as has been often observed for negative regulators and their targets in other systems (Amit et al., 2007; Segal et al., 2003) To test this hypothesis, in vitro differentiation and MOG recall assays on TOSO$^{-/-}$ cells were performed. Differentiation of TOSO$^{-/-}$ cells showed a defect in the production of pro-inflammatory cytokine IL-17A for both differentiation conditions (FIG. 5F), which was confirmed by ELISA (FIG. 5G). Moreover, memory cells stimulated with IL-23 show a lack of IL-17A production (FIG. S4A). Consistently, in a MOG recall assay, CD3$^+$CD4$^+$ Toso$^{-/-}$ T cells showed no production of IL-17a across a range of MOG$_{35-55}$ concentrations (FIG. 5H). This supports a role for TOSO as a promoter of pathogenicity.

To further explore this, RNA-seq analysis of Toso$^{-/-}$ Th17 cell populations, differentiated in vitro under non-pathogenic conditions for 96 hours was performed. Loss of TOSO results in suppression of the key regulatory genes (e.g., IL-24 (FC=0.08), IL-9 (FC=0.33) and Procr (FC=0.41) (Table S6 (Gaublomme 2015), Table 7), consistent with the reduction of IL-10 production as measured by ELISA (FIG. S4C), and a reduced number of FOXP3+ cells under Treg differentiation conditions (FIG. S4B). On the other hand, in pathogenic conditions, IL-17a (FC=0.21) is down regulated in the absence of TOSO. Enrichment analysis with respect to PC1 of the non-pathogenic differentiation condition suggests that TOSO knockout cells, rather than up-regulating regulatory genes, down-regulate genes associated with a more pro-inflammatory cell phenotype (FIG. 5E). Taken together, the data suggest that TOSO plays a critical role as a positive regulator of Th17-cell mediated pathogenicity.

MOG-stimulated Plzp$^{-/-}$ cells have a defect in generating pathogenic Th17 cells. PLZP (ROG), a transcription factor, is a known repressor of (the Th2 master regulator) GATA3 (Miaw et al., 2000), and regulates cytokine expression (Miaw et al., 2000) in T-helper cells. Since Plzp is co-expressed with the pro-inflammatory module, it was hypothesized that it may regulate pathogenicity in Th17 cells.

While in vitro differentiated Plzp$^{-/-}$ cells produced IL-17A at comparable levels to wild-type (FIG. S5A), a MOG-driven recall assay revealed that Plzp$^{-/-}$ cells do have a defect in IL-17A production that becomes apparent with increasing MOG concentration during restimulation (FIG. 5I). Furthermore, Plzp$^{-/-}$ cells also produced less IL-17A than wild-type cells when reactivated in the presence of IL-23, which acts to expand previously in vivo generated Th17 cells (FIG. S5B). Finally, Plzp$^{-/-}$ T cells secreted less IL-17A, IL-17F (FIG. 5J), IFN-γ, IL-13 and GM-CSF (FIG. S5C). These observations suggest that PLZP regulates the expression of a wider range of inflammatory cytokines. Based on RNA-Seq profiles, at 48 hours into the non-pathogenic differentiation of Plzp$^{-/-}$ cells, Irf1 (FC=5.2), Il-9 (FC=1.8) and other transcripts of the regulatory module are up regulated compared to WT (Table S6 (Gaublomme 2015), Table 7), whereas transcripts from the pro-inflammatory module, such as Ccl-20 (FC=0.38), if (FC=0.10) and Il-17a (FC=0.42), are repressed. A similar pattern is observed with respect to PC1, where genes characterizing the more pro-inflammatory cells are strongly enriched among the down-regulated genes in Plzp$^{-/-}$ T cells (FIG. 5E).

DISCUSSION: Genome-wide analysis of single-cell RNA expression profiles opens up a new vista for characterizing cellular heterogeneity in ensembles of cells, previously studied as a population. By profiling individual Th17 cells from the LN and CNS at the peak of EAE, it was found that Th17 cells adopt a spectrum of cellular states, ranging from cells with a self-renewing gene signature, to pro-inflammatory Th1-like effector or memory-like cells, to a dysfunctional/senescent phenotype. These findings shed light on the controversy in the field on whether Th17 cells are short-lived, terminally differentiated, effector cells (Pepper et al., 2010) or long-lived self-renewing T cells (Muranski et al., 2011). The analysis also shows that Th17 cells present in the lymph node and CNS generally appear to have different transcriptional profiles and that the only group of Th17 cells that transcriptionally overlap are those that attain a pre-Th1-like state with acquisition of cytokine receptors (like IL-18R) that push Th17 cells into a Th1 phenotype. This fits well with the data that most Th17 cells begin to co-express Th1 genes in the CNS and become highly pathogenic.

The Th1-like phenotype of Th17 cells observed in the CNS might facilitate memory cell formation, as the entry of Th1 cells into the memory pool is well established (Harrington et al., 2008; Sallusto et al., 1999). It is unclear if cells that adopt a Th1 phenotype are stable 'double producers' or if they show plasticity towards a Th1 fate. IL-23, which induces a pathogenic phenotype in Th17 cells has been shown to induce IFN-g in Th17 cells. Consistent with this data, IL-23R-deficient mice have lower frequencies of double producers (McGeachy et al., 2009) and chronic exposure of Th17 cells to IL-23 induces IFN-g production from Th17 cells. Additionally, a conversion from a Th17 to a Th1-like phenotype is also documented in other disease models and these are considered to be the most pathogenic T cells (Bending et al., 2009; Lee et al., 2009; Muranski et al., 2011; Palmer and Weaver, 2010; Wei et al., 2009b).

Despite being differentiated under the same culture conditions, in vitro differentiated Th17 cells also exhibit great cellular diversity, with a pathogenic, pro-inflammatory state on the one end of the spectrum and an immunosuppressive, regulatory state on the other end. A comparative analysis of in vivo and in vitro derived cells with respect to immune-related genes reveals that in vitro polarization towards a pathogenic Th17 phenotype (with IL-1β+IL-6+IL-23) produces cells that resemble more the Th17/Th1 memory cells in the CNS found during EAE (FIG. 3A).

Single cell RNA-seq further showed that pro-inflammatory genes that render Th17 cells pathogenic and regulatory genes that render Th17 cell nonpathogenic are expressed as modules in groups of Th17 cells. This allowed for dissection of factors that relate to this specific facet of Th17 cell functionality, rather than their general differentiation. Strong correlation (either positive or negative) between two genes suggests that their biological function may be linked. In this study, strong co-variation with key Th17 genes allowed us to recover many known regulators, but also to identify many promising novel candidates that were coexpressed with either a proinflammatory or a regulatory module in Th17 cells. For example, Gpr65 positively correlated with the in vitro derived pro-inflammatory gene module. Consistently, Gpr65$^{-/-}$ CD4 T cells reconstituted to Rag1 mice were incapable of inducing EAE and had compromised IL-17A production. There are many genes similarly highlighted by this analysis, including Gem, Cst7, and Rgs2, all of which significantly correlate with the in vitro derived pro-inflammatory gene module and are highly expressed in the in vivo Th17/Th1-like memory subpopulation the are present in the CNS during peak inflammation. Foxp1, on the other hand, one of the genes negatively correlated with the pro-inflammatory module, was lowly expressed in the inflammatory Th17/Th1-like subpopulations in vivo, but was highly expressed in the LN-derived Th17 self-renewing subpopulation (p<10$^{-7}$, KS test; Table S4 (Gaublomme 2015), Table 6). In line with this finding, in T follicular helper cells, Foxp1 has very recently been shown to directly and negatively regulate IL-21 (Wang et al., 2014), a driver of Th17 generation (Korn et al., 2007; Nurieva et al., 2007; Zhou et al., 2007), and to dampen the expression of the co-stimulatory molecule ICOS and its downstream signaling at the early stages of T-cell activation (Wang et al., 2014). Further functional studies with Foxp1 knockout mice in the context of EAE could elucidate its potential role in regulating Th17 cell differentiation and development of autoimmune tissue inflammation.

Importantly, it should be noted that the co-variation of a gene with the pro-inflammatory or regulatory module does not necessarily indicate a pro-inflammatory or regulatory function to this gene. For example, one of the follow-up genes, Toso, co-varies with the regulatory module, but its absence protects mice from EAE (Brenner et al., 2014) and compromises IL-17A production, suggesting Toso does not serve as a regulatory factor. This is consistent with previous studies—from yeast (Segal et al 2003) to human (Amit et al 2007), showing how regulators with opposite, antagonistic functions, are co-regulated.

Examining the single-cell RNA-seq data together with ChIP data reveals transcription factors that regulate various cellular states observed in the study. For example, Zfx was identified as a strong candidate regulator of the self-renewing state of Th17 cells in the LN, because its targets are strongly enriched in this subpopulation, it is a known regulator of self-renewal in stem cells (Cellot and Sauvageau, 2007; Galan-Caridad et al., 2007; Harel et al., 2012), and it prevents differentiation in leukemias (Weisberg et al., 2014). In contrast, for the pathogenic effector and memory cells observed in the CNS during EAE, a prominent role is assigned to known Th17/Th1 transcription factors such as Hif1a, Fosl2, Stat14 and Rel, and it is specified in which subpopulations their regulatory mechanisms contribute to disease. As such, this study elaborates on Th17 pathogenicity beyond differentiation and development. This data suggests that processes such as self-renewal, observed in the lymph node, may provide a pool of cells that are precursors for differentiating Th17 cells to effector/memory formation in the CNS that may contribute to Th17 pathogenicity in EAE. These cellular functional states enable us to map the contribution of novel and known genes to each of these processes during Th17 differentiation and function. Whereas population-based expression profiling has enabled identification of cytokines and transcription factors that set the differentiation states of Th17 cells, using single cell RNA-seq new granularity is provided in the transcriptome of a rather homogenous population of T cells. Many of the novel regulators that identified by single cell RNA-seq are regulating pathogenic vs. nonpathogenic functional states in Th17 cells. These novel regulators will allow the manipulation of pathogenic Th17 cells without affecting nonpathogenic Th17 cells that may be critical for tissue homeostasis and for maintaining barrier functions.

Figure 16A:
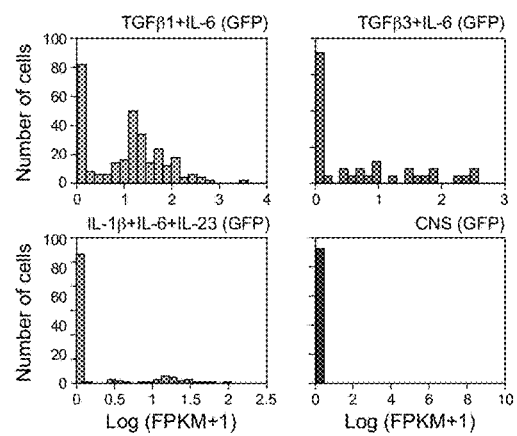
Figure 16B:
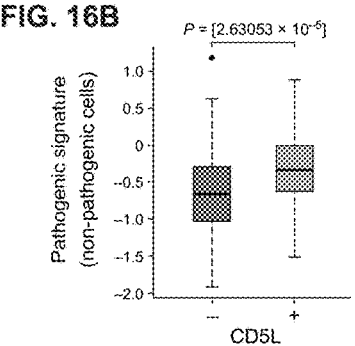
Figure 16C:
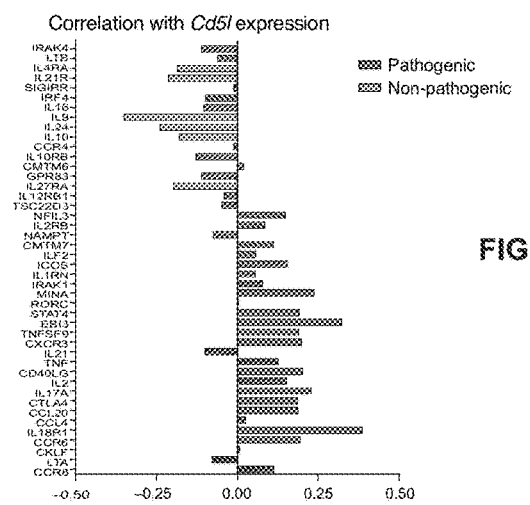

Single-cell RNA-seq identifies CD5L as a candidate regulator of pathogenicity. Cd5l is one of the high-ranking genes by single-cell analysis of potential regulators, exhibiting two surprising features: although Cd5l is expressed in Th17 cells derived under non-pathogenic conditions (FIG. 16A), in these non-pathogenic cells, Cd5l positively correlates with the first PC of in-vitro derived cells and co-varies with other genes in the pro-inflammatory module (FIG. 19A, B, C). In addition, Cd5l positively correlates with the cell pathogenicity score (FIG. 16B, C). Comparing Cd5l expression at the single-cell level in Th17 cells (sorted IL-17.GFP+) derived in vitro showed ~80% of Th17 cells derived with IL-1β+IL-6+IL-23 lacked Cd5l expression, whereas Th17 cells differentiated with TGF-β1+IL-6 predominantly expressed Cd5l (FIG. 16A). Neither Th17 cells differentiated under an alternative pathogenic condition (TGF-β3+IL-6) nor encephalitogenic Th17 cells sorted from the CNS of mice undergoing active EAE expressed Cd5l at the single-cell level (FIG. 16A). However, Cd5l expressed in nonpathogenic Th17 cells (unsorted single-cell analysis, FIG. 19A) correlates with the first PC and co-varies with the pro-inflammatory module (FIG. 19B) that is indicative of the pathogenic signature (FIG. 19C) as previously defined (Lee et al., 2012). Furthermore, Cd5l correlates with the defining signature of the pro-inflammatory module, and negatively correlates with that of the regulatory module (FIG. 16C). Finally, it is among the top 8 genes in the single cell based pro-inflammatory module whose expression most strongly correlates with the previously defined pathogenic gene signature (FIG. 16B, p=2.63 10^-5). CD5L is a member of the scavenger receptor cysteine rich superfamily (Sarrias et al., 2004). It is expressed in macrophages and can bind cytosolic fatty acid synthase in adipocytes following endocytosis (Miyazaki et al., 1999). CD5L is also a receptor for pathogen associated molecular patterns (PAMPs), and may regulate innate immune responses (Martinez et al., 2014). However, its expression has not been reported in T cells, and its role in T-cell function has not been identified.

CD5L expression is associated with non-pathogenic Th17 cells in vitro and in vivo. Applicants determined that the preferential expression of CD5L in non-pathogenic Th17 cells, but in association with the pro-inflammatory module, may reflect a unique role for CD5L in regulating the transition between a non-pathogenic and pathogenic state. While co-expression with the proinflammatory module (FIG. 16C) and correlation with a pathogenicity signature (FIG. 16B) per se could suggest a function as a positive regulator of pathogenicity, the apparent absence of CD5L from Th17 cells differentiated in vitro under the pathogenic conditions or isolated from lesions in the CNS (FIG. 16A) suggested a more nuanced role. Applicants hypothesized that CD5L is a negative regulator of pathogenicity, explaining its absence from truly pathogenic cells. In fact, mRNAs encoding negative regulators of cell states are often positively co-regulated with the modules they suppress in eukaryotes from yeast (Pe'er et al., 2002; Segal et al., 2003) to human (Amit et al., 2007).

Figure 16D:
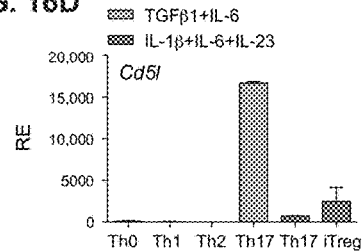
Figure 16E:
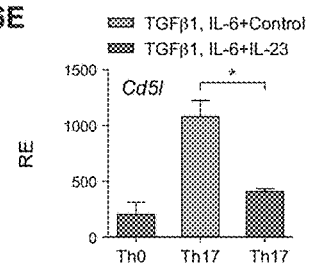
Figure 16F:
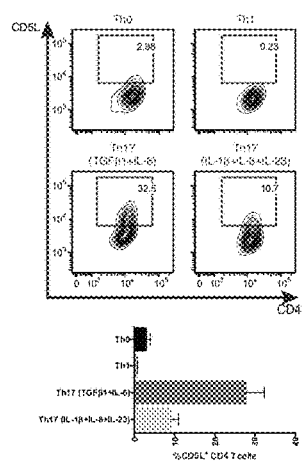

Applicants first validated and extended the initial finding that CD5L is uniquely expressed in nonpathogenic Th17 cells by analyzing naïve CD4 T cells cultured under various differentiation conditions using qPCR and flow cytometry (FIG. 16D, E, F). At the mRNA level, Applicants found little Cd5l expression in Th0, Th1 or Th2 helper T cells, high expression in Th17 cells differentiated with TGF-β1+IL-6, but low expression in Th17 cells differentiated with IL-1β+IL-6+IL-23 or in iTregs (FIG. 16D). Protein measurements confirmed the presence of CD5L in a large proportion of non-pathogenic Th17 cells (FIG. 16F).

Figure 16G:
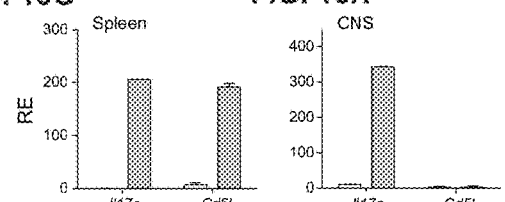
Figure 16I:
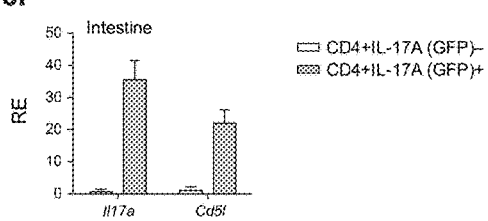

Next, Applicants explored whether CD5L expression is associated with less pathogenic Th17 cells in vivo. Applicants analyzed Th17 cells isolated from mice induced with EAE. Th17 cells (CD3+CD4+IL-17.GFP+) sorted from the spleen expressed Cd5l but IL-17-T cells did not (FIG. 16G). In contrast, Cd5l was not expressed in Th17 cells from the CNS despite significant expression of Il17(FIG. 16H), consistent with the single-cell RNA-seq data (FIG. 16A). Next, Applicants analyzed Th17 cells from mesenteric lymph nodes (mLN) and lamina propria (LP) of naïve mice, where Th17 cells contribute to tissue homeostasis and mucosal barrier function. IL-17+ but not IL-17− T cells harvested from mLN and LP expressed high levels of Cd5l (FIG. 16I and data not shown). Thus, CD5L is a gene expressed in non-pathogenic but not pathogenic Th17 cells in vivo. Applicants asked if IL-23, known to make Th17 cells more pathogenic, can regulate Cd5l expression. Applicants hypothesized that if CD5L is a positive regulator of IL-23-dependent pathogenicity, its expression will be increased by IL-23, whereas if it is a negative regulator, its expression will be suppressed. As IL-23R is induced after T-cell activation, Applicants differentiated naïve T cells with TGF-β1+IL-6 for 48h and expanded them in IL-23 in fresh media. IL-23 suppressed Cd5l (FIG. 16E), consistent with these cells acquiring a pro-inflammatory module and becoming pathogenic Th17 cells, and with our hypothetical assignment of CD5L as a negative regulator of pathogenicity. CD5L expression can be promoted by STAT3 but not RORγt (FIG. 19D, E), as IL-23 can enhance STAT3 function further studies are required to elucidate the pathways involved in regulating CD5L expression.

Figure 17H:
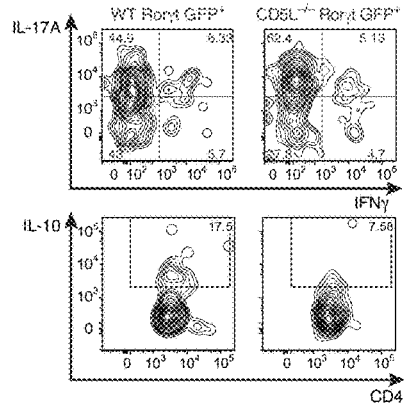

CD5L represses effector functions without affecting Th17 differentiation. To analyze the functional role of CD5L in vivo, Applicants immunized mice with MOG35-55/CFA to induce EAE. CD5L-/- mice exhibited more severe clinical EAE that persisted for at least 28 days, whereas wildtype (WT) mice began recovering 12 days post immunization (FIG. 17A). Similar frequencies of FoxP3+CD4+ Treg cells were found in WT and CD5L-/- mice, suggesting that the increased severity of the disease was not due to changes in the number of Tregs in CD5L-/- mice (FIG. 12A). In contrast, more CD4 T cells produced IL-17 and fewer cells produced IFNγ in the CNS of CD5L-/- mice (FIGS. 17A, 12B). In response to MOG reactivation in vitro, cells from the draining lymph nodes of CD5L-/- mice showed higher proliferative responses and produced more IL-17 (FIG. 12C, 12D). These observations are consistent with either a direct or indirect role for CD5L in defining Th17 cell function. Applicants studied the impact of CD5L on Th17 cells differentiated from naïve WT and CD5L-/- T cells by analyzing signature gene expression. CD5L deficiency did not affect Th17 differentiation as measured by 11-17 expression (FIG. 17B, C), nor did it affect other Th17 signature genes including Il7f, Il21, Il23r, Rorc or Rorα (FIG. 17D). Of note, under the non-pathogenic differentiation condition, CD5L-/- Th17 cells made less IL-10 (FIG. 17C, D). These observations suggest that changes in differentiation alone cannot explain the increased susceptibility to EAE in CD5L-/- mice, but that CD5L may indeed affect the internal state of differentiated Th17 cells. Applicants determined if CD5L regulates effector/memory Th17 cells by differentiation of nonpathogenic Th17 cells from naïve cells. Upon restimulation, more CD5L-/- Th17 cells produced IL-17 and expressed IL-23R without affecting viability (FIG. 17E and data not shown), suggesting that CD5L deficiency leads to more stable expansion of Th17 cells. Consistently, CD5L-/- Th17 cells expressed more Il17 and Il23r, less Il10 and similar levels of Rorc or Rorα (FIG. 17F). Thus, CD5L does not regulate Th17 cell differentiation, but affects Th17 cell expansion and/or effector functions over time. Similarly, effector memory cells (CD4+CD62LCD44+) isolated ex vivo from CD5L-/- mice have higher frequencies of IL-17+ and lower frequencies of IL-10+ cells (FIGS. 17G, 12E), possibly reflecting the greater stability of Th17 cells that persist in the repertoire of CD5L-/- mice. To address if Th17 cells isolated in vivo also produced more IL-17 per-cell, Applicants sorted RORγt+(GFP+) effector/memory T cells from WT and CD5L-/- mice and found more IL-17+ and fewer IL-10+ cells in CD5L-/- cells, suggesting RORγt+ cells are better IL-17 producers in the absence of CD5L (FIGS. 17H, 12F).

Figure 20B:
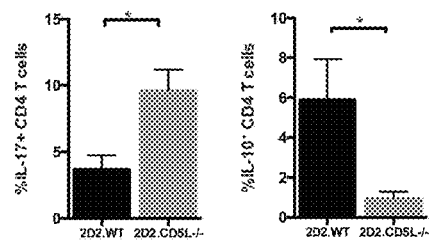
Figure 20C:
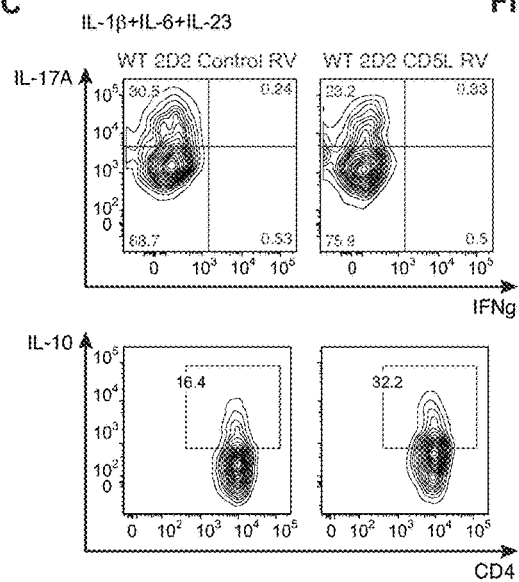
Figure 20D:
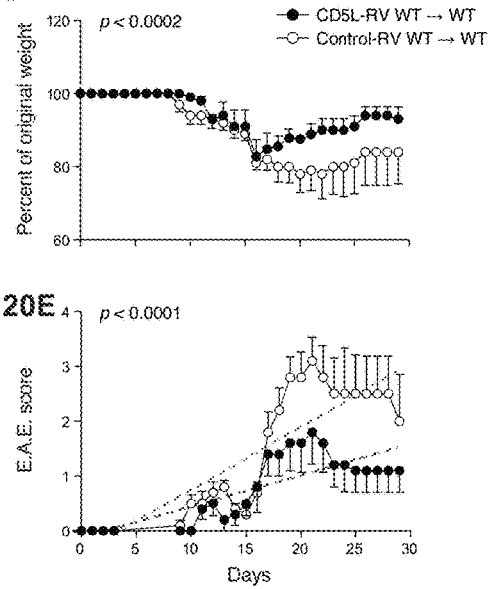
Figure 20E:
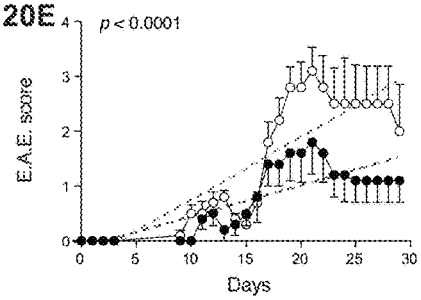
Figure 20F:
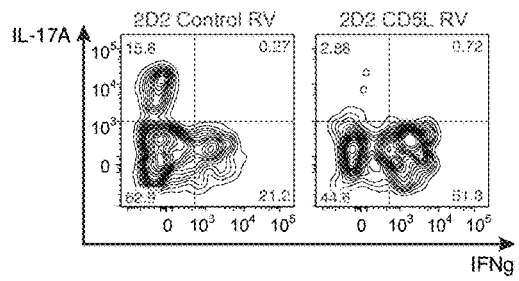

CD5L is a major switch that regulates Th17 cells pathogenicity. To determine if loss of CD5L can convert non-pathogenic Th17 cells into disease-inducing Th17 cells, Applicants crossed CD5L-/- mice to 2D2 transgenic mice expressing a T-cell receptor specific for MOG35-55/IAb (Bettelli et al., 2003). Naïve CD5L-/- 2D2 T cells were differentiated with the nonpathogenic (TGF-β1+IL-6) Th17 condition and transferred into WT recipients. Applicants analyzed the phenotype of T cells from the CNS of mice undergoing EAE. The 2D2 CD5L-/- Th17 cells retained more IL-17+ and fewer IL-10+ cells (FIG. 20A). A considerable proportion of endogenous T cells produced IL-10 compared to transferred 2D2 T cells (FIG. 20A), suggesting that extracellular IL-10 is not sufficient to restrain the pathogenicity of CD5L-/- Th17 cells. WT 2D2 T cells also acquired IFNγ expression in vivo, whereas CD5L-/- 2D2 T cells produced little IFNγ, suggesting CD5L may also regulate Th17 cell stability. Consistently, naïve CD5L-/- 2D2 T cells transferred into WT hosts immunized with MOG35-55/CFA without inducing EAE made more IL-17 and little IL-10 in contrast to WT 2D2 T cells (FIG. 20B). As IL-23 suppresses CD5L (FIG. 16E) and CD5L restrains Th17 cell pathogenicity, Applicants reasoned that sustained CD5L expression should antagonize IL-23-driven pathogenicity. To test this hypothesis, Applicants generated a retroviral vector for ectopic expression of CD5L. Naïve 2D2 T cells were differentiated with IL-1β+IL-6+IL-23, transduced with CD5L, transferred into WT recipients, and followed for weight loss and the development of clinical EAE (Experimental Procedures). 2D2 T cells transduced with CD5L (CD5L-RV 2D2) had a small reduction in IL-17 and higher IL-10 levels (FIG. 20C). Ectopic expression of CD5L in pathogenic Th17 cells reduced their pathogenicity as CD5L-RV 2D2 recipients had reduced weight loss and a significant decrease in the incidence and peak severity of EAE (FIG. 20D, E). Furthermore, CD5L-RV 2D2 Th17 cells transferred in vivo lost IL-17 production and began producing IFNγ (FIG. 20F). Therefore, sustained expression of Cd5l in pathogenic Th17 cells converts them to a less pathogenic and less stable phenotype in that these cells lose the expression of IL-17 and acquire an IFNγ-producing phenotype in vivo. This observation, combined with the observation that the loss of CD5L converts non-pathogenic Th17 cells into pathogenic Th17 cells in vivo, unequivocally supports the role of CD5L as a negative regulator of the functional pathogenic state of Th17 cells.

CD5L shifts the Th17 cell lipidome balance from saturated to unsaturated lipids, modulating Rorγt ligand availability and function: Since CD5L is known to regulate lipid metabolism, by binding to fatty acid synthase in the cytoplasm of adipocytes (Kurokawa, Arai et al. 2010), it was speculated that CD5L may also regulate Th17-cell function by specifically regulating lipid metabolites in T cells. To test this hypothesis, it was analyzed whether lipid metabolism is regulated by CD5L and is associated with the increased pathogenicity observed in Th17 cells from CD5L, mice. The lipidome of WT and CD5L$^{-/-}$ Th17 cells differentiated under the non-pathogenic (TGFβ1+IL-6) and pathogenic (TGFβ1+IL-6+IL-23) conditions was profiled. It was possible to resolve and identify around 200 lipid metabolites intracellularly or in the supernatant of differentiating Th17 cells using mass spectrometry and liquid chromatography (Table 3 herein). Of those metabolites that were differentially expressed between WT and CD5L, a striking similarity between the lipidome of CD5L$^{-/-}$ Th17 cells differentiated under the non-pathogenic condition and WT Th17 cells differentiated under the pathogenic condition (FIG. 11A) was observed. Among other metabolic changes, CD5L deficiency significantly increased the levels of saturated lipids (SFA), including metabolites that carry saturated fatty acyl and cholesterol ester (CE) as measured by liquid chromatography and mass spectrometry (FIG. 11B), and free cholesterol as shown by microscopy (FIG. 11D). Moreover, the absence of CD5L resulted in a significant reduction in metabolites carrying poly-unsaturated fatty acyls (PUFA) (FIG. 11B). Similar increase in CE and reduction in PUFA is observed in the lipidome of Th17 cells differentiated under either of two pathogenic conditions (IL-1β+IL-6+IL-23 and TGFβ3+IL-6+IL-23) compared to non-pathogenic WT cells (FIG. 11C). Thus, Th17 cell pathogenicity is associated with a shift in the balance of lipidome saturation as reflected in the increase in saturated lipids and decrease in PUFA metabolites.

Cholesterol metabolites, such as oxysterols, have been previously reported to function as agonistic ligands of Rorγt (Jin, Martynowski et al. 2010, Soroosh, Wu et al. 2014). Previous ChIP-Seq analysis (Xiao, Yosef et al. 2014) suggests that Rorγt binds at several sites in the promoter and intronic regions of Il23r and Il17 (FIG. 11D) and near CNS-9 of Il10, where other transcription factors, such as cMaf, which regulates Il10 expression, also binds. As showed above, CD5L restrains the expression of IL-23R and IL-17 and promotes IL-10 production in Rorγt$^+$ Th17 cells, and because CD5L-deficient Th17 cells contain higher cholesterol metabolite and lower PUFA (FIG. 11A, B). Putting these data together, it was hypothesized that CD5L regulates the expression of IL-23R, IL-17 and IL-10 by affecting the binding of Rorγt to these targets, through affecting the SFA-PUFA balance.

Figure 11L:
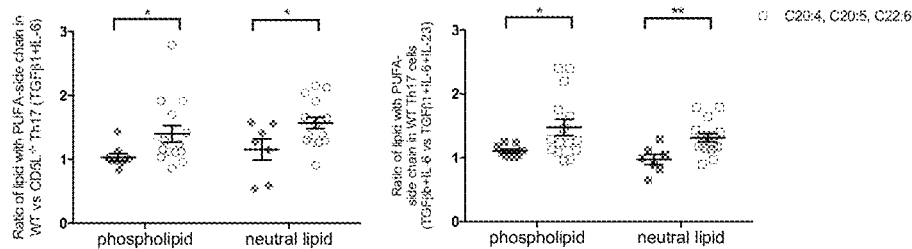
Figure 11M:
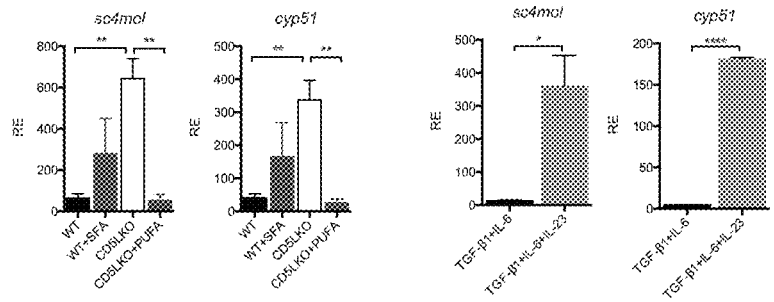

Applicants hypothesized that CD5L could regulate Th17-cell function by regulating fatty acid (FA) profiles in T cells. Applicants asked if lipid metabolites are regulated by CD5L and if any such changes are associated with the increased pathogenicity of CD5L−/− Th17 cells. Applicants profiled the lipidome of WT and CD5L−/− Th17 cells differentiated under the non-pathogenic (TGF-β1+IL-6) and pathogenic (TGF-β1+IL-6+IL-23) conditions using a non-targeted approach. Applicants detected 178 lipid metabolites from Th17 cells, 39 of which showed differences among various Th17 polarizing conditions (FIG. 11A, p<0.05, fold change >1.5; Table 4). Strikingly, non-pathogenic WT Th17 cells had a unique lipidome profile that was distinct from those of CD5L−/− Th17 cells and WT Th17 cells differentiated with TGF-β1+IL-6+IL-23 (FIG. 11A). Applicants analyzed the FA profile and lipid class in the Th17 cell lipidome. As Applicants did not detect free FA except myristic acid, Applicants analyzed the FA content (sidechain) of the lipids in FIG. 11A. WT non-pathogenic Th17 cells (compared to CD5L−/− Th17 cells of the same conditions) have increased polyunsaturated fatty acid (PUFA), accompanied by a decrease in lipids containing saturated (SFA) and monounsaturated fatty acids (MUFA) (FIG. 11K). Applicants then extended this analysis to the 178 lipids detected. Not all PUFA are different in WT vs. CD5L−/− Th17 cells: linoleic acid (C18:2) and linolenic acid (C18:3) are equally distributed in the lipidome, whereas downstream PUFA, in particular arachidonic acid (C20:4), are elevated in WT non-pathogenic Th17 cells (FIG. 21B). In contrast, MUFA is equivalently distributed and the corresponding SFA is decreased in WT non-pathogenic Th17 cells (FIG. 21C). The PUFA increase in WT non-pathogenic Th17 is equivalently distributed among the phospholipid and neutral lipid compartments (FIG. 11L), whereas the relative decrease of SFA is only significant in phospholipid (FIG. 11L). Finally, comparing the difference in specific lipid species (FIG. 21D), Applicants found a higher level of cholesterol ester (CE), lysophosphatidylcholine (LPC) and phosphatidylcholine (PC), as well as decreased triacylglyceride (TAG) in both the CD5L−/− and more pathogenic cells (FIG. 21D). Taken together, these findings suggest CD5L predominantly regulates FA composition in Th17 cells, resulting in elevation of PUFA and changes in specific lipid species, including cholesterol metabolites. Similar changes are also observed in WT Th17 cells differentiated under the pathogenic condition. Cholesterol metabolites, such as oxysterols, can function as agonists of Rorγt (Jin et al., 2010; Soroosh et al., 2014), and the cholesterol synthesis pathway has been linked to the production of endogenous Rorγt ligand. While Applicants did not detect any oxysterols or intermediates of cholesterol synthesis, the higher level of cholesterol esters (FIG. 21D) prompted us to further investigate the cholesterol pathway. Applicants confirmed the higher intensity of free cholesterol in CD5L−/− Th17 cells using microscopy (FIG. 21E). Next, Applicants analyzed the expression of cyp51 and sc4 mol, two enzymes of the cholesterol synthesis pathway responsible for generating endogenous Rorγt ligands (Santori et al., 2015), and found both increased in CD5L−/− Th17 cells or in pathogenic WT Th17 cells (FIG. 11M), suggesting this may be a common mechanism by which Th17 cells regulate their function. Applicants asked if the change in FA profile in CD5L−/− Th17 cells is responsible for the regulation of cyp51 and sc4 mol. Indeed, while SFA had a modest effect, PUFA abolished the increased expression of the enzymes in CD5L−/− Th17 cells (FIG. 11M). Thus CD5L can regulate fatty acid composition in Th17 cells and alter the cholesterol synthesis pathway, a source of Rorγt ligand.

CD5L and PUFA/SFA profile regulate Rorγt function in a ligand-dependent manner. Applicants analyzed if CD5L and the PUFA/SFA profile can alter Rorγt binding and function. Our previous chromatin immunoprecipitation (ChIP)-Seq analysis (Xiao et al., 2014) suggested Rorγt binds at several sites in the promoter and intronic regions of Il23r and Il17 and near CNS-9of Il10 (FIG. 54 WO2015130968) where other Il10-regulating transcription factors, such as cMaf, also bind (Xiao et al., 2014). As CD5L restrains IL-17 and promotes IL-10 in Rorγt+Th17 cells (FIG. 46 WO2015130968) and CD5L−/− Th17 cells have more cholesterol metabolites and lower PUFA (FIGS. 11A, 11K, 11M, 21E), Applicants hypothesized that CD5L regulates the expression of IL-23R, IL-17, IL-10 and, in turn, pathogenicity by affecting the binding of Rorγt to these targets by changing the SFA/PUFA profile and cholesterol biosynthesis. Applicants assessed if CD5L regulates Rorγt binding and transcription using ChIP-PCR and luciferase reporter assays. ChIP of Rorγt showed higher binding in the Il17 and Il23r region and reduced binding to the Il10 region in CD5L−/− Th17 cells despite similar Rorγt expression compared to WT (FIG. 18A, B, FIG. 54 WO2015130968). Further, CD5L overexpression was sufficient to suppress Rorγt dependent transcription of Il17 and Il23r luciferase reporters (FIG. 18C, FIG. 54 WO2015130968) and to enhance the transcription of the Il10 reporter (FIG. 54 WO2015130968). This effect of CD5L is not observed with PPARγ, another regulator of Il10, further supporting the hypothesis that the effect of CD5L depends on Rorγt (FIG. 54 WO2015130968). Applicants then examined whether changing the lipidome of WT Th17 cells with exogenous SFA or PUFA can regulate Rorγt binding to genomic regions (FIG. 18A, B and FIG. 54 WO2015130968). SFA enriched binding of Rorγt at Il17 and Il23r loci and PUFA decreased such binding (FIG. 15A, FIG. 54 WO2015130968). Instead, PUFA increased Rorγt binding to the Il10 CNS-9 locus (FIG. 18B), suggesting that manipulation of the lipid content of Th17 cells can indeed modulate Rorγt binding to DNA. Applicants reasoned that if CD5L regulates Rorγt transcriptional activity by limiting Rorγt ligand, adding exogenous agonists of Rorγt would rescue CD5L-induced suppression. Indeed, 7β, 27-dihydroxycholesterol, previously shown as an endogenous ligand of Rorγt (Soroosh et al., 2014), rescued the CD5L-driven suppression of Il17 reporter transcription, suggesting ligand availability partly contributes to the regulation of Rorγt function by CD5L (FIG. 18D). Consistently, CD5L inhibited IL-17 expression in unpolarized Th0 cells with ectopic Rorγt expression and this inhibition could be partially rescued by the addition of a Rorγt ligand (FIG. 18E). Addition of Rorγt ligand also increased IL-17 production from non-pathogenic Th17 cells (FIG. 18F), suggesting that ligand restriction may be one of the mechanisms by which CD5L regulates Th17 cell pathogenicity. Applicants then determined if SFA/PUFA regulate Rorγt activity through Rorγt ligand. While Rorγt strongly transactivates the Il23r enhancer in the presence of an agonistic ligand, the addition of PUFA to the agonist ligand inhibited Rorγt-mediated Il23r transactivation and enhanced Il10 transactivation (FIG. 48 WO2015130968). Similarly, adding SFA alone had little impact on Rorγt-dependent transcription, but it modified the transcriptional effect of oxysterol (FIG. 48 WO2015130968). Thus, PUFA/SFA can modulate Rorγt transcriptional activity via a Rorγt-ligand dependent mechanism, although the precise mechanism of exogenous PUFA and SFA require further studies. Taken together, these observations suggest that CD5L shifts the FA composition in the lipidome, changes Rorγt ligand availability and Rorγt genomic binding, and regulates Il23r and Il10, members of the proinflammatory vs. regulatory modules.

PUFA/SFA regulate Th17 cell and contribute to CD5L function. As CD5L-/- Th17 cells have an altered balance in lipid saturation, and PUFA/SFA modulate Rorγt binding and function, Applicants analyzed the relevance of FA moieties to Th17 cell function and their contribution to CD5L-driven Th17 cell pathogenicity. Applicants first tested the effect of PUFA/SFA on the generation of Th17 cells. WT Th17 cells were differentiated with TGF-β1+IL-6 and expanded using IL-23 in fresh media with either PUFA or SFA. PUFA suppressed IL-17 and IL-23R expression consistent with reduced transactivation in WT but not in Rorγt-/- Th17 cells, suggesting PUFA can limit pathogenic Th17 cell function in a Rorγt dependent manner (FIG. 50 WO2015130968). CD5L-/- Th17 cells differentiated with TGF-β1+IL-6 were also sensitive to PUFA treatment, resulting in reduced percentage of IL-17+CD4+ T cells (FIG. 50 WO2015130968). In contrast, addition of SFA only slightly increased the expression of both IL-17 and IL-23R expression, and this effect was not significant, possibly because pathogenic Th17 cells had already very high levels of SFA. Applicants studied the contribution of lipid saturation to Th17 cell pathogenicity. Applicants speculated that if the balance of lipid saturation distinguishes non-pathogenic WT Th17 cells and pathogenic CD5L-/- Th17 cells, the addition of SFA to WT and PUFA to CD5L-/- Th17 cells can result in reciprocal changes in the transcriptional signature relevant to Th17 cell pathogenicity. Applicants analyzed the expression of a 312 gene signature of Th17 cell differentiation and function (Yosef et al., 2013) in SFA- or control-treated WT Th17 cells and in PUFA- or control-treated CD5L-/- Th17 cells differentiated with TGF-81+IL-6. Of those genes that are differentially expressed (Table 5, >1.5 fold), PUFA-treated CD5L-/- Th17 cells resemble WT non-pathogenic Th17 cells, and SFA-treated WT non-pathogenic Th17 cells are more similar to CD5L-/- Th17 cells (FIG. 50 WO2015130968, Table 5). qPCR analysis confirmed that PUFA and SFA reciprocally regulated effector molecule expression of the pathogenicity signature (Lee et al., 2012), including Il10, Il23r, Ccl5, Csf2 and Lag3 (FIG. 50 WO2015130968). Notably, in some cases PUFA and SFA have the same effects; for example, Il22 expression is increased following either FA treatment. Taken together, these observations suggest that the balance of lipid saturation contributes to CD5L-dependent regulation of Th17 cells by regulating the Th17-cell transcriptome.

DISCUSSION. Th17 cells are a helper cell lineage capable of diverse functions ranging from maintaining gut homeostasis, mounting host defense against pathogens, to inducing autoimmune diseases. How Th17 cells can mediate such diverse and opposing functions remains a critical open question. Addressing this is especially important since anti-IL-17 and Th17-based therapies have been highly efficacious in some autoimmune diseases, but had no impact on others (Baeten and Kuchroo, 2013; Genovese et al., 2010; Hueber et al., 2012; Leonardi et al., 2012; Papp et al., 2012; Patel et al., 2013), even when Th17 cells have been genetically linked to the disease process (Cho, 2008; Lees et al., 2011). Using single-cell genomics Applicants have addressed this issue and have identified novel functional regulators of pathogenicity in Th17 cells. Here, Applicants highlight and investigate CD5L as one of the novel regulators that affect the pathogenicity of Th17 cells. Applicants show that: (1) Among CD4 T cells, CD5L is highly expressed only in non-pathogenic Th17 cells, but in them positively co-varies with a pro-inflammatory module, a pattern consistent with being a negative regulator of pathogenicity; (2) CD5L does not affect Th17 differentiation but affects their long-term expansion and function; (3) CD5L deficiency converts non-pathogenic Th17 cells into pathogenic Th17 cells; (4) CD5L regulates lipid metabolism in Th17 cells and alters their fatty acid composition; and (5) change in the lipidome in CD5L-/- Th17 cells affects the ligand availability and binding of Rorγt to its target genes.

In a seemingly paradoxical way, CD5L is expressed only in non-pathogenic Th17 cells, but in co-variance with the pro-inflammatory module. This observation led us to hypothesize that CD5L is a negative regulator of a non-pathogenic to pathogenic transition, since negative regulators are often known to co-vary in regulatory networks with the targets they repress in organisms from yeast (Segal et al., 2003) to mammals (Amit et al., 2007; Amit et al., 2009). Our functional analysis bears out this hypothesis, suggesting that CD5L might indeed be expressed to restrain the pro-inflammatory module in the non-pathogenic Th17 cells. Similarly, other genes with this specific pattern, i.e. exclusive expression in non-pathogenic cells but in co-variance with the pro-inflammatory module, may also be repressors that quench pro-inflammatory effector functions and make Th17 cells non-pathogenic. Thus, depending on the environmental context or trigger, non-pathogenic Th17 cells can be readily converted into pathogenic Th17 cells by inhibiting a single gene like CD5L. This is supported by our data showing IL-23R signalling can suppress CD5L and persistent CD5L expression inhibits the pro-inflammatory function of Th17 cells. In addition to suppressing the pro-inflammatory module, CD5L also promotes the regulatory module, acting as a switch to allow rapid responses to environmental triggers such that Th17 cells can change their functional phenotype without intermediary pathways.

Both pathogenic and non-pathogenic Th17 cells are present in peripheral lymphoid organs, but pathogenic Th17 cells appear at sites of tissue inflammation (CNS) and non-pathogenic Th17 cells appear in the gut or other mucosal surfaces. This is mirrored in the expression of CD5L. IL-23, which is present in the CNS during EAE, can suppress CD5L and convert non-pathogenic Th17 cells into pathogenic Th17 cells. At steady state, it is unknown what promotes CD5L expression and non-pathogenicity in the gut. TGF-3 could be a candidate given its abundance in the intestine and its role in both differentiation of IL-10-producing CD4 T cells in vivo (Konkel and Chen, 2011; Maynard et al., 2007) and Th17 cell differentiation (Bettelli et al., 2006; Veldhoen et al., 2006). Specific commensal bacteria (Ivanov et al., 2009; Yang et al., 2014) and metabolites from microbiota (Arpaia et al., 2013) can also regulate T cell differentiation. Notably, CD5L is reported as a secreted protein and can recognize PAMPs (Martinez et al., 2014). It is possible CD5L expressed by non-pathogenic Th17 cells in the gut can interact with the immune cells interacting with gut microbiota and maintain gut tolerance and a non-pathogenic Th17 phenotype. Other CD5L-expressing cells in the intestine may also contribute to such a function. Therefore, the two functional states of Th17 cells may be highly plastic, in that either pathogenic or non-pathogenic Th17 cells can be generated by sensing changes in the tissue microenvironment. CD5L is critical for maintaining the non-pathogenic functional state of Th17 cells, and IL-23 rapidly suppresses CD5L rendering the cells pathogenic. This hypothesis also predicts that non-pathogenic Th17 cells can be easily converted into pathogenic Th17 cells by production of IL-23 locally in the gut during inflammatory bowel disease. How does CD5L regulate Th17 cell pathogenicity? Applicants provide evidence CD5L can regulate Th17 cell function by regulating intracellular lipid metabolism and limiting Rorγt ligand. CD5L inhibits the de novo synthesis of fatty acid through direct binding to fatty acid synthase. Applicants discovered that in Th17 cells CD5L is more than a general inhibitor, as it regulates the fatty acid composition of PUFA vs. SFA and MUFA. Applicants showed CD5L suppresses the cholesterol synthesis pathway by regulating critical enzymes sc4 mol and cyp51 and the addition of PUFA could reverse this phenotype. Importantly, exogenous Rorγt ligand can rescue the suppressive effect of CD5L on IL-17 expression. PUFA metabolites can function as ligands of several transcription factors and the exact mode of function for PUFA requires further investigation. Applicants showed that PUFA limits ligand-dependent function for Rorγt, such that in the presence of CD5L or PUFA, Rorγt binding to the Il17a and Il23r loci is decreased, along with reduced transactivation of both genes, whereas binding at and expression from the Il10 locus is enhanced. Notably, Rorγt's ability to regulate Il10 expression was not reported previously. As CD5L does not impact overall Th17 cell differentiation, this suggests a nuanced effect of CD5L and lipid balance on Rorγt function, enhancing its binding to and transactivation at some loci, while reducing it in others. In Th17 cells, Stat3 and c-Maf can promote Il10 (Stumhofer et al., 2007; Xu et al., 2009). As Stat3, C-Maf and Rorγt can all bind to the same Il10 enhancer element, it is possible that, depending on the quality and quantity of the available ligands, Rorγt may interact with other transcription factors and regulate Il10 transcription. This supports a hypothesis in which the spectrum of Rorγt ligands depends, at least in part, on the CD5L-regulated PUFA vs. SFA lipid balance in the cell, and these resulting ligands can impact the specificity of Rorγt, allowing it to assume a spectrum of functional states. Several metabolic pathways are associated with Th17 cell differentiation. HIF1α regulates Th17 cells through direct transactivation of Rorγt (Dang et al., 2011; Shi et al., 2011) and acetyl-coA carboxylase influences the Th17/Treg balance through the glycolytic and lipogenic pathways (Berod et al., 2014). Mice harbouring mutations in genes that regulate Th17 cell differentiation and function acquire an obese phenotype, associating Th17 cell development with obesity (Ahmed and Gaffen, 2010; Jhun et al., 2012; Mathews et al., 2014; Winer et al., 2009). A hallmark of obesity is the accumulation of saturated fat and cholesterol and mice fed with a diet rich in PUFA were reported to have reduced severity of chronic colitis and Th17 cell polarization (Monk et al., 2013; Monk et al., 2012). In this study, Applicants provided evidence that at the cellular level, lipidome saturation can promote Th17 cell function by regulating Rorγt function.

In conclusion, by using single-cell genomics and computational analysis, Applicants identified CD5L as a novel repressor of Th17 cell pathogenicity, highlighting the power of single-cell genomics to identify molecular switches that are otherwise obscured by population-level genomic profiles. CD5L appears to be a molecular switch that does not affect Th17 differentiation per se but one that impacts the function (pathogenic vs. non-pathogenic phenotype) of Th17 cells, potentially by regulating the quality and/or quantity of available Rorγt ligands, allowing a single master regulator to possibly assume multiple functional states. Our results connect the lipidome to essential functions of immune cells, opening new avenues for sensitive and specific therapeutic intervention.

EXPERIMENTAL PROCEDURES. Mice: C57BL/6 wild-type and $CD4^{-/-}$ (2663) mice were obtained from Jackson Laboratory. IL-17A-GFP mice were from Biocytogen. All animals were housed and maintained in a conventional pathogen-free facility at the Harvard Institute of Medicine in Boston (IUCAC protocols: 0311-031-14 (V.K.K.) and 0609-058015 (A.R.)). All experiments were performed in accordance to the guidelines outlined by the Harvard Medical Area Standing Committee on Animals at the Harvard Medical School. In addition, spleens and lymph nodes from $GPR65^{-/-}$ mice were generously provided by Yang Li (IACUC protocol: 453). $PLZP^{-/-}$ mice and $TOSO^{-/-}$ mice were provided by Pier Paolo Pandolfi from Beth Israel Deaconess medical center and John Coligan from National institute of Allergy and Infectious Diseases respectively.

Cell sorting and in vitro T-cell differentiation: CD4+ T cells were purified from spleen and lymph nodes using anti-CD4 microbeads (Miltenyi Biotech) then stained in PBS with 1% FCS for 20 min at room temperature with anti-CD4-PerC$^P$, $^a$nti-$^{CD6}$21-APC and anti-CD44-PE antibodies (all Biolegend). Naïve CD4+CD62l$^{high}$CD44$^{low}$ T cells were sorted using the BD FACSAria cell sorter. Sorted cells were activated with plate-bound anti-CD3 (2 μg ml-1) and anti-CD28 (2 μg ml-1) in the presence of cytokines. For Th17 differentiation, the following reagents were used: 2 ng/ml recombinant human TGF-β1 and recombinant human TGF-β3 (Miltenyi Biotec), 25 ng/ml recombinant mouse IL-6 (Miltenyi Biotec), 20 ng/ml recombinant mouse IL-23 (R&D Biosystems) and 20 ng/ml recombinant mouse IL-1β

(Miltenyi Biotec). Cells were cultured for 48h and collected for RNA, intracellular cytokine staining, flow-fish, and flow cytometry.

Active induction of EAE and disease analysis: For active induction of EAE, mice were immunized by subcutaneous injection of 100 μg MOG(35-55) (MEVGWYRSPFSRVVHLYRNGK) in CFA, then received 200 ng pertussis toxin intraperitoneally (List Biological Laboratory) on days 0 and 2. Mice were monitored and were assigned scores daily for development of classical and atypical signs of EAE according to the following criteria (Jager et al., 2009): 0, no disease; 1, decreased tail tone or mild balance defects; 2, hind limb weakness, partial paralysis or severe balance defects that cause spontaneous falling over; 3, complete hind limb paralysis or very severe balance defects that prevent walking; 4, front and hind limb paralysis or inability to move body weight into a different position; 5, moribund state.

Isolation of T-cells from EAE mice at the peak of disease: At the peak of disease, T cells were collected from the draining lymph nodes and the CNS. For isolation from the CNS, mice were perfused through the left ventricle of the heart with cold PBS. The brain and the spinal cord were flushed out with PBS by hydrostatic pressure. CNS tissue was minced with a sharp razor blade and digested for 20 min at 37 C with collagenase D (2.5 mg/ml; Roche Diagnostics) and DNaseI (1 mg/ml; Sigma). Mononuclear cells were isolated by passage of the tissue through a cell strainer (70 μm), followed by centrifugation through a Percoll gradient (37% and 70%). After removal of mononuclear cells, the lymphocytes were washed, stained and sorted for CD3 (Biolegend), CD4 (Biolegend), 7AAD and IL-17a-GFP or FOXP3-GFP.

Memory cell isolation reactivation: Spleen and lymph nodes were isolated from indicated mice and CD4+ T cells were purified using Automacs using the manufacturers protocol (Miltenyi Biotec, CA). Cells were stained with CD44-PE, CD62L-APC and CD4-Percp antibodies prior to being sorted on the Aria FACS sorter for CD4+CD44+CD62L- cells. Cells were plated on anti-CD3/anti-CD28 (2 ug/ml each) coated flat-bottomed 96 well plate at $2\times10^5$ cells/well with or without IL-23 (20 ng/ml) for reactivation. Cells were cultured in vitro for 96 hours and then live cells (7AAD-) were analyzed for intracellular cytokine staining or sorted for harvesting prior to RNA purification.

Recall experiments: Naïve CD4 T cells (CD4+CD62L+ CD44−) were sorted from indicated KO and WT (or littermate) controls then adoptively transferred at $1\times10^6$ cells into Rag-1 KO mice for reconstitution. Two weeks post adoptive transfer; mice were immunized with 100 ug of $MOG_{35-55}$/CFA. Cells were harvested from draining LNs and spleen 8 days post immunization and restimulated with $MOG_{35-55}$ with or without IL-23 (20 ng/ml) for 4 days. Cells were harvested for intracellular cytokine analysis.

Isolation of T cells from lamina propria: Cells were isolated from the lamina propria of the large intestine from 3-6 month old IL-17GFP KI mice using Miltenyi Biotec Lamina Propria Dissociation kit following the manufacturer's protocol (Miltenyi Biotec, Calif.). GFP+CD4+ TCRb+ 7AAD− T cells were sorted using a MoFlow Astrios into RLT lysis buffer (Qiagen RNeasy micro kit) and subsequently taken through the 'RNA-seq of population controls' protocol described below.

Whole transcriptome amplification: Cell lysis and SMART-Seq (Ramskold et al., 2012) whole transcriptome amplification (WTA) was performed on the $C_1$ chip using the $C_1$ Single-Cell Auto Prep System ($C_1$ System) using the SMARTer Ultra Low RNA Kit for Illumina Sequencing (Clontech) with the following modifications: Cell Lysis Mix:

| Composition | Stock Conc. | Volume |
|---|---|---|
| $C_1$ Loading Reagent | 20× | 0.60 ul |
| SMARTer Kit RNase Inhibitor | 40× | 0.30 ul |
| SMARTer Kit 3' SMART CDS Primer II A | 12 μM | 4.20 ul |
| SMARTer Kit Dilution Buffer | 1× | 6.90 ul |

Cycling Conditions I:
a) 72° C., 3 min
b) 4° C., 10 min
c) 25° C., 1 min
Reverse Transcription (RT) Reaction Mix:

| Composition | Stock Conc. | Volume |
|---|---|---|
| $C_1$ Loading Reagent | 20.0× | 0.45 ul |
| SMARTer Kit 5× First-Strand Buffer (RNase-Free) | 5.0× | 4.20 ul |
| SMARTer Kit Dithiothreitol | 100 mM | 0.53 ul |
| SMARTer Kit dNTP Mix (dATP, dCTP, dGTP, and dTTP, each at 10 mM) | 10 mM | 2.10 ul |
| SMARTer Kit SMARTer II A Oligonucleotide | 12 uM | 2.10 ul |
| SMARTer Kit RNase Inhibitor | 40× | 0.53 ul |
| SMARTer Kit SMARTScribe ™ Reverse Transcriptase | 100.0× | 2.10 ul |

Cycling Conditions II:
a) 42° C., 90 min
b) 70° C., 10 min
PCR Mix:

| Composition | Stock Conc. | Volume |
|---|---|---|
| PCR Water | — | 35.2 ul |
| 10× Advantage 2 PCR Buffer | 10.0× | 5.6 ul |
| 50× dNTP Mix | 10 mM | 2.2 ul |
| IS PCR primer | 12 uM | 2.2 ul |
| 50× Advantage 2 Polymerase Mix | 50.0× | 2.2 ul |
| C1 Loading Reagent | 20.0× | 2.5 ul |

Cycling Conditions III:
a) 95° C., 1 min
b) 5 cycles of:
i) 95° C., 20s
ii) 58° C., 4 min
ii) 68° C., 6 min
c) 9 cycles of:
i) 95° C., 20s
ii) 64° C., 30s
ii) 68° C., 6 min
d) 7 cycles of:
i) 95° C., 30s
ii) 64° C., 30s
ii) 68° C., 7 min
e) 72° C., 10 min Single cell RNA-Seq. WTA products were harvested from the $C_1$ chip and cDNA libraries were prepared using Nextera XT DNA Sample preparation reagents (Illumina) as per the manufacturer's recommendations, with minor modifications. Specifically, reactions were run at % the recommended volume, the tagmentation step was extended to 10 minutes, and the extension time during the PCR step was increased from 30s to 60s. After the PCR step, all 96 samples were pooled without library normalization, cleaned twice with 0.9× AMPure XPSPR1 beads (Beckman Coulter), and eluted in buffer TE. The pooled libraries were quantified using Quant-IT DNA High-Sensitivity Assay Kit (Invitrogen) and examined using a high sensitivity DNA chip (Agilent). Finally, samples were sequenced deeply using either a HiSeq 2000 or a HiSeq 2500 sequencer.

Single-cell RNAseq data acquisition and analysis. Applicants profiled the transcriptome of 806 Th17 cells, either harvested in vivo or differentiated in vitro. For in vivo experiments, CD3+CD4+IL-17A.GFP+ cells were isolated from draining LNs and CNS of mice at peak of EAE. For in vitro experiments, cells were sorted at 48h post induction of differentiation of naïve CD4+ T cells under different conditions. Applicants had at least two independent biological replicates for each in vivo and in vitro condition (except for TGF-β3+IL-6 for which Applicants only had one replicate), as well as two technical replicates for two in vivo conditions.

Applicants prepared single-cell mRNA SMART-Seq libraries using microfluidic chips (Fluidigm C1) for single-cell capture, lysis, reverse transcription, and PCR amplification, followed by transposon-based library construction. For quality assurance, Applicants also profiled corresponding population controls (>50,000 cells for in vitro samples; ~2,000-20,000 cells for in vivo samples, as available), with at least two replicates for each condition. RNA-seq reads were aligned to the NCBI Build 37 (UCSC mm9) of the mouse genome using TopHat (Trapnell et al., 2009). The resulting alignments were processed by Cufflinks to evaluate the abundance (using FPKM) of transcripts from RefSeq (Pruitt et al., 2007). Applicants used log transform and quantile normalization to further normalize the expression values (FPKM) within each batch of samples (i.e., all single-cells in a given run). To account for low (or zero) expression values Applicants added a value of 1 prior to log transform. Applicants filtered the set of analyzed cells by a set of quality metrics (such as sequencing depth), and added an additional normalization step specifically controlling for these quantitative confounding factors as well as batch effects. Our analysis is based on ~7,000 appreciably expressed genes (fragments per kilobase of exon per million (FPKM)>10 in at least 20% of cells in each sample) for in vitro experiments and ~4,000 for in vivo ones. Applicants also developed a strategy to account for expressed transcripts that are not detected (false negatives) due to the limitations of single-cell RNA-seq (Deng et al., 2014; Shalek et al., 2014). Our analysis (e.g., computing signature scores, and principle components) down-weighted the contribution of less reliably measured transcripts. The ranking of regulators shown in FIG. 16 is based on having a strong correlation to at least one of the founding signature genes, and in addition, the significance of the overall pattern relative to the proinflammatory vs. regulatory signature by comparing the aggregates pattern across the individual correlations to shuffled data.

Mice. C57BL/6 wildtype (WT) was obtained from Jackson laboratory (Bar Harbor, Me.). For EAE experiment, littermate control WT was used in comparison to CD5L−/− mice in one experiment which produced similar results compared to WT from Jackson. CD5L−/− mice were provided by Dr. Toru Miyazaki from the University of Tokyo (Miyazaki et al., 1999). CD5L−/− 2D2 mice were generated by crossing CD5L−/− mice with WT 2D2 transgenic mice. IL-23R GFP reporter mice were generated as previously published (Awasthi et al., 2009). Rorγt. GFP reporter mice were provided by Dr. Dan Littman and bred at the Harvard Institute of Medicine animal facility. All experiments were performed in accordance to the guidelines outlined by the Harvard Medical Area Standing Committee on Animals at the Harvard Medical School (Boston, Mass.).

Experimental Autoimmune Encephalomyelitis (E4E). For active EAE immunization, MOG35-55 peptide was emulsified in complete freund adjuvant (CFA). Equivalent of 40 µg MOGpeptide was injected per mouse subcutaneously followed by pertussis toxin injection intravenously on day 0 and day 2 of immunization. For adoptive transfer EAE, naïve 2D2 transgenic T cells were sorted as described in T cell culture and co-cultured with irradiated APC in the presence of soluble anti-CD3 and anti-CD28 antibodies (2.5 µg/ml) and cytokines for five days. Cells were then harvested and restimulated with plate-bound anti-CD3 and anti-CD28 (2 µg/ml) for 2 days prior to transfer. For overexpression of CD5L, retroviruses, MSCV, carrying either GFP empty vector control or GFP.CD5L vector was used to infect T cell culture as outlined above one day after T cell activation. Five million cells were transferred per mouse intravenously. EAE is scored as previously published (Jager et al., 2009).

T cell differentiation culture. Naïve CD4+CD44−CD62L+CD25− T cells or Effector memory CD4+CD44+CD62L− were sorted using BD FACSAria sorter and activated with plate-bound anti-CD3 and anti-CD28 antibodies (both at 2 µg/ml) in the presence of cytokines at a concentration of $2.5 \times 10^5$ cells/ml. For Th17 differentiation: 2 ng/ml of rhTGFβ1, 2 ng/ml of rhTGFβ3, 25 ng/ml rmIL-6, 20 ng/ml rmIL-18 (all from Miltenyi Biotec) and 20 ng/ml rmIL-23 (R & D systems) were used at various combinations as specified in figures. For Th1 differentiation, 20 ng/ml rmIL-12 (R & D systems); for Th2 differentiation 20 ng/ml rmIL-4 (Miltenyi Biotec); for iTreg differentiation, 2.5 ng/ml of rhTGFβ1 were used (Miltenyi Biotec). For differentiation experiments, cells were harvested at 48 hours. For restimulation experiments, cells were differentiated for 48 hours and resuspended in fresh media with no additional cytokines for 48-72 hours. Cells were re-stimulated with PMA/ionomycin for four hours before analysis for cytokines by intracellular cytokine staining. For experiments with exogenous fatty acid, fatty acids were purchased and resuspended first with serum-free media containing BSA prior being added to culture.

Lipidomics. Th17 cells were differentiated from naïve WT and CD5L−/− T cells. Culture media were snap frozen. Cells were harvested at 96h. $10 \times 10^6$ cells per sample were snap frozen and extracted in either 80% methanol (for fatty acids and oxylipids) or isopropanol (for polar and nonpolar lipids). Two liquid chromatography tandem mass spectrometry (LC-MS) methods were used to measure fatty acids and lipids in cell extracts.

Fatty acid extracts (10 pL) were injected onto a 150×2 mm ACQUITY T3 column (Waters; Milford, Mass.). The column was eluted isocratically at a flow rate of 400 IL/min with 25% mobile phase A (0.1% formic acid in water) for 1 minute followed by a linear gradient to 100% mobile phase B (acetonitrile with 0.1% formic acid) over 11 minutes. MS analyses were carried out using electrospray ionization in the negative ion mode using full scan analysis over m/z 200-550 at 70,000 resolution and 3 Hz data acquisition rate. Additional MS settings were: ion spray voltage, −3.5 kV; capillary temperature, 320° C.; probe heater temperature, 300° C.; sheath gas, 45; auxiliary gas, 10; and S-lens RF level 60. Lipids extracts (2 µL) were injected directly onto a 100×2.1 mm ACQUITY BEH C8 column (1.7 µm; Waters; Milford, Mass.). The column was eluted at a flow rate of 450

μL/min isocratically for 1 minute at 80% mobile phase A (95:5:0.1 vol/vol/vol 10 mM ammonium acetate/methanol/acetic acid), followed by a linear gradient to 80% mobile-phase B (99.9:0.1 vol/vol methanol/acetic acid) over 2 minutes, a linear gradient to 100% mobile phase B over 7 minutes, and then 3 minutes at 100% mobile-phase B. MS analyses were carried out using electrospray ionization in the positive ion mode using full scan analysis over m., 200-1100 at 70,000 resolution and 3 Hz data acquisition rate. Additional MS settings were: ion spray voltage, 3.0 kV; capillary temperature, 300° C.; probe heater temperature, 300° C.; sheath gas, 50; auxiliary gas, 15; and S-lens RF level 60. Raw data from methods 1-3 were processed using Progenesis CoMet and QI software (Nonlinear Dynamics Ltd.; Newcastle upon Tyne, UK) for feature alignment, nontargeted signal detection, and signal integration. Targeted processing of a subset of known metabolites was conducted using TraceFinder software (Thermo Fisher Scientific; Waltham, Mass.).

ChIP-qPCR Chromatin ImmunoPrecipitation (ChIP) for Rorγt was performed as previously published (Xiao et al., 2014) using anti-Rorγt antibody (AFKJS-9) and RatIgG2a isotype control antibody (eBioscience, CA). qPCR was performed using the following primers: Il17a CNS2: Fwd: 5'-TGG AAA GTT TTC TGA CCC ACT T; Rv: 5'-GGA AGC TGA GTA CGA GAA GGA A; l17a Inl: Fwd: 5'-ACC AAA GGA ACA AGT GGA AAG A; Rv:5'-TTT GAG AAC CAG TCA TGT CAC C; Il17ap5: Fwd: 5'-GGG GTA GGG TCA ATC TAA AAG C; Rv: 5'-GTG TGC TGA CTA ATT CCA TCC A; Il10 CNS-9: Fwd: 5' TTA CAG AAT GGC ACT TCC AGA G; Rv: 5' CGA TGT ATT AGT TCC GGT GTG T; Il23r in3: Fwd 5'-CTT GGC ATC ACA AAG CTT ACA G: Rv: 5'-ACT GCC AGG CAA GAA TTT ACT C; Il23r in6: Fwd: 5'-TAC CTG AAA GCT GTG CAG AGA G; Rv: 5'-AAG TCC AAG CCT GTGAAA CAA T.

Nanostring nCounter. Nanostring nCounter platform (NanoString Technologies) is used to measure the number of RNA transcripts in RNA samples (FIG. 16I, FIG. 18D). A codeset containing 312 signature genes of Th17 cell differentiation and function as well as 4 additional house-keeping genes were custom-made (Yosef et al., 2013) and used in these experiments. Experimental procedures as detailed by the manufacturer is strictly followed.

Antibodies. Biotinylated anti-CD5L antibody used for flow cytometry analysis was purchased from R & D systems. All other flow cytometry antibodies were purchased from Biolegend. ELISA coating and capturing antibodies for IL-10 were from BD Biosciences and anti-IL-17 were purchased from Biolegend.

Statistical Analysis. Unless otherwise specified, all statistical analyses were performed using the two-tail student t test using GraphPad Prism software. P value less than 0.05 is considered significant (P<0.05=*; P<0.01=; P<0.001=*).

RNA-Seq of population controls. Population controls were generated by extracting total RNA using RNeasy plus Micro RNA kit (Qiagen) according to the manufacturer's recommendations. Subsequently, 1 μL of RNA in water was added to 2 μL of lysis reaction mix, thermocycled using cycling conditions I (as above). Next, 4 μL of the RT Reaction Mix were added and the mixture was thermocycled using cycling conditions II (as above). Finally, 1 μL of the total RT reaction was added to 9 μL of PCR mix and that mixture was thermocycled using cycling conditions III (as above). Products were quantified, diluted to 0.125 ng/μL and libraries were prepared, cleaned, and tested as above.

RNA-Seq preprocessing. RNA-Seq preprocessing was performed using the following. RNA-seq reads are aligned to the NCBI Build 37 (UCSC mm9) of the mouse genome using TopHat (Trapnell et al., 2009). The resulting alignments are processed by Cufflinks to evaluate the abundance (using FPKM) of transcripts from RefSeq (Pruitt et al., 2007). Log transform and quantile normalization is used to further normalize the expression values (FPKM) within each batch of samples (i.e., all single cells in a given run). To account for low (or zero) expression values a value of 1 prior to log transform was added.

Sample filtering and normalization. For each library quality scores were computed using Fastqc, Picard tools, and in-house scripts. Computed scores included: (1) Number of reads, (2) Number of aligned reads, (3) Percentage of aligned reads, (4) Percentage of transcripts identified (compared with the overall number of transcripts identified by at least one cell in the respective run), (5) Percentage of duplicate reads, (6) primer sequence contamination, (7) insert size (mean), (8) insert size (std), (9) Complexity, (10) Percentage of Ribosomal reads, (11) Percentage of Coding reads, (12) Percentage of UTR reads, (13) Percentage of Intronic reads, (14) Percentage of Intergenic reads, (15) Percentage of mRNA reads, (16) Coefficient of variation of coverage, (17) mean 5' Bias, (18) mean 3' Bias, (19) mean 5' to 3' Bias.

Libraries are excluded from further analysis with poor values in either the number of aligned reads, the percentage of aligned reads, or the percentage of identified transcripts. To this end, for a given performance measure x, a minimum cutoff value cx was set by taking the maximum over: {AVG(x)−1.645*STD(x), MED(x)−1.645*MAD(x)} (MED stands for median and MAD is the median absolute deviation). For the latter two performance measures, a Gaussian mixture model is fit to x; if x fits a multi-modal distribution rather than a single Gaussian (using Bayesian Information Criteria to determine the best model), then an additional cutoff z determined as the boundary between the right-most distribution and the other distributions is used. Finally, hard lower bounds (hlb) are introduced for the cutoff values (#aligned reads >25k; percentage of aligned reads>20%; percentage of identified transcripts>20%). Then the cutoff is re-set to be max{cx, z, hlb}. Only cells are retained that scored above the cutoff in all three cases.

As an additional pre-processing step a normalization technique (Risso et al., 2011) is employed to reduce the effects of the quality scores. To this end, a principal component analysis (PCA) is computed over the quality score matrix (a matrix with columns corresponding to cells and rows corresponding to quality scores). Then a global-scaling normalization approach (previously used for GC content normalization in RNA-Seq data (Risso et al., 2011) is used to remove the effects of the top principal components (PCs), until >90% of the variance in the quality matrix is covered (Notably, the quality scores are correlated, and usually the top one or two principal components are sufficient). For a given PC, the cells are divided into 10 equally-sized bins based on their projected values. The normalized expression measures are defined as:

$$E'(i,j)=E(i,j)-\text{Median}(\{E(i,j'), \text{s.t.} \quad j' \in k(j)\})+\text{Median}(\{E(i,:)\})$$

where E(i,j) is the original expression value of gene i in cell j; k(j) denotes the PC-value bin to which cell j belongs; and E(i,:) denotes the median value of gene i across all cells.

This approach was validated by computing PCA on the expression data (before filtering, after filtering, but before normalization, and after filtering and normalization) and calculating the correlation between the quality scores and the top PCs. It was found that before filtering and normalization the main PCs highly correlate with the various library quality scores; indicating that the dominant signal in the pre-normalization data might reflect experimental artifacts. These correlations are reduced after normalization, indicating that the remaining signal is less affected by artifacts (FIG. 6).

Batch correction. Two or more replicates for the majority of the analyzed conditions were obtained. Since the replicates were divided into batches, a procedure to eliminate the pertaining batch effects was applied. Due to substantial differences in the number of detected genes between in vivo and in vitro samples, this analysis is performed separately for the in vivo and the in vitro samples. For a given sample, its filtered gene set is defined as the genes that have an expression level exceeding 10 FPKM in at least 20% of the cells. For a given set of samples (in vivo or in vitro), only the genes that appear in the filtered set of at least two of the samples are retained. This results in ~4,000 genes for the in vivo data and ~7,000 genes for the in vitro. Batch correction is then performed on the resulting matrices (generated by combining all the samples and filtering for the selected genes) using the COMBAT software (Johnson et al., 2007; Novershtern et al.). To eliminate the effects of quality scores on the resulting matrix (i.e., systematic differences in the quality of different samples, rather than cells within a sample), the correction procedure described in the previous section was re-applied.

Taking into account false negatives using weighted analysis. The estimation of transcript abundance as zero can be attributed to false-negatives in the RNA-Seq data. Different individual cells within a sample can have different rates of false-negatives, depending on the quality of the library, and cell integrity. To account for this, for every cell a false-negative curve (FNC) was constructed using the following. The cell-specific FNC represents the false-negative rate as a function of transcript abundance in the bulk population. The FNC is built by taking all the housekeeping genes that are detectable (non zero estimated abundance) in the bulk population and in at least one cell, and arranging them into 30 bins. Then for every bin, the ratio of housekeeping genes that are detectable is computed. Finally, a sigmoid function is fitted to the estimated values (See, e.g., FIG. 6C). These values are used to weigh down possible false-negatives in the subsequent analysis: (1) For correlation-based analysis weighted correlations are used where a zero-value of a gene i in cell j is weighted by the value associated in the FNC of j with the expression of i in the bulk population. For lowly expressed genes the weight will be lower, indicating a higher chance for them to be false-negatives. Notably, the PCA analysis is done by computing the eigenvectors of the weighted covariance matrices. (2) For signature-based scores a weighted version of the gene set enrichment analysis algorithm is used, described next.

RNA Flow-Fish analysis of RNA-expression. Cells prepared under the same conditions as the RNA-seq samples were prepared with the QuantiGene® ViewRNA ISH Cell Assay kit from Affymetrix following the manufacturers protocol. High throughput image acquisition at 60× magnification with an ImageStream X MkII allows for analysis of high-resolution images, including brightfield, of single cells. Genes of interest were targeted by type 1 probes, housekeeping genes by type 4 probes, and nuclei were stained with DAPI. Single cells were selected based on cell properties like area, aspect ratio (brightfield images) and nuclear staining. As a negative control, Bacterial DapB gene (Type 1 probe) were used. Spot counting was performed with the amnis IDEAS software to obtain the expression distributions.

Weighted gene signature scores and gene set enrichment analysis. To interpret the functional implications of the variation between cells, a set of gene signatures was assembled that are indicative of various cell states, using the following. A typical signature is comprised of a "plus" subset and a "minus" subset. A strong match will have extreme, and opposite values for the expression of genes in the two sets (e.g., high values for the "plus" genes and low values for the "minus" genes). The signatures from the following sources are assembled: (1) The immunological signature (ImmSig) collection from MSigDB ((Liberzon et al., 2011); denoted as collection C7): ~2,000 gene sets (each divided into "plus" subset and a "minus" subset) found by comparing immune cells under different conditions (e.g., knockout vs. WT, different stimulations, time post infection etc.). (2) Cell cycle gene sets from M SigDB (Liberzon et al., 2011) and based on the gene ontology database (Huntley et al., 2009); (3) TheNetPath database (Kandasamy et al., 2010): a collection of gene sets (each divided into "plus" subset and a "minus" subset) that are downstream of various immune signaling and are either positively or negatively regulated. (4) Signatures of T helper cell subsets, based on previous work (Wu et al., 2013)(Xiao et al., 2014). (5) Signatures of exhausted and memory T cells (Crawford et al., 2014); (6) Microarray data from Sarkar et al (Sarkar et al., 2008), comparing memory vs. effector CD8+CT cells; (7) Microarray data from Muranski et al (Muranski et al., 2011), tracking the development of Th17 and Th1 cell in an adoptive transfer model. (8) Microarray data from Kurachi et al (Kurachi et al., 2014), tracking the development of CD4+ and CD8+ T cells in acute and chronic infection models. (9) Microarray data comparing IL-23R knockout mice $CD4^+$ T cells differentiated in IL-1β+IL-6+IL-23 to WT (Y. L. and V. K. K, unpublished data). Notably, while sources 1-5 already provide processed gene sets, analysis of the remaining sources is based on the raw data (microarrays). This data was analyzed to infer differentially expressed genes. To this end, all genes with a fold change over 1.5 are reported; if there are at least two replicates, consistent (up or down) and >1.5 fold change in all pairwise comparisons is required (all replicates of condition "A" vs. all replicates of condition "B" must show fold change above the cutoff). To avoid spurious fold levels due to low expression values a small constant is added to the expression values (c=50) prior to the analysis. To search for signatures that are significantly expressed in a subset of cells the following test was performed: First, standardizing the rows of the expression matrix (i.e., every cell is normalized w.r.t. the other cells) and weighing down zero entries as above (multiplying the respective entries in the Z-normalized matrix by (1−probability for false negative)). Given a signature S={$S^+$,$S^-$}, a gene set enrichment analysis (GSEA) for every cell independently is performed, using the values in the standardized, weighted matrix. To account for the direction, the values in the rows that correspond to the genes in $S^-$ are negated. The standard GSEA formulation with 250 randomizations is used, where in each randomized run a random selection of S is considered, and 50 randomly selected cells. The reported p-values are computed empirically by comparing to the resulting 12,500 random scores. A 5% FDR cutoff is computed using the Benjamini-Hochberg scheme (Benjamini and Hochberg (1995) and only signatures that had a p-value below the cutoff in at least 10% of the cells is reported. To associate gene signatures with cell's location along the principle components, for every cell a signature score is computed. For every cell-signature pair, Applicants estimated whether the expression of genes in the signature significantly varied either: (1) across cells of the same source or (2) between conditions (e.g., LN vs. CNS). A subset of the results for this analysis are presented in FIGS. 2 and 4. The complete result set is provided in Table S2 (Gaublomme 2015). To identify signatures that significantly vary between conditions, Applicants then compute for every cell a signature score. Given a signature $S=\{S^+,S^-\}$, Applicants define the score as the weighted mean of the genes in $S^+$ minus the weighted mean of the genes in $S^-$. Applicants use the gene expression values under the same normalization and weighting scheme as in the weighted PCA analysis above. Signatures that significantly vary between two given conditions ("A", "B") were identified by comparing the distributions of signature scores of cells from condition "A" vs. cells of condition "B" (Kolmogorov-Smirnov (KS) test, FDR<$10^{-4}$). For the signatures with significant variation in at least one of the two tests above, Applicants next investigated whether they are significantly associated with the main PCs. To this end, Applicants computed a Pearson correlation coefficient between the signature score and each of the first two PCs (i.e., comparing two vectors whose length equals the number of cells: one vector is the signature scores, the other vector is the projection value (i.e., x- or y-coordinate) of that cell in the PC space; FIGS. 2-4 and Table S2 (Gaublomme 2015)). Applicants plotted selected correlations on a normalized PCA map (for example: FIG. 2A, numbered open circles).

TF binding enrichment analysis. TFs were looked for with a significant overlap between their previously annotated target genes and the genes that correlated with each principal component using the following. TF-target interaction data is obtained from public databases (Chen et al., 2011; Ciofani et al., 2012a; Lachmann et al., 2010; Liberzon et al., 2011; Linhart et al., 2008). To select the set of genes for a given PC (PC1 or PC2), for every gene the Pearson correlation between its log expression value in every cell (adding a value of 1 to avoid effects of low expression levels) and the projection of this cell to that PC (i.e., the X [for PC1] or Y [for PC2] coordinate in the PC plot) is computed. Only genes with a p-value lower than a 5% FDR cutoff are retained. For every TF in the database, the statistical significance of the overlap between its putative targets and each of the groups defined above using a Fisher's exact test is computed. Cases where $p<5*10^{-5}$ and the fold enrichment >1.5 are included. Finally, in FIG. 2, only cases in which the TF was expressed above a minimal level (5 FPKM) in at least one of the respective bulk population conditions are reported.

Relating the in vitro differentiated cells to their in vivo counterparts. To perform the analysis presented in FIG. 3B, C genes are identified that are significantly up- or down-regulated in each sub-population of in-vivo cells (FDR<0.05; one-vs-all KS test; Table S4 (Gaublomme 2015), Table 6). A signature is then defined by retaining only genes that are annotate with immune response function based on the gene ontology database (Huntley et al., 2009). Finally, the signature analysis above is repeated to score the in-vitro derived cells.

Voronoi diagrams. Voronoi diagrams were used in order to delineate areas (in the space of the first two principle components (PC)) that are most strongly associated with given signatures. Specifically, given a set of signature $S=\{s\_1, \ldots, s\_k\}$ is computed for every cell k signature scores (one for each signature). For each signature i the top 5 high-scoring cells are selected, and point $c\_i$ is computed as the centroid of these points in the PC map (be averaging over their x and y coordinates). Given a set of centroid points $\{c\_1, \ldots, c\_k\}$, the Voronoi diagram divides the space into respective regions $r\_1, \ldots, r\_k$ such that for every $1 \leq i \leq k$, $c\_i$ is the closest centroid to all the points in r i. Given a set of signatures that were significantly associated with the PC map in FIG. 2a, the above procedure was followed to compute the Voronoi diagram in FIG. 2b.

Defining biomodal genes. To quantify the shape of heterogeneity in the expression levels of genes across cells, the following scheme was devised: First, a number of statistical tests are applied in order to identify genes that exhibit a bimodal distribution: (1) Hartigans Dip Test (with a p-value cutoff of 5%); (2) Gaussian mixture model—comparing a 2- or 3-Gaussian model to a 1-Gaussian model using the Bayesian Information Criteria; (3) More than 10% of cells deviate from the mean by more than 2.32 times the standard deviation (corresponding to a p-value of 1%), (4) More than 10% of cells deviate from the median by more than 2.32 times the median absolute deviation. For genes identified by at least one of the tests, two mixture models are fit using expectation maximization: (1) Exponential (for "non-expressing" cells) and normal (for "expressing" cells); and (2) Uniform (for "non-expressing" cells) and normal (for "expressing" cells). The model with the best fit us retained. Using this model a cutoff x is determined for each gene such that cells with expression higher than x are considered "expressing cells". x is determined as the maximum between {0, the boundary between the Gaussian distribution and the alternative distribution (for bi-modal genes)}. Finally, to define the set of bimodal genes, it is required (in addition to the aforementioned tests) that the percentage of "expressing cells" is smaller than 90%.

Gene ranking. An unbiased approach was used to select potential regulator of Th17 pathogenicity. The ranking is based on: (1) Correlation with the first principle component in the in-vitro derived Th17 cells (using Tgfb1+IL6; FIG. 4c). To this end, the correlation between the expression of a given gene in each cell and the PC1 projection value of each cell (X coordinate in FIG. 4b) is computed. A 5% FDR cutoff is computed using the Benjamini-Hochberg scheme and only correlations below that cutoff are reported. (2), (3) A similar analysis is performed for correlations with the first and second principle components in the in-vivo derived Th17 cells (FIG. 2a). (4) Correlation with immune-related genes in the anti-correlated modules in FIG. 4b (a "single cell pathogenicity signature" consisting of a pro-inflammatory module: Ccr6, Il18r1, Ccl4, Ccl20, Ctla4, Il17a, Il2, Cd40lg, Tnf, Il21, Cxcr3, Tnfsf9, Ebi3, and Stat4; and a regulatory module: Ccr4, Il10, Il24, IL9, Il16, Irf4, Sigirr, Il21r, and Il4ra). (5) A similar analysis using a curated pathogenicity signature (genes that are positively or negatively associated with pathogenic Th17). In the following the analysis done to evaluate selection criteria (4) and (5) is explained. For a given gene, and a signature (consisting of two opposing subsets; e.g., pro-inflammatory genes and regulatory genes) it is desirable to evaluate the statistical relationship between them. To this end, the values x1 and x2 are computed as its average correlation with the two opposing subsets respectively. Then for cases where sign (x1)!=sign(x2) its score is designated as sign(x1)*min{abs (x1), abs(x2)}. To estimate the significance of this score the original expression matrix is shuffled, and the test is repeated for 50 times. The shuffling is done independently for each row (gene), but it retains the original values of the gens in the signature. This way it conserves the expression distribution of each gene, as well as correlations between the member genes of the signature. Only genes that "failed" at most twice are reported, when compared against the shuffled data (empirical p-value<=0.04). Finally, the genes are ranked based on their scores (correlation values for criteria (1)-(3) and an aggregate score for criteria (4)-(5)). Here genes are stratified into groups of 5 (first five genes are ranked $1^{st}$; next five genes are ranked $2^{nd}$, etc.). The final score is set as the second best rank among criteria (1-5), thus requiring a gene to perform well in at least two tests. This score is amended to prioritize (ranking $1^{st}$) genes that come up both in the in-vitro analysis (criteria 1, 4, 5; top 95%) and the in-vivo analysis (criteria 2, 3; top 75%). To break the ties between equally ranked genes, the following features are used, which are based on bulk-population studies: (a) whether the gene is significantly induced during Th17 differentiation (using previous analysis (Yosef et al., 2013), which considers only cases where the induction happened after 4 hours to exclude non-specific hits); (b) whether the gene was differentially expressed in response to Th17-related perturbations in previous studies, using the same collection of knockouts used for ranking in previous work (Yosef et al., 2013). (c) Whether the gene is bound by key Th17 transcription factors, and is affected by their perturbation during Th17 differentiation. To this end, the combined score computed by Ciofani et al. (Ciofani et al., 2012b) is used.

Population based studies used to compare top ranking genes found by bulk population vs. single-cell analysis: Population based data was based on either a compendium of 41 studies of Th17 cells from our labs, (Table S7 (Gaublomme 2015)), or a literature based ranking (Ciofani et al., 2012). Each study from our labs is a comparison of two treatments (e.g., Th17 cells with or without sodium) for which Applicants identified differentially expressed genes (as described in the Methods section "Signature scores and gene set enrichment analysis"). Applicants then ranked each gene according to the number of studies (0-41) in which it was identified as differentially expressed. The literature based study (Ciofani et al., 2012) considers a combination of RNA-seq and ChIP-seq data, prioritizing genes that are differentially expressed, and bound by key Th17 transcription factors, such as Rorc.

Flow cytometry and intracellular cytokine staining. Sorted naïve T cells were stimulated with phorbol 12-myristate 13-acetate (PMA) (50 ng/ml, Sigma-aldrich), ionomycin (1 μg/ml, Sigma-aldrich) and a protein transport inhibitor containing monensin (Golgistop) (BD Biosciences) for 4 h before detection by staining with antibodies. Surface markers were stained in PBS with 1% FCS for 20 min at room temperature, then subsequently the cells were fixed in Cytoperm/Cytofix (BD Biosciences), permeabilized with Perm/Wash Buffer (BD Biosciences) and stained with Biolegend conjugated antibodies, that is, Brilliant violet 650 anti-mouse IFN-γ (XMG1.2) and allophycocyanin-anti-IL-17A (TC11-18H10.1), diluted in Perm/Wash buffer as described (Bettelli et al., 2006). Foxp3 staining was performed with the Foxp3 staining kit by eBioscience (00-5523-00) in accordance with their 'One-step protocol for intracellular (nuclear) proteins'. Data were collected using either a FACS Calibur or LSRII (Both BD Biosciences), then analysed using Flow Jo software (Treestar).

Analysis of RNA-Seq data from knockout cells. RNA-Seq was used to identify genes that are differentially expressed in knockout T cells, (compared with WT). To this end, replicate data was used to empirically infer a decision cutoff, above which the genes are reported. The decision cutoff is defined as a function of the magnitude of gene expression—genes that are lowly expressed are associated with a higher decision cutoff. To infer the cutoffs, first a set of replicate RNA-Seq experiments is collected. For each pair of replicates, the fold difference across all genes is calculated. The genes are then stratified into 10 bins (taking 10 quartiles), and then for each bin i the standard deviation d_i of fold changes between all pairs of replicates is computed. The fold change cutoff is then determined in each bin i to be mar {1.5, d_i}. As an additional stringent step, the obtained fold change cutoffs is smoothed, such that if the cutoff for a bin i is lower than bin i+1 (which includes genes with higher expression levels) then the cutoff of bin i+1 is set to that of bin i. For given knockout experiments with n "cases" and m "controls", differentially expressed only cases are expressed in which more than (n×m)/2 comparisons are above the cutoff, and all comparisons are consistent (i.e., up- or down-regulation). As above, to avoid spurious fold levels due to low expression values a small constant to the expression values (5 FPKM) prior to the analysis is added. For the analysis in FIG. 5E Applicants define the sets of all genes that either positively or negatively correlate with the first PC in cells differentiated with TGF-β1+IL-6 (FIG. 4C; Pearson correlation, FDR<5%). Applicants then evaluate the significance of overlaps between these sets and the knockout-affected genes using a hypergeometric test. Applicants use the same approach to identify genes that are differentially expressed in the gut vs. the LN or CNS.

RNA Flow-Fish. RNA-fish using QuantiGene® Flow-RNA Assay was performed in accordance with manufacturers guidelines for suspension cells, with minor modifications such as pipetting instead of vortexing, cells were stained with dapi and type 1 gene probes only. Cells were imaged using an ImageStream X MkII with a 60× objective. As a negative control, the expression of the bacterial DapB gene, in addition to Csf2, Itgax and Scd1, which are not expressed on Th17 cells in the TGF-β1/IL-6 condition at 48h was checked.

Quantification of cytokine secretion using ELISA. Naïve T cells from knockout mice and their wild-type controls were cultured as described above, their supernatants were collected after 48h and 96h, and cytokine concentrations were determined by ELISA (antibodies for IL-17 and IL-10 from BD Bioscience) or by cytometric bead array for the indicated cytokines (BD Bioscience), according to the manufacturers' instructions.

TABLES

The following Tables form a part of this disclosure:

TABLE 1

Sample information:
Columns Name; indicates sample origin,
Batch; samples with the same batch number originated from the same animal
(in addition, batch 1&2 also come from the same animal and serve as technical replicates),
Cells before filtering; the number of captured, viable single cells on the Fluidigm C1 chip,
Cells after filtering; number of cells that survived filtering criteria (Experimental Procedures),
Sequencing Reads; Number of reads sequenced on Illumina HiSeq (average across all cells),
% Aligned reads: percentage of reads that align to the NCBI Build 37 (UCSC mm9)
of the mouse genome using TopHat (average across all cells)

| Name | Batch | #Cells after filtering | #Cells before filtering | Average #Sequencing Reads | Average % Aligned reads |
|---|---|---|---|---|---|
| EAE-CNS-IL-17A/GFP+ | 1 | 48 | 86 | 2890292 | 41,134266 |
| EAE-CNS-IL-17A/GFP+ | 2 | 61 | 75 | 2728575 | 45,292021 |
| EAE-CNS-IL-17A/GFP+ | 4 | 57 | 68 | 2800285 | 48,0711565 |
| EAE-LN-IL-17A/GFP+ | 1 | 39 | 33 | 2990609 | 35,9401461 |
| EAE-LN-IL-17A/GFP+ | 2 | 40 | 38 | 2593529 | 45,8093984 |
| EAE-LN-IL-17A/GFP+ | 3 | 57 | 70 | 3025209 | 74,5995014 |
| TGFB1_IL6-48h | 5 | 56 | 80 | 5468975 | 69,3823763 |
| TGFB1_IL6-48h | 6 | 74 | 93 | 2229856 | 67,1002098 |
| TGFB1_IL6-48h-IL-17A/GFP+ | 7 | 67 | 86 | 1945212 | 63,6447485 |
| TGFB1_IL6-48h-IL-17A/GFP+ | 8 | 67 | 94 | 3460935 | 61,2721476 |
| TGFB1_IL6-48h-L-17A/GFP+ | 9 | 17 | 77 | 6316929 | 56,1096561 |
| IL1B_IL6_IL23-48h-IL-17A/GFP+ | 8 | 69 | 90 | 3208148 | 61,2153719 |
| IL1B_IL6_IL23-48h-IL-17A/GFP+ | 7 | 70 | 86 | 1936425 | 65,2173455 |

TABLE 2

Ranking of potential regulators of Th17 pathogenicity. Table 2: Potential
regulators of Th17 pathogenicity (rows in FIG. 4B) are ranked based on: (1) Correlation with
the first principle component in the in vitro derived Th17 cells (using TGF-β1 + IL-6; FIG. 4C).
(2, 3) Correlations with the first and second principle components in the in vivo derived Th17
cells (FIG. 2A). (4) Correlation with immune-related genes in the columns of FIG. 4B. (5) A
Correlation with a curated pathogenicity signature (genes that are positively or negatively
associated with pathogenic TH17 cells, (Lee et al., 2012)). The values in these respective
columns indicate the rank (percentile) of the gene in the respective test, relative to all other
candidate genes. Highly scoring genes are the ones that are bound by key Th17 transcription
factors, and affected by perturbation of these factors during Th17 differentiation. The values in
the respective column indicate the rank (percentile) of the gene, relative top all other candidate
genes. Negative values indicate a negative correlation.

Sources for single-cell score

| Gene | Description | Rank | Attributes | Known | Profiled | Score | In-vivo | PC1 rank |
|---|---|---|---|---|---|---|---|---|

In-vivo PC2 rank     In-vitro (Tgfb1 + IL6) PC1 rank  Rank by correlation with single-cell pathogenicity signature (FIG. 4c) Rank by correlation with curate pathogenic signature (Lee et al. 2012)

| Gene | Description | Rank | Attributes | Known | Profiled | Score | In-vivo | PC1 rank |
|---|---|---|---|---|---|---|---|---|
| CTLA4 | cytotoxic T-lymphocyte-associated protein 4 | 1 | | | | "ImmuneResponse, Known, CellSurface" | | |
| | 1 | 0 | 1 | 0 | 0.994565217 | −0.804347826 | 0.777173913 | 0.913043478 |
| GPR65 | G-protein coupled receptor 65 | 1 | | 0 | 1 | 1 | 0 | 0.967391304 |
| | −0.369565217 | 0.586956522 | 0.777173913 | | | | | |
| REL | reticuloendotheliosis oncogene | 1 | | | "TF, Known, PathogenicSignature (pos)" | | | 1 |
| | 0 | 1 | 0 | 0.967391304 | −0.804347826 | 0.722826087 | 0.451086957 | |
| TMEM109 | transmembrane protein 109 | 1 | | 0 | 0 | 1 | −0.967391304 | 0 |
| | −0.614130435 | 0.668478261 | 0.804347826 | | | | | |
| CD226 | | 1 | CellSurface | 0 | 0 | 1 | 0.967391304 | −0.423913043 |
| | 0.695652174 | | | | | | | |
| BCL2A1B | | 1 | 0 | 0 | 1 | 0 | 0.994565217 | −0.994565217 | 0.75 |
| | 0.913043478 | | | | | | | |
| GBP2 | guanylate binding protein 2 | 1 | | PathogenicSignature (pos) | | 0 | 0 | 1 |
| | 0.967391304 | 0.831521739 | 0.777173913 | 0 | 0 | | | |
| ECE1 | endothelin converting enzyme 1 | | 1 | 0 | 0 | 1 | 0 | |
| | 0.967391304 | −0.47826087 | 0.668478261 | 0.885869565 | | | | |
| RAMP1 | receptor (calcitonin) activity modifying protein 1 | | | 1 | | PathogenicSignature (pos) | | |
| | 0 | 0 | 1 | 0 | 0.967391304 | −0.695652174 | 0.559782609 | 0.695652174 |
| BCL2A1D | | 1 | ImmuneResponse | 0 | 0 | 1 | 0 | 0.994565217 | −0.994565217 |
| | 0.722826087 | 0.994565217 | | | | | | |
| PLEK | pleckskin | 1 | TF | 0 | 0 | 1 | 0.994565217 | 0.885869565 | — |
| 0.858695652 | 0.722826087 | 0.940217391 | | | | | | |
| BCL2A1A | | 1 | | 0 | 0 | 1 | 0.858695652 | 0.994565217 | −0.994565217 |
| | 0.777173913 | 0.967391304 | | | | | | |
| ABCG1 | "ATP-binding cassette, sub-family G (WHITE), member 1" | | | 1 | | 0 | 0 | |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|------|-------------|------|------------|-------|----------|-------|---------|----------|
| IL2 | interleukin 2 | 1 | 0.967391304 | −0.91304378 | 0.940217391 | −0.858695652 | −0.614130435 | |
| | | 2 | | "ImmuneResponse, Known, CytokineChemokine" | | 1 | 0 | |
| | | 0.994565217 | 0 | 0 | −0.994565217 | 0.913043478 | 0.885869565 | |
| FAIM3 | | 3 | | 0 | 1 | 0.967391304 | 0 | 0 | 0.885869565 | — |
| | 0.994565217 | | −0.994565217 | | | | | | |
| 1600014C10RIK | RIKEN cDNA 1600014C10 gene | 3 | | 0 | 0 | 0.967391304 | 0 | |
| | 0 | 0.967391304 | −0.940217391 | −0.940217391 | | | | | |
| PDCD1 | programmed cell death 1 | 3 | | "PathogenicSignature (neg), CellSurface" | | 0 | |
| | 0 | 0.967391304 | 0 | 0.777173913 | −0.967391304 | 0.858695652 | 0.722826087 | |
| ID3 | inhibitor of DNA binding 3 | 3 | | "ImmuneResponse, TF, Known, PathogenicSignature (pos)" | | | |
| | 1 | 0 | 0.967391304 | 0 | 0 | −0.967391304 | 0.858695652 | 0.994565217 |
| SLFN2 | schlafen 2 | 3 | | 0 | 0 | 0.967391304 | 0 | −0.967391304 |
| | 0.777173913 | 0.641304348 | | | | | | | |
| ZBTB32 | zinc finger and BTB domain containing 32 | 3 | | TF | 0 | 1 | 0.967391304 |
| | 0 | 0 | −0.967391304 | 0.967391304 | 0.994565217 | | | | |
| NFKBID | | 4 | 0 | 0 | 0.940217391 | 0 | 0.75 | −0.994565217 |
| | 0.831521739 | 0.586956522 | | | | | | | |
| IL16 | interleukin 16 | 4 | | "Known, CytokineChemokine" | 1 | 0 | 0.940217391 | 0 |
| | −0.940217391 | 0.913043478 | 0.451086957 | 0.505434783 | | | | | |
| SLA | src-like adaptor | 4 | | PathogenicSignature (pos) | 0 | 0 | 0.940217391 |
| | 0 | 0.804347826 | −0.75 | 0.831521739 | 0.994565217 | | | | |
| GM2792 | | 4 | 0 | 0 | 0.940217391 | 0 | 0.831521739 | −0.885869565 |
| | 0.967391304 | 0.967391304 | | | | | | | |
| MS4A4B | "membrane-spanning 4-domains, subfamily A, member 4B" | | 5 | | | | |
| | PathogenicSignature (pos) | 0 | 0 | 0.913043478 | 0 | 0 | −0.586956522 | |
| | 0.885869565 | 0.913043478 | | | | | | | |
| TGTP2 | | 5 | PathogenicSignature (pos) | 0 | 0 | 0.913043478 | 0.913043478 |
| | 0.695652174 | 0.913043478 | 0.369565217 | 0.39673913 | | | | | |
| TGTP1 | | 5 | 0 | 0 | 0.913043478 | 0.940217931 | 0.75 | 0.913043478 |
| | −0.559782609 | −0.586956522 | | | | | | | |
| IL17A | interleukin 17A | 6 | | "ImmuneResponse, PathogenicSignature (neg), Known, CytokineChemokine" | 1 | 0 |
| | 0.885869565 | 0 | 0 | −0.913043478 | 0.451086957 | 0.804347826 | | | |
| ACSL4 | acyl-CoA synthetase long-chain family member | 4 | 6 | | PathogenicSignature (neg) |
| | 0 | 0 | 0.885869565 | 0.885869565 | 0.885669565 | −0.641304348 | 0 | | |
| | 0.260869565 | | | | | | | | |
| SOCS2 | suppressor of cytokine signaling 2 | 6 | | | | | | |
| | "PathogenicSignature (neg), Known, CytokineChemokine" | 1 | 0 | 0.885869565 | 0 | | | |
| | 0 | 0.885869565 | −0.967391304 | −0.885869565 | | | | | |
| FOXP1 | forkhead box P1 | 6 | | "ImmuneResponse, TF" | 0 | 0 | 0.885869565 |
| | 0.885869565 | −0.994565217 | 0.206521739 | 0.288043478 | 0 | | | | |
| SYTL3 | synaptotagmin-like 3 | 6 | | 0 | 0 | 0.885869565 | −0.858695652 |
| | 0.940217391 | 0.858695652 | 0.913043478 | 0.858695652 | | | | | |
| MAPKAPK3 | | 6 | | "Kinase, PathogenicSignature (neg)" | 0 | 0 | 0.885869565 |
| | 0 | 0.940217391 | −0.885869565 | 0 | 0.179347826 | | | | |
| PRKCSH | protein kinase C substrate 80K-H | 6 | | 0 | 0 | 0.885869565 | |
| | 0.885869565 | 0 | −0.315217391 | 0.994565217 | 0.940217391 | | | | |
| GNG10 | "guanine nucleotide binding protein (G protein), gamma 10" | 6 | | 0 | 0 |
| | 0.885869565 | 0.940217391 | 0.885869565 | 0 | 0 | 0.423913043 | | | |
| GM2833 | | 6 | 0 | 0 | 0.885869565 | 0 | 0.885869565 | −0.804347826 |
| | 0.885869565 | 0.831521739 | | | | | | | |
| PPID | | 6 | 0 | 0 | 0.885869565 | −0.885869565 | 0.75 | −0.940217391 |
| | 0.668478261 | 0.233695652 | | | | | | | |
| CD5L | CD5 antigen-like | 6 | | CellSurface | 0 | 1 | 0.858695652 | 0 | 0 |
| | −0.858695652 | 0.940217391 | 0.967391304 | | | | | | |
| TNF | tumor necrosis factor | 6 | | "ImmuneResponse, Known, CytokineChemokine" | 1 | 0 |
| | 0.858695652 | 0.858695652 | 0.858695652 | −0.559782609 | 0.39673913 | 0.423913043 | | | |
| IFI47 | interferon gamma inducible protein 47 | 6 | | 0 | 0 | 0.858695652 | 0 |
| | 0 | 0.940217391 | −0.804347826 | −0.668478261 | | | | | |
| CD44 | CD44 antigen | 6 | | CellSurface | 0 | 0 | 0.858695652 | 0 | 0.858695652 |
| | −0.804347826 | 0.858695652 | 0.858695652 | | | | | | |
| GADD45B | growth arrest and DNA-damage-inducible 45 beta | | | 6 | | 0 | 0 |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|---|---|---|---|---|---|---|---|---|
| SH2D1A | | | | 0.858695652 | 0.858695652 | 0.913043478 | −0.505434783 | 0.641304348 0.559782609 |
| | | 6 | "ImmuneResponse, PathogenicSignature (pos)" | 0 | 0 | | 0.858695652 | |
| GATM | | 0 | 0 | −0.3639565217 | 0.994565217 | 0.858695652 | | |
| | glycine amidinotransferase (L-arginine: glycine amidinotransferase) | | | | | 7 | | 0 |
| | | 0 | 0.831521739 0 | 0 | 0.831521739 | −0.831521739 | −0.858695652 | |
| N4BP1 | NEDD4 binding protein 1 | 7 | | 0 | 0 | 0.831521739 0 | | 0 |
| | 0.722826087 | −0.913043478 | −0.913043478 | | | | | |
| NEK6 | NIMA (never in mitosis gene a)-related expressed kinase 6 | | | | | 7 | | |
| | "Kinase, PathogenicSignature (neg)" | 0 | 0 | | 0.831521739 | 0 | 0 | — |
| | 0.831521739 | 0.641304348 | 0.75 | | | | | |
| SUSD3 | 7 | 0 | 0 | 0.831521739 | −0.831521739 | 0.858695652 | 0.75 | |
| | 0 | 0 | | | | | | |
| MOV10 | Moloney leukemia virus 10 | 7 | | 0 | 0 | 0.831521739 0 | | 0 |
| | 0.75 | −0.967391304 | −0.831521739 | | | | | |
| DUSP4 | 7 | 0 | 0 | 0.831521739 | 0 | 0 | −0.831521739 | |
| | 0.831521739 | 0.641304348 | | | | | | |
| IER3 | immediate early response 3 | 8 | PathogenicSignature (neg) | 0 | 0 | | | |
| | 0.804347826 | 0.994565217 | 0.804347826 0 | 0 | 0.75 | | | |
| EEA1 | early endosome antigen 1 | 8 | | 0 | 0 | 0.804347826 0 | | 0 |
| | −0.940217931 | 0.804347826 | 0.315217391 | | | | | |
| BCAT1 | "branched chain aminotransferase 1, cytosolic" | | | 8 | | 0 | 0 | |
| | 0.804347826 | 0 | 0 | −0.913043478 | 0.39673913 | 0.423913043 | | |
| MAPKAPK2 | MAP kinsae-activate protein kinase 2 | 8 | "Kinase, PathogenicSignature (neg)" | | | | | |
| | 0 | 0 | 0.804347826 | 0.913043478 | 0.804347826 0 | | −0.668478261 | — |
| | 0.804347826 | | | | | | | |
| SASH3 | SAM and SH3 doman containing | 3 | 8 | ImmuneResponse | 0 | | 0.804347826 | |
| | −0.913043478 | −0.804347826 | 0.586956522 | 0.423913043 | 0.451086957 | | | |
| STAT4 | signal transducer and activator of transcription 4 | | | | | 8 | | |
| | "ImmuneResponse, TF, Known, PathogenicSignature (pos)" | 1 | 0 | | 0.804347826 | 0 | | |
| | 0.858695652 | −0.315217391 | 0.885869565 | 0.804347826 | | | | |
| CTLA2B | cytotoxic T lymphocyte-associated protein 2 beta | | | 9 | | 0 | 0 | |
| | 0.777173913 | 0 | 0 | 0.831521739 | −0.885869565 | −0.777173913 | | |
| CCL20 | chemokine (C—C motif) ligand 2 | 0 | 9 | "ImmuneResponse, Known, CytokineChemokine" | | | | |
| | 1 | 0 | 0.777173913 | 0 | −0.722826087 | 0.532608696 | 0.777173913 | |
| PDGFB | "platelet derived growth factor, B polypeptide" | | | 9 | PathogenicSignature (neg) | | | |
| | 0 | 0 | 0.777173913 | 0 | 0 | −0.777173913 | 0.315217391 | 0.342391304 |
| TNFSF9 | "tumor necrosis factor (ligand) superfamily, member 9" | | | | | 9 | | |
| | "ImmuneResponse, Known, CellSurface, CytokineChemokine" | 1 | 0 | | 0.777173913 | 0 | | |
| | 0.777173913 | −0.47826087 | 0.75 | 0.940217391 | | | | |
| IFI35 | interferon-induced protein 35 | 9 | TF | 0 | 0 | 0.777173913 0 | | |
| | 0.804347826 | 0.695652174 | −0.695652174 | −0.777173913 | | | | |
| 1810029B16RIK | RIKEN cDNA 180029B16 gene | 9 | | 0 | 0 | | 0.777173913 | 0 |
| | 0 | −0.532608696 | 0.614130435 | 0.913043478 | | | | |
| GEM | GTP binding protein (gene overexpressed in skeletal muscle) | | | | | 10 | | |
| | PathogenicSignature (pos) | 0 | 0 | 0.75 | 0 | 0.831521739 | −0.423913043 | |
| | 0.369565217 | 0.75 | | | | | | |
| IL4RA | "interleukin 4 receptor, alpha" | | | 10 | | | | |
| | "ImmuneResponse, SurfaceReceptor, Known, CellSurface, CytokineChemokine" | | | 1 | 0 | | | |
| | 0.75 | 0.885869565 | 0.722826087 | 0.451086957 | −0.505434783 | −0.641304348 | | |
| INPP5B | inositol polyphosphate-5-phosphatase B | 10 | | 0 | 0 | 0.75 | 0 | |
| | 0.722826087 | −0.532608696 | 0.722826087 0.75 | | | | | |
| RHOF | 10 | 0 | 0 | 0.75 | 0 | 0.75 | −0.75 | 0.695652174 |
| | 0.559782609 | | | | | | | |
| PPAN | peter pan homolog (*Drosophila*) | 10 | | 0 | 0 | 0.75 | 0 | 0 |
| | −0.940217391 | 0.75 | 0.179347826 | | | | | |
| MAGOHB | mago-nashi homolog B (*Drosophila*) | 10 | | 0 | 0 | 0.75 | −0.913043478 | |
| | 0 | −0.75 | 0.532608696 | 0.532608696 | | | | |
| TYW3 | 10 | 0 | 0 | 0.75 | 0 | 0 | −0.777173913 | 0.777173913 |
| | 0.668478261 | | | | | | | |
| IRF1 | interferon regulatory factor 1 | 11 | | | | | | |
| | "ImmuneResponse, TF, Known, PathogenicSignature (pos)" | 1 | 0 | | 0.722826087 | 0 | | |
| | 0 | 0.885869565 | 0.369565217 | 0 | | | | |
| CD40LG | CD40 ligand | 11 | "ImmuneResponse, Known, CellSurface, CytokineChemokine" | 1 | 0 | | | |
| | 0.722826087 | 0 | 0.75 | −0.722826087 | 0.641304348 | 0.614130435 | | |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|---|---|---|---|---|---|---|---|---|
| BCL2L1 | BCL2-like 1 | 11 | PathogenicSignature (neg) | 0 | 0 | 0.722826087 | 0.722826087 | 0 |
| | | | | -0.804347826 | 0.342391304 | 0.369565217 | | |
| SLC35A1 | | 11 | | 0 | 0 | 0.722826087 | -0.777173913 | 0 |
| | | | | 0.614130435 | 0.315217391 | | | |
| RPF2 | | 11 | | 0 | 0 | 0.722826087 | 0 | -0.722826087 |
| | | | | 0.206521739 | 0 | -0.858695652 | | |
| TM2D3 | TM2 domain containing 3 | 11 | | 0 | 0 | 0.722826087 | 0 | 0 |
| | | | | -0.722826087 | 0.777173913 | 0.722826087 | | |
| IRF4 | interferon regulatory factor 4 | 12 | "ImmuneResponse, TF, PathogenicSignature (neg), Known" | 1 | 0 | 0.695652174 | 0 | 0 |
| | | | | 0.559782609 | -0.75 | -0.722826087 | | |
| IL18R1 | interleukin 18 receptor 1 | 12 | "ImmuneResponse, SurfaceReceptor, Known, CellSurface, CytokineChemokine" | 1 | 0 | 0.695652174 | 0 | |
| | | | | 0.695652174 | 0 | 0.940217391 | 0 | 0.722826087 |
| ZFP36 | zinc finger protein 36 | 12 | | 0 | 0 | 0.695652174 | 0.994565217 | 0 |
| | | | | 0.695652174 | -0.586956522 | 0.423913043 | | |
| ASRGL1 | asparaginase like 1 | 12 | | 0 | 0 | 0.695652174 | 0 | 0 |
| CBWD1 | COBW domain containing 1 | 12 | | 0 | 0 | 0.695652174 | 0 | 0 |
| | | | | -0.777173913 | 0.505434783 | 0.668478261 | | |
| GTPBP4 | GTP binding protein 4 | 12 | | 0 | 0 | 0.695652174 | 0 | -0.885869565 |
| | | | | -0.695652174 | 0.206521739 | 0.206521739 | | |
| IRF2 | interferon regulatory factor 2 | 12 | TF | 0 | 0 | 0.695652174 | | |
| | | | | 0.913043478 | -0.695652174 | 0.233695652 | 0.179347826 | 0.668478261 |
| HIVEP3 | human immunodeficiency virus type I enhancer binding protein 3 | 13 | TF | 0 | 0 | 0.668478261 | 0 | -0.668478261 |
| | | | | | | | 0.233695652 | 0.206521739 |
| MS4A6B | "membrane-spanning 4-domains, subfamily A, member 6B" | 13 | "PathogenicSignature (pos), CellSurface" | 0 | 0 | 0.668478261 | 0 | — |
| | | | | 0.668478261 | 0 | 0.967391304 | 0.722826087 | |
| OLFM2 | | 13 | | 0 | 0 | 0.668478261 | -0.668478261 | 0 |
| | | | | 0.152173913 | | | | |
| CCR6 | chemokine (C—C motif) receptor 6 | 13 | "SurfaceReceptor, PathogenicSignature (neg), Known, CellSurface, CytokineChemokine" | 1 | 0 | | | |
| | | | | 0 | 0.641304348 | 0 | -0.913043478 | -0.641304348 0 | 0.369565217 |
| COG6 | component of oligomeric golgi complex 6 | 13 | "ImmuneResponse, Known" | 1 | 0 | | | |
| | | | | 0.641304348 | 0 | 0 | 0 | -0.559782609 | -0.641304348 |
| PIK3R1 | "phosphatidylinostol 3-kinase, regulatory subunit, polypeptide 1 (p85 alpha)" | 13 | | | | | | 13 |
| | | | | 0 | 0 | 0.641304348 | 0.831521739 0 | 0.451086957 | -0.614130435 |
| | | | | 0.315217391 | | | | |
| IL21R | interleukin 21 receptor | 13 | "ImmuneResponse, SurfaceReceptor, Known, CellSurface, CytokineChemokine" | 1 | 0 | | | |
| | | | | 0.641304348 | 0 | 0 | 0.668478261 | -0.804347826 | 0.206521739 |
| IMP2 | inositol (myo)-1 (or 4)-monophosphatase 2 | 13 | | 0 | 0 | | 0 | 0.641304348 |
| | | | | 0 | 0 | 0.641304348 | 0.179347826 | -0.668478261 | |
| RSPH3A | | 13 | | 0 | 0 | 0.641304348 | 0 | 0.532608696 | — |
| | | | | 0.940217391 | | -0.722826087 | | |
| CDS2 | CDP-diacylglycerol synthase (phosphatidate cytidylyltransferase) 2 | 13 | PathogenicSignature (neg) | 0 | 0 | 0.641304348 0 | 0 | 0.641304348 |
| | | | | -0.69562174 | 0.39673913 | | | |
| CD42A | CD24a antigen | 13 | "ImmuneResponse, PathogenicSignature (pos), CellSurface" | | | | | 0 |
| | | | | 0 | 0.614130435 | 0 | 0 | -0.614130435 | 0.559782609 | 0.233695652 |
| IL24 | interleukin 24 | 13 | "PathogenicSignature (neg), Known, CytokineChemokine" | 1 | 0 | | | |
| | | | | 0.614130435 | 0 | 0 | 0.614130435 | -0.994565217 | -0.940217391 |
| SLC15A3 | "solute carrier family 15, member 3" | 13 | PathogenicSignature (neg) | 0 | 0 | | | |
| | | | | 0.614130435 | 0 | 0.913043478 | -0.47826087 | 0.233695652 | 0.614130435 |
| IKZF3 | | 13 | TF | 0 | 0 | 0.614130435 | 0 | 0 | 0.559782609 | — |
| | | | | 0.940217391 | -0.858695652 | | | |
| HIST1H4D | | 13 | | 0 | 0 | 0.614130435 | -0.994565217 | 0 |
| | | | | 0.505434783 | 0.152173913 | -0.614130435 | | |
| ITGAV | integrin alpha V | 13 | CellSurface | 0 | 0 | 0.614130435 | 0 | |
| | | | | 0.831521739 | -0.586956522 | 0 | 0.342391304 | | |
| PROCR | "protein C receptor, endothelial" | 13 | "ImmuneResponse, SurfaceRecpetor, CellSurface" | | | | | |
| | | | | 0 | 0 | 0.614130435 | 0 | 0.288043478 | -0.913043478 | -0.831521739 |
| TPR | translocated promoter region | 13 | | 0 | 0 | 0.614130435 | | -0.967391304 |
| | | | | 0 | 0 | 0.614130435 | 0.614130435 | | |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|---|---|---|---|---|---|---|---|---|
| IL9 | interleukin 9 | 14 | | "ImmuneResponse, PathogenicSignature (neg), Known, CytokineChemokine" | 1 | 0 | 0.586956522 | 0 |
| | | | | | 0 | 0.559782609 | -0.994565217 | -0.967391304 |
| CD84 | CD84 antigen | 14 | CellSurface | 0 | 0 | 0.586956522 | 0 | 0 |
| | 0.586956522 | | 0.315217391 | 0.342391304 | | | | — |
| TREML2 | | 14 | | 0 | 0 | 0.586956522 | 0 | 0 |
| | 0.668478261 | | -0.804347826 | | | | 0.532608696 | — |
| POLB | "polymerase (DNA directed), beta" | | 14 | | 0 | 0 | 0.586956522 | 0 |
| | 0 | -0.668478261 | 0.858695652 | 0.233695652 | | | | |
| SMAP1 | stromal membrane-associated protein 1 | | 14 | | 0 | 0 | 0.559782609 | 0 |
| | 0 | 0.260869565 | -0.641304348 | -0.641304348 | | | | |
| INSL6 | insulin-like 6 | 14 | | 0 | 0 | 0.559782609 | 0 | 0 |
| | 0.451086957 | 0.559782609 | | | | | | -0.451086957 |
| CYLD | | 14 | | 0 | 0.559782609 | 0 | -0.858695652 | 0 |
| | 0.47826087 | 0.559782609 | | | | | | |
| MAPRE2 | "microtubule-associated protein, RP/EB family, member 2" | | | | 15 | | 0 | 0 |
| | 0.532608696 | 0 | 0.940217391 | -0.423913043 | 0.559782609 | | 0.532608696 | |
| STK38L | | 15 | Kinase | 0 | 0.532608696 | 0 | 0 | -0.858695652 |
| | 0.423913043 | | 0.260869565 | | | | | |
| DOT1L | | 15 | | 0 | 0.532608696 | 0 | 0.777173913 | -0.532608696 |
| | 0.260869565 | | 0.260869565 | | | | | |
| BDH2 | | 15 | | 0 | 0.532608696 | 0 | 0 | -0.451086957 |
| | 0.315217391 | | 0.831521739 | | | | | |
| ACAT3 | | 15 | | 0 | 0.32608696 | 0 | 0 | 0.233695652 |
| | 0.586956522 | | -0.586956522 | | | | | — |
| BTBD19 | | 16 | | 0 | 0.505434783 | 0 | 0 | -0.505434783 |
| | 0.369565217 | | 0.39673913 | | | | | |
| BC031181 | cDNA sequence BC031181 | 16 | | 0 | 0 | 0.505434783 | 0 | |
| | 0.777173913 | -0.39673913 | 0 | 0.505434783 | | | | |
| SP3 | trans-acting transcription factor 3 | | 16 | TF | 0 | 0 | 0.505434783 | |
| | 0.967391304 | 0 | 0 | -0.614130435 | 0.505434783 | | | |
| IRAK1 | interleukin-1 receptor-associated kinase 1 | | 16 | "ImmuneResponse, Kinase, Known, CytokineChemokine" | 1 | 0 | 0.505434783 | |
| | 0.940217391 | 0 | -0.206521739 | 0.505434783 | 0.505434783 | | | |
| EXOSC1 | exosome component 1 | 16 | | 0 | 0 | 0.505434783 | 0 | 0 |
| | 0.505434783 | 0.315217391 | 0.586956522 | | | | | — |
| EBI3 | Epstein-Barr virus induced gene 3 | | 17 | "Known, CytokineChemokine" | 1 | | 0 | |
| | 0.47826087 | 0 | 0 | -0.315217391 | 0.831521739 | 0.967391304 | | |
| ACIN1 | apoptotic chromatin condensation inducer 1 | | 17 | TF | 0 | | 0 | 0.47826087 |
| | 0 | 0 | 0.315217391 | -0.505434783 | -0.75 | | | |
| FASTKD2 | FAST kinase domains 2 | 17 | | 0 | 0 | 0.47826087 | 0 | 0 |
| | 0.858695652 | 0 | 0 | | | | | — |
| PPP1R8 | "protein phosphatase 1, regulatory (inhibitor) subunit 8" | | | 17 | | 0 | 0 | |
| | 0.47826087 | -0.940217391 | 0 | 0 | -0.586956522 | 0.47826087 | | |
| MAF1 | MAF1 homolog (S. cerevisiae) | 17 | TF | 0 | 0 | 0.47826087 | 0 | 0 |
| | 0.47826087 | 0.342391304 | 0.586956522 | | | | | |
| TRMU | | 17 | | 0 | 0 | 0.47826087 | 0 | 0 |
| | 0.804347826 | 0.695652174 | | | | | | -0.451086957 |
| STAT5B | signal transducer and activator of transcription 5B | | 18 | | "ImmuneResponse, TF, Known" | | | |
| | 1 | 0 | 0.451086957 | 0 | 0 | 0.288043478 | 0.423913043 | 0.451086957 |
| LTA | lymphotoxin A | 18 | | "ImmuneResponse, Known, CytokineChemokine" | 1 | | 0 | |
| | 0.451086957 | 0 | 0.722826087 | -0.206521739 | 0.423913043 | | 0.451086957 | |
| EGR2 | early growth response 2 | | 18 | "TF, PathogenicSignature (neg)" | 0 | | 0 | |
| | 0.451086957 | 0 | 0.695652174 | -0.369565217 | 0.369565217 | | 0.39673913 | |
| SIRT6 | | 18 | TF | 0 | 0 | 0.451086957 | 0 | 0.559782609 |
| | 0.233695652 | | | | | | | 0 |
| EXT1 | exostoses (multiple) 1 | 19 | | 0 | 0 | 0.423913043 | 0 | 0 |
| | 0.39673913 | 0.423913043 | | | | | | 0 |
| NHEJ1 | nonhomologous end-joining factor 1 | | 19 | | 0 | 0 | 0.423913043 | 0 |
| | 0 | 0.423913043 | -0.47826087 | -0.695652174 | | | | |
| SERPINF1 | "serine (or cysteine) peptidase inhibitor, clade F, member 1" | | | | 20 | | | |
| | 0 | 0 | 0.39673913 | 0 | 0 | -0.39673913 | 0.695652174 | 0.831521739 |
| TGM2 | "transglutaminase 2, C polypeptide" | | 20 | | 0 | 0 | 0.39673913 | 0 |
| | 0 | 0.39673913 | -0.885869565 | -0.885869565 | | | | |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|---|---|---|---|---|---|---|---|---|
| ADI1 | acireductone dioxygenase 1 | 20 | | 0 | 0 | 0.39673913 | 0 | 0 |
| | 0 | −0.47826087 | −0.532608696 | | | | | |
| RNF181 | ring finger protein 181 | 20 | | 0 | 0 | 0.39673913 | 0 | 0 |
| | −0.39673913 | 0.179347826 | 0.179347826 | | | | | |
| METT10D | | 20 | | 0 | 0 | 0.39673913 | 0 | 0 | −0.342391304 |
| | 0.586956522 | 0.532608696 | | | | | | |
| NIP7 | nuclear import 7 homolog (S. cerevisiae) | 20 | | | 0 | 0 | 0.39673913 |
| | 0 | 0 | −0.831521739 | 0.39673913 | 0 | | | |
| PSRC1 | proline/serine-rich coiled-coil 1 | 20 | | 0 | 0 | 0.369565217 | 0 |
| | 0 | 0.369565217 | 0.288043478 | 0.288043478 | | | | |
| TBL2 | transducin (beta)-like 2 | 20 | | 0 | 0 | 0.369565217 | 0 | 0 |
| | 0.369565217 | 0.288043478 | 0.342391304 | | | | | |
| PQLC3 | PQ loop repeat containing | 20 | | 0 | 0 | 0.369565217 | 0 | 0 |
| | 0.641304348 | −0.47826087 | 0.233695652 | | | | | |
| NIF3L1 | Ngg1 interacting factor 3-like 1 (S. pombe) | 20 | | 0 | 0 | 0.369565217 |
| | 0 | 0 | −0.586956522 | 0.342391304 | 0.369565217 | | | |
| CYSLTR1 | cysteinyl leukotrine receptor 1 | 21 | PathogenicSignature (neg) | | 0 | 0 |
| | 0.342391304 | 0 | 0 | 0.342391304 | −0.804347826 | 0.179347826 | | |
| PDLIM5 | PDZ and LIM domain 5 | 21 | PathogenicSignature (neg) | 0 | 0 | 0.342391304 |
| | 0 | 0 | −0.614130435 | 0 | 0 | | | |
| LAG3 | lymphocyte-activation gene 3 | 21 | "ImmuneResponse, PathogenicSignature (pos), CellSurface" | | 0 | 0 | 0.342391304 |
| | 0 | 0.777173913 | −0.260869565 | 0.940217391 | 0.315217391 | | | |
| SLC25A13 | "solute carrier family 25 (mitochondrial carrier, adenine nucleotide translocator), member 13" | 21 | | 0 | 0 | 0.342391304 | 0 | 0 |
| | 0.342391304 | 0 | 0.451086957 | | | | | — |
| GTF2E1 | | 21 | TF | 0 | | 0.342391304 | 0 | −0.614130435 | 0 |
| | 0.342391304 | | | | | | | |
| TSPAN6 | tetraspanin 6 | 22 | PathogenicSignature (neg) | 0 | 0 | 0.315217391 | 0 |
| | 0 | −0.505434783 | 0 | 0 | | | | |
| CHD2 | | 22 | "TF, PathogenicSignature (pos)" | 0 | 0 | 0.315217391 | 0 | 0 |
| | 0.668478261 | 0.179347826 | 0.152173913 | | | | | |
| ASB3 | ankyrin repeat and SOCS box-containing 3 | 22 | | 0 | 0 | 0.315217391 |
| | 0 | 0 | 0.315217391 | 0.233695652 | 0.260869565 | | | |
| DAPL1 | | 23 | | 0 | 0 | 0.288043478 | 0 | 0 | 0.913043478 |
| | 0.885869565 | | | | | | | |
| UBA3 | ubiquitin-like modifier activating enzyme 3 | 23 | | 0 | 0 | 0.288043478 |
| | 0 | 0 | −0.288043478 | 0.233695652 | 0.559782609 | | | |
| ZUFSP | zinc finger with UFM1-specific peptidase domain | 23 | TF | 0 | 0 |
| | 0.288043478 | 0 | 0 | −0.288043478 | 0.641304348 | 0.315217391 | | |
| MED21 | mediator complex subunit 21 | 23 | | 0 | 0 | 0.288043478 | 0 |
| | 0.831521739 | 0 | 0.260869565 | 0.288043478 | | | | — |
| NGDN | "neuroguidin, EIF4E binding protein" | 23 | | | 0 | 0.288043478 | 0 | 0.288043478 | 0 |
| | −0.913043478 | 0 | 0 | 0.288043478 | | | | |
| PIN4 | | 23 | | 0 | 0 | 0.288043478 | 0 | 0.288043478 | 0 |
| | 0.260869565 | 0 | | | | | | |
| BCDIN3D | BCDIN3 domain containing | 23 | | 0 | 0 | 0.288043478 | 0 | 0 |
| | −0.342391304 | 0.532608696 | 0.152173913 | | | | | |
| RIPK3 | receptor-interacting serine-threonine kinase 3 | 24 | Kinase | 0 | 0 |
| | 0.260869565 | −0.940217391 | 0 | 0 | 0 | 0.260869565 | | |
| CENPM | centromere protein M | 24 | | 0 | 0 | 0.260869565 | 0 | 0 |
| | 0 | 0.260869565 | | | | | | |
| TACC3 | "transforming, acidic coiled-coil containing protein 3" | 24 | | | 0 | 0 |
| | 0.260869565 | −0.994565217 | 0 | 0.260869565 | 0.233695652 | 0 | | |
| STAG1 | | 24 | TF | 0 | 0 | 0.260869565 | 0 | 0 | 0 |
| | 0.505434783 | | | | | | | 0.451086957 |
| PDSS1 | "prenyl (solanesyl) diphosphate synthase, subunit 1" | 24 | | 0 | 0 |
| | 0.260869565 | 0 | 0 | −0.260869565 | 0 | −0.532608696 | | |
| CEP57 | | 24 | | 0 | 0 | 0.260869565 | 0 | 0 | 0.39673913 |
| | 0.315217391 | 0 | | | | | | |
| MRPS22 | mitochondrial ribosomal protein S22 | 24 | | 0 | 0 | 0.260869565 | 0 |
| | 0 | −0.260869565 | 0.47826087 | 0 | | | | |
| KIF5B | kinesin family member 5B | 25 | PathogenicSignature (neg) | 0 | 0 |
| | 0.233695652 | 0 | −0.695652174 | −0.233695652 | 0.423913043 | 0 | | |

TABLE 2-continued

Ranking of potential regulators of Th17 pathogenicity. Table 2: Potential regulators of Th17 pathogenicity (rows in FIG. 4B) are ranked based on: (1) Correlation with the first principle component in the in vitro derived Th17 cells (using TGF-β1 + IL-6; FIG. 4C). (2, 3) Correlations with the first and second principle components in the in vivo derived Th17 cells (FIG. 2A). (4) Correlation with immune-related genes in the columns of FIG. 4B. (5) A Correlation with a curated pathogenicity signature (genes that are positively or negatively associated with pathogenic TH17 cells, (Lee et al., 2012)). The values in these respective columns indicate the rank (percentile) of the gene in the respective test, relative to all other candidate genes. Highly scoring genes are the ones that are bound by key Th17 transcription factors, and affected by perturbation of these factors during Th17 differentiation. The values in the respective column indicate the rank (percentile) of the gene, relative top all other candidate genes. Negative values indicate a negative correlation.

Sources for single-cell score

| Gene | Description | Rank | Attributes | Known | Profiled | Score | In-vivo | PC1 rank |
|---|---|---|---|---|---|---|---|---|
| BC055324 |  | 25 | 0 | 0 | 0.233695652 | 0 | 0 | 0 |
|  |  |  |  |  |  |  | 0.75 | 0.695652174 |
| CAMTA1 |  | 25 | TF | 0 | 0 | 0.233695652 | 0 | 0 |
|  | 0.532608696 |  | 0.47826087 |  |  |  | 0.233695652 | — |
| C2CD3 | C2 calcium-dependent domain containing 3 | 26 |  |  | 0 |  | 0 |  |
|  | 0 | 0 | 0.342391304 | 0.206521739 | 0.206521739 |  |  | 0.206521739 |
| NGLY1 | N-glycanase 1 | 27 | 0 | 0 | 0.179347826 | 0 | 0 |  |
|  | 0 | 0 |  |  |  |  |  | 0.47826087 |
| DEGS1 | degenerative spermatocyte homolog 1 (Drosophila) |  |  |  | 27 |  | 0 | 0 |
|  | 0.179347826 | 0 | 0 | −0.423913043 | 0.39673913 | 0 |  |  |
| GALK1 | galactokinase 1 | 28 | Kinase | 0 | 0 | 0.152173913 | 0 | 0 |
|  | 0 | 0.39673913 |  |  |  |  |  |  |
| SPSB3 | splA/ryanodine receptor domain and SOCS box containing 3 |  |  |  | 28 |  | 0 | 0 |
|  | 0.152173913 | 0 | 0 | 0 | 0 | 0.152173913 |  |  |
| CSNK1E | "casein kinase 1, epsilon" | 29 | Kinase | 0 | 0 | 0.125 | 0 | 0 |
|  | 0.342391304 | 0.369565217 |  |  |  |  |  |  |
| TTC27 | tetratricopeptide repeat domain 27 |  | 29 |  | 0 | 0 | 0.125 | 0 | 0 |
|  | −0.233695652 | 0.288043478 | 0 |  |  |  |  |  |
| LINS |  | 29 | 0 | 0 | 0.125 | 0 | 0 | −0.206521739 |
|  |  |  |  |  |  |  |  | 0 | 0 |
| INO80C | INO80 complex subunit C | 30 |  |  | PathogenicSignature (neg) |  | 0 | 0 |
|  | 0.097826087 | 0 | 0 | 0 | 0.288043478 | 0.288043478 |  |  |
| FDX1 | ferredoxin 1 | 30 |  | 0 | 0 | 0.097826087 | 0 | 0 |
|  | 0.260869565 | 0.288043478 |  |  |  |  |  |  |
| ITM2A | integral membrane protein 2A |  | 31 |  | 0 | 0 | 0.070652174 | 0 | 0 |
|  | 0 | 0.206521739 | 0.206521739 |  |  |  |  |  |
| MTPAP |  | 31 | 0 | 0 | 0.070652174 | 0 | 0.695652174 | 0 |
|  | 0.505434783 | 0 |  |  |  |  |  |  |
| DHX9 | DEAH (Asp-Glu-Ala-His) box polypeptide 9 |  | 32 |  | 0 | 0 | 0 | 0.043478261 |
|  | 0 | 0 | 0.152173913 | 0.152173913 |  |  |  |  |
| CEP55 | centrosomal protein 55 | 33 |  | 0 | 0 | 0 | 0 | 0 |
|  | 0.451086957 | 0.47826087 |  |  |  |  |  | — |
| FAM118A | "family with sequence similarity 118, member A" |  | 33 |  | 0 | 0 | 0 | 0 |
|  | 0 | 0 | 0 | 0 | 0 |  |  |  |
| 2500003M10RIK | RIKEN cDNA 2500003M10 gene |  | 33 |  | 0 | 0 | 0 | 0 |
|  | 0 | 0 | 0 |  |  |  |  |  |
| ICAM1 | intercellular adhesion molecule 1 |  | 33 |  | "ImmuneResponse, CellSurface" | 0 | 0 |
|  | 0 | 0 | 0 | 0 | 0 | 0.369565217 |  |  |
| GNPDA2 | glucosamine-6-phosphate deaminase 2 |  | 33 |  | 0 | 0 | 0 | 0 |
|  | 0 | 0.342391304 | 0 |  |  |  |  |  |
| MTA3 | metastasis associated 3 | 33 | TF | 0 | 0 | 0 | 0 | 0.722826087 |
|  | 0 | 0.260869565 | 0 |  |  |  |  |  |
| CCDC9 | coiled-coil domain containing 9 |  | 33 |  | 0 | 0 | 0 | 0 | 0 |
|  | 0 | 0.206521739 | 0.179347826 |  |  |  |  |  |
| 2210016L21RIK | RIKE cDNA 2210016L21 gene |  | 33 |  | 0 | 0 | 0 | 0 | 0 |
|  | 0 | 0.179347826 | 0 |  |  |  |  |  |

TABLE 3

Normalized data of lipidome analysis. WT and CD5L$^{-/-}$ naïve T cells were differentiated. Cells and supernatant were harvested at 96 hours and subjected to MS/LC. Three independent mouse experiments were performed.

| Method | Compound | TGFb1 + IL6_no cells (2_media, 4a_media, 6b_media, 3_cells) | TGFb1 + IL6_WT (2a_media, 3a_cells) | TGFb1 + IL6_CD5LKO (4b_media, 1_cells) | TGFb1 + IL6 + IL23_no cells (2b_media, 1a_cells, 3b_cells) | TGFb1 + IL6 + IL23_WT (5_media) | TGFb1 + IL6 + IL23_CD5LKO (3_media, 5a_media, 1b_cells, 4_cells) | m/z | RT | HMDB ID | Metabolite | TGFb1 + IL6_CD5LKO (1a_media, 3b_media, 2a_cells, 4b_cells) | TGFb1 + IL6_WT (1_media, 5b_media, 2_cells) | TGFb1 + IL6 + IL23_CD5LKO (6_media) | TGFb1 + IL6 + IL23_WT (1b_media, 4_media, 6a_media, 2b_cells) |
|---|---|---|---|---|---|---|---|---|---|---|---|---|---|---|---|
| C18-NEG | TF1 | 26815668 26815668 26815668 32190232 32190232 | | | | | | 355.2417 | 10.85 | | Internal Standard PGE2-d4 | 26815668 26815668 26815668 32190232 32190232 | | | 26815668 26815668 26815668 32190232 32190232 |
| C18-NEG | TF16 3904 | 4592 | | 5454 | | | | 227.2006 4140 | 16.5 | HMDB00806 4734 | Myristic acid 6041 | 22362 5120 | | | 4171 |
| C18-NEG | TF18 5595 | | | | | | | 255.2319 415325 | 17.6 | HMDB00220 | Palmitic acid 6114 | | | | 6669 |
| C18-NEG | TF22 5586 | 16628 | 3937 | | 4288 | | | 283.2632 | 18.45 | HMDB00827 | Stearic acid 4573 | 5506 | | | |
| C18-NEG | TF6 | 9894 | 25493 | | 5592 50636 | | | 303.2319 | 16.95 | 4119 HMDB01043 | Arachidonic acid 5192 | | | | |
| C18-NEG | TF9 212733 4403 392193 | 190235 | | 9756 27006 | | | | 327.2319 | 16.7 | HMDB02183 | Docosahexaenoic acid | 181344 | 214866 | | 172799 |
| C18-NEG | TF3 17816 20151 | | | | | | | 295.2279 | 14.3 | HMDB04667 4821 | 13-S-HODE 24376 17034 | 388565 32547 85814 17395 | 391793 5135 28776 41146 | | 7338 458935 4137 36384 63454 |
| C18-NEG | TF5 | | | | | | | 319.2268 | 15 | HMDB11134 | 5-HETE 5686 | 13028 | 27430 | | 23621 |
| C18-NEG | TF2 | | | | | | | 319.2268 | 14.85 | HMDB06111 | 12-HETE 605651 | 571461 | 616076 | | 619527 |
| C18-NEG | TF4 | | | | | | | 319.2268 | 14.6 | HMDB03876 | 15-HETE 7666 PGE2 25361 100092 143503 | 29546 165627 92244 138440 | 75971 105953 150043 | | 48717 137472 96506 132273 |
| C18-NEG | TF20 119832 111171 160265 | 128956 166567 | | 156919 145815 | 133633 151644 | | 10.85 | 351.2166 | | HMDB01220 105390 150862 | PGE2 94502 113499 116128 | | | | |
| C18-NEG | TF21 48552 | 4726 | | | | | | 378.2404 | 12.9 | HMDB00277 | Sphingosine 1-Phosphate 4961 | | 28965 | | 9479 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| Category | ID | 17886 / 32157 | 24158 / 26314 | 12678 / 41178 | 86777 / 13.7 | 199953 / HMDB | 50675 | (Compound) | 66831 | 42635 | 87122 | 55959 | 58936 |
|---|---|---|---|---|---|---|---|---|---|---|---|---|---|
| C18-NEG | TF7 | 945565 / 1055547 / 4172 | 959861 / 1066135 / 158405 | 878522 / 279570 | 914774 / 14865 | 963595 / 45923 (HMDB00619) | 874981 / 22873 | Cholic acid | 915457 / 84326 | 841312 / 1044979 / 291472 | 829989 / 973879 / 8592 | 1895854 / 1012834 / 74745 | 1060513 / 1083731 / 249696 |
| C18-NEG | TF8 | 33842 / 22469 / 143146 | 391.2843 | 66746 / 70604 / 11419 / 26116 | 13.7 | 24917 / 65810 / 5832 | 87301 / 79792 | | 146975 | 30651 / 5174 | 56847 / 61510 | 45052 | 28222 / 72116 |
| C18-NEG | TF13 | 446981 / 464895 / 245261 | 432.3109 / 464141 / 434862 / 143848 | 452405 / 599613 / 236992 | 420928 / 306566 | 417936 / 191381 (HMDB00698) | 453376 / 221224 | Glycolithocholic acid | 399497 | 450928 / 228104 | 417387 / 218413 | 358320 / 494639 / 348429 | 307449 / 474051 / 112692 | 804941 / 511277 / 233360 |
| C18-NEG | TF10 | 16730744 / 8790607 / 287994 | 448.3058 / 9130167 / 416282 | 9175994 / 9715621 / 2624579 | 8925907 / 9130630 / 298221 | 8566471 / 9973976 / 653840 (HMDB00637) | 8185757 / 2371148 | Glycochenodeoxycholic acid | 8624925 / 514553 | 8045296 / 301446 | 8373366 / 319299 | 7723861 / 8707438 / 342475 | 7584903 / 9173126 / 2720397 |
| C18-NEG | TF12 | 1526275 / 1682132 / 813426 | 448.3058 / 1473921 / 1596115 / 70296 | 1432269 / 1620654 / 214418 | 1381864 / 732878 | 1434129 / 147574 (HMDB00631) | 1344172 / 106136 | Glycodeoxychtilic acid | 1235504 | 1371185 / 96251 | 1294337 / 1455338 / 870148 | 1218407 / 1530555 / 94741 | 2895264 / 1537222 / 1119858 |
| C18-NEG | TF14 | 77979 / 28917 | 448.3058 / 26688 | 14758 / 28088 | 6136 / 30834 | 9701 (HMDB00708) | 21662 | Glycoursodeoxycholic acid | 14785 | | 9364 | 27507 / 38008 | 25021 / 22933 |
| C18-NEG | TF11 | 3555056 / 3631694 / 545384 | 464.3007 / 3419546 / 3399351 / 75607 | 3325521 / 3897272 / 127209 | 3185794 / 443415 | 3293510 / 113351 (HMDB0138/) | 3182289 / 32011 | Glycocholic acid | 3084720 | 3266052 / 66765 | 3319168 / 50376 | 3041840 / 3482238 / 51569 | 6885427 / 3297525 / 58617 |
| C18-NEG | TF27 | 3637940 / 3569226 / 953183 | 482.2935 / 3436786 / 3390069 / 55880 | 3187052 / 3871627 / 86020 | 3098266 / 678802 | 3137579 / 178585 (HMDB00722) | 3268503 / 5896 | Taurolithocholic acid | 2985852 | 3226234 / 13015 | 3153783 / 36954 | 2843408 / 3478013 / 948858 | 6610292 / 3486687 / 43382 |
| C18-NEG | TF23 | 21765418 / 10569920 / 10615260 | 498.2884 | 10814147 / 9857044 / 10721686 | 10085203 | 11432901 (HMDB00951) | 10135701 | Taurochenodesoxycholic acid | 10500138 | 10387928 | | 9711333 / 10774996 | 9187433 |
| C18-NEG | TF25 | 867034 / 1097889 / 1520099 / 1012843 | 498.2884 / 921101 / 1204800 / 1145610 / 535227 | 3540079 / 1186702 / 1164120 / 539591 | 833310 / 1291165 / 1108272 | 10601011 / 946736 / 1138396 / 802664 (HMDB00896) | 3469976 / 1062944 / 673835 | Taurodeoxycholic acid | 11106218 / 813296 / 1244038 / 495822 | 10588339 / 1033422 / 1081470 / 718123 | 3005206 / 1274941 / 1293712 / 1114176 / 1028133 | 983454 / 1299344 / 1028242 / 564107 | 508378 / 2209563 / 1053480 / 564084 |
| C18-NEG acid/Tauroursodeoxycholic acid | TF26 | 347874 / 858965 | 498.2884 / 292734 / 683257 | 365255 / 700081 | 317061 / 687038 | 607603 / 314646 / 778814 (HMDB00874) | 530169 / 277955 / 613338 | Taurohyodeoxycholic | 749503 / 320850 / 617107 | 565618 / 281048 / 530759 | 460525 / 298726 / 465380 | 409550 / 914503 | 364218 / 837410 |
| C18-NEG | TF24 | | 514.2833 | | 10.35 | HMDB00036 | | Taurocholic acid | | | 3683215 | 3788120 | 8155464 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | | | | |
|---|---|---|---|---|---|---|---|---|---|---|---|
| C8-pos | 4289030 4454412 945912 | 4360551 4209047 412479 | | 4078206 4584683 395216 | 3939955 1022009 | 3860197 609445 | 3750381 530472 | 3862014 487087 | 4076709 504578 | 4195779 1079071 | 4073666 478051 | 3961542 474946 |
| C8-pos | 2646 1161771 1059405 | 622.4444 1043447 1018984 | | 1087052 998964 | 6.88 1030377 | | Internal Standard 1023566 | C24:0 PC 1013596 | 1032116 | 1012539 921771 | 1158015 1088590 | 996417 1006026 |
| C8-pos | 1266 7970 8432 9238 | 468.3088 7902 5929 6158 | | 3713 8833 | 4.58 6841 8161 | HMDB10379 6850 6353 | 5416 12478 | C14:0 LPC 7519 9865 | 6661 7275 | 2679 9638 8962 | 5141 8547 5614 | 5977 9207 8336 |
| C8-pos | 1392 14635 42162 10960 | 494.3243 12487 25977 8711 | | 7561 7062 | 4.75 10624 9879 | HBDB10383 11967 8556 | 11642 13284 | C16:1 LPC 13026 10300 | 7014 42413 10118 | 5646 43253 12133 | 8282 46059 7968 | 13214 39641 9734 |
| C8-pos | 1685 351653 602325 371463 | 496.3400 316290 451796 287901 | | 164849 408232 | 5.12 308496 274878 | HMDB10382 316058 300060 | 293955 310202 | C16:0 LPC 316343 378407 | 280511 255703 | 185047 602681 344659 | 284161 657403 258328 | 287427 558708 314892 |
| C8-pos | 1536 3136 29300 1520 | 520.3412 1558 20841 778 | | 161 1254 | 4.95 895 1762 | HMDB10386 1467 2827 | 2115 1230 | C18:2 LPC 1490 1764 | 1991 692 | 1653 31806 1427 | 1606 23260 975 | 2623 27216 2009 |
| C8-pos | 1817 65990 331960 122626 | 522.3559 54998 212335 109496 | | 37484 74725 | 5.31 53044 95810 | HMDB02815 53484 121857 | 58851 138419 | C18:1 LPC 60620 130839 | 51574 100262 | 33235 323141 120798 | 47063 340550 109338 | 54536 305699 114039 |
| C8-pos | 2049 156320 541318 496284 | 524.3716 139282 380513 398060 | | 78631 515430 | 5.73 143240 389585 | HMDB10384 140446 382528 | 115978 305556 | C18:0 LPC 144991 425178 | 131814 306964 | 93212 484891 483268 | 150175 539919 341639 | 106945 452124 377311 |
| C8-pos | 1565 1078 45103 | 544.3408 957 25078 | | 341 | 4.98 713 | HMDB10395 386 | 1538 | C20:4 LPC 1720 | 315 47160 | 546 48570 | 33948 | 2629 43474 |
| C8-pos | 1686 161620 273364 175532 | 518.3222 140310 205344 138138 | | 73814 172119 | 5.12 147798 123723 | HMDB10393 143482 131367 | 135002 139487 | C20:3 LPC 147118 169528 | 135323 118266 | 79703 278500 154304 | 133563 302446 116932 | 127294 252437 147822 |
| C8-pos | 1543 207 13541 | 568.3409 363 8409 | | | 4.96 | HMDB10404 | 399 | C22:6 LPC 194 | 494 16424 | 16085 | 13036 | 584 13927 |
| C8-pos | 1716 365 22 3299 | 434.2916 25 290 1874 | | 48 6251 | 5.15 114 3178 | HMDB11503 310 2516 | 357 2983 | C16:0 LPE 69 3123 | 476 42 2481 | 111 213 4162 | 111 17 1790 | 799 50 3408 |
| C8-pos | 1843 1209 | 480.3093 2123 | | 4672 | 5.33 1704 | HMDB11506 1918 | 1684 | C18:1 LPE 2263 | 2218 2374 | 1466 1885 | 1394 1870 | 1398 1811 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | 1519 | 10950 | 10311 | 12382 | 14075 | 12409 | 8842 | 12639 | 9670 | 11071 | 13057 |
|---|---|---|---|---|---|---|---|---|---|---|---|---|
| C8-pos | 2302 10742 2057 35416 1516 | 482.3243 9984 30237 | 24614 | 5.75 20595 4.89 7203 | HMDB11130 26391 HMDB11517 7444 | 19130 6125 | C18:0 LPE 19611 C20:4 LPE 8659 | 31352 8705 | 21418 | 24054 | 30243 | 25746 |
| C8-pos | 13129 3036 19814 1314 2511736 | 704.5219 9742 21383 2193 2342464 | 8024 57018 3179497 | 8.17 15177 2637808 | HMDB07870 13329 2115223 | 18092 3934853 | C30:1 PC 17893 2521297 | 16663 2762885 | 6801 14998 1456 2291782 | 7602 25161 2479 2105914 | 9012 22315 2480 1788641 | 7862 25216 1441 3155606 |
| C8-pos | 3174 104080 19556 11464986 | 706.5381 121173 9024 | 263005 23932912 8510608 | 8.50 100045 11003330 | HMDB07869 97722 13680597 | 103152 8981976 | C30:0 PC 103096 9555005 12883235 | 99173 11495872 | 95742 18413 12142872 | 139255 22625 11288552 | 118195 18592 11754712 | 139529 15786 |
| C8-pos | 3094 619 41 1617004 | 730.5376 26079 1602014 | 669 1907726 | 8.32 1312863 | HMDB07874 2753385 | 328 1927112 | C32:2 PC 1911619 | 1924029 | 294 1592890 | 3697 1274248 | 1418 2097057 | 1476 40 1740467 |
| C8-pos | 3294 231946 83548 27784163 26605312 | 732.3539 242071 51104 | 498537 55194967 27670368 | 8.66 210272 | HMDB07873 231474 33848332 25706127 | 222549 | C32:1 PC 207147 22246803 22602306 | 203388 | 205285 97691 35107212 32424675 | 286601 86987 | 262106 90542 26193771 29776663 | 282180 71470 |
| C8-pos | 3502 321514 285151 16731527 18037146 | 734.5693 354180 190297 | 391822 33287969 121179174 | 8.96 311399 | HMDB07871 324195 25702073 19370270 | 329510 | C32:0 PC 336354 16236254 16431600 | 318227 | 309174 287073 16464607 17890462 | 390337 278414 | 393097 320104 16426187 21505865 | 385227 264113 |
| C8-pos | 3164 | 756.5530 702 | | 8.49 | HMDB08006 | | C34:3 PC | | | | | |
| C8-pos | 875171 3370 212089 152171 25560517 2226117 | 988856 758.5690 187074 104600 | 673483 402369 26166733 23405347 | 1023525 8.80 163864 | 867319 HMDB07973 177569 26958332 22095533 | 827735 164380 | 701311 C34:2 PC 162867 20067830 20436688 | 723025 167024 | 644826 169769 188001 33686135 25485037 | 810044 212274 150595 | 783009 214180 175966 26641163 23869850 | 740564 212897 139347 |
| C8-pos | 3631 1558530 1523100 111146354 119131624 | 760.5849 1672468 1105535 | 2162247 178901591 117279402 | 9.11 1493713 | HMDB07972 1715862 143335374 122152546 | 1471713 | C34:1 PC 1477760 109157114 109711913 | 1479214 | 1437013 1619969 104342448 123307892 | 1781135 1562252 | 1933722 1751912 104833865 123029810 | 1716678 1444734 |
| C8-pos | 3853 102842 102705 7612206 | 762.6004 109523 67949 5900373 | 108969 8968825 | 9.40 102870 7919729 | HMDB07970 117047 5888575 | 106010 4726055 | C34:0 PC 107085 6062746 | 99058 5415346 | 93512 126394 4727828 | 121057 106850 7213126 | 127626 122762 6142124 | 122565 97715 6076837 |
| C8-pos | 3481 173027 194530 8164057 | 784.5846 186187 125204 7771753 | 191142 7160245 | 8.93 161841 9618295 | HMDB08105 161995 7714713 | 153635 8676343 | C36:3 PC 170015 7795045 | 158580 8314128 | 147616 199672 6651223 | 187415 189187 7610487 | 202520 215520 7721078 | 172746 175659 6945637 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | |
|---|---|---|---|---|---|---|---|---|
| C8-pos | 3732<br>501205<br>454378<br>92168585<br>86428868 | 786.6005<br>547609<br>327946 | | 9.24<br>467091 | HMDB08039<br>522166<br>94507728<br>86054248 | 430865 | C36:2 PC<br>451021<br>89183697<br>86270047 | 454155 | 463073<br>502200<br>104034202<br>80643093 | 626529<br>468531 | 642678<br>516696<br>90569180<br>88651540 | 540064<br>427261 |
| C8-pos | 3995<br>962494<br>1039898<br>6054259<br>63205618 | 788.6163<br>1020635<br>714352 | 1132092<br>80860255<br>91632373 | 9.53<br>934110<br>100494858<br>55954680 | HMDB08038<br>1093301<br>77489842<br>71002509 | 915048 | C36:1 PC<br>916238<br>61738737<br>60173420 | 903430 | 888964<br>1180935<br>47157821<br>59028380 | 1120466<br>1052607 | 1153888<br>1154069<br>55637534<br>68769288 | 1063681<br>935346 |
| C8-pos | 3355<br>124626<br>153478<br>496703 | 806.5687<br>127378<br>101856<br>475949 | 84574<br>731004 | 8.77<br>121859<br>908514 | HMDB07991<br>139186<br>411716 | 107861<br>737076 | C38:6 PC<br>115065<br>484366 | 114944<br>515978 | 102208<br>186101<br>497744 | 137870<br>151302<br>443482 | 139801<br>164681<br>419329 | 127593<br>144477<br>556145 |
| C8-pos | 3619<br>137341<br>161637<br>1357728 | 810.6002<br>151632<br>109067<br>1458638 | 95753<br>1119481 | 9.11<br>129561<br>1728422 | HMDB08048<br>153570<br>1303515 | 119951<br>1786146 | C38:4 PC<br>128201<br>1480693 | 117325<br>1516861 | 116733<br>162699<br>1485202 | 150165<br>152936<br>1370926 | 163751<br>176914<br>1331765 | 136678<br>139421<br>1448781 |
| C8-pos | 3856<br>385841<br>475247<br>3038207 | 812.6144<br>425796<br>324421<br>2840122 | 299347<br>3239362 | 9.40<br>376452<br>3647621 | HMDB08047<br>428895<br>2833978 | 383143<br>2728332 | C38:3 PC<br>386432<br>2922200 | 367059<br>3106003 | 338892<br>523006<br>2670371 | 418953<br>455579<br>2841476 | 471728<br>527243<br>2684190 | 409861<br>426327<br>2651238 |
| C8-pos | 4068<br>55413<br>64364<br>7578026 | 814.6319<br>74436<br>36744<br>8600347 | 154969<br>9293840<br>8689160 | 9.62<br>58418<br>9520856 | HMDB08270<br>76390<br>10010844 | 57351 | C38:2 PC<br>52099<br>8082374 | 57746<br>8421060 | 49919<br>75316<br>9506227 | 73027<br>64649<br>8312101 | 94939<br>72867<br>8578760 | 71994<br>48600<br>8643930 |
| C8-pos | 3148<br>17634<br>3350<br>52277<br>66559<br>152956 | 826.5356<br>26748<br>828.5511<br>59335<br>40590<br>141857 | 5024<br>35165<br>194698 | 8.45<br>32216<br>8.77<br>52676<br>287249 | HMDB08511<br>9203<br>HMDB08731<br>56700<br>130844 | 8120<br>49452<br>220042 | C40:10 PC<br>8531<br>C40:9 PC<br>47562<br>150639 | 7348<br>47608<br>144369 | 1796<br>42395<br>80225<br>158304 | 18414<br>52578<br>64631<br>133617 | 3967<br>58279<br>74621<br>123826 | 6035<br>50320<br>59199<br>183219 |
| C8-pos | 3540<br>29954<br>35893<br>347813 | 834.5999<br>35209<br>28580<br>331729 | 22163<br>396980 | 9.01<br>29520<br>487550 | HMDB08057<br>41487<br>307629 | 25526<br>580470 | C40:6 PC<br>27385<br>379342 | 27412<br>413709 | 28677<br>43491<br>364802 | 40315<br>39109<br>296967 | 45841<br>46984<br>313224 | 42134<br>35182<br>412487 |
| C8-pos | 3518<br>11398 | 740.5557<br>2515 | 2578<br>9752434 | 8.97<br>59001<br>6913124 | HMDB11212<br>1064<br>4965803 | 1221<br>8048403 | C34:4 PC<br>3052<br>5528922 | plasmalogen<br>2890<br>5895548 | 466<br>6481230 | 4797<br>5421549 | 9848<br>4687022 | 5518<br>6946355 |
| C8-pos | 5858720<br>3632<br>18086<br>5643<br>10856382 | 5478828<br>744.5894<br>6210<br>6107 | 10566<br>3172<br>8503632 | 9.11<br>70877<br>11686985<br>7728070 | HMDB11210<br>7970<br>9822941<br>8689498 | 8550<br>11672448 | C34:2 PC<br>7945<br>8418221 | plasmalogen<br>6070<br>8025822 | 6583<br>11282617 | 12454<br>7207 | 22450<br>3521<br>8657446 | 18110<br>6094<br>92213773 |
| C8-pos | 3851<br>233131<br>70629<br>57590148<br>62086543 | 746.6058<br>157412<br>80503 | 181046<br>54294<br>60744260<br>57585328 | 9.40<br>693064<br>113475188 | HMDB11208<br>142337 | 154211<br>75081287 | C34:1 PC<br>145569<br>60648808 | plasmalogen-A<br>147135<br>58906427 | 140333<br>53946198 | 182689<br>95137<br>59320720 | 244679<br>84314<br>63244389 | 236142<br>94238 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | | | |
|---|---|---|---|---|---|---|---|---|---|---|
| C8-pos | 3653<br>12744<br>2480<br>4063852 | 768.5889<br>7914<br>3621<br>3774816 | 7883<br>953<br>3949412 | 30428<br>4637122 | 9.13 | HMDB11310<br>7626<br>7535900 | 6416<br>3963202 | C36:4 PC<br>6726<br>1920937 | plasmalogen<br>4042<br>3908563 | 4683<br>4539379 | 5720<br>2645<br>4602133 | 15177<br>5287<br>3752765 | 13211<br>3711<br>3707617 |
| C8-pos | 3756<br>4909<br>3912<br>2477037 | 770.6051<br>6389<br>2784<br>2254783 | 3488<br>2092<br>2423949 | 8348<br>3162551 | 9.27 | HMDB11244<br>2732<br>3313974 | 1648<br>2496483 | C36:3 PC<br>3257<br>3416792 | plasmalogen<br>2956<br>2665852 | 3199<br>2772151 | 3089<br>2696<br>3002241 | 7963<br>2295<br>2361016 | 6406<br>2585<br>2289667 |
| C8-pos | 3978<br>28970<br>6204<br>10216946 | 772.6202<br>13453<br>5842<br>11686965 | 22793<br>4795<br>12949917 | 101233<br>12949917 | 9.52 | HMDB11243<br>13874<br> | 19007<br>11791730 | C36:2 PC<br>13005<br> | plasmalogen<br>9935<br>10168997 | 9837<br> | 16843<br>8362<br>12408535 | 30521<br>8253<br> | 33682<br>5283<br>9858472 |
| C8-pos | 4219<br>24992<br>2422<br>11310871 | 774.6368<br>9785<br>3980<br>11170466 | 11869<br>2867<br>11488631 | 121498<br>29604612 | 9.82 | HMDB11241<br>6439<br> | 8920<br>15726047 | C36:1 PC<br>6577<br>13056046 | plasmalogen<br>7868<br>14923394 | 8346<br>9810601<br>9890993<br>9199747<br>10393625<br>11734350 | 17902<br>2825<br>10393625 | 30859<br>3981<br>11681531 | 33665<br>5139 |
| C8-pos | 12285980<br>3654<br>24637<br>15960<br>1900370 | 790.575<br>16221<br>22703<br>1741635 | 21351<br>16047<br>1798776 | 20049<br>2077724 | 9.13 | HMDB11229<br>20981<br>3170292 | 26327<br>1773291 | C38:7 PC<br>19250<br>2377221 | plasmalogen<br>17832<br>1907951 | 21398<br>2113604 | 17836<br>15472<br>2111468 | 25239<br>19294<br>1714617 | 28831<br>24064<br>1634288 |
| C8-pos | 3752<br>7860<br>7786<br>898017 | 792.5868<br>6572<br>6268<br>870846 | 9847<br>4227<br>884659 | 3222<br>902722 | 9.26 | HMDB11319<br>4317<br>1142487 | 9704<br>912151 | C38:6 PC<br>8082<br>1196680 | plasmalogen<br>7415<br>981880 | 1953<br>984157 | 8525<br>11168<br>1041252 | 7806<br>7556<br>822009 | 7202<br>14587<br>812605 |
| C8-pos | 3909<br>768371<br>3912 | 796.6202<br>987283<br>818.6024<br>295190 | 1078238<br>373860 | 776557<br>270756 | 9.43<br>9.44 | HMDB11252<br>928342<br>338174<br>HMDB11294 | 837424<br>294254 | C38:4 PC<br>905446<br>C40:7 PC<br>315094 | plasmalogen<br>843780<br>plasmalogen<br>290149 | 727237<br>247372 | 736031<br>244937 | 760104<br>273112 | 798661<br>266929 |
| C8-pos | 262422<br>3313<br>547852<br>3061 | 690.5064<br>447388<br>692.5223 | 270517<br>108515 | 356301<br>110176 | 8.67<br>8.25 | HMDB08924<br>320563<br>HMDB08923<br>101764 | 333391<br>122280 | C32:1 PE<br>291585<br>C32:0 PE<br>91945 | 317531<br>100596 | 265621<br>84567<br>7869 | 360641<br>125078<br>11352 | 344883<br>116680<br>12481 | 322313<br>112959<br>11974 |
| C8-pos | 198216<br>3342<br>6597<br>5861<br>558652 | 188000<br>720.5538<br>9271<br>5549<br>509220 | 8556<br>955429 | 7874<br>1117347 | 8.74 | HMDB08925<br>9767<br>458844 | 7340<br>457968 | C34:0 PE<br>8328<br>495784 | 8680<br>535348 | 13062<br>383557 | 8673<br>494401 | 7546<br>421738 | 7099<br>501847 |
| C8-pos | 3415<br>146129<br>3484 | 740.5222<br>218649<br>742.5376 | 118460<br>450084 | 142636<br>506655 | 8.83<br>8.95 | HMDB08937<br>124663<br>HMDB09060<br>416406 | 131621<br>447064 | C36:4 PE<br>118010<br>C36:3 PE<br>416794 | 129102<br>385030 | 104233<br>424752 | 149847<br>417774 | 143295<br>438176 | 130559<br>414984 |
| C8-pos | 340121<br>3733<br>5651<br>181<br>3680246 | 509273<br>744.5332<br>5681<br>319<br>3786859 | 52821<br>3395962 | 2602<br>4208916 | 9.24 | HMDB08994<br>5455<br>4122531 | 2245<br>5055936 | C36:2 PE<br>4945<br>3923968 | 4081<br>4165180 | 12784<br>866<br>4448509 | 14671<br>541<br>3569714 | 13163<br>873<br>3960404 | 10983<br>1086<br>3807167 |
| C8-pos | 3999<br>23969 | 746.5684<br>34287 | 47783 | 20802 | 9.33 | HMDB08993<br>26522 | 19924 | C36:1 PE<br>20270 | 19321 | 24108<br>18675 | 35440<br>13018 | 31141<br>18511 | 41722<br>11254 |

TABLE 3-continued

Normalized data of lipidome analysis. WT and CD5L⁻/⁻ naïve T cells were differentiated. Cells and supernatant were harvested at 96 hours and subjected to MS/LC. Three independent mouse experiments were performed.

| | | | | | | | | | | |
|---|---|---|---|---|---|---|---|---|---|---|
| C8-pos | 19085 1855181 3357 | 16742 1744152 | | | | | | | | |
| C8-pos | 51149 | 764.5222 48056 | 2005824 25196 | 2363433 8.77 34992 | 1503895 28201 | 1642338 19572 | C38:6 PE | 1754345 30478 | 1592292 21866 | 1947173 27910 | 1688759 26143 | 1726200 21786 |
| C8-pos | 3506 256395 | 766.5356 514281 | 489954 | 8.96 539670 | 472317 | 397375 | C38:5 PE | 396650 | 472420 | 403384 | 414368 | 435699 |
| C8-pos | 3765 666081 | 768.5530 903253 | 709029 | 9.28 539081 | 633779 | 568470 | C38:4 PE | 699881 | 651459 | 591925 | 705578 | 672680 |
| C8-pos | 4080 61436 | 772.5843 71717 | 68990 | 9.63 65029 | 65347 | 50958 | C38:2 PE | 54137 | 62557 | 56708 | 51835 | 56264 |
| C8-pos | 3700 72994 | 792.5522 96534 | 44341 | 9.21 26155 | 47544 | 29885 | C40:6 PE | 41811 | 45483 | 47390 | 48158 | 42202 |
| C8-pos | 3637 3508 313 | 700.5269 1001 | 9.11 3435 | 10436 1676374 | 927 1504813 | 994 1473490 | C34:3 PE plasmalogen | 2013 1601491 | 1205 1663959 | 315 1502088 | 3268 4529 529 1403889 | 3581 1554480 |
| C8-pos | 1577519 3854 67685 14565 7174980 | 1566274 702.5428 44678 20190 7402199 | 9.40 5975.5 16468 7251904 | 129783 8486385 | 55681 7398272 | C34:2 PE 58357 7744044 | plasmalogen 53175 7174122 | 41392 7703723 | 74128 14817 7111560 | 87657 18415 7030362 | 81951 15351 7049910 |
| C8-pos | 3640 48563 13172 4634771 | 724.5267 37771 16303 5015778 | 9.11 40184 15677 5044780 | 73760 3922581 | 34243 4908445 | C36:5 PE 30355 4965877 | plasmalogen 34889 484283 | 26915 5262135 | 40752 10737 5122346 | 54305 13546 4843266 | 52833 13344 4855766 |
| C8-pos | 3748 1317246 3985 | 726.5419 1424357 | 1566291 | 9.26 1262383 | 1335926 | C36:4 PE 1440304 | plasmalogen 1465597 | 1265627 | 1204243 | 1257516 | 1382164 |
| C8-pos | 2039071 4193 | 728.5581 1925675 | 2110833 | 9.53 2005479 | 2067346 | C36:3 PE 2197766 | plasmalogen 2208121 | 1776859 | 1969337 | 2019556 | 2059995 |
| C8-pos | 2973411 4416 | 730.5743 4179185 | 3190190 | 9.81 3372145 | 2732591 | C36:2 PE 2758344 | plasmalogen 2800156 | 2969895 | 2947390 | 2717266 | 2933454 |
| C8-pos | 8091 3575 5394 375 1987230 | 732.5890 15518 | 11039 | 10.09 9973 | 4934 | C36:1 PE 6683 | plasmalogen 2890 | 10220 | 8834 | 1331 | 8348 |
| C8-pos | 3673 5818 3498 2775695 | 748.5270 3730 211 2149232 | 5437 1235 2042178 | 9.05 16837 2187170 | 6788 1919386 | C38:7 PE 3101 2068196 | 5421 2006011 | 3898 2193189 | 4996 727 1979745 | 7387 904 1993973 | 4712 514 1841759 |
| C8-pos | 3895 913 868 802626 | 750.5424 5381 2401 3103546 | 4312 3124 3128792 | 9.17 15021 2584653 | 3285 3002272 | C38:6 PE 2400 3250981 | 3689 3055968 | 3794 3338845 | 2809 2585 3050214 | 6062 3186 2818721 | 4439 2475 2867826 |
| C8-pos | 4271 | 752.5580 1473 1119 863949 | 1931 1878 855063 | 9.42 1042 728946 | 1391 808932 | C38:5 PE 1237 845912 | plasmalogen 934 841931 | 1487 958588 | 1511 564 821804 | 2365 798 762124 | 1670 1074 779000 |
| C8-pos | | 756.5900 | | 9.89 | | C38:3 PE | plasmalogen | | | | |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | 173311 | 150214 | 188897 | 121355 | 136541 | 163291 | 113677 | 134051 | 161849 | 109697 | 151354 |
|---|---|---|---|---|---|---|---|---|---|---|---|
| C8-pos | 143403 3669 5289 2944 57141 | 796.5231 29862 | 34910 | 9.16 47359 | n/a 36147 | plasmalogen 28431 | 25429 | | | | |
| C8-pos | | 772.5462 39515 | 28147 | 7.88 24783 | n/a 28719 | plasmalogen 19626 | 33047 | 23444 | 28781 | 32426 | 30383 |
| C8-pos | 1809 5610 8009 5822 6297 | 300.2896 5986 7013 | 3683 3544 | 5.30 5785 5081 | HMDB00252 6437 7277 | sphingosine 5782 7569 | 6186 6961 | 6279 5987 7978 | 6262 6595 5487 | 5717 5958 5982 | 5830 6481 7425 |
| C8-pos | 3317 5381 386 | 538.5193 2857 | 2784 | 8.68 6412 935229 | HMDB04949 2148 2245895 | (d18:1) 1640 649030 | C16:0 Ceramide 1377 719654 | (d18:1) 2053 667782 | 2312 172 553474 | 11317 202 704804 | 4392 545020 |
| C8-pos | 777682 4349 | 826322 622.6131 278913 | 679639 453439 | 10.02 152636 | HMDB04952 145634 | 139831 | C22:0 Ceramide 162430 | (d18:1) 182508 | 143835 | 167696 | 179750 |
| C8-pos | 141571 4556 7208 537 1097076 | 650.6444 3892 461 1074958 | 2117 1163 872705 | 10.42 1429 1809880 | HMDB04956 604 2396651 | 2579 1066298 | C24:0 Ceramide 3121 985035 | (d18:1) 2785 867055 | 2098 866 1032546 | 9698 1150 1083149 | 5789 1290 871600 |
| C8-pos | 4396 | 648.6287 763334 | 1162889 | 10.07 576791 | HMDB04953 515576 | 603086 | C24:1 Ceramide 578682 | (d18:1) 548454 | 518092 | 554878 | 595973 |
| C8-pos | 567193 3000 9142 11087 255549 | 673.5434 11591 4828 237241 | 12733 350938 | 8.04 9087 253737 | HMDB12097 9217 254918 | C14:0 SM 7770 214284 | 8883 227967 | 7959 12181 228444 | 9559 11585 238444 | 9222 9391 220909 | 10776 12347 230001 |
| C8-pos | 3051 63943 39520 499032 | 701.5591 57057 611116 | 57853 522262 | 8.20 62362 517495 | C16:1 SM 57874 489869 | 55303 541404 | 54686 70316 520994 | 68168 77401 481286 | 67177 78069 444595 | 64258 63207 509098 | 63072 69809 535642 |
| C8-pos | 3204 667158 729767 8195012 | 703.5750 695108 510351 7790921 | 627640 16896485 7269105 | 8.54 662029 | HMDB10169 730328 8378801 | C16:0 SM 625295 7242786 | 632621 7114819 | 620807 795200 7189596 | 740512 868058 6518633 | 748856 821109 7548428 | 733877 673210 6816746 |
| C8-pos | 3328 41978 49478 65233 | 729.5909 44233 31248 56986 | 26625 119011 | 8.70 40095 78464 | HMDB12101 46620 70080 | C18:1 SM 40347 57517 | 37361 63719 | 36412 61111 59973 | 45594 48186 62651 | 47549 52419 65769 | 44730 43633 61558 |
| C8-pos | 3555 136149 153438 310293 | 731.6061 146125 111808 268467 | 96927 855269 | 9.02 119938 386046 | HMDB01348 142660 297581 | C18:0 SM 125791 241201 | 121110 248992 | 117458 132121 256835 | 142563 157719 323721 | 158800 173907 305762 | 141233 142351 297472 |
| C8-pos | 3948 24083 35600 58215 | 759.6374 28883 20834 49057 | 13444 201123 | 9.47 24970 86391 | HMDB12102 30886 61387 | C20:0 SM 22376 48140 | 23359 39850 | 22951 39154 68887 | 27503 38233 67020 | 34023 38767 03427 | 26421 30489 58245 |
| C8-pos | 4071 | 785.6531 | | 9.62 | HMDB12104 | C22:1 SM | | 73484 | 99878 | 106308 | 94758 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | | | | | |
|---|---|---|---|---|---|---|---|---|---|---|---|---|
| C8-pos | 92451<br>114689<br>63953 | 99558<br>68821<br>62029 | 60658<br>185200 | 83489<br>97669 | 107560<br>93334 | 88959<br>54181 | 89952<br>61902 | 85549<br>51257 | 127628<br>72809 | 106901<br>79917 | 117027<br>86646 | 95753<br>58221 |
| C8-pos | 4287<br>182556<br>248143<br>226269 | 787.6685<br>203372<br>140499<br>177955 | 120739<br>702174 | 9.90<br>173962<br>289858 | HMDB12103<br>224541<br>252521 | 175775<br>230953 | 178380<br>178482 | C22:0 SM<br>165709<br>174751 | 164665<br>254378<br>279662 | 202116<br>226522<br>242316 | 213210<br>242826<br>214210 | 196619<br>198254<br>253557 |
| C8-pos | 4305<br>358027<br>439178<br>1673533 | 813.6845<br>368273<br>285569<br>1680676 | 255992<br>4502687 | 9.94<br>343329<br>1892962 | HMDB12107<br>404465<br>2121997 | 347245<br>1786867 | 344153<br>1625235 | C24:1 SM<br>320583<br>1458200 | 319121<br>474535<br>2070210 | 385323<br>415063<br>1783827 | 410943<br>462816<br>1848098 | 382997<br>370610<br>1981652 |
| C8-pos | 4505<br>109528<br>143329<br>788961 | 815.7001<br>105809<br>75575<br>723401 | 73061<br>2659819 | 10.32<br>100043<br>1030387 | HMDB11697<br>108323<br>915854 | 104885<br>1131635 | 101794<br>742938 | C21:0 SM<br>99062<br>730826 | 97691<br>147764<br>1153685 | 117738<br>136788<br>877032 | 128094<br>140707<br>731189 | 112782<br>111109<br>1077622 |
| C8-pos | 5101<br>24454<br>38303<br>19236 | 614.5885<br>26809<br>136617<br>38826 | 12157<br>21564 | 11.99<br>25499<br>51135 | HMDB06725<br>32126<br>60333 | 21322<br>19828 | 20646<br>52552 | C14:0 CE<br>25565<br>32618 | 20792<br>29736<br>33034 | 28098<br>26721<br>357217 | 35585<br>34784<br>67047 | 32731<br>23149<br>16887 |
| C8-pos | 5147<br>637519<br>903438<br>103872 | 640.6030<br>705343<br>516247<br>140093 | 443695<br>68186 | 12.07<br>623115<br>152396 | HMDB00658<br>759708<br>186523 | 633693<br>106968 | 599442<br>172453 | C16:1 CE<br>608399<br>153775 | 572917<br>774345<br>129404 | 702793<br>826925<br>131617 | 720891<br>913589<br>200886 | 675160<br>674051<br>91436 |
| C8-pos | 5331<br>455614<br>611127<br>68309 | 642.6188<br>583547<br>361132<br>66424 | 310548<br>38921 | 12.41<br>488377<br>100318 | HMDB00885<br>616083<br>94829 | 443440<br>51778 | 429573<br>88738 | C16:0 CE<br>457486<br>72865 | 456623<br>509366<br>69459 | 544473<br>582357<br>83747 | 562196<br>662568<br>96204 | 436316<br>423166<br>54128 |
| C8-pos | 5059<br>115511<br>164341<br>2183 | 664.6030<br>127138<br>91743<br>2988 | 78785<br>1748 | 11.88<br>106565<br>5216 | HMDB10370<br>131011<br>1989 | 109779 | 111157<br>3445 | C18:3 CE<br>111078<br>2797 | 103755<br>152048 | 106548<br>148947<br>1895 | 128366<br>160984<br>7354 | 118564<br>122979 |
| C8-pos | 5207<br>1475380<br>2046971<br>87550 | 666.6183<br>1592270<br>1209840<br>72046 | 1059467<br>35675 | 12.17<br>1575118<br>131075 | HMDB00610<br>1732351<br>86733 | 1488233<br>63029 | 1453388<br>86322 | C18:2 CE<br>1429105<br>150520 | 1361063<br>1752063<br>55482 | 1579498<br>1737348<br>102986 | 1711370<br>2161111<br>87598 | 1542494<br>1526199<br>43174 |
| C8-pos | 5396<br>2443677<br>3302551<br>563798 | 668.6341<br>2524289<br>1885560<br>817379 | 1662052<br>273554 | 12.49<br>2457691<br>659720 | HMDB00918<br>2963070<br>1032233 | 2322218<br>577948 | 2264956<br>1004224 | C18:1 CE<br>2286733<br>745875 | 2131567<>br>2816063<br>698951 | 2566278<br>2947078<br>662546 | 2741344<br>3734819<br>946763 | 2514407<br>2490701<br>461988 |
| C8-pos | 5559<br>43456<br>73417<br>45764 | 670.6496<br>50426<br>42521<br>72789 | 22610<br>46484 | 12.89<br>43185<br>78197 | HMDB10368<br>59923<br>106649 | 40826<br>16117 | 38444<br>93063 | C18:0 CE<br>40030<br>55116 | 38324<br>62024<br>61185 | 46335<br>58531<br>73524 | 51370<br>81333<br>90995 | 38640<br>51476<br>29667 |
| C8-pos | 4997<br>98552<br>132126 | 688.6028<br>101133<br>75271 | 65609 | 11.74<br>90393 | HMDB06731<br>106798 | 94865 | 87704 | C20:5 CE<br>87362 | 81281<br>123068 | 94461<br>122341 | 100730<br>129070 | 97839<br>99677 |
| C8-pos | 5107<br>2073841 | 690.6184<br>2087516 | 1416513 | 12.01<br>1930944 | HMDB06726<br>2369481 | 2050243 | 1967259 | C20:4 CE<br>1878830 | 1831098<br>2412243 | 2095091<br>2362367 | 2347139<br>2666967 | 2110729<br>2126271 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | | | | | |
|---|---|---|---|---|---|---|---|---|---|---|---|---|
| C8-pos | 2679860 68892 | 1516435 10559 | 12434 | 88353 | 16176 | 33519 | 125364 | 16232 | 19814 | 71971 | 22654 | 20978 |
| C8-pos | 5256 207090 291995 | 692.6343 221011 184042 | 134211 | 12.28 224788 | HMDB06736 244533 | 210119 | C20:3 CE 190141 | 200855 | 189943 263401 | 217622 246441 | 244177 316787 | 220165 224163 |
| C8-pos | 5050 227977 301789 2070 | 714.6184 230159 166812 1674 | 150814 447 | 11.87 217444 5984 | HMDB06733 248072 693 | 224341 | C22:6 CE 211038 3830 | 220477 | 200437 275331 | 226618 284378 2475 | 254381 288663 346 | 228037 235494 |
| C8-pos | 5169 30010 47488 | 716.6337 35279 16790 | 14882 | 12.11 277978 | HMDB10375 41248 | 21732 | C22:5 CE 25922 | 27832 | 23888 42449 | 31949 44796 | 36043 52757 | 36006 33758 |
| C8-pos | 1468 4748 5922 4284 | 318.2641 5265 5192 4770 | 4819 2293 | 4.80 4187 3382 | HMDB11562 4631 4456 | 4910 5693 | C14:1 MAG 5004 5288 | 4866 4732 | 4800 4967 5838 | 5000 4862 3899 | 4238 5080 4271 | 5011 4698 5093 |
| C8-pos | 1856 64680 74608 64817 | 346.2952 64346 63049 67822 | 63207 35331 | 5.33 64010 52234 | HMDB11565 64584 69621 | 64508 82482 | C16:1 MAG 65003 76327 | 63064 74667 | 61100 60145 85447 | 64093 67370 57468 | 67173 63131 60548 | 64524 61735 76804 |
| C8-pos | 2302 846754 843379 303618 | 376.3422 884764 886238 842776 | 863507 400440 | 6.19 832565 690212 | HMDB11131 875628 889459 | 869287 1003586 | C18:0 MAG 841534 982395 | 819586 989857 | 1155974 872784 997477 | 887122 833236 767027 | 818196 906529 767494 | 894474 1174404 975103 |
| C8-pos | 2744 59809 64660 59466 | 430.3893 68593 58310 61118 | 61639 29805 | 7.29 59519 52964 | HMDB11582 60572 64071 | 62221 74037 | C22:1 MAG 58657 70243 | 62191 71888 | 60148 57795 73082 | 64987 61219 58127 | 69591 64238 56793 | 60714 57780 69763 |
| C8-pos | 3571 35039 29191 234491 | 558.5093 39350 33609 177298 | 36322 315638 | 9.04 32217 239799 | HMDB07011 36286 152405 | 35543 243928 | C30:0 DAG 36333 217691 | 34588 165348 | 34891 31794 195972 | 39777 35529 205369 | 43685 34388 157756 | 42156 32658 264527 |
| C8-pos | 3436 7226 3683 | 582.5093 63790 8382 | 6454 | 8.86 25430 6024 | HMDB07128 21102 HMDB07099 | 10618 5339 | C32:2 DAG 11192 C32:1 DAG 5423 | 14884 4936 | 3917 6253 4288 | 13268 8049 6340 | 15458 6538 4953 | 7174 9031 5884 |
| C8-pos | 5628 4425 372323 | 584.5246 5182 265994 | 7167 334952 | 9.18 475015 | 6521 255061 | 569607 | 421645 | 299463 | 413401 | 352685 | 265995 | 438176 |
| C8-pos | 3958 240784 222946 1487483 | 591.4960 231703 234768 1030933 | 224520 1026254 | 9.48 230244 1182690 | HMDB07098 233669 877121 | 241661 1417285 | C32:0 DAG 244424 1335693 | 222337 897664 | 230834 215569 1173511 | 309105 229119 1389598 | 232115 230259 996304 | 244291 237316 1608300 |
| C8-pos | 3796 144.576 4054 7436 3612 1334361 | 610.5404 394267 612.5560 7494 7475 1023250 | 156413 16464 1506955 | 9.31 371997 9.61 6012 1703845 | HMDB07103 294663 HMDB07102 7927 1119435 | 187924 4042 1520909 | C34:2 DAG 241902 C34:1 DAG 7814 1346234 | 244659 6816 1007241 | 172468 7545 7559 1440289 | 249012 12588 5270 1389832 | 254769 10737 4753 1097630 | 166382 11297 2951 1433900 |
| C8-pos | 4292 | 614.5720 | | 9.91 | HMDB07100 | | C34:0 DAG | | 292394 | 280602 | 287972 | 279073 |

TABLE 3-continued

Normalized data of lipidome analysis. WT and CD5L−/− naïve T cells were differentiated. Cells and supernatant were harvested at 96 hours and subjected to MS/LC. Three independent mouse experiments were performed.

| Mode | Col1 | Col2 | m/z | Col4 | RT | Col6 | HMDB ID | Col8 | Lipid | Col10 | Col11 | Col12 | Col13 | Col14 | Col15 | Col16 |
|---|---|---|---|---|---|---|---|---|---|---|---|---|---|---|---|---|
| C8-pos | 257524 / 272960 / 1110093 | 265547 / 253428 / 775022 | 636.5556 | 242016 / 971688 | 9.44 | 275783 / 794560 | HMDB07219 | 263176 / 887137 | C36:3 DAG | 249314 / 921584 | 255239 / 702180 | 274650 / 907993 | 250588 / 1051245 | 260634 / 826812 | 305939 / 1019799 | |
| C8-pos | 3921 / 18961 / 514261 | 117295 / 382395 | 638.5716 | 64187 / 598305 | 9.73 | 50166 / 986304 | HMDB07218 | 34538 / 810333 | C36:2 DAG | 35467 / 545140 | 41778 / 695589 | 36017 / 656042 | 43252 / 574819 | 43153 / 708836 | 29550 / 689206 | |
| C8-pos | 4154 / 833 / 746 | 961 | | 1463 | | 1348 | | 3717 | | 799 | 1588 | 1320 | 3629 | 2047 | 2802 / 258 | |
| C8-pos | 4369 / 3661 / 514 | 3542 / 1164 / 533043 | 640.5872 | 848 / 968136 | 10.03 | 2312 / 567275 | HMDB07216 | 3559 / 608300 | C36:1 DAG | 1843 / 643713 | 936 / 482239 | 2121 / 2264 / 629550 | 6443 / 550 / 701081 | 2613 / 849 / 556750 | 3865 / 617 / 682088 | |
| C8-pos | 696032 / 4503 / 343892 | 342740 / 338549 / 353108 | 642.6030 | 323635 / 303614 | 10.31 | 369944 / 366236 | HMDB07158 | 368085 / 406492 | C36:0 DAG | 333929 / 408882 | 328988 / 414941 | 508832 / 403680 / 426119 | 372153 / 355330 / 340417 | 387710 / 398580 / 332082 | 379161 / 566272 / 410756 | |
| C8-pos | 370959 / 366333 / 4826 | 375734 / 217481 | 740.6763 | 52502 / 265627 | 11.25 | 59302 / 225393 | n/a | 38684 / 109815 | C42:0 TAG | 35630 / 117394 | 37369 / 37042 / 97206 | 43923 / 43723 / 98394 | 48718 / 44105 / 112797 | 48554 / 39706 / 107826 | 40169 / 48263 / 98858 | |
| C8-pos | 49632 / 36782 / 112682 | 39459 / 120722 | | 39625 / 98713 | | 105263 | | | | | | | | | | |
| C8-pos | 4806 / 4567 / 5851 / 17821 | 5254 / 20116 | 764.6759 | 5909 / 19471 | 11.16 | 5523 / 22108 | n/a | 3516 / 16403 | C44:2 TAG | 5324 / 20781 | 5545 / 3659 / 13182 | 8885 / 5314 / 13510 | 9390 / 5215 / 37054 | 6005 / 3754 / 12137 | 5122 / 4250 / 16879 | |
| C8-pos | 4859 / 58227 / 56365 / 289403 | 55775 / 353201 | 766.6918 | 55086 / 388320 | 11.36 | 59302 / 225393 | n/a | 55884 / 240562 | C44:1 TAG | 57732 / 289308 | 55147 / 51945 / 227513 | 64327 / 57483 / 257786 | 70035 / 57147 / 322758 | 61652 / 53991 / 239002 | 54715 / 64503 / 254194 | |
| C8-pos | 4936 / 211935 / 217189 / 634995 | 209117 / 180753 / 673130 | 768.7075 | 193037 / 744969 | 11.59 | 199574 / 647869 | HMDB42063 | 198534 / 588998 | C44:0 TAG | 189270 / 667889 | 182887 / 677918 | 178738 / 186303 / 556458 | 194756 / 212158 / 690896 | 227900 / 186566 / 703949 | 226558 / 170578 / 610664 | |
| C8-pos | 4913 / 36670 / 102817 / 315800 | 94319 / 90730 / 363068 | 792.7073 | 81370 / 529890 | 11.51 | 103115 / 351965 | HMDB10419 | 94476 / 353238 | C46:2 TAG | 86713 / 332568 | 89858 / 372316 | 83651 / 80248 / 318760 | 101588 / 99211 / 316671 | 95120 / 86847 / 450181 | 102028 / 88469 / 315919 | |
| C8-pos | 4976 / 249655 / 277546 / 1949270 | 273855 / 225823 / 2164580 | 794.7231 | 237058 / 2609179 | 11.69 | 270928 / 2048813 | HMDB10412 | 240293 / 1552798 | C46:1 TAG | 2415345 / 1745015 | 228513 / 1964234 | 224904 / 227298 / 1670872 | 260251 / 259268 / 1976636 | 278319 / 248006 / 2335415 | 284146 / 236908 / 1717551 | |
| C8-pos | 5070 / 488767 / 580670 / 2415192 | 560364 / 456426 / 2296616 | 796.7388 | 483196 / 2759877 | 11.94 | 583093 / 2403404 | HMDB10411 | 489897 / 1843221 | C46:0 TAG | 475003 / 2277657 | 467858 / 2397312 | 461228 / 479370 / 1716677 | 566849 / 518846 / 2521591 | 578068 / 502407 / 2601075 | 583191 / 458390 / 1931286 | |
| C8-pos | 4923 / 489 / 971 / 133041 | 1360 / 1147 / 153543 | 818.7228 | 540 / 225768 | 11.54 | 1054 / 160536 | HMDB05432 | 1419 / 136250 | C48:3 TAG | 1253 / 139403 | 160147 | 209 / 104767 | 1494 / 594 / 130187 | 1534 / 868 / 175511 | 1958 / 476 / 110337 | |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| Mode | m/z | RT | HMDB ID | Lipid | | | | | |
|---|---|---|---|---|---|---|---|---|---|
| C8-pos | 820.7387 | 11.79 | HMDB05376 | C48:2 TAG | 226866 | 277617 | 291382 | 296356 | |
| | 5017 | 240393 | 286231 | 239610 | 230134 | 250176 | 239586 | 220812 | |
| | 246870 | 2990127 | 2420528 | 2007367 | 1768998 | 2225242 | 2674619 | 1883797 | |
| | 287917 | | | 241095 | | | | | |
| | 2137050 | | | 1767866 | | | | | |
| C8-pos | 822.7547 | 12.03 | HMDB05359 | C48:1 TAG | 442318 | 567443 | 570644 | 561138 | |
| | 5127 | 472466 | 565226 | 459583 | 476449 | 531643 | 540101 | 450695 | |
| | 472862 | 14690946 | 11586953 | 9809551 | 8000614 | 8568680 | 5922305 | | |
| | 532438 | 11195516 | 6761667 | 9053389 | | | 475726 | | |
| | 449152 | | | | | | 9539363 | | |
| | 588147 | | | | | | | | |
| | 421709 | | | | | | | | |
| | 10202122 | | | | | | | | |
| C8-pos | 824.7697 | 12.30 | HMDB05356 | C48:0 TAG | 515393 | 608742 | 634496 | 637841 | |
| | 5268 | 571423 | 606066 | 519445 | 512039 | 543511 | 630404 | 498694 | |
| | 518976 | 5428185 | 4748081 | 4267458 | 3012102 | 5686474 | 5210582 | 3386390 | |
| | 597758 | | | | | 544968 | | | |
| | 625044 | | | | | 3021429 | | | |
| | 524206 | | | | | | | | |
| | 537950 | | | | | | | | |
| | 5396347 | | | | | | | | |
| | 5011027 | | | | | | | | |
| | 4259963 | | | | | | | | |
| C8-pos | 844.7386 | 11.65 | HMDB05435 | C50:4 TAG | 152575 | 69267 | 100758 | 104266 | |
| | 4954 | 81132 | 94366 | 76652 | 87259 | 110639 | 115424 | 108401 | |
| | 133168 | 2186154 | 117971 | 84203 | 75601 | 89680 | 92789 | 77011 | |
| | 5054 | | | 1480312 | 1167374 | 1568078 | 2045959 | 1172454 | |
| | 90772 | | | | 100328 | | | | |
| | 119449 | 83616 | HMDB05433 | C50:3 TAG | | | | | |
| | 218410 | | | 76652 | | | | | |
| | 78272 | | | 1262113 | | | | | |
| | 111913 | | | | | | | | |
| | 70843 | | | | | | | | |
| | 1430166 | | | | | | | | |
| | 1592102 | | | | | | | | |
| C8-pos | 848.7699 | 12.13 | HMDB05377 | C50:2 TAG | 274652 | 367013 | 389715 | 370911 | |
| | 5181 | 332783 | 354176 | 274108 | 284678 | 308581 | 371907 | 275917 | |
| | 289828 | 13292884 | 16369602 | 13821058 | 7431549 | 10423726 | 11754062 | | |
| | 327021 | | | 14919640 | 11427553 | | | | |
| | 370283 | | | | | | | | |
| | 291410 | | | | | | | | |
| | 10706423 | | | | | | | | |
| C8-pos | 850.7853 | 12.38 | HMDB05360 | C50:1 TAG | 325014 | 448769 | 454143 | 415848 | |
| | 5302 | 393750 | 445769 | 317759 | 352894 | 410302 | 451401 | 324123 | |
| | 344924 | | | 19590463 | 10135680 | 13695408 | | | |
| | 408051 | | | 22104686 | 12548564 | 18665895 | | | |
| | 430529 | | | | | 338992 | | | |
| | 314018 | | | | | | | | |
| | 16210693 | 24354437 | 20387591 | | | | | | |
| | 17287267 | 11243472 | 22401227 | | | | | | |
| C8-pos | 852.8023 | 12.66 | HMDB05357 | C50:0 TAG | 163122 | 222828 | 233162 | 230123 | |
| | 5461 | 191481 | 212823 | 165080 | 201973 | 208703 | 208102 | 160029 | |
| | 195689 | 4729959 | 4760887 | 4249729 | 2668501 | 6074739 | 5181511 | 3170897 | |
| | 204302 | | | 192575 | | | | | |
| | 170824 | | | 2591195 | | | | | |
| | 188776 | | | | | | | | |
| | 4613212 | | | | | | | | |
| | 4078311 | | | | | | | | |
| C8-pos | 870.7531 | 11.84 | HMDB05380 | C52:5 TAG | 675 | 1873 | 1754 | 2272 | |
| | 5038 | 2501 | 2131 | 1184 | 789 | | 915 | 5 | |
| | 408 | 264430 | 117707 | 59933 | 45008 | 90787 | 125838 | 38998 | |
| | 1401 | | | 688 | | | | | |
| | 429 | | | 43983 | | | | | |
| | 122400 | | | | | | | | |
| | 82395 | 622 | | | | | | | |
| | 76295 | 80698 | | | | | | | |
| C8-pos | 872.7693 | 11.98 | HMDB05363 | C52:4 TAG | 4663 | 14837 | 15257 | 11073 | |
| | 5088 | 4424 | 15324 | 4181 | 5854 | 9360 | 8703 | 4635 | |
| | 10729 | 1264170 | 984175 | 756156 | 572291 | 868565 | 1129926 | 546278 | |
| | 5167 | | | 5887 | | | | | |
| | 22401 | | | 610178 | 3576 | | | | |
| | 4405 | | | | 822231 | | | | |
| | 933225 | | | | | | | | |
| | 749902 | | | | | | | | |
| | 804516 | | | | | | | | |
| C8-pos | 874.7856 | 12.23 | HMDB05384 | C32:3 TAG | 76035 | 111588 | 123729 | 98141 | |
| | 5239 | 94645 | 101753 | 62681 | 86090 | 80429 | 103045 | 81090 | |
| | 87433 | 7074262 | 6815650 | 5369150 | 3934292 | 60107329 | 7482990 | 3764748 | |
| | 99840 | | | 83664 | | | | | |
| | 109895 | | | 4092145 | | | | | |
| | 90060 | | | | | | | | |
| | 75256 | | | | | 74607 | | | |
| | 5147894 | | | | | 5024709 | | | |
| | 5293073 | | | | | | | | |
| C8-pos | 876.8006 | 12.48 | HMDB05369 | C52:2 TAG | 216419 | 309244 | 331857 | 290766 | |
| | 5368 | 261403 | 307597 | 217432 | 232763 | 259660 | 310781 | 214528 | |
| | 251983 | | | 29911870 | 14306323 | | 19022015 | | |
| | 266518 | | | 31515704 | 16648978 | | 23527421 | | |
| | 186873 | | | | | 220341 | | | |
| | 217777 | 26039568 | | | | | | | |
| | 32020579 | 28574897 | | | | | | | |
| | 280596 | | | | | | | | |
| | 22074541 | | | | | | | | |
| | 15644212 | | | | | | | | |
| | 24598791 | | | | | | | | |
| | 5677924 | | | | | | | | |
| C8-pos | 878.8167 | 12.75 | HMDB05367 | C52:1 TAG | 93308 | 143165 | 145841 | 121055 | |
| | 5500 | | | | | | | | | |

TABLE 3-continued

Normalized data of lipidome analysis. WT and CD5L−/− naïve T cells were differentiated. Cells and supernatant were harvested at 96 hours and subjected to MS/LC. Three independent mouse experiments were performed.

| | | | | | | | | | | | |
|---|---|---|---|---|---|---|---|---|---|---|---|
| C8-pos | 103945 120885 12426254 | 108591 104117 | 110988 15934169 8874614 | 97290 19194773 | 122275 15497335 | 100814 18549077 | 106406 16709333 | 106518 9938402 | 101216 7202164 15084759 | 98972 13365588 | 105375 13784123 | 102183 |
| C8-pos | 5614 84875 104111 2370374 | 880.8327 98707 90553 1835281 | 8874614 82340 2169808 | 13.06 92627 2086724 | HMDB05365 104488 2209777 | 86197 1073673 | C52:0 TAG 78099 1691964 | 75535 1672756 | 77655 89258 1480353 | 101915 94413 3157899 | 100396 99162 2529786 | 108753 82382 1446319 |
| C8-pos | 5013 1988 565 30312 | 894.7562 1532 566 30120 | 1964 61911 | 11.76 1943 107826 | HMDB05447 1581 51498 | 1614 28755 | C54:7 TAG 1304 23372 | 1258 41171 | 1712 1922 23504 | 1612 1279 37626 | 1835 1163 50395 | 1508 1361 20679 |
| C8-pos | 5102 29072 8941 150105 | 896.7682 14490 27157 158620 | 30686 268344 | 11.99 26757 465398 | HMDB05391 18124 226361 | 17973 103193 | C54:6 TAG 33584 126192 | 25938 175891 | 24726 30347 77425 | 11704 14979 187077 | 19208 24544 272371 | 12277 24956 73058 |
| C8-pos | 5284 41779 46060 710805 | 898.7851 46111 33745 753468 | 35255 852825 | 12.10 40502 1402450 | HMDB05385 47315 902521 | 40548 539037 | C54:5 TAG 52340 696995 | 38500 746485 | 45839 57529 543680 | 47637 56038 785829 | 41436 52330 1014925 | 50813 51168 496383 |
| C8-pos | 5284 3407822 2975426 5044262 | 900.8078 2822252 3077615 5404865 | 3377080 3452580 | 12.32 3209017 4694005 | HMDB05370 3024770 5560806 | 3348597 4623356 | C54:4 TAG 3329543 5176966 | 3340020 5203833 | 3186895 3163787 5224874 | 2931103 3108891 5238530 | 2937012 3207740 5881843 | 2912884 3323080 4977277 |
| C8-pos | 5437 1095539 994191 11546223 | 902.8160 887826 1072922 | 1091229 12686211 8639554 | 12.58 1049941 14222512 | HMDB05405 1004249 12014459 | 1114526 16189069 | C54:3 TAG 1079602 15064281 | 1120857 8142347 | 1015086 1061604 7882052 11122552 | 916038 1060923 11100007 | 957776 1084945 12073765 | 914912 1050798 |
| C8-pos | 5539 617872 576931 11753355 | 904.8320 607071 593008 | 648497 14785027 8030046 | 12.85 602083 16230612 | HMDB05403 570480 12449009 | 635317 16291399 | C54:2 TAG 655183 15060181 | 658020 8645345 | 609741 623058 6405154 12428285 | 581598 627414 11402769 | 603193 588417 12451251 | 539757 662444 |
| C8-pos | 5645 399533 387199 3598771 | 906.8480 366077 420771 3336165 | 421354 4527640 | 13.14 384306 3581595 | HMDB05395 360391 3941310 | 413574 1984355 | C54:1 TAG 431978 2770636 | 428456 3109555 | 388587 384376 2668140 | 328353 374731 4892882 | 358229 406145 4351790 | 356214 426703 2645219 |
| C8-pos | 5045 29238 5165 427333 | 920.7696 81933 922.7846 639806 | 34039 391359 | 11.85 17018 12.09 159598 | HMDB05392 21029 HMDB05462 223479 | 25236 246039 | C56:8 TAG 6251 C56:7 TAG 177444 | 19036 304798 | 37027 396523 | 13212 161746 | 13406 252993 | 24675 287899 |
| C8-pos | 5292 624616 5362 1207940 | 924.8010 973633 926.8155 1599057 | 720460 1528301 | 12.34 385051 12.45 681656 | HMDB05456 520191 HMDB05406 922026 | 582461 1162332 | C56:6 TAG 372169 C56:5 TAG 738401 | 607606 1295519 | 769519 1617719 | 366005 692806 | 526222 1041186 | 555357 1160337 |
| C8-pos | 5478 1472214 | 928.8318 1396382 | 1611175 | 12.69 620597 | HMDB05398 1073538 | 1154684 | C56:4 TAG 706598 | 1513989 | 1684181 | 752946 | 1147682 | 1249745 |
| C8-pos | 5575 2460671 | 930.8478 1936380 | 2567613 | 12.94 989546 | HMDB05410 1570627 | 1843540 | C56:3 TAG 1292129 | 2484273 | 2674311 | 1211022 | 1728121 | 2008602 |
| C8-pos | 5674 2439948 | 932.8636 1739238 | 2119900 | 13.24 905634 | HMDB05404 1458441 | 1649493 | C56:2 TAG 1327623 | 2392210 | 2259069 | 1385794 | 1616184 | 1710332 |

TABLE 3-continued

Normalized data of lipidome analysis. WT and CD5L$^{-/-}$ naïve T cells were differentiated. Cells and supernatant were harvested at 96 hours and subjected to MS/LC. Three independent mouse experiments were performed.

| | | | | | | | | |
|---|---|---|---|---|---|---|---|---|
| C8-pos | 5784 | 934.8792 | | 688916 | HMDB05396 720330 | C56:1 TAG 622476 | 1122804 | 954629 | 673128 | 921504 | 754286 |
| C8-pos | 1149546 862836 851145 | | 473841 | | | | | |
| C8-pos | 5219 | 948.8011 | | 222760 | HMDB05413 208380 | C58:8 TAG 138605 | 196049 | 287264 | 128092 | 164740 | 187556 |
| C8-pos | 166519 308720 263297 | 12.18 175703 | | | | | | |
| C8-pos | 5274 | 930.8160 | 12.30 | 86387 | HMDB05471 69912 | C58:7 TAG 42279 | 94168 | 131536 | 46198 | 59664 | 79383 |
| C8-pos | 87442 144435 115307 | 58099 | | | | | | |
| C8-pos | 5424 | 952.8316 | 12.56 | 207320 | HMDB05458 196952 | C58:6 TAG 124707 | 261118 | 315760 | 116415 | 209967 | 221993 |
| C8-pos | 305241 335779 295146 | 109192 | | | | | | |
| C8-pos | | 887.5597 | 8.94 | | HMDB09813 | C38:4 PI 274277 | | | | | |
| C8-pos | 478504 264239 130272 | 243273 | | 197145 | 236428 | 272264 | 283494 | 360193 | 207122 |
| C8-pos | | 706.4654 | 3.8 | | HMDB12333 | C30:1 PS | | | | | |
| C8-pos | 41451 54468 43314 | 39993 | | 48893 | 47442 | 41921 | 39816 | 47219 | 42692 | 48479 |
| C8-pos | 38012 36694 17902 | 36204 | | 46292 | 44207 | 50873 | 43167 | 38690 | 45510 | 42707 |
| C8-pos | 41000 45056 | | | | | | 59917 | 32869 | 41585 | 46242 |
| C8-pos | | 764.5431 | 8.5 | | HMDB12356 | C34:0 PS | | | | | |
| C8-pos | 182478 218389 103411 | 220445 | | 154758 | 162547 | 151109 | 139892 | 111202 | 175856 | 167202 | 144916 |
| C8-pos | | 808.5092 | 8.50 | | HMDB12362 | C38:6 PS | | | | | |
| C8-pos | 94649 100121 67324 | 125913 | | 84159 | 79702 | 102703 | 73505 | 60471 | 110177 | 82964 | 81884 |
| C8-pos | 3134 | 808.5071 | 8.41 | | HMDB10167 | C40:6 PS | | | | | |
| C8-pos | 9208 10603 14548 | 13971 | | 12764 | 11043 | 8192 | 11421 | 11597 | 17160 | 15134 | 12448 |
| C8-pos | 17050 8731 | | | | | | | 19682 | 14296 | 16584 | 14854 |
| C8-pos | 630754 590984 743019 | 646047 | | 572721 | 515868 | 559644 | 557435 | 614265 | 577272 | 496869 | 663441 |

TABLE 4

Figure 21A:
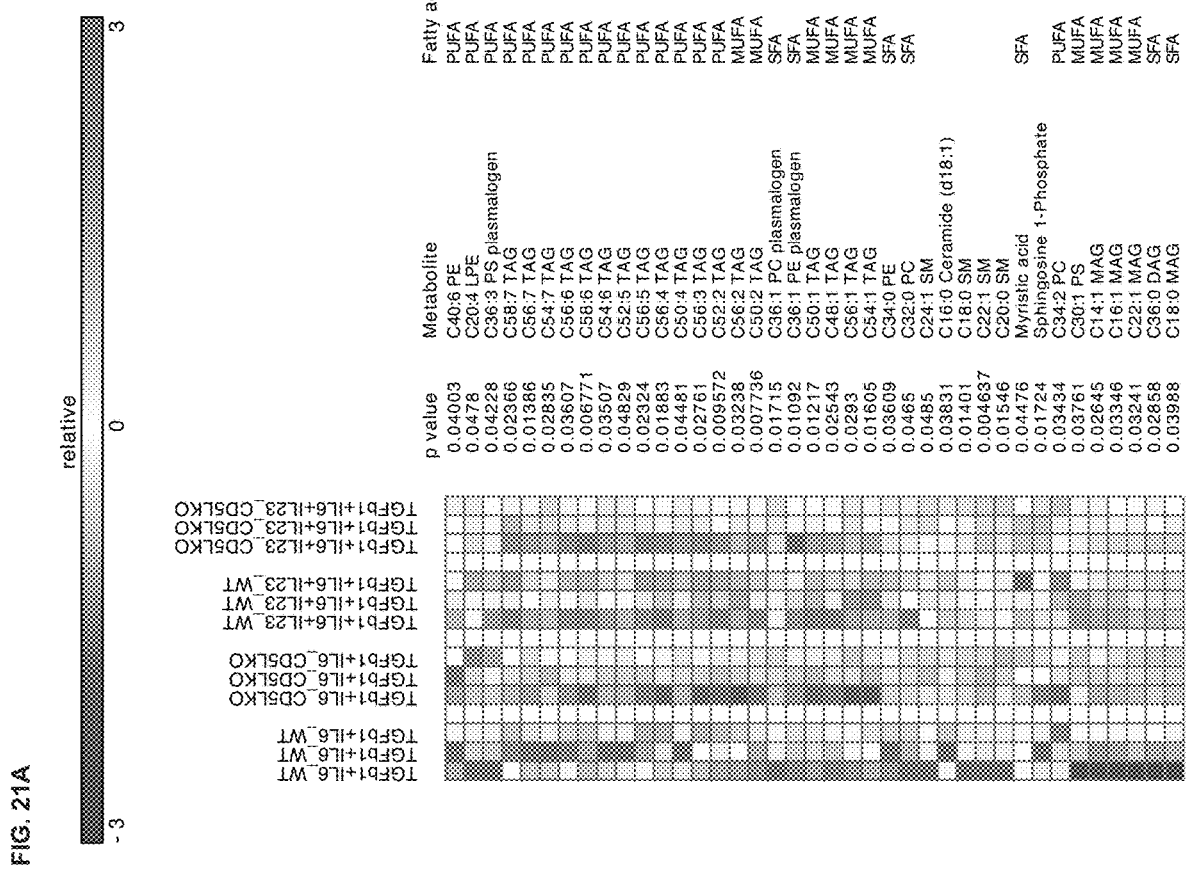
Figure 21B:
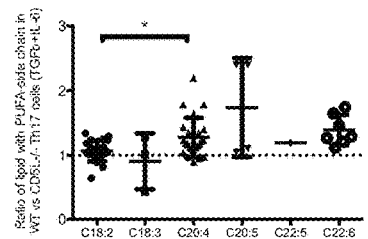
Figure 21C:
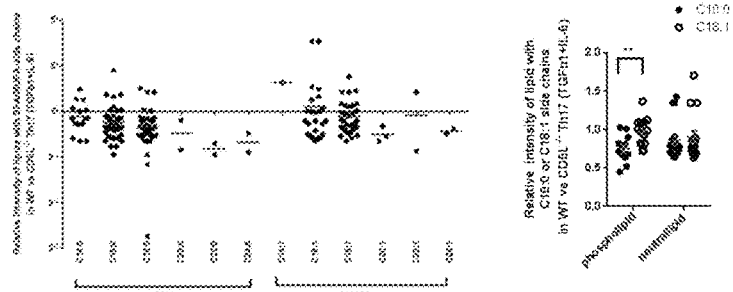
Figure 21D:
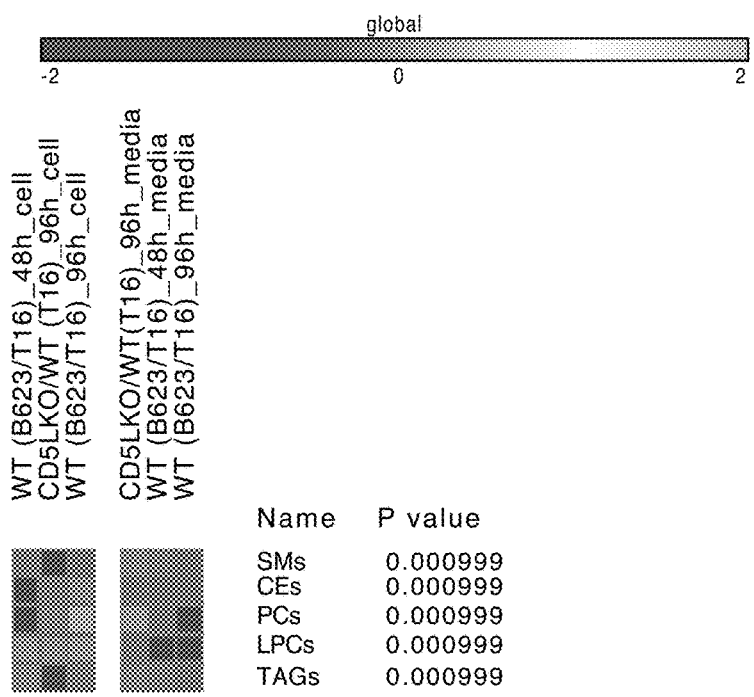
Figure 21E:
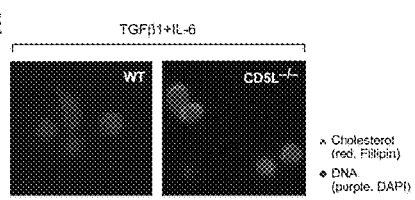

Lipidomics data showing all lipids detected except those shown in FIG. 21A. Data shown are normalized to WT (TGFb1 + IL-6) condition showing average of 3 independent biological experiments.

| Lipids that are not significantly different or have a fold change less thatn 1.5 | Min P value | WT (TGFb1 + IL-6) | CDSL−/− (TGFb1 + IL-6) | WT (TGFb1 + IL-6 + IL-23) | CDSL−/− (TGFb1 + IL-6 + IL-23) |
|---|---|---|---|---|---|
| 12-HETE | N/A | undetected | N/A | N/A | N/A |
| 13-S-HODE | 0.212 | 1 | 0.849 | 1.649 | 1.161 |
| 15-HETE | N/A | undetected | N/A | N/A | N/A |
| 5-HETE | N/A | undetected | N/A | N/A | N/A |
| Arachidonic acid | N/A | undetected | N/A | N/A | N/A |
| C14:0 CE | 0.096 | 1 | 0.789 | 1.021 | 0.563 |
| C14:0 LPC | 0.124 | 1 | 1.269 | 0.957 | 1.016 |
| C14:0 SM | 0.039 | 1 | 0.742 | 0.800 | 0.839 |
| C16:0 CE | 0.043 | 1 | 0.912 | 1.066 | 0.807 |
| C16:0 LPC | 0.277 | 1 | 0.960 | 0.922 | 0.991 |
| C16:0 LPE | 0.181 | 1 | 0.693 | 0.706 | 0.718 |
| C16:0 SM | 0.052 | 1 | 0.668 | 0.647 | 0.721 |
| C16:1 CE | 0.107 | 1 | 1.064 | 1.135 | 0.836 |
| C16:1 LPC | 0.140 | 1 | 1.245 | 1.185 | 1.153 |
| C16:1 SM | 0.072 | 1 | 0.978 | 0.876 | 0.935 |
| C18:0 CE | 0.083 | 1 | 0.710 | 0.976 | 0.641 |
| C18:0 LPC | 0.111 | 1 | 0.806 | 0.866 | 0.988 |
| C18:0 LPE | 0.052 | 1 | 0.732 | 0.802 | 0.887 |
| C18:1 CE | 0.163 | 1 | 1.184 | 1.174 | 0.938 |
| C18:1 LPC | 0.113 | 1 | 1.264 | 1.187 | 1.184 |
| C18:1 LPE | 0.366 | 1 | 1.050 | 0.992 | 1.004 |
| C18:1 SM | 0.059 | 1 | 0.658 | 0.704 | 0.687 |
| C18:2 CE | 0.165 | 1 | 1.183 | 0.971 | 0.800 |
| C18:2 LPC | 0.133 | 1 | 0.631 | 0.714 | 0.737 |
| C18:3 CE | 0.204 | 1 | 1.046 | 1.550 | 0.866 |
| C20:3 CE | N/A | undetected | N/A | N/A | N/A |
| C20:3 LPC | 0.141 | 1 | 1.000 | 0.944 | 1.080 |
| C20:4 CE | 0.276 | 1 | 1.495 | 0.977 | 0.857 |
| C20:4 LPC | N/A | undetected | N/A | N/A | N/A |
| C20:4 LPE | 0.048 | 1 | 0.672 | 0.782 | 0.792 |
| C20:5 CE | N/A | undetected | N/A | N/A | N/A |
| C22:0 Coramide (d18:1) | 0.086 | 1 | 0.509 | 0.552 | 0.553 |
| C22:0 SM | 0.063 | 1 | 0.469 | 0.592 | 0.529 |
| C22:5 CE | N/A | undetected | N/A | N/A | N/A |
| C22:6 CE | N/A | 1 | 1.613 | 0.594 | 0.788 |
| C22:6 LPC | N/A | undetected | N/A | N/A | N/A |
| C24:0 Coramide (d18:1) | 0.083 | 1 | 0.570 | 0.583 | 0.594 |
| C24:0 SM | 0.153 | 1 | 0.566 | 0.600 | 0.562 |
| C24:1 Coramide (d18:1) | 0.088 | 1 | 0.667 | 0.657 | 0.686 |
| C30:0 DAG | 0.128 | 1 | 0.886 | 0.790 | 0.955 |
| C30:0 PC | 0.015 | 1 | 0.726 | 0.604 | 0.780 |
| C30:1 PC | 0.121 | 1 | 1.162 | 0.868 | 1.010 |
| C32:0 DAG | 0.076 | 1 | 1.183 | 1.153 | 1.337 |
| C32:0 PE | 0.006 | 1 | 0.676 | 0.560 | 0.717 |
| C32:1 DAG | 0.194 | 1 | 1.212 | 0.969 | 1.011 |
| C32:1 PC | 0.064 | 1 | 0.800 | 0.683 | 0.798 |
| C32:1 PE | 0.026 | 1 | 0.798 | 0.691 | 0.812 |
| C32:2 DAG | 0.086 | 1 | 0.738 | 0.387 | 0.489 |
| C32:2 PC | 0.072 | 1 | 1.368 | 0.993 | 1.131 |
| C34:0 DAG | 0.170 | 1 | 0.884 | 0.981 | 1.022 |
| C34:0 PC | 0.045 | 1 | 0.711 | 0.794 | 0.860 |
| C34:0 PS | 0.065 | 1 | 1.066 | 0.798 | 0.968 |
| C34:1 DAG | 0.222 | 1 | 0.895 | 0.907 | 0.876 |
| C34:1 PC | 0.002 | 1 | 0.743 | 0.809 | 0.847 |
| C34:1 PC plasmalogen-A | 0.112 | 1 | 0.718 | 0.728 | 0.739 |
| C34:2 DAG | 0.163 | 1 | 1.229 | 0.948 | 0.964 |
| C34:2 PC plasmalogen | 0.157 | 1 | 0.929 | 0.863 | 0.858 |
| C34:2 PE plasmalogen | 0.020 | 1 | 0.906 | 0.897 | 0.924 |
| C34:3 PC | 0.014 | 1 | 1.071 | 0.815 | 0.920 |
| C34:3 PE plasmalogen | 0.303 | 1 | 1.007 | 0.992 | 1.020 |
| C34:4 PC plasmalogen | 0.160 | 1 | 0.900 | 0.767 | 0.845 |
| C36:1 DAG | 0.090 | 1 | 0.737 | 0.802 | 0.813 |
| C36:1 PC | 0.049 | 1 | 0.679 | 0.781 | 0.797 |
| C36:1 PE | 0.043 | 1 | 0.797 | 0.850 | 0.856 |
| C36:2 DAG | 0.178 | 1 | 1.221 | 1.004 | 0.997 |
| C36:2 PC | 0.050 | 1 | 1.084 | 0.998 | 0.967 |
| C36:2 PC plasmalogen | 0.037 | 1 | 0.930 | 0.906 | 0.828 |
| C36:2 PE | 0.073 | 1 | 1.121 | 1.021 | 0.961 |
| C36:2 PE plasmalogen | 0.022 | 1 | 0.740 | 0.812 | 0.803 |
| C36:3 DAG | 0.124 | 1 | 0.899 | 0.684 | 0.700 |
| C36:3 PC | 0.046 | 1 | 1.012 | 0.898 | 0.934 |

TABLE 4-continued

Lipidomics data showing all lipids detected except those shown in FIG. 21A. Data shown are normalized to WT (TGFb1 + IL-6) condition showing average of 3 independent biological experiments.

| Lipids that are not significantly different or have a fold change less thatn 1.5 | Min P value | WT (TGFb1 + IL-6) | CDSL−/− (TGFb1 + IL-6) | WT (TGFb1 + IL-6 + IL-23) | CDSL−/− (TGFb1 + IL-6 + IL-23) |
|---|---|---|---|---|---|
| C36:3 PC plasmalogen | 0.056 | 1 | 0.987 | 0.853 | 0.829 |
| C36:3 PE | 0.088 | 1 | 1.054 | 0.944 | 0.978 |
| C36:3 PE plasmalogen | 0.058 | 1 | 1.095 | 1.019 | 1.013 |
| C36:4 PC plasmalogen | 0.081 | 1 | 0.829 | 0.748 | 0.731 |
| C36:4 PE | 0.029 | 1 | 0.826 | 0.727 | 0.877 |
| C36:4 PE plasmalogen | 0.113 | 1 | 0.978 | 0.925 | 0.930 |
| C36:5 PE plasmalogen | 0.280 | 1 | 1.051 | 1.034 | 1.029 |
| C38:2 PC | 0.005 | 1 | 0.902 | 0.886 | 0.863 |
| C38:2 PE | 0.011 | 1 | 0.911 | 0.829 | 0.815 |
| C38:3 PC | 0.051 | 1 | 0.901 | 0.843 | 0.877 |
| C38:3 PE plasmalogen | 0.051 | 1 | 0.822 | 0.799 | 0.789 |
| C38:4 PC | 0.068 | 1 | 1.152 | 1.009 | 1.027 |
| C38:4 PC plasmalogen | 0.009 | 1 | 0.940 | 0.812 | 0.819 |
| C38:4 PE | 0.043 | 1 | 0.766 | 0.843 | 0.865 |
| C38:4 PI | 0.140 | 1 | 0.775 | 0.871 | 0.975 |
| C38:5 PE | 0.084 | 1 | 1.137 | 1.005 | 0.994 |
| C38:5 PE plasmalogen | 0.044 | 1 | 1.085 | 0.969 | 1.034 |
| C38:6 PC | 0.084 | 1 | 0.847 | 0.663 | 0.745 |
| C38:6 PC plasmalogen | 0.038 | 1 | 1.069 | 0.905 | 0.897 |
| C38:6 PE | 0.059 | 1 | 0.699 | 0.578 | 0.610 |
| C38:6 PE plasmalogen | 0.025 | 1 | 1.090 | 0.987 | 1.018 |
| C38:6 PG | 0.206 | 1 | 1.106 | 0.903 | 1.049 |
| C38:7 PC plasmalogen | 0.045 | 1 | 0.911 | 0.778 | 0.775 |
| C38:7 PE plasmalogen | 0.055 | 1 | 0.978 | 0.908 | 0.964 |
| C40:10 PC | 0.093 | 1 | 1.003 | 0.358 | 0.575 |
| C40:6 PC | 0.056 | 1 | 1.152 | 0.818 | 0.916 |
| C40:6 PS | 0.019 | 1 | 0.887 | 0.886 | 0.990 |
| C40:7 PC plasmalogen | 0.010 | 1 | 1.008 | 0.833 | 0.854 |
| C40:9 PC | 0.116 | 1 | 0.840 | 0.678 | 0.780 |
| C42:0 TAG | 0.130 | 1 | 0.949 | 0.880 | 0.911 |
| C44:0 TAG | 0.091 | 1 | 0.872 | 0.880 | 0.888 |
| C44:1 TAG | 0.056 | 1 | 0.750 | 0.802 | 0.777 |
| C44:2 TAG | 0.084 | 1 | 0.615 | 0.661 | 0.486 |
| C46:0 TAG | 0.047 | 1 | 0.785 | 0.823 | 0.800 |
| C46:1 TAG | 0.029 | 1 | 0.685 | 0.779 | 0.759 |
| C46:2 TAG | 0.136 | 1 | 0.859 | 0.882 | 0.808 |
| C48:0 TAG | 0.022 | 1 | 0.740 | 0.893 | 0.813 |
| C48:2 TAG | 0.015 | 1 | 0.708 | 0.784 | 0.738 |
| C48:3 TAG | 0.096 | 1 | 0.824 | 0.776 | 0.750 |
| C50:0 TAG | 0.033 | 1 | 0.742 | 0.987 | 0.873 |
| C50:3 TAG | 0.038 | 1 | 0.783 | 0.849 | 0.745 |
| C52:0 TAG | 0.015 | 1 | 0.686 | 1.109 | 0.874 |
| C52:1 TAG | 0.030 | 1 | 0.685 | 0.968 | 0.806 |
| C52:3 TAG | 0.020 | 1 | 0.753 | 0.875 | 0.735 |
| C52:4 TAG | 0.025 | 1 | 0.688 | 0.808 | 0.660 |
| C54:2 TAG | 0.046 | 1 | 0.699 | 0.959 | 0.793 |
| C54:3 TAG | 0.053 | 1 | 0.768 | 0.982 | 0.788 |
| C54:4 TAG | 0.098 | 1 | 1.095 | 1.192 | 1.125 |
| C54:5 TAG | 0.052 | 1 | 0.628 | 0.742 | 0.621 |
| C56:6 TAG | 0.072 | 1 | 0.436 | 0.429 | 0.353 |
| C58:6 TAG | 0.065 | 1 | 0.822 | 0.842 | 0.650 |
| Cholic acid | 0.126 | 1 | 0.315 | 1.101 | 1.211 |
| Deoxycholic acid/ Chenodeoxycholic acid | 0.204 | 1 | 0.470 | 0.846 | 1.010 |
| Docosahexaenoic acid | N/A | undetected | N/A | N/A | N/A |
| Glycochenodeoxycholic acid | 0.128 | 1 | 0.208 | 1.076 | 1.122 |
| Glycocholic acid | 0.117 | 1 | 0.199 | 1.253 | 1.271 |
| Glycodeoxycholic acid | 0.132 | 1 | 0.204 | 1.099 | 1.113 |
| Glycolithocholic acid | 0.114 | 1 | 0.551 | 0.966 | 0.871 |
| Glycoursodeoxycholic acid | N/A | undetected | N/A | N/A | N/A |
| Palmitic acid | 0.058 | 1 | 0.372 | 0.450 | 0.000 |
| PGE2 | 0.083 | 1 | 0.912 | 0.872 | 0.962 |
| sphingosine | 0.057 | 1 | 1.442 | 1.223 | 1.229 |
| Stearic acid | 0.208 | 1 | 0.453 | 0.204 | 0.223 |
| Taurochenodesoxycholic acid | 0.100 | 1 | 0.436 | 1.011 | 1.010 |
| Taurocholic acid | 0.080 | 1 | 0.616 | 0.940 | 0.811 |
| Taurodeoxycholic acid | 0.063 | 1 | 0.672 | 0.834 | 0.808 |

TABLE 4-continued

Lipidomics data showing all lipids detected except those shown in FIG. 21A. Data shown are normalized to WT (TGFb1 + IL-6) condition showing average of 3 independent biological experiments.

| Lipids that are not significantly different or have a fold change less thatn 1.5 | Min P value | WT (TGFb1 + IL-6) | CDSL-/- (TGFb1 + IL-6) | WT (TGFb1 + IL-6 + IL-23) | CDSL-/- (TGFb1 + IL-6 + IL-23) |
|---|---|---|---|---|---|
| Taurohyodeoxycholic acid/ Tauroursodeoxycholic acid | 0.000 | 1 | 0.793 | 0.770 | 0.585 |
| Taurolithocholic acid | 0.125 | 1 | 0.058 | 1.214 | 1.269 |

TABLE 5

PUFA/SFA treatment recapitulates the transcriptome (restricted) of WT versus CD5L-/- Th17 cells. Data used to generate heatmap shown in WO2015130968 FIG. 50. Nanostring data are shown using a Th17 cell codeset Applicants previously generated containing 312 genes. 3 independent experiments were performed and the median values are normalized to WT. Only genes that show differential expression (1.5 fold) among any of the four groups are included.

| | CD5LKO.PUFA | WT | CD5LKO | WT.SFA |
|---|---|---|---|---|
| Ccr4 | 1.69 | 1.00 | 0.33 | 0.61 |
| Lgals3bp | 1.34 | 1.00 | 0.34 | 0.58 |
| Il12rb1 | 0.80 | 1.00 | 0.35 | 0.39 |
| Vav3 | 1.20 | 1.00 | 0.41 | 0.56 |
| Ifng | 0.93 | 1.00 | 0.43 | 0.55 |
| Il10 | 1.01 | 1.00 | 0.44 | 0.12 |
| IL-33 | 0.66 | 1.00 | 0.44 | 1.33 |
| Klrd1 | 0.63 | 1.00 | 0.46 | 0.92 |
| Elk3 | 1.04 | 1.00 | 0.47 | 0.58 |
| Itga3 | 0.76 | 1.00 | 0.47 | 0.50 |
| nrp1 | 0.90 | 1.00 | 0.47 | 0.74 |
| Sult2b1 | 0.61 | 1.00 | 0.48 | 0.38 |
| Tmem229b | 1.52 | 1.00 | 0.51 | 0.69 |
| Cxcr3 | 1.44 | 1.00 | 0.52 | 0.48 |
| Klf9 | 0.75 | 1.00 | 0.55 | 0.68 |
| Peli2 | 0.83 | 1.00 | 0.55 | 0.88 |
| Acvr2a | 1.32 | 1.00 | 0.55 | 0.66 |
| Ccl20 | 0.84 | 1.00 | 0.55 | 0.31 |
| Gusb | 0.94 | 1.00 | 0.56 | 1.02 |
| Spp1 | 0.66 | 1.00 | 0.56 | 1.10 |
| Maf | 0.84 | 1.00 | 0.56 | 0.79 |
| Tcf4 | 1.29 | 1.00 | 0.59 | 0.72 |
| Rasgrp1 | 1.21 | 1.00 | 0.60 | 0.75 |
| Cxcr5 | 1.42 | 1.00 | 0.60 | 1.17 |
| Rela | 0.96 | 1.00 | 0.60 | 0.70 |
| Stat6 | 1.13 | 1.00 | 0.60 | 0.73 |
| Hip1r | 0.89 | 1.00 | 0.60 | 0.70 |
| Tgfb1 | 0.68 | 1.00 | 0.62 | 0.83 |
| Grn | 1.16 | 1.00 | 0.62 | 0.78 |
| Ubiad1 | 1.16 | 1.00 | 0.62 | 0.94 |
| Bcl11b | 1.03 | 1.00 | 0.62 | 0.82 |
| Irf4 | 0.65 | 1.00 | 0.62 | 0.68 |
| Ccr8 | 0.71 | 1.00 | 0.63 | 0.74 |
| Trat1 | 0.85 | 1.00 | 0.63 | 0.61 |
| Ifih1 | 1.25 | 1.00 | 0.63 | 0.87 |
| Map3k5 | 1.49 | 1.00 | 0.64 | 0.80 |
| Foxo1 | 1.03 | 1.00 | 0.64 | 0.79 |
| Bcl2l11 | 0.71 | 1.00 | 0.64 | 0.82 |
| Il6st | 0.89 | 1.00 | 0.64 | 0.87 |
| Ski | 0.86 | 1.00 | 0.64 | 0.88 |
| Il7r | 1.37 | 1.00 | 0.64 | 0.85 |
| Il2ra | 0.99 | 1.00 | 0.65 | 0.71 |
| Serpinb1a | 0.77 | 1.00 | 0.65 | 0.56 |
| Il10ra | 0.95 | 1.00 | 0.65 | 0.71 |
| Litaf | 0.61 | 1.00 | 0.65 | 1.48 |
| Rfk | 1.07 | 1.00 | 0.66 | 0.79 |
| Slc6a6 | 1.03 | 1.00 | 0.66 | 0.79 |
| Socs3 | 1.38 | 1.00 | 0.66 | 0.78 |
| Smad3 | 1.03 | 1.00 | 0.66 | 0.81 |
| Lad1 | 1.18 | 1.00 | 0.66 | 0.91 |
| Tnip2 | 0.78 | 1.00 | 0.66 | 0.90 |
| Tgfbr3 | 0.94 | 1.00 | 0.68 | 0.58 |
| Ahr | 1.08 | 1.00 | 0.68 | 0.83 |
| Mina | 1.08 | 1.00 | 0.68 | 0.72 |
| Stat4 | 1.21 | 1.00 | 0.68 | 0.77 |
| Il27ra | 1.55 | 1.00 | 0.68 | 0.70 |
| Mbnl3 | 1.30 | 1.00 | 0.69 | 0.71 |
| Jak3 | 1.27 | 1.00 | 0.69 | 0.91 |
| Tal2 | 1.52 | 1.00 | 0.69 | 1.15 |
| Gmfg | 0.76 | 1.00 | 0.70 | 0.62 |
| Irf7 | 1.17 | 1.00 | 0.70 | 0.54 |
| Abcg2 | 1.20 | 1.00 | 0.70 | 0.77 |
| Il4ra | 1.13 | 1.00 | 0.72 | 0.75 |
| Notch2 | 1.20 | 1.00 | 0.72 | 0.78 |
| Clcf1 | 1.25 | 1.00 | 0.72 | 0.74 |
| Foxp1 | 1.25 | 1.00 | 0.72 | 0.77 |
| Stat5b | 1.19 | 1.00 | 0.73 | 0.82 |
| Bcl3 | 1.13 | 1.00 | 0.73 | 0.85 |
| Ikzf3 | 1.06 | 1.00 | 0.74 | 0.82 |
| Il12rb2 | 1.60 | 1.00 | 0.74 | 0.88 |
| Tgfb3 | 1.67 | 1.00 | 0.75 | 0.88 |
| Irf8 | 1.29 | 1.00 | 0.75 | 0.99 |
| Nfkbie | 1.52 | 1.00 | 0.76 | 0.69 |
| Trps1 | 1.44 | 1.00 | 0.77 | 0.84 |
| Trim25 | 1.17 | 1.00 | 0.77 | 0.89 |
| Tgm2 | 1.51 | 1.00 | 0.78 | 0.78 |
| Ercc5 | 0.66 | 1.00 | 0.79 | 0.90 |
| Etv6 | 1.70 | 1.00 | 0.79 | 0.94 |
| Xrcc5 | 1.27 | 1.00 | 0.80 | 0.93 |
| Il1r1 | 1.36 | 1.00 | 0.82 | 0.61 |
| Csf2 | 1.20 | 1.00 | 0.83 | 0.97 |
| Fli1 | 1.35 | 1.00 | 0.83 | 0.84 |
| Klf10 | 1.30 | 1.00 | 0.83 | 0.91 |
| Arl5a | 1.33 | 1.00 | 0.84 | 0.93 |
| Jun | 0.64 | 1.00 | 0.84 | 1.11 |
| Flna | 1.10 | 1.00 | 0.84 | 0.65 |
| Foxp3 | 1.22 | 1.00 | 0.85 | 0.71 |
| Inhba | 0.81 | 1.00 | 0.86 | 0.60 |
| Cd247 | 1.32 | 1.00 | 0.88 | 0.81 |
| Faim3 | 1.31 | 1.00 | 0.89 | 0.61 |
| Pstpip1 | 1.24 | 1.00 | 0.90 | 1.16 |
| Kat2b | 1.22 | 1.00 | 0.90 | 0.69 |
| Gja1 | 0.66 | 1.00 | 0.93 | 0.94 |
| Cd86 | 1.73 | 1.00 | 0.94 | 0.99 |
| Lpxn | 1.39 | 1.00 | 0.94 | 0.85 |
| Ccl1 | 0.67 | 1.00 | 0.95 | 0.58 |
| Plagl1 | 1.07 | 1.00 | 0.95 | 2.19 |
| Ctla4 | 1.63 | 1.00 | 0.96 | 0.81 |
| Cd9 | 1.27 | 1.00 | 0.97 | 0.84 |
| Pou2af1 | 0.86 | 1.00 | 1.00 | 1.30 |
| Pmepa1 | 1.19 | 1.00 | 1.00 | 0.74 |
| Prkd3 | 1.51 | 1.00 | 1.00 | 0.73 |
| Il17f | 0.71 | 1.00 | 1.04 | 0.90 |

TABLE 5-continued

PUFA/SFA treatment recapitulates the transcriptome (restricted) of WT versus CD5L$_{-/-}$ Th17 cells. Data used to generate heatmap shown in WO2015130968 FIG. 50. Nanostring data are shown using a Th17 cell codeset Applicants previously generated containing 312 genes. 3 independent experiments were performed and the median values are normalized to WT. Only genes that show differential expression (1.5 fold) among any of the four groups are included.

| | CD5LKO.PUFA | WT | CD5LKO | WT.SFA |
|---|---|---|---|---|
| EBF1 | 1.64 | 1.00 | 1.11 | 0.51 |
| Gimap5 | 1.58 | 1.00 | 1.18 | 1.05 |
| Tsc22d3 | 0.66 | 1.00 | 1.18 | 1.06 |
| Gem | 0.73 | 1.00 | 1.18 | 1.00 |
| Gap43 | 0.68 | 1.00 | 1.21 | 1.30 |
| Maff | 0.77 | 1.00 | 1.22 | 0.99 |
| pou2f1 | 0.66 | 1.00 | 1.23 | 1.34 |
| Atf4 | 0.73 | 1.00 | 1.23 | 1.11 |
| Rel | 0.73 | 1.00 | 1.23 | 1.20 |
| Frmd4b | 1.28 | 1.00 | 1.26 | 1.05 |
| Nkg7 | 1.40 | 1.00 | 1.31 | 0.62 |
| Casp4 | 1.52 | 1.00 | 1.32 | 0.95 |
| Mt2 | 0.84 | 1.00 | 1.33 | 1.33 |
| BC021614 | 1.04 | 1.00 | 1.34 | 0.96 |
| ATF2 | 0.89 | 1.00 | 1.38 | 1.18 |
| Cxcr4 | 0.87 | 1.00 | 1.39 | 1.00 |
| Bhlhe40 | 0.70 | 1.00 | 1.43 | 1.22 |
| Il17a | 1.11 | 1.00 | 1.44 | 0.96 |
| Casp3 | 0.71 | 1.00 | 1.45 | 1.21 |
| Sap30 | 0.81 | 1.00 | 1.47 | 1.23 |
| Tnfrsf4 | 1.05 | 1.00 | 1.51 | 1.28 |
| Plac8 | 0.85 | 1.00 | 1.51 | 1.04 |
| Il23r | 1.11 | 1.00 | 1.51 | 1.12 |
| Rab33a | 1.50 | 1.00 | 1.55 | 1.23 |
| Sema7a | 1.04 | 1.00 | 1.60 | 1.44 |
| Il21 | 0.97 | 1.00 | 1.65 | 1.64 |
| Oas2 | 0.82 | 1.00 | 1.66 | 1.28 |
| Fxd7 | 0.72 | 1.00 | 1.71 | 1.07 |
| Rorc | 1.52 | 1.00 | 1.80 | 1.25 |
| Mt1 | 0.79 | 1.00 | 1.85 | 1.56 |
| Spry1 | 1.02 | 1.00 | 2.04 | 1.57 |
| Egr2 | 1.64 | 1.00 | 2.21 | 1.53 |
| Il3 | 1.45 | 1.00 | 2.24 | 2.11 |
| Cd83 | 0.88 | 1.00 | 2.33 | 1.23 |
| Cd70 | 0.77 | 1.00 | 2.51 | 0.89 |
| Cxcl10 | 1.64 | 1.00 | 3.05 | 3.83 |

TABLE 6

Shown are genes that are significantly up or down regulated in different sections of the Voronoi diagram (subpopulations) (corresponding to FIG. 2C). Differentially expressed genes in in-vivo sub-populations

| Th17/Th1-like memory | Th17/Th1-like effector-LN | | Th17/Th1-like effector-CNS | | Th17/Th1-like effector |
|---|---|---|---|---|---|
| STMN1 | OSTF1 | STMN1 | PSPH | STMN1 | RAB1 | STMN1 |
| RRM2 | BCL2A1B | RRM2 | CCDC21 | RRM2 | TNFSF11 | RRM2 |
| 2810417H13RIK | AA467197 | 2810417H13RIK | PRDX4 | 2810417H13RIK | PAPOLA | 2810417H13RIK |
| HMGN2 | UBE2F | HMGN2 | XPO1 | HMGN2 | CNOT6 | HMGN2 |
| TOP2A | TMEM128 | TOP2A | NOL12 | TOP2A | HIST2H2AA2 | TOP2A |
| SMC2 | GIT2 | SMC2 | SNRNP25 | SMC2 | DHRS3 | SMC2 |
| GM7125 | GM10247 | GM7125 | CAB39L | GM7125 | HIST2H2AA1 | GM7125 |
| SSNA1 | IFITM3 | SSNA1 | MRPL15 | NUTF2-PS1 | AC131675.1 | NUTF2-PS1 |
| BIRC5 | RGS1 | HIST1H4D | CLDND1 | SSNA1 | VAMP4 | SSNA1 |
| PCNA | BHLHE40 | SNRPA1 | ILF2 | HIST1H4D | NUBP1 | HIST1H4D |
| H2AFV | GOT1 | UBE2C | H2-KE2 | SNRPA1 | USP1 | SNRPA1 |
| NDUFA5 | RAB11A | BIRC5 | UCHL5 | UBE2C | STK39 | UBE2C |
| ASF1B | 5430421N21RIK | CKS1B | PPP1R8 | BIRC5 | AP3S1 | BIRC5 |
| NME1 | SELL | CDCA3 | UCHL3 | CKS1B | RAB4B | CKS1B |
| BCAP31 | PTPRS | MRPS16 | POLE4 | MRPL42 | GPS1 | MRPL42 |
| 2700094K13RIK | GGH | H2AFV | HSP90B1 | AC161456.1 | RIOK1 | AC131456.1 |
| TYMS | PGAM1 | ASF1B | SNRPB2 | ANP32E | CASP3 | ANP32E |
| TACC3 | GM2574 | CCNB2 | NUP214 | PCNA | PPME1 | PCNA |
| SNRPB | GPR171 | TIPIN | PDLIM1 | CDCA3 | PDLIM2 | CDCA3 |
| GM11276 | RAMP1 | 2700094K13RIK | MRPL53 | MRPS16 | IPO7 | MRPS16 |
| HIST1H2AO | ITK | TIMM17A | RPAIN | H2AFV | ACTR1A | H2AFV |
| NUF2 | H13 | TYMS | BZW2 | NDUFA5 | HMOX2 | NDUFA5 |
| HIST1H2AE | GM5138 | TACC3 | WDR12 | ASF1B | NEDD1 | ASF1B |
| HMGB2 | P2RX7 | GMNN | VRK1 | RANBP1 | NUDC | RANBP1 |
| MRPS14 | RPL31 | GM11276 | PHPT1 | CCNB2 | CSDA | CCNB2 |
| BANF1 | HIF1A | HIST1H2AO | UFC1 | NME1 | LARP7 | NME1 |
| CDCA8 | SMARCC1 | NUF2 | C330027C09RIK | CDK1 | COPB2 | CDK1 |
| MRPL18 | PDHA1 | HIST1H2AE | NFU1 | BCAP31 | GM9396 | BCAP31 |
| DDX39 | HIGD2A | HMGB2 | DPH3 | PSMD14 | TSPAN32 | PSMD14 |
| NDUFA4 | RPL30-PS8 | CDCA8 | MRPL11 | TIPIN | SEPW1 | TIPIN |
| MDH2 | ARHGAP4 | DDX39 | ATP6V1H | 2700094K13RIK | GM10036 | 2700094K13RIK |
| SNRPD2 | RGS16 | NDUFA4 | NUP93 | CDC123 | GM10071 | CDC123 |
| SDHB | NDUFS1 | RRM1 | GABARAPL2 | GM10349 | PPP2R4 | GM10349 |
| TK1 | GM3272 | MAD2L1 | MKKS | TIMM17A | RPS23 | TIMM17A |

TABLE 6-continued

Shown are genes that are significantly up or down regulated in different sections of the Voronoi diagram (subpopulations) (corresponding to FIG. 2C).
Differentially expressed genes in in-vivo sub-populations

| | | | | | | |
|---|---|---|---|---|---|---|
| SPC25 | LGALS3 | SPC25 | GNG5 | TYMS | ARMC1 | TYMS |
| CDK4 | ANXA5 | PSMB7 | DHX15 | TACC3 | GM9000 | TACC3 |
| PMF1 | STK38 | DCTPP1 | PRKAG1 | EXOSC8 | GM7808 | EXOSC8 |
| KIF23 | ITGB1BP1 | FBXO5 | TRAT1 | GMNN | RSRC1 | GMNN |
| AURKB | 2510002D24RIK | PMF1 | NGDN | DBI | NDFIP1 | DBI |
| HIST1H2AG | SERPINE2 | KIF23 | CCNC | SNRPB | RPS27A | SNRPB |
| PSAT1 | ECE1 | HIST1H2AG | HMGN1 | GM11276 | UBAP2 | GM11276 |
| ERH | GM2792 | NDUFB7 | PTCD2 | HIST1H2AO | GM7536 | HIST1H2AO |
| TAGLN2 | MED13 | PSAT1 | CCDC69 | SNRPD1 | HIST1H1C | SNRPD1 |
| BUB3 | MAPKAPK3 | CDKN3 | FAM111A | NUF2 | SMC6 | NUF2 |
| NUSAP1 | GIMAP3 | ERH | CCR6 | HIST1H2AE | CD2BP2 | HIST1H2AE |
| NDC80 | GPR65 | MRPL54 | 4930453N24RIK | LSM6 | RPL10A | LSM6 |
| EMG1 | RPS13 | H2AFZ | BAD | HMGB2 | SF1 | HMGB2 |
| SEC13 | MAP3K8 | BUB3 | ELP2 | TUBA1B | RPL19 | TUBA1B |
| TPX2 | EIF4EBP1 | NUSAP1 | PPP2R5A | MRPS14 | MAP2K3 | MRPS14 |
| CCNB1 | RCSD1 | RFC3 | PMPCB | BANF1 | SETD8 | BANF1 |
| HMGB3 | RPL15-PS2 | TPX2 | RNASEK | RAN | UQCRFS1 | RAN |
| HINT1 | OSBPL9 | CCNB1 | MAPKSP1 | CDCA8 | ELK3 | CDCA8 |
| RBBP7 | BPTF | HMGB3 | IL16 | DPY30 | RPL27 | MRPL18 |
| TUBB5 | PBRM1 | HINT1 | DEDD | PSMB6 | NOL7 | 2900010M23RIK |
| CLSPN | MGST2 | TUBB5 | TNFRSF25 | DDX39 | HAVCR2 | DPY30 |
| DTYMK | GM9858 | MRPL51 | CMAH | KIF22 | GM9846 | PSMB6 |
| BAT1A | RARS | CL5PN | GPATCH8 | NDUFA4 | TUBB6 | DDX39 |
| ETFA | TRPC4AP | DTYMK | PSMG4 | NSMCE2 | NCBP1 | KIF22 |
| TUBB2C | FTH1 | UHRF1 | NAA15 | MDH2 | DGAT1 | NDUFA4 |
| CASC5 | ARHGAP1 | 0610007P14RIK | NUDT3 | LSMD1 | AC119211.2 | NSMCE2 |
| SNRPE | UBE2G1 | CASC5 | DLD | REXO2 | GM10237 | MDH2 |
| PSMC1 | COTL1 | D2ERTD750E | PRPF4 | FAM36A | FAM65B | LSMD1 |
| CDCA2 | UBE2J1 | ERGIC2 | DDRGK1 | RRM1 | ATAD2 | REXO2 |
| 170029F09RIK | GM4609 | CDCA2 | PIN1 | MAD2L1 | RPL10 | PSMC2 |
| RPP21 | CMC1 | LBR | E2F4 | TK1 | MED21 | FAM36A |
| WBP5 | PDE4B | SLBP | TNFRSF9 | CCT5 | EIF4A1 | RPS27L |
| LBR | TNFRSF9 | MCM7 | CKB | SPC25 | OSBPL3 | RRM1 |
| TUBG1 | TOX | POLD3 | GM3150 | CDK4 | 2010002N04RIK | SDHB |
| SLBP | FAM110A | MNS1 | ARF6 | DCTPP1 | RPS12 | MAD2L1 |
| TNFRSF4 | HNRPL | TUBA4A | PIM1 | FBXO5 | STX11 | TK1 |
| MCM7 | D16ERTD472E | MCM3 | ZFP488 | RFC4 | TSPO | CCT5 |
| HMMR | CSF2 | FH1 | RGS10 | MRPS18C | SMARCA4 | SPC25 |
| ANP32A | RFC1 | KPNA2 | NR4A1 | PMF1 | SFPQ | PSMB7 |
| ORC6 | TMEM87A | RPA1 | GM3550 | HPRT | AA467197 | DCTPP1 |
| LGALS1 | BSCL2 | KIF2C | PAN3 | DUT | AC134548.2 | FBXO5 |
| GTF2A2 | AGXT2L2 | AAAS | JUND | YWHAH | TMEM128 | RFC4 |
| CD3G | H2-K1 | MRPS33 | TNFRSF1B | PSMA1 | GM16477 | MRPS1BC |
| TMEM49 | LARS | ANAPC5 | IFI27L2B | LSM5 | ACADL | PMF1 |
| PLP2 | REEP5 | ACTL6A | ATN1 | KIF23 | GM8730 | HPRT |
| MCM3 | LZTR1 | HMGB1 | KIF24 | AURKB | GM10247 | DUT |
| KPNA2 | DHX40 | PTMA | RABGAP1L | HIST1H2AG | IFITM3 | SEC11C |
| ATP5G3 | GM7665 | GM6104 | GM10313 | NHP2 | TMED9 | YWHAH |
| NDUFV3 | HNRNPA3 | SPC24 | BTG2 | COMMD1 | SCAND3 | PSMA1 |
| RPA1 | STK24 | MRPL4 | IG42R | FKBP3 | SELL | LSM5 |
| ACOT7 | DDX42 | ACO87117.1 | SKIL | PSAT1 | PGAM1 | KIF23 |
| WDR61 | ZNHIT1 | ATPSK | RAB10 | CDKN3 | CCDC59 | AURKB |
| GM10108 | PRKCH | IMMT | RPL21-PS7 | STRA13 | EIF2S2 | HIST1H2AG |
| CKS2 | ELF2 | RFC2 | RPL21-PS11 | ERH | GTPBP1 | NDUFB7 |
| RBBP4 | OBFC2A | CIT | SRRM2 | COMMD3 | STAG1 | NHP2 |
| KIF2C | SS18 | ZWINT | RPL29-PS2 | MRPL54 | RPL31 | COMMD1 |
| COX17 | RBPSUH-RS3 | CCDC34 | GM10291 | H2AFZ | BIRC2 | FKBP3 |
| ANAPC5 | EHD1 | MKI67 | GM10327 | TAGLN2 | RPS27 | PSAT1 |
| HP1BP3 | SAMSN1 | NUDT1 | GM5507 | BUB3 | RPL30-PS8 | CDKN3 |
| HMGB1 | XRN2 | EXOSC9 | GM6316 | NUSAP1 | PFDN5 | STRA13 |
| PTMA | HNRPDL | PHF5A | ALKBH5 | NDC80 | RGS16 | ERH |
| BC021614 | GM10155 | TIMM22 | MLL2 | RFC3 | CNOT2 | COMMD3 |
| SNRPG | ZFP148 | NAA38 | INSIG1 | 2310028O11RIK | MRP63 | MRPL54 |
| GM6104 | CYB5B | HELLS | GM8909 | 3200002M19RIK | FAU | H2AFZ |
| NT5C | RUNX2 | NGFRAP1 | GN11127 | PSMA4 | RPL27-PS1 | TAGLN2 |
| RPS17 | NFKBIA | RNASEH2B | H2-Q2 | TPX2 | RPL17 | BUB3 |
| MEAF6 | ITM2B | | CDKN1B | 1810027O10RIK | ORC5 | NUSAP1 |
| GNG10 | BNIP3 | | NOTCH2 | CCNB1 | TSHZ1 | NDC80 |
| EEF1B2 | GM5518 | | SGIP1 | HMGB3 | RPL5 | NDUFB2 |

TABLE 6-continued

Shown are genes that are significantly up or down regulated in different
sections of the Voronoi diagram (subpopulations) (corresponding to FIG. 2C).
Differentially expressed genes in in-vivo sub-populations

| | | | | | |
|---|---|---|---|---|---|
| BRD8 | GM10358 | NR4A3 | HINT1 | AC127419.1 | MED10 |
| SPC24 | IFITM2 | GVIN1 | TAF9 | VAMP3 | NDUFV2 |
| DRG1 | NEDD9 | | RBBP7 | ING1 | RFC3 |
| ANAPC13 | SF3B3 | | CDC45 | SHISA5 | 2310028O11RIK |
| AC087117.1 | CHSY1 | | 0610010K14RIK | RAP2C | 3200002M19RIK |
| FIGNL1 | CDK7 | | TUBB5 | GPR65 | PSMA4 |
| NKG7 | TCOF1 | | MRPL51 | TAP1 | TPX2 |
| S100A4 | FOXN2 | | CISD3 | RPS13 | 1810027O10RIK |
| SRPK1 | TAGAP | | CLSPN | RPL15-PS2 | CCNB1 |
| CIT | CCPG1 | | NDUFC2 | GM9858 | HMGB3 |
| ZWINT | MGA | | CENPA | GM5148 | HINT1 |
| CXCR6 | MAST4 | | NDUFB6 | HSPH1 | TAF9 |
| GM6169 | GM5220 | | RP23-378I13.5 | FTL1 | RBBP7 |
| MRPL41 | RPS19-PS2 | | BAT1A | APOL7B | CDC45 |
| CCDC34 | POLR2A | | ETFA | TOX | EIF4A3 |
| GM6984 | GPSM3 | | LIG1 | FAM110A | CHCHD1 |
| MKI67 | CREM | | MPHOSPH6 | RFC1 | THOC7 |
| 2610029G23RIK | POLR3C | | UHRF1 | RAPGEF6 | TUBB5 |
| RPL22L1 | TCF7 | | TUBB2C | GM7665 | MRPL51 |
| BZW1 | EPS15 | | NRM | RALBP1 | TMEM14C |
| FAM60A | CCDC50 | | CASC5 | SLC24A5 | PA2G4 |
| EXOSC9 | ATP2B4 | | SNRPE | EHD1 | CLSPN |
| CD2 | P4HA1 | | D2ERTD750E | RPS8-PS1 | NDUFC2 |
| ECH1 | FBXO46 | | ATP5B | AC120410.1 | DTYMK |
| CBX3 | IKBKB | | ERGIC2 | XRN2 | CENPA |
| HNRNPA2B1 | CCR2 | | CBX5 | GM10155 | NDUFB6 |
| CDCA7 | PLIN1 | | SUMO2 | SEC61G | RP23-378I13.5 |
| ANXA2 | ISG20 | | CDCA2 | CYB5B | BAT1A |
| NAA38 | ZYX | | RBM3 | RUNX2 | ETFA |
| PRC1 | UBASH3B | | WBP5 | GM5518 | SRP19 |
| DNAJC9 | RORA | | TCP1 | GM12666 | POLR2G |
| TNFRSF18 | GEM | | LBR | GM10358 | LIG1 |
| DKC1 | SLC15A3 | | TUBG1 | NKAP | MPHOSPH6 |
| DNAJC8 | PSD4 | | NAP1L1 | CHSY1 | UHRF1 |
| HNRNPF | 1110007A13RIK | | MRPS17 | ZRANB2 | TUBB2C |
| TPI1 | SFT2D1 | | TNFRSF4 | GM5220 | 0610007P14RIK |
| ENO1 | ZC3HC1 | | MCM7 | DYNLT1C | NRM |
| CCDC21 | YTHDC1 | | HMMR | DDX21 | PCMT1 |
| DDX47 | IFNGR1 | | MRPL23-PS1 | RPS19-PS2 | NDUFS8 |
| NSMCE1 | GOLGA7 | | POLD3 | POM121 | CASCS |
| TIGIT | IL18R1 | | PHGDH | GABARAP | SNRPE |
| TMEM50A | LITAF | | NUDT21 | HNRNPL | DZERTD750E |
| GNG2 | ATF6 | | ORC6 | TCF7 | ATP5B |
| CORO1A | DOT1L | | MNS1 | CCND2 | ERGIC2 |
| CAB39L | TAB2 | | LGALS1 | UAP1 | CBX5 |
| DNAJC15 | USP4 | | HIST1H1E | A830010M20RIK | UQCR10 |
| GM5506 | AC151275.1 | | LCK | RPL7A-PS5 | AURKAIP1 |
| EZH2 | INPP5F | | SSB | SERBP1 | NDUFB9 |
| APOBEC3 | CD44 | | LAT | LAMC1 | VDAC3 |
| ISY1 | KLF6 | | CISD1 | GM10136 | SUMO2 |
| DLGAP5 | PTP4A1 | | TMEM49 | WDR9 | HAT1 |
| CENPE | ZFP295 | | PLP2 | U2AF1 | FXC1 |
| BCAS2 | GM5561 | | MCM3 | RPL27A | CDCA7 |
| H2-KE2 | RASGRP1 | | FH1 | LITAF | 1700029F09RIK |
| SLC25A5 | ATXN1 | | KPNA2 | MDN1 | RBM3 |
| PSMD6 | CD27 | | ATPSG3 | YY1 | WBP5 |
| COX6C | SLC2A3 | | RPA1 | TACC1 | DEK |
| PPP1R8 | ZFML | | ACOT7 | AC151275.1 | TCP1 |
| UCHL3 | TNFAIP3 | | TXN1 | GM5561 | LBR |
| UBL4 | CORO2A | | NDUFAB1 | GM6139 | TUBG1 |
| CCL1 | RPRD2 | | MCM6 | CORO2A | NAP1L1 |
| XRCC6 | NRIP1 | | GTF2H5 | PRPF39 | SLBP |
| CTLA4 | CCR1 | | ASNS | SLAMF6 | MRPS17 |
| 2900073G15RIK | VPS54 | | GM10108 | GM10054 | MCM7 |
| NDE1 | PRPF39 | | CKS2 | SON | HMMR |
| GLRX | SPIN1 | | GM10053 | RPL13-PS3 | POLD3 |

TABLE 6-continued

Shown are genes that are significantly up or down regulated in different sections of the Voronoi diagram (subpopulations) (corresponding to FIG. 2C). Differentially expressed genes in in-vivo sub-populations

| | | | | | |
|---|---|---|---|---|---|
| HNRNPR | SLAMF6 | | KIF2C | ZGPAT | CCT2 |
| LPXN | EIF2C2 | | HN1 | GM5805 | PSMA6 |
| SDF4 | UBL3 | | AAAS | GM3940 | PHGDH |
| CAPG | CD200R1 | | 2310061C15RIK | GM7589 | NUDT21 |
| NUP214 | INPP4A | | COX17 | WDR70 | ORC6 |
| PRKAR1A | SON | | ANAPC5 | RPL12-PS1 | MNS1 |
| CST7 | RPL13-PS3 | | CKAP5 | QSOX1 | LGALS1 |
| PDLIM1 | ADAM19 | | MCM4 | HSD3B2 | HIST1H1E |
| SERPINB1A | GM5805 | | RANGAP1 | AC156282.1 | PSMC3 |
| CDC26 | GRINA | | TUBA1C | GM10481 | SSB |
| DERL2 | ARAP2 | | HMGB1 | TNRC6B | LAT |
| YARS | CKB | | PTMA | RPS2-PS6 | CISD1 |
| GCLM | SQSTM1 | | SSBP1 | 2310016C08RIK | TUBA4A |
| IFNG | GM7589 | | EIF3L | GM5619 | PLP2 |
| SNRNP70 | WDR70 | | BC021614 | GM3150 | MCM3 |
| PPIL2 | BCL2A1A | | SNRPG | REL | FH1 |
| FAM33A | VGLL4 | | TFF1 | GM8910 | KPNA2 |
| FAM162A | RPL12-PS1 | | GM6104 | GM6180 | ATP5G3 |
| PSMD2 | ARIH1 | | PPP1CA | UTRN | SRSF7 |
| 4933434E20RIK | ZFAND5 | | GM3090 | CCRN4L | CWC15 |
| CAPZA2 | HSD3B2 | | ELOF1 | BC005537 | RPA1 |
| SUPT16H | TEX10 | | MEAF6 | TRIM12A | ACOT7 |
| OGDH | CTSD | | MTHFD2 | RPL21-PS3 | TXN1 |
| RPS20 | GM10481 | | ANP32B | NSA2 | NDUFAB1 |
| BZW2 | 2310016C08RIK | | GNG10 | ACSL4 | CD48 |
| SFXN1 | KPNA1 | | SPC24 | AL844854.1 | TXNDC17 |
| RPSA-PS10 | RUNX1 | | C79407 | CDKN1A | MCM6 |
| ATP5L | RNF13 | | 2700029M09RIK | 4921517L17RIK | GTF2H5 |
| VRK1 | DENND4A | | CHCHD3 | GM6807 | ASNS |
| CD226 | DCTN4 | | COPS6 | FURIN | WDR61 |
| SF3A3 | HK2 | | RQCD1 | COQ10B | GM108 |
| NASP | REL | | AC087117.1 | KLF13 | CKS2 |
| SYTL3 | GM8910 | | FIGNL1 | UPF1 | TRP53 |
| HERPUD1 | CD81 | | NKG7 | RAB8B | GM10053 |
| TXNDC9 | HSF2 | | CD6 | ARF5 | KIF2C |
| RPL8 | WDFY1 | | RFC2 | PRKACA | GLO1 |
| CSNK2A1 | TRIM12A | | PRDX1 | CT033780.1 | HN1 |
| MRPL10 | TOB1 | | GOLT1B | WTAP | MRPL33 |
| PRR13 | ZBP1 | | LSM2 | CAPS2 | AAAS |
| RPLP1 | FAM102A | | PFDN1 | GM8815 | MRP533 |
| DDT | ACSL4 | | CUTA | TSC22D3 | 2310063C15RIK |
| LUC7L3 | CDKN1A | | TMPO | BAT2L2 | COX17 |
| ZCCHC17 | SRSF2IP | | SMC4 | ARF6 | 1810009A15RIK |
| BC031181 | GM6807 | | 6-Sep | GM10012 | ANAPC5 |
| 2310036O22RIK | FURIN | | SSRP1 | GM10154 | ACTL6A |
| HJURP | IL4RA | | ZC3H15 | AC117259.1 | CKAP5 |
| MTIF2 | COQ10B | | SET | TGOLN1 | MCM4 |
| ALDOA | TNF | | MCM5 | 193.412F15RIK | RANGAP1 |
| TSG101 | PDE4D | | CLIC1 | GM5453 | TUBA1C |
| PFKP | D14ABB1E | | CIT | GM10063 | HMGB1 |
| TAF6 | GM8815 | | PDZD11 | GM5908 | PSMD7 |
| LXN | ARF6 | | FKBP2 | AC155816.1 | DNAJC19 |
| CD40LG | PHC3 | | SMC1A | LRRC58 | PTMA |
| CDK5RAP2 | RALGPS2 | | GM10123 | RPL36-PS3 | SSBP1 |
| SKP1A | ANXA1 | | GM6169 | AMD1 | EIF3L |
| S100A6 | JMJD1C | | PSMA5 | CFLAR | BC021614 |
| GABARAPL2 | GABARAPL1 | | SUMO3 | MACF1 | SNRPG |
| RPLP2 | SMPDL3A | | AIP | FOXP1 | YWHAQ |
| TBC1D10C | RPL36-PS3 | | FDPS | PPP1R12A | UQCRC2 |
| HNRNPM | SEC62 | | CCDC34 | MLL5 | TFF1 |
| PSMD5 | FAM177A | | GM6984 | SP110 | GM6104 |
| RPS15 | FOXP1 | | FABP5 | CDC42SE2 | PPP1CA |
| NCL | CAMK2D | | MKI67 | ZMYND8 | GM3090 |
| CISH | ZMYND8 | | 2610029G23RIK | KRR1 | NAA10 |
| GM200 | ANKRD12 | | MRPL34 | ANKRD12 | SRPR |
| RPS29 | NFKBIZ | | SLC29A1 | GM8054 | ELOF1 |
| RPL28 | GM8054 | | POP4 | AMD2 | PPIG |
| TMSB4X | LARP4 | | TFDP1 | GSK3B | MRPL28 |

TABLE 6-continued

Shown are genes that are significantly up or down regulated in different
sections of the Voronoi diagram (subpopulations) (corresponding to FIG. 2C).
Differentially expressed genes in in-vivo sub-populations

| | | | | | |
|---|---|---|---|---|---|
| CCR8 | MAPKAPK2 | | TTC1 | AC108412.1 | MEAF6 |
| RPS25 | SLFN1 | | ECH1 | SPOPL | MTHFD2 |
| LLPH | RBPJ | | CBX3 | GM7592 | ANP32B |
| HCST | RNF19A | | MYG1 | MNDAL | GNG10 |
| WBSCR22 | 1500012F01RIK | | GM4737 | ZFP488 | COX7A2 |
| NUCKS1 | CTNNA1 | | UBE2A | AC142450.1 | PPIB |
| RIF1 | RGS10 | | CALM2 | AC117184.1 | SPC24 |
| IL1R2 | CHD7 | | RDM1 | JARID2 | DRG1 |
| CD69 | SEMA4B | | HELLS | TMEM71 | C79407 |
| RPL35 | NR4A1 | | PRC1 | SEMA4B | 2700029M09RIK |
| BC016495 | KLRD1 | | DNAJC9 | GM2026 | ICT1 |
| GM11353 | GM3839 | | NUTF2 | GM7609 | CHCHD3 |
| CBX1 | RBM47 | | PPIA | AMD-PS3 | COPS6 |
| POLR2E | ZFP187 | | PCIF1 | GM14305 | C5 |
| GM10073 | GM9104 | | RPP30 | GM14434 | MRPL4 |
| SSU72 | RABGEF1 | | HSPA14 | EMD | RQCD1 |
| PGK1 | ASAH1 | | CNIH | LY6C1 | AC087117.1 |
| POLR2B | GPR132 | | MRPS11 | GM3839 | ATP5K |
| BCLAF1 | CTSB | | HDGF | GM10916 | DERA |
| AC124742.1 | ECM1 | | STIP1 | A230046K03RIK | PDCD5 |
| GM5559 | CSRNP1 | | NSMCE1 | GM9104 | FIGNL1 |
| 5-Sep | ZEB2 | | AHSA1 | LARS2 | CD6 |
| RPS15A | GM10293 | | GARS | B4GALT1 | RFC2 |
| GM12033 | ANKRD17 | | TIGIT | HNRNPUL1 | PRDX1 |
| TRAT1 | AI848100 | | XPO1 | KHSRP | GOLT1B |
| NGDN | SMAD7 | | CHMP2A | GM14391 | LSM2 |
| ELOVL1 | CCL4 | | CD160 | GM11167 | NDUFA9 |
| TPRKB | GP49A | | PTGES3 | RAD9 | PFDN1 |
| IL2RA | PELI1 | | SNRNP2S | H2-GS10 | PSMB3 |
| PSMD4 | XRN1 | | IL18RAP | 0610031J06RIK | CUTA |
| KPNB1 | PLAC8 | | TMEM109 | SPNA2 | TMPO |
| RPL21 | NRP1 | | MCM2 | GADL1 | SMC4 |
| TTC39B | RPL21-PS10 | | NUP210 | FAM113B | PPIE |
| HMGN1 | RAB11FIP1 | | RPA3 | GPBP1L1 | SSRP1 |
| CCDC55 | GADD45B | | EZH2 | PTEN | BC056474 |
| PPP1R16B | BTG1 | | D17WSU104E | GM10S66 | ZC3H15 |
| TNFSF11 | CHD1 | | NXT1 | GM10293 | SET |
| PAPOLA | LGALS3BP | | ISY1 | ACOT2 | MCM5 |
| GM10250 | JUND | | DLGAP5 | AC159008.1 | ICOS |
| GAPDH | TNFRSF1B | | PSMB1 | GM3550 | CLIC1 |
| CCR6 | PLD3 | | CENPE | RPL7A-PS3 | CIT |
| ANAPC11 | CTSC | | SLC25A5 | RALB | PDZD11 |
| DHRS3 | TTF1 | | CYC1 | NIPBL | ZWINT |
| MIER1 | ANKFY1 | | COX6C | UBXN11 | FKBP2 |
| FXYD5 | ANXA4 | | UCHL5 | LNPEP | COPS3 |
| S100A11 | EFHD2 | | ACTB | RRM2B | SMC1A |
| CD4 | HEXB | | HMGN5 | PSMB10 | GM10123 |
| SRGN | ATN1 | | LSM4 | PRPF4B | CCDC101 |
| GM10359 | GM3222 | | ADH5 | PPIP5K1 | P5MD1 |
| ORC3 | SLAMF7 | | DPYSL2 | HEXDC | USMG5 |
| IL2RB | GBP7 | | 2900073G15RIK | KDM5B | P5MA5 |
| SRSF1 | H2-DMA | | RNPS1 | PAN3 | CCDC56 |
| ABLIM1 | C330021F23RIK | | NFYB | RPL21-PS10 | SUMO3 |
| KLRC1 | SP3 | | MRPS25 | RPS6-PS1 | AIP |
| ID2 | NFIL3 | | EFTUD2 | GM5921 | FDPS |
| GM4963 | DUSP5 | | GTL3 | RPGRIP1 | CCDC34 |
| PPP2R5A | GM10313 | | AI314976 | BTG1 | GM6984 |
| SNX5 | BTG2 | | SNX3 | CLASP2 | FABP5 |
| BCL2A1D | PPMIK | | PDHB | LRRC8D | NDUFB3 |
| GM10263 | IGF2R | | SNRPB2 | CAP1 | PRPS1 |
| AC129078.1 | TGTP1 | | NDUFAF2 | RSBN1L | MKI67 |
| RPL15 | SKIL | | SNAPC5 | RPL7A-PS10 | 2610029G23RIK |
| UNC13D | RAB10 | | HNRNPAB | JUND | IMPA1 |
| CENPQ | GBP2 | | PRKAR1A | AP2A2 | MRPL34 |
| RECQL | RPL21-PS7 | | AHCY | DYNC1H1 | ZFP207 |
| 0910001L09RIK | C1QA | | VDAC1 | 4632428N05RIK | SLC29A1 |
| EIF3A | IER3 | | AP1S1 | IFI27L2B | 10-Sep |

TABLE 6-continued

Shown are genes that are significantly up or down regulated in different
sections of the Voronoi diagram (subpopulations) (corresponding to FIG. 2C).
Differentially expressed genes in in-vivo sub-populations

| | | | | | |
|---|---|---|---|---|---|
| GM2606 | IFRD1 | | PPID | GAS2L3 | MRPL40 |
| FOLR4 | RPL21-PS11 | | BLMH | TTF1 | CACYBP |
| HSPA5 | SIK1 | | TPD52L2 | ANKFY1 | POP4 |
| GM6636 | TET2 | | 2810428I15RIK | DNAJB14 | EXOSC9 |
| LONP2 | GBP6 | | FAM125A | GM10362 | TFDP1 |
| FTSJ3 | SPTY2D1 | | HAUS3 | TLCD1 | PSMB4 |
| ZFR | RPL21-PS6 | | ACTG1 | RAP2B | TTC1 |
| EXOSC2 | NR4A2 | | CALM1 | DDX6 | CD5 |
| GM9396 | MED13L | | YARS | PYHIN1 | TIMM22 |
| TSPAN32 | RRBP1 | | 0610037P05RIK | CAPN12 | ECH1 |
| GM10036 | RASSF2 | | CRBN | SYNRG | CBX3 |
| SYPL | LILRB4 | | GM10076 | ATN1 | SMU1 |
| SUCLG2 | AHNAK | | IFNG | TRPM2 | HNRNPA2B1 |
| LTA | RGS2 | | UBASH3A | GM3222 | CDCA7 |
| IL16 | PLEK | | TSN | MTMR2 | MYG1 |
| TRA2B | FOSL2 | | FAM33A | KIF24 | GM4737 |
| VPS35 | DUSP1 | | POLA1 | C330021F23RIK | PPP6C |
| GM2833 | PER1 | | PSIP1 | IL7R | UBE2A |
| GM10240 | GM10327 | | OGDH | MS4A4C | BLVRA |
| ERMN | IRF2BP2 | | ARL1 | MLL3 | SRP9 |
| DENND2D | GM5507 | | ABCF2 | 2810422J05RIK | CNIH4 |
| FAM165B | TOB2 | | KIF15 | PBXIP1 | CALM2 |
| RPS28 | GM6316 | | TIPRL | GM2058 | TIMM8B |
| CTSW | KDM6B | | ACTN4 | JHDM1D | NAA38 |
| AQR | GM6109 | | CORO1C | KTN1 | RDM1 |
| TMEM147 | JUN | | SYTL3 | ELMOD2 | HELL5 |
| NDFIP1 | ALKBH5 | | OXCT1 | ABHD2 | PRC1 |
| RPS27A | JUNB | | C330027C09RIK | GM10313 | NGFRAP1 |
| SAP30BP | CD63 | | WDR33 | DTX3L | DNAJC9 |
| UTP14A | MNDA | | SNRPA | PPM1K | ITPRIPL1 |
| SIN3A | INSIG1 | | HIST1H4I | GM8225 | NUTF2 |
| BSG | RNF213 | | AC5L5 | RUNX3 | ATP5J2 |
| SUZ12 | FOSB | | FAM96B | IGF2R | PPIA |
| 0610011F06RIK | PSAP | | 9130401M01RIK | MYCBP2 | VIM |
| RPL10A | 9930111J21RIK2 | | BAZ1B | SKIL | PCIF1 |
| MAP4K1 | CCL5 | | ZCCHC17 | SMG1 | RNASEH2B |
| GATA3 | GM11127 | | THOC4 | ABCG1 | RPP30 |
| PTPN22 | EGR1 | | 2310036O22RIK | AL732476.1 | PSPH |
| YIF1A | APOE | | HJURP | RPL21-PS7 | AK2 |
| MUM1 | NOTCH2 | | IFT27 | NPC2 | HSPA14 |
| CMAH | CCRL2 | | SLC35D1 | RPL21-PS11 | NUDT5 |
| YTHDF2 | NR4A3 | | EXOSC5 | SIK1 | CNIH |
| GBA | GM4070 | | SLC1A5 | AC163269.1 | HNRNPF |
| LIMD2 | GM7030 | | NUP93 | TNRC6C | MRPS11 |
| MAP2K3 | GVIN1 | | PPP1R11 | 4930470H14RIK | HDGF |
| SETD8 | CD86 | | L7RN6 | SRRM2 | MRPS18A |
| DDX5 | PRDX5 | | RNASEH2C | GM10718 | STIP1 |
| TAPBP | AIF1 | | TAF6 | IFI203 | CCDC21 |
| LAPTM5 | H2-AB1 | | CDK5RAP2 | RPL21-PS6 | H3F3A |
| DGKA | H2-EB1 | | SH3BGRL3 | HMHA1 | 1500032L24RIK |
| HAUS2 | LYZ2 | | CDKN2AIPNL | MED13L | NSMCE1 |
| CST3 | GRN | | DNMT1 | RPL29-PS2 | AHSA1 |
| ITGAV | C1QB | | RAD21 | RASSF2 | MRPL46 |
| HAVCR2 | LY86 | | MEMO1 | NCOA3 | PRDX4 |
| SLC3A2 | FCER1G | | MRPS24 | STAT1 | NUDCDZ |
| MAPRE2 | TYROBP | | CISH | FMO1 | GARS |
| CLK3 | | | PRPF38A | GM10291 | XPO1 |
| GPATCH8 | | | CCDC124 | RPL17-PS3 | MRPL45 |
| ATP6V1G1 | | | MRPS6 | SLC39A1 | CD160 |
| SH2D2A | | | UBB | GM10327 | PTGES3 |
| DGAT1 | | | GTF2A1 | BIRC6 | NOL12 |
| EIF1AD | | | MKKS | IRF2BP2 | GDI2 |
| MRPS26 | | | TRIM28 | GM5507 | SNRNP25 |
| AW112010 | | | CCR8 | MAP3K1 | TUBA1A |
| FAM65B | | | PUF60 | GM10800 | 5930416I19RIK |
| NUMA1 | | | TMED2 | TOB2 | IL18RAP |
| EMB | | | NEBL | GM6316 | SIVA1 |
| 2010111I01RIK | | | HCFC1 | KDM6B | TMEM109 |

TABLE 6-continued

Shown are genes that are significantly up or down regulated in different sections of the Voronoi diagram (subpopulations) (corresponding to FIG. 2C). Differentially expressed genes in in-vivo sub-populations

| | | | |
|---|---|---|---|
| MED21 | D930014E17RIK | GM6109 | MCM2 |
| 2310004N24RIK | EIF4H | LY6C2 | NUP210 |
| ARPC5L | NUCKS1 | ZFP36L1 | RPA3 |
| AC114648.1 | LNP | JUN | EZH2 |
| SDF2 | SCAMP2 | ALKBH5 | TAF12 |
| THEMIS | GALM | MLL2 | CLDND1 |
| S1PR1 | 2810407C02RIK | PDCD4 | GLTP |
| IL12RB2 | CENPL | INSIG1 | NT5C3L |
| GM9234 | UFSP2 | RNF213 | NXT1 |
| B2M | DCTN3 | GM8909 | ILF2 |
| ZFP825 | DKKL1 | C030046E11RIK | DLGAP5 |
| GM5160 | RPS21 | PSAP | PSMB1 |
| MIIP | HIST1H2BC | 9930111J21RIK2 | CENPE |
| NSD1 | UBE2S | ARID1B | H5D17B12 |
| SATB1 | RPL12 | GM11127 | H2-HE2 |
| | AP2S1 | H2-Q2 | SLC25A5 |
| | | CDKN1B | HAUS1 |
| | | NOTCH2 | FGFR1OP2 |
| | | SLFN5 | CYC1 |
| | | SGIP1 | COX6C |
| | | GM4070 | UCHL5 |
| | | BMP2K | PPP1R8 |
| | | GM7030 | UCHL3 |
| | | GVIN1 | UBL4 |
| | | ZFP36 | XRCC6 |
| | | LYZ2 | YWHAE |
| | | H2-AA | HMGN5 |
| | | CTSS | CIAPIN1 |
| | | CD74 | LSM4 |
| | | | PFDN4 |
| | | | PQLE4 |
| | | | ADH5 |
| | | | DPYSL2 |
| | | | 2900073G15RIK |
| | | | DCP5 |
| | | | M6PR |
| | | | RNPS1 |
| | | | NFYB |
| | | | MRPS25 |
| | | | EFTUD2 |
| | | | HSPE1 |
| | | | ESD |
| | | | MFF |
| | | | GTL3 |
| | | | AI314976 |
| | | | SNX3 |
| | | | ATP5C1 |
| | | | PDHB |
| | | | H47 |
| | | | SNRPB2 |
| | | | NDUFAF2 |
| | | | NUP214 |
| | | | SNAPC5 |
| | | | HNRNPAB |
| | | | AHCY |
| | | | LSM10 |
| | | | PAK1IP1 |
| | | | GM10736 |
| | | | MRPL53 |
| | | | VADC1 |
| | | | AP1S1 |
| | | | MAD2L2 |
| | | | PPID |
| | | | UBA1 |
| | | | BLMH |
| | | | TPDS2L2 |
| | | | MAGOHB |
| | | | 2810428I15RIK |
| | | | RUVBL2 |
| | | | FAM125A |
| | | | HAUS3 |
| | | | CALM1 |
| | | | YARS |
| | | | VBP1 |
| | | | 0610037P05RIK |
| | | | CRBN |

TABLE 6-continued

Shown are genes that are significantly up or down regulated in different
sections of the Voronoi diagram (subpopulations) (corresponding to FIG. 2C).
Differentially expressed genes in in-vivo sub-populations GM10076
UBASH3A
TSN
FAM33A
PQLA1
SBDS
PSIP1
QGDH
ARL1
PPIH
ABCF2
KIF15
CNPY4
TIPRL
ACTN4
POLR3K
CORO1C
SSSCA1
SF3A3
SYTL3
OXCT1
C330027C09RIK
WDR33
SNRPA
ORC4
HI5T1H4I
ACSL5
NRF1
9130401M01RIK
MRPL11
CINP
BAZ1B
LUC7L3
ZCCHC17
PPIL1
MRPS36
GABPB2
THQC4
2310036O22RIK
HJURP
IFT27
NOP58
SLC9A3R1
SLC35D1
SLA2
EXOSC5
SLC1A5
NUP93
PPP1R11
IMPDH2
L7RN6
PSMD13
RNASEH2C
CRMP1
UTP3
LJXT
CDKSRAP2
CDKN2AIPNL
DNMT1
RAD21
ADPRH
MEMO1
ITPA
RNF7
EXOSC3
PRPF38A
CCDC124
MRPS6
MKKS
TRIM28
CCR8
POLR2H
PLIF60
LTA4H
TMED2
NEBL TABLE 6-continued Shown are genes that are significantly up or down regulated in different sections of the Voronoi diagram (subpopulations) (corresponding to FIG. 2C). Differentially expressed genes in in-vivo sub-populations

| | | | | | | HCFC1 |
|---|---|---|---|---|---|---|
| Th17/Th1-like effector | Th17/pre-Th1-like effector | | Th17 self-renewing | | T17 Dysfunctional/senescent | |
| ATOX1 | CKS2 | RPS8-PS1 | TOP2A | EZR | STMN1 | AC127419.1 |
| LYAR | FIGNL1 | XAF1 | UBE2C | GM10237 | 2810417H13RIK | 4833420G17RIK |
| GNG5 | CIT | TXLNG | BIRC5 | LEF1 | HMGN2 | SNRNP200 |
| RWDD1 | MRPL27 | NCK2 | NDUFA5 | FAM65B | TOP2A | FTH1 |
| D930014E17RIK | DOK2 | CDK7 | CCNB2 | HK1 | SMC2 | SYT11 |
| EIF4H | PPP1R8 | MGA | NME1 | EMB | GM7125 | GM5148 |
| NUCKS1 | HSPE1 | ISCA1 | TIPIN | 2010111I01RIK | NUTF2-PS1 | 5830405N20RIK |
| APIP | CDC26 | POM121 | SNRPB | MED21 | SSNA1 | MYSM1 |
| RIF1 | IL22 | LARP4B | NDUFA4 | COMT1 | HIST1H4D | WAS |
| EIF2S3X | YARS | POLR3C | NSMCE2 | 2310004N24RIK | SNRPA1 | RNF5 |
| LNP | IFNG | TNFRSF26 | FAM36A | THADA | CKS1B | AGXT2L2 |
| DHX15 | TBL3 | TCF7 | SNRPD2 | SDF2 | MRPL42 | IRGM1 |
| EXOSC10 | ALDOA | MRPS7 | DUT | FARSB | ANP32E | RP23-71J17.1 |
| 2610039C10RIK | CD7 | RASSF1 | SEC11C | H2-Q7 | PCNA | AC120410.1 |
| CD3E | CCR8 | CPNE8 | KIF23 | THEMIS | MRPS16 | HNRPDL |
| 2400001E08RIK | MICAL1 | TTC5 | COMMD1 | NUCB1 | H2AFV | GM10155 |
| SYNCRIP | SDHC | GPR68 | STRA13 | S1PR1 | NDUFA5 | FXR1 |
| HIST1H2BG | RPS15A | GRIPAP1 | H2AFZ | BRP44L | ASF1B | GM10358 |
| POLR2B | TNFSF11 | SFI1 | TAGLN2 | OSBPL3 | RANBP1 | SF3B3 |
| HSPA4 | CCR6 | LITAF | EMG1 | B2M | NME1 | USP50 |
| MRPS36-PS1 | ASRGL1 | AC151275.1 | 1810027O10RIK | TTC39C | BCAP31 | GM5220 |
| AKR1A4 | DHRS3 | BRAP | CISD3 | 2010002N04RIK | PSMD14 | RPS19-PS2 |
| WDYHV1 | MDP1 | GM5561 | SRP19 | NDFIP2 | GM10349 | GPSM3 |
| 2810407C02RIK | GGPS1 | ADO | LIG1 | RPS12 | TIMM17A | ATP2B4 |
| CENPL | POT1A | WBP11 | MPHOSPH6 | APOL7E | EXOSC8 | CNOT3 |
| UFSP2 | ORC3 | EZH1 | UHRF1 | DDX18 | GMNN | EXOC1 |
| LGTN | ODF2 | GM10054 | ERGIC2 | NSD1 | SNRPB | SERBP1 |
| KPNB1 | TMEM154 | GM3940 | TXN2 | BCL2L1 | NUF2 | ZC3HC1 |
| DCTN3 | LSG1 | GM7589 | MRPS17 | SATB1 | TUBA1B | YTHDC1 |
| DKKL1 | UTP23 | RPL12-PS1 | TNFRSF4 | SFPQ | MRPS14 | RPL27A |
| HIST1H2BC | PMPCA | EXOC4 | HMMR | CAR5B | MRPL18 | GM11273 |
| CCNC | SYPL | HSD3B2 | MANF | OSTF1 | DPY30 | AC151275.1 |
| FAIM | CDKAL1 | SOCS2 | LGALS1 | BCL2A1B | PSMB6 | GM5561 |
| UBE2S | ERMN | 2310016C08RIK | CISD1 | UBAP2L | PSMC2 | 2810474O19RIK |
| CTCF | TRAF2 | KPNA1 | TMEM49 | AA467197 | FAM36A | GM6139 |
| RPL12 | CTSW | IL10RB | PLP2 | AC134548.2 | CCT5 | FRMD4B |
| AP2S1 | AGTPBP1 | HK2 | EMP3 | UBE2F | CDK4 | GM100S4 |
| FAM111A | DEGS1 | REL | SRSF7 | LY6G5B | DCTPP1 | RPL13-PS3 |
| RAB1 | SIKE1 | GM6180 | ACOT7 | ACADL | MRPS18C | GM5805 |
| ACP1 | PFKL | RPL21-PS3 | NOP56 | GM10247 | HPRT | SMG7 |
| PAPOLA | PIGU | CDKN1A | TXN1 | IFITM3 | YWHAH | GM7589 |
| CNOT6 | MUM1 | IL4RA | CD48 | RGS1 | H2AFZ | QSOX1 |
| SNX4 | TAF1 | ZBTB20 | TXNDC17 | BHLHE40 | NDC80 | SAMHD1 |
| ANAPC1 | MAP2K3 | D14ABB1E | CKS2 | HDLBP | NDUFB2 | RPS2-PS6 |
| ANAPC11 | DNPEP | GM8815 | RBBP4 | PFDN2 | EMG1 | GM6180 |
| TRNT1 | RINT1 | GM10012 | SEC61B | FAM129A | MED10 | NSA2 |
| HIST2H2AA2 | SLC3A2 | HERC2 | COX17 | WDR43 | SEC13 | AL844854.1 |
| AGPAT3 | NSF | GM10154 | KRTCAP2 | SELL | NDUFV2 | 4921517L17RIK |
| BAD | FAM65B | IFNGR2 | HP1BP3 | GGH | HMGB3 | SRP54A |
| HIST2H2AA1 | WIBG | 4930412F15RIK | TMEM208 | PGAM1 | TAF9 | GM6807 |
| AC131675.1 | UBR1 | GM10063 | TFF1 | RAMP1 | 0610010K14RIK | WTAP |
| VAMP4 | UPF3B | GABARAPL1 | GM3090 | ITK | EIF4A3 | GM10695 |
| NUBP1 | ARPC5L | KDM6A | CCT8 | MTA3 | THOC7 | GCNT2 |
| USP1 | IL27RA | LRRC58 | RPS17 | BAX | TUBB5 | GM8815 |
| STK39 | AHCYL2 | RPL36-PS3 | GNG10 | EIF4G1 | MRPL51 | MEX3C |

TABLE 6-continued

Shown are genes that are significantly up or down regulated in different sections of the Voronoi diagram (subpopulations) (corresponding to FIG. 2C). Differentially expressed genes in in-vivo sub-populations

| | | | | | | |
|---|---|---|---|---|---|---|
| AP351 | ZFP825 | AP1B1 | EFF1B2 | PRKACB | PA2G4 | GM10012 |
| RAB4B | GM5160 | KRR1 | SPC24 | RPL31 | NDUFB6 | ZZEF1 |
| SRSF1 | MIIP | 1500012F01RIK | 31-Aug | HIF1A | SSR2 | GM10154 |
| GPS1 | CLEC2 | NR4A1 | NDUFA1 | KHDRB51 | POLR2G | AC117259.1 |
| ELP2 | AA467197 | CREBL2 | IMMT | ALKBH4 | UHRF1 | GM8991 |
| THOC6 | POGLUT1 | H2-GS10 | NKG7 | DNAJB6 | PCMT1 | 4930412F15RIK |
| RIOK1 | HAUS8 | CSRNP1 | HSD17B10 | PD55A | CBX5 | GM5453 |
| CASP3 | IFITM3 | GADL1 | S100A4 | RPS27 | HAT1 | GM10063 |
| ZCRB1 | 2410002O22RIK | ISCU | GM10120 | RPL30-PS8 | MRPS21 | GM5908 |
| PPP2R5A | MTPN | UBXN11 | CRIP1 | MAGT1 | 1810006K21RIK | AC155816.1 |
| PDLIM2 | COX10 | PLAC8 | SRPK1 | GOLM1 | ORC6 | RPL36-PS3 |
| IPO7 | SSBP2 | RPL21-PS10 | SET | GTPBP4 | NDUFB11 | MT1 |
| PMPCB | PHKG2 | RPS6-PS1 | S100A10 | DHX9 | LGALS1 | ZMYND8 |
| SMC3 | TEX261 | MS4A6C | CIT | RGS16 | LAT | GM8054 |
| DDOST | BCAT2 | TPDS2 | ZWINT | DDRGK1 | ANXA6 | MAPKAPK2 |
| MRPL35 | PLDN | TTF1 | FKBP2 | MRP63 | POLR2F | AC142450.1 |
| UBE2B | PDHA1 | ATN1 | NAP1L4 | LGALS3 | MRPL21 | AC117184.1 |
| ACTR1A | MAGT1 | LY6I | CXCR6 | LMAN2 | TRAPPC1 | GM3839 |
| SNRPC | RGS16 | C330021F23RIK | GM6169 | ANXA5 | CWC15 | GM10916 |
| DDB1 | TAF13 | NK1RAS1 | MRPL41 | WBP2 | MCM6 | A230046K03RIK |
| CENPQ | 2510002D24RIK | ABHD2 | AIP | STK38 | GTF2H5 | GM9104 |
| RECQL | GM4759 | BAZ2B | UQCR11 | RPL17 | GLO1 | LARS2 |
| HMOX2 | MAPKAPK3 | RPL21-PS11 | FABP5 | RBM38 | ANAPC5 | HNRNPUL1 |
| RPL9-PS4 | GPR65 | RPL21-PS6 | RPL22L1 | ACTN2 | HMGB1 | KHSRP |
| RNASEK | EIF4EBP1 | RPL29-PS2 | 10-Sep | ORC5 | PSMD7 | IRAK1 |
| DDX27 | ARHGAP1 | LILRB4 | ZAP70 | RPL5 | PTMA | GM11167 |
| STARD3NL | COTL1 | KLHL24 | POP4 | FAM49B | VPS25 | RAD9 |
| NEDD1 | 4732418C07RIK | FOSL2 | FIF5A | AC127419.1 | EIF3L | H2-GS10 |
| SSR4 | TOX | GM6316 | PTPRCAP | 4833420G17RIK | TMEM208 | RC3H1 |
| PDCL3 | MYD88 | GM6109 | HNRNPA2B1 | EIF4A2 | GM6104 | GADL1 |
| FTSJ3 | DDHD2 | LY6C2 | ANXA2 | ECE1 | PPP1CA | GM10566 |
| SMS | ARL5C | GM8909 | TNFRSF18 | GM2792 | ARHGDIA | GM10293 |
| NUDC | | CTSH | PSMG2 | ATP6V08 | SRPR | AC159008.1 |
| CSDA | | GM11127 | DKC1 | MAPKAPK3 | 2700029M09RIK | GM3550 |
| GOT2 | | EGR1 | VIM | PIK3CD | MRPL4 | ISCU |
| RPL37 | | NR4A3 | CCT7 | GPR65 | PHB | RPL7A-PS3 |
| LARP7 | | GM7030 | CNIH | TAP1 | GM10120 | UBXN11 |
| CCDC41 | | SDC4 | HNRNPF | RPS13 | PPIE | PICALM |
| COPB2 | | H2-AB1 | TPI1 | MAP3K8 | VDAC2 | MYO1E |
| SEPW1 | | C1QB | ENO1 | STK4 | NAP1L4 | PPIP5K1 |
| GM10071 | | | DDX47 | RPL15-PS2 | SMC1A | HEXDC |
| PPP2R4 | | | 1500032L24RIK | HBS1L | GM10123 | CLINT1 |
| KCNAB2 | | | PARK7 | IL1R1 | SUMO3 | PAN3 |
| APIS | | | HSP90AA1 | PRDM1 | CCDC34 | MFSD11 |
| SUGT1 | | | TIGIT | GM9858 | XLR4C | RPL21-PS10 |
| PRPF18 | | | GNG2 | APPL1 | MRPL34 | RPS6-PS1 |
| TARS | | | CAMK4 | FTH1 | PTTG1 | GM5921 |
| RPS23 | | | CORO1A | RBM5 | PPP6C | RNF149 |
| ARMC1 | | | IL18RAP | LIN7C | DCTN6 | LRRC8D |
| GM9000 | | | DNAJC15 | ARHGAP1 | TIMM8B | RPL7A-PS10 |
| RSRC1 | | | TCEB2 | CNP | PQBP1 | JUND |
| UBAP2 | | | SUSD3 | GM5148 | HELLS | TMEM123 |
| GM7536 | | | GM5506 | UBE2J1 | SARNP | MXD1 |
| HIST1H1C | | | ISY1 | SERINC3 | NUTF2 | GAS2L3 |
| SIN3A | | | EEF1G | RNGTT | OLA1 | TTF1 |
| SUZ12 | | | HSD17B12 | LRRFIP1 | PCIF1 | TGFBR2 |
| SMC6 | | | BCAS2 | 5830405N20RIK | NSMCE1 | ANKFY1 |
| MAP4K1 | | | CTLA4 | CMC1 | EIF3C | DNAJB14 |
| SF1 | | | PKP3 | TULP4 | PTPN2 | CAMK2G |
| RPL19 | | | 2900073G15RIK | PDE48 | UBE2V2 | GM10362 |

TABLE 6-continued

Shown are genes that are significantly up or down regulated in different sections of the Voronoi diagram (subpopulations) (corresponding to FIG. 2C).
Differentially expressed genes in in-vivo sub-populations

| | | | | |
|---|---|---|---|---|
| SETD8 | ADSL | TNFRSF9 | GIMAP4 | TLCD1 |
| UQCRFS1 | PSMC4 | MYSM1 | ANAPC16 | RAP2B |
| GM8394 | 1810037I17RIK | APOL7B | ADSL | DDX6 |
| IK | LPXN | TEX2 | TRMT112 | PYHIN1 |
| RPL27 | SDF4 | YME1L1 | CST1 | TRAFD1 |
| ITGAV | CAPG | TOX | BRIX1 | CAPN12 |
| NOL7 | SNX3 | FAM110A | TPD52L2 | SYNRG |
| GPX1 | ADK | 1700123O20RIK | UFD1L | BAT2L |
| GM9846 | PRKAR1A | RBMS1 | DCAF1 | ATN1 |
| MSL3 | RPLP0 | D16ERTD472E | MRPS18B | TRPM2 |
| DNAJC2 | PDLIM1 | CSF2 | ESF1 | GM3222 |
| NCBP1 | CSNK2B | RFC1 | EIF3D | MAP3K14 |
| GPATCH8 | 2810428I15RIK | TMEM874 | PSIP1 | C330021F23RIK |
| EIF1AD | ACTG1 | SNX2 | BZW2 | MLL3 |
| ARGLU1 | CALM1 | DNAJB1 | WDR12 | ELMOD2 |
| CCDC107 | YARS | H2-K1 | KIF15 | ABHD2 |
| AC119211.2 | EIF3K | FAM98B | UCF1 | ADIPOR1 |
| GM10237 | IFNG | TMEM149 | C330027C09RIK | GM10313 |
| ATAD2 | S100A13 | REEP5 | WDR33 | DTX3L |
| TPT1 | TMEM176B | GM7665 | 2410001C21RIK | PPM1K |
| OSBPL3 | GSTP2 | MPHOSPH10 | MRPL48 | GM8225 |
| UCP2 | FAM162A | 2610101N10RIK | ZCCHC17 | MYCB92 |
| 2010002N04RIK | GTF2E2 | STK24 | GABPB2 | SMG1 |
| A430093F15RIK | PSMD2 | ZNHIT1 | NOP58 | RAB10 |
| RPS12 | CPSF3L | CNOT1 | PNRC2 | AL732476.1 |
| TSPO | CDC42 | F2R | 2610030H06RIK | RPL21-PS7 |
| SMARCA4 | RPS20 | SS18 | ACADVL | NPC2 |
| SFPQ | BZW2 | RBPSUH-RS3 | TMED2 | RPL21-PS11 |
| GATAD1 | SLAMF1 | EHD1 | CLP1 | SIK1 |
| AC134548.2 | RPSA-PS10 | GNL3 | RIF1 | AC163269.1 |
| NAA15 | ATP5L | RP58-PS1 | SDHC | TNRC6C |
| GM16477 | HAX1 | NSG2 | SCAMP4 | 4930470H14RIK |
| ACADL | CD226 | SAMSN1 | BIN2 | GM10718 |
| GM8730 | HSP90AB1 | AC120410.1 | CPM | IFI203 |
| SF3A1 | PSMB8 | XRN2 | GM10250 | RPL21-PS6 |
| TMED9 | NASP | GLUL | ARAF | MED13L |
| SCAND3 | SYTL3 | GM10155 | CCR6 | RPL29-PS2 |
| MTPN | OXCT1 | FASL | GIMAP6 | RASSF2 |
| KIF2A | RPL36A | XAF1 | 4930453N24RIK | STAT1 |
| PUM2 | RPL8 | RASA3 | RPL18 | AHNAK |
| GTPBP1 | GM8759 | RUNX2 | AC131675.1 | ARID5B |
| STAG1 | TBCB | NFKBIA | RRP1B | FMO1 |
| MED29 | RPS8 | HOPX | LONP2 | GM10291 |
| SMN1 | RPSA | ITM2B | EEF1E1 | RPL17-PS3 |
| SREK1 | RPL7 | GM5518 | ENY2 | SLC39A1 |
| RPL31 | 2410001C21RIK | PLEKHB2 | GM10257 | TAX1BP3 |
| HMGA1 | PRR13 | GM10358 | PRPF18 | GM10327 |
| KHDRBS1 | RPLP1 | PUM1 | GM7808 | BIRC6 |
| BIRC2 | YWHAZ | NXF1 | PPP1R7 | IRF2BP2 |
| RPS27 | DDT | ELK4 | YIF1A | GM5507 |
| FMR1 | PPP1CC | ARHGEF3 | INTS7 | GM10800 |
| RPL30-PS8 | ZCCHC | IFITM2 | TPT1 | GM6316 |
| PFDN5 | MRP536 | NEDD9 | PSME2B-PS | KDM6B |
| RGS16 | CALM3 | CHSY1 | GM9234 | GM6109 |
| 2810008M24RIK | SLC35D1 | CDK7 | ATP6V1F | PNRC1 |
| MRP63 | SLA2 | ZRANB2 | TSPO | ZFP36L1 |
| PIN1 | PIH1D1 | CHD4 | RAB27A | ALKBH5 |
| GNL3L | ALDOA | PPP1CB | GM2574 | MLL2 |
| FAU | TSG101 | TCOF1 | GM5138 | JUNB |
| RPL27-PS1 | NDUFA13 | NOL8 | SREK1 | PDCD4 |
| RPL17 | L7RN6 | MDM4 | ING5 | INSIG1 |
| ORC5 | LXN | TRPS1 | PFDN5 | GM8909 |
| TSHZ1 | CRMP1 | AL732569.1 | GTPBP4 | C030046E11RIK |
| RPL5 | SH3BGRL3 | ZFP91 | DHX9 | PSAP |

TABLE 6-continued

Shown are genes that are significantly up or down regulated in different sections of the Voronoi diagram (subpopulations) (corresponding to FIG. 2C).
Differentially expressed genes in in-vivo sub-populations

| | | | | |
|---|---|---|---|---|
| FAM49B | S100A6 | AKNA | GM3272 | ARID1B |
| AC127419.1 | GABARAPL2 | MGA | RPL27-PS1 | GM11127 |
| VAMP3 | RPLP2 | GM5220 | RPL5 | H2-Q2 |
| ING1 | RAD21 | RPS19-PS2 | | CDKN1B |
| KRCC1 | TBC1D10C | ZFP106 | | NOTCH2 |
| SHISA5 | GM4294 | BCL2A1C | | SLFN5 |
| GPR65 | SEC22B | DYRK1A | | SGIP1 |
| TAP1 | RPS15 | CREM | | NR4A3 |
| RPS13 | NCL | TNFSF10 | | GM4070 |
| RPL15-PS2 | G3BP1 | SEMA4A | | BMP2K |
| GM9858 | MRPS24 | SRSF5 | | GM7030 |
| GM5148 | ATP5G2 | CASP8 | | GVIN1 |
| GM4609 | NPTN | TSC22D4 | | ZFP36 |
| HSPH1 | CISH | GLTSCR2 | | LY22 |
| FTL1 | PRPF38A | TCF7 | | GRN |
| WBP4 | GM2000 | 1600014C10RIK | | |
| RFC1 | RPL3 | ATP2B4 | | |
| GM6736 | RPS29 | CDK11B | | |
| GM10116 | RPL28 | PSMD9 | | |
| REEP5 | TMSB4X | CCND2 | | |
| D19BWG1357E | RPL7A | LAG3 | | |
| GM7665 | RPL38 | PTPN18 | | |
| RALBP1 | CCR8 | CCR2 | | |
| DDX42 | TIMM17B | TMEM66 | | |
| RP23-71117.1 | RP53A | PLIN2 | | |
| RPS8-PS1 | SLA | EROIL | | |
| AC120410.1 | ATOX1 | UAP1 | | |
| XRN2 | RPS25 | COX16 | | |
| HNRPDL | RPS18 | GPR68 | | |
| GM10155 | LLPH | NVL | | |
| PCBP1 | RP53 | ARHGAP26 | | |
| BRD9 | RWDD1 | ZYX | | |
| SEC61G | EIF4H | GIMAP7 | | |
| CYB5B | 1700012B07RIK | PMAIP1 | | |
| RUNX2 | TMSB10 | UBASH3B | | |
| ITM2B | RIF1 | RORA | | |
| GM5518 | IL1R2 | APAF1 | | |
| GM10358 | RPL35 | PIAS1 | | |
| USP50 | SNRNP27 | RNF20 | | |
| NFATC2 | BC016495 | SLC15A3 | | |
| GM5220 | RPL22 | PSD4 | | |
| DYNLT1C | LASS2 | 1110007A13RIK | | |
| RPS19-PS2 | GM11353 | WDR4SL | | |
| GABARAP | RPL14 | YTHDC1 | | |
| LARP4B | POLR2E | RHOH | | |
| HNRNPL | NACA | GM10136 | | |
| TCF7 | RPS19 | IFNGR1 | | |
| GRCC10 | RPL39 | DNAIC1 | | |
| CCND2 | GM10073 | IL18R1 | | |
| TLN1 | POLR2B | RPL27A | | |
| A830010M20RIK | BCLAF1 | USP7 | | |
| GIMAP7 | AC124742.1 | C330019G07RIK | | |
| RPL7A-P55 | MRP536-PS1 | DNAJB4 | | |
| SERBP1 | COMMD6 | LITAF | | |
| WDR45L | 5P1 | GNGT2 | | |
| GM10136 | GM5559 | MDN1 | | |
| WDR92 | GM6472 | DDX46 | | |
| RPL27A | RP59 | IFI35 | | |
| MDN1 | RP518-PS3 | TAB2 | | |
| DDX46 | 5-Sep | DMTF1 | | |
| AC151275.1 | RPL35A | AC151275.1 | | |
| GM5561 | GM12033 | CPD | | |
| 2810474O19RIK | TRAT1 | CD44 | | |
| GM6139 | NGDN | KLF6 | | |
| UBQLN1 | IL2RA | GM5561 | | |
| WBP11 | MRPL32 | SPARC | | |
| PRPF39 | GNA15 | EHMT1 | | |
| EZH1 | SPAG7 | NMNAT1 | | |

TABLE 6-continued

Shown are genes that are significantly up or down regulated in different sections of the Voronoi diagram (subpopulations) (corresponding to FIG. 2C). Differentially expressed genes in in-vivo sub-populations

| | | |
|---|---|---|
| GM10054 | 2810407C02RIK | PION |
| SON | TMEM179B | ATXN1 |
| RPL13-PS3 | CENPL | CD27 |
| ZGPAT | RPS24 | SLC2A3 |
| GM5805 | GM10020 | GM6139 |
| GM3940 | DCTN3 | CASP4 |
| GM7589 | ACOT9 | TNFAIP3 |
| WDR70 | RP510 | CORO2A |
| RPL12-PS1 | RPS7 | MAF |
| QSOX1 | RPL21 | SOAT1 |
| HSD3B2 | RPS21 | BIRC3 |
| AC110247.1 | HIST1H2BC | NRIP1 |
| AC156282.1 | RPS13-PS1 | CCR1 |
| GM10481 | TTC39B | VP554 |
| TNRC6B | HMGN1 | PRPF39 |
| RPS2-PS6 | CCDC55 | RELL1 |
| GM5619 | RP516 | SPIN1 |
| GM3150 | GM10119 | FRMD4B |
| RBM15 | AC154908.2 | RBM26 |
| GM8910 | RPL12 | AIM1 |
| GM6180 | CTLA2A | SLAMF6 |
| SLC38A6 | TNFSF11 | UBL3 |
| UTRN | SPNB2 | INPP4A |
| CCRN4L | ERGIC3 | GM10054 |
| BC005537 | RPL30 | SON |
| TRIM12A | DENR | ANKRD44 |
| RPL21-PS3 | PECI | ADAM19 |
| N5A2 | RPL7L1 | FRYL |
| ACSL4 | GAPDH | ARAP2 |
| AL844854.1 | CCR6 | CKB |
| CDKN1A | HNRNPA0 | SQSTM1 |
| 4921517L17RIK | P4HB | WDR70 |
| GM6807 | MEDI1 | BCL2A1A |
| FURIN | AGPAT3 | QSOX1 |
| KLF13 | DHR53 | CTSD |
| UPF1 | GIMAP6 | CLIC4 |
| ARF5 | FXYD5 | CCR7 |
| PRKACA | DGUOK | APIS2 |
| CT033780.1 | RPS27A-PS2 | RPS2-PS6 |
| WTAP | RPL18 | SOC52 |
| PDE4D | 5100A11 | 2310016C08RIK |
| GM10695 | GM10159 | RUNX1 |
| CAPS2 | VAMP4 | NFAT5 |
| GM8815 | SRGN | IGTP |
| EDEM1 | GM10359 | RNF13 |
| BAT2L2 | PIGX | DENND4A |
| ARF6 | TRAF3IP3 | KBTBD11 |
| GM10012 | ACTR2 | DCTN4 |
| ZZEF1 | AEBP2 | HK2 |
| GM10154 | IL2RB | REL |
| AC117259.1 | LAGE3 | GM8910 |
| TGOLN1 | GM10335 | ARL15 |
| GM8991 | ABLIM1 | HSF2 |
| 4930412F15RIK | KLRC1 | WDFY1 |
| GM5453 | H2-Q8 | CCRN4L |
| GM10063 | GGNBP2 | TRIM12A |
| GM5908 | CDC42SE1 | ENTPD7 |
| AC155816.1 | RPL9-PS6 | ZBP1 |
| LRRC58 | ID2 | FAM102A |
| ESCO1 | ZCRB1 | ACSL4 |
| RPL36-PS3 | GM4963 | CDKN1A |
| FNBP1 | CD37 | SRSF2IP |
| UBR4 | PPP2R5A | GM6807 |
| AMD1 | SNX5 | FURIN |
| SEC62 | BCL2A1D | COQ10B |
| CFLAR | GM10263 | VCPIP1 |
| MACF1 | DDOST | PRKACA |
| TXNIP | AC129078.1 | ATPBD4 |

TABLE 6-continued

Shown are genes that are significantly up or down regulated in different
sections of the Voronoi diagram (subpopulations) (corresponding to FIG. 2C).
Differentially expressed genes in in-vivo sub-populations

| | | |
|---|---|---|
| PPP1R12A | RPL15 | 1110007C09RIK |
| MLL5 | RPL6 | TNF |
| SP110 | CYLD | PDE4D |
| ZMYND8 | EEF2 | GCNT2 |
| KRR1 | 1810046I19RIK | BAT2L2 |
| TNRC6A | CCM2 | UPF2 |
| GM8054 | SNRPC | RALGPS2 |
| AMD2 | GM5879 | GM10012 |
| GSK3B | RPL9PS4 | GATAD2A |
| AC108412.1 | 0910001L09RIK | AP2B1 |
| SPOPL | EIF3A | GM10154 |
| UBE2H | RAC1 | AC117259.1 |
| 2310035C23RIK | GM2606 | TGOLN1 |
| GM7592 | FKBP5 | GM8991 |
| MNDAL | MYO1G | GM5453 |
| SLFN1 | FOLR4 | GM10063 |
| RBPJ | IFI27L2A | GM5908 |
| ZFP488 | RPS6 | KDM6A |
| AC142450.1 | GM6636 | FOXO1 |
| AC117184.1 | STARD3NL | ESCO1 |
| SEMA4B | CHMP5 | AMD1 |
| GM2026 | ZFR | AP1B1 |
| GM7609 | RPL23A | MFSD4 |
| AMD-PS3 | RPL37 | MACF1 |
| GM14434 | GM9396 | SAMD9L |
| EMD | TSPAN32 | FOXP1 |
| IRAK2 | SEPW1 | CAMK2D |
| LY6C1 | RPL9 | PPP1R12A |
| GM3839 | RPL18A | SP110 |
| GM10916 | RPL37A | MT1 |
| NBR1 | GM10036 | PDCD11 |
| ZFP187 | SYPL | H2-T10 |
| A230046K03RIK | GM10071 | ZMYND8 |
| GM9104 | SIRT2 | FOXN3 |
| LARS2 | IL16 | NFKBIZ |
| B4GALT1 | TSPAN31 | TNRC6A |
| HNRNPUL1 | 5UGT1 | GM8054 |
| H2-Q6 | TRA2B | AMD2 |
| KH5RP | FKBP8 | ACTN1 |
| GM14391 | RPS23 | HELZ |
| GM11167 | GM10268 | CDK13 |
| RAD9 | GM2833 | 2310035C23RIK |
| H2-GS10 | AKAP13 | RBP1 |
| 0610031J06RIK | GM10240 | ZFP488 |
| TECPR1 | AC124399.1 | CTNNA1 |
| SPNA2 | ERMN | TMEM71 |
| RC3H1 | GM9000 | SEMA4B |
| GADL1 | DENND2D | AMD-PS3 |
| FAM113B | RPS28 | EMD |
| GPBP1L1 | RPL36 | NR4A1 |
| PTEN | CTSW | IRF2 |
| GM10566 | ADRBK1 | GM10916 |
| SETD2 | MAT2A | RBM47 |
| UBN2 | ODC1 | ZFP187 |
| GM10293 | PPP1R7 | ARHGAP31 |
| ACQT2 | CSTB | A230046K03RIK |
| AC159008.1 | AC114007.1 | CD9 |
| GM3550 | TMEM147 | GM9104 |
| BRWD1 | NDFIP1 | ASAH1 |
| RPL7APS3 | RPS27A | RBBP6 |
| AI848100 | RBMX | KH5RP |
| TRIM24 | PFKL | CT5B |
| NIPBL | GM7536 | PTEN |
| RNASET2A | BSG | ZEB2 |
| UBXN11 | RPL26 | ACOT2 |
| LNPEP | RPL10A | ISCU |
| RRM2B | MRPL55 | SMAD7 |
| PRPF4B | MAP4K1 | UBXN11 |
| RNASET2B | RPL19 | GP49A |
| PPIP5K1 | CMAH | KIF21B |
| HEXDC | LIMD2 | RRM2B |
| KDM5B | SETD8 | PRPF4B |

TABLE 6-continued

Shown are genes that are significantly up or down regulated in different
sections of the Voronoi diagram (subpopulations) (corresponding to FIG. 2C).
Differentially expressed genes in in-vivo sub-populations

| | | |
|---|---|---|
| PAN3 | TMEM176A | PLAC8 |
| NRP1 | BTLA | CLJNT1 |
| RPL21-PS10 | GM54S1 | PAN3 |
| RPS6-PS1 | DGKA | MFSD11 |
| GM5921 | CST3 | NRP1 |
| RPGRIP1 | RPL27 | RPL21-PS10 |
| BTG1 | ITGAV | RAB11FIP1 |
| CLASP2 | HAVCR2 | GADD45B |
| LRRC8D | GM9846 | BTG1 |
| CAP1 | MAPRE2 | RNF149 |
| LGALS3BP | TUBB6 | LGALS3BP |
| RSBN1L | U2AF1L4 | TNFRSF1B |
| RPL7A-PS10 | VAMP8 | SKI |
| JUND | DGAT1 | SSH2 |
| DOCK8 | RPS6KA1 | MXD1 |
| AP2A2 | AC119211.2 | IFI27L2B |
| DYNC1H1 | AW112010 | GAS2L3 |
| 4632428N05RIK | | CTSC |
| GBP10 | | ANKFY1 |
| IFI27L2B | | ANXA4 |
| GAS2L3 | | GM10362 |
| TTF1 | | TLCD1 |
| ANKFY1 | | SYNRG |
| DNAJB14 | | ATN1 |
| GM10362 | | LY6I |
| TLCD1 | | SQD2 |
| RAP2B | | GBP7 |
| DDX6 | | C330021F23 |
| SYNRG | | IL7R |
| CYTH4 | | KTN1 |
| ATN1 | | PPT1 |
| TRPM2 | | ASH1L |
| GM3222 | | NFIL3 |
| MTMR2 | | ADIPOR1 |
| SQD2 | | BTG2 |
| KIF24 | | PPM1K |
| C330021F23RIK | | GM3225 |
| IL7R | | H2-OA |
| MS4A4C | | RUNX3 |
| MLL3 | | MYCBP2 |
| 2810422I05RIK | | SKIL |
| GBP8 | | SMG1 |
| PBXIP1 | | ABCG1 |
| GM205B | | RAB10 |
| JHDM1D | | AL732476.1 |
| KTN1 | | IFRD1 |
| MLL1 | | RPL21-PS11 |
| ELMOD2 | | SEPP1 |
| ASH1L | | SIK1 |
| ABHD2 | | TET2 |
| GM10313 | | 4930470H14RIK |
| ZCCHC6 | | SRRM2 |
| BTG2 | | CD38 |
| DTX3L | | SPTY2DI |
| PPM1K | | RPL21-PS6 |
| GM8225 | | NR4A2 |
| RUNX3 | | HMHA1 |
| IGF2R | | RPL29-PS2 |
| MYCBP2 | | RRBP1 |
| SKIL | | RASSF2 |
| TRP53INP1 | | LILRB4 |
| SMG1 | | AHNAK |
| ABCG1 | | PLEK |
| RAB10 | | FMO1 |
| AL732476.1 | | FQSL2 |
| RPL21-PS7 | | TAXIBP3 |
| NPC2 | | MS4A6D |
| RPL21- | | BIRC5 |

TABLE 6-continued

Shown are genes that are significantly up or down regulated in different sections of the Voronoi diagram (subpopulations) (corresponding to FIG. 2C). Differentially expressed genes in in-vivo sub-populations PS11
SIK1
AC163269.1
PPP1R15A
TNRC6C
2610036A22RIK
TET2
GBP6
E430029J22RIK
4930470H14RIK
SRRM2
GM10718
IFI203
RPL21-
PS6
HMHA1
MED13L
RPL29-
PS2
CD27A
RASSF2
NCOA3
KLHL24
STAT1
AHNAK
ARID5B
FMO1
GM10291
RPL17-
PS3
SLC39A1
GM10327
BIRC6
IRF2BP2
GM5570
MAP3K1
GM10800
TOB2
GM6316
KDM6B
GM6109
LY6C2
ZFP36L1
JUN
ALKBH5
MLL2
JUNB
PDCD4
MNDA
INSIG1
RNF213
GM8909
C030046E11RIK
PARP4
PSAP
9930111J21RIK2
ARID1B
GM11127
H2-Q2
CDKN1B
NOTCH2
SLFN5
SGIP1
GM4070
PCF11
BMP2K
GM7030
GVIN1
ZFP36
LYZ2
H2-AA
CTSS
FCER1G

MAP3K1
GM10800
GM6109
JUN
MLL2
JUNB
INSIG1
FQSB
CCL5
LGMN
APOE
NOTCH2
SGIP1

NR4A3
GM4070
BMP2K

SDC4
AIF1
LYZ2
H2-AA
GRN
C1QB
FCER1G

TABLE 7

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL.6 + IL.23-96 h-1 | | GPR65-KO- TGFB1 + IL.6-96 h-1 | | PLZP-KO- IL1B + IL.6 + IL.23-48 h-1 | | PLZP-KO- TGFB1 + IL.6-48 h-1 | | TOSO-KO- IL1B + IL.6 + IL.23-96 h | | TOSO-KO- IL1B + IL.6 + IL.23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| CT025533.1 | 638.963 | LY6G | 72.0601 | CR478112.1 | 4828.97 | AC112970.1 | 997.832 | AC090432.1 | 19.4613 | LY6G | 20.5027 |
| GM11042 | 219.403 | CD3G | 35.7993 | AC163094.2 | 705.836 | AC163330.1 | 0.00100217 | GM10999 | 17.1617 | GM10139 | 0.0744158 |
| AC163330.1 | 57.6454 | H2-Q8 | 20.2139 | GM11035 | 469.257 | AC118017.2 | 691.521 | FAM132A | 0.0731972 | CCDC56 | 12.7227 |
| GM10695 | 52.9557 | ROMO1 | 18.4077 | AC090563.1 | 181.836 | GM10974 | 0.00177299 | NDUFC1 | 12.6321 | GM10192 | 12.3271 |
| IL17F | 20.8104 | ATP5J | 16.4856 | GM10774 | 127.093 | GM10774 | 0.00786822 | IL24 | 0.0840608 | IL24 | 0.0852024 |
| GM11035 | 15.2049 | MPP1 | 15.7176 | GM11074 | 86.5719 | GM11074 | 120.52 | A2LD1 | 9.99009 | PAM16 | 0.0870993 |
| 2210012G02RIK | 14.137 | UFM1 | 14.9395 | GM11032 | 0.0235315 | SND1 | 114.79 | 2010107H07RIK | 9.64576 | HMGA1-RS1 | 0.0887043 |
| GM10222 | 12.7776 | LY6I | 14.4088 | CISD3 | 0.0267441 | DEDD | 0.00957397 | NHEJ1 | 9.40856 | UCKL1 | 0.09253 |
| S100A1 | 0.0863747 | LY6C2 | 14.2462 | IFI27L2A | 29.7388 | NUDT1 | 59.2046 | RNF121 | 7.96782 | PIH1D1 | 8.8086 |
| SLC15A3 | 11.4418 | GM10774 | 13.9351 | TBC1D17 | 0.0363317 | GM10222 | 0.017264 | GM10495 | 7.43442 | GNAQ | 8.75423 |
| MUTYH | 10.8353 | LY6C1 | 12.7774 | AL732569.1 | 0.0430873 | GM6293 | 0.0203867 | NTAN1 | 0.152127 | CCDC9 | 8.65022 |
| TEAD2 | 13.3068 | IL17F | 12.2224 | EWSR1 | 21.7177 | H2-Q8 | 48.6847 | LSMD1 | 0.153423 | MYCBP | 0.12853 |
| GM10490 | 9.71233 | CCL5 | 0.0827434 | AC121566.1 | 0.0476118 | GM11032 | 47.0127 | MED6 | 6.4984 | FRG1 | 0.132368 |
| IFFO2 | 8.85699 | SGK1 | 11.4417 | LIN37 | 0.052081 | ATOX1 | 45.8514 | MED7 | 6.43439 | BCCIP | 7.46098 |
| TBCB | 8.74941 | 2010107E04RIK | 11.366 | FAM36A | 19.0056 | AC121566.1 | 44.8555 | CTSE | 6.37075 | 0610037L13RIK | 0.141592 |
| AC102609.1 | 8.69175 | BANF1 | 11.1666 | GM10721 | 18.9873 | PFN1 | 37.3129 | TM2D3 | 0.160132 | RABL3 | 6.66246 |
| CATSPER4 | 8.30689 | TIMM8B | 11.0647 | AC132391.1 | 0.0537352 | AL845291.1 | 0.0348296 | CCDC101 | 6.24144 | COX6B2 | 6.63466 |
| CCBL2 | 8.27697 | VPS36 | 10.7432 | AC163993.1 | 0.0554745 | 2310004I24RIK | 0.0365274 | SLC12A4 | 6.04047 | MRP530 | 0.150918 |
| GM11074 | 8.19721 | GAA | 9.86035 | 2310030N02RIK | 18.0003 | SNX14 | 0.0369612 | SAP30BP | 5.90169 | E130306D19RIK | 6.53277 |
| LINS | 8.16618 | COX7A1 | 9.68942 | GM11167 | 17.8147 | STRA13 | 26.8007 | UBASH3B | 5.82363 | KLHDC1 | 6.48342 |
| 1700029F09RIK | 8.12329 | AC087540.1 | 9.67077 | GM10106 | 17.065 | 1700054O19RIK | 25.0357 | 8430419L09RIK | 5.78915 | FBXO9 | 6.32457 |
| MCFD2 | 0.123502 | NDUFC1 | 9.66605 | CCDC34 | 16.9601 | 4930423O20RIK | 24.9749 | CT030170.2 | 5.45632 | TMEM209 | 6.15855 |
| TMEM33 | 7.73635 | PPP2R5C | 9.6414.3 | AC131780.4 | 16.6801 | 1110051M20RIK | 0.0422463 | GOLGA1 | 5.358 | FAM1898 | 0.164908 |
| 4930425F17RIK | 7.56473 | LY6A | 9.61981 | LYRM2 | 0.060334 | GCDH | 0.0422702 | SRSF9 | 5.31367 | SETD4 | 6.03598 |
| CLEC12A | 7.52948 | IFI27L2A | 9.53003 | WBP11 | 16.5356 | ARRDC1 | 22.4399 | ZMPSTE24 | 5.2634 | H2-QS | 5.89529 |
| MCTS1 | 7.4317 | LSMD1 | 9.38183 | CES5A | 16.1643 | PAM | 22.1904 | TOMM5 | 0.190338 | GM7367 | 5.88087 |
| 2010107G23RIK | 7.38844 | NGFRAP1 | 9.37045 | MLLT10 | 16.0522 | MED27 | 0.0482159 | TSC22D1 | 5.2077 | MRPS36 | 5.83917 |
| UQCC | 7.377 | COX5B | 9.302 | AC125405.1 | 15.7217 | NMNAT3 | 0.048537 | PGLYRP1 | 5.16763 | LEPREL1 | 5.77011 |
| BCCIP | 7.04936 | GIMAP3 | 9.18091 | GM10800 | 15.3943 | NDUFS5 | 0.0489343 | PACSIN3 | 5.13269 | ATF7IP | 0.177348 |
| XPA | 7.02998 | SPAG7 | 9.17137 | RWDD1 | 0.0660117 | PSENEN | 20.1098 | ZFP688 | 5.09008 | WARS | 0.180546 |
| RAB34 | 7.02805 | GMFG | 9.11872 | AC131780.2 | 15.0009 | D8ERTD738E | 18.1426 | PPAN | 0.196514 | ZCCHC17 | 5.50318 |
| DFFA | 6.96773 | TFG | 8.71842 | GM10720 | 14.7899 | MRPS23 | 0.0512351 | 1700120B22RIK | 5.073 | A53003D15RIK | 0.182743 |
| GNG12 | 6.94052 | XPA | 0.117077 | FANCE | 14.53 | POLR1D | 17.8188 | ZFP523 | 5.04854 | HINT2 | 5.43973 |
| ARL3 | 0.146797 | MRPL2 | 8.47401 | UBE2A | 0.0707408 | GMFG | 17.5188 | BSDC1 | 0.198872 | GM1968 | 5.3797 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL6-96 h-1 | | GPR65-KO- IL1B + IL6 + IL23-96 h-1 | | PLZP-KO- IL1B + IL6 + IL23-48 h-1 | | PLZP-KO- TGFB1 + IL6-48 h-1 | | TOSO-KO- IL1B + IL6 + IL23-96 h | | TOSO-KO- IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| TDP1 | 6.76641 | CR974466.3 | 8.47128 | CKLF | 13.7256 | MRP55 | 17.1812 | WDFY1 | 5.02185 | GTPBP6 | 0.189111 |
| SPG20 | 6.7321 | AC118017.2 | 0.11863 | PRNP | 13.6676 | GM10311 | 0.0585203 | MUP11 | 4.90405 | TMUB1 | 5.23194 |
| CYTH1 | 0.150294 | RPS6KA3 | 0.119074 | LYRM7 | 13.446 | RNASEK | 16.9543 | DIABLO | 0.205542 | BCL2L12 | 5.09994 |
| GM10238 | 6.62969 | PAIC5 | 8.38958 | GM10718 | 13.4418 | 2410015M20RIK | 0.0598462 | NUMB | 4.81845 | DOK2 | 0.196929 |
| HNRNPR | 6.59627 | TSPO | 8.35239 | A830010M20RIK | 13.4368 | 42256 | 16.5496 | HMGN3 | 4.79371 | GM10416 | 5.05178 |
| DRAM2 | 0.153594 | GM10416 | 8.2616 | GM10719 | 13.3625 | MRPS18A | 15.8322 | FBXO6 | 0.210289 | ACER2 | 5.04034 |
| 1810020D17RIK | 0.154415 | GM5215 | 8.11489 | AEN | 13.0909 | RFC5 | 15.7095 | HMGA1-RS1 | 0.213347 | PYGO2 | 0.198435 |
| CHCHD8 | 0.159584 | NRBP1 | 7.90454 | GM6396 | 12.781 | LSM12 | 0.0640507 | LACTB2 | 4.66939 | CLEC16A | 5.02465 |
| LZIC | 6.22633 | GM7713 | 7.86697 | GM10717 | 12.3342 | 18I003SL17RIK | 0.0643269 | 1110051M20RIK | 4.65484 | MLEC | 4.95276 |
| PSMD13 | 6.14569 | ATRX | 7.85905 | 2010107H07RIK | 11.8908 | SPC25 | 15.407 | SERTAD3 | 4.65467 | ATPAF2 | 0.204293 |
| PPDPF | 6.0768 | CCDC109B | 7.85490 | CCL3 | 11.8036 | ORC5 | 15.3066 | HRSP12 | 4.64663 | FBXW20 | 0.206001 |
| TCF4 | 0.164742 | PAPOLA | 0.128481 | ZFP668 | 0.0856954 | GM11011 | 0.0660117 | HIAT1 | 4.60585 | 9430002A10RIK | 4.84791 |
| FASTK | 6.03114 | FUNDC2 | 7.75996 | DPH3 | 11.5057 | IPO9 | 0.0670124 | IL17A | 0.217419 | DFFA | 4.83616 |
| SAFB2 | 5.93824 | LEPREL1 | 7.71451 | MRPL52 | 11.4306 | ANAPC13 | 14.8538 | UBAP1 | 4.57328 | AKAP9 | 0.206832 |
| WDR54 | 5.77242 | DBI | 7.66514 | POLR2H | 0.0878308 | 281002112RIK | 0.0687575 | CIC | 4.56612 | CBX5 | 0.208348 |
| MED28 | 5.70363 | PSMG4 | 7.54057 | PIK3R1 | 0.0898843 | PDCD2 | 0.09698 | MMP16 | 4.56577 | TULP4 | 4.79559 |
| MOSPD3 | 5.68319 | RGS19 | 7.53778 | AC025786.1 | 0.0900128 | PAF1 | 14.2702 | PQBP1 | 4.55228 | DOCK7 | 4.79084 |
| RENBP | 5.65082 | AC112970.1 | 0.132869 | MAPK3 | 0.0902236 | CKLF | 0.0702488 | SEC61A2 | 4.54133 | CRTC1 | 4.77533 |
| ALDOB | 5.63858 | GM5830 | 7.43749 | HMGXB4 | 11.8908 | SLC39A14 | 14.0594 | RRP8 | 4.49549 | AC154631.1 | 4.75579 |
| HELLS | 5.48094 | POLR2J | 7.35784 | MRPL54 | 0.0906724 | AC132837.1 | 13.9914 | IFT140 | 4.48953 | 2310003F16RIK | 4.74871 |
| GM11444 | 5.45078 | TARBP2 | 7.2882 | FBXL12 | 0.0941317 | EXOSC3 | 0.0716036 | CCDC109B | 0.224915 | DEB1 | 4.72541 |
| TNFRSF22 | 5.41408 | RSRC1 | 7.25371 | 4930431F12RIK | 10.5765 | ZCCHC7 | 13.8323 | DSN1 | 4.43985 | 4930431F12RIK | 4.66373 |
| AC114625.1 | 5.37391 | HSCB | 7.21689 | AC127590.1 | 10.5317 | 231061C15RIK | 13.8171 | PHF20 | 4.43522 | LHPP | 4.66082 |
| GM6003 | 5.33337 | 0610037L13RIK | 7.19607 | SEMA4F | 0.0952178 | BDH1 | 0.0726258 | NPM3 | 4.38892 | CSNK1G1 | 4.60268 |
| GALE | 5.25036 | NOP56 | 7.16844 | MPND | 0.956693 | HACL1 | 13.7256 | RCAN3 | 4.37872 | BC049349 | 0.217973 |
| GTDC1 | 5.21537 | PIGK | 7.16261 | SLCO3A1 | 0.0961635 | CCNE2 | 13.6676 | MKNK1 | 4.3396 | DRAM2 | 4.51794 |
| PHF21A | 0.192406 | RPL21-PS6 | 7.16 | OPCML | 10.354 | GM9758 | 0.0731656 | EXOC6B | 4.31007 | | 0.219853 |
| ARHGAP4 | 5.17683 | ANAPC13 | 7.05292 | ZCCHC10 | 0.0984483 | TMEM107 | 13.5403 | ENPP2 | 0.233365 | PCID2 | 4.5141 |
| DLC1 | 5.16934 | PDRG1 | 7.00334 | AC155646.1 | 0.0995017 | CCDC55 | 13.4463 | ZC3H10 | 4.26288 | GRAMD1B | 4.50702 |
| FMNL1 | 0.199325 | ARRDC1 | 6.94928 | PPP2R2B | 9.89 | GRCC10 | 13.3862 | PIGF | 0.23674 | RUNX2 | 0.22212 |
| PUSL1 | 4.98071 | NAP1L4 | 6.94591 | PDIK1L | 9.83923 | SCP2 | 13.1902 | LY6C2 | 4.21301 | GM5900 | 4.50071 |
| 2610030H06RIK | 4.94004 | PQP5 | 6.91452 | EMP3 | 9.79589 | GM16372 | 0.0762153 | TRNAU1AP | 0.237682 | 1200016B10RIK | 4.49989 |
| MECR | 4.89871 | 0610037P05RIK | 6.90089 | MRPS12 | 9.73996 | RDM1 | 0.0768956 | TRMU | 4.20472 | GM16380 | 0.222513 |
| TNFAIP8 | 0.204512 | CK51B | 6.88764 | GM10192 | 9.67502 | MRPL23-PS1 | 12.9196 | HIRIP3 | 4.18487 | TRAFD1 | 4.49287 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h |  |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| HRSP12 | 4.4833 | A93005H10RIK | 6.87052 | GM10801 | 9.62219 | ENTPD1 | 12.8249 | 2210016L21RIK | 4.16073 | FAM165B | 4.45428 |
| RHOQ | 0.207277 | GM10506 | 0.145568 | GM10715 | 9.35018 | INSL6 | 0.0791878 | MDN1 | 4.15504 | TMEM5 | 4.44872 |
| GPATCH8 | 0.20735 | CLK1 | 6.80099 | 1700026D08RIK | 9.29877 | AC125405.1 | 12.6184 | SELK | 0.244008 | AIM1L | 4.41539 |
| IFNAR1 | 4.82106 | PRDX4 | 6.78434 | GM10842 | 0.107607 | MRPL19 | 12.6066 | FBXL12 | 4.06574 | FAM129B | 0.227632 |
| TAF12 | 0.207562 | WDR75 | 6.78281 | XRCC4 | 0.10761 | GNGT2 | 12.4445 | LLGL2 | 4.0643 | NUP85 | 4.36604 |
| RASAL3 | 0.207598 | SMEK2 | 6.76563 | IL9 | 0.109536 | AW112010 | 12.3828 | MZT2 | 4.03573 | HIST2H3B | 4.33905 |
| CCL4 | 4.78481 | TMEM85 | 6.7621 | A630001G21RIK | 0.109616 | AC102609.1 | 12.2887 | MAD1L1 | 0.247878 | FAM175A | 0.231044 |
| FAM69A | 0.209402 | DPM2 | 6.6864 | ENTPD1 | 9.07642 | ATPBB2 | 0.0822643 | ZCRB1 | 0.247973 | YAF2 | 0.232974 |
| ME3 | 4.7724 | UBL4 | 6.67639 | IER3IP1 | 9.0603 | GNG12 | 12.1127 | DEB1 | 4.02094 | GM10355 | 0.23349 |
| MPND | 4.77191 | CLEC16A | 0.151024 | AC122006.1 | 8.8707 | TMEM222 | 0.0832766 | KLRC1 | 3.98576 | NAB1 | 0.233585 |
| NMB | 4.67907 | MPHOSPH8 | 6.58917 | MED7 | 0.11446 | EDF1 | 11.9815 | HIBCH | 3.97739 | ADCK3 | 0.233826 |
| SLC1A5 | 0.216752 | PCMTD1 | 0.152472 | MMADHC | 0.115059 | TIMM10 | 11.9333 | A530032D15RIK | 3.96486 | PEX11B | 0.234331 |
| C1APIN1 | 4.5998 | PREB | 6.55723 | NSUN3 | 8.60642 | BC057079 | 11.8981 | MTX1 | 0.252901 | BTBD10 | 0.235263 |
| 2810432D09RIK | 4.56386 | GM8394 | 6.54589 | PHF10 | 0.116796 | GM11110 | 0.0850470 | UNC45A | 3.93916 | ACNAT1 | 4.24866 |
| POLR2F | 4.54568 | FKBP3 | 6.5407 | AC131780.1 | 8.51373 | SLC35A1 | 0.0854511 | KIT | 3.9252 | HIST1H4F | 4.24366 |
| LSM4 | 4.53477 | FAM165B | 6.54065 | SNAP47 | 8.47662 | POLR2I | 0.0856321 | NPAT | 3.8405 | CYSLTR1 | 0.235958 |
| PNRC1 | 0.222174 | BCCIP | 6.50692 | RAB11A | 8.44774 | UBE2B | 11.6779 | MLLT10 | 3.82477 | PSMB9 | 4.21107 |
| PUF60 | 4.47952 | PPIG | 6.50177 | EXOC4 | 8.44629 | ASAH1 | 0.0863792 | 1110005A03RIK | 0.26263 | NEBL | 0.237823 |
| 1110001J03RIK | 4.47334 | NSMCE4A | 6.47025 | HIST1H2BH | 0.119207 | MRPL28 | 11.5026 | DPY19L3 | 3.9252 | HRSP12 | 4.20275 |
| MLLT10 | 0.223694 | CEPT1 | 6.39179 | TRAFD1 | 8.36382 | PCID2 | 0.087048 | CDKAL1 | 0.263647 | PDIK1L | 0.238132 |
| 0610010O12RIK | 4.42709 | SPCS1 | 6.36876 | ATF7 | 0.119705 | SRP9 | 11.4865 | 0610010O12RIK | 3.79286 | GM10482 | 0.238435 |
| GM10482 | 0.226172 | WDR61 | 6.36703 | 4930470H14RIK | 8.2969 | NISCH | 11.4306 | C1D | 0.263877 | POLR2I | 4.19095 |
| SLC25A11 | 4.39262 | FANCC | 6.33444 | SOD1 | 8.20086 | GM2178 | 11.3855 | MANBA | 3.78609 | RPL21-PS4 | 0.239361 |
| HDAC8 | 0.230041 | RAD23A | 6.20533 | 1700064H15RIK | 0.121984 | FUBP1 | 11.3077 | SIN3A | 3.78214 | TEME48 | 0.239496 |
| THAP7 | 4.34098 | RNF5 | 6.20083 | FASTK | 0.122115 | FANCE | 11.298 | NASP | 3.76321 | CLN3 | 0.240092 |
| ECM1 | 4.33421 | CKLF | 6.13147 | EVI2A | 8.17236 | RAB8A | 11.2824 | IQSEC1 | 3.7207 | GABPA | 0.240205 |
| JUP | 4.3205 | CDK5RAP3 | 6.11741 | GALK2 | 8.15188 | RPL30-PS6 | 0.0889991 | WBP1G | 0.270456 | ITGAV | 0.240239 |
| 1110004E09RIK | 4.31718 | DCAF17 | 0.163649 | AC131780.3 | 8.14542 | FAM64A | 11.2121 | RALGPS1 | 3.69553 | AC114625.1 | 4.15154 |
| TOR2A | 4.30601 | U2AF1L4 | 6.09837 | DNAJC24 | 0.122813 | TOR1AIP2 | 0.0899992 | ARMC7 | 3.68615 | MBTPS2 | 4.12905 |
| ZFP54 | 4.29205 | HMGB1 | 6.04354 | 4930534B04RIK | 8.12667 | PSMG3 | 11.0633 | SNRPC | 0.271861 | 1810074P20RIK | 0.242547 |
| GM6990 | 0.233534 | PSMD6 | 5.99621 | 2310045N01RIK | 0.123579 | ALDH7A1 | 10.9234 | CASP9 | 3.67579 | CSNK1E | 4.11864 |
| AC1SS646.1 | 0.233606 | AC132391.1 | 5.97323 | SERGEF | 8.03129 | TSPAN32 | 10.724 | KLHL15 | 3.67081 | SELENBP2 | 4.11852 |
| MTX1 | 4.27561 | LY6K | 5.94919 | GGNBP1 | 0.124804 | SSBP2 | 10.6665 | MBTD1 | 3.67015 | STYK1 | 4.09169 |
| AL845291.1 | 4.2534 | CD209C | 0.16859 | 5730437N04RIK | 7.93924 | PPAPDC1B | 0.093832 | 1110065P20RIK | 3.66259 | UFSP2 | 0.24606 |
| GTF2H1 | 0.235342 | DLG4 | 5.93042 | DEB1 | 7.91466 | UBL4 | 10.5765 | NENF | 0.273259 | PHLDA3 | 0.24686 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| IER3 | 0.235664 | VILL | 5.92894 | MTHF5 | 7.87981 | MED28 | 10.5684 | EIF4ENIF1 | 3.64441 | KLC1 | 0.248587 |
| AKTIP | 0.235925 | WDR13 | 5.90818 | GM10576 | 7.8766 | TRIM28 | 10.5317 | ZFAND3 | 3.64348 | PRL8A1 | 4.02006 |
| WBSCR22 | 0.241006 | HFMK1 | 5.89641 | TTC39A | 0.127576 | GIMAP7 | 0.0953338 | PDUM1 | 0.276107 | GM12166 | 4.01965 |
| LY6K | 0.241404 | SLC35A1 | 5.83336 | COX7A1 | 7.82902 | IVD | 10.4803 | 1110007A13RIK | 3.61404 | DUSP22 | 0.249121 |
| BRIX1 | 4.14223 | NDUFB6 | 5.81576 | HSPA4 | 0.128114 | HIST1H4C | 10.4707 | THNSL2 | 3.61171 | CCDC23 | 4.00206 |
| DNAJC24 | 4.12988 | PRP51 | 5.7819 | RAB9 | 0.128579 | AC025786.1 | 0.0955993 | MYO1B | 3.61009 | NT5DC1 | 0.250004 |
| ZMYND8 | 4.11359 | IFI27L1 | 5.75922 | DHODH | 0.128681 | UBR4 | 10.3681 | ECE1 | 0.27729 | RNF185 | 0.25078 |
| RNF141 | 0.244327 | ZMPSTE24 | 5.69972 | PEX19 | 7.69973 | PIGZ | 0.0967107 | SIVA1 | 0.277827 | METTL1 | 3.97941 |
| DDX49 | 4.07132 | DEK | 5.68906 | DHPS | 7.60305 | MAGOHB | 10.2556 | TIPIN | 0.277841 | POLR3G | 3.95579 |
| SPAG5 | 4.06089 | SERPINB1A | 5.68805 | CAP1 | 0.13167 | KCTD9 | 10.2384 | PSIP1 | 3.59527 | H2-Q6 | 3.95138 |
| 2010107H07RIK | 0.246574 | KCNAB2 | 5.68346 | AC102876.1 | 7.47393 | CNDP2 | 10.2284 | USP11 | 3.59442 | GM10495 | 0.253919 |
| TRIAP1 | 0.247873 | NPRL2 | 5.65002 | SSSCA1 | 7.4544 | AC163993.1 | 10.1311 | BATF3 | 0.278394 | RAC3 | 0.256158 |
| DHDPSL | 4.03073 | 9030619P08RIK | 5.64316 | 201030SA19RIK | 7.43256 | POP1 | 0.0992703 | RALY | 3.58739 | 1700054O19RIK | 3.89993 |
| CCDC130 | 4.01695 | MAPRE1 | 5.63223 | NDUFB2 | 7.39808 | DHDDS | 10.0429 | MTHFS | 3.5871 | TMEM38B | 3.89356 |
| CPSF3L | 4.00615 | UFD1L | 5.6314 | GAA | 7.38646 | YIPF1 | 10.0231 | 3110001D03RIK | 3.56035 | BCAT2 | 0.257108 |
| GUK1 | 4.0013 | IL2 | 5.63133 | HIST1H2BN | 7.29384 | RBM4B | 9.97471 | 1500002O20RIK | 3.55877 | BATF3 | 3.85665 |
| TMEM85 | 3.98691 | CPOS7B | 5.61304 | DNAJC19 | 7.28404 | MED24 | 7.28404 | D6MMSE | 3.55478 | 2310061I04RIK | 3.85025 |
| ACTRT2 | 3.96478 | TEX14 | 0.178636 | CLN3 | 0.1375 | R3HDM2 | 9.89625 | RIT1 | 3.55126 | BMYC | 0.260139 |
| PPIL3 | 0.252903 | 42262 | 5.5932 | PUS7L | 7.24213 | MTBP | 9.84994 | SYTL3 | 3.53773 | CBX7 | 0.26126 |
| RSRC1 | 0.253147 | RNASEH2C | 5.58174 | FAM188A | 7.23481 | PUS7L | 9.83923 | GGT1 | 3.5364 | EGFL7 | 0.261514 |
| ZFP68 | 3.9485 | PPOX | 5.56957 | IL3 | 0.139557 | TNF | 0.101767 | ETFB | 0.283229 | AC125405.1 | 3.81229 |
| SEL1L | 3.94649 | NUDT2 | 5.56538 | GGNBP2 | 7.15053 | SURF2 | 0.102144 | GGPS1 | 0.283765 | NDUFB2 | 3.79385 |
| SLC12A6 | 3.93412 | CD27 | 0.180344 | ZFP353 | 7.12168 | TPPT | 10.0259 | ZFP58 | 3.51272 | ING3 | 0.264762 |
| YBX1 | 0.254705 | MOCS2 | 5.52865 | VKORC1 | 7.08262 | CERKL | 10.0267 | RTEL1 | 0.285742 | THG1L | 0.265805 |
| ARID5A | 3.92361 | RGS1 | 5.52352 | POPS | 0.142477 | GM10506 | 9.73403 | BCL3 | 3.49539 | TMEM147 | 3.74181 |
| CCDC52 | 0.254901 | LXN | 5.51705 | TXNL4A | 0.142821 | TAF12 | 0.102745 | MFSD11 | 0.287788 | ZCCHC10 | 3.73683 |
| DULLARD | 3.91929 | PTPN6 | 5.47051 | ZCRB1 | 0.142824 | ALGS | 9.71286 | SPSB1 | 3.47315 | POLR3GL | 0.267958 |
| CD209C | 3.91841 | GM10999 | 0.183075 | GM14420 | 6.99722 | GM7075 | 9.58803 | PRL7B1 | 3.46403 | CD72 | 3.72884 |
| TTC33 | 3.90685 | PESI | 5.45618 | AL732476.1 | 6.98499 | FAM96B | 9.58165 | MAPRE2 | 0.288947 | 1110051M20RIK | 3.72461 |
| RBKS | 0.256393 | SNRPD2 | 0.256393 | PARS2 | 0.143242 | MYLPF | 0.104864 | CHAF1B | 0.289552 | MBD6 | 3.71439 |
| PARP3 | 3.89675 | ANKRD37 | 5.44157 | 2610044O15RIK | 6.96583 | KDM4C | 10.0517 | AP2A1 | 3.43984 | RNF38 | 3.70742 |
| FAM71F2 | 0.257088 | CDCA2 | 0.183865 | AC117259.1 | 6.9419 | CTSW | 9.48133 | SCYL3 | 3.41864 | GGT7 | 0.270077 |
| 2810040SK02RIK | 3.88632 | E130306D19RIK | 5.42898 | GRSF1 | 0.144906 | 5730469M10RIK | 9.47232 | LRIG1 | 3.47102 | C630004H02RIK | 0.271104 |
| GM10720 | 3.603 | WDR83 | 5.3926 | BNIP2 | 6.93192 | SH3KBP1 | 0.105824 | RFK | 3.40993 | ORC5 | 3.67903 |
| CSE1L | 3.85295 | EIF2B2 | 5.37028 | PNKD | 0.144915 | FBXL17 | 9.42315 | MFSD10 | 3.40474 | PHTF2 | 3.67589 |
| ANKRD40 | 3.85008 | MAF1 | 5.35371 | GM10203 | 6.8613 | A330049M08RIK | 9.37675 | H2-Q8 | 3.40278 | 4930425F17RIK | 3.67327 |
| MCART6 | 3.80306 | 2310003L22RIK | 5.35207 | SLC7A4 | 0.146352 | MAGFD2 | 9.37124 | MAFK | 3.40214 | TMEM199 | 0.272294 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information includes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| 1700093K21RIK | 0.26331 | IFNAR2 | 5.34873 | POLR2I | 6.82307 | NCF4 | 0.106786 | HIATL1 | 0.29417 | POLRMT | 3.66929 |
| MYC | 3.79416 | EIF2S3Y | 0.187055 | TMEM223 | 6.78242 | SNRNP25 | 9.334236 | GM8923 | 3.39724 | CNOT6L | 0.273167 |
| AC131780.2 | 3.77596 | ASNS | 5.33487 | TMSB15B1 | 0.148173 | ABAT | 9.31561 | ETV6 | 0.294593 | EXOC5 | 0.274182 |
| GM10719 | 3.75154 | PDLIM2 | 5.33001 | R3HCC1 | 0.148619 | CD3G | 9.29877 | 2310079N02RIK | 0.294964 | ARLSC | 3.63451 |
| MGAT4C | 3.74852 | NAA16 | 5.32749 | TMUB1 | 0.150806 | PIGX | 9.28618 | CC2D1B | 0.296056 | PHYHD1 | 3.61167 |
| MTA2 | 3.73852 | GSOT1 | 5.31579 | CWC27 | 0.151624 | 2410017P09RIK | 0.107927 | MTCH2 | 3.37335 | BC055324 | 0.277808 |
| MAGOH | 0.267975 | GM101120 | 5.28972 | B4GALT3 | 0.15171 | 1700128F08RIK | 9.20197 | POU2F2 | 0.296735 | VHAF1B | 3.59632 |
| TSPAN4 | 3.73086 | MKNK1 | 5.25695 | AC142104.1 | 0.152305 | PTPN2 | 9.18199 | WWOX | 3.36062 | ARIH1 | 0.278113 |
| GM11167 | 3.72546 | IFRD1 | 5.24842 | ACIN1 | 0.153182 | POLR2A | 0.108941 | SUFU | 3.35608 | ROBLD3 | 0.280033 |
| CLYBL | 3.71736 | SDCBP | 5.24642 | SYTL3 | 0.153335 | CCDC9 | 9.15689 | NMI | 3.34913 | TNFRSF14 | 3.57066 |
| GM10717 | 3.71066 | UBE2NL | 5.24562 | DNASE1 | 6.49588 | PTPMT1 | 9.1473 | WDR11 | 3.34188 | FUCA2 | 0.280098 |
| ACTR1B | 3.70995 | TMEM60 | 5.23158 | GM16372 | 0.154587 | TMEM85 | 9.07642 | GM16416 | 3.33749 | GM11275 | 3.54481 |
| BOLA3 | 3.70413 | GM8909 | 5.22564 | MLLT3 | 6.46887 | PLXND1 | 9.04785 | MRPL27 | 3.3349 | HERC3 | 3.53754 |
| CEPT1 | 3.67288 | GM9762 | 5.20942 | RBM22 | 6.4636 | GM8054 | 0.110711 | COPZ2 | 3.33482 | PSMD14 | 0.283245 |
| LUC7L | 3.67232 | LZIC | 5.1977 | FKBP1A | 0.155468 | SEPSECS | 0.110944 | ZFP318 | 3.33439 | TTC7 | 0.284516 |
| LAIR1 | 3.67033 | INSL6 | 5.1949 | PLA2G16 | 6.4322 | COX15 | 8.9846 | APPL1 | 3.33289 | AGPAT2 | 3.51269 |
| MRPL17 | 3.67024 | GM10925 | 5.17227 | TMEM126A | 0.156135 | P4HA2 | 8.97898 | TCF4 | 3.33168 | AC152721.1 | 3.50828 |
| ASAH1 | 0.273768 | CDK11B | 5.16631 | METTL11A | 0.156575 | EED | 8.97733 | TMEM126A | 3.3264 | RAD23A | 3.49641 |
| SMARCD2 | 3.64906 | ANXA5 | 5.1584 | RPL21-PS7 | 6.35423 | MAT2B | 8.96162 | VWA5A | 3.32388 | ADAR | 3.48718 |
| GM10718 | 3.64245 | GPN3 | 5.13763 | ZFP280C | 0.158142 | FUCA2 | 8.94968 | MED10 | 0.300958 | STX4A | 0.286919 |
| RUVBL2 | 3.63161 | FXR2 | 5.13594 | AC132837.1 | 6.32254 | NDUFB4 | 0.111736 | COX19 | 3.32126 | LIAS | 0.287101 |
| TTC35 | 3.63095 | TMBIM4 | 5.13572 | MAP3K5 | 6.30122 | ACAD8 | 0.112277 | GM13147 | 3.31654 | 2210016L21RIK | 3.47446 |
| TPST2 | 3.62066 | ELF2 | 5.09157 | IL24 | 0.159647 | WBSCR22 | 8.88424 | IRF1 | 3.31264 | IL15RA | 3.47047 |
| GM7713 | 3.60269 | PDCD5 | 5.06988 | SRCRB4D | 0.159836 | SMS | 0.112965 | BUB1 | 3.30274 | 9030617O03RIK | 0.289013 |
| CCDC107 | 3.59403 | TTC4 | 5.05311 | HCST | 6.24208 | NBR1 | 8.8219 | LYAR | 3.29979 | TRPC2 | 3.45442 |
| GOSR2 | 0.278504 | MED6 | 5.05201 | GM6096 | 6.23421 | INSIG2 | 8.80943 | KLHL22 | 3.29245 | MPP6 | 3.44593 |
| 1110003E01RIK | 3.58679 | PTP4A2 | 5.02647 | RRP8 | 0.160473 | TMEM147 | 8.8022 | TSR2 | 3.28397 | TEAD2 | 0.290337 |
| FAM175B | 3.58168 | FBXO6 | 5.02333 | ALKBH3 | 0.1605 | AC160471.1 | 0.1139 | WFDC12 | 3.27084 | DYNLT1B | 3.43878 |
| CCNDBP1 | 0.281381 | KCTD13 | 0.199541 | KLHL15 | 6.22658 | POLE3 | 0.11417 | METTL8 | 3.26973 | HIST1H4C | 3.43302 |
| HCST | 3.55104 | AA467197 | 5.00576 | SLC15A2 | 0.215 | CDC25B | 8.73177 | ST6GAL1 | 0.306454 | BX679668.1 | 3.42595 |
| ZMPSTE24 | 3.51831 | CREM | 4.97069 | GMPPA | 6.20253 | MMP16 | 8.69991 | CLEC16A | 0.307168 | AQR | 3.42194 |
| SUCLA2 | 0.28494 | MYCBP | 0.201252 | GM10695 | 6.2007 | CAR9 | 8.6955 | FOXJ3 | 0.308099 | GLRX | 3.42051 |
| IRF5 | 3.50011 | CUL1 | 4.96085 | SPATA24 | 0.161365 | 4930425F17RIK | 8.65193 | MEN1 | 3.23788 | AW112010 | 3.3997 |
| SNX11 | 3.49777 | 0610010K14RIK | 4.95445 | 1700128F08RIK | 6.18163 | TEAD2 | 8.50191 | CREB1 | 0.309475 | MKI67IP | 0.29428 |
| CLN6 | 3.48154 | RARS | 4.95308 | PRMT1 | 0.163087 | TRPM7 | 0.117774 | WDR91 | 3.22232 | MKI67IP | 3.38602 |
| HEMK1 | 3.48009 | MLX | 4.94267 | CENPT | 6.11819 | GM6396 | 0.118058 | RPUSD3 | 3.19808 | PACSIN3 | 3.3842 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL-6-96 h-1 | | PLZP-KO- IL1B + IL-6 + IL-23-48 h-1 | | PLZP-KO- TGFB1 + IL-6-48 h-1 | | TOSO-KO- IL1B + IL-6 + IL-23-96 h | | TOSO-KO- IL1B + IL-6 + IL-23-96 h | |
|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| AC139042.1 | 0.287734 | BC029214 | 4.92756 | VAMP8 | 0.163897 | IFI27L2B | 8.45495 | MAN1A2 | 3.19268 | CDCA3 | 3.38042 |
| MOSC2 | 3.46365 | HCFC1R1 | 4.92552 | FAM132A | 6.1003 | CLPP | 8.44774 | KDM4B | 3.3133014 | SLCO3A1 | 0.295842 |
| ADAMTSL4 | 3.44653 | IDH3G | 4.9087 | ANKRD12 | 6.08043 | 4930431F12RIK | 8.44682 | RPS6KA1 | 3.18481 | GABPB1 | 0.296055 |
| ENTPD1 | 3.44534 | GM11027 | 0.203723 | MED12 | 6.05937 | GM14326 | 0.118615 | OPCML | 0.314452 | PPIL1 | 3.36445 |
| HEATR7A | 3.43505 | CTSW | 4.88659 | USP48 | 0.165395 | GM14399 | 0.118719 | PSPC1 | 3.17489 | GM13145 | 3.35155 |
| RBMX2 | 3.43505 | H2-T22 | 4.88453 | ARF2 | 6.0275 | TMEM41B | 0.118866 | GEMIN6 | 3.16916 | HNRNPUL1 | 0.299266 |
| H2-KE6 | 0.291348 | UBAC1 | 4.88373 | EP400 | 0.165979 | FAM173A | 0.118928 | RSRC1 | 0.315601 | HIST1H4D | 3.33023 |
| ACADM | 0.291727 | LRRC42 | 4.8802 | SEC22A | 6.02034 | PARL | 0.11911 | PHRF1 | 0.316104 | SRSF9 | 0.300436 |
| ACAT1 | 0.292164 | COMMD2 | 4.87675 | POP4 | 0.167588 | PFDN5 | 8.37525 | MTMR2 | 3.16217 | YIPF1 | 3.3284 |
| TTC4 | 0.29297 | UFC1 | 4.87361 | CUL4A | 5.96554 | DUSP22 | 0.119563 | CBX6 | 3.1587 | CCDC12 | 0.301017 |
| MPP1 | 3.41016 | EHMT1 | 4.85546 | RHBDD2 | 5.95536 | USP46 | 8.34247 | NIPSNAP3B | 0.316638 | FXR2 | 0.301391 |
| DNAJB6 | 0.293362 | TSPAN32 | 4.85182 | MED13 | 0.16848 | RGS10 | 8.298 | ZFP560 | 3.148 | SEPP1 | 3.3074 |
| PEX3 | 3.40686 | NDUFA5 | 4.84453 | GRIPAP1 | 0.168836 | ZNHIT1 | 8.28155 | PENK | 3.14719 | CTSE | 3.30526 |
| TM2D3 | 3.40459 | SHBG | 0.206932 | POLB | 0.168936 | TMEM68 | 8.24996 | DNAJC12 | 3.14601 | GM16415 | 0.302846 |
| ING3 | 3.39927 | NDUFAF1 | 4.83055 | AC117184.1 | 5.91584 | MYD88 | 8.23977 | ALAS1 | 3.146 | LY6C1 | 3.29529 |
| BC003331 | 0.294189 | H2-Q2 | 4.82529 | FAM45A | 5.91331 | ADRBK1 | 0.12153 | ATHL1 | 3.1458 | STT3B | 0.304407 |
| GM10721 | 3.3823 | NAA38 | 4.82184 | ATP8B2 | 5.90572 | 4933424B01RIK | 0.121798 | TRIM23 | 3.14356 | ABHD10 | 3.28355 |
| GM7204 | 3.37432 | REXO4 | 4.81173 | HIRIP3 | 5.88779 | SQSTM1 | 8.20789 | RPA3 | 0.31917 | SKINT8 | 3.27906 |
| GM11110 | 3.36481 | ADRM1 | 4.75358 | TPRKB | 0.170218 | GM11007 | 0.122161 | MYSM1 | 0.319182 | FANCE | 0.304979 |
| CLUAP1 | 3.35826 | GEMIN7 | 4.74963 | BRP44 | 0.170503 | GM14430 | 0.122161 | PI4K2B | 3.12907 | GSR | 0.306238 |
| CASP2 | 0.298264 | GM16372 | 4.7397 | GNAQ | 0.170757 | GM14432 | 0.122161 | AKR1B10 | 0.320108 | IL10RB | 3.24925 |
| PXT1 | 3.3411 | INPP4B | 4.73513 | IMPA1 | 5.84994 | GM2007 | 0.122161 | AP1G2 | 3.11828 | CCDC12 | 3.24378 |
| IFT81 | 3.34066 | MRPS33 | 4.73216 | FXR2 | 0.170976 | RNF214 | 8.18285 | POLR2A | 3.11809 | GM9726 | 0.308711 |
| INPP5B | 3.34042 | DRAM2 | 4.73138 | ZCCHC11 | 0.172462 | BBS5 | 8.18151 | HOMEZ | 3.10679 | 8430419L09RIK | 0.308795 |
| KIN | 0.299378 | H2-Q7 | 4.72653 | YY1 | 0.173566 | PLA2G4C | 8.17236 | TCFE3 | 3.09882 | 0610011L14RIK | 3.23236 |
| GLUD1 | 0.30071 | PHF5A | 4.72302 | ZFP687 | 0.173904 | TIMM17B | 8.16695 | BLVRA | 0.322872 | RFC4 | 0.309401 |
| ADCK5 | 3.30721 | TANK | 4.69966 | ASAH1 | 5.73409 | ITGB4 | 8.12447 | PPP1R10 | 3.09185 | CD69 | 3.21508 |
| RANGRF | 3.30264 | STOML2 | 4.69151 | 1110018G07RIK | 0.174577 | STAM2 | 0.123152 | FUCA1 | 3.0907 | CCDC58 | 0.311259 |
| OBFC1 | 3.3018 | TBCA | 4.6727 | MT2 | 5.71646 | RNMT | 0.123306 | WHSC1 | 0.323879 | MCEE | 0.311593 |
| PREB | 0.303249 | GDI1 | 4.65362 | COMTD1 | 5.68962 | KIN | 0.12338 | CLYBL | 3.0825 | GM10576 | 3.20521 |
| BRI3 | 3.27993 | FAIM3 | 4.63947 | SNAPC5 | 0.176233 | GNG2 | 8.10003 | SLC10A3 | 3.0807 | RDH9 | 3.20507 |
| GM5116 | 0.304959 | ELMOD3 | 4.6303 | EIF3G | 5.66822 | HSPB11 | 8.08051 | PTPN5 | 3.08056 | SDF2L1 | 3.20341 |
| NNJ1 | 0.305402 | ACBD5 | 4.62748 | RASAL3 | 0.176644 | TRMU | 8.06635 | MSL1 | 0.324943 | FAM53B | 3.19661 |
| ANKRD5 | 3.27329 | MCM7 | 4.61003 | NBR1 | 0.176732 | CCDC53 | 8.0588 | PPP1CC | 0.324984 | ZFP687 | 3.19627 |
| NAPA | 3.27263 | CDK1 | 0.217436 | MKNK1 | 0.176948 | ZFP120 | 0.124245 | BOLC1S1 | 3.07662 | TOR1AIP1 | 3.1931011 |
| PNPK | 3.27166 | LIMS1 | 4.5884 | SFXN5 | 0.177569 | 2310045N01RIK | 0.12338 | RUNX2 | 0.325457 | TSPAN5 | 0.313131 |
| MRPL12 | 3.2648 | CD53 | 4.58769 | PRPSAP2 | 0.177826 | WDR54 | 0.124942 | ECHS1 | 3.06707 | CASKIN2 | 0.313155 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| SMS | 3.26183 | PCNP | 4.58745 | CISH | 5.61993 | ZFP277 | 7.98906 | BECN1 | 3.06641 | TSEN34 | 0.313224 |
| FTSJ3 | 0.306978 | LTA | 4.57147 | WHSC1 | 0.178333 | GM5830 | 7.96854 | HINT3 | 3.06058 | PLXNA3 | 0.313512 |
| ALKBH7 | 3.25685 | LST1 | 4.5675 | PDCD6 | 5.60468 | LST1 | 7.96261 | RIN3 | 3.05864 | DNTTIP2 | 0.314457 |
| GTPBP2 | 0.307896 | GM129 | 4.56142 | A830080D01RIK | 5.58829 | GGNBP2 | 7.9446 | STK38 | 3.03842 | DEDD | 0.314807 |
| GIT2 | 3.24272 | YWHAE | 4.53645 | GM9805 | 0.179155 | STX4A | 0.125957 | CD74 | 0.329393 | LSM7 | 3.17454 |
| EDC4 | 3.23745 | SNRPA1 | 4.52685 | 1700019E19RIK | 0.179583 | ITGA3 | 0.126311 | RIPK2 | 3.03454 | CD209C | 3.17324 |
| KIF18B | 0.309756 | CCDC55 | 0.221266 | MTF1 | 0.179724 | B9D1 | 0.126396 | PLK4 | 0.330137 | NPRL2 | 3.17313 |
| MESDC2 | 0.311201 | SIN3B | 4.50388 | NUDT1 | 5.54265 | CASP8AP2 | 7.91164 | NSUN5 | 0.33078 | 2010317E24RIK | 3.16942 |
| 320002M19RIK | 3.21272 | BUD31 | 4.49958 | THAP3 | 0.180812 | 2310004N24RIK | 7.8659 | CCDC124 | 0.330746 | COPS8 | 0.315522 |
| TOP2B | 0.311371 | CAMTA1 | 0.222475 | ABCB8 | 0.181246 | GM10192 | 7.84084 | UBE2L6 | 3.02117 | 1700128F08RIK | 3.16253 |
| DCTN5 | 3.20361 | TSPAN31 | 4.49444 | TOP2B | 0.181282 | EZH2 | 7.83613 | D2WSU81E | 3.02012 | ALDH16A1 | 0.31636 |
| 2310061I04RIK | 0.312456 | GM7075 | 4.48701 | AL844854.1 | 5.51339 | MRPL47 | 0.127977 | NUP85 | 0.31187 | FBLIM1 | 3.15478 |
| CTNNBL1 | 0.314975 | NUP43 | 4.48542 | SLMAP | 0.181459 | GM10576 | 7.80195 | BC023829 | 3.01789 | GM5356 | 3.15448 |
| RASL2-9-PS | 3.17011 | TMEM223 | 4.47551 | POLD3 | 0.182126 | GIMAP5 | 7.78292 | CLTC | 3.00802 | TRADD | 0.317215 |
| IDH1 | 0.31565 | 0610007C21RIK | 4.47073 | SCLY | 5.46754 | MAPKSP1 | 7.76362 | COG6 | 3.00697 | EBNA1BP2 | 0.317965 |
| KIF3A | 3.16623 | ZFP68 | 4.46896 | JKAMP | 0.183242 | MFHAS1 | 0.129244 | 2310039H08RIK | 0.332595 | ABCC1 | 0.318111 |
| LSM12 | 3.15031 | CD2 | 4.46617 | RFT1 | 0.183557 | ARHGAP23 | 7.71607 | MNT | 3.00475 | PDCL | 3.13806 |
| GM221 | 3.14642 | NUSAP1 | 4.46516 | C1D | 0.184599 | STARD4 | 0.129674 | PCYOX1 | 0.333752 | CCDC43 | 0.318846 |
| AC131780.3 | 3.14591 | AGPAT3 | 4.46119 | CCDC59 | 0.184704 | 1600002K03RIK | 0.1297 | B23O312A22RIK | 2.99448 | 4933474N05RIK | 3.1328 |
| FAHD2A | 3.14433 | AC156550.1 | 4.45543 | KDELC1 | 0.184761 | SDR39U1 | 7.71011 | CCNE1 | 2.98388 | PDLIM2 | 3.12896 |
| DOLPP1 | 3.13618 | CDCA8 | 4.44608 | ADCK3 | 5.41193 | NFYB | 0.129757 | NDUFS5 | 2.98382 | CCDC34 | 3.12826 |
| STAM | 3.13571 | BTF3L4 | 4.44441 | SEPSEC5 | 0.184985 | GRAP | 7.6721 | 1110004E09RIK | 2.98052 | SRSF1 | 3.12446 |
| TIMM10 | 0.319394 | DDX52 | 4.44187 | VEGFA | 0.185212 | LUZP1 | 7.63923 | HMGB1 | 2.98022 | DPP7 | 3.12375 |
| GM10203 | 3.12599 | NDUFS5 | 4.42774 | SC5D | 5.39603 | HCST | 7.61544 | GTF2IRD2 | 2.97923 | IL1F9 | 3.1218 |
| NUBP1 | 0.320316 | CDC42SE1 | 4.41984 | FNBP1 | 5.39015 | ZFP637 | 7.60926 | TMED5 | 2.97866 | SLC4A11 | 0.320514 |
| NAT9 | 0.320397 | UCHL5 | 4.41338 | SRP19 | 5.38091 | OSGEPL1 | 7.57363 | FAF2 | 2.97736 | ALG14 | 3.11635 |
| RB1 | 0.320964 | PIGYL | 4.40893 | AIMP1 | 0.18622 | TMEM199 | 7.56543 | CCR4 | 0.336944 | MFSD2A | 0.321052 |
| H2-GS10 | 3.11528 | PDLIM7 | 4.4059 | 1810020D17RIK | 5.36392 | SENP3 | 7.48781 | NTNG2 | 2.9583 | RB1CC1 | 0.321173 |
| MYCBP | 3.11017 | VDAC3 | 4.40259 | ECHDC1 | 0.18951 | TSEN2 | 7.4544 | RNF44 | 0.339022 | FXR1 | 0.321184 |
| AC132391.1 | 3.1075 | 4933424B01RIK | 4.38958 | MTIF3 | 5.33494 | GBP2 | 7.43783 | NDUFAF3 | 0.339379 | PINX1 | 3.11098 |
| IPO13 | 0.322049 | PPP6C | 4.38589 | RAPSN | 0.187887 | CIB1 | 7.4126 | IFT20 | 0.340482 | D4ERTD22E | 3.11053 |
| PIP4K2B | 3.10511 | SUCLA2 | 4.37852 | MPHOSPH8 | 0.185212 | IFRD1 | 7.40784 | 2310008H09RIK | 0.340502 | GNG2 | 3.10972 |
| 4930522L14RIK | 3.10127 | ENPP2 | 4.36614 | GM15401 | 0.188117 | 3110003A17RIK | 7.40034 | CAMK2B | 2.93204 | ERLEC1 | 3.10554 |
| 1810043H04RIK | 3.09951 | HCST | 4.35327 | TBCB | 0.18951 | 2010107H07RIK | 7.38496 | COQ2 | 0.341951 | ARMCX1 | 3.10231 |
| PSPH | 0.323327 | GNPDA1 | 4.34901 | 5830405N20RIK | 0.189633 | ZFP51 | 5.2627 | MRPL53 | 2.91647 | GSTK1 | 3.09987 |
| GM10106 | 3.0872 | BAT1A | 4.34702 | AC161001.1 | 0.135464 | | | CD44 | 0.342897 | UBE2D2 | 0.322793 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-TGFB1 + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| ZFP451 | 3.08594 | ZFP738 | 0.230576 | AC156282.1 | 5.26252 | ARHGAP15 | 7.37653 | NFKBIL2 | 0.343165 | HIST2H3C1 | 3.09785 |
| R3HCC1 | 3.08076 | MBD2 | 4.32965 | GLUL | 5.25996 | POLD1 | 0.136672 | RGS1 | 2.91313 | 8430426H19RIK | 0.323762 |
| CHCHD2 | 3.07856 | PRR13 | 4.32946 | LIME1 | 5.22859 | TTLL12 | 0.13693 | POLR2K | 2.9129 | SMARCD2 | 0.323887 |
| PCCA | 3.07753 | DPY19L3 | 4.32468 | CCDC43 | 0.191352 | MAN1A2 | 0.136938 | RNPC3 | 2.91133 | BDP1 | 3.08415 |
| WDR45 | 3.07381 | GM6180 | 4.32311 | DNAJC1 | 5.22394 | HAUS1 | 7.29384 | ARL5B | 0.344485 | MPV17 | 3.07741 |
| CFHR1 | 3.0702 | SLC25A19 | 4.31144 | MRPS24 | 5.22365 | 1700034H14RIK | 7.27853 | SLC2A6 | 0.344806 | MPHOSPH6 | 0.325279 |
| EMD | 0.327152 | TTF2 | 0.232143 | IMMP2L | 0.191798 | PGAP2 | 7.26564 | TBC1D9B | 2.89908 | CDCA5 | 3.07215 |
| BCL2L11 | 0.3276 | RPAIN | 4.29849 | COQ6 | 0.192374 | RASA1 | 0.137688 | B230208H17RIK | 0.345136 | 1700106N22RIK | 3.07201 |
| AC131780.1 | 3.04934 | CARS | 4.27862 | PIGK | 5.17747 | JMJD6 | 7.24938 | ZBTB49 | 2.89711 | ACADSB | 0.325735 |
| VTA1 | 0.328216 | RCC2 | 4.26834 | IL15RA | 0.193169 | AC132391.1 | 7.20559 | WDR12 | 2.89619 | AC125099.1 | 3.06864 |
| ZMAT5 | 3.04487 | DPF2 | 0.234501 | VPS25 | 0.193271 | COX16 | 0.139135 | PTOV1 | 2.89529 | SELENBP1 | 3.06799 |
| PITPNA | 0.328621 | PHF10 | 4.24475 | GM5116 | 5.16527 | SDCCAG3 | 7.18597 | SRR | 2.8933 | PLA2G16 | 3.06358 |
| HNRNPH1 | 0.329638 | BBS9 | 0.235876 | PRM1 | 5.15044 | 2500003M10RIK | 7.17577 | 2010111I01RIK | 2.88992 | HIST1H1B | 3.06348 |
| STX17 | 3.02886 | RPP21 | 0.236253 | CCLS | 0.194269 | SLC25A14 | 0.139358 | BLCAP | 0.347386 | 1810030N24RIK | 0.326736 |
| TFAM | 3.01805 | VMN2R7 | 0.236701 | GRAMD1B | 5.1398 | TCTEX1D2 | 0.13985 | PHF20L1 | 2.86916 | ARID4B | 0.327308 |
| MXRA8 | 3.00578 | EWSR1 | 4.20549 | CAPS2 | 5.13789 | 4930447C04RIK | 7.14502 | FBXW4 | 2.86808 | NOX4 | 3.05421 |
| ACADSB | 3.00199 | BLOC1S1 | 4.2011 | RPS6KB1 | 5.13778 | MRPL53 | 7.13183 | PHLDB1 | 0.348714 | NEK8 | 3.04829 |
| RPL21 | 2.99721 | GOLT1B | 4.18881 | TBCA | 0.194723 | TMEM39A | 7.07725 | RAPH1 | 0.349641 | BLCAP | 3.28174 |
| HAT1 | 2.99666 | PFKL | 4.184 | CUAP1 | 0.194896 | MTIF2 | 7.06029 | PIH1D1 | 2.85572 | FAM49B | 3.283 |
| AC151573.1 | 0.333857 | FAM132A | 4.17661 | PUS1 | 0.195037 | SOD1 | 7.0561 | CREG1 | 2.85346 | RHBDD3 | 0.328672 |
| PHPT1 | 0.334679 | GSN | 4.17321 | NAT9 | 5.11575 | GM14391 | 0.142113 | LMF1 | 2.85313 | ECHDC1 | 0.328928 |
| TMEM120A | 2.98268 | UGDH | 4.16843 | TMEM219 | 0.19559 | GM16519 | 7.03028 | BC003267 | 2.85291 | UFD1L | 0.329148 |
| PEPD | 0.335518 | NR2C2 | 4.16575 | ANAPC11 | 5.10652 | ZWILCH | 7.02727 | NELF | 2.83614 | MGAT4C | 3.03683 |
| UXT | 2.97617 | MECR | 0.240318 | SEC63 | 0.196009 | LENEP | 0.142993 | TTC9C | 2.8299 | SRD5A3 | 3.03372 |
| AC131780.4 | 2.95956 | ACAA2 | 4.14731 | EIF2C4 | 5.09769 | BC031181 | 6.98719 | EPT1 | 2.82973 | ZFP874A | 0.329847 |
| UCP2 | 2.94585 | GM10028 | 4.14033 | TRNAU1AP | 5.09474 | UNC5C1 | 6.96583 | NEK8 | 2.82961 | UGDH | 0.329891 |
| PML | 2.92902 | REXO2 | 4.13396 | DIABLO | 0.196302 | CHUK | 0.144161 | MPND | 0.353903 | CUL1 | 0.330359 |
| GM5531 | 2.92779 | ATM | 4.13183 | CEP55 | 0.196627 | SPIC | 6.92498 | MOBKL1A | 2.82546 | CMAH | 3.02473 |
| GM10715 | 2.91891 | NOPR1 | 4.13177 | GM7075 | 5.05552 | HOOK3 | 0.144541 | ZFP287 | 2.82431 | LPL | 3.02258 |
| POLR3GL | 2.91406 | GM10203 | 0.242035 | AIFM2 | 5.04453 | DLG4 | 6.91142 | TBCE | 2.82358 | SIDT2 | 3.01548 |
| LSM1 | 2.91027 | TAGLN2 | 4.11826 | NUP210 | 0.198274 | ARMCK6 | 0.145354 | MARK2 | 2.81506 | YBX1 | 0.333036 |
| GM11152 | 0.343815 | NBR1 | 4.11699 | FAHD2A | 0.198849 | HIST1H1B | 0.145354 | GBA2 | 2.81383 | IL9 | 0.333116 |
| STAT6 | 2.90777 | CPT2 | 4.1068 | ARHGAP29 | 0.19898 | APIP | 0.14542 | FBF1 | 2.80213 | PNPO | 2.99467 |
| DLG4 | 2.90687 | GM1968 | 4.10351 | MAN2C1 | 5.02447 | DET1 | 0.145604 | MRPS23 | 2.8007 | CENPH | 2.9921 |
| MTCH1 | 0.344018 | DERL2 | 4.09817 | SPINK10 | 5.02384 | CENPV | 0.145745 | MXRA8 | 2.80045 | LITBP1 | 2.98882 |
| MAGED2 | 0.344848 | ERGIC2 | 4.09157 | HSPB11 | 5.01869 | GTF2F2 | 6.8613 | GOSR1 | 2.80035 | USP20 | 0.335411 |
| SLC10A3 | 2.89944 | PHOSPHO2 | 0.244986 | 2810428I15RIK | 0.199368 | COMMD6 | 6.83834 | TAF11 | 0.357693 | CD40LG | 0.33575 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information includes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL-6-96 h-1 | | PLZP-KO- IL1B + IL-6 + IL-23-48 h-1 | | PLZP-KO- TGFB1 + IL-6-48 h-1 | | TOSO-KO- IL1B + IL-6 + IL-23-96 h | | TOSO-KO- IL1B + IL-6 + IL-23-96 h | |
|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| CKLF | 0.345303 | ATP6V1D | 4.08007 | MFF | 0.199484 | B4GALT3 | 6.82285 | CHCHD7 | 2.79479 | CLP1 | 0.336059 |
| RAE1 | 0.345495 | LSM10 | 4.07981 | TIMD2 | 5.0101 | AARSD1 | 0.146637 | TRIP11 | 2.79204 | CBX8 | 0.33665 |
| MED27 | 0.2884 | ZNRD1 | 4.07458 | UFD1L | 0.19963 | IFT46 | 6.8108 | SQRDL | 0.358218 | TRNT1 | 0.336673 |
| CTSE | 0.28808 | LGTN | 4.07031 | SDHC | 0.199634 | MAD2L1BP | 6.80448 | TIA1 | 2.79049 | RG9MTD3 | 0.336739 |
| IFT57 | 2.88579 | WSB1 | 4.06913 | 1110001J03RIK | 5.00685 | NDUFB6 | 6.79376 | EXOC5 | 2.78989 | 2610029I01RIK | 2.95916 |
| GM10217 | 0.346567 | MTIF3 | 4.06886 | GM11175 | 0.199973 | 0910001L09RIK | 0.147261 | 1190007I07RIK | 2.78892 | BRE | 0.338296 |
| ALPL | 0.347105 | RNF7 | 4.05685 | STYK1 | 4.98328 | GLRX2 | 6.7192 | LYSMD2 | 2.78888 | CHCHD6 | 2.95512 |
| CIB1 | 0.347157 | AC116115.1 | 0.247894 | RAD51L1 | 4.97228 | CHD8 | 0.149339 | ZFP317 | 0.358667 | ZFP451 | 0.338711 |
| HINT3 | 0.347171 | 2810474O19RIK | 4.02276 | MED6 | 0.201969 | 1110008F13RIK | 0.149452 | CDC34 | 0.35947 | SEC61A2 | 0.338805 |
| TSC22D4 | 0.34724 | LUC7L3 | 4.00597 | CNN2 | 0.202084 | THAP7 | 0.149641 | CCDC28A | 2.77955 | MAP3K14 | 0.338859 |
| CDC23 | 2.87725 | TNFRSF4 | 3.9988 | PLAC8 | 4.93497 | ATP5L-PS1 | 6.67932 | BRD7 | 2.77765 | SLC25A19 | 2.94723 |
| RPL21-PS14 | | | | | | | | | | | |
| UPP1 | 0.347912 | OGT | 3.99743 | MRRF | 0.203165 | MED4 | 0.149821 | SLC39A1 | 0.360242 | RG9MTD2 | 2.94721 |
| AI314180 | 0.348802 | TNNC1 | 0.250444 | DPM2 | 0.203226 | SNX15 | 0.149921 | CRTC2 | 2.77523 | PQLC3 | 2.94393 |
| KBTBD4 | 0.348425 | GM12942 | 3.97863 | 3110001D03RIK | 4.89187 | AHSA2 | 0.15006 | ATP6AP2 | 2.77394 | PPL2 | 2.94232 |
| 2700094K13RIK | 0.348921 | JTB | 3.97698 | SMAD4 | 0.205077 | PDCD1 | 6.62636 | USP18 | 2.77391 | TMTC2 | 2.94055 |
| H2-Q6 | 2.85926 | WBP5 | 3.97449 | RGS10 | 0.205674 | 1110058L19RIK | 6.61022 | FANCL | 2.7726 | MRPL53 | 0.340076 |
| ORC4 | 2.85828 | 4930522L14RIK | 3.97073 | 4933427D14RIK | 0.205823 | WFDC12 | 0.151538 | PAFAH1B1 | 2.77096 | 2610001J05RIK | 0.3403 |
| SDR39U1 | 2.8579 | PHRF1 | 3.96914 | TOR1A | 0.205923 | UFM1 | 6.59687 | SVIL | 2.76036 | CHCHD6 | 0.340666 |
| USP3 | 2.85678 | CCDC56 | 3.96355 | DUT | 4.85312 | MRP525 | 6.5844 | MRPS25 | 2.75866 | 4931406P16RIK | 0.340949 |
| H2-D1 | 2.85498 | LMAN2L | 0.252321 | SNX12 | 4.83276 | CISH | 0.151934 | NUDT3 | 2.7582 | DIP2A | 2.93247 |
| SLC1A2 | 2.85043 | ISCA2 | 3.9591 | CAMTA1 | 4.82271 | ACER3 | 6.58143 | ATN1 | 2.75811 | STAB1 | 2.92744 |
| CARM1 | 0.350989 | PARL | 3.93771 | EXOC7 | 4.81229 | SLAMF1 | 6.5452 | OLFR816 | 2.75542 | BC017647 | 2.92608 |
| TPK1 | 2.8438 | TMEM135 | 0.255381 | COQ7 | 0.207907 | ACTR1B | 6.53341 | 2310044H10RIK | 2.75278 | ELP2 | 0.342265 |
| GM11678 | 0.352289 | IFT52 | 3.90514 | RNF130 | 0.208222 | GM6096 | 6.50942 | CHD6 | 2.75194 | ARHGAP4 | 0.342484 |
| ALPL | 2.83596 | PSAT1 | 3.90383 | FAM58B | 0.208634 | ELP4 | 6.50917 | SNRPB2 | 0.363667 | AP351 | 0.34362 |
| H2AFY | 2.83378 | STX18 | 0.256366 | GPD1L | 4.79143 | TM4SF5 | 6.50305 | NUCB1 | 0.364479 | PTPN3 | 0.344161 |
| MRPL32 | 0.353268 | ANXA2 | 3.89173 | SEC24B | 0.208746 | PXMP4 | 6.49205 | DLGAP4 | 2.74225 | KDM1A | 0.344246 |
| RASSF7 | 0.354535 | AEN | 0.257495 | MBD2 | 4.76196 | SPATA6 | 0.154734 | DCXR | 0.364747 | PVR | 2.90195 |
| GM14420 | 2.81884 | TADA3 | 3.86131 | ARMC6 | 0.210289 | SNAPC4 | 0.154947 | AHCY | 2.74099 | ERH | 0.344634 |
| IGBP1 | 0.355248 | MAT2B | 3.86108 | GM10125 | 4.74057 | AA467197 | 0.155267 | 1110008P14RIK | 0.365256 | PPOX | 0.344666 |
| NDFIP1 | 0.355598 | 42249 | 3.85924 | 9930111J21RIK2 | 4.73875 | SUPV3L1 | 6.41432 | TIAM1 | 0.365257 | XLR4B | 0.345325 |
| UHRF1 | 2.81099 | NUDT1 | 0.259245 | 0610011F06RIK | 4.73797 | DHPS | 0.156039 | EIF2B1 | 2.72536 | GM2938 | 2.88665 |
| TRIM50 | 2.81049 | RHOF | 3.85418 | CNPY2 | 4.72965 | DDIT3 | 0.156589 | 5830405N20RIK | 2.7248 | PAIP2B | 2.88615 |
| CCDC43 | 0.355835 | IMMP2L | 3.84533 | CHCHD8 | 4.7235 | BOD1 | 0.156685 | GM11276 | 0.367251 | FBXW2 | 0.348007 |
| GTF2F2 | 0.355977 | CELF2 | 3.83589 | ACBD6 | 4.71636 | 9030625A04RIK | 6.35456 | HIST1H2AO | 0.367251 | MPST | 2.8706 |
| | | DENND2A | 0.260843 | ABT1 | 4.71447 | COX5A | 6.33911 | RASSF2 | 2.72257 | C2 | 2.85795 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL6-96 h-1 | | GPR65-KO- IL1B + IL6 + IL23-96 h-1 | | PLZP-KO- IL1B + IL6 + IL23-48 h-1 | | PLZP-KO- TGFB1 + IL6-48 h-1 | | TOSO-KO- IL1B + IL6 + IL23-96 h | | TOSO-KO- IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| TNFRSF13B | 2.80894 | FAM114A1 | 0.357441 | 1810032O08RIK | 0.261077 | HERC3 | 0.212175 | CRADD | 2.72066 | FAM78A | 0.350322 |
| TADA2A | 2.79953 | EXOSC9 | 3.82852 | JUP | 4.71286 | PPIG | 0.158134 | SLCO4A1 | 0.367988 | C33002IF23RIK | 2.85429 |
| YIF1B | 2.79885 | RPL37-PS1 | 3.8276 | C130022K22RIK | 4.70846 | APITD1 | 0.158176 | ISCA2 | 0.368981 | CDC25B | 2.85421 |
| NFKB1 | 0.357441 | NCK1 | 0.262234 | CDK14 | 4.70157 | 2310008H09RIK | 6.31859 | MRPL2 | 0.369111 | ZFP369 | 2.85328 |
| H2-K1 | 2.79752 | SNX15 | 3.79972 | HTRA2 | 4.69693 | MBOAT1 | 0.158372 | STOM | 0.369478 | BET1 | 0.350498 |
| IFI27L2B | 2.79246 | RNASEH2A | 3.79724 | EIF2B2 | 0.213067 | LMO4 | 0.158933 | BAG1 | 0.370334 | MRPS22 | 0.351299 |
| IDH3B | 0.359126 | CNP | 3.79312 | ACBD5 | 4.688 | STK19 | 0.159019 | WSB2 | 2.70026 | MTFR1 | 0.351334 |
| MRPL55 | 0.359918 | ACADVL | 3.79189 | GNGT2 | 4.68529 | PHB | 6.28423 | BOP1 | 0.370403 | INPP5D | 2.83909 |
| CDC40 | 0.359945 | MRPL22 | 3.78887 | 0610031J06RIK | 0.213485 | UPP1 | 0.159191 | FBXO18 | 2.69642 | DNMT3B | 2.83849 |
| COMMD5 | 2.77285 | SELK | 3.7873 | AI314180 | 0.21373 | SLC15A2 | 6.28071 | SERPINB6B | 2.69283 | D16H22S680E | 0.352514 |
| STXBP2 | 0.361123 | MRPS24 | 0.264476 | GM10417 | 4.66524 | MOC52 | 6.27195 | 5730494N06RIK | 0.372059 | UGGT2 | 2.83121 |
| FAS | 0.361673 | ICOS | 3.77963 | CTPS2 | 0.214964 | USE1 | 6.26846 | BLOC1S2 | 0.372809 | HRAS1 | 2.82848 |
| CTR9 | 2.76177 | CSDE1 | 3.77373 | CLEC4A2 | 4.65076 | DCTN5 | 6.26381 | LAP3 | 2.68166 | PDLIM5 | 2.82108 |
| STT3A | 0.363716 | SNX2 | 3.7713 | GM7665 | 4.64326 | TLE6 | 6.26098 | CD48 | 0.373303 | TTLL4 | 0.354725 |
| H2-T23 | 2.74839 | EFTUD1 | 3.76083 | SPINT2 | 0.215713 | STX18 | 6.2564 | CHCHD1 | 2.67635 | ALKBH3 | 0.355442 |
| GATAD1 | 0.364231 | SLC25A5 | 3.75199 | SPA17 | 0.215945 | BCL2A1B | 0.159862 | MAPK1IP1 | 2.67331 | SFI1 | 2.8129 |
| RBM17 | 0.366844 | SEMA4A | 0.266764 | TBC1D1 | 0.215945 | CCNDBP1 | 0.23421 | METTL4 | 0.374093 | SYNJ1 | 0.355614 |
| TIMM22 | 0.367561 | FBXO4 | 3.74721 | GM14399 | 0.216145 | PHKG2 | 6.2254 | ZFP605 | 2.67043 | 4930422I07RIK | 0.356305 |
| TMEM106A | 2.71516 | FXC1 | 3.74327 | PRKRIP1 | 4.60596 | GM10495 | 6.21918 | SLC35A4 | 2.67036 | PRKCZ | 2.80052 |
| AL732569.1 | 0.368325 | DGAT1 | 3.73403 | ZSCAN2 | 0.219106 | RRP36 | 0.161141 | PEA15A | 2.66759 | GGNBP2 | 0.35727 |
| SDF2 | 0.368758 | NSMCE1 | 3.73272 | PRIM2 | 4.55993 | POLR1E | 0.161376 | IQCE | 0.375067 | PRPS2 | 2.79576 |
| AC132837.1 | 0.369262 | GBP2 | 3.73272 | QDPR | 0.219302 | ARFIP2 | 6.16931 | MTG1 | 0.375758 | NADSYN1 | 2.77753 |
| 5930416I19RIK | 0.369793 | IL10RB | 3.73038 | CDCA5 | 0.219692 | KRAS | 6.16237 | RALGAPA2 | 2.65799 | NDUFAF1 | 0.360265 |
| TUBA8 | 2.70237 | GRHPR | 3.73034 | SCFD2 | 0.219781 | MAD2L2 | 0.162373 | NOL7 | 0.376463 | LYSMD2 | 2.77269 |
| H2-OB | 0.370064 | DNAIC15 | 3.72675 | HADHA | 0.220075 | EIF2B2 | 6.15565 | FAIM3 | 0.37671 | NUSAP1 | 2.77163 |
| MED6 | 0.371113 | IMMP1L | 3.72299 | GM4893 | 0.220436 | 8430423G03RIK | 0.162475 | RAB3D | 0.377163 | PXMP2 | 0.360913 |
| RSU1 | 0.371744 | ARMC7 | 3.72249 | RABB8 | 0.22074 | SGSM3 | 0.162516 | 2700094K13RIK | 0.377586 | SNX14 | 0.361047 |
| TMEM179B | 0.371842 | CYP11A1 | 0.269039 | STAP1 | 0.220747 | NSMCE4A | 0.163059 | LDB1 | 0.377679 | BLOC152 | 2.76953 |
| FLT3L | 2.68853 | EIF4G1 | 3.71276 | FAM175A | 4.51023 | IPO13 | 0.163484 | ADRBK1 | 2.64366 | HIST1H4I | 2.7683 |
| TMC4 | 2.6825 | LGAL59 | 0.269833 | TPST1 | 0.222301 | GM561 | 6.09075 | EPSTI1 | 2.64135 | MUC2 | 2.76605 |
| MORF4L2 | 0.373036 | ECHDC2 | 3.69407 | FAM32A | 4.4939 | GALK2 | 6.08225 | NRF1 | 2.6405 | PPP1R13L | 2.76466 |
| DHPS | 0.373179 | SI00A13 | 3.69165 | MTUS2 | 0.222665 | YIPF6 | 0.16479 | PIGT | 0.378962 | PARVG | 2.76232 |
| BC030499 | 2.67153 | RNASEH2B | 3.69113 | CCNL1 | 4.47916 | ASTE1 | 0.165034 | TADA1 | 2.6381 | CBARA1 | 2.75891 |
| SYCE2 | 0.374728 | ARPC5 | 3.67632 | MLKL | 0.223832 | MRPL55 | 6.05937 | CLTB | 0.379157 | EXOSC3 | 2.7582 |
| ZRSR2 | 2.66741 | ARPC3 | 3.66651 | DNPEP | 4.46494 | HSD17B12 | 0.165137 | TSEN34 | 2.6373 | SRSF5 | 0.36266 |
| RNMT | 0.374968 | CYTIP | 3.66609 | GM11276 | 4.46139 | GM6843 | 0.165668 | GM9774 | 0.380122 | FBXL12 | 2.75597 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| GPCPD1 | 0.375571 | RPA2 | 0.274174 | HIST1H2AO | 4.46139 | ME3 | 6.03518 | GM2833 | 2.62465 | 1500001M20RIK | 0.363356 |
| JAK1 | 2.66069 | MRPL21 | 3.64363 | CDK2APL | 0.224199 | ABLIM2 | 6.01497 | WBSCR22 | 2.62229 | MANF | 2.74877 |
| MT2 | 0.375898 | DYNLRB1 | 3.63555 | ZFP35 | 4.45623 | RPS12 | 0.1669 | 2410089E03RIK | 2.61843 | BECN1 | 0.363818 |
| WAC | 0.376308 | MUS81 | 0.275812 | SECISBP2 | 4.45206 | VMN1R58 | 5.97815 | UHRF1 | 0.382247 | PSTK | 2.74776 |
| THOC6 | 0.376726 | GM10566 | 3.62112 | NEK8 | 0.224899 | AKIRIN1 | 5.97705 | UBE2E1 | 2.61472 | TMEM29 | 0.364208 |
| USE1 | 2.65108 | NINJ1 | 3.6157 | 42070 | 4.44642 | TAF13 | 5.97344 | GSTZ1 | 2.61459 | PUS7 | 0.36489 |
| THAP3 | 0.377346 | BLZF1 | 3.59783 | GM5474 | 4.43605 | 2400001E08RIK | 5.96702 | EIF3L | 0.382819 | CIT | 0.365716 |
| GM9574 | 0.377779 | MRPL10 | 3.59223 | TIMM44 | 4.43373 | 1110001J03RIK | 5.94875 | NPLOC4 | 2.61217 | MLLT10 | 0.365901 |
| MRPS6 | 0.377989 | PRODH | 3.58928 | PPDPF | 4.43157 | ALKBH6 | 5.94376 | BC026585 | 2.61077 | PAQR3 | 2.73185 |
| AC160471.1 | 0.378247 | C1D | 3.58896 | IFI35 | 4.42972 | DGKZ | 5.9229 | VPS29 | 0.383109 | NUDT3 | 0.36641 |
| FAM173A | 2.64377 | D10WSU52E | 3.57659 | CENPL | 4.41587 | MUS81 | 5.9194 | GMS610 | 0.383109 | NUDT3 | 0.366644 |
| VEZT | 2.64154 | NUPS4 | 3.5669 | CDC7 | 4.41328 | DCUN1D1 | 0.168965 | PDLIM5 | 2.60311 | LBR | 0.367002 |
| TMUB1 | 2.64146 | OGFOD2 | 3.56196 | AASDH | 0.226953 | CLNS1A | 0.16917 | SNTB1 | 2.60288 | KCTD13 | 2.72178 |
| LITAF | 2.64108 | RBM43 | 0.281272 | ZMAT5 | 0.227216 | SLC35C2 | 5.9112 | GPR107 | 0.384602 | CCDC109A | 0.367499 |
| CALD1 | 2.64051 | GM5506 | 3.55487 | PPAPDC1B | 4.3942 | CNN2 | 5.89954 | 1810035L17RIK | 0.384739 | SSRP1 | 2.71716 |
| MAPRE1 | 0.378721 | TXN1 | 3.5524 | 3110009E18RIK | 0.228199 | LRRC40 | 5.89635 | AEN | 0.385092 | SPIC | 2.71485 |
| USP5 | 0.378759 | ASL | 3.55025 | GPR19 | 4.38073 | PRIM2 | 5.88398 | USP25 | 2.59227 | PDAP1 | 2.71339 |
| PSMG2 | 2.6364 | CD68 | 3.54467 | SLC11A2 | 4.37804 | ARFRP1 | 5.87869 | FAM183B | 0.38684 | SNX32 | 2.71032 |
| MRPL41 | 0.37975 | GM11444 | 3.54297 | ARL2 | 0.22845 | MND1 | 0.170847 | OAS1A | 2.584 | CTSC | 0.369527 |
| SERHL | 0.379928 | CCNL2 | 3.54173 | DCTN3 | 0.228615 | MOBKL3 | 0.170936 | N4BP3 | 2.5831 | NOL6 | 0.369607 |
| GCC2 | 0.379996 | DPH3 | 3.54104 | DNAJC12 | 0.22918 | THOC7 | 0.171761 | NCKIPSD | 2.57772 | ZWILCH | 0.370438 |
| CRYGN | 0.380065 | C0300391L03RIK | 0.282425 | BC057079 | 4.36401 | UTY | 0.171829 | RIOK2 | 2.57744 | OPRM1 | 2.69491 |
| ABI1 | 0.380254 | ENTPD1 | 0.282635 | TMEM188 | 4.35828 | GBA | 5.81696 | ASB7 | 2.57699 | MRPS7 | 2.69191 |
| XLR4C | 2.62803 | H2-Q6 | 3.52238 | ARL3 | 4.3356 | TMEM33 | 5.80804 | ETOH11 | 2.57488 | MMP16 | 2.6919 |
| MBOAT1 | 0.380531 | WDR3 | 3.51936 | FBXL17 | 4.3512 | EIF4BP1 | 5.79065 | IL1R2 | 0.388562 | PRDM11 | 2.69182 |
| TMED3 | 2.62714 | DHX8 | 3.51485 | MUL1 | 4.34233 | GTF2H1 | 5.78757 | CYP4F13 | 2.57031 | CCT6A | 0.37176 |
| GIMAP3 | 2.62097 | NUBP2 | 3.5116 | NUP188 | 4.33967 | TUBGCP4 | 0.173065 | NKG7 | 2.56692 | VAV2 | 2.6868 |
| NSUNS | 2.61944 | GM10324 | 3.50986 | RBL2 | 4.33662 | CD2 | 5.77675 | GM14391 | 2.56275 | DTL | 2.68598 |
| WIPF1 | 0.381938 | NFIB | 0.284944 | MECR | 4.32577 | AFF1 | 0.173118 | GRHPR | 2.55795 | ELOVL5 | 0.372757 |
| CCT4 | 2.6093 | IMPA2 | 3.50901 | AI462493 | 4.32377 | TANK | 0.17324 | PARP3 | 2.55783 | PDPK1 | 0.372828 |
| GPS2 | 0.38457 | DDX1 | 3.50543 | ZFP26 | 4.31551 | 2310036O22RIK | 0.173257 | HDAC5 | 0.391103 | TMEM69 | 2.68202 |
| NAA35 | 2.60468 | TNFAIP8L2 | 0.3049 | GIMAP5 | 0.231722 | 4930473A06RIK | 5.76841 | SUPT3H | 2.5565 | RPA1 | 0.37316 |
| RARS2 | 0.38393 | ARL6IP4 | 3.50285 | CYBSRL | 0.231826 | EPN2 | 5.75899 | STRA6 | 0.391227 | ITM2A | 0.374049 |
| NGFRAP1 | 0.384268 | GM10324 | 3.50197 | RPS19BP1 | 4.31053 | PNP2 | 0.173642 | EHD1 | 2.55424 | ERCC5 | 2.67242 |
| IL1F9 | 2.59869 | TMEM128 | 0.28566 | CPM | 0.232819 | STIM2 | 0.173743 | MRPL17 | 0.391555 | BRD8 | 2.67235 |
| TNFAIP8L2 | 0.384814 | AC139042.1 | 3.49905 | GM13147 | 4.29271 | ZFP62 | 0.173835 | TBC1D20 | 0.391907 | CLDN7 | 0.374323 |
| TMEM161A | 0.38506 | SLAMF8 | 0.286743 | 1110021L09RIK | 4.2791 | CAP2B | 0.173926 | TBCA | 2.54932 | SFT2D1 | 2.67093 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| GM10842 | 2.5922 | CDC20 | 3.48721 | PSMD10 | 4.27034 | BCL2A1C | 0.17394 | ARHGEF18 | 2.54846 | MRPS10 | 0.374692 |
| CTTN | 2.59036 | FMNL1 | 3.4823 | VIPAR | 0.234174 | TGS1 | 0.174071 | ARL16 | 0.392431 | ACAD11 | 2.66233 |
| MLKL | 0.386417 | SEPP1 | 3.47958 | CENPA | 0.234317 | PPIL3 | 0.174089 | 1500011H22RIK | 0.392571 | HDAC6 | 0.375756 |
| GGTA1 | 0.386703 | RPS17 | 3.47038 | R3HDM2 | 4.26772 | AC166169.1 | 0.174396 | PTPN3 | 2.54622 | RNF6 | 0.376193 |
| METT11D1 | 2.5361 | GPR18 | 3.46365 | UBE2W | 0.234509 | FUS | 0.174416 | SETX | 2.54107 | CARKD | 0.377398 |
| TAF1D | 0.387516 | CTLA4 | 3.46255 | TSC22D4 | 0.234692 | PPIH | 5.71612 | ZDHHC13 | 0.393563 | SBF2 | 2.64709 |
| 2310045N01RIK | 2.57617 | TMEM9 | 3.45673 | OLA1 | 0.234852 | MED11 | 0.174944 | PHF7 | 2.53974 | OSBPL7 | 2.64258 |
| RNASEH2B | 0.388575 | EIF4E | 3.45672 | TATDN3 | 0.234926 | MANBA | 5.71117 | MDFIC | 2.53954 | ZBTB7B | 0.37856 |
| THOC5 | 0.388575 | PIH1D2 | 3.44643 | CHKA | 4.25282 | TMEM223 | 5.7077 | SUSD3 | 0.394206 | RGS3 | 2.6388 |
| RPL21-PS12 | 0.389232 | GM8815 | 3.44583 | RBM14 | 0.235463 | BC017643 | 5.70458 | RNMT | 2.53629 | DULLARD | 0.379202 |
| MRE11A | 0.389622 | HDAC7 | 3.4423 | CHM | 4.24299 | ZZZ3 | 5.69466 | GM12942 | 2.53483 | NUDT14 | 0.380537 |
| 4621228N05RIK | 0.390117 | SLC25A39 | 3.44154 | FAM3C | 0.235902 | L7RN6 | 5.69185 | INO80C | 2.53474 | TYMS | 2.62736 |
| IMMP1L | 0.390261 | COMMD1 | 3.43923 | MS4A6D | 4.23668 | POLK | 0.175794 | ZDHHC4 | 2.53286 | SETD6 | 2.62561 |
| 8430419L09RIK | 0.390402 | CSTAD | 0.290846 | GM5900 | 4.23525 | NUP43 | 5.68573 | PBK | 2.53258 | INP5F | 2.6251 |
| CCNC | 2.56046 | INSL3 | 3.43606 | HDAC8 | 0.236014 | IFT140 | 0.176033 | NUDC | 0.395065 | CNPY2 | 2.62114 |
| PSD4 | 0.390742 | AKR1A4 | 3.43343 | NRK | 4.22303 | DDHH | 5.67803 | ATPAF2 | 0.395464 | NFIC | 0.381718 |
| IL15RA | 0.390915 | AP1S1 | 0.291393 | VMN1R58 | 4.22215 | SIRT2 | 5.63162 | RACGAP1 | 2.52856 | HPS5 | 0.382031 |
| ALKBH1 | 0.390984 | DUSP19 | 3.43144 | ANAPC2 | 0.237303 | MRP534 | 0.177826 | REC4 | 0.395695 | GM16181 | 2.60756 |
| CINP | 2.55745 | PIH1D1 | 0.291703 | BC055324 | 4.2104 | ST6GAL1 | 0.178039 | METTL10 | 2.52633 | CHMP4B | 2.60726 |
| PFN1 | 2.55449 | 4930402H24RIK | 0.291965 | IFT20 | 0.237727 | TGMA4 | 5.61281 | CDC45 | 2.52427 | MNS1 | 2.60505 |
| E03003010106RIK | 0.391747 | LSM5 | 3.41724 | WDR85 | 4.19078 | USP5 | 5.60719 | CASP6 | 0.396329 | DDA1 | 0.383999 |
| 2700062C07RIK | 0.392185 | LAMA5 | 3.4158 | 1700047G07RIK | 4.18925 | LRRC31 | 0.178434 | PDZD11 | 2.52099 | BUB1B | 0.384036 |
| GTL3 | 2.54873 | DBP | 0.292969 | GM11110 | 0.238794 | SNAPC5 | 5.60413 | FOXRED1 | 2.51945 | MAP3K1 | 2.60194 |
| AC087117.1 | 2.54855 | BAD | 0.293991 | PFDN5 | 4.18382 | AIP | 5.59989 | GM9762 | 0.397014 | 2900010M23RIK | 2.60193 |
| ATF7IP | 0.392441 | PFKFB3 | 0.294121 | METTL5 | 4.17327 | PHF20 | 5.59826 | MGLL | 0.397019 | REXO1 | 0.384764 |
| CEP250 | 0.392457 | SNRPB2 | 3.39522 | RHBDL2 | 4.16203 | ACP6 | 0.178677 | 2310036O22RIK | 2.51867 | FKBP2 | 2.59551 |
| HIST1H4I | 2.54658 | KCTD14 | 3.39439 | AKAP13 | 4.15011 | FAM3A | 0.179502 | NMT1 | 2.51497 | CES5A | 2.59475 |
| TNFRSF25 | 2.545 | TNFRSF18 | 3.39091 | HIBADH | 4.14954 | 2610528E23RIK | 0.1799 | 2410002F23RIK | 2.51263 | RBMX | 0.385616 |
| GMFB | 0.393779 | EDF1 | 3.39068 | ING2 | 0.241135 | U2AF1L4 | 5.55635 | USP21 | 2.51209 | 2500003M10RIK | 0.385865 |
| PARVG | 2.53884 | TM9SF4 | 3.38904 | KIN | 0.241463 | MYSM1 | 0.180108 | STAP1 | 2.50944 | ABI3 | 0.386054 |
| ACPL2 | 0.393929 | MRPS36-PS1 | 3.38588 | SNX14 | 4.13506 | SPAG5 | 0.180124 | TMEM120A | 2.50846 | PNPT1 | 2.59012 |
| N6AMT2 | 0.395451 | CCNE2 | 3.38245 | BRD7 | 0.242433 | CHAC2 | 5.55104 | LY6I | 2.50636 | RPE | 0.386085 |
| B230208H17RIK | 0.396264 | C030048B08RIK | 3.38235 | LSM2 | 4.12415 | FAM118B | 0.180146 | IKZF3 | 2.50618 | GFM1 | 2.58967 |
| 3010026O09RIK | 2.52186 | TASP1 | 3.38082 | GM71 | 0.242591 | 2310003H01RIK | 5.54767 | CLK2 | 0.399108 | KPNA3 | 0.386292 |
| MTIF3 | 2.51817 | GMNN | 3.37777 | SUGP2 | 0.24264 | SUSD3 | 5.54412 | CSDA | 0.39964 | DEDD2 | 0.386389 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h |  |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| BIN2 | 2.51792 | SIT1 | 3.37462 | WDR26 | 4.121 | PIA2 | 0.180634 | IFIT2 | 2.50035 | BTBD9 | 0.387014 |
| DCTPP1 | 0.397437 | DAPP1 | 3.37257 | CAB39L | 4.12023 | CHST12 | 5.52136 | RFTN1 | 2.49718 | ZZEF1 | 2.582 |
| TM9SF4 | 0.397746 | TUBA1A | 3.37022 | GM6132 | 4.1164 | ZFP61 | 0.181115 | U2AF1 | 0.400739 | TWSG1 | 0.387342 |
| PROP1 | 0.397841 | PLIN2 | 3.36978 | PSMC3IP | 0.242976 | A830010M20RIK | 5.50564 | LZTR1 | 2.49469 | ASB6 | 2.58105 |
| 2310003C23RIK | 0.397982 | ACTB | 3.36773 | IFI27L1 | 4.09596 | LRRC59 | 0.181713 | 903025P20RIK | 2.49125 | TRAF3 | 2.58057 |
| ATP1B3 | 2.51244 | TMEM97 | 3.36432 | GCC2 | 0.244318 | PIA1 | 0.182048 | RRAS | 2.49102 | SUFU | 2.57907 |
| PHAX | 0.398858 | TIMM22 | 0.298029 | TRIP4 | 0.244704 | RBM14 | 5.47441 | NGFRAP1 | 0.401506 | HAUS6 | 2.57873 |
| KDM4C | 0.399245 | MRPS14 | 3.35244 | 6330416L07RIK | 4.08248 | SNX1 | 5.46754 | TBRG4 | 2.49007 | IRF3 | 0.387819 |
| RRAS | 2.50304 | WDR54 | 3.35107 | CASP2 | 4.08 | MPDUL | 5.46415 | 1110034B05RIK | 0.402464 | E330020D12RIK | 2.57835 |
| GM6483 | 0.39999 | PHB2 | 3.34915 | PPWD1 | 0.245456 | GM4830 | 0.183093 | H2-M2 | 2.48448 | JMJD5 | 2.57693 |
| TCTEX1D2 | 2.49548 | CISD3 | 0.29859 | ISL2 | 0.245584 | PEX19 | 5.4617 | CCDC76 | 2.48072 | TRIAP1 | 0.388319 |
| U2AF1L4 | 0.401416 | FKBP1A | 3.34809 | AC117232.1 | 0.245801 | H2-Q6 | 5.45725 | ANKRD12 | 2.47797 | LSM2 | 2.57473 |
| HMOX1 | 0.401474 | SLC25A11 | 3.34521 | MMP16 | 4.06537 | RBM22 | 5.45222 | ZKSCAN14 | 2.4722 | ZMAT5 | 2.57136 |
| AC166169.1 | 0.401762 | AC090563.1 | 0.299305 | APOBEC1 | 4.06336 | MFN2 | 0.184369 | CITED2 | 2.47108 | AC132320.1 | 2.57098 |
| SMEK2 | 0.40177 | ATP6AP2 | 3.33938 | CCDC40 | 4.06246 | GM6710 | 0.184704 | ING3 | 2.46922 | UNC45A | 2.56806 |
| TGDS | 2.46387 | PFDN1 | 3.33829 | TIAL1 | 4.05923 | KIF2C | 5.39762 | ATP6V1D | 2.46538 | ZBTB20 | 0.389732 |
| BBC3 | 0.402395 | SNX1 | 3.33024 | MRFAP1 | 0.246888 | TBPL1 | 5.38661 | KCNK7 | 0.406665 | NXF1 | 0.391 |
| CBARA1 | 2.48476 | LUC7L | 3.32473 | GADL1 | 0.247037 | CDC123 | 5.38034 | HNRNPL | 0.406792 | GMEB1 | 0.391028 |
| XRN2 | 0.403258 | EIF4B | 3.32463 | SERPINF1 | 0.247061 | RAG1AP1 | 5.37712 | SPG11 | 2.45809 | CIRH1A | 0.391777 |
| 2810428I15RIK | 0.403471 | FYB | 3.31789 | KIF5B | 4.04619 | 493342I11RIK | 5.37001 | MIPOL1 | 2.45699 | OAS1B | 2.55216 |
| LGALS3 | 0.403629 | KNG1 | 0.302111 | CORO1B | 0.247187 | AC127590.1 | 5.35724 | COL4A3 | 2.45583 | ARRB1 | 0.392411 |
| S100A3 | 2.4669 | LPCAT3 | 0.302157 | LRRK1 | 4.04349 | 493051ZM02RIK | 5.3539 | HSF2BP | 2.45561 | MRPL43 | 2.54414 |
| GM6396 | 0.405591 | GGA3 | 0.302824 | TMEM104 | 4.04072 | TREX1 | 5.34849 | GM12789 | 2.45047 | GM14443 | 2.54154 |
| ITGA6 | 2.46387 | ANKRD16 | 0.303006 | ZFP488 | 4.0366 | MRPL2 | 0.18728 | AU022870 | 2.45027 | SPAG5 | 2.53887 |
| HMGN1 | 0.407101 | ZSCAN21 | 0.303014 | 2310001H12RIK | 0.247861 | 42248 | 5.33353 | VAMP4 | 2.44973 | ZFAND6 | 0.393917 |
| EED | 0.407365 | VTA1 | 3.29714 | GNB1L | 0.248459 | CUL4A | 5.33054 | CIAPIN1 | 0.408638 | AC068006.1 | 2.53464 |
| DNAJC21 | 0.407973 | SATB1 | 3.29571 | RPS2 | 0.248605 | CENPL | 0.187671 | COQ5 | 2.44616 | CD27 | 2.53458 |
| NDUFS1 | 0.408024 | NDUFS3 | 0.303751 | ILK | 0.248648 | AU019823 | 0.187717 | TATDN1 | 0.408903 | PLBD2 | 2.52362 |
| GM5617 | 2.44984 | JKAMP | 3.29212 | COMMD2 | 4.01665 | TRADD | 5.32189 | RNF7 | 0.408986 | RAB2A | 2.52042 |
| WTIP | 0.408332 | SKAP2 | 3.28684 | CQQ9 | 0.248966 | SNX12 | 0.188894 | ATR | 2.44494 | ATRIP | 2.52039 |
| CD48 | 0.408816 | H2-Q10 | 3.28673 | D930014E17RIK | 0.24934 | LLPH | 5.29397 | H2-Q6 | 2.44355 | SEC16A | 0.396912 |
| MFF | 0.408963 | COMMD3 | 3.28433 | AC142450.1 | 4.0057 | TNFRSF13B | 5.28839 | PTPN2 | 2.4435 | MED31 | 2.5165 |
| SRSF2 | 0.408024 | MYSM1 | 3.28378 | CLCF1 | 0.249709 | MRE11A | 0.189138 | ATG4B | 0.409998 | PCCA | 0.397718 |
| SLC39A11 | 0.410655 | 1810020D17RIK | 0.304718 | AC102609.1 | 3.99958 | IMPA1 | 5.27732 | MED18 | 2.43574 | SNAP23 | 0.398389 |
| PPCS | 2.42455 | GM10800 | 3.28046 | ORC4 | 0.250401 | GALT | 0.189633 | 1110049F12RIK | 2.43525 | IKBKE | 2.5098 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| RPE | 2.42392 | TMEM50A | 3.27816 | YTHDC1 | 0.250938 | LY6C2 | 5.27335 | SPR | 0.410802 | NOP10 | 2.50758 |
| BC049349 | 0.412584 | CAPZA2 | 3.27751 | MRPS23 | 3.98124 | RP23-369M17.1 | 0.190228 | TMEM121 | 2.43406 | D19ERTD386E | 0.399471 |
| LRRC33 | 2.42129 | MAP2K3 | 3.27284 | TNFSF9 | 3.97682 | LY6I | 0.190318 | BAK1 | 0.411164 | CUL4A | 2.50226 |
| GM4953 | 2.42053 | MDH2 | 3.27146 | LSM12 | 3.97426 | KIF1B | 0.190499 | WDR26 | 2.43141 | MRPL12 | 2.50001 |
| SMAD2 | 0.413406 | CD3D | 3.27114 | POLD4 | 3.94804 | EIF3G | 5.24109 | MAPK3 | 0.411846 | NCKAP5 | 2.4997 |
| PTPRV | 0.413851 | PEX11B | 3.27019 | CEP57 | 0.253563 | TMEN219 | 0.191107 | CD226 | 2.42794 | GM10125 | 2.49936 |
| KLC1 | 2.4143 | AHSA1 | 3.26954 | SAMSN1 | 3.94248 | 4930529M08RIK | 5.23014 | TBC1D13 | 2.42405 | GM5607 | 2.49751 |
| CISH | 2.41248 | SPINK10 | 0.305927 | 2300009A05RIK | 3.93763 | H2AFV | 5.22596 | TIMM50 | 0.412533 | FANCG | 0.400578 |
| 1700007K09RIK | 0.415149 | BC017643 | 3.26754 | AC156948.1 | 3.93241 | DNAJC9 | 5.22093 | 1810020D17RIK | 0.412683 | FBXO44 | 0.400767 |
| PIGZ | 0.415217 | A630001G21RIK | 0.306225 | S100A1 | 3.91733 | TKI | 5.21873 | CUX2 | 2.42237 | BIRCC | 0.400962 |
| PTTG1 | 0.415544 | TBC1D10C | 3.26649 | GMDS | 3.91583 | RADS1AP1 | 0.191965 | C130026I21RIK | 2.42004 | 2310044H10RIK | 0.401107 |
| BC017643 | 2.40337 | PARD6A | 3.26276 | CAR5 | 0.255555 | DHX33 | 5.20461 | PRMT7 | 0.413402 | BC048355 | 2.48897 |
| YIF1A | 0.416415 | PAM16 | 2.3571 | MRPL21 | 3.90612 | IRF1 | 5.20163 | LUC7L3 | 2.41893 | 5930416I19RIK | 2.48462 |
| FBXO5 | 0.4165 | SCN9A | 0.307586 | PEA15A | 0.256257 | CAT | 0.192378 | TM2D1 | 0.413569 | PTPN4 | 2.48407 |
| PSEN2 | 2.39813 | MAP2K2 | 3.25054 | ACP6 | 0.256389 | CFLAR | 0.19253 | SUV420H2 | 0.19253 | ANKRD13C | 0.402613 |
| LASS2 | 2.39778 | MOBKL2A | 3.24581 | DHDDS | 0.256606 | BRP44 | 0.192542 | MAPK7 | 2.41704 | DNAJC16 | 0.40297 |
| AC135633.1 | 2.39558 | SRSF7 | 3.23621 | RAB7L1 | 0.256733 | ST7 | 5.19068 | NDUFAF4 | 0.414396 | SMARCB1 | 2.47527 |
| LAMC1 | 2.39358 | OTUB1 | 0.309121 | B9D1 | 0.256824 | MS4A6B | 5.18831 | SLC35C2 | 2.41267 | ZEP488 | 2.47522 |
| PQBP1 | 0.418668 | ATP5SL | 3.2329 | GAPTCH8 | 3.89108 | LXN | 5.18433 | FBXW17 | 2.40956 | 1110004E09RIK | 2.47062 |
| YIPF6 | 2.38573 | LDHA | 3.23201 | NTSC3 | 0.257359 | NRD1 | 0.193068 | GM6055 | 0.415127 | DUSP10 | 2.40978 |
| PPP1R15A | 2.38156 | CTPS2 | 3.22448 | 2410017P09RIK | 0.257389 | 1110002B05RIK | 5.17424 | COL11A2 | 2.40794 | 2610030H06RIK | 0.406121 |
| PHF20 | 0.420072 | GLMN | 3.22116 | UTY | 3.87871 | AL844854.1 | 5.17249 | 1700034H14RIK | 2.4071 | SSSCA1 | 0.40619 |
| GM9775 | 0.420155 | ZMAT5 | 0.310823 | 1110012L19RIK | 0.258256 | MCCC2 | 5.16899 | HNRNPM | 2.40693 | LGLS3BP | 2.46169 |
| H2-Q10 | 2.37859 | COMMD4 | 3.2157 | CCNH | 3.86755 | MRPL17 | 5.15904 | BOLA1 | 0.415547 | MTM1 | 2.45805 |
| PHB2 | 2.37696 | PIGP | 3.21334 | ANKRD32 | 0.258792 | RPP38 | 0.194425 | MNDAL | 2.40581 | ENTPD5 | 0.40683 |
| BTF3L4 | 2.37421 | CNPY2 | 3.21207 | TBC1D7 | 3.85399 | LGTN | 5.13435 | BIRC5 | 2.40443 | TBCB | 2.4579 |
| HSCB | 2.36574 | CHCHD8 | 3.21086 | XLR4A | 3.85399 | GM16181 | 5.13293 | FOXP1 | 2.40424 | GM2178 | 0.406996 |
| A930005H10RIK | 0.122718 | HNRNPH1 | 3.20272 | NINJ1 | 0.259964 | ORC4 | 0.19501 | ANKRD13D | 2.4039 | CCDC77 | 2.45456 |
| PPP2R2C | 0.422829 | LCORL | 3.20242 | 2610001J05RIK | 0.260073 | SCARB1 | 5.12455 | AI452195 | 2.40212 | ZEP259 | 0.407721 |
| ATG13 | 2.36443 | TMEM69 | 3.20107 | 4930579G24RIK | 0.260613 | DOT1L | 5.11575 | ARL8A | 0.416667 | ZDHHC12 | 0.407944 |
| AATF | 2.36391 | S100A6 | 3.19886 | GM14326 | 0.260714 | MRPL23 | 5.11274 | ARMCX6 | 0.4168 | GSK3B | 0.408054 |
| CDK1 | 0.423207 | NFX1 | 3.19883 | STARD3NL | 3.83561 | COMMD3 | 0.19575 | TRIM56 | 2.42794 | RMND1 | 0.408142 |
| RABGGTB | 0.423371 | PDCD6IP | 3.19865 | VPS39 | 3.83015 | FLAD1 | 0.195774 | RAB43 | 2.39609 | GM13147 | 0.40828 |
| PNRC2 | 0.423764 | ZRSR2 | 3.19603 | ERCC1 | 3.82564 | MRPS11 | 5.10387 | FGD3 | 2.39565 | AIM2 | 2.44856 |
| HDAC1 | 2.35879 | ABHD11 | 3.19565 | APPL2 | 3.82255 | IFNGR2 | 5.10147 | TRIM37 | 2.39431 | UHRF1 | 2.44582 |
| GTF3C2 | 2.35778 | CNBP | 3.18437 | MKRN1 | 0.26168 | COX10 | 0.196107 | NDUFB4 | 2.3924 | DUSP19 | 0.409179 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| PPIL2 | 2.35711 | GM10801 | 3.18078 | PTP4A1 | 0.261791 | ENDOG | 0.196494 | DUT | 0.417992 | BC023814 | 2.44176 |
| TUBB2C | 2.35326 | H2-D1 | 3.17421 | STK11 | 3.80655 | GLS | 5.08921 | INSR | 2.38695 | TBX21 | 2.44142 |
| UBE2W | 2.35082 | SPATA5 | 3.17178 | GM10490 | 3.80099 | UBE2E3 | 5.08578 | MTF1 | 0.419149 | LIFR | 2.43915 |
| NEIL1 | 2.34342 | PSG23 | 0.315546 | TMEM50B | 0.263502 | MRPL41 | 0.196729 | FANCE | 0.419595 | COMMD5 | 0.410351 |
| UBE2A | 0.426773 | BRD3 | 3.16708 | GALT | 0.264371 | NUBP1 | 5.08253 | 0610037L13RIK | 2.38209 | RGP1 | 2.43434 |
| SLC25A39 | 0.427532 | CAPZA1 | 3.16705 | NAA35 | 0.264406 | DGUOK | 5.0798 | STK32C | 2.3794 | DCAF17 | 2.43375 |
| SIL1 | 2.33407 | ADAM33 | 0.315962 | PCIF1 | 0.26458 | TTC1 | 0.197229 | MRM1 | 0.420347 | TAZ | 0.411156 |
| LY6C1 | 2.33251 | AC131780.2 | 3.16492 | AI413582 | 0.264792 | NUPL2 | 5.06885 | FKBP5 | 2.37896 | THAP7 | 0.411234 |
| H2-KE2 | 2.32733 | A83001N09RIK | 3.15992 | MRPL16 | 0.265274 | FKBP1A | 5.06112 | RPL21-PS14 | 2.37893 | TRAPPC3 | 0.411335 |
| 0910001L09RIK | 2.32723 | GPR19 | 0.31673 | CETN4 | 0.266008 | ABHD10 | 5.05799 | TMEM209 | 0.420712 | MINK1 | 2.42966 |
| RGS1 | 2.32238 | ARHGDIB | 3.1569 | RNMTL1 | 0.266008 | GNPDA2 | 5.05258 | PPP2R2D | 2.37506 | FBXO11 | 0.411741 |
| MFAP3 | 0.4308 | PSPH | 3.14818 | LPL | 3.75591 | UBE2E3 | 5.05027 | SNAP23 | 2.37461 | MCM3 | 0.411754 |
| MTMR4 | 0.430925 | GFPT1 | 3.14709 | SPRYD4 | 0.266657 | 4930470H14RIK | 5.04453 | CHD4 | 0.421301 | UAP1 | 0.412061 |
| ABHD11 | 0.431066 | RC3H2 | 0.31779 | IFT80 | 3.74813 | AMPD2 | 0.198234 | ZFP110 | 2.37356 | 6330577E15RIK | 0.412524 |
| THY1 | 2.3178 | PIAK | 3.146 | GSN | 3.74534 | ZFP386 | 5.03395 | VPS26A | 2.37266 | SEPW1 | 2.42171 |
| 1500031L02RIK | 2.3116 | TIMM23 | 3.14596 | PDCL | 3.74384 | LMF1 | 0.198661 | PNKP | 0.421521 | BAIAP2 | 2.41981 |
| PEMT | 0.432817 | PSMA1 | 3.14408 | AGTPBP1 | 3.7416 | IL2 | 5.02774 | TMEM63B | 0.422363 | USF2 | 0.413563 |
| CDK2AP1 | 0.432935 | FANCE | 0.318156 | LUC7L | 3.73929 | ANKHD1 | 0.199012 | DNAIB11 | 2.36543 | FOLR4 | 2.41563 |
| RAD54L | 0.434173 | CDCA7 | 0.319438 | ECE2 | 0.267644 | TSPAN14 | 5.01152 | TYMP | 2.36431 | RAB14 | 0.414768 |
| SMU1 | 0.434279 | RPP30 | 3.12774 | 1810074P20RIK | 3.73582 | AC122006.1 | 5.01152 | NDUFA10 | 0.423107 | CRYZL1 | 0.415122 |
| SMPD2 | 0.434936 | ME2 | 3.12344 | GTF2H4 | 3.72869 | MAP3K5 | 0.199854 | DARS2 | 2.36275 | BRCC3 | 0.415153 |
| IFI27L1 | 2.29594 | NAA20 | 3.12119 | 1110058L19RIK | 0.268254 | CASP2 | 0.4978 | CUL1 | 2.36253 | WDR3 | 0.41543 |
| RSL24D1 | 2.29428 | PKP4 | 0.320792 | GM10212 | 3.72679 | TTC23 | 4.99638 | PAPD5 | 0.423809 | FAM60A | 0.415574 |
| SFRS18 | 0.436007 | FYTTD1 | 3.1168 | TMEM93 | 3.72279 | GM10695 | 4.9814 | 2700097O09RIK | 2.35561 | CAPN2 | 0.415688 |
| PIK3CD | 0.436753 | PKN1 | 3.11594 | GRCC10 | 3.7191 | ETV4 | 4.97154 | D4ERTD22E | 2.35549 | ADPGK | 0.415859 |
| HVCN1 | 2.28932 | 4933421E11RIK | 3.11448 | TFG | 3.71634 | HSD3B2 | 0.201313 | GTF3A | 0.424646 | ADSSL1 | 0.41591 |
| SEMA4D | 0.436848 | CDC23 | 3.09954 | BRCC3 | 0.269708 | ESF1 | 4.94502 | ARNT | 2.35173 | MARCKSL1 | 0.415994 |
| BC003266 | 2.28841 | CLDND1 | 3.09523 | PDK3 | 3.70624 | SNX17 | 0.201338 | PARD6A | 0.3498 | AGTPBP1 | 2.40301 |
| FAM165B | 0.43747 | ACTR2 | 3.08416 | GGCT | 0.269918 | CCND3 | 0.202376 | INTS2 | 2.34851 | RUFY1 | 0.417223 |
| IL24 | 2.28483 | ESF1 | 3.07944 | TM9SF1 | 3.70468 | NSMCE2 | 4.93656 | ATPSK | 2.34778 | PROCR | 0.41754 |
| TBPL1 | 2.28311 | STAT1 | 3.07825 | EDC3 | 0.270247 | TYM5 | 4.93404 | DNAJA1 | 2.34478 | HSD3B2 | 2.39353 |
| CPNE8 | 0.438106 | FPR2 | 0.325105 | OSBPL9 | 3.69825 | KRT19 | 4.93225 | ADK | 0.426564 | L7RN6 | 0.418484 |
| ANKRD37 | 2.28006 | 1700047G07RIK | 0.32513 | ACADM | 0.270559 | STXBP3A | 4.91429 | ABHD11 | 2.34376 | VWA5A | 0.41858 |
| MSL3 | 2.27915 | PLEKHA2 | 3.07279 | 2900010J23RIK | 0.270662 | RHOQ | 4.90855 | GM5830 | 2.34002 | TESC | 2.38873 |
| PIGF | 0.439112 | EIF3E | 3.07275 | PMS1 | 0.270738 | CRCP | 4.90201 | KPNB1 | 2.33972 | LAP3 | 0.419111 |
| EPHX4 | 2.27228 | POR | 3.07274 | 6530401N04RIK | 3.68326 | 1700049G17RIK | 0.204421 | IFNAR1 | 2.33894 | BIN3 | 2.38331 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL6-96 h-1 | | GPR65-KO- IL1B + IL6 + IL23-96 h-1 | | PLZP-KO- IL1B + IL6 + IL23-48 h-1 | | PLZP-KO- TGFB1 + IL6-48 h-1 | | TOSO-KO- IL1B + IL6 + IL23-96 h | | TOSO-KO- IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| 1500002O20RIK | 2.26953 | NSUN5 | 0.325629 | DLGAP4 | 0.271558 | FOXM1 | 0.204562 | DNAJB4 | 0.427629 | ZDHHC21 | 2.38218 |
| BCAT1 | 0.440655 | BHMT2 | 0.325884 | PAFAH1B3 | 0.271558 | TLCD2 | 4.88197 | XPO6 | 2.33846 | TRAF3IP3 | 2.37848 |
| ZFP58 | 0.440674 | ACAT1 | 3.06557 | UTP3 | 0.271746 | RDH9 | 4.8736 | FAR1 | 2.33826 | SLC25A10 | 0.420602 |
| AHSA2 | 0.441142 | SLC12A8 | 0.326475 | GM7609 | 3.67655 | DBFC2B | 0.205823 | RAB31 | 0.42773 | WDR73 | 2.37632 |
| AC154631.1 | 0.441629 | MRPL23 | 3.05711 | C630004H02RIK | 0.272053 | LSM2 | 4.85528 | POLR2L | 2.33638 | PIF1 | 2.37403 |
| FERMT3 | 2.2639 | MAPK8IP3 | 0.327393 | SIRT4 | 0.272685 | WAC | 4.8472 | CYB561D2 | 0.429112 | SUV420H2 | 2.36921 |
| PDCD2L | 0.441746 | SUMO1 | 3.05309 | 2700007P21RIK | 0.273377 | 1700021F05RIK | 4.83563 | KPNA2 | 0.429464 | PHYHIPL | 2.36779 |
| LYRM4 | 0.442065 | TESC | 3.05301 | TRIT1 | 0.273748 | DSN1 | 4.82271 | 5730601F06RIK | 0.429723 | TMEM97 | 2.36561 |
| PHOSPHO2 | 0.4425 | TMEM9B | 3.05154 | TMC5 | 3.65153 | GM9894 | 0.207352 | PIGQ | 0.429912 | HOOK2 | 0.422724 |
| OIP5 | 2.582 | ZFP637 | 3.04922 | GM5244 | 3.63364 | FBXW9 | 0.207469 | AURKB | 0.430777 | GMFG | 2.36501 |
| PGAM5 | 2.25599 | MRPL24 | 3.04409 | GDE1 | 0.275214 | PGAM5 | 4.81491 | TH1L | 2.32119 | NOL11 | 0.422881 |
| GM6293 | 2.25379 | TBCB | 3.04279 | GTF2H3 | 3.62942 | GM5576 | 0.207801 | FAM184A | 0.42773 | CLTB | 2.3623 |
| PDSS1 | 0.444757 | ETS1 | 3.04198 | GNPAT | 0.27554 | SNAP23 | 4.81051 | GSTT3 | 0.431811 | FAM136A | 2.35444 |
| VBP1 | 0.445036 | SDR39U1 | 3.04125 | HSD3B2 | 0.3278 | C2CD3 | 4.81043 | CHD8 | 0.432011 | MOSPD3 | 0.425477 |
| IFT46 | 0.445227 | SERPINB1C | 3.03727 | DCP1B | 0.275893 | HMOX1 | 4.80258 | ODF2 | 2.31431 | PHF7 | 2.34785 |
| GPR174 | 0.445264 | FABP5 | 3.03405 | DHX32 | 0.275893 | HDDC2 | 0.208325 | GM16380 | 0.432609 | ITGB1 | 0.426033 |
| TES | 0.445357 | 1110003E01RIK | 0.329743 | GM5617 | 3.62459 | HSPA12B | 4.79693 | DHX32 | 2.31124 | TWF1 | 2.34335 |
| H2-Q2 | 2.24237 | UQCRC2 | 3.02946 | ZCCHC7 | 0.275933 | CCDC34 | 4.79632 | CELF2 | 0.432691 | CTSO | 2.33801 |
| GAPVD1 | 0.446533 | MGAT4C | 0.330276 | CASP8AP2 | 0.276211 | TMU82 | 4.79307 | TUT1 | 2.31019 | ACP5 | 0.427721 |
| PANX1 | 0.447449 | TIPIN | 3.02717 | DPF2 | 0.276612 | AC142104.1 | 4.79143 | AFF1 | 2.30981 | RBM43 | 2.33786 |
| RBM38 | 2.23439 | RPS6KB1 | 3.02517 | MBD5 | 3.61261 | CDK5RAP1 | 0.209144 | POMP | 0.432971 | TMC5 | 0.427846 |
| PUM1 | 0.448127 | APOBEC3 | 3.02458 | CERKL | 3.60774 | TMBIM1 | 4.77378 | PITRM1 | 2.30782 | GM3435 | 2.33728 |
| PER1 | 2.22917 | POLR2F | 3.02026 | THUMPD3 | 0.277258 | IL11 | 0.209998 | CYBSD1 | 2.3069 | WASL | 0.42835 |
| MAEA | 0.44936 | TMEM218 | 3.01908 | LMF1 | 3.60375 | NIPSNAP3B | 4.75276 | MED25 | 0.434109 | ANKRD16 | 0.429125 |
| RBP7 | 0.449786 | 1700123O20RIK | 3.01794 | ARRDC1 | 3.60208 | CDC40 | 0.210631 | MTUS2 | 2.30321 | GM5577 | 2.32926 |
| PPIL5 | 2.22281 | OSBPL2 | 3.01609 | GIMAP9 | 3.59942 | ZC3H10 | 4.74138 | AAGAB | 0.434276 | 1810009A15RIK | 2.3291 |
| TIMM8B | 0.450513 | RBMXRT | 0.3158 | CIZ1 | 0.278323 | DEPDC5 | 4.73809 | GTPBP5 | 2.30251 | LRRC40 | 0.429404 |
| TKT | 0.4519 | PTMA | 3.01477 | ALG9 | 3.59128 | CDCD6 | 4.73184 | SLAIN1 | 2.3004 | 42068 | 0.429453 |
| GM4877 | 2.21139 | RBM22 | 0.331773 | ADRBK1 | 0.278702 | ZDHHC12 | 0.211334 | ZFP609 | 2.30028 | ACSS2 | 2.32433 |
| TTC23 | 0.452772 | SAT1 | 3.01393 | INSL6 | 3.57822 | 4930522L14RIK | 4.72965 | TRUB2 | 0.434877 | GM4825 | 2.32323 |
| DPYD | 0.452878 | 2410004P03RIK | 0.332288 | KANK3 | 0.278823 | METTL8 | 0.211536 | VMAC | 2.29809 | H2-Q7 | 0.430584 |
| FAM103A1 | 0.45312 | ADAMTSL4 | 0.332405 | VPS4B | 0.279789 | DCTN3 | 4.72301 | S100A1 | 0.435407 | STARD3 | 0.431148 |
| CYB5R3 | 0.453256 | D4WSU53E | 3.00463 | PTTG1IP | 0.279925 | BCCIP | 0.211808 | TOMM40L | 2.29491 | MPHOSPH9 | 0.432089 |
| GPR89 | 2.20106 | GM6104 | 0.333215 | ZFP738 | 3.56755 | CDKN2AIPNL | 4.71636 | INTS12 | 0.435833 | METT5D1 | 0.432492 |
| PICK1 | 0.454538 | PRPSAP1 | 0.33323 | NDRG1 | 3.5565 | PIGN | 4.71511 | BC031181 | 2.29133 | MYG1 | 2.31213 |
| ARL6IP4 | 2.19989 | GM10979 | 0.333439 | CENPH | 3.55546 | PIGQ | 0.212219 | ZFP60 | 2.29105 | PPIH | 0.432492 |
| | 2.1967 | ING3 | 2.99657 | MLH1 | 0.281258 | RBM28 | 0.212315 | DBR1 | 0.436565 | EIF5 | 0.433605 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| H2-K2 | 2.19661 | SMARCA5 | 2.99274 | GIT2 | 3.5547 | TARBP2 | 4.70756 | RBM34 | 2.29054 | SNRNP35 | 0.433755 |
| GDE1 | 0.455548 | SRP19 | 2.98391 | CDC20 | 0.281777 | AC161001.1 | 4.70369 | KIF21B | 2.2878 | 0610011F06RIK | 0.43426 |
| AC079644.1 | 2.19361 | INPP5F | 0.335351 | EXOSC4 | 3.54589 | CDK14 | 4.70157 | UBN2 | 2.28747 | PPAN | 0.434394 |
| GM16381 | 2.19361 | STX6 | 0.335692 | TRPM1 | 0.282101 | RAD18 | 0.212948 | BAT5 | 2.28739 | ATP13A3 | 0.434517 |
| GM2001 | 2.19361 | GM10123 | 2.97672 | CMAS | 3.54427 | DPY19L4 | 4.69293 | RGS19 | 2.2834 | ELOVL1 | 0.434824 |
| GM5670 | 0.455882 | CCT5 | 2.97616 | HCFC2 | 3.53925 | HIBADH | 4.68299 | TM9SF1 | 0.438314 | GM7935 | 0.435003 |
| LEPR | 2.1916 | NT5C3 | 2.97287 | ADIG | 3.53563 | HNRNPL | 0.213539 | XBP1 | 0.43854 | 2310045N01RIK | 2.29852 |
| HOPX | 2.1894 | PIM2 | 2.97224 | CATSPER4 | 3.53563 | FAM175A | 4.68088 | H6PD | 2.27792 | 4930555F03RIK | 2.2952 |
| CLSPN | 2.18611 | LY6E | 2.96994 | HERPUD1 | 0.282919 | SYTL3 | 4.66871 | SEMA4A | 0.438999 | MRPL16 | 0.435779 |
| AKR1B8 | 0.457558 | TTLL4 | 2.96786 | IQCC | 0.282927 | GGA3 | 4.653 | RABEP2 | 2.27703 | CYBASC3 | 0.436256 |
| GRCC10 | 2.18497 | PTPRC | 2.95901 | EIF2B4 | 0.283034 | IFFO2 | 4.65076 | RG9MTD3 | 2.27613 | HIST1H2BB | 2.29128 |
| POLE4 | 0.457719 | PKM2 | 2.95759 | S100A6 | 0.2837 | POLB | 4.64779 | 2610020H08RIK | 0.439923 | GBP5 | 2.29067 |
| GPRASP2 | 0.457873 | SYCP1 | 2.95358 | TGS1 | 0.283813 | GM2938 | 4.64434 | MPDU1 | 2.27308 | WDR77 | 0.436786 |
| BC056474 | 2.18157 | ACOT13 | 2.95291 | PCCB | 0.283949 | GRAMD3 | 4.64089 | HEMK1 | 2.27166 | 1700034H14RIK | 0.436958 |
| CIDEC | 0.458486 | ADAM19 | 0.339011 | FOXK2 | 3.52152 | 9430023L20RIK | 4.63579 | NDOR1 | 0.440514 | RBM7 | 0.437622 |
| FNBP1 | 0.458881 | 1110065P20RIK | 2.94794 | LY6C2 | 3.51312 | ATPBD4 | 4.63232 | BZRAP1 | 0.440638 | BRWD1 | 0.437664 |
| SAE1 | 2.17964 | AIMP2 | 2.94187 | METT11D1 | 3.50825 | CREBL2 | 4.62929 | SRBD1 | 2.26829 | WDR46 | 2.28303 |
| TFIP11 | 0.458874 | RDM1 | 2.9385 | ARID4B | 0.285507 | HDHD3 | 0.216275 | RDH14 | 2.26786 | 4930534B04RIK | 2.28142 |
| RPL30-PS6 | 2.17678 | ZCRB1 | 0.340327 | SGK1 | 3.4986 | GSS | 4.62133 | DAZAP1 | 0.441077 | 4933427I04RIK | 2.27929 |
| ADAR | 0.459489 | DAPK2 | 0.340716 | 8430423G03RIK | 3.49655 | POLD4 | 4.61637 | TRIB3 | 0.441663 | BC023829 | 0.439785 |
| PGS1 | 2.17398 | LRRC41 | 0.341072 | EXTL2 | 3.49509 | DNAJB11 | 4.61387 | 2810422O20RIK | 2.26358 | SGSM3 | 2.27323 |
| GPP107 | 0.460142 | STARD3NL | 2.93172 | CENPK | 0.286116 | CDK2AP2 | 4.60874 | STX2 | 2.26259 | TOR1B | 0.440344 |
| TIMM17B | 2.17137 | GM11152 | 0.341478 | PAM16 | 4.935 | VPS36 | 4.60218 | GABPB2 | 2.26178 | FLAD1 | 0.440699 |
| STAM2 | 2.1672 | MRPS18A | 2.91805 | RALB | 3.49078 | FAM126A | 0.217596 | FAM126A | 2.26122 | VEPH1 | 2.26833 |
| GAA | 0.461615 | ORMDL3 | 0.343151 | ZBED4 | 3.48917 | TMEM106C | 4.58509 | TFB2M | 2.25777 | 6030422M02RIK | 2.26531 |
| TRAPPC3 | 0.461743 | GHITM | 2.91234 | STIM2 | 3.48912 | ZFP353 | 4.58439 | ECHDC1 | 2.25729 | SCARB2 | 0.44166 |
| PAFAH13B | 2.16551 | STRN4 | 0.343765 | 4930547N16RIK | 0.286625 | PHRF1 | 4.57943 | ANKRD32 | 2.25421 | ST6GALNAC6 | 2.26353 |
| PRAMEL6 | 0.461853 | AZI2 | 2.90738 | TRPC2 | 0.286652 | PDDC1 | 0.218373 | EPHA2 | 0.444115 | NRF1 | 0.442264 |
| LPHN3 | 0.462371 | GM7030 | 2.90617 | ING3 | 3.4874 | CORO7 | 4.57843 | NSUN3 | 0.444483 | GJC3 | 2.26072 |
| PCBP3 | 2.16243 | RTP3 | 0.34424 | DGCR6 | 3.48344 | GIT2H4 | 4.57703 | SHARPIN | 2.24975 | PPPDE2 | 0.442814 |
| SRSF3 | 0.46284 | COPS2 | 2.90125 | BOLA1 | 0.287478 | TTC35 | 4.57584 | LRRC8C | 2.24954 | L1CAM | 0.442979 |
| PET112L | 0.465325 | GM10451 | 0.344691 | HIST1H4D | 0.287839 | 6030408B16RIK | 4.56696 | ATP2B4 | 0.2494 | RPAP2 | 2.25699 |
| 1500012F01RIK | 0.465366 | CALM2 | 2.90089 | GM2938 | 3.46952 | JAK1 | 4.55797 | RASL118 | 2.2486 | DPY19L4 | 0.443354 |
| SHISA5 | 2.14857 | ICAM1 | 2.89977 | PSAP | 3.45928 | PRAMEF8 | 4.55729 | TTI1 | 2.24819 | MFN2 | 0.443758 |
| SH2D3C | 0.46601 | HSPA14 | 2.89926 | AC161211.2 | 3.45693 | GTPBP8 | 4.55576 | RFXAP | 2.24717 | CCDC84 | 0.444341 |
| MRPS28 | 0.466172 | MED14 | 2.8974 | SLC16A6 | 0.289278 | FAM162A | 0.219795 | LRRC33 | 2.24323 | NR4A2 | 0.444708 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| IL4 | 0.467198 | EBP | 2.89522 | GNPDA2 | 0.289466 | CNOT6L | 0.219928 | AC101875.1 | 2.23945 | PARVA | 2.24781 |
| HNRNPC | 0.467546 | ACAT3 | 2.89508 | COX17 | 3.44155 | MTUS2 | 4.54291 | CDK5RAP1 | 2.23785 | CCPG1 | 0.445004 |
| RTF1 | 2.13572 | 2310035K24RIK | 2.89501 | MPDU1 | 3.44092 | ZMYND11 | 4.53646 | SETDB1 | 0.447154 | H2AFX | 2.2465 |
| IDH3G | 2.13392 | BC057079 | 0.345461 | PNPLA7 | 3.4408 | SFPQ | 0.220524 | TELO2 | 0.447155 | MRPL1 | 2.24561 |
| MF5D2A | 0.469366 | CRISP4 | 0.345759 | COX10 | 0.291276 | THUMPD3 | 0.22081 | VTA1 | 2.2359 | 2900097C17RIK | 2.2443 |
| CLN3 | 0.470116 | SNRNP25 | 0.346171 | SETD5 | 3.43074 | DNAJB6 | 4.52642 | ZFP426 | 2.23532 | ADI1 | 2.24225 |
| CYP51 | 0.470341 | ARRB1 | 0.346338 | TNF | 3.42383 | CENPH | 0.221034 | MSL3 | 2.23499 | GRAP2 | 0.446283 |
| CARS | 2.12414 | GM10719 | 2.88708 | TRAPPC6B | 0.292286 | STK38L | 4.51851 | SSNA1 | 2.23311 | IKZF3 | 2.24007 |
| ACAT3 | 0.471553 | AL603711.1 | 0.346453 | ERI3 | 3.4132 | ZFP110 | 0.221331 | SNRPG | 0.448137 | UTP6 | 0.44674 |
| ETFB | 2.11968 | SLC25A1 | 2.88624 | USP33 | 0.29313 | ZDHHC6 | 4.51423 | SLC28A2 | 0.448712 | LCORL | 0.447019 |
| ATRIP | 0.472654 | CLK2 | 2.88431 | DIAP1 | 0.293347 | GMS623 | 2.27748 | EXOSC7 | 2.27748 | SEC23B | 2.23703 |
| NSMCE1 | 2.11554 | GM11042 | 0.346709 | PKP3 | 0.293441 | HIST1H4K | 4.51023 | HELZ | 0.44939 | LEPREL2 | 2.23611 |
| DHRS1 | 0.473178 | LGALS4 | 0.347111 | DCBLD2 | 3.40187 | UBE2K | 0.221837 | MGAT4A | 2.22469 | GM9762 | 0.447916 |
| GM10250 | 0.473386 | CCDC97 | 2.87776 | IKBKB | 0.293957 | AL732476.1 | 4.5064 | C330027C09RIK | 2.22406 | SLC25A23 | 0.448019 |
| SVOP | 2.11244 | PDCD1 | 0.347471 | PRPF3 | 0.294636 | RPF1 | 0.222192 | FAM33A | 2.22079 | MRPS33 | 2.23185 |
| GBP3 | 0.473443 | CAPRIN2 | 0.347865 | FNBP4 | 3.39347 | EFTUDI | 0.222611 | DIS3L2 | 2.22056 | CDRO2A | 0.448298 |
| TSPO | 2.11212 | NDUFB11 | 2.87217 | PHOSPHO2 | 0.294693 | METTL6 | 0.222665 | PRPS2 | 0.450339 | STK17B | 0.448479 |
| FAM45A | 0.473528 | SLC5A11 | 0.34834 | NFYC | 0.294786 | AGA | 0.222796 | ELP4 | 2.21858 | YKT6 | 0.44781 |
| NEK2 | 2.1112 | NDUFA8 | 2.86842 | MCOLN2 | 3.3836 | MGST2 | 4.486 | GLRX2 | 2.21715 | RCBTB2 | 0.449053 |
| DGAT1 | 0.474097 | BUB1B | 2.86674 | DPAP1 | 0.295633 | PMPC8 | 4.47916 | TCP11L1 | 2.21687 | GIT1 | 2.2222 |
| CENPH | 0.474097 | RHBDL2 | 0.349214 | NFYB | 3.37877 | LZTFL1 | 0.223606 | NFS1 | 2.21653 | AC156948.1 | 2.22018 |
| SGSM3 | 0.474555 | CYBS | 2.86303 | MRPL2 | 0.296363 | DTWD1 | 4.47201 | TMC6 | 0.451846 | LEO1 | 0.450433 |
| TRIM30B | 0.474604 | PDCD1 | 2.86295 | DTWD1 | 0.29648 | REPS1 | 4.46966 | MYEOV2 | 2.11222 | MVP | 0.45048 |
| FDXR | 0.47544 | CAPRIN2 | 0.349369 | GM10033 | 3.37291 | REXD4 | 4.46788 | PFDN2 | 0.452543 | RDM1 | 2.21862 |
| TOMM20 | 2.10061 | DHRS1 | 0.349492 | STRN4 | 3.36855 | MRPS15 | 4.46494 | TMEM161A | 2.20829 | FAM192A | 2.2176 |
| PDAP1 | 0.477104 | SH3GLB1 | 2.85718 | SEC61A2 | 0.296884 | RAC1 | 0.223967 | CHRM4 | 2.2041 | TBL3 | 2.21522 |
| PTPMT1 | 2.09393 | TCF4 | 0.350483 | ACER2 | 3.3672 | EIF4ENIF1 | 4.43929 | E130309D02RIK | 0.453787 | 1110008L16RIK | 2.21368 |
| SIGMAR1 | 0.478621 | TRIAP1 | 2.85065 | BUB1B | 0.297187 | NRF1 | 4.43836 | NPEPPS | 2.20295 | UVRAG | 0.452127 |
| BBS7 | 0.47905 | FUBP3 | 2.84969 | GTDC1 | 3.36386 | SPINT2 | 0.225426 | DNAJB2 | 0.454667 | GLRX5 | 2.20846 |
| TNFSF13B | 0.479792 | CENPF | 0.351001 | GADD45G | 3.36234 | PLOD2 | 4.43373 | GM2178 | 0.454756 | 2510003E04RIK | 0.452882 |
| PARP2 | 2.08299 | LY6F | 2.84688 | TM2D2 | 0.297412 | NDUFAF2 | 4.43157 | MS4A6B | 2.19789 | NUFIP2 | 0.453053 |
| NUDT3 | 2.08262 | GM14181 | 0.35151 | TOMM34 | 3.35824 | ABHD6 | 0.225748 | DOS | 2.19472 | TK1 | 0.453355 |
| TTC5 | 2.08224 | TPI1 | 2.84474 | DYNLL2 | 0.297932 | GTF3C5 | 4.42774 | TBX21 | 2.19238 | PPP1R12A | 0.453602 |
| LRRC24 | 0.480779 | LMNA | 2.83893 | MTERFD1 | 3.35647 | TXNIP | 4.41587 | FBXO44 | 0.456012 | MAX | 2.20405 |
| NAA20 | 0.48164 | TMEM55B | 0.352678 | TFAM | 3.35624 | SNX3 | 0.226596 | CTLA2B | 2.1924 | PLIN2 | 0.453764 |
| EIF1AX | 0.481816 | IFI47 | 2.82703 | FLT3L | 3.34759 | TM9SF4 | 4.41067 | 4921517L17RIK | 2.19238 | DNAJA2 | 0.453795 |
| MRPS36 | 0.481983 | GMS145 | 2.82597 | NOL7 | 0.298838 | BBS9 | 4.40793 | AC165266.1 | 0.456577 | MTF2 | 0.453888 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- TGFB1 + IL6-96 h-1 | | PLZP-KO- IL1B + IL6 + IL23-96 h-1 | | PLZP-KO- IL1B + IL6 + IL23-48 h-1 | | PLZP-KO- TGFB1 + IL6-48 h-1 | | TOSO-KO- IL1B + IL6 + IL23-96 h | | TOSO-KO- IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| COX6B2 | 0.482287 | ADK | 2.82127 | CTSE | 3.34344 | SEC23A | 4.40537 | PPRC1 | 2.18911 | F2RL1 | 2.16781 |
| GTPBP8 | 0.482307 | AC149585.1 | 0.35473 | 281042210SRIK | 3.34306 | UBLCP1 | 4.40451 | BCAS3 | 0.457248 | FBXO3 | 0.455736 |
| CHI3L1 | 0.482918 | NAT9 | 2.81543 | MIA1 | 3.34135 | NT5C | 4.40436 | PSMB6 | 0.457575 | GM10417 | 2.19193 |
| SIGIRR | 2.07058 | XRN2 | 2.81516 | EIF4H | 0.299847 | POLR2H | 4.40262 | TMEM120B | 0.457765 | ZER1 | 0.456295 |
| GM11273 | 2.06922 | SCMH1 | 0.355375 | THAP7 | 0.300809 | CDC42SE1 | 4.40229 | CDK16 | 2.1831 | PREX1 | 0.456446 |
| GM9830 | 0.483586 | GM5160 | 2.81271 | CREB1 | 3.32323 | TNFAIP3 | 0.227358 | 2310011J03RIK | 2.18273 | RPL21-PS7 | 0.456737 |
| DBR1 | 0.483831 | HFM1 | 0.355716 | GM2833 | 0.300988 | PRR15 | 0.227365 | GPR89 | 0.458367 | IGSF8 | 0.456869 |
| LEPREL1 | 0.483856 | D18ERTD653E | 2.80732 | SRSF9 | 0.301296 | TNFSF13B | 4.3957 | ARL5C | 2.18109 | MAPK3 | 0.457086 |
| CRYZL1 | 0.485628 | ADAMTSL5 | 0.356243 | PFDN2 | 0.301424 | NUDC | 0.227573 | GSTK1 | 0.45855 | 5730469M10RIK | 2.1868 |
| CCDC127 | 0.484085 | ARHGAP4 | 2.80704 | PIGYL | 3.31608 | ZFPL1 | 4.3942 | DSTN | 2.18006 | SEMA4D | 0.457713 |
| RNF7 | 2.05833 | PRAMEF8 | 2.80697 | GM8055 | 3.31475 | C2 | 0.227783 | SEC23B | 0.458803 | MYCBP2 | 2.18452 |
| ACTC1 | 2.05784 | CCR7 | 2.80169 | REST | 0.30191 | NGRN | 0.227815 | FTSJ1 | 2.17933 | STX8 | 2.17767 |
| GM8815 | 2.05722 | G3BP1 | 2.80063 | SP100 | 3.31134 | CRYZL1 | 4.38778 | MEF2A | 0.459317 | NOL12 | 2.17683 |
| TBC1D10C | 2.05628 | HSD17B12 | 0.357385 | OAS1G | 0.302131 | PSMD5 | 4.38291 | CDK2AP1 | 2.17715 | TOP3B | 0.460001 |
| OSCAR | 0.486345 | HSDL2 | 2.80704 | PFDN2 | 3.30054 | CBLL1 | 0.229251 | TANK | 2.1771 | HECTD2 | 0.460161 |
| GM8909 | 2.05336 | SDHD | 2.79789 | RASA1 | 3.29877 | FOLR4 | 4.36204 | AC125221.1 | 0.459349 | IKBKAP | 0.460335 |
| NCOA7 | 2.05066 | LRRK1 | 2.79732 | MAPKAPK5 | 0.303347 | PRMT1 | 4.36011 | MPHOSPH6 | 2.17579 | DGUOK | 0.460441 |
| TRNT1 | 0.487822 | PSMD5 | 0.35776 | SLC4A1AP | 3.29316 | OPCML | 4.35887 | GM7367 | 2.1738 | R3HDM2 | 0.460494 |
| AIRE | 2.04966 | HSD17B12 | 2.79458 | SQSTM1 | 3.29302 | CD200 | 0.229479 | AC163101.1 | 0.460169 | STIM2 | 2.17149 |
| MRPS18B | 0.48936 | KIF18B | 0.357954 | COX19 | 0.303672 | HSD17B7 | 4.34864 | CALD1 | 2.17236 | IPO9 | 0.460607 |
| AC113307.1 | 0.490348 | GTF2E2 | 2.79364 | GM12184 | 0.304115 | OTUD7B | 4.34571 | ZFP125 | 2.17183 | TCP11L1 | 2.17006 |
| PA2G4 | 0.490583 | RP23-147O14.1 | 2.79357 | MAPKAP1 | 0.304377 | ZCCHC9 | 4.3401 | ALG5 | 0.460528 | UQCRC1 | 0.46127 |
| | | | | TRMU | | | | | | | |
| VPS8 | 0.490681 | ACNAT1 | 2.79048 | ITGB1 | 0.30453 | ITGAM | 0.230433 | CNIH4 | 2.17113 | DYNC1H1 | 2.16781 |
| UBE2F | 0.490797 | GOSR2 | 2.78985 | 8430410A17RIK | 3.28293 | TIAL1 | 0.230539 | GM10180 | 2.17074 | TM7SF3 | 2.16685 |
| DDX50 | 0.491492 | SNRPE | 2.78815 | TMEM106B | 3.27349 | KATNAL2 | 4.33361 | NAPG | 0.460711 | PAPOLG | 2.16558 |
| LCTL | 0.491521 | 3110057O12RIK | 2.78673 | TUBD1 | 0.305922 | FTD | 0.231057 | CCNK | 0.460907 | UBEIY1 | 2.16452 |
| PWP1 | 2.03349 | TBPL1 | 2.78564 | GET4 | 3.26735 | SLC12A8 | 4.3262 | 1110014N23RIK | 0.461185 | COPG | 0.462215 |
| TMEM167 | 0.491829 | 5730437N04RIK | 2.78518 | ZFP560 | 0.306077 | GM6624 | 4.32377 | NDEL1 | 2.16644 | CREB3 | 0.46359 |
| TRABD | 2.0272 | FGGY | 0.359534 | RG9MTD3 | 0.307657 | CEP63 | 0.231391 | TOM1L2 | 2.16555 | DHX32 | 2.15693 |
| PCNA | 2.02689 | MAP4K2 | 2.77986 | RPS6KB2 | 3.24669 | TM9SF3 | 0.231488 | VARS2 | 2.16514 | PHRF1 | 2.15662 |
| SFT2D1 | 0.493485 | DIAP1 | 2.77962 | 1500011B03RIK | 0.308119 | ASCC1 | 4.31053 | BBS9 | 0.461886 | RNF220 | 2.15494 |
| IFRD1 | 0.494308 | TUBA1C | 2.7781 | MAP2K5 | 0.308611 | TBCE | 4.30615 | ERH | 0.461997 | DNAJB6 | 0.464138 |
| RPS6KA6 | 0.495289 | AI462493 | 2.77233 | GMS890 | 0.308934 | ELMOD2 | 4.3011 | EVL | 2.1623 | 2210012G02RIK | 0.464892 |
| FBXO4 | 0.495816 | N6AMT2 | 2.77103 | LSM6 | 0.30901 | SMARCD2 | 4.3011 | FAM58B | 2.1614 | TFPT | 0.464973 |
| IRF6 | 2.01593 | PPIA | 2.76671 | SESTD1 | 0.309995 | BUB3 | 4.2996 | 1810014F10RIK | 0.462829 | | 2.14718 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| TIMM13 | 2.0151 | A430093F15RIK | 2.76654 | AIG1 | 3.22462 | SLC20A1 | 4.29733 | BPNT1 | 0.463089 | H2-DMA | 2.14258 |
| HEATR3 | 0.497245 | TSR1 | 2.76595 | SLC25A14 | 0.310115 | GPN2 | 0.233055 | AKAP9 | 2.15875 | UQCRQ | 2.14201 |
| CNN3 | 0.497368 | AC120410.1 | 2.76426 | TMEM39A | 3.22291 | SLU7 | 0.233292 | SLC30A4 | 2.15757 | RBBP6 | 2.14017 |
| GM6351 | 0.498605 | TGOLN1 | 2.76399 | 0610010K14RIK | 3.21932 | M54A6D | 4.27783 | UBTF | 2.15703 | WBSCR27 | 0.467399 |
| RTN3 | 2.00547 | 1810012P15RIK | 0.361885 | AC132397.1 | 0.311155 | VTI1B | 4.27576 | TSR1 | 0.463691 | NLRC3 | 2.13944 |
| OLFR345 | 0.499759 | GM4979 | 0.362023 | WWOX | 3.21153 | PI4KA | 4.27384 | INTS9 | 0.463911 | NAAA | 2.13651 |
| CCDC55 | 0.500381 | TMED7 | 0.362038 | RP9 | 3.20928 | GM10208 | 0.234478 | AC132391.1 | 2.15509 | SRR | 0.468115 |
| GARI | 0.502431 | TRP53 | 2.758 | CHCHD5 | 0.311661 | MLX | 4.25504 | FKBP15 | 2.15391 | BC016423 | 0.468265 |
| CCR8 | 1.98996 | CETN3 | 2.75738 | RANGAP1 | 0.311673 | HAUS7 | 0.235016 | GM13308 | 2.15066 | TMPRSS11BNL | 2.13355 |
| HSDL2 | 1.9894 | CTNNBL1 | 2.75612 | FYN | 0.311934 | ARGLU1 | 4.25041 | TXNRD2 | 0.46555 | MCM6 | 0.468971 |
| RTCD1 | 0.502788 | USMG5 | 2.75505 | GPLD1 | 3.2021 | TGIF1 | 0.235529 | PWP1 | 0.465791 | GABARAP12 | 2.13081 |
| 2900092E17RIK | 1.98882 | ORF19 | 0.363004 | DNAJA1 | 3.1971 | GTF3C2 | 0.235537 | TMEM220 | 2.14674 | MYC | 2.12935 |
| ACLY | 1.9886 | RP23-389D15.1 | 0.363122 | 42253 | 0.312944 | ADM | 0.235992 | PDE7A | 2.14661 | P5ENEN | 2.1288 |
| 1110059E24RIK | 0.503225 | COROIC | 0.363195 | IL23A | 0.313055 | DSCR3 | 0.236114 | CGRRF1 | 0.466117 | ADCK4 | 2.12453 |
| CAPRIN1 | 0.503311 | AC131780.1 | 2.75298 | PRL8A1 | 3.19363 | RNF13 | 4.23063 | IL17F | 0.466476 | 2610020H08RIK | 2.1236 |
| FAM129B | 1.98337 | KBTBD4 | 2.75195 | SEPP1 | 0.313428 | PPAP2C | 4.22014 | HIST4H4 | 0.466639 | COQ6 | 0.470918 |
| MTHFS | 0.504917 | RPL7A-PS10 | 2.75035 | NDUFB7 | 3.18801 | GM129 | 0.237507 | ALDH4A1 | 0.466655 | TRRAP | 2.12216 |
| STAU1 | 1.97701 | 2610204G22RIK | 0.364174 | WDR35 | 0.31374 | CRTC2 | 4.20833 | MRPL20 | 2.14273 | ERGIC2 | 0.471759 |
| TLE6 | 0.505982 | GM10750 | 0.364482 | CSF2 | 0.313826 | ANKRD46 | 4.20651 | CLEC4A2 | 0.466949 | HYOU1 | 0.471895 |
| 1190002H23RIK | 1.97612 | IKZF5 | 0.364538 | RER1 | 0.314012 | TOR1A | 0.237885 | UBXN2A | 2.13985 | PTPRCAP | 2.1184 |
| CD40LG | 1.97553 | NPEPPS | 2.73802 | RECQL | 3.18209 | ZNF512B | 4.19972 | FAM82B | 0.467589 | TOMM70A | 0.472127 |
| STAT5A | 0.506535 | 4932425I24RIK | 0.36533 | STAG1 | 0.314267 | SPRED1 | 0.238232 | HIST1H1B | 0.467605 | TCIRG1 | 0.472379 |
| FHDC1 | 0.506963 | GNL2 | 2.73438 | NKAP | 3.18169 | MRPL50 | 4.19615 | MAP2K5 | 2.13721 | MRPL35 | 2.11517 |
| NRBP1 | 0.507055 | UGT1A6A | 0.366222 | PTGR2 | 3.1815 | ZC3H15 | 0.238561 | STRN | 2.13357 | BRP16 | 2.1119 |
| RHOC | 0.507238 | STAG1 | 0.366399 | SIRT3 | 3.18125 | GINS4 | 0.238992 | GM10736 | 2.13349 | CYB5R1 | 0.473998 |
| SIDT2 | 0.507307 | UBE2I2 | 0.366474 | CCBL1 | 0.314523 | 1700020C11RIK | 0.239037 | CDKN2C | 2.1312 | PFKP | 0.474076 |
| LPCAT4 | 0.507401 | NIPSNAP1 | 0.366488 | KIF3A | 3.17297 | KDELR3 | 0.239351 | EPS15 | 2.13044 | TIMM22 | 0.474165 |
| 1700009P17RIK | 0.50749 | UBC | 2.72581 | 2310061C15RIK | 0.315197 | DUSP23 | 0.239468 | 2510002D24RIK | 0.469557 | PRDX1 | 0.474435 |
| GPN3 | 0.508025 | PDIK1L | 0.367074 | PDHX | 3.17102 | ACAD11 | 4.17327 | VTI1A | 2.12789 | TOP1MT | 2.10729 |
| POP7 | 1.96773 | PFKFB2 | 0.36714 | GALNT6 | 0.316141 | CLCC1 | 4.17103 | CCR8 | 0.469985 | COX15 | 0.474648 |
| TMEM106C | 0.508505 | CCDC93 | 0.367484 | ALG1 | 0.316257 | NDUFA10 | 4.16873 | IRGM1 | 2.12683 | 4934321E11RIK | 0.475088 |
| GBA2 | 0.509279 | ZFP260 | 2.72025 | ORAOV1 | 0.316266 | SEPP1 | 4.16486 | UBE2M | 0.47037 | AIF1L | 2.10471 |
| ING1 | 0.509737 | RNF38 | 0.367695 | PEX3 | 0.316448 | ATG13 | 4.16056 | RELT | 0.470413 | PATZ1 | 0.475465 |
| ATP5G2 | 0.50999 | ADD1 | 2.71941 | TRIM12C | 3.15835 | ING2 | 4.15707 | GBP8 | 2.12493 | NDRG1 | 0.476038 |
| ZMYND15 | 0.510139 | EEF1G | 2.71874 | CR974466.3 | 3.1556 | GM1354D | 0.24064 | MFSD5 | 0.471448 | GM6404 | 2.09989 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h |  |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| RAMP1 | 1.95994 | MARK2 | 0.368465 | WIPI2 | 0.316989 | H2-M3 | 0.240682 | LCMT1 | 0.471778 | SLC35C1 | 0.476217 |
| TUBE1 | 1.95881 | KLF7 | 2.71385 | TRIB2 | 0.317126 | ERP44 | 0.240825 | KPNA6 | 2.1164 | EPB4.1 | 0.476245 |
| COMMD2 | 0.510898 | 5730403B10RIK | 0.368507 | HTT | 0.317342 | OVGP1 | 4.14954 | TMX1 | 2.116 | IL5RA | 2.09889 |
| FAM76A | 0.511198 | TMEM176B | 2.713 | GM10355 | 0.317373 | TEX264 | 0.241296 | BET1L | 2.1144 | DPH3 | 2.09784 |
| OSGIN1 | 0.511961 | IL1F9 | 0.36898 | PABPC1 | 0.317586 | GSPT1 | 4.14142 | ADARB1 | 0.473036 | MED30 | 0.476857 |
| GM10479 | 0.512029 | RNH1 | 2.709 | METTL1 | 3.14705 | MRPL24 | 4.14044 | RPL30-PS6 | 0.473359 | FGF13 | 0.477104 |
| CCDC155 | 0.512097 | TXNDC17 | 2.70692 | BIN3 | 0.317891 | NARFL | 4.13729 | FBXL8 | 2.11176 | LRCH1 | 2.09545 |
| AP2S1 | 0.513282 | ARI3 | 2.70455 | EIF1AD | 0.318045 | HMBOX1 | 0.241991 | CTSL | 0.47388 | PHACTR4 | 0.477394 |
| GM5356 | 1.94757 | NAPG | 2.70085 | SLC7A3 | 0.318191 | MRPL40 | 4.13221 | 0610007C21RIK | 2.10994 | ENTPD1 | 2.09064 |
| GM2004 | 0.513559 | COX5A | 2.69935 | ACSL6 | 3.14156 | AP3M1 | 0.244216 | AMDHD2 | 0.473971 | ELF4 | 0.478486 |
| ZMYM1 | 1.94678 | ARFGAP3 | 2.69573 | TIMP1 | 3.14129 | RILPL2 | 4.12217 | IFITM7 | 2.10784 | 5133401N09RIK | 2.08776 |
| YIPF3 | 1.94037 | B230208H17RIK | 0.371107 | H2-M3 | 0.318527 | BC056474 | 0.242985 | PRKD3 | 2.10658 | GM5244 | 2.08734 |
| NDUFB4 | 1.93997 | CCT2 | 2.69382 | HNRNPD | 0.318867 | LAMC1 | 0.243258 | DPP7 | 0.474707 | TXNDC5 | 0.479354 |
| SLC5A6 | 1.9379 | EXTL1 | 0.371383 | SMARCE1 | 0.318939 | C1GALT1C1 | 0.243391 | AHCYL1 | 0.475079 | DBR1 | 0.479424 |
| SLPI | 0.516184 | 2210418O10RIK | 0.371465 | FYTTD1 | 0.318977 | UTP6 | 4.10415 | SNRPE | 0.475442 | PSME2 | 2.08388 |
| STXBP3B | 0.516692 | PAK2 | 0.371564 | ZFP68 | 0.319157 | HELQ | 0.243841 | KDM1A | 2.10326 | GLB1 | 0.481116 |
| ODF2 | 1.93096 | MANIB1 | 0.371606 | GRK4 | 3.13139 | CNPY2 | 4.0997 | ASAH1 | 2.10298 | PYGL | 0.481326 |
| MYO1B | 1.92966 | ABHD14A | 2.68887 | NCALD | 3.12826 | CTSE | 4.09769 | NBEAL2 | 2.1018 | ZNRD1 | 2.07589 |
| PABPN1 | 0.51825 | AQP3 | 2.68602 | VDAC2 | 0.320477 | FUNDC2 | 4.09626 | TMEM223 | 2.1006 | DDB1 | 0.482269 |
| FAM119A | 0.519745 | GM14443 | 0.372325 | WDR5 | 3.11549 | AATF | 0.244143 | BC016495 | 2.09905 | RDH1 | 2.07068 |
| HSP90B1 | 0.519761 | PTS | 2.68215 | PIGN | 3.11357 | BAZ2B | 4.09403 | MTMR14 | 0.477007 | 1810006K21RIK | 2.06959 |
| FAAH | 1.92212 | COX7A2 | 2.67593 | 4933411K20RIK | 3.10909 | NPRL2 | 0.244258 | TMEM194B | 2.09601 | SCAI | 2.06911 |
| GNAQ | 1.92071 | TMX1 | 2.67553 | UBFD1 | 0.321659 | STRN3 | 0.244485 | ANK | 2.0958 | GMPPA | 2.06901 |
| YWHAZ | 0.521058 | LIMD2 | 0.373978 | USF1 | 0.321783 | RBMX2 | 4.08875 | PPP1R8 | 2.09564 | OTUB1 | 2.06728 |
| FAM98B | 1.91469 | SEC14L3 | 0.374268 | EPB4.1 | 0.322107 | TMEM161B | 0.244574 | GM11092 | 2.09303 | MRPL54 | 2.06611 |
| SYNGR1 | 0.523142 | GM13247 | 0.37523 | DNAJC9 | 3.10335 | RHOT1 | 4.08433 | ZHX2 | 0.477808 | TNFSF9 | 2.06593 |
| SHARPIN | 0.523917 | AB11 | 2.6648 | SPEN | 0.322519 | MOBKL2B | 4.08057 | IDE | 0.478085 | TPCN2 | 0.484625 |
| PSMA4 | 1.90774 | FAM53A | 2.66272 | MCEE | 0.322623 | ANKLE1 | 4.0788 | HSBP1 | 0.478165 | GPS2 | 2.0626 |
| AMZ2 | 0.525351 | SEC13 | 2.65611 | CENPO | 0.322861 | HTATIP2 | 0.245456 | BC029127 | 2.091 | APPL2 | 2.06132 |
| GM5590 | 0.525698 | SUN1 | 0.376637 | EBI3 | 3.09731 | CORO1B | 4.07192 | PLSCR1 | 0.478294 | GMIP | 0.485289 |
| PXMP4 | 0.525848 | GTDC1 | 0.376912 | NDUFS3 | 3.09465 | D030074E01RIK | 0.245584 | MAVS | 0.478734 | EIF2AK4 | 0.485579 |
| ESRRG | 0.525993 | 4933427D14RIK | 2.65234 | ASH2L | 0.32334 | SERTAD2 | 4.06939 | GM129 | 2.08859 | TMLEM123 | 0.485769 |
| PFDN1 | 1.90048 | UIMC1 | 2.6522 | NAGK | 3.08875 | ITGA6 | 0.246102 | TFPT | 0.478798 | UBE3B | 0.486341 |
| CCDC21 | 1.89879 | PSMB2 | 2.64775 | WDR37 | 0.323944 | SPEN | 4.05653 | 4931429L15RIK | 2.08706 | SEC11A | 0.486873 |
| MUS81 | 1.89522 | SNX12 | 2.64757 | MOBKL2A | 3.08572 | DAP | 0.246516 | BC056474 | 0.479157 | 4934319F18RIK | 0.486967 |
| RBM3 | 0.52776 | GM5623 | 2.64667 | PPP1R7 | 3.08366 | DGCR6 | 4.0543 | FAM96A | 0.479384 | OLFR613 | 2.0521 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| DLGAP4 | 0.52777 | TEX13 | 0.377913 | MOBKL3 | 0.324337 | GRAMD1B | 0.246709 | TAF6 | 2.08572 | KCTD10 | 2.05136 |
| PSMG1 | 0.528081 | GM10222 | 0.378032 | 2410017P07RIK | 3.08185 | ATPSS | 0.246942 | BRCC3 | 0.479527 | CAST | 0.487554 |
| ABCF2 | 0.528096 | HIST1H4D | 0.378041 | TMC6 | 3.08041 | SEL1L | 4.04563 | 0610007P08RIK | 2.08457 | RAPGEF2 | 2.05031 |
| A43000SL14RIK | 1.89358 | OLFR592 | 0.378312 | RCC1 | 0.324706 | LTBP1 | 4.04427 | THYN1 | 0.480007 | RPL23A-PS1 | 2.05018 |
| PARS2 | 1.89236 | DEF836 | 0.378563 | FAM98A | 0.324901 | BC002059 | 0.247311 | PLRG1 | 0.480248 | PKP4 | 2.05014 |
| DDX23 | 0.529333 | MAGEB18 | 0.378797 | GSTO1 | 3.07349 | FKBP2 | 4.04349 | PEX19 | 0.480576 | TTF2 | 0.487781 |
| TRADD | 0.529472 | PRKRA | 2.63855 | ADI1 | 3.07244 | PIH1D1 | 0.24734 | MSRB2 | 0.48109 | SNX11 | 0.488012 |
| BRWD1 | 0.529774 | ZCWPW1 | 2.63355 | CAD | 3.07003 | CAMK4 | 0.247613 | SGSM3 | 0.481319 | AKIRIN1 | 0.489518 |
| HOOK1 | 0.529863 | TECR | 2.63226 | PRKAB1 | 0.326859 | EPB4.1 | 4.03552 | GOLPH3 | 0.482346 | SHPRH | 0.48972 |
| BZW1 | 0.530277 | ESCO2 | 0.380025 | IDS | 3.05883 | TMEM120A | 4.03342 | TNFRSF1B | 0.482373 | MS4A6B | 2.03976 |
| CIZ1 | 0.531406 | PPID | 2.63042 | PIGS | 3.05691 | ACY1 | 4.03144 | NUDT1 | 0.48239 | TAF6 | 2.03951 |
| LPIN3 | 0.531659 | SRP68 | 2.62526 | UBE2K | 3.05691 | FBXO7 | 0.24829 | PAG1 | 0.482728 | STK25 | 0.490473 |
| RHOG | 1.87916 | TXNRD2 | 2.62157 | DHTKD1 | 3.27149 | 2700062C07RIK | 4.0248 | EAPP | 2.06911 | RGS14 | 2.0743 |
| TDRD7 | 0.534047 | 493025F17RIK | 0.381826 | PNPO | 0.327168 | SLAMF7 | 0.248459 | ADHS | 0.483443 | APEX1 | 0.491194 |
| BRCC3 | 1.87235 | ODF2 | 0.381901 | ATOX1 | 3.0533 | ECHDC1 | 0.248583 | CHEK2 | 2.0683 | WDR37 | 0.49142 |
| NME2 | 0.534089 | EEF1A1 | 0.381766 | MTA1 | 3.05263 | INPPSD | 4.0219 | ZDHHC5 | 0.483838 | BC005624 | 2.03429 |
| COMMD9 | 0.534538 | GM4609 | 2.61683 | MPP7 | 0.327679 | OGFOD1 | 4.02036 | SPATA2 | 0.483905 | TAX1BP1 | 0.4917 |
| CUL1 | 0.534786 | EIF251 | 2.61263 | ENO3 | 0.327796 | PPIL5 | 0.248734 | AKR1B8 | 0.484074 | VAPA | 0.491756 |
| FGFR1OP2 | 1.86828 | REPS1 | 2.61067 | CTLA2B | 0.328106 | CD84 | 0.248964 | TMEM160 | 0.484123 | MFSD4 | 0.492919 |
| GM5495 | 0.535808 | HEXDC | 0.383138 | TRMT5 | 3.0478 | AC142450.1 | 4.01427 | TADA2A | 2.06517 | C130026I21RIK | 2.02849 |
| STARD4 | 0.536393 | NUBPL | 0.383279 | L7RN6 | 0.328111 | TUBB4 | 4.0125 | BFAR | 2.06511 | GTF2H1 | 0.49316 |
| SLC4A2 | 0.536914 | H2-K1 | 2.60702 | FBXO18 | 0.328843 | HIGD2A | 4.01059 | CD55 | 2.06327 | GUK1 | 2.02764 |
| ACBD7 | 0.537082 | 3110003A17RIK | 2.60608 | OBFC2B | 0.328937 | ITPRIPL1 | 0.249459 | CDYL2 | 2.0612 | BAT4 | 0.493262 |
| NUP188 | 0.537166 | SLC12A9 | 0.384014 | UBE2R2 | 0.329711 | BOLA2 | 4.00643 | 5730460C07RIK | 2.05794 | PXN | 0.494138 |
| CCDC67 | 0.537188 | CDADC1 | 2.60389 | JAGN1 | 3.02432 | TUBA3A | 0.249604 | 583041BK08RIK | 2.05734 | BOLA3 | 0.494476 |
| SCO2 | 0.537268 | ATP6V1A | 2.6038 | DNASE2A | 3.02216 | UNC50 | 4.00364 | LARP1B | 2.05711 | INSIG1 | 0.494544 |
| RPL7A-PS8 | 0.537795 | MLF2 | 0.384558 | STX7 | 0.331134 | PHF14 | 0.250137 | NRD1 | 2.05564 | CARM1 | 2.02201 |
| SYNGR3 | 0.538227 | MGST3 | 0.538249 | PI4KA | 3.01903 | FAM114A2 | 0.250261 | GPT2 | 0.486763 | LGALS4 | 2.01707 |
| 6720456B07RIK | 0.538249 | CTSD | 2.59728 | WASF2 | 3.01724 | AMT | 3.99346 | LGALS8 | 0.486918 | STIM1 | 0.496023 |
| SBDS | 0.539336 | FIGNL1 | 0.385147 | RRBP1 | 0.331763 | DHRS13 | 0.250712 | G6PDX | 2.05221 | FAF1 | 0.496116 |
| SRFBP1 | 0.539387 | 1110054O05RIK | 0.385579 | LRPPRC | 0.332031 | AC117259.1 | 3.98473 | R3HDM2 | 2.05198 | 0610030E20RIK | 2.0156 |
| MANBA | 0.539715 | STXBP3A | 2.58956 | FAH | 3.00849 | FAM103A1 | 3.98124 | ATP5H | 2.05144 | TUSC3 | 0.496643 |
| MARK2 | 0.540156 | RPS6 | 2.58683 | SPC24 | 3.00563 | ALKBH1 | 3.97894 | TRAF3IP3 | 0.487575 | BZW1 | 0.497008 |
| CRNKL1 | 0.542027 | GST2 | 2.58677 | IPP | 3.33073 | CYSLTR1 | 3.97682 | GNG12 | 0.487806 | CYP4X1 | 2.00703 |
| RAB8B | 0.542064 | TUBA1B | 2.58618 | SFMBT1 | 3.00142 | DRAM2 | 0.251573 | SLC25A10 | 0.488253 | EROIL | 0.498334 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or II-1β + IL-6 + IL-23), and the duration of differentiation before harvesting for RNA-seq analysis (48 or 96 h). All differentiations were conducted as for the single cell in vitro data.

Differentially expressed genes for GPR65−/−, PLZP−/− and TOSO−/− Th17 cells

| GPR65-KO TGFB1 + IL6-96 h-1 | | GPR65-KO IL1B + IL6 + IL23-96 h-1 | | PLZP-KO IL1B + IL6 + IL23-48 h-1 | | PLZP-KO TGFB1 + IL6-48 h-1 | | TOSO-KO IL1B + IL6 + IL23-96 h | | TOSO-KO IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| CREBL2 | 0.542531 | TEC | 2.58595 | CSTF2 | 3.00105 | CKMT1 | 0.251619 | B9D1 | 0.488281 | LAMC1 | 0.498656 |
| CRLF3 | 0.543038 | OLFR57 | 0.386892 | TCP11L1 | 3.00088 | 9930111J21RIK2 | 3.97353 | MAPK11P1L | 0.488444 | 1110038D17RIK | 2.00509 |
| MBD6 | 0.543651 | ZPFS8 | 2.58133 | BCAS3 | 3.00008 | AIM2 | 3.97193 | ETL4 | 2.04704 | CD52 | 0.498934 |
| MPHOSPH8 | 0.544274 | GM1840 | 2.57924 | WBSCR22 | 0.333521 | TASP1 | 3.96539 | ABR | 2.04692 | ACSL4 | 0.499223 |
| ORAOV1 | 0.545472 | OPHN1 | 2.57923 | XIAP | 2.99495 | TRIP13 | 3.95438 | SMPDL3A | 2.04613 | LETMD1 | 2.003 |
| EFTUD1 | 0.546074 | CENPH | 0.388323 | CTLA2A | 2.9872 | IDH3B | 3.95381 | PSMD6 | 0.488833 | C1AD1 | 0.499491 |
| SYNE2 | 0.546379 | 42253 | 0.388438 | CCDC30 | 2.98622 | PRAMEL6 | 3.94997 | GATA3 | 0.488935 | NARS | 0.499662 |
| GM16519 | 0.546936 | GM8325 | 2.57395 | ESF1 | 0.335338 | H2-AB1 | 3.94804 | MFN2 | 0.489162 | GM10845 | 1.99974 |
| GZMA | 0.547503 | CDKN2AIPNL | 2.57245 | RBBP9 | 2.98171 | KPNA6 | 3.94607 | RPP21 | 2.14171 | ATP5SL | 0.500147 |
| SSBP3 | 0.547555 | RASA1 | 2.57058 | FRYL | 0.335625 | PSMB4 | 0.253314 | PARK7 | 0.489843 | TNK2 | 0.500251 |
| AC154908.2 | 0.548873 | MMAB | 2.57045 | WSB1 | 0.335422 | FOXP1 | 3.94607 | PTPN7 | 2.14112 | TRPM7 | 0.500309 |
| TEX10 | 0.549138 | HNRNPA2B1 | 2.56681 | GTF3C5 | 2.97883 | PCCB | 0.25368 | VTI1B | 2.04051 | HEXDC | 1.99764 |
| ENTPD8 | 0.54997 | DYNC1LI1 | 0.390009 | MAN1A2 | 2.97865 | CAS21 | 0.253707 | SYPL | 2.03922 | C79407 | 0.500689 |
| CLU | 0.550086 | ACOT8 | 0.390187 | CHURC1 | 2.97706 | 2310061104RIK | 3.94086 | SLC35C1 | 0.490401 | SMG5 | 0.500951 |
| ATP6AP1 | 0.550153 | GM6578 | 2.56122 | APOO | 2.9741 | EDA | 3.94086 | GM10226 | 0.490733 | ERCC1 | 0.501052 |
| EXOC4 | 0.550339 | RCAN3 | 2.56117 | SPARC | 2.97331 | PDSSA | 0.25396 | FBXO22 | 2.036 | ALKBH6 | 1.99384 |
| AC121959.1 | 0.55083 | PIGU | 0.390626 | RABL3 | 2.9712 | CLEC16A | 3.93383 | BNIP3L | 2.03506 | GARS | 0.501551 |
| CLDND1 | 0.550984 | A430078G23RIK | 0.390774 | AC163269.1 | 0.337272 | URM1 | 3.92678 | SUV420H1 | 2.03379 | CINP | 0.502082 |
| PELP1 | 0.552241 | CRIP2 | 2.55862 | MDM2 | 0.337421 | CDK2 | 3.92492 | WDR77 | 2.03303 | PHF20 | 0.502194 |
| IAH1 | 0.552825 | DPP6 | 0.391064 | BC004004 | 0.337925 | 2900062L11RIK | 2.95574 | WDR47 | 2.03231 | CBX6 | 2.02539 |
| UFSP2 | 1.80831 | ZFP772 | 0.391224 | 1810006K21RIK | 0.338721 | TMCO4 | 3.91832 | SUGP1 | 0.492191 | PI15 | 1.98937 |
| PSAT1 | 0.553274 | MRPS5 | 2.55298 | SMARCA5 | 0.339057 | YIPF3 | 3.91359 | GFER | 2.03044 | HTATSF1 | 1.9889 |
| RPL21-PS1 | 1.8074 | TIMM13 | 2.55225 | SMC4 | 0.33909 | GM6531 | 3.90986 | TNFAIP3 | 2.02887 | MTHFD1L | 0.502804 |
| ATAD3A | 0.553998 | WDR70 | 0.39246 | TLCD1 | 2.94781 | TADA3 | 3.90802 | SLC19A2 | 0.493046 | CTPS2 | 0.502812 |
| FANCC | 0.554128 | RPS8-PS1 | 2.54258 | ZMYM4 | 2.94475 | AC157595.1 | 3.907 | GGA2 | 2.02625 | RPL31 | 1.98629 |
| RPL7A-PS3 | 0.556195 | CIZ1 | 0.393323 | CR1L | 2.93625 | RIN3 | 3.9052 | MARK4 | 0.493923 | IPO8 | 1.98393 |
| DTWD1 | 0.556841 | PDCD2L | 2.54149 | AC154908.2 | 2.929 | NDUFV3 | 3.90298 | ATP11A | 0.494052 | GM7964 | 0.504708 |
| SOD1 | 0.558599 | HAT1 | 0.39379 | TRAT1 | 0.341417 | SLC29A1 | 0.256339 | KATNAL2 | 2.02335 | SLC7A11 | 1.97586 |
| SPEN | 0.55987 | UROS | 0.393838 | ARL1 | 2.92184 | TOR1AIP1 | 0.25649 | TPRKB | 2.02206 | GM9924 | 0.506625 |
| FAM58B | 0.561243 | CENPM | 2.53785 | FH1 | 0.342486 | DPF1 | 0.256606 | RABGGTA | 0.495179 | AC159008.1 | 0.97165 |
| KLHDC10 | 0.56306 | KIF1B | 0.394297 | MSL1 | 2.91958 | GEMIN4 | 3.89371 | HEG1 | 2.01904 | UBE4B | 1.96929 |
| MMADHC | 0.564054 | TNNI3 | 0.394472 | SLC4A11 | 0.342529 | ARMC7 | 3.89219 | CHD2 | 2.01572 | STAM | 0.508236 |
| GNA13 | 0.564115 | GEMIN6 | 0.394833 | GEMIN6 | 0.342677 | WARS | 0.257273 | ATF1 | 0.496124 | SERPINF1 | 0508625 |
| 1110001A16RIK | 1.77005 | DCUNID1 | 2.53234 | PDXDC1 | 0.343355 | 2610001005RIK | 3.88639 | GZMB | 2.01541 | SERPINF1 | 0.509771 |
| AC112970.1 | 0.565013 | RADS2 | 2.5261 | TRAPPC2 | 0.344281 | AC154908.2 | 0.257344 | IKBIP | 2.01523 | CAPN7 | 0.51015 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information inlcdes; the knockout mouse (GPR65-/-, PLZP-/- or TOSO-/-), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65-/-, PLZP-/- and TOSO-/- Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| MRPL47 | 0.565422 | TNIP2 | 0.395921 | CTSA | 2.90317 | EBAG9 | 0.257504 | HPYC-PS | 2.01226 | UPA1L1 | 0.510379 |
| BCORL1 | 0.5655 | GM4945 | 2.52316 | CDK5RAP1 | 0.344497 | MFNG | 3.88175 | MFAP1B | 0.496986 | SF3A3 | 1.95914 |
| GM16514 | 0.566314 | CHST12 | 2.52284 | CIAO1 | 2.89879 | HK1 | 3.88042 | KAT2B | 0.497207 | DTX3 | 0.510586 |
| DENR | 0.567381 | CSN3 | 0.396734 | SMYD4 | 2.89716 | MRP510 | 0.257769 | PIN4 | 2.01112 | CTXN1 | 0.510613 |
| ZBTB20 | 0.567625 | DRG2 | 2.52055 | GRHPR | 0.345239 | PIGYL | 3.87436 | SPRED2 | 2.0094 | ATP13A2 | 0.510873 |
| IPO4 | 0.567981 | 4930431F12RIK | 0.396971 | BATF | 0.345388 | RBM17 | 0.258107 | CPM | 2.0084 | KPNA1 | 0.511448 |
| CSTF1 | 0.568261 | GM12216 | 0.397362 | IFT46 | 2.8929 | 2310001H12RIK | 0.258201 | CRYZ | 2.00822 | NUP160 | 0.511725 |
| DNA1C1 | 0.569127 | VEGFB | 2.51584 | HEXDC | 2.89157 | CDADC1 | 2.89521 | PRDM9 | 2.00768 | DOHH | 0.511747 |
| PPOX | 0.570301 | NDUFV1 | 2.51426 | LIMS1 | 2.89128 | EIF3K | 3.86656 | D17WSU104E | 0.498499 | CD84 | 0.95194 |
| RP23-378I13.5 | 1.75336 | WAC | 2.50759 | MTM1 | 2.88984 | 9330129D05RIK | 3.86585 | SLC25A23 | 0.498819 | PPME1 | 0.51334 |
| GSTT1 | 1.75265 | PSMD7 | 2.50723 | EMID2 | 0.346445 | NADK | 3.86219 | SIT1 | 0.498906 | GM8113 | 1.94732 |
| UBAC1 | 0.570886 | SET | 2.50644 | VPS36 | 0.346491 | CISD3 | 3.85639 | H2AFX | 2.00404 | RELT | 0.513763 |
| FAM114A2 | 1.75083 | DAZAP2 | 2.50634 | CSNK1G1 | 2.88601 | 2610021521RIK | 3.85623 | MED29 | 0.499274 | SIN3A | 1.94621 |
| ATP6V1D | 0.571885 | MRPS9 | 2.50611 | MRPS9 | 2.88388 | TNNC1 | 3.84669 | SPECC1L | 2.00133 | MAP2K2 | 0.514433 |
| NUP210 | 0.572376 | MYG1 | 2.50566 | AC163101.1 | 2.87474 | COPG2 | 3.84545 | CFLAR | 2.00132 | GAD1 | 0.515378 |
| FKBP4 | 0.573039 | TRAP6 | 2.50285 | CTSS | 2.87188 | GPS1 | 0.260265 | POLK | 0.499794 | 2010106G01RIK | 0.516083 |
| SF3B5 | 1.74422 | 2410002F23RIK | 0.399637 | ABCF3 | 0.348441 | TWF2 | 0.260267 | STX1A | 0.500013 | PIGX | 1.93751 |
| GNAS | 0.57567 | SLC1A5 | 2.50163 | ATF2 | 0.348658 | TRIAP1 | 3.83902 | AAK1 | 1.99721 | 2510039O18RIK | 0.516461 |
| 1600002K03RIK | 0.57703 | KATNAL1 | 0.399924 | SND1 | 0.34901 | GM12184 | 0.260714 | OSBPL3 | 0.500811 | TRAPPC4 | 0.516634 |
| TRIM27 | 1.73294 | SH15A5 | 2.49998 | GM4978 | 2.86399 | CNOT3 | 0.260816 | TES | 0.501326 | PYCR2 | 0.517569 |
| MTA3 | 0.577892 | PLXNA2 | 0.400344 | KBTBD4 | 2.86249 | IER3 | 3.83412 | FAM76A | 0.501609 | GM7334 | 1.93156 |
| CDKN1A | 1.7286 | ENSA | 2.49638 | PDE7A | 0.349459 | PUM1 | 3.8327 | THUMPD3 | 0.501862 | VPS24 | 0.517816 |
| LY6I | 1.72847 | PTPN2 | 2.49413 | RPL30 | 0.349535 | MRPS9 | 3.83118 | ADORA2B | 1.9918 | ZBTB44 | 0.518369 |
| MRPL4 | 1.72501 | CCR8 | 2.49156 | SRD5A3 | 0.349732 | GLUL | 0.261028 | DLAT | 0.502327 | ZBTB25 | 1.92887 |
| STK16 | 0.582641 | GPR171 | 2.49065 | CCDC101 | 0.349885 | TAF1D | 0.261034 | RCBTB2 | 1.98949 | CDCA7L | 1.92825 |
| FAM19A1 | 0.582755 | EAF2 | 0.401732 | ZFP828 | 0.350727 | 2700060F02RIK | 3.8289 | BC003331 | 1.98914 | DPP8 | 0.5189 |
| 1700022I11RIK | 1.71165 | LYZL6 | 0.401936 | CNOT6L | 0.34999 | RAD52 | 0.261605 | CYFIP1 | 1.98797 | FOXRED1 | 0.519651 |
| CCDC58 | 0.58524 | SIGLEC5 | 2.48747 | BET1 | 2.84451 | CELF2 | 3.81935 | 2400001E08RIK | 1.98759 | PSG28 | 1.92329 |
| NPC2 | 1.70688 | NUMB | 0.402097 | ATP5J2 | 2.84365 | 2410002D22RIK | 0.261916 | RNPEP | 0.503512 | CDCA4 | 0.520308 |
| CASC1 | 0.586183 | SMOX | 2.48543 | MTA2 | 0.351893 | PTTG1IP | 0.262322 | KIF2A | 1.98526 | NMT2 | 0.520384 |
| FIGNL1 | 0.587311 | PRKRIP1 | 2.48495 | TSR2 | 2.84151 | LRP1B | 3.812 | CNOT7 | 1.98499 | SLC25A3 | 0.520812 |
| GM10947 | 0.587706 | 1700040L02RIK | 2.48404 | APOO-PS | 2.84093 | 1700084I12RIK | 0.262448 | ACER2 | 1.98398 | TBCE | 0.520816 |
| USP4 | 0.588948 | HOMER3 | 0.402929 | SRP9 | 0.352207 | AM22 | 0.262804 | CTNNB1 | 0.504068 | FGFR1OP | 0.521589 |
| IPO9 | 0.59223 | AKT1S1 | 0.402934 | CHD6 | 0.352869 | TWF1 | 0.262902 | 2310001H12RIK | 0.504076 | UPB1 | 1.91671 |
| GLUL | 0.592284 | CCDC52 | 2.48127 | ST13 | 0.353181 | 9130011E15RIK | 0.263089 | 1200016B10RIK | 0.504231 | ACO2 | 0.521775 |
| | 0.593623 | MLXIPL | 0.403803 | GM10126 | 0.353969 | PGM2 | 3.79693 | COQ9 | 0.504426 | ARID1A | 1.91419 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| IK | 0.594284 | FAM96B | 2.47507 | YME1L1 | 0.35435 | ZFP119B | 0.263371 | GM9920 | 1.98207 | SCO1 | 0.522445 |
| SMN1 | 0.598734 | FAM192A | 2.47499 | LARS2 | 0.35468 | MS4A4C | 0.263921 | LSR | 0.504704 | STK19 | 1.91279 |
| RPF1 | 0.600117 | D2WSU81E | 2.47422 | XRCC2 | 2.81685 | BSCL2 | 3.78787 | A230046K03RIK | 1.98068 | SLC9A7 | 1.9123 |
| EIF3F | 0.600944 | KARS | 2.4733 | PPT1 | 0.35564 | GPAA1 | 3.78783 | PAPI2 | 0.505006 | MEF2A | 0.523401 |
| STAMBPL1 | 0.601806 | ZEB2 | 2.47291 | ATP6V1G1 | 0.355986 | SLC6A9 | 3.78783 | NAB2 | 0.505161 | 4732465J04RIK | 1.90773 |
| NAP1L4 | 0.601861 | EIF3I | 2.47183 | LRRC59 | 0.356649 | RABEPK | 0.264159 | IBTK | 1.97881 | TRIM26 | 1.90526 |
| SUMO3 | 1.66089 | CCT7 | 2.47169 | DAP | 0.366992 | POLR3G | 0.264569 | SCMH1 | 0.505617 | PDLIM7 | 0.525343 |
| ZFYVE20 | 1.65953 | H2AFZ | 2.46948 | E130309D02RIK | 0.357077 | PHB2 | 3.77815 | BC031353 | 1.9776 | RAB84 | 0.525506 |
| SNX6 | 1.64709 | CLIP1 | 0.405064 | HMGB3 | 0.357559 | VPS25 | 3.77655 | UPF3A | 1.97507 | FAM172A | 1.90216 |
| TMEM208 | 0.608069 | FLNA | 2.46297 | USP45 | 0.358041 | APPL2 | 3.77447 | FDXACB1 | 1.97505 | HSP90B1 | 0.526021 |
| CDYL2 | 1.64066 | CMAH | 0.406825 | UBE2G2 | 0.358728 | NAGA | 0.264986 | LY6C1 | 1.97364 | TRAF2 | 1.90049 |
| MRPS23 | 1.62324 | PSMB3 | 2.45744 | SLC13A4 | 0.35893 | ZFP444 | 0.265217 | RBBP6 | 1.97358 | RTN3 | 0.526287 |
| SDCCAG8 | 0.618133 | NUP188 | 2.45588 | DCTN6 | 0.359605 | BTD | 3.7705 | DNAJC15 | 0.506779 | HAT1 | 0.526603 |
| GM10180 | 0.6231 | TMEM50B | 0.407658 | BC005537 | 0.359731 | ERCC8 | 0.265289 | TBX6 | 1.97285 | AI480653 | 0.52694 |
| NFKBIL2 | 0.62363 | PDIA6 | 2.45116 | 4930473A06RIK | 0.360025 | 2310011103RIK | 0.265376 | IRS2 | 1.97257 | WDR13 | 0.527264 |
| TREX1 | 1.60079 | SLC2A9 | 0.408452 | NUP35 | 0.360156 | SLC3A2 | 3.76824 | ZFP260 | 0.506964 | RPS12 | 1.89526 |
| NMT1 | 0.629225 | FBXO18 | 2.44665 | DUS1L | 0.360992 | ADI1 | 0.265536 | A630010A05RIK | 1.97099 | H2-GS10 | 1.89495 |
| BOLA2 | 1.58747 | IL2RG | 2.44447 | RNF25 | 2.76455 | GST21 | 0.265792 | SYTL1 | 0.507613 | RBPSUH-RS3 | 0.527976 |
| RPS12-PS3 | 0.635083 | SNRNP200 | 2.44421 | ATP6V1D | 0.362458 | MTG1 | 0.265886 | LYN | 1.96963 | CTNNA1 | 0.528139 |
| EIF3K | 0.640023 | APLF | 0.409141 | AGK | 0.362486 | PPM1M | 3.76093 | ZMYND8 | 0.507888 | POLD1 | 0.528232 |
| RNF8 | 0.640552 | TTC16 | 0.409214 | EIF4E3 | 0.362549 | MYBBP1A | 0.265955 | TGTP2 | 1.90875 | FNDC3A | 0.530053 |
| GIMAPS | 0.641094 | FAM171A2 | 0.409287 | PNO1 | 0.363285 | TUSC2 | 0.266008 | 1600014C10RIK | 0.507938 | ECT2 | 0.530097 |
| ICOS | 1.57747 | RDH11 | 2.44145 | RPAP2 | 2.74578 | CCDC40 | 0.266274 | COG6 | 0.508092 | ZBTB48 | 0.531218 |
| AAAS | 0.645299 | GM9867 | 0.409753 | CRYBG3 | 2.74507 | RCCD1 | 3.75553 | EIF1B | 1.96748 | AIMP2 | 0.531318 |
| AACS | 1.54713 | SH3GL2 | 0.410064 | YBX1 | 0.364351 | UBE2G2 | 3.75208 | AKR7A5 | 0.508268 | GEM | 0.532475 |
| CLTB | 0.646466 | TGDS | 2.43712 | BBS9 | 2.74435 | ZCCHC11 | 3.75014 | A430033K04RIK | 0.508386 | SMOX | 0.532485 |
| TSTA3 | 0.64683 | GM12355 | 2.43594 | CCNC | 0.364551 | RFT1 | 3.74624 | GNPTG | 1.96637 | GRK1 | 1.87782 |
| GLTPD1 | 0.647385 | SLC17A1 | 0.410597 | ORC6 | 2.74063 | BFAR | 3.74384 | CDC42SE2 | 1.96594 | HSPH1 | 0.532596 |
| USP33 | 0.652032 | CHCHD2 | 2.43431 | PSTK | 2.74002 | MLL5 | 0.267206 | UBAC1 | 0.509005 | EEF2 | 0.532776 |
| HSF2BP | 0.65726 | 2310004I24RIK | 0.411066 | PHF20 | 0.365273 | AB041803 | 0.267228 | STT3A | 1.96405 | SESN3 | 0.53345 |
| EIF2B2 | 1.51353 | RFC4 | 2.43237 | GBP4 | 2.7348 | EIF4E1B | 3.74213 | MEA1 | 1.96388 | TMEM16B | 0.534151 |
| GM9846 | 0.661306 | GM5449 | 2.43162 | ATP2A2 | 0.365747 | NUP54 | 0.267326 | ALG6 | 1.96135 | UBE2O2 | 0.534491 |
| AC068006.1 | 1.51037 | RNMT | 2.42932 | CSDA | 0.36588 | TMEM111 | 3.74061 | MAP2K4 | 0.510181 | RASSF7 | 1.86971 |
| BCL2A1D | 0.663782 | KIN | 2.42826 | CBR4 | 0.366082 | GYG | 0.267383 | DAPK3 | 1.95949 | MAVS | 0.535261 |
| EPHX1 | 0.664393 | CRX | 0.412069 | CCDC111 | 2.73013 | WAPAL | 0.267453 | GM6132 | 1.95886 | FAM32A | 1.86815 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-<br>IL1B + IL6 + IL23-<br>96 h-1<br>Fold.Change<br>(KO/WT) | Gene | GPR65-KO-<br>TGFB1 + IL6-96 h-1<br>Fold.Change<br>(KO/WT) | Gene | PLZP-KO-<br>IL1B + IL6 + IL23-<br>48 h-1<br>Fold.Change<br>(KO/WT) | Gene | PLZP-KO-<br>TGFB1 + IL6-48 h-1<br>Fold.Change<br>(KO/WT) | Gene | TOSO-KO-<br>IL1B + IL6-48 h + IL23-<br>96 h<br>Fold.Change<br>(KO/WT) | Gene | TOSO-KO-<br>IL1B + IL6 + IL23-<br>96 h<br>Fold.Change<br>(KO/WT) |
|---|---|---|---|---|---|---|---|---|---|---|---|
| | | NOSTRIN | 2.42669 | MBTPS2 | 0.366424 | POLA1 | 3.73713 | LRP1 | 0.511141 | SMG7 | 0.535301 |
| | | TPMT | 2.42108 | GLA | 0.36763 | SCFD2 | 3.73631 | VMN1R15 | 1.95617 | CBLB | 1.86343 |
| | | RIN2 | 0.414077 | TUBGCP4 | 2.70223 | ZBTB25 | 0.267644 | 2010005H15RIK | 0.511384 | VPS33B | 0.537968 |
| | | MRPS21 | 2.41435 | PTPN22 | 2.70201 | CCDC137 | 3.73303 | PUS1 | 1.955 | RERE | 0.538233 |
| | | LSS | 0.41427 | FAM82B | 0.370392 | GM16380 | 3.73135 | HOXB1 | 1.95471 | RAB7 | 0.539009 |
| | | ERCC6L | 0.414813 | OCIAD1 | 0.370722 | ZFP870 | 0.268254 | PTPN1 | 0.511705 | TMEM222 | 1.8546 |
| | | CDH7 | 0.415362 | PHF14 | 0.371514 | BC021614 | 3.72679 | TOP3A | 1.9542 | CDC26 | 0.539305 |
| | | FLT1 | 0.415599 | BC017643 | 0.371595 | CENPQ | 3.72435 | 42066 | 1.95403 | ARRB2 | 0.540067 |
| | | NHLRC3 | 2.40576 | TAF12 | 2.6907 | RGS11 | 0.268513 | FAM65A | 1.95385 | REEP4 | 0.540384 |
| | | RAC2 | 2.4055 | B230208H17RIK | 2.68825 | SIDT2 | 0.268642 | TRA2A | 1.95347 | NFKBIL1 | 0.5408 |
| | | TTC35 | 0.416079 | SMOX | 2.68797 | BHMT2 | 3.72138 | CCDC34 | 1.95296 | LUC7L | 1.84785 |
| | | SERTAD2 | 2.40336 | SNX1 | 0.372894 | PRPSAP1 | 0.26896 | SEC61B | 0.512119 | GM7263 | 1.84588 |
| | | BCL3 | 2.40316 | GM10491 | 2.67982 | ZNRD1 | 3.71802 | UBTD1 | 0.512319 | SGIP1 | 0.541977 |
| | | QRAOV1 | 0.416262 | GLIPR1 | 2.67168 | ZFP566 | 0.269243 | BCAP29 | 0.512497 | 1810029B16RIK | 1.83701 |
| | | GM10192 | 0.416457 | CDC55 | 2.66151 | TFG | 0.269249 | F730047E07RIK | 0.512933 | GPR98 | 1.8369 |
| | | GM10576 | 0.416531 | BCKDK | 2.655 | PIH1D2 | 3.7134 | GTF2E2 | 0.512934 | SYPL | 1.83272 |
| | | 1810062G17RIK | 0.416542 | OLFR613 | 0.65279 | ATG4A | 3.71131 | BPTF | 1.94905 | TARDBP | 0.546266 |
| | | ATF7 | 0.416542 | MRPS28 | 0.378022 | GRINA | 0.269574 | SURF6 | 0.513101 | PAFAH1B3 | 1.82962 |
| | | PYGL | 0.416898 | GOSR2 | 2.64246 | SIL1 | 0.269867 | CDK4 | 1.94802 | SNAPC1 | 0.547069 |
| | | B4GALT7 | 2.39738 | SNX10 | 0.379113 | FAM54B | 3.70403 | OAT | 0.513348 | PNRC1 | 0.547422 |
| | | SHKBP1 | 0.417187 | PTPN7 | 2.63711 | H2-Q7 | 3.70298 | HSPBP1 | 0.513387 | DHCR24 | 0.547732 |
| | | NEIL3 | 0.417589 | RPL21-<br>PS6 | 2.6325 | LGAL54 | 3.70086 | RP23-<br>7IJ17.1 | 0.51361 | EPT1 | 0.548464 |
| | | ARHGAP23 | 0.417865 | CDK2AP2 | 0.380398 | FZR1 | 0.27031 | MINK1 | 0.513728 | SERINC3 | 1.82304 |
| | | CCDC73 | 0.417948 | LRRC33 | 0.38045 | PAFAH1B3 | 3.69605 | GPN2 | 0.513745 | TRIM16 | 0.549268 |
| | | SERINC3 | 2.39241 | PXMP4 | 2.62462 | NFKB1 | 0.270657 | LANCL1 | 0.514143 | EIF4H | 0.549483 |
| | | IRF3 | 2.39082 | MAP3K1 | 2.62401 | TAF8 | 3.69444 | RNF214 | 0.514319 | SERINC1 | 0.55107 |
| | | REEP3 | 0.418667 | LCLAT1 | 0.381754 | CD44 | 0.270938 | NFURL3 | 1.94432 | NFE2L2 | 0.551235 |
| | | NAPA | 2.38692 | TADA2A | 2.61838 | SLC12A6 | 3.68795 | GJA1 | 1.94426 | PSG16 | 1.80771 |
| | | RCCD1 | 2.38312 | SBF2 | 2.61665 | ADPRHL1 | 3.68326 | CTPS | 0.514334 | PSD4 | 0.553898 |
| | | ZBTB48 | 0.419638 | MED11 | 0.382379 | GSTT2 | 0.271538 | EPHB6 | 0.514382 | BRP44L | 1.80508 |
| | | ENO1 | 2.38291 | SDR39U1 | 0.382638 | NDUFS3 | 3.68165 | SC4MOL | 1.94234 | NDUFS8 | 1.79949 |
| | | SRA1 | 2.38251 | FLII | 0.38277 | WWOX | 0.271617 | GOLGB1 | 1.94176 | PRKAG1 | 0.556035 |
| | | NRN1 | 2.3825 | CCDC58 | 2.60645 | GALNT1 | 3.67991 | FAM53B | 1.94035 | VEGFA | 0.557177 |
| | | RBMX2 | 2.38229 | DCAF17 | 2.60515 | AK157302 | 0.271878 | AZIN1 | 0.515598 | PML | 0.557223 |
| | | PLSCR2 | 0.419896 | DPYSL5 | 2.60017 | VPS52 | 0.271994 | TBC1D7 | 1.93891 | ZFP277 | 1.79357 |
| | | MRPL27 | 2.37937 | D17WSU104E | 2.59814 | TPRGL | 0.272112 | GMS148 | 0.516057 | EAPP | 0.557704 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | Fold.Change (KO/WT) GPR65-KO- IL1B + IL6 + IL23- 96 h-1 | Gene | Fold.Change (KO/WT) GPR65-KO- TGFB1 + IL6-96 h-1 | Gene | Fold.Change (KO/WT) PLZP-KO- IL1B + IL6 + IL23- 48 h-1 | Gene | Fold.Change (KO/WT) PLZP-KO- TGFB1 + IL6-48 h-1 | Gene | Fold.Change (KO/WT) TOSO-KO- IL1B + IL6 + IL23- 96 h | Gene | Fold.Change (KO/WT) TOSO-KO- IL1B + IL6 + IL23- 96 h |
|---|---|---|---|---|---|---|---|---|---|---|---|
| | | GM9920 | 0.420306 | CRBN | 0.384986 | SDCCAG38 | 0.272155 | GM15446 | 0.516669 | UBR1 | 1.79211 |
| | | SNX11 | 0.420689 | COMMD3 | 2.59712 | JMY | 0.272284 | RPS19BP1 | 0.517113 | NUP210 | 0.558386 |
| | | CCDC127 | 2.37554 | GARS | 0.385447 | ZFP68 | 3.67263 | BAT2L | 1.93341 | TRAF4 | 0.559497 |
| | | GM12166 | 2.37455 | ADD1 | 0.385754 | KDELR1 | 3.66723 | THOC2 | 1.93184 | NSMCE4A | 1.78532 |
| | | CHCHD5 | 2.37221 | IGF2BP1 | 2.5918 | PRPSAP2 | 0.272685 | GM7204 | 0.51812 | TUBG1 | 0.560497 |
| | | PSMC1 | 2.37129 | 4930422I07RIK | 0.385953 | 4921521F21RIK | 3.66495 | N4BP2L1 | 1.92934 | HERC4 | 0.560835 |
| | | CDCA3 | 2.37031 | SLC5A6 | 2.59072 | AMDHD2 | 0.272858 | DDB2 | 0.518393 | TMEM128 | 0.561113 |
| | | HIGD1A | 2.3696 | STK38L | 2.58657 | SREK1 | 0.272866 | UBR1 | 0.518747 | ACP6 | 0.561274 |
| | | HK2 | 2.36845 | PIGQ | 2.58532 | SPATA5 | 3.6635 | CCDC64 | 1.92739 | RAE1 | 1.77899 |
| | | HAX1 | 2.36709 | CCNE2 | 0.387262 | YWHAB | 3.653 | TIMM17A | 0.519287 | CRK | 1.77824 |
| | | GM6616 | 0.422601 | RNFT1 | 0.387617 | AGPAT4 | 3.65153 | NOL6 | 0.519525 | PKM2 | 0.563075 |
| | | GOLGA2 | 2.36616 | WDR83 | 2.5794 | C130022K22RIK | 3.64762 | SNF8 | 0.519544 | RAB3D | 0.563213 |
| | | IDH3A | 2.36555 | TMEM208 | 2.57819 | AAMP | 0.274362 | ZFAND2B | 0.519692 | ERI2 | 0.565008 |
| | | TUFT1 | 0.422771 | LDHB | 2.57679 | BTNL7 | 0.274362 | MAP2K6 | 1.92378 | RAD9 | 1.76762 |
| | | IARS | 2.36517 | HIGD2A | 0.388263 | FARS2 | 0.274534 | RPA2 | 1.92376 | TRIM12C | 0.566937 |
| | | SNRPC | 0.423025 | TRMT2A | 2.57556 | TMEM138 | 3.63884 | FLCN | 0.519922 | BHLHE40 | 0.567591 |
| | | TAGAP1 | 2.36305 | 1810029B16RIK | 0.388697 | DHRS1 | 0.274822 | CCDC109A | 1.92333 | GOLGA3 | 0.568098 |
| | | ESRRB | 2.36259 | WDR11 | 2.57205 | FAM45A | 0.274896 | MICAL1 | 1.92329 | DHODH | 0.568201 |
| | | EGLN2 | 0.423727 | PRPF4 | 0.389138 | LRRC51 | 3.63652 | YTHDF1 | 0.520077 | CD2BP2 | 0.568371 |
| | | GNB3 | 2.3696 | GM129 | 2.56113 | HBP1 | 3.63527 | 6330512M04RIK | 1.92214 | NUP50 | 0.568502 |
| | | CETN2 | 2.35631 | RNF8 | 0.390462 | TM9SF1 | 0.275183 | ARFGAP3 | 1.92052 | RBBP4 | 0.570096 |
| | | SRSF2 | 2.35537 | ENOPH1 | 2.55864 | GM10125 | 3.63363 | AHSA1 | 0.520838 | SYCE2 | 0.57057 |
| | | GM6984 | 2.35439 | CCDC21 | 2.55839 | VPS4B | 3.63172 | KCTD20 | 1.91971 | SDHB | 0.57114 |
| | | ZDHHC2 | 0.424965 | POLR3C | 2.5568 | SMYD4 | 0.275947 | OLFR309 | 1.91784 | IKZF1 | 0.571504 |
| | | ACTR5 | 2.35309 | LZIC | 0.391656 | KDELC1 | 3.63101 | 1200011M11RIK | 1.91752 | TPM3 | 0.571603 |
| | | BNIP1 | 0.425006 | SMARCAL1 | 2.54702 | RIOK2 | 3.62388 | FUZ | 0.52165 | GNPDA2 | 0.572931 |
| | | FUNDC1 | 2.34964 | CASP9 | 0.392795 | ACTG2 | 0.276442 | FBXL20 | 0.521882 | BBS5 | 0.573259 |
| | | TMEM106C | 2.3483 | ATAD3A | 2.54526 | ACSL5 | 3.6173 | CHCHD4 | 1.91611 | WIPI1 | 0.575804 |
| | | RPL27A-PS2 | 2.34643 | CREM | 0.393101 | IFT80 | 0.275947 | CCDC99 | 1.91608 | GM10126 | 1.72328 |
| 2610020H08RIK | 2.3461 | NUSAP1 | 2.54381 | C1Q8P | 3.61566 | CNOT8 | 0.522017 | EIF2B3 | 0.581782 | | |
| ALOXE3 | 0.426314 | INTS4 | 2.54359 | SAR1A | 0.276578 | RMND5A | 0.522092 | UBAP1 | 1.71853 | | |
| HELZ | 2.34235 | UBE3B | 2.54343 | EIF5 | 0.276583 | VRK3 | 0.52243 | SPSB1 | 0.582234 | | |
| FAM58B | 2.34033 | 2210012G02RIK | 2.54314 | ZDHHC4 | 3.61425 | TMEM70 | 0.52249 | ALG1 | 0.583562 | | |
| TMEM29 | 2.33863 | DCLRE1C | 2.54308 | RHEB | 3.61261 | WDR62 | 1.91337 | EIF4G1 | 0.585375 | | |
| CCT8 | 2.33681 | HUS1 | 0.393319 | DEGS1 | 0.27711 | PLA2G4C | 0.52267 | GM10154 | 1.69708 | | |
| BRD7 | 0.42797 | UROS | 0.39347 | SETD3 | 0.277125 | APLP2 | 1.91309 | ARPC2 | 0.590214 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-TGFB1 + IL6-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| PSMD4 | 2.33652 | CDCA2 | 2.54124 | SNX5 | 3.60658 | HEXB | 0.522921 | SIN3B | 0.590385 |
| AC087117.1 | 2.33628 | ATP5G2 | 0.393622 | 1700026D08RIK | 3.60065 | ITGA7 | 0.523022 | NADK | 0.591149 |
| CCNB1 | 2.33545 | CHCHD2 | 2.53764 | F730047E07RIK | 3.59942 | DDX3X | 0.523083 | SNX15 | 0.59177 |
| GLRX2 | 0.428297 | RNF7 | 2.53293 | AC102876.1 | 3.59924 | LY75 | 1.90982 | SLIGP1 | 0.592918 |
| PRKAR1A | 2.33459 | ZFP871 | 0.394855 | STRADA | 3.59782 | AMN1 | 0.523642 | WBP11 | 0.593785 |
| FER1L4 | 0.428392 | HDAC3 | 2.5311 | MTCH1 | 3.59294 | GM10126 | 1.9084 | EIF4B | 0.594521 |
| SERF1 | 2.33264 | GM11444 | 0.395169 | CLUAP1 | 0.278452 | TBC1D14 | 1.90609 | KPNA6 | 0.599164 |
| GLB1 | 2.33197 | TRMT6 | 0.395306 | TXNL4A | 3.59025 | TTC14 | 1.90396 | EIF3G | 0.603438 |
| RPL17-PS3 | 2.33185 | PSMB4 | 0.395713 | 2010002N04RIK | 3.5887 | POLR2I | 1.90363 | CHCHD3 | 0.603518 |
| PCID2 | 2.32949 | PSMB10 | 2.52609 | WDR83 | 3.58864 | CORO2A | 0.525557 | BLMH | 0.604504 |
| SLC35A5 | 2.32855 | FDPS | 0.396001 | ALG1 | 3.58642 | CTSF | 1.90247 | NDUFV2 | 0.608703 |
| ACOT9 | 2.32667 | PUS7 | 0.396696 | SLC25A20 | 0.27883 | CPEB4 | 1.90227 | AC121959.1 | 0.60898 |
| XPO6 | 2.32366 | H2-T10 | 0.396761 | C1D | 0.27899 | ACAD11 | 1.90142 | 1700021K19RIK | 0.612295 |
| DULLARD | 0.430551 | CDK6 | 2.52008 | WDR5B | 0.27904 | ACADL | 1.90024 | JUNB | 0.61636 |
| MBTPS2 | 0.430966 | STXBP3A | 0.397055 | FBXW17 | 0.279342 | USP34 | 1.89966 | GM16372 | 0.620202 |
| GLRX3 | 2.31916 | PRDX4 | 0.397077 | MRPS2 | 3.57822 | HECTD2 | 1.89902 | TRIOBP | 0.622737 |
| FBXO7 | 0.431201 | CAMK2D | 0.397755 | PARP2 | 0.279468 | FAM18B | 1.89846 | SLC23A2 | 0.623297 |
| RFC1 | 2.31754 | SURF6 | 0.397919 | PVR | 0.27983 | SUB1 | 0.527024 | TIMP1 | 0.62437 |
| BACH2 | 0.431518 | NMT1 | 0.398118 | SLC38A6 | 3.57343 | GM4953 | 1.89734 | NG2 | 0.627746 |
| EDIL3 | 0.431846 | MRPL12 | 2.50676 | CCDC117 | 0.280162 | ORAOV1 | 0.527263 | TM92F2 | 0.630655 |
| MAPKAPK3 | 2.31328 | UBA3 | 2.50203 | SRSF1 | 3.56743 | ARL13B | 0.527358 | BCL2L1 | 0.631318 |
| ACSL3 | 2.31253 | CCDC53 | 0.400055 | CCDC37 | 0.280558 | VPS37A | 0.527394 | CR974466.3 | 0.632526 |
| EIF2B1 | 2.31248 | ARPC4 | 2.49874 | NDUFA5 | 0.280768 | RAD23B | 1.89356 | 2410002F23RIK | 0.637736 |
| RAB34 | 0.432762 | SIP1 | 2.49633 | LAPTM4A | 0.280976 | KLHDC1 | 1.89321 | TIMD2 | 0.65466 |
| HIST1H1B | 2.30999 | DUSP11 | 0.40093 | RHBDD3 | 3.55902 | ACTN1 | 1.89312 | GM10092 | 0.662806 |
| FAM86 | 2.30926 | AQR | 0.401972 | CHURC1 | 3.55842 | RNASEH1 | 0.528473 | | |
| USP20 | 0.433214 | PRPF6 | 2.48721 | SRP72 | 0.281468 | MFSD4 | 0.528688 | | |
| ARRDC4 | 2.30811 | SMCHD1 | 2.4853 | VAPA | 3.54427 | PHKB | 1.89121 | | |
| GNB1L | 2.30491 | TOE1 | 0.402448 | VCAM1 | 0.282146 | FEN1 | 0.529469 | | |
| OXSM | 0.433947 | ETF1 | 0.402612 | C130026I21RIK | 0.282669 | HK2 | 0.529593 | | |
| KDELR1 | 2.30246 | CSNK2B | 0.402876 | TAX1BP1 | 3.535 | ZFP64 | 0.529764 | | |
| PPWD1 | 0.434447 | MRPL23 | 0.403481 | H2-KE2 | 3.53448 | CBFA2T2 | 0.529815 | | |
| MTCH1 | 0.43445 | PIP4K2B | 2.47823 | LRRC57 | 0.282927 | NUDT2 | 1.88732 | | |
| UBE2K | 2.30119 | GEMIN5 | 0.403858 | MCFD2 | 0.282948 | TRIM26 | 1.88656 | | |
| MCM3 | 2.30089 | MPP6 | 2.47593 | RPUSD4 | 0.283046 | CAPN1 | 1.88608 | | |
| RAB26 | 2.29972 | CHCHD3 | 2.47563 | AHCTF1 | 3.53299 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| | | COQ5 | 2.29929 | BCAP29 | 0.404156 | 2610015P09RIK | 0.28318 | GPRASP2 | 0.530205 | | |
| | | PPP1R12B | 0.43505 | HAX1 | 0.404298 | AC161211.2 | 3.53132 | WDR83 | 0.53028 | | |
| | | GM1673 | 0.435322 | RAB1 | 0.404338 | GM10845 | 3.52711 | ATP6V0A1 | 0.530309 | | |
| | | BAT4 | 2.29618 | 2310008H09RIK | 2.47301 | RRP9 | 3.52632 | 1810012P15RIK | 0.5304 | | |
| | | HHAT | 0.436199 | PLEKHA2 | 0.404372 | HKAMP | 3.52345 | GNPDA2 | 1.88521 | | |
| | | IL11 | 0.4364 | MRPS11 | 2.47198 | BEND5 | 0.283881 | 1200011I18RIK | 1.88463 | | |
| | | TERF2IP | 0.436546 | GM10247 | 0.40515 | RBM18 | 3.52106 | RNF220 | 1.88316 | | |
| | | TOP1 | 0.43657 | RFC3 | 2.46815 | PFN2 | 0.284257 | D11WSU47E | 0.531055 | | |
| | | PIGO | 0.43692 | C130026I21RIK | 2.46687 | COQ3 | 0.284301 | UBXN11 | 0.531091 | | |
| | | GAK | 2.28802 | ETFDH | 0.40565 | CYC1 | 3.51628 | GSPT1 | 1.88263 | | |
| | | SLC35B4 | 2.28551 | 2810474O19RIK | 2.46509 | GRINL1A | 3.51511 | FUS | 1.88159 | | |
| | | RWDD1 | 2.28476 | ZMYM1 | 0.405929 | CMTM5 | 3.51179 | MAPK6 | 0.531495 | | |
| | | ARFGAP1 | 2.28443 | MYH9 | 2.46303 | UVRAG | 0.284938 | 2810006K23RIK | 1.88005 | | |
| | | RNG207 | 0.437931 | RNF135 | 2.46229 | SLC2A1 | 3.50806 | TUBB6 | 0.532162 | | |
| | | 4933434E20RIK | 2.28268 | GBP2 | 2.46228 | DCUN1D5 | 3.50632 | BC003266 | 1.87822 | | |
| | | 1700049G17RIK | 0.438122 | RABGGTB | 0.406451 | RMND1 | 3.50373 | ZKSCAN5 | 1.87779 | | |
| | | MYST2 | 0.438131 | BCL2L11 | 2.4598 | PRKCQ | 0.285425 | PPARD | 0.532756 | | |
| | | HNRNPLJ | 0.438283 | CORO7 | 0.407067 | BOLA1 | 3.50029 | TOMM70A | 0.532804 | | |
| | | A2LD1 | 0.43857 | CAB39 | 0.407257 | 2900010I23RIK | 0.285879 | ZCCHC10 | 1.87629 | | |
| | | WDR67 | 0.438638 | PFKFB4 | 2.45371 | CLSPN | 3.49183 | LPIN2 | 0.533743 | | |
| | | MAPKAPK5 | 0.438737 | THOC4 | 2.45298 | NUDT19 | 3.48855 | MOCOS | 1.87267 | | |
| | | MRPL23-PS1 | 2.27896 | R3HDM1 | 0.407704 | TRP53BP1 | 0.286692 | CCDC17 | 0.534254 | | |
| | | BC046331 | 0.43885 | LAMC1 | 0.407777 | USP8 | 0.286742 | PIK3AP1 | 0.534386 | | |
| | | GM4666 | 0.43888 | RBM4B | 0.407937 | 2310008H04RIK | 0.286929 | SPNS1 | 0.534407 | | |
| | | ADSL | 2.27559 | SERF2 | 0.408298 | NR2C2 | 0.286973 | EIF3B3 | 0.534832 | | |
| | | VSIG10 | 0.439492 | CINP | 2.44822 | CD97 | 3.48148 | ACD | 0.534847 | | |
| | | ATP281 | 2.27493 | KPNB1 | 0.408474 | PGM3 | 0.287426 | PTPMT1 | 1.8695 | | |
| | | UCP2 | 2.27177 | TAP1 | 0.409023 | CLEC4A2 | 3.47531 | UBA5 | 0.535227 | | |
| | | GM8279 | 0.440209 | EIF3F | 2.44425 | FCRL1 | 0.287744 | SOCS1 | 1.86833 | | |
| | | SSR4 | 2.27155 | 2700094K13RIK | 2.43966 | RAD51L1 | 0.287889 | TRIM12A | 1.86742 | | |
| | | IGSF8 | 0.440973 | CPNE8 | 2.43946 | HIBCH | 3.47339 | KANK3 | 1.866 | | |
| | | DAGLB | 0.44098 | AP1G2 | 2.43878 | METTL7A1 | 0.288049 | CSTF3 | 0.535954 | | |
| | | UBB | 2.26697 | CNN3 | 0.410269 | FAM58B | 3.4704 | RREB1 | 0.535999 | | |
| | | KLHL18 | 0.441715 | NUP93 | 2.43383 | GM5507 | 0.288649 | GM10749 | 1.86475 | | |
| | | SNRNP35 | 0.441746 | SNAP23 | 0.410876 | KCNQS | 3.46359 | NCOA2 | 1.86434 | | |
| | | DPM3 | 2.26299 | IL17A | 0.411163 | D630004N19RIK | 0.288787 | ABCD1 | 1.86396 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-<br>IL1B + IL6 + IL23-<br>96 h-1<br>Fold.Change<br>(KO/WT) | Gene | GPR65-KO-<br>TGFB1 + IL6-96 h-1<br>Fold.Change<br>(KO/WT) | Gene | PLZP-KO-<br>IL1B + IL6 + IL23-<br>48 h-1<br>Fold.Change<br>(KO/WT) | Gene | PLZP-KO-<br>TGFB1 + IL6-48 h-1<br>Fold.Change<br>(KO/WT) | Gene | TOSO-KO-<br>IL1B + IL6 + IL23-<br>96 h<br>Fold.Change<br>(KO/WT) | Gene | TOSO-KO-<br>IL1B + IL6 + IL23-<br>96 h<br>Fold.Change<br>(KO/WT) |
|---|---|---|---|---|---|---|---|---|---|---|---|
| | | BCD49349 | 0.442184 | SCD3 | 2.43123 | SLC25A39 | 3.46276 | FOXO3 | 0.536658 | | |
| | | HECTD3 | 2.26147 | RRP36 | 0.41212 | 3110001D03RIK | 3.46125 | ASH2L | 0.536841 | | |
| | | MUM1 | 0.442346 | WDR77 | 0.412209 | ACRBP | 3.45928 | CD1D1 | 1.862 | | |
| | | GM5879 | 2.26 | 1110059E24RIK | 2.42555 | 2610301B20RIK | 0.289335 | EXOSC3 | 1.86032 | | |
| | | ANAPC5 | 2.25775 | RAB4B | 2.42419 | TIMM22 | 3.4562 | 2700073G19RIK | 1.85974 | | |
| | | MSN | 2.25766 | FAS | 0.412615 | ERCC3 | 0.289451 | CLP1 | 0.537757 | | |
| | | PRKAB1 | 0.44338 | CDV3 | 0.41273 | TTLL1 | 0.289466 | GFM1 | 0.53782 | | |
| | | OBFC2B | 0.443448 | TARS | 0.412962 | CYP4X1 | 3.45405 | ANGEL1 | 0.537921 | | |
| | | 2010002N04RIK | 2.25414 | MCTS1 | 2.42132 | FANCC | 0.289578 | TMEM55B | 0.537935 | | |
| | | GBA | 2.25281 | ADK | 0.41902 | ACP2 | 0.289725 | AI314976 | 0.537974 | | |
| | | WFDC12 | 0.444838 | LUM | 0.413837 | BC068281 | 0.2898 | FRG1 | 1.85879 | | |
| | | HSD17B10 | 2.24676 | DDB2 | 0.414031 | STARD7 | 3.45065 | IFI47 | 1.85754 | | |
| | | RSF1 | 0.44561 | CHCHD1 | 0.414192 | PLACB | 3.44922 | SLC39A14 | 0.538616 | | |
| | | DHR53 | 0.445627 | HAUSS | 0.414267 | RPL21-<br>PS4 | 3.44832 | RPL10A-<br>PS2 | 0.539089 | | |
| | | APEX1 | 2.2438 | GRAMD3 | 0.414562 | AA960436 | 0.290163 | MRPL12 | 1.85427 | | |
| | | TULP4 | 0.445693 | STAG2 | 2.41193 | CBR1 | 3.44506 | RAPGEF6 | 1.8531 | | |
| | | KLHL6 | 2.2427 | KIF23 | 2.41134 | UROD | 0.290278 | ETFA | 1.85182 | | |
| | | TSTD2 | 0.445908 | FANCG | 0.444815 | 1110018G07RIK | 3.44241 | IL4RA | 0.540125 | | |
| | | SFXN5 | 0.445941 | 42249 | 2.40807 | GABARAP | 0.290549 | BCL2L11 | 1.85096 | | |
| | | A530064D06RIK | 0.445959 | MRPS5 | 2.40689 | RFTN1 | 0.290802 | CKAP5 | 0.8501 | | |
| | | RG9MTD2 | 0.446327 | 9330129D05RIK | 0.415476 | TOR1B | 3.43761 | PPP1R11 | 1.84947 | | |
| | | POLR3K | 2.24048 | MYCBP | 0.40489 | SIRT6 | 0.290991 | MGAT1 | 0.540891 | | |
| | | ZFAND1 | 2.24028 | SMYD5 | 2.3976 | HYAL2 | 0.291252 | ACTL6A | 0.540991 | | |
| | | CHN2 | 0.446849 | ZFP605 | 2.39591 | AA415398 | 0.291482 | PRR3 | 0.541067 | | |
| | | GNA13 | 2.23782 | POLR2F | 0.418289 | LAPTM4B | 0.291771 | TSPAN3 | 0.541238 | | |
| | | LRRC57 | 2.23676 | TCTN2 | 0.3902 | ACOT9 | 3.42735 | SDHA | 0.541254 | | |
| | | RORA | 2.23615 | ZC3HAV1 | 2.38878 | RIT1 | 0.291982 | IRAK1 | 0.541435 | | |
| | | STK38 | 0.447501 | 2410002I01RIK | 0.419639 | GATAD2B | 2.38206 | GM16372 | 0.541465 | | |
| | | SDF4 | 2.23205 | TOMM7 | 2.38206 | GM454 | 3.42131 | PRR13 | 0.541563 | | |
| | | EMG1 | 2.23131 | TBC1D9B | 2.38033 | RUSC1 | 0.292286 | PHF21A | 1.84613 | | |
| | | FAM69A | 0.448401 | AC166253.1 | 0.37846 | 2610029G23RIK | 0.292435 | CCNDBP1 | 1.84601 | | |
| | | IKBKG | 0.448482 | ID2 | 0.420475 | MAX | 3.41678 | WBSCR16 | 0.5418 | | |
| | | AC170752.1 | 2.22847 | NUP43 | 0.420972 | CIR1 | 3.41407 | SURF2 | 0.542203 | | |
| | | IAH1 | 0.448838 | CLINT1 | 0.421182 | SLC45A4 | 3.41407 | HEATR7A | 0.542304 | | |
| | | ARMC6 | 2.22769 | BAZ2B | 2.37372 | LEPROT | 3.41029 | UPF2 | 1.84338 | | |
| | | RIMKLB | 0.449006 | NFS1 | 0.421373 | DTWD2 | 0.29323 | ZDHHC2 | 1.84324 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO-IL1B + IL6 + IL23-96 h-1 | | GPR65-KO-TGFB1 + IL6-96 h-1 | | PLZP-KO-IL1B + IL6 + IL23-48 h-1 | | PLZP-KO-TGFB1 + IL6-48 h-1 | | TOSO-KO-IL1B + IL6 + IL23-96 h | | TOSO-KO-IL1B + IL6 + IL23-96 h |
|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| | | ZNF512B | 0.449096 | CD40LG | 0.421523 | TMEM126A | 3.40481 | ZSWIM7 | 0.542856 | | |
| | | PSMB1 | 2.22377 | SEPHS1 | 0.421566 | TSPAN6 | 3.40187 | SNAPIN | 1.84112 | | |
| | | SPIC | 0.449745 | MSH2 | 2.37021 | 1700052N19RIK | 3.40139 | H2-OA | 0.543218 | | |
| | | NDUFB5 | 2.22266 | 1110001A16RIK | 2.36988 | ZFP239 | 3.40051 | HIST1H3G | 0.543763 | | |
| | | ACTL6A | 0.45008 | IL16 | 2.36962 | 2410002I01RIK | 3.39923 | SH3BPS | 1.83895 | | |
| | | PLA2G2C | 0.450326 | SEC11A | 2.36893 | CST3 | 3.39793 | ECT2 | 1.83892 | | |
| | | RPL3 | 2.21903 | UXT | 0.422554 | SLC9A3R1 | 0.294297 | 4933421E11RIK | 0.544024 | | |
| | | CLUAP1 | 2.21787 | DECR2 | 2.3663 | ZFP82 | 3.39489 | CYB5R1 | 0.544334 | | |
| | | S100A7A | 0.45141 | DPCD | 0.422754 | CABLES2 | 3.39347 | GM10349 | 0.544527 | | |
| | | USP7 | 0.451836 | POLE | 0.422899 | RNF38 | 3.39295 | PDCD1 | 0.544637 | | |
| | | 2900092E17RIK | 0.452171 | INPP5K | 0.422982 | 2410002F23RIK | 3.38695 | PPP2R5E | 1.83563 | | |
| | | TUBG1 | 0.452948 | FOXRED1 | 2.36406 | HMGN5 | 0.295251 | WHRN | 0.545202 | | |
| | | PECI | 2.20688 | VPS4A | 2.36323 | GALNT7 | 0.295262 | WDYHV1 | 0.545738 | | |
| | | DHX40 | 2.20161 | BIRC3 | 2.3623 | CRK | 0.295838 | GNPNAT1 | 1.83227 | | |
| | | PAQR3 | 0.45431 | GM10395 | 0.423351 | 1810063B05RIK | 3.37945 | 630416G13RIK | 0.545776 | | |
| | | AL592187.1 | 0.454499 | 3110043O21RIK | 0.423484 | PPP2R2D | 0.295906 | QDPR | 0.545929 | | |
| | | MIF4GD | 2.20019 | SATB1 | 0.424146 | AHNAK | 0.295931 | ZRANB2 | 1.83121 | | |
| | | ABAT | 0.454636 | AC132320.1 | 2.35533 | PTK2B | 0.296081 | GM71 | 1.83056 | | |
| | | PBX1 | 0.454434 | QRICH1 | 0.424793 | ATP6AP2 | 3.37424 | FBXW11 | 0.546354 | | |
| | | MLPH | 0.455592 | TRP53 | 0.425101 | WEE1 | 0.29648 | GIMAP4 | 1.83026 | | |
| | | WDR77 | 0.455613 | SLC25A36 | 2.35234 | LRRC41 | 3.37149 | AGFG1 | 1.82946 | | |
| | | FBXO44 | 2.19411 | PIGX | 2.35214 | CENPQ | 0.296665 | AMIGO1 | 0.546986 | | |
| | | PFDN2 | 0.455822 | ASB13 | 0.425366 | ATP6V1B2 | 0.297223 | NDUFB9 | 0.547145 | | |
| | | SULF2 | 0.456066 | POP1 | 0.425439 | NGFRAP1 | 3.36353 | TMEM43 | 0.5472 | | |
| | | 4632433K11RIK | 0.456427 | TTC19 | 0.425544 | GM4922 | 0.297412 | EPHX1 | 0.547367 | | |
| | | AP1B1 | 0.456439 | AC087117.1 | 2.34081 | HAUS3 | 0.297412 | RALB | 0.547377 | | |
| | | MRPL20 | 2.18844 | ZDHHC21 | 2.34042 | IL1RL2 | 0.297412 | SPATA7 | 1.82669 | | |
| | | HINT1 | 2.18827 | TCHP | 0.427295 | 2610018G03RIK | 0.297753 | KHK | 0.547649 | | |
| | | 6330439K17RIK | 0.457064 | DPY30 | 2.33847 | RPL13-PS3 | 3.35846 | CYTH2 | 1.82538 | | |
| | | ANP32A | 0.457393 | NTAN1 | 0.427809 | 3110009E18RIK | 0.297797 | FAAH | 0.5479 | | |
| | | H2-T23 | 2.18171 | PFDN4 | 0.428353 | LDHC | 3.35647 | R3HCC1 | 0.548164 | | |
| | | SAG | 0.458865 | SH3KBP1 | 2.33449 | NHEDC2 | 0.298441 | 1700057G04RIK | 0.548299 | | |
| | | CTSZ | 2.1802 | GM10063 | 0.428916 | MKLN1 | 0.298486 | AHR | 1.82235 | | |
| | | GM10699 | 0.458737 | CAML | 0.428973 | FBXL4 | 3.34996 | RTCD1 | 1.82138 | | |
| | | DGUOK | 2.17906 | LRRFIP1 | 0.429017 | GM6816 | 3.34996 | PLOD3 | 1.82037 | | |
| | | PARP1 | 2.17543 | SEMA4D | 2.33063 | CORO1C | 3.34844 | PSMD10 | 0.549959 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information inlcldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
|---|---|---|---|---|---|---|---|---|---|
| | GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h |
| | | UNC45B | 0.459794 | TRAPPC1 | 2.32803 | SETX | 0.298789 | USMG5 | 0.551139 |
| | | H2-K2 | 2.17147 | ZFP655 | 0.429566 | USP21 | 0.298838 | CCDC127 | 0.551167 |
| | | POLD4 | 2.17121 | CD209C | 2.32591 | APEX2 | 3.3449 | BRIX1 | 1.81416 |
| | | ZFP53 | 2.16957 | PPPDE1 | 2.32456 | TMEM69 | 3.34327 | BGLAP-RS1 | 1.81269 |
| | | VP554 | 2.16948 | DEPDC5 | 0.431528 | LRPPRC | 0.299236 | POLD1 | 0.551766 |
| | | H2-OA | 0.460969 | EIF2B5 | 2.3157 | CMTM6 | 3.33853 | YWHAZ | 0.551889 |
| | | CCDC124 | 0.46117 | AP1B1 | 2.31379 | RER1 | 3.33853 | PRPF3 | 0.551942 |
| | | TLCD2 | 0.461632 | RNASEH2B | 0.432267 | CDK8 | 0.29975 | HIST1H2BG | 1.81161 |
| | | LIMCH1 | 0.461684 | RNF20 | 0.432732 | KPNB1 | 0.299805 | 4930445C21RIK | 0.55247 |
| | | C1YBL | 2.1649 | GNPDA1 | 2.30957 | GSN | 3.33504 | 2810417H13RIK | 1.80977 |
| | | 2610028H24RIK | 2.16231 | VTA1 | 0.433242 | 2010107G23RIK | 3.33144 | CHURC1 | 1.80936 |
| | | POT1B | 0.462653 | NISCH | 2.30736 | CCNL1 | 0.300171 | DNAJA3 | 0.552777 |
| | | GM10359 | 2.161 | INPP5B | 0.434037 | EIF2C4 | 3.32825 | TMEM33 | 0.552949 |
| | | FAM48A | 2.16008 | VEZT | 2.30135 | 2310039H08RIK | 3.32527 | CRTC1 | 0.552987 |
| | | SLC35A3 | 0.463086 | DDX56 | 0.434647 | GM4769 | 0.300727 | MAN2C1 | 0.553075 |
| | | VP528 | 2.15942 | MRPS18C | 2.29971 | CDKN3 | 3.32437 | TBC1D2B | 1.80746 |
| | | GM16223 | 0.463771 | TSSC1 | 2.29637 | ALG8 | 0.300988 | TMEM109 | 0.553279 |
| | | PPIL1 | 0.463844 | NIF3L1 | 0.435506 | NDUFAF1 | 3.30854 | DPH1 | 0.553309 |
| | | SEC23A | 2.15533 | ACOT9 | 0.435567 | BC026590 | 3.30791 | ZFP617 | 1.8071 |
| | | KCTD20 | 0.465161 | RTN4 | 2.29576 | VPS45 | 0.302474 | GABPB1 | 0.553583 |
| | | GM10491 | 0.465733 | ICAM1 | 0.43576 | RPL21-PS6 | 0.302832 | PBX4 | 1.80478 |
| | | GAPDH | 2.14683 | IFT52 | 0.43611 | 4932425I24RIK | 3.30203 | RPS6KB2 | 0.554403 |
| | | EML1 | 0.466 | GM10941 | 0.437625 | ZUFSP | 0.303095 | WASF2 | 1.80256 |
| | | GM11127 | 0.466028 | CUL2 | 0.43766 | FBXO25 | 0.303323 | 1810063B05RIK | 0.5548 |
| | | CTSL | 2.14528 | RABEPK | 0.437762 | CHCHD3 | 3.29527 | GTF3C5 | 0.555342 |
| | | FCGBP | 0.466372 | CCNA2 | 0.4381 | AC156282.1 | 3.29316 | NCOR1 | 1.80056 |
| | | PMPCB | 2.14362 | NFU1 | 0.4384 | APOO | 3.29302 | UFD1L | 0.555419 |
| | | GM11696 | 0.467028 | 4930512M02RIK | 2.28097 | TUBB2A | 3.29053 | INCENP | 0.555529 |
| | | EXPI | 0.467245 | MEMO1 | 0.43848 | AC154727.1 | 0.304576 | BC004004 | 1.79969 |
| | | CD70 | 0.467704 | AP2A1 | 2.28027 | METT11D1 | 3.28058 | ELOF1 | 0.555867 |
| | | MRPL13 | 0.467833 | 913001J15RIK | 0.438852 | TMEM55B | 0.305017 | ANKRD39 | 1.79863 |
| | | FAM188A | 2.13708 | NAE1 | 0.43911 | GM7792 | 0.305222 | PEX5 | 1.79857 |
| | | HELLS | 2.1366 | SET | 0.439536 | TBC1D14 | 3.2763 | PML | 1.79766 |
| | | ZDHHC12 | 0.468237 | PYCARD | 0.43988 | PRKACA | 0.305346 | PDGFA | 0.556287 |
| | | GM6843 | 0.468988 | FADS6 | 2.27168 | CHCHD5 | 3.27182 | ZMYM1 | 0.556484 |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h |
|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Fold.Change (KO/WT) |
| | | H2-KE2 | 2.13071 | NDUFB3 | 0.440946 | PUF60 | 3.26996 | RC3H2 | 0.556597 | |
| | | TTC39B | 2.12776 | CTNNB1 | 0.441276 | B230315N10RIK | 0.305922 | IFI30 | 0.556767 | |
| | | GM9104 | 2.12771 | PGAP2 | 0.441622 | CASP9 | 3.26881 | WDR74 | 0.556829 | |
| | | IFFO2 | 0.470055 | SLC1A7 | 0.441665 | CSMD3 | 3.26735 | MAPKAPK5 | 0.557062 | |
| | | UNC119 | 0.470111 | 1110007A13RIK | 2.26398 | GIT2 | 3.26251 | PLCXD1 | 0.557075 | |
| | | FARSA | 2.12375 | PARVG | 2.26374 | PARVG | 3.26132 | ABI1 | 0.55722 | |
| | | CDK5RAP1 | 0.471003 | CCNG1 | 0.441766 | JMJD1C | 0.306647 | PISD | 0.557802 | |
| | | GM10481 | 2.12193 | 1810043G02RIK | 2.2607 | EXT1 | 0.306879 | PRDX1 | 0.55786 | |
| | | HCN3 | 0.471413 | CENPN | 2.26031 | STRBP | 3.25784 | CEPT1 | 0.558251 | |
| | | WDR26 | 2.11983 | AHSA2 | 2.25986 | HSD11B1 | 3.25586 | GPSM3 | 1.79072 | |
| | | ZSCAN2 | 0.471782 | NF1 | 2.25905 | TSC22D3 | 0.307254 | EGFR | 0.558788 | |
| | | RABL2 | 0.472485 | TIMM9 | 2.25653 | FXR1 | 0.307377 | CASZ1 | 1.78932 | |
| | | LRRC8D | 0.47293 | FAM192A | 2.2561 | M6PR | 0.307753 | SAR1B | 1.78855 | |
| | | CPNE5 | 0.47295 | CPA6 | 2.25489 | CDIPT | 3.24906 | COMMD1 | 0.559244 | |
| | | WFDC5 | 0.473411 | ACO1 | 2.25226 | GM10120 | 0.30795 | SMC4 | 0.559449 | |
| | | 1110008I03RIK | 0.473831 | SUCLA2 | 2.24437 | ME2 | 3.24437 | NEDD9 | 1.78684 | |
| | | TPM1 | 0.474032 | CCS | 2.24671 | UBE2R2 | 3.24431 | GALT | 0.559741 | |
| | | TAF11 | 0.474295 | HDAC6 | 2.24613 | NUP35 | 3.24336 | FZR1 | 0.560072 | |
| | | 1110049F12RIK | 0.474416 | BCL2A1D | 0.44523 | PRP52 | 3.24211 | LRSAM1 | 0.560257 | |
| | | CCDC101 | 2.10597 | SS18 | 2.24356 | 5730403B10RIK | 3.24185 | FAM126B | 0.560396 | |
| | | 8430410A17RIK | 0.475727 | RPUSD4 | 0.446656 | GJC3 | 3.24033 | ZFP783 | 1.78415 | |
| | | GM16409 | 2.10033 | STOML2 | 2.23691 | RRP15 | 2.2377 | RHEBL1 | 0.560621 | |
| | | 4930423O20RIK | 0.476418 | TRUB2 | 2.23626 | HERC4 | 0.309176 | DLD | 0.560748 | |
| | | IPO4 | 0.47698 | LIAS | 0.447179 | PPIE | 0.309526 | AGPAT6 | 1.78293 | |
| | | OGFOD1 | 0.477246 | EME1 | 2.23473 | BRMS1 | 3.2304 | CCDC88C | 0.560936 | |
| | | GM16253 | 0.477298 | PAPD5 | 2.23455 | TOP2B | 3.22874 | TFG | 0.561088 | |
| | | AC087229.1 | 0.477627 | MKKS | 0.448136 | FBXO22 | 3.22729 | GM6404 | 1.78103 | |
| | | FTL1 | 2.09329 | HDAC7 | 2.23062 | LISP7 | 3.22585 | NUFIP2 | 1.77858 | |
| | | GM6177 | 2.09251 | 2610002J02RIK | 0.448358 | ST13 | 0.31005 | PAM16 | 0.562297 | |
| | | EIF1AX | 0.478225 | GM10222 | 0.448984 | CCDC47 | 3.22504 | ACBD4 | 0.562414 | |
| | | OXSR1 | 0.478424 | COX7B | 0.449612 | AC158559.1 | 0.310331 | PICK1 | 0.562446 | |
| | | GM11011 | 0.478426 | ARPP19 | 0.449695 | CDK16 | 0.3108356 | LRP1B | 0.562624 | |
| | | ZWILCH | 2.08967 | PYGB | 2.22223 | 2410022L05RIK | 3.21695 | TMEM141 | 0.562297 | |
| | | APH1B | 2.08549 | 1110004E09RIK | 0.451634 | IGFBP4 | 0.310854 | GADD45A | 0.562888 | |
| | | FNDC7 | 0.479946 | MRPS36 | 0.452048 | 5RSF2 | 3.21548 | PCGF1 | 0.562989 | |
| | | NUDT16L1 | 0.479973 | P4HB | 0.452445 | D1BWG0212E | 0.311108 | MGAT4C | 0.563208 | |
| | | AL589878.1 | 0.480025 | FAM103A1 | 2.20774 | FEN1 | 0.311256 | NVL | 1.77522 | |
| | | | | | | | | | 1.77516 | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO IL1B + IL6 + IL23-96 h-1 | | GPR65-KO TGFB1 + IL6-96 h-1 | | PLZP-KO IL1B + IL6 + IL23-48 h-1 | | PLZP-KO TGFB1 + IL6-48 h-1 | | TOSO-KO IL1B + IL6 + IL23-96 h | | TOSO-KO IL1B + IL6 + IL23-96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| | | 2010106G01RIK | 0.480718 | MCFD2 | 2.20704 | YBX1 | 0.311269 | PRPF40A | 1.77313 | | |
| | | AC153594.1 | 0.480831 | SLC35A2 | 0.453334 | CCNG1 | 3.21088 | TMEM101 | 0.564739 | | |
| | | RPL21-PS11 | 2.07755 | HAUS7 | 0.453406 | FAM40A | 3.20928 | CDCA3 | 0.564975 | | |
| | | ATF4 | 2.07678 | TMEM49 | 2.20502 | 5830433M19RIK | 0.311726 | SLFN8 | 1.76958 | | |
| | | EMD | 2.07543 | SMAD3 | 0.454636 | CTS5 | 3.20795 | FUNDC2 | 0.565211 | | |
| | | ABHD4 | 2.06755 | MADD | 2.19501 | CLIP1 | 3.20692 | 1810013D10RIK | 0.565296 | | |
| | | PATZ1 | 0.483944 | ZFP277 | 2.19468 | GM10482 | 0.311832 | RNASEH2 | 0.565395 | | |
| | | 1700061G19RIK | 0.48396 | 5930416I19RIK | 2.19421 | PRAMEL5 | 3.20611 | GSN | 0.565571 | | |
| | | ERH | 2.06622 | HDGF | 0.455778 | GM10088 | 3.20581 | PLCG1 | 1.768 | | |
| | | SNX17 | 0.4842 | CHRAC1 | 2.18984 | ATP5L | 0.312179 | 1600002H07RIK | 0.56563 | | |
| | | RHBDD2 | 0.484413 | NUP214 | 2.18975 | ZC3HAV1 | 3.20328 | SYNGR1 | 0.565632 | | |
| | | ILF2 | 2.06414 | AGPAT6 | 2.18953 | ING3 | 0.312252 | MRPL13 | 1.76635 | | |
| | | GHM5045 | 2.06252 | CUL1 | 0.456742 | UPF3B | 3.2021 | CLPTM1L | 0.566179 | | |
| | | TRPM1 | 0.485193 | FAM48A | 2.18865 | GM4885 | 3.19919 | ATP5G1 | 0.566213 | | |
| | | FURIN | 0.486329 | ADAMTSL4 | 0.45754 | D2WSU81E | 3.19707 | ERN1 | 0.566827 | | |
| | | GM7964 | 2.05608 | PRDM11 | 2.1834 | SMC4 | 0.312889 | SMYD3 | 1.76394 | | |
| | | GPKOW | 2.05294 | BC026585 | 2.18302 | POT1A | 0.313051 | PLAGL1 | 0.567379 | | |
| | | IRGM1 | 2.05135 | AKAP9 | 0.458226 | PRKAB1 | 3.1937 | MARCKSL1 | 1.762 | | |
| | | METTL5 | 2.05114 | DSTN | 0.458411 | BANF1 | 3.19157 | ALDOART2 | 0.567735 | | |
| | | PGAM1 | 2.0511 | GOT2 | 0.459847 | CDC20 | 3.18913 | SELP | 0.567803 | | |
| | | MYBBP1A | 0.487549 | POLR2J | 2.1702 | TRMT61A | 0.313689 | DCTN4 | 0.568542 | | |
| | | NUDT7 | 2.0507 | GM15887 | 0.461531 | MKKS | 3.18457 | CDK2 | 0.568548 | | |
| | | 2410017P09RIK | 0.487772 | CREB3 | 0.463233 | 1110002N22RIK | 3.1836 | PLA2G16 | 0.568624 | | |
| | | NXT1 | 0.487864 | NUP54 | 0.46331 | 4930555F03RIK | 3.18179 | 672048N17RIK | 0.569815 | | |
| | | HNRNPAB | 0.487941 | GM10495 | 2.15552 | CGN | 3.17972 | 1110007C09RIK | 0.570179 | | |
| | | PPP1R3F | 2.04769 | INPPSF | 2.14687 | KRT222 | 3.17941 | USE1 | 0.570337 | | |
| | | LEO1 | 2.04707 | LGALS1 | 2.14651 | SARNP | 3.17917 | VPS39 | 0.570866 | | |
| | | CMTM6 | 2.04648 | TIMM17A | 0.466884 | ARL6 | 3.17793 | ATG9A | 0.570933 | | |
| | | MFF | 0.48865 | SURF4 | 0.467147 | P2RX4 | 3.17721 | ILF2 | 1.75104 | | |
| | | PCBP3 | 0.488893 | PSMC6 | 0.467773 | COX18 | 3.17615 | 42068 | 0.571351 | | |
| | | KLC1 | 0.489024 | NDUFB11 | 2.1347 | TADA2A | 0.314846 | YIF1A | 0.571751 | | |
| | | GM9808 | 2.04453 | PSMD13 | 0.468583 | TUFT1 | 0.314984 | CIB1 | 1.74844 | | |
| | | CBX1 | 2.0445 | SSB | 0.475177 | RIOK1 | 3.17343 | TNFRSF14 | 1.74806 | | |
| | | IL4RA | 2.04176 | SDF4 | 0.479001 | NUDT16L1 | 0.31515 | AC090123.1 | 1.74715 | | |
| | | 2310045N01RIK | 0.489897 | RPL22L1 | 0.484688 | 0610009B22RIK | 3.17238 | AMFR | 0.572472 | | |
| | | CCT4 | 2.03971 | NME1 | 2.05839 | NAPA | 3.17114 | MAPKAP1 | 0.572544 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| GPR65-KO- IL1B + IL6 + IL23- 96 h-1 | | GPR65-KO- TGFB1 + IL6-96 h-1 | | PLZP-KO- IL1B + IL6 + IL23- 48 h-1 | | PLZP-KO- TGFB1 + IL6-48 h-1 | | TOSO-KO- IL1B + IL6 + IL23- 96 h | | TOSO-KO- IL1B + IL6 + IL23- 96 h | |
|---|---|---|---|---|---|---|---|---|---|---|---|
| Gene | Fold.Change (KO/WT) | Gene | Fold.Change (KO/WT) | Gene | Fold.Change (KO/WT) | Gene | Fold.Change (KO/WT) | Gene | Fold.Change (KO/WT) | Gene | Fold.Change (KO/WT) |
| | | BDH1 | 2.03947 | RPS15A | 0.489007 | FNBP1 | 3.16923 | GM13154 | 1.74582 | | |
| | | GM10845 | 0.49045 | ANP32A | 0.495753 | CTPS | 3.16817 | PAFAH2 | 0.573079 | | |
| | | NUDC | 2.03722 | GM10036 | 0.501126 | FAM195A | 3.16733 | EVI2A | 0.57309 | | |
| | | T5FM | 2.03532 | KDM5A | 1.98696 | ATP6V1E1 | 0.316043 | CD69 | 0.573096 | | |
| | | UHRF1 | 0.491655 | MRPL20 | 1.98423 | C330021F23RIK | 3.16359 | 4930453N24RIK | 0.573176 | | |
| | | CHD3 | 0.491889 | UBA1 | 1.98506 | 2810004N23RIK | 3.15863 | PLEK | 0.573959 | | |
| | | PI4KA | 0.491991 | CRIP1 | 1.94192 | FUT8 | 0.316765 | PIK3CD | 0.573988 | | |
| | | CD247 | 0.492074 | AT5B | 0.516133 | PSMB5 | 0.316776 | AKTIP | 0.574124 | | |
| | | PSG29 | 0.492256 | TOPMM5 | 1.92215 | RNF14 | 0.316879 | NUP50 | 0.574382 | | |
| | | DDXS6 | 0.492881 | VPS29 | 1.89828 | GM6498 | 3.15505 | GM10108 | 0.574638 | | |
| | | MGST2 | 0.493199 | LY6A | 1.89024 | PPOX | 3.15469 | SF3B4 | 0.57473 | | |
| | | PIPSK1A | 0.493439 | GPI1 | 0.529736 | LIAS | 3.15234 | BC052040 | 1.73993 | | |
| | | SCD2 | 2.02514 | APEX1 | 0.536689 | LIN37 | 0.317121 | MFSD2A | 1.73981 | | |
| | | TNNI1 | 0.494042 | 1810009A15RIK | 0.537057 | CACNA1F | 0.317155 | PHLDA3 | 0.574792 | | |
| | | SAA1 | 0.494437 | | | FBXO18 | 3.15288 | GFPT1 | 0.574973 | | |
| | | GM11092 | 0.494518 | | | ARHGDIA | 3.15288 | CDC26 | 1.73847 | | |
| | | OLFR316 | 0.49502 | | | BCL3 | 3.15234 | CYP11A1 | 0.575584 | | |
| | | MARCKSL1 | 0.495066 | | | NUBPL | 3.15086 | MKKS | 0.576672 | | |
| | | CCDC61 | 0.496047 | | | NARS2 | 3.1491 | TMEM123 | 1.73129 | | |
| | | HIST1H1E | 0.496819 | | | POP4 | 3.14837 | SF3A2 | 0.577604 | | |
| | | SIGMAR1 | 0.496855 | | | RNF34 | 0.317653 | RNF125 | 0.57771 | | |
| | | EIF4G3 | 0.49691 | | | EIF285 | 3.14724 | A630033E08RIK | 0.577835 | | |
| | | NFKBID | 0.496946 | | | MYG1 | 3.14567 | CIR1 | 0.577934 | | |
| | | UNC50 | 0.496963 | | | M54A15 | 0.31794 | RCSD1 | 0.577976 | | |
| | | AI314976 | 2.01113 | | | DDX41 | 0.317994 | MANEA | 1.72905 | | |
| | | TRIM43A | 0.4973 | | | ARL3 | 0.318146 | GIMAP9 | 0.578676 | | |
| | | RAB7L1 | 0.497891 | | | AEN | 3.14104 | TMEM138 | 0.578809 | | |
| | | PI16 | 0.498177 | | | BPGM | 0.318753 | ALDH7A1 | 0.579051 | | |
| | | 1110007A13RIK | 0.498318 | | | ARMC10 | 0.318867 | JMJD6 | 0.579408 | | |
| | | BTBD11 | 0.498889 | | | 6330416G13RIK | 3.1361 | LZIC | 0.57939 | | |
| | | WDR69 | 0.499266 | | | SNUPN | 3.13603 | NAT9 | 1.72561 | | |
| | | CDK2 | 0.499306 | | | GORASP2 | 0.319013 | UN13D | 0.5797 | | |
| | | SEPW1 | 0.499344 | | | WDR53 | 3.13378 | MSI2 | 1.72493 | | |
| | | ZBTB43 | 0.499355 | | | CCDC58 | 0.319208 | UBE2B | 0.579806 | | |
| | | RELB | 2.00243 | | | KDM1A | 3.13242 | STK16 | 0.580011 | | |
| | | RPL10 | 2.00217 | | | BC011426 | 0.319263 | RAB14 | 0.58029 | | |
| | | AL845291.1 | 0.499614 | | | TMEM164 | 0.31954 | AA467197 | 0.581573 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-TGFB1 + IL6-96 h-1 Fold.Change (KO/WT) | Gene | PLZP-KO-IL1B + IL6 + IL23-48 h-1 Fold.Change (KO/WT) | Gene | PLZP-KO-TGFB1 + IL6-48 h-1 Fold.Change (KO/WT) | Gene | TOSO-KO-IL1B + IL6 + IL23-96 h Fold.Change (KO/WT) | Gene | TOSO-KO-IL1B + IL6 + IL23-96 h Fold.Change (KO/WT) |
|---|---|---|---|---|---|---|---|---|---|
| GM4883 | 0.499929 | | | MBTPS2 | 3.12778 | EPN2 | 0.581642 | | |
| FAM160A2 | 0.500259 | | | QDPR | 3.12635 | MTMR1 | 1.71705 | | |
| SLC22A23 | 0.501166 | | | TFIP11 | 3.12476 | FLII | 0.582556 | | |
| ECHDC1 | 0.501544 | | | BC003267 | 3.12306 | A630007B06RIK | 1.71539 | | |
| EFCAB1 | 0.501729 | | | 2210404I11RIK | 0.320322 | GPR98 | 1.71429 | | |
| CIAPIN1 | 0.502094 | | | NSG2 | 0.320617 | ISYNA1 | 0.583808 | | |
| PGAM5 | 0.502382 | | | SGIP1 | 3.11884 | SNRNP200 | 1.71092 | | |
| ZDHHC19 | 0.502393 | | | GIMAP6 | 3.11626 | HIST1H3C | 1.7103 | | |
| PRDM10 | 1.99024 | | | ATG16L2 | 3.11474 | TFPI | 0.585092 | | |
| RPL39L | 0.502504 | | | NUPR1 | 3.11474 | COX6A1 | 0.586233 | | |
| RDH9 | 0.50263 | | | GM10343 | 0.321806 | GFM2 | 0.586276 | | |
| ITPA | 1.98861 | | | TSPAN18 | 3.10729 | PPIL3 | 0.586625 | | |
| PTGES3 | 1.98596 | | | KIF5B | 0.32193 | 1810032O08RIK | 1.70368 | | |
| PTMS | 0.503584 | | | RPL27A-PS1 | 3.10625 | KHDRBS1 | 0.587185 | | |
| RNF135 | 0.50392 | | | VPS72 | 3.10624 | TMEM159 | 1.70133 | | |
| MRPL50 | 1.98425 | | | GM4978 | 0.322117 | ALDOC | 1.70114 | | |
| BRAP | 0.504061 | | | FASTKD2 | 0.322465 | SMAP1 | 0.588077 | | |
| TMEM45B | 0.504185 | | | LUC7L3 | 3.10094 | TM9SF4 | 1.7001 | | |
| COMMD9 | 0.504361 | | | STX11 | 0.322483 | SUPT5H | 0.58832 | | |
| CNTN1 | 0.504447 | | | NME7 | 3.09872 | TMEM149 | 1.69819 | | |
| ANO3 | 0.504602 | | | TGFBR1 | 3.09731 | ATP6V1H | 0.589251 | | |
| DCTN4 | 0.504703 | | | 5HQ1 | 3.09603 | KCTD11 | 0.589528 | | |
| MAPRE2 | 0.504727 | | | LMAN1 | 3.09465 | SOCS4 | 0.589616 | | |
| HIST4H4 | 0.505159 | | | HIP1R | 3.09349 | WASL | 1.69599 | | |
| 1500032L24RIK | 0.505228 | | | CSTB | 3.09201 | SMPD4 | 0.58987 | | |
| DOK2 | 0.505314 | | | GM5145 | 3.08822 | FAM125A | 0.590039 | | |
| LIN37 | 1.97879 | | | PDIA3 | 3.08642 | SIGMAR1 | 1.69479 | | |
| DCXR | 1.97873 | | | KYNU | 3.0849 | UHRF1BP1L | 0.590182 | | |
| RPS6-PS1 | 1.9786 | | | CHD4 | 0.324318 | EZH1 | 0.590285 | | |
| PMS1 | 0.505608 | | | AC117184.1 | 3.08207 | SDCCAG8 | 1.69368 | | |
| GPI1 | 1.97771 | | | SERINC1 | 0.324744 | PSMB9 | 1.69186 | | |
| INSIG2 | 1.97708 | | | UBE2E1 | 3.07896 | MRPL19 | 0.591074 | | |
| CEP250 | 0.505932 | | | YWHAH | 3.07799 | A130022I5RIK | 0.591458 | | |
| TRMU | 0.50683 | | | OXNAD1 | 3.07753 | DNAJC11 | 0.591491 | | |
| AU017455 | 0.50733 | | | TTC5 | 0.325023 | SRSF4 | 0.591655 | | |
| 8430426H19RIK | 0.50749 | | | RWDD4A | 3.07464 | GM8973 | 0.591773 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | 9030625A04RIK | 0.507881 | | | RPL26-PS2 | 3.07285 | ARHGAP4 | 0.592326 | | |
| | | ELMOD2 | 0.508684 | | | PDHX | 3.07277 | SEPHS1 | 1.68819 | | |
| | | MFN1 | 0.508852 | | | GALE | 3.07244 | IL2 | 0.592404 | | |
| | | GNGT1 | 1.96518 | | | PHOH | 3.07071 | PRNP | 1.68801 | | |
| | | LRRTM4 | 0.509206 | | | TAFIB | 3.06934 | LSP1 | 0.592415 | | |
| | | HBXIP | 1.96377 | | | GM10916 | 0.325935 | QPRT | 0.592438 | | |
| | | OBSL1 | 0.509404 | | | CCDC132 | 0.326324 | C80913 | 0.592481 | | |
| | | RRP9 | 0.509527 | | | SMCHD1 | 3.06355 | LRRC24 | 0.59293 | | |
| | | SR1 | 1.96225 | | | CRIP2 | 3.06351 | YTHDF2 | 0.592945 | | |
| | | 4930579K19RIK | 0.509665 | | | GRPEL2 | 0.326535 | PYGB | 0.593102 | | |
| | | 1700016D06RIK | 0.509699 | | | PARP4 | 3.06245 | SEMA4F | 0.593194 | | |
| | | SEPHS1 | 0.509782 | | | M5L3 | 0.326656 | RILPL2 | 0.593397 | | |
| | | OXNAD1 | 0.509827 | | | AAR5 | 0.326762 | AITC | 0.593821 | | |
| | | RPE | 0.51997 | | | TMEM179B | 3.06001 | CPNE3 | 1.68383 | | |
| | | RPL7A-PS8 | 1.954 | | | PYCRL | 0.327028 | IKBKG | 0.594093 | | |
| | | SLC15A3 | 0.511777 | | | LPL | 3.05767 | VHL | 0.594121 | | |
| | | GM561 | 0.511922 | | | 0030046E11RIK | 3.05746 | MRPL35 | 1.68226 | | |
| | | FBXO3 | 1.95304 | | | ZC3H12D | 0.327301 | H47 | 0.594489 | | |
| | | OSGIN2 | 0.51206 | | | 2700007P21RIK | 0.327512 | ZNHIT1 | 0.594596 | | |
| | | PXMP4 | 0.512182 | | | 4930583H14RIK | 3.05263 | ITPR2 | 1.68152 | | |
| | | FXYD3 | 0.512375 | | | ACAP2 | 0.327587 | GP49A | 1.67993 | | |
| | | PLEKHG2 | 0.512695 | | | CPNE8 | 0.327879 | XLR4C | 0.595291 | | |
| | | MDH1 | 1.9488 | | | LCMT1 | 0.327899 | KPNA4 | 1.67867 | | |
| | | LMO3 | 0.513707 | | | CES2B | 3.04897 | DPF1 | 0.595754 | | |
| | | THAP7 | 1.94632 | | | MARK2 | 3.0478 | ZFYVE20 | 0.595924 | | |
| | | SLC1A7 | 0.513853 | | | CDK2AP1 | 0.328236 | FAF1 | 0.596011 | | |
| | | PHPT1 | 0.514348 | | | PLEK | 0.328688 | POLB | 0.596191 | | |
| | | TOMM5 | 1.94408 | | | THOC1 | 0.328704 | RPL37 | 1.67707 | | |
| | | HNRPDL | 1.94367 | | | GTPBP2 | 3.04092 | MOCS1 | 0.596294 | | |
| | | WDR31 | 0.514637 | | | CBWD1 | 0.329216 | GNAI2 | 0.596532 | | |
| | | TOR1AIP2 | 0.514874 | | | BBS12 | 0.329239 | YME1L1 | 1.67359 | | |
| | | MYO1B | 0.515039 | | | TMEM167 | 0.32943 | GPAA1 | 0.597772 | | |
| | | RNF125 | 1.93985 | | | CSDA | 0.329624 | INSL3 | 0.597842 | | |
| | | 2310016C08RIK | 1.93825 | | | CCDC22 | 0.329876 | DNLZ | 1.67102 | | |
| | | NARFL | 0.516157 | | | VAMP4 | 3.02859 | CLK4 | 1.66998 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | APEX2 | 0.516321 | | | VPS16 | 3.02752 | APBB1IP | 1.66987 | | |
| | | RANBP1 | 1.93556 | | | SH3GLB1 | 3.02432 | MRPS11 | 0.599032 | | |
| | | HMCN1 | 0.517013 | | | ZC3H14 | 0.330652 | MAGED2 | 0.599116 | | |
| | | AAGAB | 0.517197 | | | TRMT11 | 0.330748 | ESCO1 | 0.599233 | | |
| | | PSG16 | 0.517263 | | | ABI3 | 0.331024 | AC151578.1 | 1.66877 | | |
| | | 2610044O15RIK | 0.517356 | | | HBA-A2 | 3.02035 | GPN1 | 0.60056 | | |
| | | TMEM49 | 1.93192 | | | NOP14 | 3.02006 | UTRN | 0.602289 | | |
| | | FCER1G | 0.517759 | | | ENOPH1 | 3.01903 | BDP1 | 1.65868 | | |
| | | KIF24 | 0.518046 | | | SLC44A1 | 0.331232 | AC148768.1 | 0.603 | | |
| | | MEA1 | 0.51844 | | | GM5614 | 3.01688 | RPL35 | 1.65822 | | |
| | | DHODH | 0.518678 | | | GM8225 | 0.332032 | ENO2 | 1.65807 | | |
| | | GM9574 | 0.519645 | | | CD47 | 3.00969 | DRAM2 | 1.65765 | | |
| | | HNRNPK | 1.92367 | | | FTSJ1 | 0.332414 | ATXN2 | 0.603542 | | |
| | | NOC4L | 0.520174 | | | 1700030K09RIK | 0.33275 | ABHD10 | 0.603967 | | |
| | | AW146154 | 0.520334 | | | PPP1CC | 3.00449 | TPRGL | 0.605694 | | |
| | | INTU | 0.520955 | | | NOL8 | 0.333129 | OSGIN2 | 0.605746 | | |
| | | YPEL5 | 1.91937 | | | WSB1 | 3.00142 | APOO-PS | 0.605872 | | |
| | | PTOV1 | 0.521626 | | | WBP11 | 0.333203 | RPL34 | 0.60602 | | |
| | | GM11057 | 0.521738 | | | MTERFD1 | 0.333307 | GM16514 | 0.607024 | | |
| | | 4930429B21RIK | 0.521955 | | | VPS26A | 0.333475 | GNL3L | 0.607071 | | |
| | | LAPTM5 | 1.91483 | | | ADAM17 | 2.99801 | FXYD7 | 0.607867 | | |
| | | NTNG2 | 0.522288 | | | NUP188 | 0.333567 | LIMK2 | 0.608276 | | |
| | | CCM2 | 0.522776 | | | ZFAND6 | 0.333577 | ELAC2 | 0.608326 | | |
| | | RPL9 | 1.9115 | | | HPS5 | 0.334144 | AW112010 | 1.64378 | | |
| | | MS4A6D | 0.523227 | | | NUP85 | 0.334404 | KIF2C | 1.64323 | | |
| | | USH2A | 0.523684 | | | GM5528 | 2.99039 | GM14085 | 1.6432 | | |
| | | PANX1 | 0.523705 | | | PEX11B | 0.334418 | MTOR | 0.608838 | | |
| | | 5430437P03RIK | 1.90784 | | | AL593857.1 | 0.334998 | IMPA2 | 0.60909 | | |
| | | DDX28 | 0.524218 | | | CYFIP1 | 0.33539 | RIC8 | 0.609158 | | |
| | | PDXDC1 | 0.524505 | | | 4930451C15RIK | 2.98157 | GPR108 | 0.609424 | | |
| | | 1700025C18RIK | 0.52592 | | | SERBP1 | 0.335462 | CD63 | 1.64047 | | |
| | | PIN4 | 1.90123 | | | PRL8A1 | 2.96933 | EIF2S2 | 1.63999 | | |
| | | 9130011J15RIK | 1.9008 | | | GIMAP3 | 0.336894 | TBCB | 1.63952 | | |
| | | NEK11 | 0.526292 | | | SCFD1 | 0.337001 | USP6NL | 0.610349 | | |
| | | 1700057G04RIK | 0.526551 | | | KDMSC | 0.337333 | PIK3R5 | 0.610793 | | |
| | | CSF2RA | 0.527 | | | THYN1 | 0.337668 | RABIF | 0.610904 | | |
| | | CDC14B | 0.527155 | | | RARS2 | 0.337682 | YBX1 | 1.63684 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | ARID1A | 0.527197 | | | MLH3 | 0.337695 | IFT52 | 0.61108 | | |
| | | ABTB2 | 0.527331 | | | RUVBL2 | 2.95935 | CCS | 0.611143 | | |
| | | GLIPR1 | 0.527729 | | | GADL1 | 2.95707 | ADRM1 | 0.611145 | | |
| | | ABL1 | 0.52888 | | | SMARCB1 | 0.338306 | FAM69A | 1.63587 | | |
| | | LRRC31 | 0.528966 | | | HYOU1 | 0.339143 | LRRC61 | 1.63562 | | |
| | | PTN | 0.529347 | | | 603042M02RIK | 2.94463 | GM10257 | 1.63531 | | |
| | | CTSH | 1.88706 | | | SPC24 | 0.3399 | SDCBP | 0.611715 | | |
| | | STXBP2 | 1.88643 | | | PAPD5 | 2.9409 | DGKZ | 0.612086 | | |
| | | CHMP4B | 0.530156 | | | EIF2S2 | 0.340636 | ZFP113 | 0.61223 | | |
| | | ZBTB7B | 0.530163 | | | EPHA2 | 2.93381 | YWHAE | 1.63332 | | |
| | | THNSL1 | 1.88547 | | | RPL21-PS13 | 0.341839 | GM2382 | 1.6316 | | |
| | | BCHE | 0.530597 | | | RALGPS1 | 0.343168 | H13 | 0.612962 | | |
| | | NPNT | 0.530949 | | | WDR34 | 2.91354 | TPST2 | 0.613058 | | |
| | | SLC25A12 | 1.8827 | | | TCOF1 | 0.343472 | UTP18 | 1.63081 | | |
| | | GM11744 | 0.531659 | | | RAMP1 | 0.3436 | DPF2 | 0.613245 | | |
| | | MEN1 | 0.531763 | | | AC132320.1 | 2.91022 | SRSF10 | 1.62946 | | |
| | | TDG | 1.88037 | | | 1810046I19RIK | 2.90959 | GM6723 | 1.62727 | | |
| | | SLCO1A4 | 0.532108 | | | GM10071 | 2.90557 | RPL21-PS4 | 0.614851 | | |
| | | GM3150 | 1.87932 | | | GTF2A2 | 2.90346 | MRPL23 | 0.61524 | | |
| | | DHTKD1 | 0.532265 | | | RSRC1 | 2.90081 | CKLF | 1.62516 | | |
| | | WFDC3 | 0.532408 | | | ZFP738 | 0.345153 | BCL2L12 | 0.61548 | | |
| | | LY6G6C | 0.532747 | | | SEPW1 | 2.89617 | SLC25A35 | 0.615825 | | |
| | | SARS | 1.87699 | | | ICOS | 0.345799 | FABP5 | 0.615904 | | |
| | | SMYD5 | 1.87569 | | | CHSY1 | 0.346137 | PRPF19 | 0.616463 | | |
| | | CC2D1B | 0.533576 | | | LSM6 | 0.346562 | ACAD9 | 1.6219 | | |
| | | DLEC1 | 0.533793 | | | AU022252 | 2.88303 | HSF2 | 0.617283 | | |
| | | INVS | 0.534027 | | | MYO19 | 0.346902 | SDC1 | 0.617848 | | |
| | | COPA | 0.534307 | | | TULP4 | 2.88204 | GM7551 | 1.61851 | | |
| | | HHEX | 0.534463 | | | SCD1 | 0.347362 | CRELD1 | 0.618095 | | |
| | | TMEM43 | 0.534548 | | | CD83 | 0.347481 | IL21 | 0.618323 | | |
| | | TMSB4X | 1.8707 | | | SIN3A | 0.348585 | LSG1 | 0.618479 | | |
| | | NDUFAF2 | 0.534784 | | | TMEM128 | 0.348728 | BNIP1 | 0.618645 | | |
| | | NUDT19 | 0.534909 | | | ARF2 | 0.349221 | SLC2SA14 | 0.618958 | | |
| | | GM10125 | 0.534953 | | | YME1L1 | 0.349654 | PSMG2 | 1.61508 | | |
| | | SLC12A6 | 0.535677 | | | PLEKHA1 | 0.350085 | RWDD1 | 1.61433 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | 0610017F06RIK | 1.86601 | | | CDC23 | 2.85513 | 493043IF12RIK | 0.619471 | | |
| | | TMEM149 | 1.86387 | | | CWC22 | 0.350444 | FAM53A | 1.6121 | | |
| | | GPR143 | 0.536753 | | | RHOF | 0.350505 | 9130011J15RIK | 0.620392 | | |
| | | LRPAP1 | 0.537166 | | | HMGN2 | 2.85272 | AMD-PS3 | 0.621165 | | |
| | | AIP | 1.86093 | | | PFDN1 | 0.350644 | XKRX | 1.60901 | | |
| | | CCDC142 | 0.537379 | | | DMTF1 | 0.350683 | ZFP382 | 0.622107 | | |
| | | ITSN1 | 0.537442 | | | CCDC56 | 2.84927 | COMMD10 | 0.622673 | | |
| | | PRAMEL6 | 0.537628 | | | ANAPC11 | 2.84924 | COPA | 0.623015 | | |
| | | COPE | 1.8586 | | | PPP2R3C | 0.351018 | IMMP1L | 0.623121 | | |
| | | SYNE1 | 0.538865 | | | KBTBD4 | 0.351941 | AC114007.1 | 1.6038 | | |
| | | HBP1 | 1.85527 | | | ATP11A | 0.352003 | 2210012G02RIK | 0.624415 | | |
| | | YPEL1 | 0.539064 | | | CD226 | 0.352127 | HIPK3 | 0.624904 | | |
| | | TMX2 | 1.85357 | | | CEP97 | 2.83567 | ZEB1 | 0.62508 | | |
| | | 5730403M16RIK | 0.540161 | | | FDPS | 0.352866 | C230096C10RIK | 0.62563 | | |
| | | TECTB | 0.540828 | | | BRCA1 | 0.353625 | CCDC45 | 0.62605 | | |
| | | AC132837.1 | 1.84883 | | | ZFP71-RS1 | 2.82321 | CCPG1 | 0.626144 | | |
| | | NDUFAF4 | 0.541102 | | | DNAJA3 | 0.354683 | HRAS1 | 0.626281 | | |
| | | GCDH | 0.541261 | | | BAZ1B | 2.81913 | EIF2B5 | 0.626283 | | |
| | | SCARB1 | 0.541408 | | | SMC3 | 0.355663 | RELB | 1.59645 | | |
| | | UBASH3A | 1.8468 | | | DHODH | 2.80861 | CCDC84 | 0.626489 | | |
| | | ZZZ3 | 0.541756 | | | INO80E | 0.356211 | ARF2 | 0.626727 | | |
| | | MEGF6 | 0.543478 | | | SELPLG | 0.356485 | AP1S1 | 0.628649 | | |
| | | RPL9-PS6 | 1.83817 | | | BBS4 | 0.356769 | ZFP640 | 0.628656 | | |
| | | AWAT2 | 0.544553 | | | 2700050L05RIK | 0.356786 | PRMT10 | 1.58977 | | |
| | | BTBD16 | 0.544948 | | | WDR43 | 0.356853 | GTF3C2 | 0.62908 | | |
| | | GCNT2 | 1.83502 | | | NUDCD3 | 0.356972 | DMTF1 | 1.58942 | | |
| | | ARSK | 0.545347 | | | RARS | 2.79838 | GOSR2 | 0.629196 | | |
| | | AASDH | 0.545482 | | | CYBASC3 | 0.357406 | SAAL1 | 0.62955 | | |
| | | TRMT2B | 0.545657 | | | BCKDK | 0.357639 | PTMS | 0.629922 | | |
| | | HIST1H4A | 1.8326 | | | PAIP2 | 0.357925 | PSMD1 | 0.630357 | | |
| | | EFTUD2 | 0.546041 | | | RNMTL1 | 0.358145 | CD72 | 1.58599 | | |
| | | DTWD2 | 0.546128 | | | LSG1 | 2.7903 | EIF2S3Y | 1.58457 | | |
| | | GM10417 | 0.546155 | | | 1700008F21RIK | 2.78487 | NCBP2 | 0.631746 | | |
| | | NGDN | 0.546662 | | | CPA6 | 2.78487 | COG8 | 0.632996 | | |
| | | HOXB1 | 0.54707 | | | 2700029M09RIK | 0.359429 | GM6396 | 0.633102 | | |
| | | D11WSU47E | 0.547455 | | | WDR12 | 2.77938 | ERP29 | 0.633491 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-<br>IL1B + IL6 + IL23-<br>96 h-1<br>Fold.Change<br>(KO/WT) | Gene | GPR65-KO-<br>TGFB1 + IL6-96 h-1<br>Fold.Change<br>(KO/WT) | Gene | PLZP-KO-<br>IL1B + IL6 + IL23-<br>48 h-1<br>Fold.Change<br>(KO/WT) | Gene | PLZP-KO-<br>TGFB1 + IL6-48 h-1<br>Fold.Change<br>(KO/WT) | Gene | TOSO-KO-<br>IL1B + IL6 + IL23-<br>96 h<br>Fold.Change<br>(KO/WT) | Gene | TOSO-KO-<br>IL1B + IL6 + IL23-<br>96 h<br>Fold.Change<br>(KO/WT) |
|---|---|---|---|---|---|---|---|---|---|---|---|
| | | GM10691 | 0.547725 | | | NAT6 | 0.360026 | NUBPL | 0.634143 | | |
| | | DHRS2 | 0.548037 | | | GM7627 | 0.360486 | ATP5L-PS1 | 0.634633 | | |
| | | SRGN | 1.82428 | | | AP1B1 | 0.360615 | ASNS | 0.6348 | | |
| | | GM14420 | 0.548174 | | | DYNC1H1 | 0.360627 | DTNB | 1.57523 | | |
| | | NUP210 | 0.548315 | | | ANAPC1 | 2.77169 | GM6843 | 1.5748 | | |
| | | TMEM66 | 1.82364 | | | ARAF | 2.76739 | TPT1 | 1.57464 | | |
| | | 4931408A02RIK | 0.54868 | | | GDI1 | 2.76562 | LYRM2 | 0.635092 | | |
| | | CCDC60 | 0.54869 | | | RPL21 | 0.361663 | WAC | 0.635559 | | |
| | | VTI1B | 0.549696 | | | ADK | 0.36299 | TRIOBP | 0.63562 | | |
| | | PCYT2 | 1.81919 | | | AIFM1 | 0.363256 | GSDMD | 0.636216 | | |
| | | RPL13A-PS1 | 0.549725 | | | PSD4 | 2.73921 | NFKBIA | 0.636642 | | |
| | | GM6320 | 1.81274 | | | H2-K1 | 2.7367 | PLEKHF2 | 0.636936 | | |
| | | UBE2A | 0.551724 | | | CEP57 | 0.365624 | ZMIZ1 | 0.637048 | | |
| | | TOP38 | 0.551816 | | | USP48 | 0.365786 | DFFA | 0.637145 | | |
| | | TRAPPC6A | 0.552441 | | | NDUFA13 | 0.365819 | THOP1 | 0.637365 | | |
| | | RPL7 | 1.81007 | | | PPP2R5D | 0.366459 | GSS | 0.63771 | | |
| | | DAZAP1 | 0.552963 | | | COMT1 | 2.72784 | BANF1 | 0.63781 | | |
| | | CHD6 | 0.552991 | | | EYA3 | 2.72297 | MAP2K2 | 0.637887 | | |
| | | SPRR1A | 0.553582 | | | PECR | 0.367285 | WSB1 | 0.638066 | | |
| | | PHF20 | 1.80464 | | | CFDP1 | 0.368433 | CUL5 | 1.56587 | | |
| | | VPS72 | 0.554352 | | | IL4RA | 0.368673 | SHKBP1 | 0.638955 | | |
| | | 1700057K13RIK | 0.55457 | | | SDF2 | 0.369416 | TECR | 0.639414 | | |
| | | TRIM24 | 0.555522 | | | 4732418C07RIK | 2.69688 | TMEM29 | 0.639476 | | |
| | | GM14296 | 0.55609 | | | ZFP446 | 0.370858 | TWF1 | 0.640301 | | |
| | | TXNDC11 | 0.556915 | | | VGLL4 | 0.37087 | HYOU1 | 0.641183 | | |
| | | 1700093K21RIK | 0.557875 | | | COG6 | 0.371414 | 1810049H13RIK | 0.641337 | | |
| | | SPP1 | 0.55804 | | | COMMD1 | 0.372521 | NFIA | 0.641587 | | |
| | | IVD | 0.558086 | | | CDC27 | 0.372858 | DERL2 | 0.641603 | | |
| | | YY1 | 0.560429 | | | RPL26-PS4 | 0.373203 | AKR1B3 | 1.55771 | | |
| | | AC125405.1 | 0.560436 | | | SLC11A2 | 0.373532 | TSEN15 | 0.642102 | | |
| | | CCDC18 | 0.561413 | | | TUBA8 | 0.374051 | ZFP593 | 1.55675 | | |
| | | CTSC | 0.562011 | | | 5RPR | 0.374362 | IL10RB | 1.55656 | | |
| | | GM4953 | 1.77831 | | | STXBP2 | 0.37487 | BID | 0.642473 | | |
| | | AL672068.1 | 0.563077 | | | IKZF5 | 0.375049 | SLC4A2 | 0.642706 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information includes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO IL1B + IL6 + IL23-96 h-1 Fold.Change (KO/WT) | Gene | GPR65-KO TGFB1 + IL6-96 h-1 Fold.Change (KO/WT) | Gene | PLZP-KO IL1B + IL6 + IL23-48 h-1 Fold.Change (KO/WT) | Gene | PLZP-KO TGFB1 + IL6-48 h-1 Fold.Change (KO/WT) | Gene | TOSO-KO IL1B + IL6 + IL23-96 h Fold.Change (KO/WT) | Gene | TOSO-KO IL1B + IL6 + IL23-96 h Fold.Change (KO/WT) |
|---|---|---|---|---|---|---|---|---|---|---|---|
| | | PSRC1 | 1.77182 | | | RNF20 | 0.37522 | HSD17B12 | 1.55536 | | |
| | | KAT2B | 0.565 | | | RPS12-PS2 | 0.375391 | SNRPB | 0.643816 | | |
| | | TMED4 | 1.76822 | | | EIF1AX | 0.37563 | PRDM2 | 0.644808 | | |
| | | OLFR1055 | 0.565775 | | | NAT10 | 0.375687 | PSMF1 | 0.645237 | | |
| | | ME3 | 0.56733 | | | GPATCH4 | 0.375755 | TMEM106B | 0.645351 | | |
| | | ETL4 | 0.567722 | | | PFAS | 0.375796 | BCAS2 | 0.645699 | | |
| | | LRRC33 | 0.56973 | | | SLC35B1 | 0.375953 | EBNA1BP2 | 0.645891 | | |
| | | FBXL21 | 0.569879 | | | BLVRA | 0.376773 | RORC | 0.646421 | | |
| | | 2810417H13RIK | 1.75076 | | | KPNA3 | 2.65139 | SMYD2 | 1.54653 | | |
| | | DCBLD2 | 0.571483 | | | STAG2 | 0.377564 | GGA1 | 0.647033 | | |
| | | RALGDS | 0.57227 | | | CRNKL1 | 2.64761 | PSME3 | 0.647243 | | |
| | | SYF2 | 1.747 | | | SVOP | 0.378 | SEL1L | 1.54484 | | |
| | | ALG13 | 0.572541 | | | I0C0044D17RIK | 0.378094 | BCCIP | 0.647653 | | |
| | | FDXR | 1.74544 | | | TMEM80 | 2.63584 | SRA1 | 0.648219 | | |
| | | TCTEX1D2 | 0.573273 | | | UQCC | 2.63526 | SERPINB1A | 0.648369 | | |
| | | SLC25A42 | 0.573647 | | | CCL20 | 0.379952 | PRKB1 | 0.648723 | | |
| | | ID2 | 1.73951 | | | ISY1 | 0.380229 | SYT11 | 1.54006 | | |
| | | 1110008P14RIK | 0.57645 | | | IF147 | 2.62916 | ENTPD4 | 0.649691 | | |
| | | METTL14 | 0.577951 | | | ASNS | 0.3804 | NDUFB5 | 0.650471 | | |
| | | TXNDC16 | 0.580239 | | | NAA40 | 0.380451 | TRP53BP1 | 0.651022 | | |
| | | RP57 | 1.72318 | | | CCNE1 | 0.380776 | PIP5K1C | 0.651315 | | |
| | | FAM184A | 0.580454 | | | D330012F22RIK | 0.381723 | CMC1 | 0.652247 | | |
| | | SNAP47 | 1.7222 | | | CDK5RAP2 | 0.382085 | RPS6KC1 | 0.652501 | | |
| | | RAD18 | 1.72044 | | | 1700123O20RIK | 0.383244 | PAPOLA | 1.53209 | | |
| | | MAP3K7 | 1.72015 | | | T5G101 | 2.60705 | 111003I02RIK | 0.653034 | | |
| | | H2-AB1 | 1.71789 | | | MTHFS | 2.60336 | IL15RA | 0.653215 | | |
| | | COLEC12 | 0.583908 | | | RTN4IP1 | 0.38439 | DDT | 0.653474 | | |
| | | LIAS | 0.584048 | | | ADAMTSL4 | 0.384451 | LXN | 0.653775 | | |
| | | VGLL4 | 1.71021 | | | POLE | 0.384793 | CAML | 0.654098 | | |
| | | STAM2 | 0.584817 | | | BCAP29 | 0.384893 | NME6 | 0.654537 | | |
| | | E230001N04RIK | 0.585026 | | | CD5 | 0.385786 | GHDC | 0.655175 | | |
| | | SEL1L | 0.585038 | | | GLE1 | 0.385815 | NTSC3L | 1.52508 | | |
| | | H2AFY | 1.70815 | | | SMC5 | 0.386445 | DDX18 | 0.655943 | | |
| | | R3HDM2 | 0.585866 | | | MPI | 2.5868 | 2900010J23RIK | 0.656538 | | |
| | | SPEN | 0.586272 | | | ARIH1 | 2.58613 | RB1 | 0.656729 | | |
| | | NCSTN | 0.58805 | | | OXCT1 | 0.387007 | HIST1H3H | 0.656763 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-IL1B + IL6 + IL23-96 h-1 Fold.Change (KO/WT) | Gene | GPR65-KO-TGFB1 + IL6-96 h-1 Fold.Change (KO/WT) | Gene | PLZP-KO-IL1B + IL6 + IL23-48 h-1 Fold.Change (KO/WT) | Gene | PLZP-KO-TGFB1 + IL6-48 h-1 Fold.Change (KO/WT) | Gene | TOSO-KO-IL1B + IL6 + IL23-96 h Fold.Change (KO/WT) | Gene | TOSO-KO-IL1B + IL6 + IL23-96 h Fold.Change (KO/WT) |
|---|---|---|---|---|---|---|---|---|---|---|---|
| | | PRL8A1 | 0.588641 | | | PDPK1 | 2.57756 | DPP3 | 0.657155 | | |
| | | MRPS15 | 1.69495 | | | PRODH | 0.388288 | DLG2 | 0.657191 | | |
| | | GIGYF2 | 0.591335 | | | DDX47 | 0.388346 | ZFP703 | 1.52155 | | |
| | | DERA | 1.6895 | | | 2610507B11RIK | 2.57237 | AC090563.1 | 1.52069 | | |
| | | GM12033 | 1.068909 | | | DPM1 | 0.389039 | HCFC1 | 0.657862 | | |
| | | TM95F1 | 0.594558 | | | ANXA7 | 0.389075 | MRPS30 | 0.657906 | | |
| | | UCHL4 | 0.594589 | | | KEAP1 | 0.389438 | NBR1 | 0.658347 | | |
| | | XRCC4 | 0.59578 | | | 4930453N24RIK | 2.56778 | BC029214 | 0.65973 | | |
| | | AC068006.1 | 0.597766 | | | CREM | 0.38953 | CARS2 | 0.659736 | | |
| | | AUTS2 | 0.598334 | | | RPP14 | 0.389539 | SNAP47 | 0.659889 | | |
| | | NPDC1 | 0.599026 | | | IFT20 | 2.56423 | D6ERTD738E | 0.660079 | | |
| | | CT033780.1 | 0.599051 | | | 1810022K09RIK | 0.390263 | RBM33 | 0.66011 | | |
| | | 1110001J03RIK | 1.66896 | | | GALM | 0.390284 | DYNLT3 | 1.51481 | | |
| | | AUH | 0.599389 | | | GFM1 | 0.390367 | HNRNPAB | 0.66032 | | |
| | | GBP5 | 0.601504 | | | PDAP1 | 0.391077 | MRPS36-PS1 | 0.661543 | | |
| | | OAS3 | 0.602776 | | | CUX1 | 0.391626 | PPP5C | 0.661659 | | |
| | | MTG1 | 0.606137 | | | SP100 | 2.54971 | CLN6 | 0.661741 | | |
| | | PNPLA8 | 0.606206 | | | PPP4R2 | 0.392231 | MEMO1 | 0.661783 | | |
| | | 1500011B03RIK | 0.606396 | | | CAND1 | 2.54938 | LSM7 | 0.661841 | | |
| | | ZFP575 | 0.606493 | | | CBX3 | 2.54808 | ELK3 | 1.51042 | | |
| | | RPL30-PS6 | 0.608551 | | | BUD13 | 0.393549 | CUTA | 0.662154 | | |
| | | ZFP560 | 0.610421 | | | SACM1L | 0.393831 | RPRD18 | 1.50924 | | |
| | | INADL | 0.611092 | | | PRKCH | 0.393957 | LAMP1 | 1.50915 | | |
| | | CAMK2D | 1.63545 | | | SUMO3 | 2.53558 | INPP5D | 0.662713 | | |
| | | 1700054O19RIK | 0.612794 | | | UBA6 | 0.394606 | UTY | 1.50869 | | |
| | | ATG4A | 0.612875 | | | TIMELESS | 2.53153 | SMAP2 | 0.662836 | | |
| | | TMEM219 | 1.63077 | | | 2410091C18RIK | 0.395525 | DNAJC19 | 0.662901 | | |
| | | SNF8 | 0.613773 | | | GTF2E2 | 0.396167 | GM6666 | 0.663179 | | |
| | | DDX58 | 0.615491 | | | DLGAP5 | 0.396602 | MRPS10 | 0.663256 | | |
| | | GPAA1 | 0.617882 | | | SGDL1 | 2.52105 | PDE6D | 0.663286 | | |
| | | MID1 | 1.61553 | | | SRPK1 | 0.396828 | PCBP1 | 0.663767 | | |
| | | PSMD2 | 0.61948 | | | HCLS1 | 0.39702 | ZAP70 | 0.663792 | | |
| | | EEF1E1 | 1.61071 | | | BRD7 | 0.397033 | AI480653 | 1.50628 | | |
| | | SRPK1 | 0.623737 | | | MTA3 | 0.397085 | NEK2 | 0.663933 | | |
| | | ZFP259 | 0.623906 | | | WDR26 | 0.397789 | PGLYRP2 | 1.50557 | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | KCNH6 | 0.625341 | | | NFRKB | 0.398091 | ANAPC4 | 0.664398 | | |
| | | RPL18A | 0.625821 | | | TMED9 | 0.398144 | UBE4A | 0.664403 | | |
| | | AC110247.1 | 0.626334 | | | AC125221.1 | 2.51118 | PRDX5 | 0.665043 | | |
| | | CKS2 | 1.59547 | | | MYBL2 | 0.398438 | GTPBP3 | 0.666361 | | |
| | | SEC63 | 0.626857 | | | BAX | 0.398521 | | | | |
| | | MDM2 | 0.630367 | | | USPL1 | 0.398688 | | | | |
| | | BLOC152 | 0.630729 | | | SLC31A1 | 0.399003 | | | | |
| | | TMEM154 | 0.631156 | | | ELAVL1 | 0.400468 | | | | |
| | | SBNO1 | 1.5767 | | | GM14443 | 2.49621 | | | | |
| | | RPRD1B | 0.634263 | | | LY6C1 | 2.49202 | | | | |
| | | CFLAR | 0.638629 | | | DCPS | 0.401308 | | | | |
| | | MAP3K5 | 0.638837 | | | INPP5F | 2.48702 | | | | |
| | | ATP6V1B2 | 0.639371 | | | THOC5 | 0.402952 | | | | |
| | | ALDH7A1 | 0.640159 | | | GM6736 | 2.4789 | | | | |
| | | WBP7 | 1.55732 | | | HIPK3 | 2.4774 | | | | |
| | | EXOC4 | 0.642436 | | | HSPA4 | 0.403747 | | | | |
| | | AIFM1 | 0.643759 | | | NDUFV1 | 0.403761 | | | | |
| | | PUM1 | 0.645538 | | | SYT11 | 2.47641 | | | | |
| | | SLC38A6 | 0.646337 | | | COX8A | 0.40383 | | | | |
| | | NMT1 | 0.648082 | | | E230001N04RIK | 0.404113 | | | | |
| | | ING1 | 0.64957 | | | ELOF1 | 0.404182 | | | | |
| | | STX1A | 0.650026 | | | VBP1 | 0.404242 | | | | |
| | | AA960436 | 1.53269 | | | TDP1 | 0.404604 | | | | |
| | | HMGCR | 0.652542 | | | COP57A | 2.47145 | | | | |
| | | TUFM | 0.653859 | | | TBRG1 | 0.404881 | | | | |
| | | RBMS2 | 0.654071 | | | RAD54L | 0.405062 | | | | |
| | | ABHD5 | 0.654691 | | | GM15887 | 0.40524 | | | | |
| | | ITGB1BP3 | 0.656226 | | | GPR171 | 0.405533 | | | | |
| | | H2-DMA | 1.52224 | | | RFWD3 | 0.405537 | | | | |
| | | DSN1 | 0.657136 | | | SMEK2 | 0.406438 | | | | |
| | | FAM18B | 0.657681 | | | D19ERTD386E | 0.406513 | | | | |
| | | FXYD5 | 1.51958 | | | PMF1 | 0.407169 | | | | |
| | | PEX1 | 0.659458 | | | COMMD8 | 2.45588 | | | | |
| | | PAFAH2 | 0.663406 | | | ACOX2 | 2.45558 | | | | |
| | | AP2S1 | 0.663464 | | | FAM54A | 0.407283 | | | | |
| | | CT025683.2 | 0.664094 | | | WDR89 | 0.407385 | | | | |
| | | TIGIT | 0.665111 | | | SAMSN1 | 2.45027 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | GM5436 | 0.66616 | | | ATP6V1D | 2.44873 | | | | |
| | | AC121959.1 | 0.666529 | | | FYTTD1 | 2.44867 | | | | |
| | | | | | | NDUFB2 | 2.44813 | | | | |
| | | | | | | RAD1 | 0.408477 | | | | |
| | | | | | | OTUD68 | 0.408922 | | | | |
| | | | | | | RBM39 | 2.44457 | | | | |
| | | | | | | EBNA1BP2 | 0.409552 | | | | |
| | | | | | | 1810013L24RIK | 0.410077 | | | | |
| | | | | | | STAT3 | 0.410132 | | | | |
| | | | | | | RNASEH2A | 2.43243 | | | | |
| | | | | | | MLL1 | 0.411438 | | | | |
| | | | | | | PIGA | 0.411634 | | | | |
| | | | | | | KIF24 | 2.42673 | | | | |
| | | | | | | AP3B1 | 0.412271 | | | | |
| | | | | | | RAD21 | 0.412759 | | | | |
| | | | | | | ZFP330 | 0.412968 | | | | |
| | | | | | | ACER2 | 2.41598 | | | | |
| | | | | | | DHX9 | 0.4141 | | | | |
| | | | | | | INTS9 | 0.041427 | | | | |
| | | | | | | BC031781 | 0.415611 | | | | |
| | | | | | | RCBTB1 | 0.416923 | | | | |
| | | | | | | SUPT7L | 2.39515 | | | | |
| | | | | | | NARF | 0.417643 | | | | |
| | | | | | | MCM10 | 0.417936 | | | | |
| | | | | | | TGTP2 | 2.39105 | | | | |
| | | | | | | FAD56 | 2.39042 | | | | |
| | | | | | | 2310035K24RIK | 2.38318 | | | | |
| | | | | | | FAM60A | 2.38162 | | | | |
| | | | | | | PSMC3IP | 0.41999 | | | | |
| | | | | | | RNF25 | 2.379 | | | | |
| | | | | | | LPXN | 2.37549 | | | | |
| | | | | | | IL17A | 0.421247 | | | | |
| | | | | | | TMEM176B | 2.37084 | | | | |
| | | | | | | GNL2 | 0.422463 | | | | |
| | | | | | | MYCBP2 | 2.36498 | | | | |
| | | | | | | ALKBH5 | 2.36021 | | | | |
| | | | | | | CALU | 2.36001 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or II-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-IL1B + IL6 + IL23-96 h-1 Fold.Change (KO/WT) | Gene | GPR65-KO-TGFB1 + IL6-96 h-1 Fold.Change (KO/WT) | Gene | PLZP-KO-IL1B + IL6 + IL23-48 h-1 Fold.Change (KO/WT) | Gene | PLZP-KO-TGFB1 + IL6-48 h-1 Fold.Change (KO/WT) | Gene | TOSO-KO-IL1B + IL6 + IL23-96 h Fold.Change (KO/WT) | Gene | TOSO-KO-IL1B + IL6 + IL23-96 h Fold.Change (KO/WT) |
|---|---|---|---|---|---|---|---|---|---|---|---|
| | | | | | | RBPJ | 0.423864 | | | | |
| | | | | | | RINT1 | 0.424041 | | | | |
| | | | | | | GM9396 | 2.35258 | | | | |
| | | | | | | GCSH | 0.425617 | | | | |
| | | | | | | SPARC | 2.34917 | | | | |
| | | | | | | GLO1 | 2.3482 | | | | |
| | | | | | | 2410089E03RIK | 2.34731 | | | | |
| | | | | | | DPY19L3 | 2.34681 | | | | |
| | | | | | | MCM6 | 2.34553 | | | | |
| | | | | | | B020018G12RIK | 0.426889 | | | | |
| | | | | | | SNRPF | 2.34229 | | | | |
| | | | | | | TRP53 | 2.34163 | | | | |
| | | | | | | C79407 | 2.34024 | | | | |
| | | | | | | PAM16 | 0.427458 | | | | |
| | | | | | | SNRNP27 | 2.33875 | | | | |
| | | | | | | TMEM11 | 0.429165 | | | | |
| | | | | | | CRIP1 | 2.32956 | | | | |
| | | | | | | RPL18 | 2.32709 | | | | |
| | | | | | | MT2 | 2.32658 | | | | |
| | | | | | | ITK | 2.32166 | | | | |
| | | | | | | CTSA | 2.32073 | | | | |
| | | | | | | MPP1 | 0.431271 | | | | |
| | | | | | | DERL2 | 0.431818 | | | | |
| | | | | | | CUL1 | 0.432041 | | | | |
| | | | | | | UHRF1 | 2.31278 | | | | |
| | | | | | | ALDOART1 | 2.31234 | | | | |
| | | | | | | USP14 | 0.43273 | | | | |
| | | | | | | FAM172A | 2.30775 | | | | |
| | | | | | | GM4825 | 0.433418 | | | | |
| | | | | | | PDCD5 | 0.433425 | | | | |
| | | | | | | MED12 | 0.433605 | | | | |
| | | | | | | PPIL2 | 2.30371 | | | | |
| | | | | | | INTS10 | 2.30127 | | | | |
| | | | | | | CCNL2 | 0.434666 | | | | |
| | | | | | | LYGA | 2.2994 | | | | |
| | | | | | | 1110057K04RIK | 2.29924 | | | | |
| | | | | | | 2310028O11RIK | 2.29643 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | | | | | SCAI | 2.29301 | | | | |
| | | | | | | GRK4 | 2.29277 | | | | |
| | | | | | | BIRC5 | 2.29248 | | | | |
| | | | | | | RAD23A | 2.29189 | | | | |
| | | | | | | G3BP1 | 2.29103 | | | | |
| | | | | | | SDCCAG1 | 0.437 | | | | |
| | | | | | | SMC6 | 0.437145 | | | | |
| | | | | | | NSUN5 | 2.28523 | | | | |
| | | | | | | FAM48A | 0.438003 | | | | |
| | | | | | | NSF | 0.438358 | | | | |
| | | | | | | HARS | 2.2809 | | | | |
| | | | | | | 2510006D16RIK | 2.27804 | | | | |
| | | | | | | TRABD | 2.27559 | | | | |
| | | | | | | SYNCRIP | 0.439523 | | | | |
| | | | | | | SNX10 | 2.27209 | | | | |
| | | | | | | SEC11A | 0.440221 | | | | |
| | | | | | | SEC61A1 | 2.2693 | | | | |
| | | | | | | CSTF3 | 2.26916 | | | | |
| | | | | | | HELLS | 2.26881 | | | | |
| | | | | | | LIG3 | 0.441041 | | | | |
| | | | | | | ARL1 | 2.26717 | | | | |
| | | | | | | ZFP488 | 2.26453 | | | | |
| | | | | | | HCFC2 | 0.442179 | | | | |
| | | | | | | CDC7 | 0.442591 | | | | |
| | | | | | | HEATR6 | 2.25775 | | | | |
| | | | | | | ETFDH | 2.25742 | | | | |
| | | | | | | GM9034 | 2.2546 | | | | |
| | | | | | | TAPBPL | 2.25428 | | | | |
| | | | | | | IER3IP1 | 2.25291 | | | | |
| | | | | | | BTRC | 0.4439 | | | | |
| | | | | | | AFF4 | 0.444174 | | | | |
| | | | | | | WDR11 | 0.444467 | | | | |
| | | | | | | CDC26 | 0.445353 | | | | |
| | | | | | | HAGH | 2.24485 | | | | |
| | | | | | | NUP205 | 0.445805 | | | | |
| | | | | | | BRIX1 | 2.24139 | | | | |
| | | | | | | 2310016M24RIK | 2.23958 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO-IL1B + IL6 + IL23-96 h-1 Fold.Change (KO/WT) | Gene | GPR65-KO-TGFB1 + IL6-96 h-1 Fold.Change (KO/WT) | Gene | PLZP-KO-IL1B + IL6 + IL23-48 h-1 Fold.Change (KO/WT) | Gene | PLZP-KO-TGFB1 + IL6-48 h-1 Fold.Change (KO/WT) | Gene | TOSO-KO-IL1B + IL6 + IL23-96 h Fold.Change (KO/WT) | Gene | TOSO-KO-IL1B + IL6 + IL23-96 h Fold.Change (KO/WT) |
|---|---|---|---|---|---|---|---|---|---|---|---|
| | | | | | | PRDX6 | 2.23838 | | | | |
| | | | | | | CHMP2A | 0.44701 | | | | |
| | | | | | | MRPS21 | 0.447083 | | | | |
| | | | | | | TTPAL | 2.23388 | | | | |
| | | | | | | MYO1B | 2.23376 | | | | |
| | | | | | | EMB | 2.23361 | | | | |
| | | | | | | ANAPC16 | 2.23213 | | | | |
| | | | | | | LSP1 | 2.22932 | | | | |
| | | | | | | BRP44L | 2.22887 | | | | |
| | | | | | | ASL | 2.22792 | | | | |
| | | | | | | XPNPEP2 | 2.22638 | | | | |
| | | | | | | SOAT2 | 0.499889 | | | | |
| | | | | | | GM5745 | 2.22194 | | | | |
| | | | | | | LPCAT3 | 0.450215 | | | | |
| | | | | | | TOMM5 | 0.450963 | | | | |
| | | | | | | PSMA3 | 2.21527 | | | | |
| | | | | | | DENR | 0.452926 | | | | |
| | | | | | | NEK6 | 2.20784 | | | | |
| | | | | | | POGLUT1 | 0.453388 | | | | |
| | | | | | | BCL2A1A | 0.453814 | | | | |
| | | | | | | 1110007A13RIK | 2.20188 | | | | |
| | | | | | | GGTA1 | 0.454425 | | | | |
| | | | | | | HK2 | 0.454714 | | | | |
| | | | | | | BSG | 2.1981 | | | | |
| | | | | | | WDR76 | 0.455091 | | | | |
| | | | | | | BAT2L2 | 0.455459 | | | | |
| | | | | | | IARS | 0.455491 | | | | |
| | | | | | | GM6483 | 2.19173 | | | | |
| | | | | | | PNP | 0.456278 | | | | |
| | | | | | | TMX1 | 2.1891 | | | | |
| | | | | | | TBRG4 | 2.18888 | | | | |
| | | | | | | SDHD | 0.45686 | | | | |
| | | | | | | RPP21 | 2.18707 | | | | |
| | | | | | | PLCG1 | 0.457433 | | | | |
| | | | | | | TRAP1 | 2.18582 | | | | |
| | | | | | | ACO1 | 0.458043 | | | | |
| | | | | | | GTF2H5 | 2.17756 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or Il-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | | | | | LCP2 | 0.459844 | | | | |
| | | | | | | GM10719 | 2.17187 | | | | |
| | | | | | | METTL2 | 2.16859 | | | | |
| | | | | | | GM7263 | 0.461366 | | | | |
| | | | | | | TMEM109 | 2.16707 | | | | |
| | | | | | | TSTA3 | 2.16432 | | | | |
| | | | | | | 2310003F16RIK | 2.16375 | | | | |
| | | | | | | MRPL12 | 2.16216 | | | | |
| | | | | | | RPS7 | 0.463462 | | | | |
| | | | | | | 0610010K14RIK | 0.465093 | | | | |
| | | | | | | ASF1B | 2.13197 | | | | |
| | | | | | | EBP | 0.470037 | | | | |
| | | | | | | ACOT7 | 2.12369 | | | | |
| | | | | | | AC101875.1 | 2.12289 | | | | |
| | | | | | | ARL5C | 0.472555 | | | | |
| | | | | | | TCEB2 | 0.472686 | | | | |
| | | | | | | LARS2 | 0.473056 | | | | |
| | | | | | | EIF3D | 0.478682 | | | | |
| | | | | | | PA2G4 | 0.481972 | | | | |
| | | | | | | CAPZA2 | 0.482067 | | | | |
| | | | | | | GM4838 | 0.486641 | | | | |
| | | | | | | CD82 | 2.05396 | | | | |
| | | | | | | NDUFA2 | 0.487634 | | | | |
| | | | | | | SELK | 0.489794 | | | | |
| | | | | | | COX7C | 2.04046 | | | | |
| | | | | | | 2610024G14RIK | 2.0264 | | | | |
| | | | | | | 0610007P14RIK | 0.497032 | | | | |
| | | | | | | TIMP1 | 1.9987 | | | | |
| | | | | | | GM4987 | 0.501073 | | | | |
| | | | | | | AC131780.3 | 1.99065 | | | | |
| | | | | | | NEDD8 | 0.503159 | | | | |
| | | | | | | GCN1L1 | 1.98192 | | | | |
| | | | | | | MRPL18 | 0.506898 | | | | |
| | | | | | | UBR1 | 1.96833 | | | | |
| | | | | | | ARF1 | 1.93639 | | | | |
| | | | | | | PPP1CA | 1.92795 | | | | |
| | | | | | | RPS25 | 0.519359 | | | | |

TABLE 7-continued

Listed is the fold change (defined as the expression level of the knock out cells divided by the expression level of corresponding wild type or littermate controls) of all significantly differentially expressed genes (Experimental Procedures) for a given experimental condition. Experimental condition information incldes; the knockout mouse (GPR65−/−, PLZP−/− or TOSO−/−), differentiation condition (TGF-β1 + IL-6 or IL-1β + IL-6 + IL-23), and the duration of differentiation before harvesting for RNA-seq analysis (48 h or 96 h). All differentiations were conducted as for the single cell in vitro data.

Differentially expressed genes for GPR65−/−, PLZP−/− and TOSO−/− Th17 cells

| Gene | GPR65-KO- IL1B + IL6 + IL23- 96 h-1 Fold.Change (KO/WT) | Gene | GPR65-KO- TGFB1 + IL6-96 h-1 Fold.Change (KO/WT) | Gene | PLZP-KO- IL1B + IL6 + IL23- 48 h-1 Fold.Change (KO/WT) | Gene | PLZP-KO- TGFB1 + IL6-48 h-1 Fold.Change (KO/WT) | Gene | TOSO-KO- IL1B + IL6 + IL23- 96 h Fold.Change (KO/WT) | Gene | TOSO-KO- IL1B + IL6 + IL23- 96 h Fold.Change (KO/WT) |
|---|---|---|---|---|---|---|---|---|---|---|---|
| | | | | | | SNRPD2 | 0.519897 | | | | |
| | | | | | | COX7A2 | 1.9177 | | | | |
| | | | | | | DAZAP2 | 1.91034 | | | | |
| | | | | | | COX7B | 1.90204 | | | | |
| | | | | | | GM16382 | 1.90161 | | | | |
| | | | | | | RPN2 | 1.89675 | | | | |
| | | | | | | RPL30 | 1.89126 | | | | |
| | | | | | | IL9 | 1.88491 | | | | |
| | | | | | | 8430427H17RIK | 1.88407 | | | | |
| | | | | | | RPS12-PS3 | 0.531131 | | | | |
| | | | | | | PSMD13 | 0.535643 | | | | |
| | | | | | | TUBB2C | 1.86526 | | | | |
| | | | | | | GM6807 | 0.53642 | | | | |
| | | | | | | UQCR11 | 1.85797 | | | | |

REFERENCES

Ahmed, M., and Gaffen, S. L. (2010). IL-17 in obesity and adipogenesis. Cytokine & growth factor reviews 21, 449-453.

Amit, I., Citri, A., Shay, T., Lu, Y., Katz, M., Zhang, F., Tarcic, G., Siwak, D., Lahad, J., Jacob-Hirsch, J., et al. (2007). A module of negative feedback regulators defines growth factor signaling. Nature genetics 39, 503-512.

Amit, I., Garber, M., Chevrier, N., Leite, A. P., Donner, Y., Eisenhaure, T., Guttman, M., Grenier, J. K., Li, W., Zuk, O., et al. (2009). Unbiased reconstruction of a mammalian transcriptional network mediating pathogen responses. Science 326, 257-263.

Annunziato, F., Cosmi, L., Santarlasci, V., Maggi, L., Liotta, F., Mazzinghi, B., Parente, E., Fili, L., Ferri, S., Frosali, F., et al. (2007). Phenotypic and functional features of human Th17 cells. The Journal of experimental medicine 204, 1849-1861.

Antebi, Y. E., Reich-Zeliger, S., Hart, Y., Mayo, A., Eizenberg, I., Rimer, J., Putheti, P., Pe'er, D., and Friedman, N. (2013). Mapping differentiation under mixed culture conditions reveals a tunable continuum of T cell fates. PLoS biology 11, e1001616.

Arpaia, N., Campbell, C., Fan, X., Dikiy, S., van der Veeken, J., deRoos, P., Liu, H., Cross, J. R., Pfeffer, K., Coffer, P. J., et al. (2013). Metabolites produced by commensal bacteria promote peripheral regulatory T-cell generation. Nature 504, 451-455.

Aust, G., Kamprad, M., Lamesch, P., and Schmucking, E. (2005). CXCR6 within T-helper (Th) and T-cytotoxic (Tc) type 1 lymphocytes in Graves' disease (GD). European journal of endocrinology/European Federation of Endocrine Societies 152, 635-643.

Awasthi, A., Riol-Blanco, L., Jager, A., Korn, T., Pot, C., Galileos, G., Bettelli, E., Kuchroo, V. K., and Oukka, M. (2009). Cutting edge: IL-23 receptor gfp reporter mice reveal distinct populations of IL-17-producing cells. Journal of immunology 182, 5904-5908.

Bachmann, M. F., Barner, M., and Kopf, M. (1999). CD2 sets quantitative thresholds in T cell activation. The Journal of experimental medicine 190, 1383-1392.

Baeten, D. L., and Kuchroo, V. K. (2013). How Cytokine networks fuel inflammation: Interleukin-17 and a tale of two autoimmune diseases. Nature medicine 19, 824-825.

Bending, D., De la Pena, H., Veldhoen, M., Phillips, J. M., Uyttenhove, C., Stockinger, B., and Cooke, A. (2009). Highly purified Th17 cells from BDC2.5NOD mice convert into Th1-like cells in NOD/SCID recipient mice. The Journal of clinical investigation 119, 565-572.

Benjamini, Y., and Hochberg, Y. (1995). Controlling the false discovery rate: a practical and powerful approach to multiple testing. Journal of the Royal Statistical Society Series B (Methodological), 289-300.

Berod, L., Friedrich, C., Nandan, A., Freitag, J., Hagemann, S., Harmrolfs, K., Sandouk, A., Hesse, C., Castro, C. N., Bahre, H., el al. (2014). De novo fatty acid synthesis controls the fate between regulatory T and T helper 17 cells. Nature medicine 20, 1327-1333.

Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH 17 and regulatory T cells. Nature 441, 235-238.

Bettelli, E., Pagany, M., Weiner, H. L., Linington, C., Sobel, R. A., and Kuchroo, V. K. (2003). Myelin oligodendrocyte glycoprotein-specific T cell receptor transgenic mice develop spontaneous autoimmune optic neuritis. The Journal of experimental medicine 197, 1073-1081.

Blaschitz, C., and Raffatellu, M. (2010). Th17 cytokines and the gut mucosal barrier. Journal of clinical immunology 30, 196-203.

Brenner, D., Brustle, A., Lin, G. H., Lang, P. A., Duncan, G. S., Knobbe-Thomsen, C. B., St Paul, M., Reardon, C., Tusche, M. W., Snow, B., el al. (2014). Toso controls encephalitogenic immune responses by dendritic cells and regulatory T cells. Proceedings of the National Academy of Sciences of the United States of America 111, 1060-1065.

Cellot, S., and Sauvageau, G. (2007). Zfx: at the crossroads of survival and self-renewal. Cell 129, 239-241.

Chai, J. G., and Lechler, R. I. (1997). Immobilized anti-CD3 mAb induces anergy in murine naïve and memory CD4+ T cells in vitro. International immunology 9, 935-944.

Chen, L., Wu, G., and Ji, H. (2011). hmChIP: a database and web server for exploring publicly available human and mouse ChIP-seq and ChIP-chip data. Bioinformatics 27, 1447-1448.

Cho, J. H. (2008). The genetics and immunopathogenesis of inflammatory bowel disease. Nature reviews Immunology 8, 458-466.

Chung, Y., Chang, S. H., Martinez, G. J., Yang, X. O., Nurieva, R., Kang, H. S., Ma, L., Watowich, S. S., Jetten, A. M., Tian, Q., el al. (2009). Critical regulation of early Th17 cell differentiation by interleukin-1 signaling. Immunity 30, 576-587.

Ciofani, M., Madar, A., Galan, C., Sellars, M., Mace, K., Pauli, F., Agarwal, A., Huang, W., Parkurst, C. N., Muratet, M., el al. (2012a). A validated regulatory network for Th17 cell specification. Cell 151, 289-303.

Ciofani, M., Madar, A., Galan, C., Sellars, M., Mace, K., Pauli, F., Agarwal, A., Huang, W., Parkurst, Christopher N., Muratet, M., el al. (2012b). A Validated Regulatory Network for Th17 Cell Specification. Cell.

Codarri, L., Gyulveszi, G., Tosevski, V., Hesske, L., Fontana, A., Magnenat, L., Suter, T., and Becher, B. (2011). RORgammat drives production of the cytokine GM-CSF in helper T cells, which is essential for the effector phase of autoimmune neuroinflammation. Nature immunology 12, 560-567.

Crawford, A., Angelosanto, J. M., Kao, C., Doering, T. A., Odorizzi, P. M., Barnett, B. E., and Wherry, E. J. (2014). Molecular and transcriptional basis of CD4(+) T cell dysfunction during chronic infection. Immunity 40, 289-302.

Dang, E. V., Barbi, J., Yang, H. Y., Jinasena, D., Yu, H., Zheng, Y., Bordman, Z., Fu, J., Kim, Y., Yen, H. R., et al. (2011). Control of T(H)17/T(reg) balance by hypoxia-inducible factor 1. Cell 146, 772-784.

De Rosa, S. C., Herzenberg, L. A., Herzenberg, L. A., and Roederer, M. (2001). 11-color, 13-parameter flow cytometry: identification of human naïve T cells by phenotype, function, and T-cell receptor diversity. Nature medicine 7, 245-248.

Deng, Q., Ramskold, D., Reinius, B., and Sandberg, R. (2014). Single-cell RNA-seq reveals dynamic, random monoallelic gene expression in mammalian cells. Science 343, 193-196.

Dolfi, D. V., Boesteanu, A. C., Petrovas, C., Xia, D., Butz, E. A., and Katsikis, P. D. (2008). Late signals from CD27 prevent Fas-dependent apoptosis of primary CD8+ T cells. Journal of immunology 180, 2912-2921.

El-Behi, M., Ciric, B., Dai, H., Yan, Y., Cullimore, M., Safavi, F., Zhang, G. X., Dittel, B. N., and Rostami, A.

(2011). The encephalitogenicity of T(H)17 cells is dependent on IL-1- and IL-23-induced production of the cytokine GM-CSF. Nature immunology 12, 568-575.

Esfandiari, E., McInnes, I. B., Lindop, G., Huang, F. P., Field, M., Komai-Koma, M., Wei, X., and Liew, F. Y. (2001). A proinflammatory role of IL-18 in the development of spontaneous autoimmune disease. Journal of immunology 167, 5338-5347.

Fang, X., Huang, Z., Zhou, W., Wu, Q., Sloan, A. E., Ouyang, G., McLendon, R. E., Yu, J. S., Rich, J. N., and Bao, S. (2014). The zinc finger transcription factor ZFX Is required for maintaining the tumorigenic potential of glioblastoma stem cells. Stem cells.

Franke, A., McGovern, D. P., Barrett, J. C., Wang, K., Radford-Smith, G. L., Ahmad, T., Lees, C. W., Balschun, T., Lee, J., Roberts, R., et al. (2010). Genome-wide meta-analysis increases to 71 the number of confirmed Crohn's disease susceptibility loci. Nature genetics 42, 1118-1125.

Galan-Caridad, J. M., Harel, S., Arenzana, T. L., Hou, Z. E., Doetsch, F. K., Mirny, L. A., and Reizis, B. (2007). Zfx controls the self-renewal of embryonic and hematopoietic stem cells. Cell 129, 345-357.

Gaffen, S. L., Hernandez-Santos, N., and Peterson, A. C. (2011). IL-17 signaling in host defense against *Candida albicans*. Immunologic research 50, 181-187.

Gattinoni, L., Zhong, X. S., Palmer, D. C., Ji, Y., Hinrichs, C. S., Yu, Z., Wrzesinski, C., Boni, A., Cassard, L., Garvin, L. M., et al. (2009). Wnt signaling arrests effector T cell differentiation and generates CD8+ memory stem cells. Nature medicine 15, 808-813.

Genovese, M. C., Van den Bosch, F., Roberson, S. A., Bojin, S., Biagini, I. M., Ryan, P., and Sloan-Lancaster, J. (2010). LY2439821, a humanized anti-interleukin-17 monoclonal antibody, in the treatment of patients with rheumatoid arthritis: A phase I randomized, double-blind, placebo-controlled, proof-of-concept study. Arthritis and rheumatism 62, 929-939.

Ghoreschi, K., Laurence, A., Yang, X. P., Tato, C. M., McGeachy, M. J., Konkel, J. E., Ramos, H. L., Wei, L., Davidson, T. S., Bouladoux, N., et al. (2010). Generation of pathogenic T(H)17 cells in the absence of TGF-beta signalling. Nature 467, 967-971.

Ghosh, S., Elder, A., Guo, J., Mani, U., Patane, M., Carson, K., Ye, Q., Bennett, R., Chi, S., Jenkins, T., et al. (2006). Design, synthesis, and progress toward optimization of potent small molecule antagonists of CC chemokine receptor 8 (CCR8). Journal of medicinal chemistry 49, 2669-2672.

Gilmore, T. D., and Gerondakis, S. (2011). The c-Rel Transcription Factor in Development and Disease. Genes & cancer 2, 695-711.

Hamann, I., Zipp, F., and Infante-Duarte, C. (2008). Therapeutic targeting of chemokine signaling in Multiple Sclerosis. Journal of the neurological sciences 274, 31-38.

Harant, H., and Lindley, I. J. (2004). Negative cross-talk between the human orphan nuclear receptor Nur77/NAK-1/TR3 and nuclear factor-kappaB. Nucleic acids research 32, 5280-5290.

Harel, S., Tu, E. Y., Weisberg, S., Esquilin, M., Chambers, S. M., Liu, B., Carson, C. T., Studer, L., Reizis, B., and Tomishima, M. J. (2012). ZFX controls the self-renewal of human embryonic stem cells. PloS one 7, e42302.

Harrington, L. E., Janowski, K. M., Oliver, J. R., Zajac, A. J., and Weaver, C. T. (2008). Memory CD4 T cells emerge from effector T-cell progenitors. Nature 452, 356-360.

Hendriks, J., Gravestein, L. A., Tesselaar, K., van Lier, R. A., Schumacher, T. N., and Borst, J. (2000). CD27 is required for generation and long-term maintenance of T cell immunity. Nature immunology 1, 433-440.

Hendriks, J., Xiao, Y., and Borst, J. (2003). CD27 promotes survival of activated T cells and complements CD28 in generation and establishment of the effector T cell pool. The Journal of experimental medicine 198, 1369-1380.

Hernandez-Santos, N., and Gaffen, S. L. (2012). Th17 cells in immunity to *Candida albicans*. Cell host & microbe 11, 425-435.

Hilliard, B. A., Mason, N., Xu, L., Sun, J., Lamhamedi-Cherradi, S. E., Liou, H. C., Hunter, C., and Chen, Y. H. (2002). Critical roles of c-Rel in autoimmune inflammation and helper T cell differentiation. The Journal of clinical investigation 110, 843-850.

Hitoshi, Y., Lorens, J., Kitada, S. I., Fisher, J., LaBarge, M., Ring, H. Z., Francke, U., Reed, J. C., Kinoshita, S., and Nolan, G. P. (1998). Toso, a cell surface, specific regulator of Fas-induced apoptosis in T cells. Immunity 8, 461-471.

Hock, H., Meade, E., Medeiros, S., Schindler, J. W., Valk, P. J., Fujiwara, Y., and Orkin, S. H. (2004). Tel/Etv6 is an essential and selective regulator of adult hematopoietic stem cell survival. Genes & development 18, 2336-2341.

Hueber, W., Sands, B. E., Lewitzky, S., Vandemeulebroecke, M., Reinisch, W., Higgins, P. D., Wehkamp, J., Feagan, B. G., Yao, M. D., Karczewski, M., et al. (2012). Secukinumab, a human anti-IL-17A monoclonal antibody, for moderate to severe Crohn's disease: unexpected results of a randomised, double-blind placebo-controlled trial. Gut 61, 1693-1700.

Hundt, M., Tabata, H., Jeon, M. S., Hayashi, K., Tanaka, Y., Krishna, R., De Giorgio, L., Liu, Y. C., Fukata, M., and Altman, A. (2006). Impaired activation and localization of LAT in anergic T cells as a consequence of a selective palmitoylation defect. Immunity 24, 513-522.

Huntley, R. P., Binns, D., Dimmer, E., Barrell, D., O'Donovan, C., and Apweiler, R. (2009). QuickGO: a user tutorial for the web-based Gene Ontology browser. Database: the journal of biological databases and curation 2009, bap010.

Ichii, H., Sakamoto, A., Arima, M., Hatano, M., Kuroda, Y., and Tokuhisa, T. (2007). Bcl6 is essential for the generation of long-term memory CD4+ T cells. International immunology 19, 427-433.

International Genetics of Ankylosing Spondylitis, C., Cortes, A., Hadler, J., Pointon, J. P., Robinson, P. C., Karaderi, T., Leo, P., Cremin, K., Pryce, K., Harris, J., el al. (2013). Identification of multiple risk variants for ankylosing spondylitis through high-density genotyping of immune-related loci. Nature genetics 45, 730-738.

International Multiple Sclerosis Genetics, C., Wellcome Trust Case Control, C., Sawcer, S., Hellenthal, G., Pirinen, M., Spencer, C. C., Patsopoulos, N. A., Moutsianas, L., Dilthey, A., Su, Z., et al. (2011). Genetic risk and a primary role for cell-mediated immune mechanisms in multiple sclerosis. Nature 476, 214-219.

Ioannidis, V., Beermann, F., Clevers, H., and Held, W. (2001). The beta-catenin-TCF-1 pathway ensures CD4(+) CD8(+) thymocyte survival. Nature immunology 2, 691-697.

Ivanov, II, Atarashi, K., Manel, N., Brodie, E. L., Shima, T., Karaoz, U., Wei, D., Goldfarb, K. C., Santee, C. A., Lynch, S. V., et al. (2009). Induction of intestinal Th17 cells by segmented filamentous bacteria. Cell 139, 485-498.

Jager, A., Dardalhon, V., Sobel, R. A., Bettelli, E., and Kuchroo, V. K. (2009). Th1, Th17, and Th9 effector cells induce experimental autoimmune encephalomyelitis with different pathological phenotypes. Journal of immunology 183, 7169-7177.

Jarboe, J. S., Anderson, J. C., Duarte, C. W., Mehta, T., Nowsheen, S., Hicks, P. H., Whitley, A. C., Rohrbach, T. D., McCubrey, R. O., Chiu, S., et al. (2012). MARCKS regulates growth and radiation sensitivity and is a novel prognostic factor for glioma. Clinical cancer research: an official journal of the American Association for Cancer Research 18, 3030-3041.

Jhun, J. Y., Yoon, B. Y., Park, M. K., Oh, H. J., Byun, J. K., Lee, S. Y., Min, J. K., Park, S. H., Kim, H. Y., and Cho, M. L. (2012). Obesity aggravates the joint inflammation in a collagen-induced arthritis model through deviation to Th17 differentiation. Experimental & molecular medicine 44, 424-431.

Jin, L., Martynowski, D., Zheng, S., Wada, T., Xie, W., and Li, Y. (2010). Structural basis for hydroxycholesterols as natural ligands of orphan nuclear receptor RORgamma. Molecular endocrinology 24, 923-929.

Johnson, W. E., Li, C., and Rabinovic, A. (2007). Adjusting batch effects in microarray expression data using empirical Bayes methods. Biostatistics 8, 118-127.

Jostins, L., Ripke, S., Weersma, R. K., Duerr, R. H., McGovern, D. P., Hui, K. Y., Lee, J. C., Schumm, L. P., Sharma, Y., Anderson, C. A., el al. (2012). Host-microbe interactions have shaped the genetic architecture of inflammatory bowel disease. Nature 491, 119-124.

Kandasamy, K., Mohan, S. S., Raju, R., Keerthikumar, S., Kumar, G. S., Venugopal, A. K., Telikicherla, D., Navarro, J. D., Mathivanan, S., Pecquet, C., el al. (2010). NetPath: a public resource of curated signal transduction pathways. Genome biology 11, R3.

Kaplan, M. H., Sun, Y. L., Hoey, T., and Grusby, M. J. (1996). Impaired IL-12 responses and enhanced development of Th2 cells in Stat4-deficient mice. Nature 382, 174-177.

Komatsu, N., Okamoto, K., Sawa, S., Nakashima, T., Ohhora, M., Kodama, T., Tanaka, S., Bluestone, J. A., and Takayanagi, H. (2014). Pathogenic conversion of Foxp3+ T cells into TH17 cells in autoimmune arthritis. Nature medicine 20, 62-68.

Konkel, J. E., and Chen, W. (2011). Balancing acts: the role of TGF-beta in the mucosal immune system. Trends in molecular medicine 17, 668-676.

Korn, T., Bettelli, E., Gao, W., Awasthi, A., Jager, A., Strom, T. B., Oukka, M., and Kuchroo, V. K. (2007). IL-21 initiates an alternative pathway to induce proinflammatory T(H)17 cells. Nature 448, 484-487.

Korn, T., Bettelli, E., Oukka, M., and Kuchroo, V. K. (2009). IL-17 and Th17 Cells. Annu Rev Immunol 27, 485-517.

Kryczek, I., Zhao, E., Liu, Y., Wang, Y., Vatan, L., Szeliga, W., Moyer, J., Klimczak, A., Lange, A., and Zou, W. (2011). Human TH17 cells are long-lived effector memory cells. Science translational medicine 3, 104ra100.

Kurachi, M., Barnitz, R. A., Yosef, N., Odorizzi, P. M., DiIorio, M. A., Lemieux, M. E., Yates, K., Godec, J., Klatt, M. G., Regev, A., et al. (2014). The transcription factor BATF operates as an essential differentiation checkpoint in early effector CD8+ T cells. Nature immunology 15, 373-383.

Lachmann, A., Xu, H., Krishnan, J., Berger, S. I., Mazloom, A. R., and Ma'ayan, A. (2010). ChEA: transcription factor regulation inferred from integrating genome-wide ChIP-X experiments. Bioinformatics 26, 2438-2444.

Lalmansingh, A. S., Arora, K., Demarco, R. A., Hager, G. L., and Nagaich, A. K. (2013). High-throughput RNA FISH analysis by imaging flow cytometry reveals that pioneer factor Foxa1 reduces transcriptional stochasticity. PloS one 8, e76043.

Lamb, JR., Zanders, E. D., Sewell, W., Crumpton, M. J., Feldmann, M., and Owen, M. J. (1987). Antigen-specific T cell unresponsiveness in cloned helper T cells mediated via the CD2 or CD3/Ti receptor pathways. European journal of immunology 17, 1641-1644.

Lang, K. S., Lang, P. A., Meryk, A., Pandyra, A. A., Boucher, L. M., Pozdeev, V. I., Tusche, M. W., Gothert, J. R., Haight, J., Wakeham, A., et al. (2013). Involvement of Toso in activation of monocytes, macrophages, and granulocytes. Proceedings of the National Academy of Sciences of the United States of America 110, 2593-2598.

Latta, M., Mohan, K., and Issekutz, T. B. (2007). CXCR6 is expressed on T cells in both T helper type 1 (Th1) inflammation and allergen-induced Th2 lung inflammation but is only a weak mediator of chemotaxis. Immunology 121, 555-564.

Laurence, A., Tato, C. M., Davidson, T. S., Kanno, Y., Chen, Z., Yao, Z., Blank, R. B., Meylan, F., Siegel, R., Hennighausen, L., et al. (2007). Interleukin-2 signaling via STAT5 constrains T helper 17 cell generation. Immunity 26, 371-381.

Lee, Y., Awasthi, A., Yosef, N., Quintana, F. J., Xiao, S., Peters, A., Wu, C., Kleinewietfeld, M., Kunder, S., Hafler, D. A., et al. (2012). Induction and molecular signature of pathogenic TH17 cells. Nature immunology 13, 991-999.

Lee, Y. K., Turner, H., Maynard, C. L., Oliver, J. R., Chen, D., Elson, C. O., and Weaver, C. T. (2009). Late developmental plasticity in the T helper 17 lineage. Immunity 30, 92-107.

Lees, C. W., Barrett, J. C., Parkes, M., and Satsangi, J. (2011). New IBD genetics. common pathways with other diseases. Gut 60, 1739-1753.

Liberzon, A., Subramanian, A., Pinchback, R., Thorvaldsdottir, H., Tamayo, P., and Mesirov, J. P. (2011). Molecular signatures database (MSigDB) 3.0. Bioinformatics 27, 1739-1740. Leonardi, C., Matheson, R., Zachariae, C., Cameron, G., Li, L., Edson-Heredia, E., Braun, D., and Banerjee, S. (2012). Anti-interleukin-17 monoclonal antibody ixekizumab in chronic plaque psoriasis. The New England journal of medicine 366, 1190-1199.

Lin, L., Ibrahim, A. S., Xu, X., Farber, J. M., Avanesian, V., Baquir, B., Fu, Y., French, S. W., Edwards, J. E., Jr., and Spellberg, B. (2009). Th1-Th17 cells mediate protective adaptive immunity against *Staphylococcus aureus* and *Candida albicans* infection in mice. PLoS pathogens S, e1000703.

Linhart, C., Halperin, Y., and Shamir, R. (2008). Transcription factor and microRNA motif discovery: the Amadeus platform and a compendium of metazoan target sets. Genome research 18, 1180-1189.

Liu, Y., Wang, X., Jiang, J., Cao, Z., Yang, B., and Cheng, X. (2011). Modulation of T cell cytokine production by miR-144* with elevated expression in patients with pulmonary tuberculosis. Molecular immunology 48, 1084-1090.

Mahad, D. J., and Ransohoff, R. M. (2003). The role of MCP-1 (CCL2) and CCR2 in multiple sclerosis and experimental autoimmune encephalomyelitis (EAE). Seminars in immunology 15, 23-32.

Maity, A., and Koumenis, C. (2006). HIF and MIF-a nifty way to delay senescence? Genes & development 20, 3337-3341.

Martinez, V. G., Escoda-Ferran, C., Tadeu Simoes, I., Arai, S., Orta Mascaro, M., Carreras, E., Martinez-Florensa, M., Yelamos, J., Miyazaki, T., and Lozano, F. (2014). The macrophage soluble receptor AIM/Api6/CD5L displays a broad pathogen recognition spectrum and is involved in early response to microbial aggression. Cellular & molecular immunology 11, 343-354.

Mathews, J. A., Wurmbrand, A. P., Ribeiro, L., Neto, F. L., and Shore, S. A. (2014). Induction of IL-17A Precedes Development of Airway Hyperresponsiveness during Diet-Induced Obesity and Correlates with Complement Factor D. Frontiers in immunology 5, 440.

Maynard, C. L., Harrington, L. E., Janowski, K. M., Oliver, J. R., Zindl, C. L., Rudensky, A. Y., and Weaver, C. T. (2007). Regulatory T cells expressing interleukin 10 develop from Foxp3+ and Foxp3− precursor cells in the absence of interleukin 10. Nature immunology 8, 931-941.

McGeachy, M. J., Chen, Y., Tato, C. M., Laurence, A., Joyce-Shaikh, B., Blumenschein, W. M., McClanahan, T. K., O'Shea, J. J., and Cua, D. J. (2009). The interleukin 23 receptor is essential for the terminal differentiation of interleukin 17-producing effector T helper cells in vivo. Nature immunology 10, 314-324.

Miaw, S. C., Choi, A., Yu, E., Kishikawa, H., and Ho, I. C. (2000). ROG, repressor of GATA, regulates the expression of cytokine genes. Immunity 12, 323-333.

Miyazaki, T., Hirokami, Y., Matsuhashi, N., Takatsuka, H., and Naito, M. (1999). Increased susceptibility of thymocytes to apoptosis in mice lacking AIM, a novel murine macrophage-derived soluble factor belonging to the scavenger receptor cysteine-rich domain superfamily. The Journal of experimental medicine 189, 413-422.

Mo, C., Chearwae, W., O'Malley, J. T., Adams, S. M., Kanakasabai, S., Walline, C. C., Stritesky, G. L., Good, S. R., Perumal, N. B., Kaplan, M. H., et al. (2008). Stat4 isoforms differentially regulate inflammation and demyelination in experimental allergic encephalomyelitis. Journal of immunology 181, 5681-5690.

Monk, J. M., Hou, T. Y., Turk, H. F., McMurray, D. N., and Chapkin, R. S. (2013). n3 PUFAs reduce mouse CD4+ T-cell ex vivo polarization into Th17 cells. J Nutr 143, 1501-1508.

Monk, J. M., Jia, Q., Callaway, E., Weeks, B., Alaniz, R. C., McMurray, D. N., and Chapkin, R. S. (2012). Th17 cell accumulation is decreased during chronic experimental colitis by (n-3) PUFA in Fat-1 mice. J Nutr 142, 117-124.

Muranski, P., Borman, Z. A., Kerkar, S. P., Klebanoff, C. A., Ji, Y., Sanchez-Perez, L., Sukumar, M., Reger, R. N., Yu, Z., Kern, S. J., et al. (2011). Th17 cells are long lived and retain a stem cell-like molecular signature. Immunity 35, 972-985.

Nakae, S., Iwakura, Y., Suto, H., and Galli, S. J. (2007). Phenotypic differences between Th1 and Th17 cells and negative regulation of Th1 cell differentiation by IL-17. Journal of leukocyte biology 81, 1258-1268.

Nguyen, X. H., Lang, P. A., Lang, K. S., Adam, D., Fattakhova, G., Foger, N., Kamal, M. A., Prilla, P., Mathieu, S., Wagner, C., et al. (2011). Toso regulates the balance between apoptotic and nonapoptotic death receptor signaling by facilitating RIP1 ubiquitination. Blood 118, 598-608.

Nishikomori, R., Usui, T., Wu, C. Y., Morinobu, A., O'Shea, J. J., and Strober, W. (2002). Activated STAT4 has an essential role in Th1 differentiation and proliferation that is independent of its role in the maintenance of IL-12R beta 2 chain expression and signaling. Journal of immunology 169, 4388-4398.

Novershtern, N., Subramanian, A., Lawton, L. N., Mak, R. H., Haining, W. N., McConkey, M. E., Habib, N., Yosef, N., Chang, C. Y., Shay, T., el al. (2011). Densely interconnected transcriptional circuits control cell states in human hematopoiesis. Cell 144, 296-309.

Nurieva, R., Yang, X. O., Martinez, G., Zhang, Y., Panopoulos, A. D., Ma, L., Schluns, K., Tian, Q., Watowich, S. S., Jetten, A. M., et al. (2007). Essential autocrine regulation by IL-21 in the generation of inflammatory T cells. Nature 448, 480-483.

Palmer, M. T., and Weaver, C. T. (2010). Autoimmunity: increasing suspects in the CD4+ T cell lineup. Nature immunology 11, 36-40.

Papp, K. A., Leonardi, C., Menter, A., Ortonne, J. P., Krueger, J. G., Kricorian, G., Aras, G., Li, J., Russell, C. B., Thompson, E. H., et al. (2012). Brodalumab, an anti-interleukin-17-receptor antibody for psoriasis. The New England journal of medicine 366, 1181-1189.

Patel, D. D., Lee, D. M., Kolbinger, F., and Antoni, C. (2013). Effect of IL-17A blockade with secukinumab in autoimmune diseases. Annals of the rheumatic diseases 72 Suppl 2, iii 16-123.

Pe'er, D., Regev, A., and Tanay, A. (2002). Minreg: inferring an active regulator set. Bioinformatics 18 Suppl 1, S258-267.

Pepper, M., Linehan, J. L., Pagan, A. J., Zell, T., Dileepan, T., Cleary, P. P., and Jenkins, M. K. (2010). Different routes of bacterial infection induce long-lived TH1 memory cells and short-lived TH17 cells. Nature immunology 11, 83-89.

Perfetto, S. P., Chattopadhyay, P. K., and Roederer, M. (2004). Seventeen-colour flow cytometry: unravelling the immune system. Nature reviews Immunology 4, 648-655.

Peters, A., Burkett, P. R., Sobel, R. A., Buckley, C. D., Watson, S. P., Bettelli, E., and Kuchroo, V. K. (2014). Podoplanin negatively regulates CD4+ effector T cell responses. The Journal of clinical investigation.

Pruitt, K. D., Tatusova, T., and Maglott, D. R. (2007). NCBI reference sequences (RefSeq): a curated non-redundant sequence database of genomes, transcripts and proteins. Nucleic Acids Res 35, D61-65.

Quintana, F. J., Jin, H., Burns, E. J., Nadeau, M., Yeste, A., Kumar, D., Rangachari, M., Zhu, C., Xiao, S., Seavitt, J., et al. (2012). Aiolos promotes TH17 differentiation by directly silencing Il2 expression. Nature immunology 13, 770-777.

Ramskold, D., Luo, S., Wang, Y.-C., Li, R., Deng, Q., Faridani, O. R., Daniels, G. A., Khrebtukova, I., Loring, J. F., Laurent, L. C., et al. (2012). Full-length mRNA-Seq from single-cell levels of RNA and individual circulating tumor cells. Nature biotechnology 30, 777-782.

Reya, T., Duncan, A. W., Ailles, L., Domen, J., Scherer, D. C., Willert, K., Hintz, L., Nusse, R., and Weissman, I. L. (2003). A role for Wnt signalling in self-renewal of haematopoietic stem cells. Nature 423, 409-414.

Risso, D., Schwartz, K., Sherlock, G., and Dudoit, S. (2011). GC-content normalization for RNA-Seq data. BMC bioinformatics 12, 480.

Rocha, P. P., Scholze, M., Bleiss, W., and Schrewe, H. (2010). Med12 is essential for early mouse development and for canonical Wnt and Wnt/PCP signaling. Development 137, 2723-2731.

Sallusto, F., Lenig, D., Forster, R., Lipp, M., and Lanzavecchia, A. (1999). Two subsets of memory T lymphocytes with distinct homing potentials and effector functions. Nature 401, 708-712.

Salminen, A., and Kaarniranta, K. (2011). Control of p53 and NF-kappaB signaling by WIP1 and MIF: role in cellular senescence and organismal aging. Cellular signalling 23, 747-752.

Santori, F. R., Huang, P., van de Pavert, S. A., Douglass, E. F., Jr., Leaver, D. J., Haubrich, B. A., Keber, R., Lorbek, G., Konijn, T., Rosales, B. N., el al. (2015). Identification of natural RORgamma ligands that regulate the development of lymphoid cells. Cell metabolism 21, 286-297.

Sarkar, S., Kalia, V., Haining, W. N., Konieczny, B. T., Subramaniam, S., and Ahmed, R. (2008). Functional and genomic profiling of effector CD8 T cell subsets with distinct memory fates. The Journal of experimental medicine 205, 625-640.

Sarrias, M. R., Gronlund, J., Padilla, O., Madsen, J., Holmskov, U., and Lozano, F. (2004). The Scavenger Receptor Cysteine-Rich (SRCR) domain: an ancient and highly conserved protein module of the innate immune system. Critical reviews in immunology 24, 1-37.

Segal, E., Shapira, M., Regev, A., Pe'er, D., Botstein, D., Koller, D., and Friedman, N. (2003). Module networks: identifying regulatory modules and their condition-specific regulators from gene expression data. Nature genetics 34, 166-176.

Sester, U., Presser, D., Dirks, J., Gartner, B. C., Kohler, H., and Sester, M. (2008). PD-1 expression and IL-2 loss of cytomegalovirus-specific T cells correlates with viremia and reversible functional anergy. American journal of transplantation: official journal of the American Society of Transplantation and the American Society of Transplant Surgeons 8, 1486-1497.

Shalek, A. K., Satija, R., Adiconis, X., Gertner, R. S., Gaublomme, J. T., Raychowdhury, R., Schwartz, S., Yosef, N., Malboeuf, C., Gnirke, A., et al. (2013). Single-cell transcriptomics reveals bimodality in expression and splicing in immune cells. Nature in press.

Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 509, 363-369.

Shi, L. Z., Wang, R., Huang, G., Vogel, P., Neale, G., Green, D. R., and Chi, H. (2011). HIF1 alpha-dependent glycolytic pathway orchestrates a metabolic checkpoint for the differentiation of TH17 and Treg cells. The Journal of experimental medicine 208, 1367-1376.

Shin, H. J., Lee, J. B., Park, S. H., Chang, J., and Lee, C. W. (2009). T-bet expression is regulated by EGR1-mediated signaling in activated T cells. Clinical immunology 131, 385-394.

Shinohara, M. L., Kim, J. H., Garcia, V. A., and Cantor, H. (2008). Engagement of the type I interferon receptor on dendritic cells inhibits T helper 17 cell development: role of intracellular osteopontin. Immunity 29, 68-78.

Snyder, C. M., Cho, K. S., Bonnett, E. L., van Dommelen, S., Shellam, G. R., and Hill, A. B. (2008). Memory inflation during chronic viral infection is maintained by continuous production of short-lived, functional T cells. Immunity 29, 650-659.

Song, Y., and Jacob, C. O. (2005). The mouse cell surface protein TOSO regulates Fas/Fas ligand-induced apoptosis through its binding to Fas-associated death domain. The Journal of biological chemistry 280, 9618-9626.

Soroosh, P., Wu, J., Xue, X., Song, J., Sutton, S. W., Sablad, M., Yu, J., Nelen, M. I., Liu, X., Castro, G., et al. (2014). Oxysterols are agonist ligands of RORgammat and drive Th17 cell differentiation. Proceedings of the National Academy of Sciences of the United States of America 111, 12163-12168.

Stumhofer, J. S., Silver, J. S., Laurence, A., Porrett, P. M., Harris, T. H., Turka, L. A., Ernst, M., Saris, C. J., O'Shea, J. J., and Hunter, C. A. (2007). Interleukins 27 and 6 induce STAT3-mediated T cell production of interleukin 10. Nature immunology 8, 1363-1371.

Sutton, C., Brereton, C., Keogh, B., Mills, K. H., and Lavelle, E. C. (2006). A crucial role for interleukin (IL)-1 in the induction of IL-17-producing T cells that mediate autoimmune encephalomyelitis. The Journal of experimental medicine 203, 1685-1691.

Symons, A., Budelsky, A. L., and Towne, J. E. (2012). Are Th17 cells in the gut pathogenic or protective? Mucosal immunology 5, 4-6.

Thierfelder, W. E., van Deursen, J. M., Yamamoto, K., Tripp, R. A., Sarawar, S. R., Carson, R. T., Sangster, M. Y., Vignali, D. A., Doherty, P. C., Grosveld, G. C., et al. (1996). Requirement for Stat4 in interleukin-12-mediated responses of natural killer and T cells. Nature 382, 171-174.

Trapnell, C., Cacchiarelli, D., Grimsby, J., Pokharel, P., Li, S., Morse, M., Lennon, N. J., Livak, K. J., Mikkelsen, T. S., and Rinn, J. L. (2014). The dynamics and regulators of cell fate decisions are revealed by pseudotemporal ordering of single cells. Nature biotechnology 32, 381-386.

Trapnell, C., Pachter, L., and Salzberg, S. L. (2009). TopHat. discovering splice junctions with RNA-Seq. In Bioinformatics, pp. 1105-1111.

Trimble, L. A., Kam, L. W., Friedman, R. S., Xu, Z., and Lieberman, J. (2000). CD3zeta and CD28 down-modulation on CD8 T cells during viral infection. Blood 96, 1021-1029.

Tsuzuki, S., and Seto, M. (2013). TEL (ETV6)-AML1 (RUNX1) initiates self-renewing fetal pro-B cells in association with a transcriptional program shared with embryonic stem cells in mice. Stem cells 31, 236-247.

Veldhoen, M., Hocking, R. J., Atkins, C. J., Locksley, R. M., and Stockinger, B. (2006). TGFbeta in the context of an inflammatory cytokine milieu supports de novo differentiation of IL-17-producing T cells. Immunity 24, 179-189.

Waite, J. C., and Skokos, D. (2012). Th17 response and inflammatory autoimmune diseases. International journal of inflammation 2012, 819467.

Wang, H., Geng, J., Wen, X., Bi, E., Kossenkov, A. V., Wolf, A. I., Tas, J., Choi, Y. S., Takata, H., Day, T. J., et al. (2014). The transcription factor Foxp1 is a critical negative regulator of the differentiation of follicular helper T cells. Nature immunology 15, 667-675.

Wei, G., Wei, L., Zhu, J., Zang, C., Hu-Li, J., Yao, Z., Cui, K., Kanno, Y., Roh, T. Y., Watford, W. T., et al. (2009). Global mapping of H3K4me3 and H3K27me3 reveals specificity and plasticity in lineage fate determination of differentiating CD4+ T cells. Immunity 30, 155-167.

Weisberg, S. P., Smith-Raska, M. R., Esquilin, J. M., Zhang, J., Arenzana, T. L., Lau, C. M., Churchill, M., Pan, H., Klinakis, A., Dixon, J. E., et al. (2014). ZFX controls propagation and prevents differentiation of acute T-lymphoblastic and myeloid leukemia. Cell reports 6, 528-540.

Welford, S. M., Bedogni, B., Gradin, K., Poellinger, L., Broome Powell, M., and Giaccia, A. J. (2006). HIF1alpha delays premature senescence through the activation of MIF. Genes & development 20, 3366-3371.

Wells, A. D., Walsh, M. C., Bluestone, J. A., and Turka, L. A. (2001). Signaling through CD28 and CTLA-4 controls two distinct forms of T cell anergy. The Journal of clinical investigation 108, 895-903.

Wherry, E. J., Ha, S. J., Kaech, S. M., Haining, W. N., Sarkar, S., Kalia, V., Subramaniam, S., Blattman, J. N., Barber, D. L., and Ahmed, R. (2007). Molecular signature of CD8+ T cell exhaustion during chronic viral infection. Immunity 27, 670-684.

Willinger, T., Freeman, T., Herbert, M., Hasegawa, H., McMichael, A. J., and Callan, M. F. (2006). Human naïve CD8 T cells down-regulate expression of the WNT pathway transcription factors lymphoid enhancer binding factor I and transcription factor 7 (T cell factor-1) following antigen encounter in vitro and in vivo. Journal of immunology 176, 1439-1446.

Winer, S., Paltser, G., Chan, Y., Tsui, H., Engleman, E., Winer, D., and Dosch, H. M. (2009). Obesity predisposes to Th17 bias. European journal of immunology 39, 2629-2635.

Wu, C., Yosef, N., Thalhamer, T., Zhu, C., Xiao, S., Kishi, Y., Regev, A., and Kuchroo, V. K. (2013). Induction of pathogenic TH17 cells by inducible salt-sensing kinase SGK1. Nature 496, 513-517.

Xiao, S., Yosef, N., Yang, J., Wang, Y., Zhou, L., Zhu, C., Wu, C., Baloglu, E., Schmidt, D., Ramesh, R., et al. (2014). Small-molecule RORgammat antagonists inhibit T helper 17 cell transcriptional network by divergent mechanisms. Immunity 40, 477-489.

Xu, J., Yang, Y., Qiu, G., Lal, G., Wu, Z., Levy, D. E., Ochando, J. C., Bromberg, J. S., and Ding, Y. (2009). c-Maf regulates IL-10 expression during Th17 polarization. Journal of immunology 182, 6226-6236.

Yosef, N., Shalek, A. K., Gaublomme, J. T., Jin, H., Lee, Y., Awasthi, A., Wu, C., Karwacz, K., Xiao, S., Jorgolli, M., et al. (2013). Dynamic regulatory network controlling TH17 cell differentiation. Nature 496, 461-468.

Zhou, L., Ivanov, II, Spolski, R., Min, R., Shenderov, K., Egawa, T., Levy, D. E., Leonard, W. J., and Littman, D. R. (2007). IL-6 programs T(H)-17 cell differentiation by promoting sequential engagement of the IL-21 and IL-23 pathways. Nature immunology 8, 967-974.

Zingoni, A., Soto, H., Hedrick, J. A., Stoppacciaro, A., Storlazzi, C. T., Sinigaglia, F., D'Ambrosio, D., O'Garra, A., Robinson, D., Rocchi, M., et al. (1998). The chemokine receptor CCR8 is preferentially expressed in Th2 but not Th1 cells. Journal of immunology 161, 547-551.

The invention is further described by the following numbered paragraphs:

1. A method of diagnosing, prognosing and/or staging an immune response involving T cell balance, comprising detecting a first level of expression, activity and/or function of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l and comparing the detected level to a control of level of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Sc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or gene product expression, activity and/or function, wherein a difference in the detected level and the control level indicates that the presence of an immune response in the subject.

2. A method of monitoring an immune response in a subject comprising detecting a level of expression, activity and/or function of one or more of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5 at a first time point, detecting a level of expression, activity and/or function of one or more signature genes or one or more products of one or more of a gene in a herein Table or a combination of genes in herein Table(s) or Toso, Ctla2b, Gatm. Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l at a second time point, and comparing the first detected level of expression, activity and/or function with the second detected level of expression, activity and/or function, wherein a change in the first and second detected levels indicates a change in the immune response in the subject.

3. A method of identifying a patient population at risk or suffering from an immune response comprising detecting a level of expression, activity and/or function of one or more of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the patient population and comparing the level of expression, activity and/or function of one or more signature genes or one or more products of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr6S, Plzp or Cd5l or any combination thereof Gpr65, Plzp or Cd5l in any combination of Gpr65, Plzp, Toso or Cd5l in a patient population not at risk or suffering from an immune response, wherein a difference in the level of expression, activity and/or function of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5 or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more thereof Gpr65, Plzp or Cd5l or any combination of Gpr6S, Plzp or Cd5l in any combination of Gpr65, Plzp, Toso or Cd5l in the patient populations identifies the patient population as at risk or suffering from an immune response.

4. A method for monitoring subjects undergoing a treatment or therapy specific for a target gene selected from the group consisting of candidates comprising a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l for an aberrant immune response to determine whether the patient is responsive to the treatment or therapy comprising detecting a level of expression, activity and/or function of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the absence of the treatment or therapy and comparing the level of expression, activity and/or function of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Slc25a13, Chd2, Ino80c, Med21, Pdss1, Galk1, (Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in the presence of the treatment or therapy, wherein a difference in the level of expression, activity and/or function of a gene in a herein Table or a combination of genes in herein Table(s) or Toso, Ctla2b, Gatm, Bdh2, Bcat1, Zfp36, Acsl4, Acal3, Adi1, Doll, Mett10d, Sirt6, Slc25a13, Chd2, Ino80c, Med21. Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gam, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more thereof Gpr65, Plzp or Cd5l or any combination of Gpr65, Plzp or Cd5l in any combination of Gpr65, Plzp, Toso or Cd5l in the presence of the treatment or therapy indicates whether the patient is responsive to the treatment or therapy.

5. The method of any one of numbered paragraphs 1 to 4 wherein the immune response is an autoimmune response or an inflammatory response.

6. The method of numbered paragraph 5 wherein the inflammatory response is associated with an autoimmune response, an infectious disease and/or a pathogen-based disorder.

7. The method of any one of numbered paragraphs 1 to 6 wherein the signature genes are Th17-associated genes.

8. The method of any one of numbered paragraphs 4 to 7, wherein the treatment or therapy is an antagonist as to expression of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce differentiation toward regulatory T cells (Tregs), Th1 cells, or a combination of Tregs and Th1 cells.

9. The method of any one of numbered paragraphs 4 to 7, wherein the treatment or therapy is an agonist that enhances or increases the expression of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce T cell differentiation toward Th17 cells.

10. The method of numbered paragraphs 4 to 7, wherein the treatment or therapy is an antagonist of a target gene selected from the group consisting of a gene in a herein Table or a combination of genes in herein Table(s) or Toso, Ctla2h, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a pathogenic to non-pathogenic signature.

11. The method of numbered paragraphs 4 to 7, wherein the treatment or therapy is antagonist that enhances or increases the expression of a target gene selected from the group consisting of a gene in a herein Table or a combination of genes in herein Table(s) or Toso, Ctla2b, Gatm, Bdh2, Bcat1, Zfp36, Acsl4, Acat3, Adi1, Doll, Mett10d, Sirt6, Slc25a13, Chd2, Ino80c, Med2l, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a non-pathogenic to a pathogenic signature.

12. The method according to any one of numbered paragraphs 8 to 11, wherein the T cell modulating agent is an antibody, a soluble polypeptide, a polypeptide agent, a peptide agent, a nucleic acid agent, a nucleic acid ligand, or a small molecule agent.

13. A method of modulating T cell balance, the method comprising contacting a T cell or a population of T cells with a T cell modulating agent in an amount sufficient to modify differentiation, maintenance and/or function of the T cell or population of T cells by altering balance between Th17 cells, regulatory T cells (Tregs) and other T cell subsets as compared to differentiation, maintenance and/or function of the T cell or population of T cells in the absence of the T cell modulating agent; wherein the T cell modulating agent is an antagonist for or of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13. Chd2, Ino80c, Med21, Pdss1, Galk1, Gnpda2 or Mtpap or any one of the foregoing or any combination thereof with one or more of Gpr65. Plzp or Cd5l or any combination thereof Gpr65, Plzp or Cd5l in any combination of Gpr65, Plzp, Toso or Cd5l in an amount sufficient to induce differentiation toward regulatory T cells (Tregs), Th1 cells, or a combination of Tregs and Th1 cells, or wherein the T cell modulating agent is an agonist that enhances or increases the expression of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more of Gpr65, Plzp or Cd5l or any combination thereof Gpr65. Plzp or Cd5l in any combination of Gpr65, Plzp, Toso or Cd5l in an amount sufficient to induce T cell differentiation toward Th17 cells, or wherein the T cell modulating agent is specific for a target gene selected from the group consisting of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l, or wherein the T cell modulating agent is an antagonist of a target gene selected from the group consisting of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a pathogenic to non-pathogenic signature, or wherein the T cell modulating agent is an agonist that enhances or increases the expression of a target gene selected from the group consisting of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a non-pathogenic to a pathogenic signature.

14. The method according to numbered paragraph 13, wherein the T cell modulating agent is an antibody, a soluble polypeptide, a polypeptide agent, a peptide agent, a nucleic acid agent, a nucleic acid ligand, or a small molecule agent.

15. The method according to numbered paragraph 13, wherein the T cells are naïve T cells, partially differentiated T cells, differentiated T cells, a combination of naïve T cells and partially differentiated T cells, a combination of naïve T cells and differentiated T cells, a combination of partially differentiated T cells and differentiated T cells, or a combination of naïve T cells, partially differentiated T cells and differentiated T cells.

16. A method of enhancing Th17 differentiation in a cell population, increasing expression, activity and/or function of one or more Th17-associated cytokines or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines or non-Th17-associated transcription regulators selected from FOXP3, interferon gamma (IFN-γ), GATA3, STAT4 and TBX21, comprising contacting a T cell with an agent that enhances expression, activity and/or function of a gene in a herein Table or a combination of genes in herein Table(s) or Toso, Ctla2b, Gatm, Bdh2, Bcat1, Zfp36, Acsl4, Acal3, Adi1, Doll, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l.

17. The method of numbered paragraph 16, wherein the agent enhances expression, activity and/or function of at least Toso.

18. The method of numbered paragraphs 16 or 17, wherein the agent is an antibody, a soluble polypeptide, a polypeptide agonist, a peptide agonist, a nucleic acid agonist, a nucleic acid ligand, or a small molecule agonist.

19. The method of numbered paragraph 18, wherein the agent is an antibody.

20. The method of numbered paragraph 19 wherein the antibody is a monoclonal antibody.

21. The method of numbered paragraph 20, wherein the antibody is a chimeric, humanized or fully human monoclonal antibody.

22. Use of an antagonist for or of a gene in a herein Table or a combination of genes in herein Table(s) or Toso, Ctla2b, Gatm, Bdh2, Bcat1, Zfp36, Acsl4, Acal3, Adi1, Dot1l, Mett10d, Sirt6, Sc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce differentiation toward regulatory T cells (Tregs), Th1 cells, or a combination of Tregs and Th1 cells for treating or Drug Discovery of or formulating or preparing a treatment for an aberrant immune response in a patient.

23. Use of an agonist that enhances or increases the expression of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to induce T cell differentiation toward Th17 cells for treating or Drug Discovery of or formulating or preparing a treatment for an aberrant immune response in a patient.

24. Use of an antagonist of a target gene selected from the group consisting of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65, Plzp or Cd5l in any combination of Gpr65, Plzp, Toso or Cd5l in an amount sufficient to switch Th17 cells from a pathogenic to non-pathogenic signature for treating or Drug Discovery of or formulating or preparing a treatment for an aberrant immune response in a patient.

25. Use of an agonist that enhances or increases the expression of a target gene selected from the group consisting of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino8Mc, Med21, Pdss1, Galk1, Gnpda2 or Mtpap or any one of the foregoing or any combination thereof with one or more thereof Gpr65, Plzp or Cd5 or any combination of Gpr65, Plzp or Cd5l in any combination of Gpr65, Plzp, Toso or Cd5l in an amount sufficient to switch Th17 cells from a non-pathogenic to a pathogenic signature for treating or Drug Discovery of or formulating or preparing a treatment for an aberrant immune response in a patient.

26. A treatment method or Drug Discovery method or method of formulating or preparing a treatment comprising any one of the methods or uses of any of the preceding numbered paragraphs.

27. The method of numbered paragraph 26 or the use of numbered paragraph 27 wherein an agent, agonist or antagonist of any of the preceding numbered paragraphs is a putative drug or treatment in Drug Discovery or formulating or preparing a treatment; and formulating or preparing a treatment comprises admixing the agent, agonist or antagonist with a pharmaceutically acceptable carrier or excipient.

28. A method of drug discovery for the treatment of a disease or condition involving an immune response involving T cell balance in a population of cells or tissue which express one or more of a gene in a herein Table or a combination of genes in herein Table(s) or Toso, Ctla2b, Gatm, Bdh2, Beall, Zfp36, Acsl4, Acat3, Adi1, Dot1I, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr6s, Plzp or Cd5l in any combination thereof Gpr65, Plzp, Toso or Cd5l comprising the steps of:

(a) providing a compound or plurality of compounds to be screened for their efficacy in the treatment of said disease or condition;

(b) contacting said compound or plurality of compounds with said population of cells or tissue;

(c) detecting a first level of expression, activity and/or function of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5l or one or more products of one or more of a gene in a herein Table or a combination of genes in herein Table(s) or Toso, Ctla2b, Gatm, Bdh2, Bcat1, Zfp36, Acsl4, Acat3, Adi1, Dot1l, Mett10d, Sirt6, Slc25a13, Chd2, Ino80c, Med21, Pdss1, Galk1, Gnpda2 or Mtpap or any one of the foregoing or any combination thereof with one or more of Gpr65, Plzp or Cd5l or any combination thereof Gpr65. Plzp or Cd5l in any combination of Gpr65, Plzp, Toso or Cd5l;

(d) comparing the detected level to a control of level of a gene in a herein Table or a combination of genes in herein Table(s) or Toso, Cd1a2b, Gatm, Bdh2, Bcat1, Zfp36, Acsl4, Acat3, Adi1, Dot1l, Mett10d, Sirt6, Slc25a13, Chd2, Ino80c, Med21. Pdss1, Galk1, Gnpda2 or Mtpap or any one of the foregoing or any combination thereof with one or more of Gpr65, Plzp or Cd5l or any combination of Gpr65, Plzp or Cd5l in any combination thereof Gpr65, Plzp, Toso or Cd5 or gene product expression, activity and/or function; and, (e) evaluating the difference between the detected level and the control level to determine the immune response elicited by said compound or plurality of compounds.

29. A method of diagnosing, prognosing and/or staging an immune response involving Th17 T cell balance in a subject, comprising detecting a first level of expression of one or more of saturated fatty acids (SFA) and/or polyunsaturated fatty acids (PUFA) in Th17 cells, and comparing the detected level to a control level of saturated fatty acids (SFA) and/or polyunsaturated fatty acids (PUFA), wherein a change in the first level of expression and the control level detected indicates a change in the immune response in the subject.

30. The method of numbered paragraph 29, further comprising determining the ratio of SFA to PUFA and comparing the ratio to a control level, wherein a shift in the ratio indicates a change in the immune response in the subject.

31. The method of numbered paragraphs 29 or 30, wherein a shift towards polyunsaturated fatty acids (PUFA) and/or away from saturated fatty acids (SFA) indicates a non-pathogenic Th17 response.

32. A method for monitoring subjects undergoing a treatment or therapy involving T cell balance comprising, detecting a first level of expression of one or more of saturated fatty acids (SFA) and/or polyunsaturated fatty acids (PUFA) in Th17 cells in the absence of the treatment or therapy and comparing the detected level to a level of saturated fatty acids (SFA) and/or polyunsaturated fatty acids (PUFA) in the presence of the treatment or therapy, wherein a difference in the level of expression in the presence of the treatment or therapy indicates whether the subject is responsive to the treatment or therapy.

33. The method of numbered paragraph 32, wherein the treatment or therapy involving T cell balance is for a subject undergoing treatment or therapy for cancer or an autoimmune disease.

34. A method of drug discovery for the treatment of a disease or condition involving an immune response involving Th17 T cell balance in a population of cells or tissue comprising:

(a) providing a compound or plurality of compounds to be screened for their efficacy in the treatment of said disease or condition;

(b) contacting said compound or plurality of compounds with said population of cells or tissue; (c) detecting a first level of expression of one or more of saturated fatty acids (SFA) and/or polyunsaturated fatty acids (PUFA) in Th17 cells;

(d) comparing the detected level to a control level of saturated fatty acids (SFA) and/or polyunsaturated fatty acids (PUFA); and, (e) evaluating the difference between the detected level and the control level to determine the immune response elicited by said compound or plurality of compounds.

A method of treatment of a disease or condition involving an immune response involving Th17 T cell balance comprising administering at least one lipid to a patient in need thereof, wherein the at least one lipid is sufficient to cause a shift in the ratio of SFA to PUFA, whereby there is a change in T cell balance.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of discovering a compound capable of altering an immune response in Th17 cells comprising the steps of:
    (a) providing a compound or plurality of compounds;
    (b) providing a population of Th17 cells which express Gpr65, Plzp, and/or Toso, and does not express Cd5l;
    (c) contacting said compound or plurality of compounds with said population of cells;
    (d) detecting a level of expression of Gpr65, Plzp, and/or Toso, and Cd5l;
    (e) comparing the detected level to a control level of a population of Th17 cells not contacted with said compound or plurality of compounds; and
    (f) evaluating the difference between the detected level and the control level to determine if the compound or plurality of compounds alters an immune response in Th17 cells.

2. The method of claim 1, wherein a compound or plurality of compounds that decreases expression of Gpr65, Plzp, and/or Toso, and increases expression of Cd5l is discovered.

3. The method of claim 1, wherein the population of Th17 cells is contacted in vitro or ex vivo.

4. The method of claim 1, wherein the population of Th17 cells are obtained from a subject having an autoimmune response or an inflammatory response.

5. The method of claim 4, wherein the autoimmune response is selected from the group consisting of multiple sclerosis (MS), psoriasis, inflammatory bowel disease, ulcerative colitis, Crohn's disease, uveitis, lupus, ankylosing spondylitis, and rheumatoid arthritis.

* * * * *